US011125739B2

(12) United States Patent
Sharei et al.

(10) Patent No.: US 11,125,739 B2
(45) Date of Patent: Sep. 21, 2021

(54) GENE EDITING THROUGH MICROFLUIDIC DELIVERY

(71) Applicants: Massachusetts Institute of Technology, Cambridge, MA (US); President and Fellows of Harvard College, Cambridge, MA (US)

(72) Inventors: Armon R. Sharei, Watertown, MA (US); Marc Lajoie, Seattle, WA (US); Klavs F. Jensen, Lexington, MA (US); Robert S. Langer, Newton, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 250 days.

(21) Appl. No.: 15/542,892

(22) PCT Filed: Jan. 12, 2016

(86) PCT No.: PCT/US2016/013113

§ 371 (c)(1),
(2) Date: Nov. 27, 2017

(87) PCT Pub. No.: WO2016/115179

PCT Pub. Date: Jul. 21, 2016

(65) Prior Publication Data

US 2018/0003696 A1 Jan. 4, 2018

Related U.S. Application Data

(60) Provisional application No. 62/102,347, filed on Jan. 12, 2015.

(51) Int. Cl.
*C12N 15/87* (2006.01)
*G01N 33/50* (2006.01)
*G01N 33/487* (2006.01)
*C12Q 1/00* (2006.01)

(52) U.S. Cl.
CPC ......... *G01N 33/5002* (2013.01); *C12N 15/87* (2013.01); *G01N 33/48721* (2013.01); *C12Q 1/00* (2013.01)

(58) Field of Classification Search
CPC ......... G01N 33/5002; G01N 33/48721; C12N 15/87; C12Q 1/00
See application file for complete search history.

(56) References Cited

U.S. PATENT DOCUMENTS 4,055,799 A 10/1977 Coster
4,835,457 A 5/1989 Hanss
5,023,054 A 6/1991 Sato et al.
5,643,577 A 7/1997 Pang et al.
5,658,892 A 8/1997 Flotte et al.
5,842,787 A 12/1998 Kopf-Sill et al.
5,951,976 A 9/1999 Segal
6,133,503 A 10/2000 Scheffler
6,156,181 A 12/2000 Parce et al.
6,186,660 B1 2/2001 Kopf-Sill et al.
6,218,166 B1 4/2001 Ravindranath et al.
6,410,329 B1 6/2002 Hansen et al.
6,461,867 B1 10/2002 Cai et al.
6,562,616 B1 5/2003 Toner et al.
7,109,034 B2 9/2006 Ormar et al.
7,704,743 B2 4/2010 Fedorov et al.
7,993,821 B2 8/2011 Chiu et al.
8,211,656 B2 7/2012 Hyde et al.
8,669,044 B2 3/2014 Chiu et al.
8,697,359 B1 * 4/2014 Zhang .................... C12N 15/85 435/6.1
8,844,570 B2 9/2014 Glick et al.
9,005,579 B2 4/2015 Nowinski et al.
9,017,991 B2 4/2015 Diefenbach
9,157,550 B2 10/2015 Wheeler et al.

(Continued)

FOREIGN PATENT DOCUMENTS

CN 101031339 A 9/2007
CN 101031641 A 9/2007

(Continued)

OTHER PUBLICATIONS

Sharei et al., Cell Squeezing as a Robust, Microfluidic Intracellular Delivery Platform, Journal of Visualized Experiments, 7 pages ( Year: 2013).*
Sharei et al., A vector-free microfluidic platform for intracellular delivery, 2013, PNAS, vol. 110, No. 6, pp. 2082-2087 (Year: 2013).*
Sharei et al., A vector-free microfluidic platform for intracellular delivery, 2013, PNAS, vol. 110, No. 6, supplemental information, 10 pages (Year: 2013).*
Adamo, Andrea et al., "Microfluidics-Based Assessment of Cell Deformability," Analytical Chemistry (Aug. 7, 2012), vol. 84, No. 15, pp. 6438-6443.
ATCC Thawing, Propagating, and Cryopreserving Protocol, NCI-PBCF-HTB81 (DU 145), Prostate Carcinoma (ATCC® htb-81), Version 1.6, 2012, 23 pages.

(Continued)

*Primary Examiner* — Catherine S Hibbert
(74) *Attorney, Agent, or Firm* — Wolf, Greenfield & Sacks, P.C.

(57) ABSTRACT

Gene editing can be performed by introducing gene-editing components into a cell by mechanical cell disruption. Related apparatus, systems, techniques, and articles are also described. The methods and systems of the invention solve the problem of intracellular delivery of gene editing components and gene editing complexes to target cells. The results described herein indicate that delivery of gene editing components, e.g., protein, ribonucleic acid (RNA), and deoxyribonucleic acid (DNA), by mechanical disruption of cell membranes leads to successful gene editing. Because intracellular delivery of gene editing materials is a current challenge, the methods provide a robust mechanism to engineer target cells without the use of potentially harmful viral vectors or electric fields.

41 Claims, 75 Drawing Sheets

Specification includes a Sequence Listing.

(56) References Cited

U.S. PATENT DOCUMENTS

| | | | |
|---|---|---|---|
| 9,255,245 | B2 | 2/2016 | Bernick et al. |
| 9,364,504 | B2 | 6/2016 | Godfrin et al. |
| 9,950,049 | B2 | 4/2018 | Godfrin et al. |
| 10,124,336 | B2 | 11/2018 | Sharei et al. |
| 10,526,573 | B2 | 1/2020 | Ding et al. |
| 10,696,944 | B2 | 6/2020 | Sharei et al. |
| 10,870,112 | B2 | 12/2020 | Sharei et al. |
| 2003/0133922 | A1 | 7/2003 | Kasha, Jr. |
| 2004/0176282 | A1 | 9/2004 | Dalby et al. |
| 2004/0197898 | A1 | 10/2004 | Nakatani et al. |
| 2005/0026283 | A1 | 2/2005 | Ormar et al. |
| 2006/0134067 | A1 | 6/2006 | Liu et al. |
| 2006/0134772 | A1 | 6/2006 | Miles et al. |
| 2006/0223185 | A1 | 10/2006 | Fedorov et al. |
| 2007/0243523 | A1 | 10/2007 | Ionescu-Zanetti et al. |
| 2007/0249038 | A1 | 10/2007 | Adamo et al. |
| 2008/0026465 | A1 | 1/2008 | Nakata |
| 2008/0311140 | A1 | 12/2008 | Lee et al. |
| 2008/0318324 | A1 | 12/2008 | Chiu et al. |
| 2009/0209039 | A1 | 9/2009 | Adamo et al. |
| 2009/0280518 | A1 | 11/2009 | Adamo et al. |
| 2010/0203068 | A1 | 8/2010 | Betz et al. |
| 2010/0249621 | A1 | 9/2010 | Ichitani |
| 2010/0323388 | A1 | 12/2010 | Chiu et al. |
| 2011/0014616 | A1 | 1/2011 | Holmes et al. |
| 2011/0030808 | A1 | 2/2011 | Chiou et al. |
| 2011/0091973 | A1 | 4/2011 | Glaser |
| 2011/0300205 | A1 | 12/2011 | Geall et al. |
| 2012/0064505 | A1 | 3/2012 | Suresh et al. |
| 2012/0107925 | A1 | 5/2012 | Li et al. |
| 2012/0207745 | A1 | 8/2012 | Godfrin et al. |
| 2012/0222143 | A1 | 8/2012 | Fahrenkrug et al. |
| 2013/0023051 | A1 | 1/2013 | Bundock et al. |
| 2013/0045211 | A1 | 2/2013 | Nowinski et al. |
| 2013/0065314 | A1 | 3/2013 | Macmillan |
| 2014/0011226 | A1 | 1/2014 | Bernick et al. |
| 2014/0273229 | A1 | 9/2014 | Meacham et al. |
| 2014/0287509 | A1 | 9/2014 | Sharei et al. |
| 2015/0184127 | A1 | 7/2015 | White et al. |
| 2015/0196913 | A1 | 7/2015 | Liu et al. |
| 2016/0017340 | A1 | 1/2016 | Wu et al. |
| 2016/0193605 | A1 | 7/2016 | Sharei et al. |
| 2016/0199837 | A1 | 7/2016 | Breinlinger et al. |
| 2017/0020926 | A1 | 1/2017 | Mata-Fink et al. |
| 2017/0326213 | A1 | 11/2017 | Jajosky et al. |
| 2018/0003696 | A1 | 1/2018 | Sharei et al. |
| 2018/0016539 | A1 | 1/2018 | Ding et al. |
| 2018/0085402 | A1 | 3/2018 | Kahvejian et al. |
| 2018/0142198 | A1 | 5/2018 | Sharei et al. |
| 2018/0201889 | A1 | 7/2018 | Sharei et al. |
| 2018/0245089 | A1 | 8/2018 | Sharei et al. |
| 2019/0017072 | A1 | 1/2019 | Ditommaso et al. |
| 2019/0030536 | A1 | 1/2019 | Sharei et al. |
| 2019/0093073 | A1 | 3/2019 | Sharei et al. |
| 2019/0111082 | A1 | 4/2019 | Gilbert et al. |
| 2019/0382796 | A1 | 12/2019 | Gilbert et al. |
| 2020/0277566 | A1 | 9/2020 | Sharei et al. |

FOREIGN PATENT DOCUMENTS

| | | | |
|---|---|---|---|
| CN | 106244543 | A | 12/2016 |
| EP | 882448 | A1 | 12/1998 |
| EP | 1225228 | A2 | 7/2002 |
| EP | 2169070 | A1 | 3/2010 |
| JP | H01196566 | A | 8/1989 |
| JP | H03257366 | A | 11/1991 |
| JP | 2010-02582 | A | 2/2010 |
| JP | 2010-025852 | A | 2/2010 |
| JP | 2011-163830 | A | 8/2011 |
| JP | 2013-536848 | A | 9/2013 |
| JP | 6235085 | B2 | 11/2017 |
| KR | 2014-0115560 | A | 10/2014 |
| WO | WO 85/00748 | A1 | 2/1985 |
| WO | WO 97/20570 | A1 | 6/1997 |
| WO | WO 00/07630 | A1 | 2/2000 |
| WO | WO 02/067863 | A2 | 9/2002 |
| WO | WO 03/020039 | A1 | 3/2003 |
| WO | WO 2004/001424 | A1 | 12/2003 |
| WO | WO 2006/010521 | A1 | 2/2006 |
| WO | WO 2006/095330 | A2 | 9/2006 |
| WO | WO 2006/0105251 | A2 | 10/2006 |
| WO | WO 2007/067032 | A1 | 6/2007 |
| WO | WO 2007/097934 | A2 | 8/2007 |
| WO | WO 2008/021465 | A2 | 2/2008 |
| WO | WO 2008/0214565 | A2 | 2/2008 |
| WO | WO 2009/056332 | A1 | 5/2009 |
| WO | WO 2010/016800 | A1 | 2/2010 |
| WO | WO 2010/077290 | A1 | 7/2010 |
| WO | WO 2010/105135 | A1 | 9/2010 |
| WO | WO 2010/129671 | A2 | 11/2010 |
| WO | WO 2010/145849 | A2 | 12/2010 |
| WO | WO 2011/051346 | A1 | 5/2011 |
| WO | WO 2011/119492 | A2 | 9/2011 |
| WO | WO 2012/069568 | A2 | 5/2012 |
| WO | WO 2012/097450 | A1 | 7/2012 |
| WO | WO 2012/106536 | A2 | 8/2012 |
| WO | WO 2012/118799 | A2 | 9/2012 |
| WO | WO 2012/162779 | A1 | 12/2012 |
| WO | WO 2013/059343 | A1 | 4/2013 |
| WO | WO 2013/185032 | A1 | 12/2013 |
| WO | WO 2014/065596 | A1 | 5/2014 |
| WO | WO 2014/106629 | A1 | 7/2014 |
| WO | WO 2014/106631 | A1 | 7/2014 |
| WO | WO 2014/120956 | A1 | 8/2014 |
| WO | WO 2014/165707 | A2 | 10/2014 |
| WO | WO 2015/023982 | A1 | 2/2015 |
| WO | WO 2015/061458 | A1 | 4/2015 |
| WO | WO 2015/153102 | A1 | 10/2015 |
| WO | WO 2015/161276 | A2 | 10/2015 |
| WO | WO 2016/003485 | A1 | 1/2016 |
| WO | WO 2016/070136 | A1 | 5/2016 |
| WO | WO 2016/077761 | A1 | 5/2016 |
| WO | WO 2016/109864 | A1 | 7/2016 |
| WO | WO 2016/115179 | A1 | 7/2016 |
| WO | WO 2016/183482 | A1 | 11/2016 |
| WO | WO 2017/005700 | A1 | 1/2017 |
| WO | WO 2017/008063 | A1 | 1/2017 |
| WO | WO 2017/041050 | A1 | 3/2017 |
| WO | WO 2017/041051 | A1 | 3/2017 |
| WO | WO 2017/106899 | A2 | 6/2017 |
| WO | WO 2017/123644 | A1 | 7/2017 |
| WO | WO 2017/123646 | A1 | 7/2017 |
| WO | WO 2017/123663 | A1 | 7/2017 |
| WO | WO 2017/192785 | A1 | 11/2017 |
| WO | WO 2017/192786 | A1 | 11/2017 |
| WO | WO 2018/089497 | A1 | 5/2018 |

OTHER PUBLICATIONS

Augustsson et al. "Microfluidic, Label-Free Enrichment of Prostate Cancer Cells in Blood Based on Acoustophoresis," Analytical Chemistry, Aug. 28, 2012 (Aug. 28, 2012), vol. 84, No. 18, pp. 7954-7962.

BD Bioscience FITC-labeled anti-CD45 antibody, 2 pages.

BD Bioscience PE-labeled anti-EpCAM antibody, 2 pages.

Boohaker, et al., "The Use of Therapeutic Peptides to Target and to Kill Cancer Cells," Curr. Med. Chem., 19(22), 26 pages, 2012.

Cancer Facts & Figures 2012. Published by the American Cancer Society in Atlanta, 68 pages.

Cross et al., "Nanomechanical analysis of cells from cancer patients," Nature Nanotechnology (Dec. 2007), vol. 2, pp. 780-783.

Downs, C. A. et al. (May 14, 2011). "Cell Culture Models Using Rat Primary Alveolar type 1 Cells", Pulmonary Pharm. & Therapeutics 24(5)577-586.

Eixarch, H. et al. "Tolerance induction in experimental autoimmune encephalomyelitis using non-myeloablative hematopoietic gene therapy with autoantigen." Molecular Therapy 17.5 (2009): 897-905.

Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).

(56) References Cited

OTHER PUBLICATIONS

European Search Opinion dated Apr. 30, 2015 from European Application No. 12 841 329, 2 pages.
Examination Report No. 1 dated Dec. 1, 2016 from Australian Application No. 2012326203, 10 pages.
Examination Report No. 2 dated Jul. 26, 2017 from Australian Application No. 2012326203, 6 pages.
Extended European Search Report for EP 14836593.5, dated Feb. 23, 2017, 9 pages.
Gasteiger, et al., "Protein Identification and Analysis Tools on the ExPASy Server," The Proteomics Handbook, Chapter 52, pp. 571-607, 2005.
Griesbeck et al., "Sex Differences in Plasmacytoid Dendritic Cell Levels of IRF5 Drive higher IFN-alpha production in Women," The Journal of Immunology (Dec. 2015), vol. 195(11):5327-5336.
Hallow et al., "Shear-Induced Intracellular Loading of Cells With Molecules by Controlled Microfluidics," Biotechnology and Bioengineering (2008), vol. 99(4):846-854.
Han, X. et al., "CRISPR-Cas9 delivery to hard-to-transfect cells via membrane deformation," Sci. Adv., Aug. 14, 2015, e1500454, 8 pages.
Hillerdal et al., "Systemic treatment with CAR-engineered T cells against PSCA delays subcutaneous tumor growth and prolongs survival of mice," BMC Cancer (Jan. 18, 2014), vol. 14, No. 30, pp. 1-9.
Hoeppener et al., "Immunomagnetic Separation Technologies," In: Ignatiadis M., Soritiou C., Pantel K. (eds.), Minimal Residual Disease and Circulating Tumor Cells in Breast Cancer. Recent Results in Cancer Research, vol. 195, pp. 43-58 (2012).
Hoskin, et al., "Studies on anticancer activitied of antimicrobial peptides," Biochimica et Biophysica Acta, v.1778, pp. 357-375, 2008.
Hosokawa, et al., "Size-Selective Microacvity Array for Rapid and Efficient Detection of Circulation Tumor Cells," Anal. Chem, 85:6629-6635, 2010.
Howarth, M. et al. (May 2008). "Monovalent, Reduced-Size Quantum Dots for Imaging Receptors on Living Cells," Nature Methods 5(5):397-399.
International Preliminary Report on Patentability dated Feb. 16, 2016 from International Application No. PCT/US2014/051343.
International Preliminary Report on Patentability, PCT/US2012/060646, dated Apr. 22, 2014, 7 pages.
International Preliminary Report on Pattentability, PCT/US2015/058489, dated May 2, 2017, 12 pages.
International Preliminary Report on Pattentability, PCT/US2015/060689, dated May 16, 2017, 10 pages.
International Search Report and Written Opinion dated Jan. 3, 2017 from International Application No. PCT/US2016/050287, 13 pages.
International Search Report and Written Opinion dated Feb. 1, 2016 from International Application No. PCT/US15/60689.
International Search Report and Written Opinion dated Feb. 25, 2013 from International Application No. PCT/US12/060646.
International Search Report and Written Opinion dated Mar. 11, 2016 from International Application No. PCT/US15/584489.
International Search Report and Written Opinion dated Mar. 21, 2016 from International Application No. PCT/US2016/013113.
International Search Report and Written Opinion dated Dec. 18, 2014 from International Application No. PCT/US2014/051343.
International Search Report and Written Opinion dated Jul. 21, 2017 from International Application No. PCT/US2017/030933, 20 pages.
International Search Report and Written Opinion dated Sep. 19, 2017 from International Application No. PCT/US2017/030932, 18 pages.
Janeway CA Jr, et al., "The structure of a typical antibody molecule," Immunobiology: The Immune System in Heath and Disease, 5th edition (2001), 5 pages.
Kim, D., et al., "Microengineered Platforms for Cell Mechanobiology," Annual Review of Biomedical Engineering, 2009, vol. 11, pp. 203-233.
Lee et al., "Nonendocytic delivery of functional engineered nanoparticles into the cytoplasm of live cells using a novel, high-throughput microfluidic device," Nano Letters (2012), vol. 12, pp. 6322-6327.
Lin et al., "Highly selective biomechanical separation of cancer cells from leukocytes using microfluidic and hydrodynamic concentrator," Biomicrofluidics (Jun. 26, 2013), vol. 7, No. 3, pp. 34114-1-34114-11.
Liu et al., "Molecular imaging in tracking tumor-specific cytotoxic T lymphocytes (CTLs)," Theranostics (Jul. 28, 2014), vol. 4, No. 10, pp. 990-1001.
Liu et al., "Spatially selective reagent delivery into cancer cells using a two-layer microfluidic culture system," Analytica Chimica Acta (Sep. 1, 2012), vol. 743, pp. 125-130.
Liu, W. et al. (Jan. 20, 2010). "Compact Biocompatible Quantum Dots Via RAFT-Mediated Synthesis of Imidazole-Based Random Copolymer Ligand," JACS 132(2):472-483.
Mattews, B.D., et al., "Cellular adaptation to mechanical stress: role of integrins, Rho, cytoskeletal tension and mechanosensitive ion channels," Journal of Cell Science, vol. 119, pp. 508-518, 2006.
Milo, R. "What is the total number of protein molecules per cell volume? A call to rethink some published values." Bioessays 35.12 (2013): 1050-1055.
Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.
Notice of Grant dated Jan. 11, 2018 for Chinese Patent Application No. 201280060689.6.
Office Action dated Dec. 1, 2016 from Chinese Application No. 201280060689.6, 4 pages.
Office Action dated Dec. 17, 2014 from Chinese Office Action No. 201280060689.6, 9 pages.
Office Action dated Jun. 23, 2017 from Chinese Application No. 201280060689.6, 4 pages.
Office Action dated May 13, 2016 from Chinese Application No. 201280060689.6, 4 pages.
Office Action dated Oct. 11, 2017 from European Application No. 12 841 329, 4 pages.
Office Action dated Sep. 6, 2015 from Chinese Office Action No. 201280060689.6, 8 pages.
Office Action dated Aug. 15, 2017 from U.S. Appl. No. 14/912,001, 32 pages.
Office Action dated Feb. 24, 2017 from U.S. Appl. No. 14/352,354, 11 pages.
Office Action dated Jul. 27, 2016 from U.S. Appl. No. 14/352,354, 9 pages.
Office Action dated Jul. 5, 2017 from Chinese Application No. 201480056295.2, 13 pages.
Office Action dated Jul. 7, 2016 from Japanese Application No. 2014-537184, 14 pages.
Office Action dated Mar. 16, 2017 from U.S. Appl. No. 14/912,001, 29 pages.
Office Action dated Mar. 23, 2017 from Russian Application No. 2014119926/10(031699), 10 pages.
Office Action dated May 1, 2017 from Japanese Application No. 2014-537184, 13 pages.
Office Action dated Oct. 26, 2016 from Russian Application No. 2014119926/10(031699), 10 pages.
Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).
Ravilla et al., "Erythrocytes as Carrier for Drugs, Enzymes and Peptides," Journal of Applied Pharmaceutical Science, vol. 2, No. 2, pp. 166-176 (2012).
Rutella et al., "Tolerogenic dendritic cells: cytokine modulation comes of age," Blood, vol. 108, No. 5, pp. 1435-1440 (2006).
Sharei et al, "Ex vivo Cytosolic Delivery of Functional Macromolecules to Immune Cells," (Apr. 13, 2015), PLoS One, vol. 10, No. 4, 12 pp. e0118803.
Sharei et al., "A vector-free microfluidic platform for intracellular delivery," Proc. Natl. Acad. Sci. USA (Feb. 5, 2013), vol. 110, No. 6, pp. 2082-2087.

(56) References Cited

OTHER PUBLICATIONS

Sharei et al., "Cell Squeezing as a Robust, Microfluidic Intracellular Delivery Platform," Journal of Visualized Experiments (Nov. 7, 2013), No. 81, 9 pages.
Sharei et al., "Plasma membrane recovery kinetics of a microfluidic intracellular delivery platform," Integrative Biology (2014), vol. 6, pp. 470-475.
Shelby et al., "A microfluidic model for single-cell capillary obstruction by Plasmodium falciparum infected erythrocytes," (Dec. 9, 2003), Proc. Nat. Acad. Sci., vol. 100, No. 25, pp. 14618-14622.
Steinman et al., "Tolerogenic dendritic cells," Annual Review of Immunology, vol. 21, pp. 685-711 (2003).
Stewart et al., "In vitro and ex vivo strategies for intracellular delivery," Nature, vol. 538, No. 7624, pp. 183-192 (2016).
Supplementary European Search Report dated Apr. 30, 2015 from European Application No. 12 841 329, 3 pp.
Swaminathan, et al., "Mechanical Stiffness Grades Metastatic Potential in Patient Tumor Cells and in Cancer Cell Lines," Cancer Research, 71(15):5075-5080, 2011.
Szeto et al., "Microfluidic squeezing for intracellular antigen loading in polyclonal B-cells as cellular vaccines," Scientific Reports, vol. 5, 10276 (May 2015), 13 pages.
Third-Party Submission dated Oct. 23, 2015 from U.S. Appl. No. 14/352,354, 21 pages.
Williams, A.R. et al. (Nov. 5, 1999). "Filtroporation: A Simple, Reliable Technique for Transfection and Macromolecular Loading of Cells", Biotechnology and Bioengineering 65(3)341-346.
Zarnitsyn et al., "Electrosonic ejector microarray for drug and gene delivery," Biomed Microdevices (2008) 10:299-308.
Extended European Search Report for EP App. No. 15859824.3 dated Sep. 11, 2018.
Extended European Search Report for EP App. No. 15855640.7 dated Sep. 5, 2018.
Ditommaso et al., Cell engineering with microfluidic squeezing preserves functionality of primary immune cells in vivo. PNAS. Oct. 2018;115(46):E10907-14.
Gossett et al., Hydrodynamic stretching of single cells for large population mechanical phenotyping. PNAS. May 2012;109(20):7630-5.
Nic an Tsaoir et al., Scalable Antibody Production from CHO Cell Line of Choice Using Flow Electroporation. MaxCyte. Jun. 2016. 1 page.
Stevenson, D. J. et al., "Single cell optical transfection," J. R. Soc. Interface, vol. 7, 863-871 (2010).
Weaver et al., A brief overview of electroporation pulse strength-duration space: A region where additional intracellular effects are expected. Bioelectrochemistry. Oct. 2012;87:236-43.
Extended European Search Report for EP App. No. 16822078.8 dated Jan. 30, 2019.
International Search Report and Written Opinion for PCT/US2016/041653 dated Oct. 4, 2016.
International Preliminary Report on Patentability for PCT/US2016/041653 dated Jan. 18, 2018 (Chapter I).
Extended European Search Report for EP App. No. 16737769.6 dated May 3, 2018.
International Preliminary Report on Patentability for PCT/US2016/013113 dated Jul. 27, 2017 (Chapter I).
Partial Supplementary European Search Report for EP App. No. 15859824.3 dated Jun. 11, 2018.
Partial Supplementary European Search Report for EP App. No. 15855640.7 dated May 30, 2018.
Banz, A. et al., "Tumor Growth Control Using Red Blood Cells as the Antigen Delivery System and Poly(I:C)," J Immunother 2012, 35(5), pp. 409-417.
Chaw et al. Multi-step microfluidic device for studying cancer metastasis. Lab on a Chip (2007), v7, p. 1041-1047.
Cremel, L. et al., "Innovative approach in Pompe disease therapy: Induction of immune tolerance by antigen-encapsulated red blood cells," Int J Pharm. Aug. 1, 2015;491(1-2), pp. 69-77.
Cremel, L. et al., "Red blood cells as innovative antigen carrier to induce specific immune tolerance," Int J Pharm. Feb. 25, 2013;443(1-2), pp. 39-49.
Ding, X. et al., "High-throughput nuclear delivery and rapid expression of DNA via mechanical and electrical cell-membrane disruption," Nature Biomedical Engineering (2017), vol. 1, No. 3, 7 pages.
Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Grimm, A. J. et al., "Memory of tolerance and induction of regulatory T cells by erythrocyte-targeted antigens," Sci Rep. Oct. 29, 2015;5:15907, 11 pages.
Kiani et al., Cas9 gRNA engineering for genome editing, activation and repression. Nature Methods. 2015;12:1051-4.
Li, J. et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Lorentz, K. M. et al., "Engineered binding to erythrocytes induces immunological tolerance to *E. coli* asparaginase," Sci Adv. Jul. 17, 2015;1(6):e1500112, 11 pages.
Mali, P. et al., "RNA-guided human Genome Engineering via Cas9," Science (2013), vol. 339, No. 6121, pp. 823-826.
Maratou et al., Glucose transporter expression on the plasma membrane of resting and activated while blood cells. European Journal of Clinical Investigation. 2007;37:282-90.
Rossi, L. et al., "Erythrocyte-mediated delivery of phenylalanine ammonia lyase for the treatment of phenylketonuria in BTBR-Pah. sup.enu2 mice," Journal of Controlled Release 194; 37-44 (2014).
Rughetti, A. et al., "Transfected human dendritic cells to induce antitumor immunity," Gene Therapy, vol. 7, pp. 1458-1466 (2000).
Stevenson, D. J. et al., "Single cell optical transfection," IEEE Transactions on Ultrasonics, Ferroelectrics and Frequency Control, vol. 53, No. 1, 863-871 (2010).
Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).
Wright et al., Rational design of a split-Cas9 enzyme complex. PNAS. Mar. 2015;112(10):2984-9.
Yin et al., "Delivery technologies for genome editing," Nature Reviews (2017), vol. 16, No. 6, pp. 387-399.
Zdobnova et al., Self-Assembling Complexes of Quantum Dots and ScFv Antibodies for Cancer Cell Targeting and Imaging. PLoS One. 2012:7(10):e48248. 8 pages.
International Search Report and Written Opinion for PCT/US2016/050288 dated Jan. 12, 2016.
Extended European Search Report dated Nov. 21, 2019 for Application No. EP 19187758.8.
Adamo et al., Microfluidic Cell Deformation As a Robust, Vector-Free Method for Cystosolic Delivery of Macromolecules. 2012 AlChE Annual Meeting. Oct. 2012;8 pages.
Alberts et al., Chapter 11: Ion Channels and the Electrical Properties of Membranes. Molecular Biology of the Cell, 4*th* Ed. New York: Garland Science. 2002. 20 pages.
Azarikia et al., Stabilization of biopolymer microgels formed by electrostatic complexation: Influence of enzyme (laccase) cross-linking on pH, thermal, and mechanical stability. Food Res Int. Dec. 2015;78:18-26. doi: 10.1016/j.foodres.2015.11.013. Epub Nov. 21, 2015.
Fagerlund et al., The Cpf1 CRISPR-Cas protein expands genome-editing tools. Genome Biol. Nov. 17, 2015;16:251. doi: 10.1186/s13059-015-0824-9.
Gilbert, T-cell-inducing vaccines—what's the future. Immunology. Jan. 2012;135(1):19-26. doi: 10.1111/j.1365-2567.2011.03517.x.
Jiang, The immunopotentiators and delivery systems for use in vaccines. Prog Microbiol Immunol. Dec. 31, 2012;(3):1-8.
Novokhatskiy et al., Problema kontaminatsii kletkami I novyie podkhody k kontroliu perevivaiemykh liniy. Voprosy virusologii. 1977;4:396-408.
Song et al., Scientific basis for the use of hypotonic solutions with ultrasonic liposuction. Aesthetic Plast Surg. Mar.-Apr. 2006;30(2):233-8. doi: 10.1007/s00266-005-0087-z.

(56) References Cited

OTHER PUBLICATIONS

Vechkanov et al., Osnovy kletochnoy inzhenerii: Study guide. Rostov-on-Don. 2012; 133 pages. Relevant pp. 15-16.
Wen et al., Shear Effects on Stability of DNA Complexes in the Presence of Serum. Biomacromolecules. Oct. 9, 2017;18(10):3252-3259. doi: 10.1021/acs.biomac.7b00900. Epub Sep. 1, 2017.
Yangulov et al., Vliyaniye razlichnykh kriozashchitnykh sred na zhiznesposobnost kriokonservirovannykh limfoblastnykh kletochnyk liniy H-9 I U-937. Problemy kriobiologii. 1991;3:46-9.
Ye, Complexation between milk proteins and polysaccharides via electrostatic interaction: principles and applications—a review. Int J Food Sci Technol. Jan. 31, 2008;43(3):406-15.
Zhdanov et al., Tayna tretiego tsarstva. Znaniye. 1975; 176 pages. Relevant pp. 124-125.
[No Author Listed], SQZ Biotech and AskBio Announce Research Collaboration to Create Immune Tolerization Products for AAV Gene Therapies. AskBio. Press Release. Nov. 7, 2019. 3 pages.
[No Author Listed], SQZ Biotech Announces Pricing of Initial Public Offering. SQZ Biotech. Press Release. Oct. 29, 2020. 2 pages.
[No Author Listed], SQZ Biotech Closes $65 Million Series D Financing. SQZ Biotech. Press Release. May 18, 2020. 2 pages.
[No Author Listed], SQZ Biotechnologies Presents Preclinical Data for their SQZ Tolerizing Antigen Carrier Platform in Antigen-Specific Immune Tolerance (ASIT) Digital Summit Invited Talk. SQZ Biotech. Press Release. Jan. 27, 2021. 4 pages.
Blagovic et al., 165 Activating antigen carriers generated with microfluidics cell squeezing drive effective anti-tumor responses. JITC. Dec. 2020;8:A98-9. doi: 10.1136/jitc-2020-SITC2020.0165.
Bosilkovski, This MIT PhD Just Raised $65 Million for His Clinical Stage Cell Therapy Company. Forbes. May 21, 2020. https://www.forbes.com/sites/igorbosilkovski/2020/05/21/meet-the-mit-phd-who-just-raised-65-million-for-his-clinical-stage-cell-therapy-company/?sh=le9a48af9809 [last accessed Jan. 28, 2021]. 3 pages.
Chen et al., Patch clamping on plane glass-fabrication of hourglass aperture and high-yield ion channel recording. Lab Chip. Aug. 21, 2009;9(16):2370-80. Epub May 14, 2009. https://doi.org/10.1039/b901025d.
Escoffre et al., What is (still not) known of the mechanism by which electroporation mediates gene transfer and expression in cells and tissues. Mol Biotechnol. Mar. 2009;41(3):286-95. doi: 10.1007/s12033-008-9121-0. Epub Nov. 18, 2008.
Golzio et al., Direct visualization at the single-cell level of electrically mediated gene delivery. Proc Natl Acad Sci U S A. Feb. 5, 2002;99(3):1292-7. doi: 10.1073/pnas.022646499. Epub Jan. 29, 2002.
Ogurtsov et al., Biotechnology. Principles and Application Training Manual. Ministry of Education and Science. 2012. 344 pages.
Paganin-Gioanni et al., Direct visualization at the single-cell level of siRNA electrotransfer into cancer cells. Proc Natl Acad Sci U S A. Jun. 28, 2011;108(26):10443-7. doi: 10.1073/pnas.1103519108. Epub Jun. 13, 2011.
Ramakrishnan et al., 1743-P: Engineering Erythrocytes with the SQZ Cell Therapy Platform to Enhance Immunotolerance. Diabetes. Jun. 2019;68(Supplement 1). https://doi.org/10.2337/db19-1743-P. Abstract.
Tran et al., Expansion of immature, nucleated red blood cells by transient low-dose methotrexate immune tolerance induction in mice. Clin Exp Immunol. Nov. 18, 2020;0:1-15. doi: 10.1111/cei.13552.
Vinulan, SQZ Biotech Lines Up an IPO on the NYSE to Fund Cell Therapy R&D. Xconomy. Oct. 12, 2020. https://xconomy.com/boston/2020/10/12/sqz-biotech-lines-up-an-ipo-on-the-nyse-to-fund-cell-therapy-rd/ [last accessed Jan. 28, 2021]. 3 pages.

* cited by examiner

TAGGGGATGACAGTGGGCTCTCCGCTTTCTCCTCCATGAAGTAACTTACATGCCCCTCAC
CCTCTGTGGGAGGGGTGTTGCAGGGGGTGCAGAACTCCCCTCGCCGGGTAGTTCAAGCAA
TGGGGACCATATCAATTCCATCTATAGGGAAACTGAGGCCTGGAGTAGGGCGAGGCCTCT
GGGAACCCAGCCCTATTCTGTCTCTTTCCCTGGCATTTCCCATCCACACATAGAGCTTCA
GATTCTCTTTCTTTCCCCAGAGACCCTCAAATATCCTCTCACTCACAGAATGGTGTCTCT
GCCTGCCTCGGGTTGGCCCTGTGATTTATTTTAGTTCTTTTCCCTTGTTTTTTTTTTTTC
AAACTCTATACACTTTTGTTTTAAAAACTGTGGTTTCTCATGAGCCCTATTATCTCATTG
ATACCTCTCACCTCTGTGGTGAGGGGAAGAAATCATATTTTCAGATGACTCGTAAAGGGC
AAAGAAAAAAACCCAAAATTTCAAAATTTCCGTTTAAGTCTCATAATCAAGAAAAGGAGA
AACACAGAGAGAGAGAAAAAAAAAAACTATGAGAACCCCTCCCCACCCCGTGATTATCAGC
GCACACACTCATCGAAAAAAATTTGGATTATTAGAAGAGAGAGGTCTGCGGCTTCCACAC
CGTACAGCGTGGTTTTTCTTCTCGGTATAAAAGCAAAGTTGTTTTTGATACGTGACAGTT
TCCCACAAGCCAGGCTGATCCTTTTCTGTCAGTCCACTTCACCAAGGTGAGTGTCCCTGC
TCTCCCCTACCAGATGTGGGCCCCATTGGAGGAGATGGCAGGGAGGTAGGCACGGCGGGG
GGGTCAGGGGCCCTCTGGTACAGTGGGATGTACCCAGCTACCGTGATTCCAGCCAGGTAA
GGTCTTTAAAAAAATAATAGAATAAATGGCAGAAGACTTAAAGGTGAAGTACTTAATGCA
TGGGCAGGGGCAAAAATAAATGAATTCATCAATTGATACGTAGATGGATAGGATTTTTAA
AATATGTCAGCTGCCAGTCTTTATGGATTTCAGAGCTTTGAACAACTTGAAATGCTGTCC
AGGTGCAACTGAAAATTTCAACTGCATCTCTCTCATCTCTTTGTCTCTTAGCTCTTGATG
CCTCTCATCCTTCTCTGTCTCTCTGCTCACCCTGTCTTGCTCTTTTACATGTTTCTCTGC
CTCTCTTTCTCCCGCCATCTGTCTGTCGCTACACTCAGACTCTCTTTCCCCGCATCTCTC
CTGGCCTCTGACCATCTCCCCTATCTCTGTCTCCTCCATCTTGACCACACTCCATCGATC
TCCTTTCCTCCATCTCTCCCGCTCTCTTTTCTTGCCTTCCCCCACCTGCCTTCCCAGCCA
GCATCCAGCCTAGAGCTTTGTACACAGCTGGCGTTTAATAATAGTAATGTCGCCGAGGAC
CTTTACATTTTATGAGAGTGAGCATCAGTTCTGTTCACCCTAGTAGCAGGAGGATTGCAA
GGTGCCGGGGCAAGCTGAGCACTTAACTGAACTTTGCTTGTATCGCTTTAGAGGAGACCC

FIG. 6

TTGGGGCGGGGGGGCAGGGAGCACTTCACACCATTGTCAACCGTAGTTTAGCTGTGTGGA
CCTACCCCAGGACTGCATGTGTGTGACCAGAGTCCATATTCAGGAAGCAAACAGGTTGTT
CAGGGCTGGGGTGAGCTCGATTCTGCAGGCTTAGCACAGCGTTTGGCACAAAGTAAGTGC
TCACGAAGTGTTAGCTATTAGTATTTCTGTAACCAAATTAGAATCATGCTATATATTGGT
TTTGTTCCTGCTTTATTCAATTAACAGTAGTGTTTTTGAAGCTTACTAAAAATTGTTTGA
ACACATGATCTTTCATGATGGACAAGACTGTCCTCACATCAGCATGAACTTTGATTGATT
TGACCAAGTGCCGATTGTTGGACATTCCGGTTGTTTCTCGTTTTTTTCTATAAACATCCC
TGACTGCTTCCTTGGATTCCTGAAAAGGGAGTTGCTGGGGCAAAGGGGGCGTGCATTTTT
AAAGTTTATGACCCTCTCTGCTAATTCTCCTTCCAAAAGGTTGTCCTATTTTATGCTCCC
TCTACTTAAGCTAACCCTAGGTGAGTATTATTATGTTTTAATTATTTCCCAACATGACAG
GTAAGAAAAACACATTATCACATTGTTGAAATTTGCATCTTGTGATTACTTTTACTATTC
ATTGGCCATTCATGCTTTTTTTTTTTTTTTTTTGGTTGTCTGGTCATGTCCTTACTCCTA
ATAGGGTGTTCATCTTATTTTTCCCTTATTGATTTGCCACAGCTCTTTATTTGGAATGGT
TATTAACCTTTCATCAGCCATTACATATATAGCAAATATTTTCCCCAATTCATCATTTGC
TTTTTTTCTATTTGTTTATGGTGTTTTTTGTGATGCTTATGATGGTTTTATACAGTCAAA
TAGGTTAGTCTTTTTTTCTGTGGCTTCTGTCTCTGGTTTTGTGCTTAGAAAGTCCTTTCC
TACTTGAAAATGAGATAAATGTTCACCTATGTTGGCTTCTAGTCTCTTTTATGGCTTCAT
TTTTTCCATTTACTATAGAGGTTAAGAGTGTGGGTACTGGAGCCAGACTGTCTGGGACAA
ACCCAGCGTCACCCCAAGCCCTATGTGTGATTTTTAGCCAGGCACTTAACCTCTCCATAC
CTCCATTTCCTCATATGTACTGCAATGGTTATAATAGTACCTTCCTCAGGAGTCTTTGTT
TAGATTAAAATTTTTAACCACAGTAAATACTTAGCACAAGGCCTGACACACAATAAACCC
AAGATCAGCATTAGGTGTTAAAACTTATATCTTGAATGGATCTGGGCATTTTAGGGTATA
TGATGATGGTGACATTTCAAACTGGGCAGGGAGGGGTTGTTGGGATAATGGACTGACTAT
TCACTCAATAACTTTATCTTCTCCCTAATTATCTCAGACACATTTGTTAAACCATACTCC
ATGGTCCTCCAGTTTGAAATGCCACATTCATCACAAATTCAGTTCTCTCCATATGTGGGT
CCATGTCCAAGCTTTCTATTCTGTTCTCTTCCCCAGTATCTGTTCTTATACCAGGCCAC
ACTGTTTTGCTGATTGTTGCTTTGCAATACAATTCAATACCCAGCCATGGGTGTCCCTGG

CACCTTGCCCTTCTTTATTCTTGATTATTTCAGGCAGCATCAGTTGAACCAGCCAGAGAC
CAGCAAATGTTCTTATTTGAGGCAATCCTCCTCTCGCACACATGCACTCTGGCTCTCCAT
GCATGTGTCCATTTCTCTCAATGTCTCTCACTATCTCTTGTTCTCTCTTGCTCGCTCTTT
GTGTGTGTCTCTTTGTCTCTATGTATCCCTATCTCTCAGCCAGTCCCCTGGATAGAGGGG
CAATTGTCAACTTGAAGCCCTGCAGACACCTAATGACTTAACCAGACAGCGTAGAAGGGC
CCTGGCCCTTGTCTACTCCACGCCTCTCCGTGCTCAGTGTAGAAGGGCAAATTGAAGACC
AGAGATCTCAGGGCCTCACCGAAATGCAGCGGCAGAGTTGAAATCCAAGCCTAGATCTCA
GGACTCTAGGTGGGACCCTGGTTCTGGCTCTCTCCCCAACTGCAGGCCTCAGTTTACCCC
TCAGCACCCAGAAGGGGGAAGGGGAACCTGGGCTACCATTCCCCCTTCTGCCTTCTCACA
CGTTGGACCCCAACTTCCCACAGGTTGGACGATCCACGATCACAGTGTGGGGCCCAGCCT
CACAAGAGCTGGGCTAGGTGAGGCCCCGGACTCCATAGGTCAGGAGGCCTAGTTGGCCAG
AGCGTGGTGATGATGGAGGCATGTCAGTCAGTCAGGCTGTGTGTCCCCAGAGCTGGTGCT
GGTCCCCGAAAACCTTGATTGTGGGGCCCCTCTAGAGAGTCTGATGATGGGCTCTGTATT
GGCGAAGGCTGAGGCTTTTCCAGCTCCCCCCATGAGGCCCAGACCAAAGGCACACCAGCC
TCAACCTCCTCCTCCCCCTGTTGCCATCTCTGGCGGAGTGGCCATGTATTTGGGAACGTT
GTTCCAGAGTGGACAGGGAGACTGAGGCCCTAGGGAGGCTGGCTCTGTTTCCAGGCCTGG
TAGGCAAGAGGCCCTATGAAGCAGCAAGCTGCCTGACTTTCAGATGGTTCCAAGGAGTTT
GGACACCAGGGACACTGGCCTACACATACTGAGACTTTGGGACCGTAGACCCCACAGTCT
GTGGTTTTGAGATTCTAGGATCCTTTAAATCTAAGAAATGCTGTTCTATGATTCTGAGGT
CCTGGTGTTATACTATTTGAAGACCCCAGGGGTCCCAGTATCTGTGGAGCCTGCCTGGCA
CTCTCAGAGCTTCAAACCTGGGTCCTCTCCACAACCCAAGAAGGGCCAGGTCTTCAGAGC
TAGGGGCTTGTCATAGTGGCCAGATGGACATCACCTACCACATCCACCAGCACCCATGTC
ACCCCACCTGGGCCAAGCCTGCTGCAGGACAGGGCAGCCAGTTCTCGGAACGAAACCTGT
GGGGTGGGGTATCTGCCCTCTTCTCTTCCTCCGTGGTGTCGATGAAGCCCGGCGCATCCG
GCCGCCATGACGTCAATGGCGGAAAAATCTGGGCAAGTCGGGGGCTGTGACAACAGGGCC
CAGATGCAGACCCCGATATGAAAACATAATCTGTGTCCCAGAAACATCCCCCATTCAGCT
TCTGAGAAACCCAGTCAGAAAGGGACGTCCCAACAGACAGTGCAGGAAGCCGGCTGCCCA

FIG. 6 (continued)

GCCCGGCCCTCTAGGTCCTCTACCCCCAGACAGATCATCTCCATGTCCCTGTCTGAGAAT
GTATCTATGCTTTGCTGAGTCAGGCCATCCCACATGTGTTTGGGGAGAATTCTTAGCTCT
GGCCAAGTGTCCAGGCAGCTTCAGAAGTGACCACAGGCCAGCCACATGGGCCAGGCCAGA
GTGGTGGAAAACATCCATTTGCACCGAAATCGGTATTAGTTTGTTCTGGCTGCTATAACA
AAGTACCACAACTGAGTGGCTTCAGCAACAGAAATTGATCATCTCACAGTTCTGGAGGCC
AGAGTCCAAGATCAAGGTGTTGCCAGGGTTGGTTCCTTCTGGGGGCCATAAGGGAGAAGC
TGCTCCAGGCCTCTCCCCCAGCTTCTGGTGGTTGCTGGCAATCTTTGTTATTTCTTGGCT
TGAAGGAGCATCACCCCATCTCTGGCTTCATTCATTCACTCACCTTCTCATCTCACCAGT
GCTCTCCCAGGCCCTTGTTCGGAGCCTCCACAGACCCACACTCCTGTTTCTCACGCAGTA
ATGTTCTAAGCCCCCAGGAGACTAAGAACTTAATACCTGGATTCTCACACTCATCTCCCT
CAGCACCACAGCTCTGACAACCACCCCCAGGAGGTGACAGCAAAGAAAGGAAGGAGCAAC
TGCTCCCCCAGAACCCTTCTATACTCCCCCGGGCTGCTCTCAGCAGCTGTGTGCCCAACT
CAGTGCTGTGAGGTGGAACGGGGAGATGGAGACACACACACACACACACCAGAGAGTTTA
TAAAATGTGCACACGGAAACACTTCCTAAAGAAAGAAGTGGAGTTCTCAAGTCACTATGG
GACTACGGAACTCGGCATCTGAGCATCCCCTTCTGTATAATGGGGTTGGCTGGGCAGTCC
CTTCCAGCTCTGGCTTCCTCTCAGACCAGGATTATAGGATCCTGAAAAGCCAGTGCTTCC
CTCAGGGAGTGGAAGGTTCTGGGGCTCAGCAGGGGGCCCGGAGCCATTGTGGAGGGCTTT
CAAGGTGAGGACAATAGAAGAGCAGGTCTTGCGTGGCTTGGACAGGGAAAGAGGAGAAGG
AGTGGGCATTTGAGGCAGGGGGTGTAGCATGAGCCAGGCTTGAGGGCCAGAAATTGGGGT
GAACTCTGATGGGGGCTGGGTAGAGAAGCTTCTACAGGCCCCAGCTCAAGAGACCCCATC
TCTCCTCCTCTCTGTCACTTGCCATGCTGGATCCGTGCATGATCACACTCCTGGACTCGC
CTCCTTGCCCTGAGATCCAGACCCCCGTATTCAGCTGCCCCCTCAGCTCCTCCACTCACA
TATTTAATGCCAGACTCTTCATGTCTATCTACACCTGCACTTTTGCACCCAATCCAACTC
CCCGCCATGTCCCCCATCTCAGGTAATGTCAGCTCGGTCCTTCCAGCTGCTCAAGCTAAA
ACCCATGTCACTTTGACTCTCCCTCTTGCCCACTACATCCAAGCTGCTAGCACTGCTCCT
GATCCAGCTTCAGATTAAGTCTCAGAATCTACCCACTTCTCGCCTTCTCCACTGCCACCA
GCCCATTCTGTGCCAGCATCATCACTTGCCAGGACTGTTACAATAGCCTCCTCACTAGCC

CCACTCACAGCAGCCAGATGAATCTTTTGAGTCCATGCCTAGTCACTGGGGCAAAATAGG
ACTCCGAGGAGAAAGTCCGAGACCAGCTCCGGCAAGATGAGCAAACACAGCCTGTGCAGG
GTGCAGGGAGGGCTAGAGGCCTGAGGCTTGAAACAGCTCTCAAGTGGAGGGGGAAACAAC
CATTGCCCTCATAGAGGACACATCCACACCAGGGCTGTGCTAGCGTGGGCAGGCAAGCCA
GGTGCTGGACCTCTGCACGTGGGGCATGTGTGGGTATGTACATGTACCTGTGTTCTTGGT
GTGTGTGTGTGTGTGTGTGTGTGTGTGTGTCTAGAGCTGGGGTGCAACTATGGGGCCCCT
CGGGACATGTCCCAGCCAATGCCTGCTTTGACCAGAGGAGTGTCCACGTGGCTCAGGTGG
TCGAGTATCTCATACCGCCCTAGCACACGTGTGACTCCTTTCCCCTATTGTCTACGCAGC
CTGCCCTTGGACAAGGACCCGATGCCCAACCCCAGGCCTGGCAAGCCCTCGGCCCCTTCC
TTGGCCCTTGGCCCATCCCCAGGAGCCTCGCCCAGCTGGAGGGCTGCACCCAAAGCCTCA
GACCTGCTGGGGGCCCGGGGCCCAGGGGGAACCTTCCAGGGCCGAGATCTTCGAGGCGGG
GCCCATGCCTCCTCTTCTTCCTTGAACCCCATGCCACCATCGCAGCTGCAGGTGAGGCCC
TGGGCCCAGGATGGGGCAGGCAGGGTGGGGTACCTGGACCTACAGGTGCCGACCTTTACT
GTGGCACTGGGCGGGAGGGGGGCTGGCTGGGGCACAGGAAGTGGTTTCTGGGTCCCAGGC
AAGTCTGTGACTTATGCAGATGTTGCAGGGCCAAGAAAATCCCCACCTGCCAGGCCTCAG
AGATTGGAGGCTCTCCCCGACCTCCCAATCCCTGTCTCAGGAGAGGAGGAGGCCGTATTG
TAGTCCCATGAGCATAGCTATGTGTCCCCATCCCCATGTGACAAGAGAAGAGGACTGGGG
CCAAGTAGGTGAGGTGACAGGGCTGAGGCCAGCTCTGCAACTTATTAGCTGTTTGATCTT
TAAAAAGTTACTCGATCTCCATGAGCCTCAGTTTCCATACGTGTAAAAGGGGGATGATCA
TAGCATCTACCATGTGGGCTTGCAGTGCAGAGTATTTGAATTAGACACAGAACAGTGAGG
ATCAGGATGGCCTCTCACCCACCTGCCTTTCTGCCCAGCTGCCCACACTGCCCCTAGTCA
TGGTGGCACCCTCCGGGGCACGGCTGGGCCCCTTGCCCCACTTACAGGCACTCCTCCAGG
ACAGGCCACATTTCATGCACCAGGTATGGACGGTGAATGGGCAGGGAGGAGGGAGCAGGT
GGGAGAACTGTGGGGAGGGGCCCCGAGTCAGGCTGAACCACAGCCCACATGTGCCCCCCA
GCTCTCAACGGTGGATGCCCACGCCCGGACCCCTGTGCTGCAGGTGCACCCCCTGGAGAG
CCCAGCCATGATCAGCCTCACACCACCCACCACCGCCACTGGGGTCTTCTCCCTCAAGGC
CCGGCCTGGCCTCCCACCTGGTAACACCTCAGCCCGTACCCCATGGCTTCACAGAACCCC

FIG. 6
(continued)

CAAGTCCCCAGATCCTTGGCTGTGAGCAGTGTAGGCTATTCTGAATTGCAGTACTCTGGG
GGTCAAAGGTGTCAGGTCTCAGAGGCTTGGAAACTCCACCCTCCAAAAAACGTCAGGTGC
AGAACCTTAAAGATGCAGAATGTCAAAATCACAAAACCACAGAGCTTTACAAAGCTAGTC
AAAATGTCAGCACCTGCGAATGGCCGTCTTTAAGCTTCTCTGCCAGAAGCCTGGGACTTT
GGGGACAGCAGAGCCCCCTGGGAGTCAGGGTTTCGAGGCTCAGGAGGGTGGGAAGCTCA
AAATGAGAGGCCTTGTGGGCCAAGCTCCAGAGCCCAGCCCACAGCCTCCATAGGTGCCCT
GTCCCCACCCACAGGGATCAACGTGGCCAGCCTGGAATGGGTGTCCAGGGAGCCGGCACT
GCTCTGCACCTTCCCAAATCCCAGTGCACCCAGGAAGGACAGGTCAGTGGACAGGGCTGG
GAAGGATCCTCGCCCTCCTATCCCCTCCCCTGACACCCTCTGTCCCCCCAGCACCCTTTC
GGCTGTGCCCCAGAGCTCCTACCCACTGCTGGCAAATGGTGTCTGCAAGTGGCCCGGATG
TGAGAAGGTCTTCGAAGAGCCAGAGGACTTCCTCAAGTGAGTGGCCCAGGCCTGTGCCAG
TCTACCGGCCCTGGCTTGTGGGGAGAGGTCTAGGGTGCAGATCTCAGCTCAGGCTTCATC
CCAATAAGTAGTAAGATGCAAGAGCTAAACTCTGAGACTGTGGGTTCAAATCCCAGCTCC
ATCCCTGACTGGCTGTGTGACCTTGGACAAATTACTTAGCTTCTCTCGACCTCAGTTTTC
TCGTATGTATAATAAGAAACGTTTGTGCTGTTATTTACCCCCATTTTACAGACAAGGAGA
CTGAGGCCAAAGAGGTTAAGTGTCTTGATCAAAATCTCCCAGTTCCTGAGTGACAGAGCT
GGGATTTGAACCCATGTAGCCAGGCTCTAGAATCTGCACTCCTGCTTTGCCCTGCTACTC
CTCATGCCAACATGCCAGCCTTATTCCACTGTTCCCAAAGTTCTAGCTCCTCTAGATGGC
TGCTGCTGCCTCCCCTCAGTCCCCCCATATGTCTCTCTCTCTCTCTCTCTCTCTCTCTCT
CTCTCTCTCTCTCTCTCTCTCTCTTTCTCTCTCTCACACACACACACACACAAATA
CACACCACACTACACACAACCCTTAGCAGCAACCCCACATGTCCTGTCCTCCTTGCAGCC
AGGCCTTTGCACAGGCCGTCCCTCCACCCAGAATGCTTTGCCCACTCTCACCTCCCTGGC
CCATTCTCAACTCACCACACTTCCAACATTATCTCCAGCACTCTGGCCAGGCTCAAGTGG
TGAGTTCAGGCCTGACATGCAGTAGGTGCTGAGGGGCATGTGTTAAGGGAACGAGGGGTG
TGAGAGGGAGACTGAGGTAGAGAGGGGAGGGGAGCTGGGGCTCAGAGGAGAGAACTCCCA
GAGGGTCTGGGCCCTCCCCATTCAGAGCATTGAGCCAGACCAGGCCTGTCGTGGTCACCT
GCATGGAATCTTCTCCCTACTTAGGCACTGCCAGGCGGACCATCTTCTGGATGAGAAGGG

FIG. 6
(continued)

CAGGGCACAATGTCTCCTCCAGAGAGAGATGGTACAGTCTCTGGAGCAGCAGGTAATGCC
AGGGCGGTGGAGGGTAAGGGATAGGGATAGTGCGCAAAACCTTCTGTCCACCATGTGCCA
GAAACCAAGTTCACCTGGGACGAGGGCTGGTATAAAGGAAGGAAGAGGAGCGGGCACTCC
CAGGGAAGACCGTAGCCTGGGCAAAGATGTGGCAGAGAAGGGCCAGGCTGAGGCCTCATG
TTTGTGCCATTTCACAGCTGGTGCTGGAGAAGGAGAAGCTGAGTGCCATGCAGGCCCACC
TGGCTGGGAAAATGGCACTGACCAAGGCTTCATCTGTGGTGAGCGACCCCAGGACTGGTG
GTGGCAGACTCAGACTGCTGGGGGGCAGGGAGGAGGTCTGCACGGTGCAGGGAACCTAAC
CTCACATTCAGGTCCTGAGAGCTAGGGGCCCCTGTCCCCAGCTCCAAACATGCCCAGACC
TGGAAATCTGTCCCCTTCTACTTACAAACCCTCTGACCCCGGCTGGGCGTGGTGGCTCAC
GCCTGTAATCCCAGCACTTTGGGAGGCCGAGGCGGGTGGATCACGAGGTCAGGAGTTCAA
GACCAGCCTCGCCAAGATGGTGAAACCCTGTGTCTACTAAAAGTACAAAAAATTAGCCAG
GCGTGGTGGCAGGTGTCTGTAGTCCCAACTACTTGGGAGGCTGAGGCAGAGAATTGCTTG
AACCTGGGAGGCGGAGTTTGCAGTGAGCTGAGATCATACCACTGCACTCCAGCCTAGGCG
ACAGATCAAGACTCCGTCTCAAGAAAAAAAAAAAAAAAAAAACCCTCTGACTCTAAGATCC
CCAAACACTGTGATCCTGAGTTGTTAAAGCAAATGCAAATAGCCAGACTTGCCAGATGCA
GGCTGTGTGCCAGCAGGACCAGCTATGTAACCTGCAGGGCCCCTTGTTCAGATTTCAAGA
TGGCGACCACAGAGCATTAAACAAAGCACAGGGTGCCACATAACCACATAGGTCACACGC
CCATGAAGCCAGCCCTGGAGGCCAGGCACTGTTTCTGAGCGCTTTGCTGGTGGTAATTTA
TTTCTCATGATGCGAATGTACAGATGAGGAATATTGAGGCCAGGGGGTTTAGGTGACTT
TCCCAAGGTCACAGTTGGGTGGTAAAGAGCCCTATTCAACCCCAGTTCATGGTCCCAGCA
TCAGTGGCCACATACGACATCCGCACCTGTGCTCTAATAAATACGGCTCATGCTGTTTTG
TGGGATTCCACCTCAGACTGGAATTTAGAAGAGGGCGTCCTTGCTTTGAAAAACACTGAT
TTAAAAATAAAGTGGAGCCAGGCGCAGTGGCTCATGCCTGTAATCCCAGCACTTTGGGAG
GCTGAAGCGGGTGGATCACATGAGGTCAGGAGTTCGAGACCAGCCTGGCTAACATGGTGA
AACCCCATCTCTACCAAAAATACAAAAATTAGCTGGGCGTAGTGACGGGCACCTGTAGTC
CCAGCTACTCGGGAGGCTGAGGCAGAAGACTTGCTTGAATCTGGGAGGTGGGGGTTGCAG
TGAGCCGAGATTGCACCACTGCACTCCAGCCTGGGCGACAGAGCAAGACTCAGTATCAAA

AAAAATAAAAAACATAAAATAGAAAGTAAAAAGTGGAAGTTTAAGCCTCTGGGTCACCA
GCCTCTCCCCCTCACCCAGGCATCATCCGACAAGGCTCCTGCTGCATCGTAGCTGCTGG
CAGCCAAGGCCCTGTCGTCCCAGCCTGGTCTGGCCCCCGGGAGGCCCCTGACAGCCTGTT
TGCTGTCCGGAGGCACCTGTGGGGTAGCCATGGAAACAGCACATTCCCAGGTAAGAATGG
TCCTTGCACTACACGGTGCCCCCAAGCTCCTAATCCTGACAGGCTCTGGGTGGAGGGTGC
AAAGGAGCTCCATGCTGCCCCTTCCCACCACCACCACCACTGCAGCTGCCGCCACTCAGC
CTTTGGGAAAATGCATCCGCTCACAAAAGCTTCCTTTCGGGATGTCCGTGGCCTGAAAGC
CCCCCATATGGTCTCGAGTGTCGGGCCCCTAGCCCTGACTCCCTTGGGGATTGGGGCCAT
GCCTCACCCACTCTGGACTCCAGCTACTATATTCGGCCATCAGAAGGGAGGGACCCTGCT
AAGTAATTCCAGGAGCACCTCCTTTCCTCCCCTGACCAAGGAAAATCGGGGTGGATTCGC
CCGAGCTCACCTATCCACTGCTCTCCACCAGGCCTGGCCTGTGGGCTTAGCAGGGATCAG
AGACCTTGACTGTCATCCTGGCTCTGCCATTTAACCTCTTGCATCCTTTGGTGTGCAAGT
TACTCCGCTTCTTTTCAACCTCGGGGAGAACTATTTTGGCAGAAGTGGTGCAAAGAATAA
ATGATACAACTTATGTCAGGTGCTCAGCAAACAGTACCTGTGCCCGTGGACACGGGTGTT
GACGGTGAGATCTCAGGCCTGTAGACTCACCTTGTAGGGGGAGGGGACAGGGAGCTAGCT
AGGAGGTCCTGCATGGGGCTTGATTCATCCCCACCCTCTGACAGAGTTCCTCCACAACAT
GGACTACTTCAAGTTCCACAACATGCGACCCCCTTTCACCTACGCCACGCTCATCCGCTG
GGTAAGCAGGGCAGCTCGGCCCCAAGGAGGAGGAAGACAAAGATGGGGTGGGGGACCTGC
CTCCCAAACTCCTGTCTCCCTCTGAGTGCCCTCAGAGTGGGTTCCTCCATTCCCAAGCCC
CAGCCCCAAGGATCCCCAAGCCGTGCCTCAAATGTGACCCCTCATGCTGGCTTCACCCCA
AACCTGTCCGCAAATCCAAACCTAAACCACCATCCAGGCCAGAGCATGCCAAATTCTGAC
CCTAAACCTACCCCTTTCCAGATGTCCACCTCAGCCCCATACCTAACCCTCTCCTGGACC
CATAAAATAGCCTAAAGCTAACCCCATCTCTGCACCTTGCCCTAAACGTACCCCAGCTCT
TACTCTAACTCCTTCCCCAGCCTTTATGCCAACCCAACCCCATCTCCTTCCCTGGCCCCA
ACGTACCCCAGTATGTCAATACACCCCCAACTGGGCACCATTCCCAACCTTTCCTTGTAA
CACCCATTTGATCCTTAACTTCATCACCCCATCCCAACTCCTTCATCTCAGCCTCCCCAA
TGCCTTCTCAGAACCTTCATCCTAGCGCCACACCTAACCCCAAACCTGAACCTCACCCCT

ACATGATACCAGATATTCCCCGACTGTCTCTGAACTGAAACCCTGACCTAGCCCCATCCT
GACTGATAGCCTCACTGCAATCATCATCGCTGACTCTGTAATCCCATTCCTGAATCCAAA
CTGATCAAATTCCCTGACCCTCAGCCTCACTCCACACCGAACCCCACAACTAACCTCATC
CTTGCCCTGAGCCTAACCACCTAACCATGTCCCTGACACGTAAGATACTCGATAATTCAA
ACCATCTCTGGCTTCTGACCTAAAGCCAAGTCATCCCATCCCTCACCCCTAGACCCCCCA
CCTGAGTCCACCCCAGCCTGACTCTTAACCCACCCCTTCCCTGACCCTTAAGTTGGCCTG
GCCCTTTACCCCTTCCAAATCCTTGACCCCACTTCTGACCCTTCACCTTCCCCAACCCTG
AAATGTCACCTCCACAGAGAACCCCAACTCCAACTCCATCCCAGACCTTTCACCTCACTT
CAGCCCTAGCCCTGAACAAGACCCCACTCCCAACCTCAGTCCTGATCCCTTACCTAATCC
CAGAACAACCATACCCACACCCATCTAACCCTGCCCAACCCGACACTTCACCCCTTTTCT
AACCCCATCTTTGACCCCATGCTTCACCCCACATCTAGTCCTGTCCCTGATTACCTGCCC
CTACAATTCCGCCCCCATGTCAGATGGCTCGGGGTAGGTCATAGCCCCTCTAAACCCCAA
GTTTGGGGAATGTGCCCCTTACCCCACCCCCCAACTTCCAGGCCATCCTGGAGGCTCCAG
AGAAGCAGCGGACACTCAATGAGATCTACCACTGGTTCACACGCATGTTTGCCTTCTTCA
GAAACCATCCTGCCACCTGGAAGGTGAGCTCCTCTGAGGTGGCGGTGACTGGGATGGCCT
CAAGTGCCATCGCAGCTCAAAGTGGGCAGGCCTGGGTCTGGGCTCATAGGCACATTGGGG
AGGAACGGGATGTGGGTTGTTGGTGGTGGCTGCTGGCCTCAGAGGTTGACGCCCACCTGC
TCCCTGTCCCCGGCCTTCCACAGAACGCCATCCGCCACAACCTGAGTCTGCACAAGTGCT
TTGTGCGGGTGGAGAGCGAGAAGGGGGCTGTGTGGACCGTGGATGAGCTGGAGTTCCGCA
AGAAACGGAGCCAGAGGCCCAGCAGGTGTTCCAACCCTACACCTGGCCCCTGACCTCAAG
ATCAAGGAAAGGAGGATGGACGAACAGGGGCCAAACTGGTGGGAGGCAGAGGTGGTGGGG
GCAGGGATGATAGGCCCTGGATGTGCCCACAGGGACCAAGAAGTGAGGTTTCCACTGTCT
TGCCTGCCAGGGCCCCTGTTCCCCCGCTGGCAGCCACCCCCTCCCCCATCATATCCTTTG
CCCCAAGGCTGCTCAGAGGGGCCCCGGTCCTGGCCCCAGCCCCCACCTCCGCCCCAGACA
CACCCCCCAGTCGAGCCCTGCAGCCAAACAGAGCCTTCACAACCAGCCACACAGAGCCTG
CCTCAGCTGCTCGCACAGATTACTTCAGGGCTGGAAAAGTCACACAGACACACAAAATGT
CACAATCCTGTCCCTCACTCAACACAAACCCCAAAACACAGAGAGCCTGCCTCAGTACAC

TCAAACAACCTCAAAGCTGCATCATCACACAATCACACACAAGCACAGCCCTGACAACCC
ACACACCCCAAGGCACGCACCCACAGCCAGCCTCAGGGCCCACAGGGGCACTGTCAACAC
AGGGGTGTGCCCAGAGGCCTACACAGAAGCAGCGTCAGTACCCTCAGGATCTGAGGTCCC
AACACGTGCTCGCTCACACACACGGCCTGTTAGAATTCACCTGTGTATCTCACGCATATG
CACACGCACAGCCCCCCAGTGGGTCTCTTGAGTCCCGTGCAGACACACACAGCCACACAC
ACTGCCTTGCCAAAAATACCCCGTGTCTCCCCTGCCACTCACCTCACTCCCATTCCCTGA
GCCCTGATCCATGCCTCAGCTTAGACTGCAGAGGAACTACTCATTTATTTGGATCCAAG
GCCCCCAACCCACAGTACCGTCCCCAATAAACTGCAGCCGAGCTCCCCACATGCTGGACT
ATCACCCCATATAAGGGTTGCGGTCAGTGGGCAGGGGTCTGGGTCCAAGGCCGCAGCAGG
AGGAACTGGACAGCGGAGGAAGTAGCTAGGGCATGTGCTTGGCCACTGCCTCCAGCACCC
CAAATCCCTGCCTGAGGCTGGGGAGAGACCTCTGCCGGCGGCTCCTCAGGCCTCCCGGAC
CCGGCCTAGGAGGCCAGCGTTCTCCTGGCGGAGGGCTCGGTAGTCCTCCCGGATCTTCTC
CAGGTTGCTGAGGGTCTTCTTGCCCAGCTCTGTCTCGATCTGAGGCAATGTGAACACATG
CCCCCTCAGCACACACAGCCCCTTTCCCAGCTCCTGCTCACCAGCCCCCATCACAGCCAC
TCTGGGCCCCTCCCACCAACTCCAACAGCCTGCTCTGTCCCATGGCCAGGCCTCGTGTGG
TGTTCCCTCTACCCAAAGCATCCTTCGCCATGTGGCAGGATTCCCCCTACATCTTTAAGC
TGAAGCCTCTGCCCATGGCCCTGGGAGGCAGACAGGAGGGCCCTTGGGGTGGAAGCTGGG
GCTCACAGTAGGCCACTTGCCTGTCCCAGGTCACAGGCACTAAGGGGCAGG

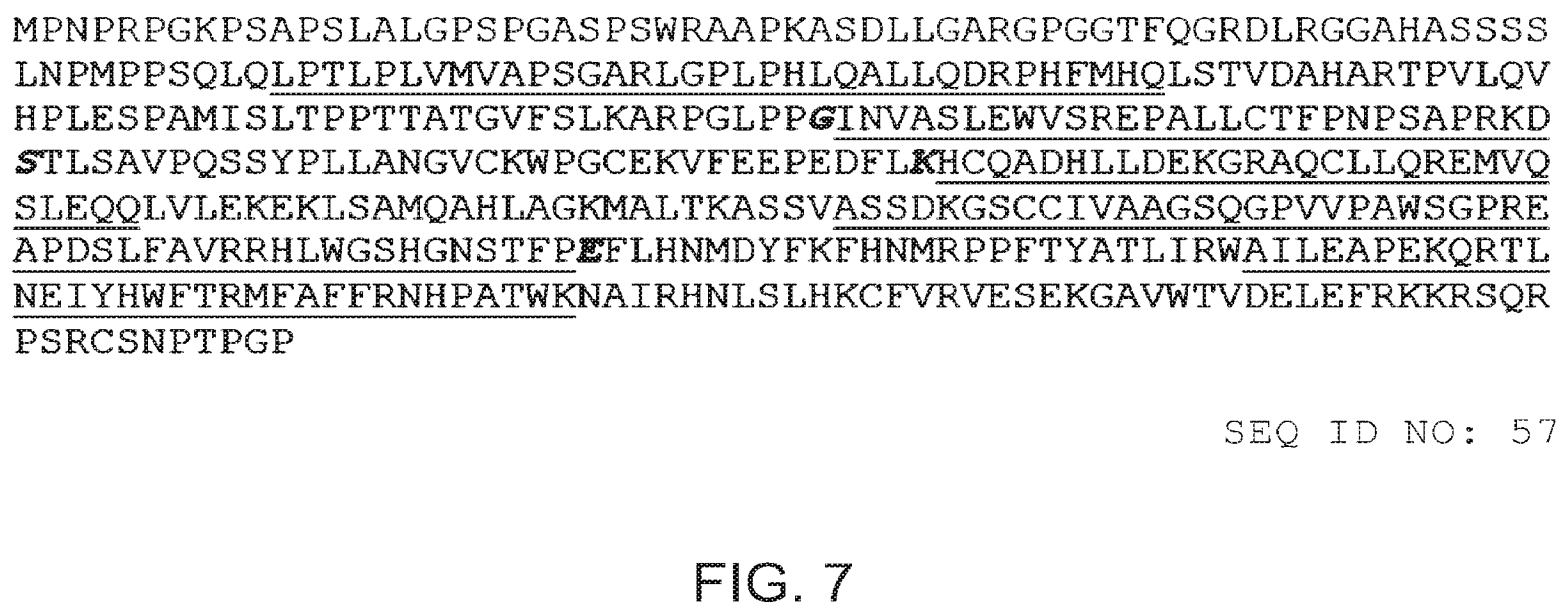

MPNPRPGKPSAPSLALGPSPGASPSWRAAPKASDLLGARGPGGTFQGRDLRGGAHASSSS
LNPMPPSQLQLPTLPLVMVAPSGARLGPLPHLQALLQDRPHFMHQLSTVDAHARTPVLQV
HPLESPAMISLTPPTTATGVFSLKARPGLPPGINVASLEWVSREPALLCTFPNPSAPRKD
STLSAVPQSSYPLLANGVCKWPGCEKVFEEPEDFLKHCQADHLLDEKGRAQCLLQREMVQ
SLEQQLVLEKEKLSAMQAHLAGKMALTKASSVASSDKGSCCIVAAGSQGPVVPAWSGPRE
APDSLFAVRRHLWGSHGNSTFPEFLHNMDYFKFHNMRPPFTYATLIRWAILEAPEKQRTL
NEIYHWFTRMFAFFRNHPATWKNAIRHNLSLHKCFVRVESEKGAVWTVDELEFRKKRSQR
PSRCSNPTPGP

SEQ ID NO: 57

FIG. 7

CATGACCCTGCCACCCCATGGGCCTGCTGCTGGTGGCAGCGTGGCCGCCTCCTGAGAGTT
GGCCCTCCCTTGTGCCACTGCCAGGGGAGGAAAGGCCTTGATGTTCCAGACAATAATAAA
TGCGCCTGTGACTTAGCCTTGGTGTCAGTCTCTTGCGGACCTGACAACCCCCATCTCTCC
TTCCCTGATTCCCTCTGCCTTTCCAGGCCCCATCCCCCTGAACAGCTCCTCCCTATGGTC
CTGGCTGGGCCTAACCCTGCCCCAGGGCCTAACCCTACCTGAGGCTCCTCCCCTTCCCCC
GGGGCAGGTTGAGAGGCTGGAGTGGGTCCCTCAGCGCCCTGGGTGGGTGGGCCTGCACAG
GGGGTACCTCCTTCTCTGAGGAACTGGGCTGTTAGGGATTTTCCTTAGGCCCTTTGGTTT
CCGCCTACGGAGAGGTTTCCCCCATTGGTTGCTCTTCCTCAGCCAGGGTTACTTCCTGGT
CTGTTCCCCTACCCAATACCCCGCCGCTCTGTCAGCTTGAGCTCCAGGTGGAGCTCCAGG
TGGCTCCTCCTCTCCCGGGGGAAGGCGGCCCTGGACCAGCAGGCGGGCCTGCTGTACTCC
CGCTTTGGGGCTGCAGGGAAGCTGGCCGCTGTGGGCGGTCTCGGGCCAGCCCCGCCCCAC
CTGTCCTTTTCCTGGAGACTATTAGTCCAGGGTTTGTCCCTGCAGTGCCATTGGCCTGGC
AGGCAGGATCGAGGAGGAAGTGGCTGATTACTGAGCGGTTCTTCCTCACCTGGCTTGGGC
CACTGTGCACAGCTGTGCCGCTGGCTCAGCCCCGCCCCCTGCGGCCCTCTGCCGTGGCTT
CCCCCTCCCTACAGAGAGATGCTGTCCCGTGGGTAAGTCCCGGGCACCATCGGGGTCCCA
GTCTCCTGTTAGTTTTGGAGGGAGGGAGGGCTTTGTTGATGCTCACTCCGACGTGTGTGA
ACGTGAGTGCGATCTGCCGCTGCCCTGCGCCTGTTTCCGGTCCCTATGAACTTCCCCTTC
CCGCAAGGTGTGAGGACCCCCGGCTCACTCATGCTCCTCTGCCCCCTCTTTAACATTTTC
CCCTGGACAAGTGTGTATCTGTTCTCTCCATTGCATTTCTACTTCCAGCCTCTGGGCTCC
TGCTTCTGCCTCCTGCTTAGGACCTGTCCCCCTGGGTAGCTCACAACACCTCAAACATAG
CAGTCAGAGGCCACCCGCGAAGGCCCTCCCACGTCCAGCCAACTTCTCCGCACTTCCCAA
CATCAGACTTTGGTCCCATCTTCTTTGTTTCCTTTCACTTCCCTTTCCCCTGCATCATTC
ATTCAACAGGTACGTGTTGAGCATCTATTATGCACCAGGTGCTGTTTAAGATGCTGGTAA
TACTGGAGTGAACAAGACAGACATGGTCTCTGCTCTCACGGAGCTTACATTCCAGTGGGA
GGTTACAGACCGAACAAATAACCCAATAAATTGGATCATTGCAGATTCTCAGAAGTATTA

CGCAGAAAATAGACAGCCTTGGCCGGGTGTAGTGGTTCACACCTGTGATCCCAGCACTGT
GGGAGGCTGAGGCGAGAGGATTGCTTGAGCCCAGGAGTTTGAGACCAGCCTGGCCAATAT
AGTGAGACCCTGTCTCTACAAAAAATAAGAAATTAGCTGGGTGTGGTGGCACACGTCCTG
TGGTTCCAGCTATGGAGAGGCTAAGGTGAGAGGCTTGCTTGAGCCTGGGAGGTCAAGGCT
GCAGTCAGCGATGATTGCACCACTGCACACCAGCCTGGGCGACAGAGTGAGACCTTGTCT
CAAAAAAAAAAAAAAAAAAAGAAAATGAACCAGCTTCATATGCTAGCAAGTGACTGGGTG
TGCAGGTGACATTACTAGCTGGAGGGATCAGGGAGGCCTTCCCGAGGAGGTGACATTTGA
GCTGAGACCCGGATGAGGAGGAAGAGGAGCTGGCCATGTGACGTAGTGATCAAGAGTCAA
GCATCTCTGGGCAGAGGAGATGGTGAGCACAAAGCCCTAATGTGGGAACAAACAAAAAAA
GGACAGTGTGCCCGTGGCAGAGGACCCTAGTGGAGCGGAGGCAGGGCCACAGCAGGTTAG
ACCATGTTGGAGCTAGGATGTTGAAAGTGAAAACCTGACGAGATGAGGTGGCGCACGTCT
GTGATCCCAGCACTTTGGGAGGCCGAAGGGGGAAGATTGCTTGAGCTCAGGAGTTTAAAA
CCAGCCTGGGCAACATAGAGAGACCCCATCTCTATTAAAAAAAAATACTGGGTATGATGG
CCCAAGCATGTGGTAGTCCTAGCAGTTTGGGAGGCTGAGGTGGGAGGATCACTTGAGCCC
AAGAGTTCAAGACCACCCTGGGCAACATAGGGAGAGACCTCATCTCTACTACGACTACGA
CTACTACTACTACTAATAAATAGCTGGATGTAGTGGCATGCACCTGTGGTCTCAGTTACT
TGGAAGGCTGAGGCAGGAGGATCACCTGAGCCAAGGAGGTCGACGCTGCAGTGAGTTGGA
TTGTGACACTGCACTTCAGCCTGGGTGATAAAGCAAGATTCTGTGTCAAAAAAAAAAAAA
AAAGAGAGGGAAGGAAAGAAGGAAGGGAAGGAAGAAAGAAAAAGAGAAAGAAGGAAAAAA
AGGAAAGAGCGAGAAAGAAGAAAGAAAAGGAAGGAAGGAAAGAAAGAAAAGAAAGGAAAG
AAAAAGAAAAAGTGACACCCAGTCGAAAGAAGAAAGGAAAGAAAAAGAAAAAGTGACAAC
CGGTCGAAAGAAAAAAGAAAAAGTGACAACCGGCTGGGCATGGTGGCTCAAGCCTGTAAT
CCCAGCACTTTGGGAGGCCGAGGCAGGTGGATCACGAGGTCAGGAGTTCAAGACCAGCCT
GGCCAACATGGTGAAACCCTGTCTCAACTAAAGATACAAAAAAAAAATTAGGCTGGCACA
GTGGTGCGCACCTGTGAGTCCCAGCTACTAGGGAGGCTGAGGCAGGAGAATTGCTTGAAC

CCAGGAGGCGGAGGTTGCAGTGAGCCGAGATTGCGTCACTGCACTCCAGCCTGAGTGCAG
CGGGAGAGACTCCATCTCAAAAAAAAAAAAAAAAGAAAAGAAAAAGTGACAACCTGCTTA
CAGAGTACTGGCGAGTTTGTGGGTGGGTGGCTCCCTAGCCCTGCTGATTCTTGCTTCTCA
CACTCATGTCTGCCCCTGCCCCAGTGCACATCTTGTCACTGTCGGCCCCACCGATGGGGT
TCCTACTGAGTCTTCTGGTCCCTGATCCCGTCTGTGGTCATTTTCCTGCCAGGTAGCTTG
GCCAGGCCTCCCCTGGTGCAGATTTCATCCTTGGTTTCTCAGCCTGGCCTTGAATGACCC
TCTACAGCAGGGTCCCCACCTCTCAGAACAACTTTGCTCCAGCCACATGGCTTGCTCACG
GCCAGGCACTGCCCATGTGGACTCTGTGCGTGCCACCTCTTTGCCCTGACCCATGTTGCC
TCTGGGGGAGCACTTCTTCCTCCACCTTCCATCATGGGCTGTGGCAGTGCCCATCCCATC
TGCCCCCGACGCTGTCTGCTGCAGTATGGTTGTTGGGGGAAAGGGCACCAGGCTCCGGCG
TCTGACAGCCGTGTTTTACCCACCTTCCTACTCACTAGCTTGTGACCTTGGGCAATTACT
TAACATCTCTGAGTCTTAGTTTCTGTTTCTAAAATTGGGTGAATAACACCTACTAAGTAG
GGTTGGCCTGAGGATTAATAGTATAATGTAAAAGCTGGCAGCACTGAAACCCTGCCACTT
ACCAGCTTTTCACATCAGTATTTGGGAAATATTGTTAAGCTCATTTGTCAGGCGGGGATT
CTGAGGCTCAGAGCAGTTCCAGAACTTTCTACAGATTATTTTGCCTTGTTTGCGCTTCCA
GACTGCCTATCTTCTTGTATCACCATTGATCTTGATCTGTATGGTTTTTAATTTTTTTTT
TTTTGAGACGGAGTTTCACTCTGTTGCCCAGGCTGGAGTGCGGTGGCATGATCTCGGCTC
ACTGCAACCTCCACCTCCTGAGAAGCTGGGATTACAGGCATGTGCCACCACACCCGGCTA
ATCTTTGTATTTTTAGTAGAGTTGGGGTTTCACTATGTTGGCCAGGCTGGTCTCGATCTC
CTGACCTCGTGATCCGCCAGCCTTGGCCTCCCAAAGTGCTGGGATTACAGGCGTGAGCCA
CTGCGCCCGGCCAACTTCACGTTTATACACACCCATGCAAACAGCATCCAGATAGAGACA
AAGAGCCTTCCCTGTACCCTAAAAGTTTCCCAGAAATTGTTCCCAGTTAGCATATTTATT
TTTATAAAGGTAATGCATGCCCATCATATAACATTCAAAAAGGTATGTAGAGAACCAAGT
GTCTCCCCCAGCCCTGTCCTCCAGCCACCCAGTTTCCCTCCCTAGGGGAAGCCACCAATA
TGTGTTTCTTATGTATCCCCTGTTGAGCTGCTTTTCCTCGTTTTGGTTTGGCGGTGTTGA

FIG. 8 (continued)

TGTTTGTATTTGGAATTACAGGTAGGCAGCATCATATACCTTAGTGTTTAGGGCCTCTAA
GATCAACCAGCCCTGAGAAAATCAGCCATGGTGAGGACCTTGTCCCCCAGCCCCCCAGGA
GATAGGCCCCCTGGTGGGAGTGCTGGGGCAGGGCAGAGGCCTAGGGACAAGAATTAGAAA
GGACCCATGTTGACAGGGCTGCTCAGGGTCATGTTGTCCATCCCTCTGCCACAGTGGCAT
GGACAAACTGCATATGTTGGTTAGAGGAGGGCACCCTTCTCTCTTGCAAGCATTGGCAAG
GTCTTAACTATTAGTCTCCTGCTCCCATGGCAGCCCCTTTGGACAAGGAGGCTCTTAATC
TCTGTTCTTTGAAGCCCTGAGGGCTGGTGTATAGGAGTTCAAAGCACTGGCTTTGGAACC
GGACTGTCTGGGTTTGAATCCTGGCACTGCAGCTGACTCACTGATGGACTCAGGCAATGC
CTTAAACTCCCTGAGCCTCAGGTTCCTTGTCTGTAAAATGATAAAGATAGCCCCTGTTTC
ATAGGGCTGTGGTGAGAAACCAATCAGACAAGGCATGTGAACGCCATTATAGCACAGCGC
CCGGCATCCAGCAGGACTCACTCGATGACAGTTGTCACCGCCATCATTGTTATTAGCGTG
GGCCAGGGAGGGCTGCGTAAAAGCAGCTGGTGGAGGAGGGAGAGATGCCGTGGGACCGTC
TGGGTTCGCATGCGTGAAGTATTATCTGGGCCTGGAGTGTGCAAGGCACACATGTGTCCT
TACTGCATGTGTTGTCACATATGTGCAATGCCATGCTCCTGAGCCTTTGATTGCAGACGT
GTGGGAAGTGGGCCCCGTCCCCACCCCCAGTGCCACCCTGCTCTGCTTCTCTTCCCTTGC
TGTGCTCTAAAACGAGAAGTACAAGTGAGTTCCCCCAAGGGGTCGGCCGCGCCTCTTCCT
GTCCCCGCCCTGCCGGCTGCCCCAGGCCAGTGGAGTGGCAGCCCCAGAACTGGGACCACC
GGGGGTGGTGAGGCGGCCCGGCACTGGGAGCTGCATCTGAGGCTTAGTCCCTGAGCTCTC
TGCCTGCCCAGACTAGCTGCACCTCCTCATTCCCTGCGCCCCCTTCCTCTCCGGAAGCCC
CCAGGATGGTGAGGTAAGGGCCTGCCACCCACGGTAGACAGGAGGCAAGGGTGCCTGGTG
CCCACGGGACCCCTCCTCACTGCCCTGCCTGGGCCGCCCAGGTGGTTTCACCGAGACCTC
AGTGGGCTGGATGCAGAGACCCTGCTCAAGGGCCGAGGTGTCCACGGTAGCTTCCTGGCT
CGGCCCAGTCGCAAGAACCAGGGTGACTTCTCGCTCTCCGTCAGGTAGGTGGGCCCCCG
CAACCCCGGGCATTTTGGCCACTCTCTTGTGCCATCCAGGCCCTGAACCACTCATTCCTG
GTTCCCCGTGGCAGTGCTGACTCCCCGTCTGTTCCCTTGCCCCCAACCCCCACACTCCCC
ATCCCTGTCTGTGCCCACCCATGCCCATGTGTGCCCCCACCCAGGACCTCAGCCGATCCC

FIG. 8
(continued)

TGCCCTCCTGCCTCTACTCCTGCACCGACTGGCCTCACCGCCTGGTGCCCTGCAGGGTGG
GGGATCAGGTGACCCATATTCGGATCCAGAACTCAGGGGATTTCTATGACCTGTATGGAG
GGGAGAAGTTTGCGACTCTGACAGAGCTGGTGGAGTACTACACTCAGCAGCAGGGTGTCC
TGCAGGACCGCGACGGCACCATCATCCACCTCAAGTACCCGCTGAACTGCTCCGATCCCA
CTAGTGAGAGGTGAGGGCTCCGCACCCCCGCCATTCCCAAGCAGGGATGAGCCGGCTCCC
ACCCTGAACAGCCAGGGAGGCAGGGAGACTGGCAGCCGGCGCTGCCTACCCTCCATCCCC
TCCCCTCCCTGCACCAGCTGGGGCTCTCAATGTCCCTCCTCCCTGCTGTCCTGGGACCTG
GTGTCTCAGAGCCTAACCTACCACCCTTTCCACCTAACCCCGAGGAAGCCACAGAAAGCT
GCCTCGCCCTACTCCGGGAGCCCTGGCCGCTGCAACCCAGGTCCCACTGGAGACAGGGAG
GCCACTGCTGGTGGCCAGCATGTCGTGCAGGCCAGCTCTGTTGTTAGAAAGCTCTTCTTC
CTCTGGAATCGAGCCTGCCTTCCTCCGTCTGCCCCTCACCCCAGCACATGTTAGGACAGT
GAGGAGCTGACACTGGGGTGAAGATGGGGATGAATGCTTGCCAAGACACTTGATGCCTTG
TCCCAGCCGCCCCGTGGGGATGGGTCTGTCCTGTGGGGTCAAATAGGTCTCCGGCCCAAA
CAGAGATCATTGAGAGCACGATGTGAAGTGTTCACCTGTGTAAAGTGTCTCACGCTGTCC
CGGGCACAGAGTAATACTCCAGGCATTTCCTTCCTGTGGCCTCCCCGACTCCTCCTGTGG
TCTCCCAAAGGCATGGGCTGGGGGCTGGGGGCTCTGAATGCTCCTCATGACACCATGGCT
CCTTTCAGCAGCCGCATCTCAATGCCAGATCCCCTTAGAGTAAAGGGCAGCGGAATAACG
CTAGGGGGTTTTCACATGCACCCCCTGGGCCAAGCCGACTTGCCCTTGCCGTGGATCCCTG
CATTCATGGATCGGTTATTGAAATGATCGGGAACCTTGCTCCTGCCAGCTTGCAGCCTCT
CTGAGATTCGGGCCTCCAAACTGCATCAATATTTTTGGTCAAGGCACTGATTGAAACTTA
GAGCTGGATTCGGTCACGGTGCAGCCCTGTGGCCCACCTGGGAGGCCTCCTTTCCTGGAT
CGGCCTCCTTCAAGGCCTTCCCTCTCTCTGTGAGCCTCACATGGCTGGCTCCGTGTCTGC
CCCCTGCCCTTCCTCTTCCCCACCGCAACACTCAGGGGGCTTTTGGCACCGAGACCCTCT
AAAGCTCATGTCCTCTCTTTCTCCTTGCCTCCAGCCAGGAGAGGAGGACGGCTGACCAG
TGCCTGGAGGTGGAAGAGAGGAGCAGGGCCCCAGGAGGCCCCTGCAGAGGAGGCTGAGGC

FIG. 8 (continued)

CTGGGTTCAAGGAGAAGAGAGAAGAGAGAGAAGGAAGGGAGGGCAGTGCCGGGGCGGGAG
GTTAAGACCAGGGAAGCCGCACTGGAGGCCCTTTTGGGTGACCCGTCCCAGGAGCCAGTG
TCACCCCTGAGCCTGGGAGTGTGTGAGAGGCTCTTTCTCCCAGGTTCTGCTGTGTCCTCT
GCCTTGTCTGTGCGCCTCCTCCTCTGCGAGAATTTGCATCTGTCCCTCGGTGGCTCTGCG
CTTCCTGTGGTCAGCCTGACATTTGCATGGAGACTTCCTCATCCTGGGGCCTGAGGGAAG
GGGCTCAGCCCCCTCCCCGCTACCTGGGGTCCTAGCCTGTCCCCAGGCGGTGGCTGAAG
TAGCCCAGTGGGGTTAGGAGGCTCTGGGGGTCTCTCGGCTGGAGTCACCTCCGGGCAGGG
GTGAGATGGGTTGGGACAGACTGGTCCTCCCCTCCTTCCCCCCATCCCTGCGGTTGGAAA
ATTTGCCCGCCCTCCCCTCGTCCCTGGGCTGAGGAAACCTCACAACCTCACTTCTCACTC
TCTCCCCAGAAGGAGTTTTGTGTTTTTTCCATCACGTGGTTTCCTGTGGGGCTGGGCTTT
GTGGGGCTACAGTTTCCTCCTGGGAAAGGGGTGTGCTTCGGGGAAAGGGCTTAGTTCTGC
TTTCTGCCCTGACAGCCCCTTCAAATCCGTTTGAACCCTGGGCTCCCCTTCAGTGACATC
ATCCAGGGCACCCCAGAACCCCCTACACCACTCTTTCCCCAGTGGGGTTGTCTTCCCCGC
CTCCCTGGCGGAGCGCACCCCATCCGCCTTCCTTGTGACTTGAGTCTGTGTGTCCATCTC
CCACCACTCCCTGTGGTGTGGCCTCGGTCTGCGTTTCTCTTTGCCTCTGGTCTCTGCTGG
GGCACAGTCCCATCCTTCACGGAGATTCATCCTTAGCTTCTCTCCTCCAAATATTTTGAA
TATTGCCAGCCTTTCTGCCTTTCAGAGGTGGGCTCTGGGTTCGAAGCCCGGTTAGAACTC
TGGAGGCTAGGATGGCTTGAACCTGGGAGGTCGAGGCTGCAGAGAGCTGTAACCGCGCCA
CTGCACTCCAGCCTGGGCAACAGAGCTCTGGAAGCTTGCCCTAGAGTCAGTCAAGGGCCC
TAGGCCAGTGAGTAACAGCTCAGCGTCAGTTTCCTCATCTATAAAATGGGGGTAATATCA
TACCTAGCTCTCAGCATGTTTGTGAGAGACCTAAATGAGGTGGTGGATTTGGAAGCATGT
AGCGCAGTGCCTGGCACACAGTAGGTGCTTGATTTCCGGCCCCTCTCTGTGAATGTCTCT
GCTCAGCGCCTTCCCCTGTGGCCTGGGTCTTACCTTCCCTGACGCTGCCTTCTCTAGGTG
GTACCATGGCCACATGTCTGGCGGGCAGGCAGAGACGCTGCTGCAGGCCAAGGCGAGCC
CTGGACGTTTCTTGTGCGTGAGAGCCTCAGCCAGCCTGGAGACTTCGTGCTTTCTGTGCT

CAGTGACCAGCCCAAGGCTGGCCCAGGCTCCCCGCTCAGGGTCACCCACATCAAGGTCAT
GTGCGAGGTAAGGCAGCCAGGCGGCGGGGGAGCCTCTGCTGAGGCTCCTGTCTGTGACCA
CAGTGTGGGTGGCAGGGAGGGTCTGCCTGGGCTTGAATTCAAGGCTGGGGACCCAGGGAG
GGAGACTCAAGTCCTGTGAATGGCCTAATTTGGCTCCCCCCAGGGTGGACGCTACACAGT
GGGTGGTTTGGAGACCTTCGACAGCCTCACGGACCTGGTGGAGCATTTCAAGAAGACGGG
GATTGAGGAGGCCTCAGGCGCCTTTGTCTACCTGCGGCAGGTCAGGGGTGGGCCCAGCTG
CCTCCCCACTTCCCCTGAGCTGTCCCCCAGATGTGAGCTTCTGGGATCTCTGAGTTGCTG
ACTTCTCGCTCTTCCCCACCCCAGCCGTACTATGCCACGAGGGTGAATGCGGCTGACATT
GAGAACCGAGTGTTGGAACTGAACAAGAAGCAGGAGTCCGAGGATACAGCCAAGGCTGGC
TTCTGGGAGGAGTTTGAGGTGCATGGTGGGGACCGGCAGGGCTGGGGCAGCTGAGGTGGT
GGCAGCGGCCTGGGGCCCCAGGCGGACACCTTCCCCTCCTTGCCCACCTCTGCTCCTGAC
CCACCCCACGTGAGCTCCCCCGATGGATGCCCTCTTTGGGAGCTGATGCTCATTTCCCCA
CCCACATCTCAGAGTTTGCAGAAGCAGGAGGTGAAGAACTTGCACCAGCGTCTGGAAGGG
CAGCGGCCAGAGAACAAGGGCAAGAACCGCTACAAGAACATTCTCCCCTGTGAGCACCCA
GGCTGCCCCATTCACCCAGGATACCGCCCCTGCCCCAGCTGCCTCCCCTCATCTCACAGG
TCTCCACCCTCCACGCCAGGAGGGGCCATCTCCCCACACCCCCCACAGAGCCTCCCCCTT
CTCCAAAAGGCCTCTACTCCTCCCAGAAGTGCCTCCCCACCACCAGCAGGCAGGTTGCCC
CCTGCTCCCAACCTCCTTGTGAACTCCCTCACTCCCTCCATACAGATGATCCCCCACCCC
TGCTGCCCACAGTCCCCCGCAAGCCTCATGGCTTCTGAGACCAGAATGGCCTGTTAGCTC
AGGAGGGTCTGACCCAGGTGTGGTGAGTCCCTGGCTAACCCAGACCATCTCGCCTCCTCT
CCGCCCACTCCCAGTTGACCACAGCCGAGTGATCCTGCAGGGACGGGACAGTAACATCCC
CGGGTCCGACTACATCAATGCCAACTACATCAAGGTCAGCAGTGTGGGCCACGTGGGAGG
AGAGGCTGGGCCCTGGGAATTCCCTGTCTGGTGGGGGGACCCTAGATCCAGAGACAGCTG
GGCAAAGCCGAAGCTGGCTTCTTGCATGGGTGAGGGTGGCAGTGGTTCAGGGCCTGTGCT
GGGCCAAGGGGCTCACTGTCTTGGGGTGCGTCTCTCCACGCTTGCGTCCAGAACCAGCTG

FIG. 8
(continued)

CTAGGCCCTGATGAGAACGCTAAGACCTACATCGCCAGCCAGGGTTGTCTGGAGGCCACG
GTCAATGACTTCTGGCAGATGGCGTGGCAGGAGAACAGCCGTGTCATCGTCATGACCACC
CGAGAGGTGGAGAAAGGCCGGGTAGGGCGCCCCCCTTCCCCGCATCCGCCCCCGTGCTT
GTGGTCATGCCATTAAGTCGAAGAGCAGTCAGATGCCAGGGCAGAAAGGGATCTCAGGGG
TGAGGGTCCGGCCCTTGTTGGGAAACTGAGGGCTAGTGACAAAGTCTCGACTACACAACG
TGACCCCCAGATCCCTGCATGCATCCCTGGGCTCTTCTGAGCTCCAGACCCAGGTTCCAG
GCTGTCCTCCTTCCTCCTACCCCTGCCCCACCTGTCTGCATCCAGGCCCCTCCTGTCCTC
CCTGCCCCATAGATCTCTCTGGAGTCTGCCCCTTACCCTGCAGGCTCCCCCTACACAGCA
CCCTCTGTGCTGCCATTGAAGTGATCCCATCCGTGACACAAACTGGGTCAAGTTCCTTCC
TTTCTGAAATCTCTTCCATGGCTCCTGGTCACCTTTGGGATAAAGTCGCACTCTAAGGCC
TGGCATTCAAGGTCTGGTGGCTTCCCTCTGACCCGCACGCTTCTCTTGAAGGCTCACCGC
CCCCAGCAGCCCCAGCTCTTTCAGGTTCCCAGCCTTTCTTTGCACAAGCTCATTTTCTGC
TAGGAAATGACTCTCTCCACACTATCTCTGCCTGGCAGATGCCTCGTTTTTGAAGACACA
GCCGGAGCGCTGCCTCCTCTGTGAATCCAGGTCTTGTTTCCTCCAGGACCTAGAGGGAGA
ATTACGTCTTTCCCAGCCACGCTCCTCAGCGCGGTGTCTCCCCCGGTCACCTGTCTCTGT
GAGCTCCTCGAGGCACAGGGGCACAGACTGGGTGTTATTTGTGTCTGTGAAGCTGTGTGG
TTTGCACAGCTTCGGGGACAATGCCTGCCCTGGCAACGTTTGTTGAATGACAAACGGATG
TACCGGTGAAGTGGCTGGCCAGGCCTCACCACCTGTTGGTGGTTGATCTGAGACGAGAGC
CCAGGTCTCCTGCCTCTCTGCCAGCCCATCCGTCCATCCAACAAATGTTTGGGCCGGTGC
CAGGCACTCAGAACATAGAGCAGGACCTGGGATGGGCCACAGTGCCCTGCTCTGTGCCTC
ATCCCCACCCGACCCTCCCTTTCCAGAACAAATGCGTCCCATACTGGCCCGAGGTGGGCA
TGCAGCGTGCTTATGGCCCTACTCTGTGACCAACTGCGGGGAGCATGACACAACCGAAT
ACAAACTCCGTACCTTACAGGTCTCCCCGCTGGACAATGTGAGTGGCCCCCACGCCCTGC
CCCATTCCGGGAGTCCCTCCCTGGACTTGTTCTCCTCTCTGGTCGGGTAGGGTGAGATGG
ATGAGGTGTTCCGAGAGAGGAGGGGGCACTGACCCTATGTCCTCGGCTTAGGGAGACCTG

ATTCGGGAGATCTGGCATTACCAGTACCTGAGCTGGCCCGACCATGGGGTCCCCAGTGAG
CCTGGGGGTGTCCTCAGCTTCCTGGACCAGATCAACCAGCGGCAGGAAAGTCTGCCTCAC
GCAGGGCCCATCATCGTGCACTGCAGGTGAGGATGATAATCCTGATGGTAGTAGTGACAG
CTGAGAAGTAAATACTGCTAAGTGCCATGAGCTGTTATAAGCAATATAAACGTTAGCTCG
CACATTGAGTGCCCTCCGCTCACCCCCGGCTTCTCCTGGGTCCCCTCATGGCTCCAGAAC
CCTGGGTGGATCGTGGCTGGAACCAGCCCCACTTTGGCCCTCTGCCTGTGGGTATCTTCC
TCAGAGCCCTCTCCGGATGTACCATCTCGCCCAACCCTGCCAAATACAGAGGAGGAGCCC
GGGACCCAGTTGCTGGCCAGGCCCAAGCTAGTCAGGGCAAGGCCGGGCAGGCACCCACAG
TAGGCCTGTGTCCCGGCTGCTCCGCTTTCTCTCGAGGTCCCATTCTGTTGGTTTCTTCTC
CCAGGAACATCTATGAGGCATGTGCTCCCCATTCCTCCTCTTTTTCCATCGGTAGCCGCA
GGGCTTCGGCTTCTTCCTGACTCTGCCCTCTCTCCCAGCTTCCCCAGGCAGTGCCCCATC
CTGGCCCCCAGGGCTGTGTGGGGATGGGTGATGCTTCTTTGGGGCTGCACATAACTCCTC
TGTCTATCTACCCGCATGTTTGTGATCAGGAGACCTCTGGTAAGGTGCAGAGGTGGGGGC
TGCAAGGAGGAGCAGGGGTTCCACAGGTGAGCCCACTGAGCTGGCCTGGCCTGGGTGGAT
GAGAGGCAGTGGGTGCAGGGCCCCTCCGCTTACCAGCTGTGTGGTCTTGGACAAATTACT
TAACTTTTCTAACCCTCAGCTTCCTCATCTGTAAAATCAGGATCTCAGGGTTGTCGTGAG
AACTCAATGAGACCCTATCGTTGTGGCTGGAATTCCGTCAGCCCTCAAAAACTGGGCGCT
GTTACTAGTTTAGTAACTCACATCAGGCAGAGAATAGGGGAATGGGAACCTGCCTTGCCC
CGGTCCCTTCCCACTCCCTCCGTGGACCCCAGGCCTGCGACGGCCTCTGGCTTCCTCCTC
TTCCCCCAGCAGCTGTTTGTCCTGGGACAGGGCAAGTCGGCTGAATCTAGAGGTGCCCCC
GATGGGCTGTCCGGGGACGCGGCTCTGTCCTGTGCTCTCTCAGGGACAGGCCCATCCCCG
AGAGCTACCCTCCTGCTCACCCGCCACACACACATTCACACACTTCTTGAAAGCCCCATG
GCCTTTATTTAGACGTTACAGGAAGGAAGTGGGTGTGGGGGGTTATTTTTGACAATCTGG

FIG. 8
(continued)

GTTTGAAATTAGACAGCGCGACTCAGGGCATCAGCTTGCTGGGCTCAGCTGAGGGTGGGC
CTGGGGTCTCCCTGAGGTCTGTTTGCCCAGGGCTGGGAAAGGAGAGAAACTTCCTACTGC
ACTGCTCCCCTGAGTCCCCTGACCCTGTGCCCCCGCACCCTGCTGTCTCAGGGCTATCCT
TTCCCTGACGTCAGGGTTTGAAGGAAAAGGGAAGTGAAGCCATGCTGAGAGACGCTCCAT
AACTCCTTCAGGGAGAGGCGGGGAGGGCTCAGGGTACCTGGGAGCCGGCAGGACAGTGGT
GGGATTTGGGGTCCCAGGTCTTCCGGGGTGGGGGCAGCCACTCACTAGGAGTGAGGAGT
CGGCGCGAGGAGTGGAGGAGGGAAGGATGGTGGCAGCTGGGGAGCCAGCGTCAGCACCGC
AGAGCCCGAGGTGGAGCGTGTCCATGCAGAGCTGGGCAAACCTCCATCATCACTTGCCCG
GTGACCCTGGGCACATTCCCTCCCATCACTGGAGGCTCAGGCTGCTCCTGTGGTGCCTGG
GGCTGGAGCTGAGCGCTGGGTACCCCCCTTCCCGGGGAGGGCTTGACTGGCCTCTGATGG
CACCCCCGTCTTTCCCCAGCGCCGGCATCGGCCGCACAGGCACCATCATTGTCATCGACA
TGCTCATGGAGAACATCTCCACCAAGGGTGAGGGGCACCTGGGGGTTTGGGGGTGGGGGG
TGAGCAGCCCCTCGGTGTCCGCCTATGCCTGGACCTGAGGTTTGACTGCCCCCCACCCAG
GCCTGGACTGTGACATTGACATCCAGAAGACCATCCAGATGGTGCGGGCGCAGCGCTCGG
GCATGGTGCAGACGGAGGCGCAGTACAAGTTCATCTACGTGGCCATCGCCCAGTTCATTG
AAACCACTAAGAAGAAGCTGGAGGTCCTGCAGGTGCGTGCAGAGCAGGGCCTGGGGGGGG
GGGGGGCTGCAGTGCAGGATGGGTGCCACCTGGCCCTGCTGGGACCACCACCTTCCCACT
GTCCCTCTGCCCACAGTCGCAGAAGGGCCAGGAGTCGGAGTACGGGAACATCACCTATCC
CCCAGCCATGAAGAATGCCCATGCCAAGGCCTCCCGCACCTCGTCCAAGTGAGTGGCCCT
GACTGCCACTGCCCGGCATCCACCCCTTTGTCCTGCCCAGCCCGATCCTCACTTTCTGGA
GAGGACAAGTGTTGCAGCTGGGGGACCTGGCTTCAAGTTCAGGCTTGGTTCTCACCCCT
TCTGTTCATAAGCATTTCCTGAGTGCCCACACGTGTGGGCCTCTGCTAGGTACCAGCAGC
GCACTCGTGTATGAGATGTAGCCTCTGTCCTCTAGGAGCTTGGAGTCTAGTGCAGGGACC
GTGGCTGCGTCACCTGTGAGACGGGGTGGCCAGAGGGGACTGCCAGTGCCGGTCCCCCT

GTGCTGTCTCCTGACCTGCACCAACTGCCTGTACTTGCCCCCCTGCACCCGGCTGCAGAC
ACAAGGAGGATGTGTATGAGAACCTGCACACTAAGAACAAGAGGGAGGAGAAAGTGAAGA
AGCAGCGGTCAGCAGACAAGGAGAAGAGCAAGGGTTCCCTCAAGAGGAAGTGAGCGGTGC
TGTCCTCAGGTGGCCATGGTACAGCTCTTCTGCCTGGGTGTCCTCCCTGCCCTGCCCTGT
GTCCTTGGCTCCACTGCCTTCCCTGGGTGGATGGGGTGGCCGCAGCCTCATTCTGTGCTT
CCCAGCTGCCCCAGACCCTCTTGTTCCACCTCCAGGTTCCAGCTACCCTCTCACTCCCTC
ACTCCCTTCTCTTGGCAGCCTCAGCCCTGACCCTGTGGAAGCATTTCGCGATGGACAGAC
TCACAACCTGAACCTAGGAGTGCCCCATTCTTTTGTAATTTAAATGGCTGCATCCCCCCC
ACCTCTCCCTGACCCTGTATATAGCCCAGCCAGGCCCCAGGCAGGGCCAACCCTTCTCCT
CTTGTAAATAAAGCCCTGGGATCACTGTGTGTCGCCTCTGAGCCCTTTGCTTGCCCAGTG
AGTGGGCGGCCAGAGGGCAGGGCAGGATGGGTAACTGTGTGTGCCTCCGTGCGTGCCTCG
CGTGAAAGCTCCGCCTTCCGTCAGACGGACGTGGGTCGGGACTCCGCCTCGCACGTGGGA
GGGTGACCGTGGGTGAAGCTCCCCAGTCTCCTTCTTTAAAATGGAGGGCGATCATAACAG
GGTGGTTGTGAAAAGCACCGAGATGACGGCTGACGATAAGACGGGCACAGTGACTCATCA
CACGCTTGCCATGTGCCCAGGCACTAAAAGACTACACACGTTAGTTCAGTCTAGGCACTT
CTGTCATTCTCATTTTACCGTGGCGGAAACTGAGGGACAGAAAAACTAAGTAACTTGGTC
ACTTGCCCAAGGTCACAGGGCTATGGAACAGTGAGGCTGGGATTCGAACCCAGGCTGTCT
GACCCCAGAGCCCACACTCCTTACCCTGGAGTTGCAGCTGGGGCCACCCTCAGGGGGGCC
CTGATCACACTCCCCTGATGCTGAGTTCCAGATCTGAACTAAGAAGAGTAGTTAACAGCC
GGAAGCGCAGACCTGAGGCCAGCCCGGCT

MVRWFHRDLSGLDAETLLKGRGVHGSFLARPSRKNQGDFSLSVRVGDQVTHIRIQNSGDF
YDLYGGEKFATLTELVEYYTQQQGVLQDRDGTIIHLKYPLNCSDPTSERWYHGHMSGGQA
ETLLQAKGEPWTFLVRESLSQPGDFVLSVLSDQPKAGPGSPLRVTHIKVMCEGGRYTVGG
LETFDSLTDLVEHFKKTGIEEASGAFVYLRQPYYATRVNAADIENRVLELNKKQESEDTA
KAGFWEEFESLQKQEVKNLHQRLEGQRPENKGKNRYKNILPFDHSRVILQGRDSNIPGSD
YINANYIKNQLLGPDENAKTYIASQGCLEATVNDFWQMAWQENSRVIVMTTREVEKGRNK
CVPYWPEVGMQRAYGPYSVTNCGEHDTTEYKLRTLQVSPLDNGDLIREIWHYQYLSWPDH
GVPSEPGGVLSFLDQINQRQESLPHAGPIIVHCSAGIGRTGTIIVIDMLMENISTKGLDC
DIDIQKTIQMVRAQRSGMVQTEAQYKFIYVAIAQFIETTKKKLEVLQSQKGQESEYGNIT
YPPAMKNAHAKASRTSSKSLESSAGTVAASPVRRGGQRGLPVPGPPVLSPDLHQLPVLAP
LHPAADTRRMCMRTCTLRTRGRRK

SEQ ID NO: 59

FIG. 9

AGGCTCAAGCAATCCTCTCACCTCAGCCTCCCGAGTAGCTGGGACTACAGGCGCGCGCCA
CCACGCCCGGCTAATTTTTGTATTTTTTGTAGAGATGGGATTTCACTATTTTGCCCGGGC
TGGTTCCCAACTCCTGGACTCAAGCGATTCGCCCGCCTCAGCCTCCCAAAGGGAAGTGCT
GGGATTTCAGGCGTGTGCCACCGCTCCCACCCCAAAGTAGTATTTATTGTAATTATTATT
ATTATTTTGAGACGGAGTCTCGCTCTATTGCCAGGCTGGAGTGCAGTGGCGCGATCTCGG
CTCAATGCAACCTCTGCCTCCCGGGTTCAAGCGATTCTCCTGCTTCAGACTCCCAAGCAG
CTGGGACTACAGGCGCCCCCCACCACGCCAGGCTAATTCTTGAATTTTTAGTGGAGACGG
GGTTTCACCATGTTGGCCAGGATGGTCTCGATCTCTTGACCTCGTGATCCGCCCACCTCG
GCCTCCCAAAGTGCTGGGATTACAGGCGTGAGCCACCGCGCCCAGCCTATTATTATTTTT
TTAGGCAGTGTCTTGCCCTGTCGCTCAGGGTGTAGTGCAGTGGCGTGATCACGACTCACT
GCAGCCCCGACTTCTCGGGCTTAAGTTATCTTCCCGCCGCAGCCTCCACGCCCGGTTAGT
TTTTTGCATTTTTTGTAGAGATGAGGTCTTGCTTTTTTGCCCAGGCTGGCCTCGAACTCC
TTGGCTTAAGCGAACCTCTTGCCGCAGCCTCCCAAAGTGTTGGGATTACGGGCGTGAACC
ACCGCGCCCAGCCTACTATCTTTATCTTACAGAAAGAAAAGAATGGAGGAAACCGAGGCT
CGGAGACAGTAGGTAATTTCCCCAAGGTTCCACAGCTAATGAGTGGAGCGGCGATTTGTG
GAACGAAATGAATGAAATCGATGTGGCAGCGGGCCCGGACGGGTCGGTGGCGTAGACGCG
GAGCGCGCAGCTCACACCTGGCGGCCGCGGTTTCCAGGAGGAAGCAAGGATGCTTTGGAC
ACTGTGCGTGGCGCCTCCGCGGAGCCCCCGCGCTGCCATTCCCGGCCGTCGCTCGGTCCT
CCGCTGACGGGAAGCAGGAAGTGGCGGCGGGCGTCGCGAGCGGTGACATCACGGGGGCGA
CGGCGGCGAAGGCGGGGGCGGAGGAGGAGCGAGCCGGGCCGGGGGGCAGCTGCACAGTC
TCCGGGATCCCCAGGCCTGGAGGGGGGTCTGTGCGCGGCCGGCTGGCTCTGCCCCGCGTC
CGGTCCCGAGCGGGCCTCCCTCGGGCCAGCCCGATGTGACCGAGCCCAGCGGAGCCTGAG
CAAGGAGCGGGTCCGTCGCGGAGCCGGAGGGCGGGAGGAACATGACATCGCGGAGGTGAG
GAGCCCCGAGGGGCCCGGCGCGGGCCTCGGCCCGGCCACCGCCGCGTTCGGTTAGCCCCG
TCCGGAAGGGGGCGCCCCGGCCGGGCTTCGGGCTCCCGCCCCGGGTCGGGGTTGGGGGCC
GGTTCCCTCCTCGTCCCCTCGCCCTCCAGGGGCCGGGGGCCGGCCCCACCGCGCCCCCAC
CCCTCGGGTCCCCATTCATTTCCTGCCTCCCCGAGTTCCGGCTGCGGCAGCCCCGGGGAT
GCCCGTCAGGCCCGGGGCAGGTAGAGCCGCCGAGGGAACCACGGGTGCCAGCGGCCAGGC
TCAGCGCCGCATTCCTGACCCATTGCCTCATGAGAATTGCCTCATGGTGATTCCGAAATA
ACCCTGCTCACTTGGGGAGGCTCCTTGGGACACGAGAGGGGAGTTGCGCGGGGCCGGGCC
CCCAGTGGTCTAGTCGTTCTGGCTCACTGTGCCACTTTCGTGCATTTGGGGACTTCACGC
AGGACCCCTGACCCTTTTATATGCCTCTTTGTGTCTTCTTTTCCTCCTACCCCTCACGTG
CCAGAAATGGAAAAACTGACTGTATCTGCAGCCACTAGAAGTATTTCCTTCCTCTGCGAT
CTTCGCTTTGGGAGATGGAAAGGAAGGGAGCCGCATCTCGTTATTTAATCCTTCACTGCA
ACCTTAACAGTCAGGTCACTTTACTGGTACCCGTTTTATGGATGAGGAAACCGAGGCCCA

FIG. 10

GAAGCAACATGCTAGTAAATGACAAGATTTGAAACTTAGGAGGATTAGTGAGTTAATGAG
ATCCTTTGAAAGGTCAGGGTAATACTACTACTAATAGCTAACATTTGCTTAGTTCTGACC
ACAGCCCTATCAGATGGCTACTATTATCCCCATTGTAAAGATGAGTAAACCGAGTTTCAG
AGGTTAAGTAAATTGCCTAACCTCACAGCTAGTAGGTGGTGGAGACAGAATCCCTACTTT
TAATCACTATGTTGCTTCTATTATTTTGTAACTATTGCTAACCATTTGTAAGCCTTAATT
TTGTTGTCAAACAGTAGTGTGACCTGTTGTTTTCAGATAGTGATCCTGCTATTTTGTATA
GTCACTCTATATACCACTCACACTTAAGACCCATTGTCTATTCTTTTCCATGATTGTTCA
ATTATGGTCACTGTCTCAGACATTTAAAAAACGATTCAAGCTATTGAGGCTATTTGAATG
AGATTTTCTTTTCTTTTTTTCTTTTTTTTTTTGGAGACGGAGGCTCACTCTGTTGCCCAG
GCTGGAGTGCAGTGGCGCAATCTCGGCTCACCACAATCTCCGCCTCCTAGGTTCAAGCGA
TTCTCCTGCCTCAGCCTCCCAAGTAACTAGGACTACAGGCGCACCACTATGCCCGGCTAA
TTTTTGTATTTTTAGTAGAGACAGGGTTTCACTATGTTGGCCAGGCTGGTCTCAAACTCC
TGACCTCGTGATCCGCCCGCCTTGGCCTCCCAAAGTGCTGGAATTACAGGCGTGAGCCAC
CGTACCCAGCCTGAATGAGATTTTTCAAAATATTAGGAATGTCTCCTCCAAACACACCTG
GCATGTTATTCATACATGGATCTGGAATTTAAAAAGGGGAGAAAAAGAAAACTGAGAACT
CGTAGGAAGTGAGTGACTTGGACAGGTCGGTTGGCAAGTGCTTACAGATCTGGGTAATAT
ATAACTGCATTTCAACAGAACAGTGTATAGCCTCAAATGTTCTAATTCTTTAGGGAGCTT
TTAAATAAACAGTTGTCTATTCTTTAATCTGTCAAATAGTCATTGAGCCTTTTGTTCCTG
GTGTCTGCTCTTCCAGACAAGTAAGGATCTGCTGCTTTAGGAGACATCAGACGGGGCTGG
GGGTTGGGAAAAGGTCTGGGTAGTAATAGACCCTACATTGTCCAGTTTGTTCATTTAGAA
GCATAGAAGTGTGGGCATAGTCAAAGTAGCAAGTGGTAAAGATGACAGTTTGAAATGGAG
TAATTCCTTCTCCCCTCCAGCCCTGGTATTATGCACCACCCAAAAAGCCGGGTTATGAAC
ATAATACACATAATTTTGAATGATTCATTATTTTTTGGATTATAAGCCTGTTTTATTTGT
TAACCAGCCTTAATGAGGTATAAATGACATGCAATTAATTGCATATATTTAAATGTACAA
TTTGATCAGTTTTGACATACATATACACTTGGGAAACCACCACCATAGTCAAGATAATGA
ACACATCTATCACCCCTGGTAATTTTGCCTTATGTTCTTTATAATCCTTCCTTTGTTCTT
AGGCAGCCACTATTCTGCTTTCTGTCACTATGTATTAGTTTGCATTTCCTAGAATTTTAT
TTTTAAAAATTTTAAAATTGTTTGAATAGAGATGGGGTCTCACTGTGTTGCCCAGGGCAG
TCTCAAACTCCTGGGTTCAAGTGATCCTCTCACCTTGGCCTCCTGAAGTGTTGGGATTAT
AGGCATGAGACACCCTGCCCAGCCCTAGAATTTTATTATTATTGTTATTATTGTGTTTTT
TTGAGATAGGGTCTCACTTTGTTGCCCAGGCTGGAGTGCAGTGGTGCAATCACTGCAGCC
TTGTTTTCCTAGGCTCAATCCATCCCCCCTCCTCAGCTTTCCGGTTACTGGGGCTACAGG
TGTGCACCACCACACCCGGCTAATTTTTGTATTTTTTTATAGAGACAGGGTTTTGCCATG
TTGGCCAGGCTGGTCTCAAACTCCCGGGCTCAAGCGATCTTCCTGCCTCGGCCTCCCAAA
GTGCTGGGATTACAGGCATGAGCTATTGCGTCCCGCCTTCAAATTACTTTAACCTAGTAT

FIG. 10
*(continued)*

TAATTCATTCAACAGGAAGTTAATGAGCCAGGCAGGATAAAGCAGTAAGATAGGAAAATA
TTGCTATTTTCATGGCTGAGAGAGAGCAGACAAACACATGACTAAATAGGGCAATTTCAG
GTAGTAATAAATTCTAGGAGGGAAAAAATCCCACAGAAATGTGAGGATGGGAGAATGCAG
TTAGTTTTGATAGGTGGTTTAGAGAAGGTGATCGTGTGAGCTGACACCTGAATGACAATT
AGTAGTCTGAATTTTGTTTTGCTTAATTATCAAAATAACTCCTCTTGGGTTCGGCTTTTA
TATGCATCCAGTAATTAAAATGTAAGTATATTCAATGTACTGATATCTCTCAGCATCATA
GGTAGGAAAACTAAGGCATTCAGCAATTAAGTGACTCCTCCCTTGATCATGTAGCAGTGA
TAGTACTGGATTTAGATTTTGAGGTTGCTTCTCTGCCCTTTTCTGCCTTTGTGAAACCAA
CAAAGCTGCCTGTATTTTCCAACTCTTCCTTCAGCATGTGGTACCTCCTTTACATCTGTT
TTTGTTGCTCTGAAATCCATACGCGACGATGAGCTGAGAGGGGCAGAAAATTGAGCTTGT
TCTGAGACTGGAGGCTTTTGGTTTATCTCTTGCAGGTCAAGTACATTTTGTCCTGGGCTC
TCCCTGGTGGCCACGTTTGTTTATCTCCTGCGGGAGTAAATAAACTTGCCTTGCTGAAAA
ATAACAGTTCTGTGTCTTTGCAGTGGAAACTGGGATGTCTTTATTAACGTTAGGTCCTGA
TGTAAGGCCAAGTTTTTGGTTAGAGTTGCTCAAGTGCAGAGGCCACTGCTAAGATGACTT
ACCCCTCGTGTCCATGGTCAATGTGGAGACTGTTATGAGTGGCACATGATGCTGGAAAAG
CAGAGCCAACTCATGTTTGTAATTGTCCTAGCAGGCCGTGGTGTACTTTGTTAGGCAGCC
ACAGAACAATAGAGAAACTCAGCTTATTCCCCTTCCCTCTGGGAAACACAGACAGTACTT
GCCATCCAACGCCAATGTTTTTAAGGAAGAAAGAGGCAAAAAGTGATGTTGGCAAGGTCT
CTGGGAGTTGTGGACCCCAACCAAGGATTGGAGACCCTGAAATGGATTCAGATGCCCTAA
AATGCAGCCCAGTTCATTACTATGAATTTTGGAGGACTTTGTGCCTTGAGCAAATGTGTA
TATGTGACGCTCTTTGACAACACTGAAATAGGAAAAATACTATCCATGTTCGCGAGGAGC
ACTGAATTTAGAGAGGGAGACAGACTTTTATGCCAGCATCAAATGAATTTGATAAAGCTA
GTACCAAAATGAAATTTGAAATTTTTTTTTTTGAAATAGAGTCTTACTCAGTCACCCAG
GCTGGAGTGCAGTGATACAATATTGGCTCACTGCAACCTCCACCTCTTGGGTTCAAACAA
TTCTTGTGCCTCAGTCTCCTGAGTAGCTGGGATTACAGGTGCGTGCCACCATGTCTGGCT
AATTTTTATATTTTTAGTAGGGATGGGGTTTCACCATGTTGGCCAGGCCGGTCTTGAACT
CCTGGCCTCAAGTGATCTGCCCACCTTGGCCTTCCAAAGTGCTGGGATTATAGGCATGAG
CTACCACACAAGCCTGAAATTTGAAATGTATTGGTATAGAATATACTGTTTAGAATGTAT
GTGTATATATGTATATTTGTATACTCATATAAACACAAATACACATTGTATGTGTTTCTG
TAATATGTATATCTGTCTACACATACATGTATATACACACATACAATGTCTTTTTTTTTT
TTTTTTTTTTTGAGACAGGGTCTTACCCTGTTGCCCAGGCTGGAGACTGCAGTGGCATA
ATCTTGGCTCACTGCAGCCTCGACCTCCTGGGCTCAAGTGATCCTCCCATCTCAGCCTCC
TGAGTAGCTGGGACTGACTACAGGCACGTGGCATCAAACTTGTCCAATTTTTCTATTTTT
TTGTAGAGTTAGGGTCTTGCTCTGTTGCCCAGGCTGGTCTCAAATTCCTGGGCTCAAGCT
GTCTGCCTGCCTCGGCCTTCCAAAGTACTAGGATTACAGATGTGAACCACTGTACCTGGC

FIG. 10
*(continued)*

CTTTACAATGTCTATTTTAAAGATAATGGTTCAAGTTTTTATCATCCCACTGGCCTACTC
TAATGAAACATCTATCCATTCATTGAAGAATTATTTATGGTGGGATAACTCTGTGCCAGG
TACCGTGCTAGGCATTGAGTATTCCAGGTTTTAGGAAACAGCACATGCAAAAGTGCTGAA
GTGGGAGAAGATCTCGGAGTGATTGAAGGCTAGGAGAGAGCAAGTGTGGGAGCTGTGAGG
CTGGGAAGGTGGGAGGTAGGTGGGAGCAGACCACATAGGGATTCTTAATGTCTTTAGTGT
CATGTGGACCATGGAGAGGAGTGTAGATTGTATTTTTAGAGCAATGCAAAATCATAGAAG
GATGTGATCGGGGGAGTGGCATGAGCTGATCTATTTAAAAATATTTCTCTGGCTGCTGTG
AAGGAAGGATTGTAGGAGGCAGGAGTAGATTCAGGGAGATGAGACAAGTGATGAGAGAGG
CTTTGAACTTGGGTAAAAGTAGTTTGTGGAAAGTCTTTTTTGGAGGTAGTTTTTGTTTAT
TGCCTTGTCATCAAAGCAGAGATGCTGACCAATGAAACTCCATGAGAAAATAGTGATTTA
TAAAGACATATCTATGCACTGCCATTAAAAAGCTGCTTGGAAAAAAAGGATAAAAAGCTG
CTTTAACAACTTTTTTTTTTGAGATGGGGTCTTACTCTGTCACCCAGGCTCACGACCTCA
GCTCACTGCAACCTCTGCCTCCCAGGCTCAAGCATTCTCCCACCTCAGCCTCCCGAGTGG
CTGGGACTGCAGGCACACGCCACCATGTCAGGCTAATTGTGTGTGTGTGTGTGTGTGTGT
ATGTGTGTGTGTGTGTGTGTGTGTGTGTGCTGGGACTGCAGGCACACACCACCATGTCAG
GCTAATTGTGTGTGTGTGTGTGTGTGTGTGTGTGTGTGTGTGTGTGTGTGTGTGTGTGTA
TGTAGAGATGGGGTTTTGCCATGTTGCCCAGGCTGGTCTCAAAATGTTGCCCAGGCTGGT
CTCAAACTCCTGAGCTCAGGTGATCCACCCGCCTCGGCCTCCAAAGTGCTGGAGATTACA
GACGTGAGCCACTGTGCCCACCTAACAACTTTAAAAAAATTTTGACATTTAGTAGGATAT
TTATTGCATTATTGTTGAGATGGCAAAATATTGGAGACAACTGAAATGTTCATCAGTGGG
GGGGGCTAGTTAAATGAAATACAGTGTAGCATGCATTAGAACACTTTTCAAGAATTTAAC
TTTTTTTGTAGCCTTTTACTTATAATGCTTGTCCCTATTGATGCCTTTTTTTTCAGCATG
ACTTACTCTTTTACTATAGGATATTAAAATTTAATTAGATTAGAAATGAGGAATATTCTT
GTAATCTGTAGAAAGTAACAAACTATAAACTTATTCCCCAAGAACAAATATAATAATTTT
TCTGGAGTAGCAGGTAAGAAAGATATAAATTTATATGTATACAAGAAACTGAAATTAGAC
TTTATACATTTAAAGGTTACAAGTGCAGTTTTATTACATGAATGTATTATCCAGCATTGA
AGTCTGGGCTTTTAGTGTAACCAGCACCTGAATAACATACATTGTACCCATTAAGTAATT
TCTCATCCCTCAAACCCCTCCCACCCTGAAATTAGACTTTGGATCCCTAGTTTAAATTCC
ACCCCTCTCTTTTTTTGAGACAAGGTCTCACTCTGTCACCCAGGCTGGAGGGCAATGTTG
CAATGATAGCTTACTGTAGCCTCAACCTCCTGGGCTCAAGGGATACACCCTCCTCAGCCT
CCTGAGTAGCTGGAACTGCAGGCGTGCACCACCACATTCAGCTAATTTTTTGATTTTTTT
ATAGAGATGAGGTCGGAACTCCTGGGCTCAAGCGATTCTCCCCAAGTGCTGGGGTTACAC
ACATGGGCCACTGCCCCCAGCCTAAACCTCCTTTCTCAGTATAGCAGCCTTGAGATGAAG
TTCCTGAAATTACTGGCCAGCTTGACTGTTTCCCCACATCACTGGAGGAGGGGGATGCAT
AGATAAAACAAAATATTCAGCATCATTGTATTTTCTTTTTTGTTTCATCAGCATCTTTTTT

FIG. 10
*(continued)*

TAAAACTCACTTGACATAAGTCCCTAGCCTCAAAGAGTAAAGCCTTTGCAGAATCTGCAT
TCAGATTTCGGGTGTGATTTCCTGACAGATAGTTCAGGTTTGTAAACTCTTTTTTTTTTC
TTTGAGACAGAGTTTCACTCTTGTAGCGCAGGCTGGAGTGCAGTGGCACCATCTTGCCTC
ACTGCAACTTCTGCCCCCTTGATTCACGCGATTCTCCTGCCTCAGCCTCCTGAGTAGCTG
GGATTACAGGCATGCGCCACCACACCTGGGTAATTTTTGTATTTTTAGTAGAGATGGGGT
TTCACCATGTTGGCCAGGCTGGTTTTGAACTCCTGACTTCAGGTGATCTACCTGCCTCAG
CCTCCCAAAGTGATGGGATTACAGGTGTGAGCCACCGCAGCCGGCCAAAACTTTGTTTTT
TTTCCTCTTTTTGTTGCTGAGAAATGTAAACTCTTACAGACACAAATTATGTCTCCCATT
TTTTAAAACCCACTCAACACAGGGGTCATGTGTAATAGGCCCTGGAGCTTATTTTAGACA
TTGATTTGAGGCTCTTTTCCCCAAGTGCTGGTTTGTGTGTGTGTGTATGTGTGTGTAAGT
CTTTCTATGAGATGAGTGGTACCTACCTGGGCTGTGTGATCTTTTTTATTTTATTTATTT
TATTTTTGTAGATACGAGGTCTCACTATGTTGCTCAGGCTGGTCTTGAACTCTGGGGCTC
AACCTATCCTCCCTCCTTGGCCTCCTAGAGTGCTGAGATTACAGGTGTGAGCCACTGCAC
CTGGCCAGCGATCCTTAATAAATATAGATAATGGCCGGGCGTGGTGGCTCACACCTATAA
TACCAGTACTTTGAGGGGCCGAGGCTGGCAGGTCACCTGAGCTGAGGAGTTTGAGACCAG
CCTGGGTAACGTGGGTGAAACCCTGTCTCTACAGAAAATAGAAAAATTAGCCAGGTGTGG
TGGTGCATGCCTGTAGTCACAGCTACTTGGGAGGTTGAGACAGGAGAATTGCTTGAACCT
GGAAGGTGGAGGTTGCAGTGAGCCGAGATCGTGTCTTTGAACTCCAGCCTGGGTGACAGA
GTGAGACCTTGTCTCAAAAAAAAATATAGATATAGGCTGGGCGTGGTGGCTCACACCTGT
AATCCCAGCACTTTGGGAGGCCGAGGCGGGTGGATCAGGAGGTCAGGAGATCGAGACCAT
CCTAGCTAACATGGTGAAACCCTGTCTCTACTAAAAATACAAACAATTAGCCAGGCCTGG
TGGTGGGTGCCTGTAGTCCCAGCTACTCGGGAGGCTGAGGCAGGAGAATGGCGTGAACCC
GGGAGGTGGAGGTTGCAGTGAGCCGAGACTGTGCCACTGCCCTCCAGCCTGGGCGACAGA
GCGAGACTCTGTCTCAAAAAAAAAAAATCTATATATCTATATATCTATATCTATATAGAT
ATAGATATAGATAATGCCAGATGATGGCTGGTTAGAAGGGATTGTCAGGGGCTGGCAGGT
TTTGCAGGTGTTAGAATGAGCAAGATGAGGAGAAGGATGCTTACTTCCCTCTCCTTGTAA
CTCTCTACCCCCTCCCCTCAGTGTTTTTTATTTTTATTTTTATTTATTTATTTTTTTTG
AGACAAGGTCTTGCTCTGTCACCCACACTGGATTGCAGTGATGCAATCATAGCTCATTGA
AGCCCAAACTCCTGGGCTCAAGTGATCCTCTTGCCTCAGCCTCCCAAGTAACTGGGACCA
CAGGTGCGTACAACTATGCCCAGTTAAGTTTTTCATTTTTTATACAGACGGGGTCTTGCT
ATGCTGTCCAGGCTGGACTTGCACTTCTGGCTTCAAGTGATTCTCTTGCCTCAGTTTCCC
AAAGTGCTGGCATTATGGGCATAAGCCACTGTGCCTAGCCCATCAGTGTCTTTTTATCCT
TTACTCCTATCAAAATTCATTCACTCAGCAGCCATTGATCAAGTGCCTACTATATACATG
TTGAGGACTGGAAATTTATTTGTCTCTTCTCATCTTATCTGGACCCTCTGTGTTAATTGT
AATTAACTGTAATCATTCTGTATTAATTGTAATAAACTTGTTGATAAACTCAAATGAGGC

FIG. 10 *(continued)*

CATACCGTTTTGCCACTTCCCCTCCTTCCAGGTTATATGGATGTACTTACATTGCAGGTT
TCATTTGTTGGTTCAGTTTTTAAACTAAGCCCTATTGTGTCAAATTATGCTAGGTGTGAG
ATGGGGAGTTCAAGCTGTGTGTTGTCTTTTTTTTTTTTTTTTTTTTGCCTCACTTACTA
ATATACAAGCGCTTATAACCTTTGAGGCTGGCCCTATACATTAAGATTTTTATTAATTCC
ACTGTTCTTTATCTTCTCTTACTAAGTTCTCAGGGTCGAATGAACTCTAACTGCTCCTTG
CTAGTGATAAGCAAGTTGCAAATTACAGAATTGTCAGTGATTGAATACACGTATTAAACC
TGTAACTGGGAAGCATTTTTGGTAATTATGAATACTTTTGGAAAAAAAAAAGCTATGGAA
GGAAAGTTTAAAATCTACGAAAGCTCAAGTAGATGGTCATGGAATAGCTATTTCAATTTC
TAACTATATATTACTTATTTATTTATTTATTTTTGAGACGGAGTTTAGCTCTTGTTGCCC
AGGCTGGAGTGTAATGGCGTGATCTCAGCTCACTGCAACCTCCACCTCCCGGGTTCAAGC
TATTCTCCTGCCTCAGCCTCCCGAGTAGCTGGGATTATAGACATGTGCCACCACGCCAGG
CTAATTTTGTATTTTTAGTAGAGACGGGGTTTCTCCACATTGGTCAGGCTGGTCTCGAAC
TCCCAACCTCAGCTGATCCGCCTGCCTCGGCCTCCCAAAGTGCTGGGATTACAGGCGTGA
GCCACCGCGTCCGGCCTCTTAACTATTGTTTGAAATAATGTAGAGACAGCTCCAGAGCCA
TGAAGAAGTGTATGAAGAAGCAGTGTTAGCTTAAATGACATACATGTCACAATTGCCTAT
GTGAAACTATCATAATTATGCATGAGAAGTATCTATCCTGCATAACCTCCACCAATAATA
ATAATGTTAATAATAGTGAAAACTAATGTTTATTAAGTCCTTACTGTCTCCAGCCTCTGT
GCTAAATACTGGTTACTAAGTTTCCCTGAAAATACTATTCTCATCTGTTTGTTCTTAATA
ACAGGATAGCATAATTGTAAGTTGTAAATGAAATAATACAGTTTATGTAATAAAAGGGTA
AAAGAGAAGACCACCTACCTTATCTTCTGTTGCTGATCTGGATGGATGTAGGTGGTGTTT
ACCTAGTTTCACCTTTGGCAGTTGAAACTACTTTTTTTTTTTTTTTTTTTTTTTTAAGA
GACAGGGTGGGCCAGGCGCAGTGGCTCACGCCTGTAATCCCCGCACTTTGGGAGGCTGAG
GCGGACAGATCACTTGAGGTCAGAAGTTCGAGACCAGCCTGGCCAACATGGTGAAACCCT
GTCTCTACTAAAAATACAGAAAAATTAACTGGGTGTGGTGGTACACACCTGTAATTCCAG
CTACGTGGGAGGCTGAAGCAGGAGAATCGCTTGAACCCGGGAGTGGAGGTTGCAGTGAGC
TGAGATTGTGCCACTGCACTCCAGCCTGGGTGACAGAGCAGGACTCCGTCTCAAAAAAAA
AAACAACAACAAAAAAAGAAATTTTTAGAAATATGAGATGACAGCAAGAATGAGGGTATT
AAAAAGAAATTTTTAGAACTAAATAGCAGAATGTAATGGTGAAAAGTTTGATTTCTCAAG
TCTGCTTTGCACACAGGCATGTGGCAAACATTCAGTAAGTATAGCTGTAATTTTAACCAG
CTGTAATGTATAATAGCCAACATATCACATTTTTCTTTTTTCTTTTTTGAGACAGAGTCT
TGCTCTGTTGCCCAGGCTGGAGTGCAGTGGCACCATCTCGGCTCACTGCAACCTCTGCCT
CCTGAGTTCAAGTGATTCTTGTGCCTCAGCCTCTCAAGTAGCTGGGATTACAGGTGTGTG
CCACCACACTCGGCTATTTTTTGCATTTTTAGTAGAGATGGGGCTGGTCTTGAACTCCCA
GCCTCAGGTGATCTGCCTGCCTCAGCCTCCCAAAGTGCTGAGATTACAGGTGTGAGCCAC
AGCGCCTGGCCATATATTGCTTTTTTCTTATTATCAGAGCCAGTTCATAATTGTGGAAAA

FIG. 10
*(continued)*

ATAGTGTTTGTAACAATGTAAGTATGGATAAATCATCTTTTTAATTTTGTGATTCATATA
GGTTTGTTGTTGTTGTTGTTGTTTTGTTTTTATCTTGAGACAGAGTCTTGGTCTGTCACC
CAGGCTGGAGTGTAATGGCACAACCATGGCTCACTGCAGCCTCAGATGCCTGGGTTCAAG
CAATCCTCCCGTCTCAGCCTCTAGAGTAGATGGGACCACAGGTGTGGGCCACCATGCCTG
GGTAATTACAAAACTTTTTTTTTTTTTCTAGAGATGAGGTCTCACTATGTTGCCCAGGC
TGGTCTCAAACCTTTGACCTCGCTTCAGCCTTTAGAGTAGCTATGACTATAGGCATGTGC
CATCACCCAGCTAATTAAAATTTTTTTTCTTTTTTTTTTTGGTGGAGATGCGGTCTTACT
TTGTTACCCAGACTGCAAGTTAGTTTCAGATATCAACATTTGGTGTTTCCAAATGCACGG
GGAGGCTTTGGAGCAAGTTTTTGGCTCATATGCATAGGTGTCCTAGACATTCACTTTGCA
AATTCTTATTAAAATGACTACAGTAGCATACAGATAGGGAAAAATATCCTTGTCAGTACC
ACCGATTGGGTGAGAAGAGACTGTATATTAAAAACAATGACCATCTTTTTGCCACATAAA
TTGCTGGTGGGGCCAGTTTGAAGAGGGCTTTGTCAGCTGCCTTCTGCCTCTTCCTCTTGA
GTACGTGGAGTTGGAGTCATCCTTGACAGCCTCCTGTTGACACCACCCGGGTCACAGATG
TGAAACTGTGTGGATGTAGGAGAGAGCAGTGATGGGGCTTACCCCAAGGTTGCTCTTCCT
TCCCTCTGGCCACAAATGTTTAGTAAGGAACTGCTCTGTATTAACCATTTGCTAGGGGCT
GCAGATACGGTGGTGAAGAAATAGACATGTTCCTACTCGGGATGCTGAGGTGGGAGGATT
GCTTGAGCCCAGGAGTTGGAGCTGCAGTGAGCCATGATCACACCACTGCACTCCAGCCTG
GGGGACAGAGCGAGACCCTATCTCTAAAAAACAATAAAAGAAATAGATGTGTCCTTCACC
CTCATGGAACTGCCAGTCTAGCCTTCAACCTGGTGACTGTAGAAATGTGTGATTAGATGC
TATATTGCCATGTTGAGTGTCACCCCTGAGAAGCAGGGTTTTTTTTGAGAAGGTAGGATG
GGGGATCTGACTGTGGGACCACCAGAGGGAAAAGCACATGTAAAAGCTGCGTGTACCAAC
TGGAGGAAATCGGAGACGTGATCAGAGAACCAGAGTCAACCAGGGGCCATGCCGTACAGG
GTCCTGTTAAGATCTGTGACTTTTTTCTAAACGTTTTCTTCTGGATAACATCTAAATTTC
TAGTTCCAAATGTGAAACTCCAAGGGCGTTCTGTGCTAAACATTTTGCATGTATTAATTA
ATTTCCACCACACAACATTGCTGTGAATTAAGACAGTTTCTAAGCATGGCAAGAAACCCA
GAAATCATAATGGAAAAATCTGATAAATTTAACAATGCCAACATGAACCTCTGTAGGAAA
AAAAATACCACAGACTAAAAAGGGGGGAAAAAAACCAGAGACAAATATTTGCAACACATA
CAGTAAAGGGTAATTTTCTGGTTATATCAAGAGCTCCTACAAATCAGTAAGAAAAAAAAT
CTAATAGGAAATGAGCAACGACAAACTGACAACTCATAGAAAAGGAAACACAAGTGGTCT
GAAAACATGAAAAAGTGCTCAGTCTCACAAAGAAATGCAAACTAACATGGTACCATTTTC
CATTAATCAGATAGACAAAGATGAAAGAGTTTGGTAATGTATGTAGTATTGGCACAAGTG
AGGGAAAACAGGGGATTTCACACTCTATGCCCGTCCAAACCAGTACCTTATTTTGAGGGT
GGTTTGACAATATTTGTCAAAATAAAAAAATTATATATAGTCATTTGCCACATAATGATG
GTTCAGTTGATGATGGACGGCATACATAATGGTGGTCCCATAAGAATATAATGGGCTGGG
TGCAGTGGCTCTCACCTGCAATCCCAGCACTTTGGGAGGCCGAGGTGGGTGGATTGCCTG

FIG. 10
*(continued)*

AGGTCAGGAGTTTGAGACCAGCCTGGCCAACATGGTGAAACCCTGTCTCTGCTAAAAACA
TACAAACAATTAGCCAGGCATGGTGGCGGGTGCCTGTAATCCCAGCTACTCAGGAGGCAG
AGGCAGGAGAATCGCTTGAACCCGGAAGGCGGAGGTTGCAGTGAGGTGAGATTGGGCCAC
TGCACTCCCATCTAGATGACAAGGCAAAACTCCATCTCAAAAAAAAAAAAAAAAAAGAAT
ATTATGGGCCCAGCCACAGTGGCTCACACCTGTAATCCCAGTACTTTGGTAGGCCAAGGC
AGGAGAATCATTTGAACTCAGGAGTTTGAGACTAGTGGGGACAACATAGCAAGACCCCAT
CTCAAAAAAAAAAGATTATGGTGGAGCTGTCCTGTATAGACATACCATTTTTAACTTTTT
TTTTTTTTGAGATGGAGTCTTGCTGTGTCACCCAGGCTGATGTGTAGTGGCGTGATCTGG
GCTTACTGAAACCTCCACCTCCTGGGTTCAAGCGATTCTCCTGCCTCAGCTTCCTGAGTA
GCTGGGACTGCAGGCGCAGGACACCATATCTGGCTAATTTTTATATATTTAGTAGAGATG
GGGTTTCACCATGTTGGCCAGGCTGGTCTTGAACTCCTGACCTCAAGTGATCCGCCTGCC
TCAGCCTCCCAAAGTGCTGGGATTACAGGCATTAGCCACCATTTACAGGCACCTGGCCAC
CATTTTTAATCTTTTATATTGTATTTAAACTGTACCTTTTCTATGTATGGATGTGTTTAG
ATACACAAATACCATTGTGTTACAGTTACTTACAGTATTCAGTACAGTAGCATGCTGTAC
AGGTGTGTAGCCTAGGAGCAATAGGTTATACCATATAGCCCAGGTGTGTAGTAGGCTCTG
CCATCTAGGTTTGTGTAAGTACGCTCCATGATGTTACCACAGTGACGAAATCGCCTAATG
ATGCATTTCTCAGAACATATTCCTGTTGTTAAGCAATGCATGACCGTATCTTGACAAAGC
CATTTTATTTCTAAAACTTTAATTTTACAGATTTATTTGTAAAAGTATGTAAAAATGATT
GTAAAGGATATGTTCTGCTGCATTATTTGTAATAACAAAAAACCAGAGGATAACATAAAT
GTCCTATAAGAAGGGTTAGATTATGGATGGCACATTCATACAATGGGGTATTATGTAGCC
ATTGAATAAAAGGGTACTGGCTGGGCGCAGTGGCTCATGCCTATAATCTCAACACTTTGG
GTGGCCAAAGAAGGAGGATTGCTTGAAGCCAGGAGCTTGGGGCCAGCCTGGGCAACATAG
CAAGACCCTATCTCTACAAAGGAAAAATAAAACAATTAGCCAGGTTTGGTATTGGACACC
TTCATGGTCCCAGCTACTGAGGAGGCTGAGATTGGAGGGATCGCTTGTGCCTGGCAGGTT
GAGGCTGTAGTGAGCCATGATTGTGCCACTGCACTCCAGGCTGGGAGATAGAGTGGGACC
CTATCTCAAAAAAACAAAAACAAAAACAAAACCTCCTGTAAAATGTCAAGAAGTCCTAGA
TGTGGGCCAGGTGTGGTGGCTCACACTTGTAATCCCTGCACTTTGGGAGGCTGAGGCCAG
GAGTTTGAGACCAGGCAGAGCAAGATAGCAAGACTCCATTTCTACAAAAAATAAAAAAAA
TTAGTTGGGCATAGTGGTGCATTCCTGTAGTCCCAGCTACTCAGGAGGCTGAGGTGGGAG
GATTGCTTGAGCCTGGGAGGTTGAGGCTGCAGTGAGCCATGATCACACCTCTGCACTCCA
ACCTGCGCAACAGAGTGAGACCCTGTCTCTAAAAACAACAACCAAAAAAACCCAGCAAAG
TACTGATAAAGATCTTTGGCTGGGCGCAGTGGCTCACACCTGTAATCCCAACACTTCAGG
AGGCTGAGGCGGGCAGGTCACAAGATCAAGAGATCAAGACCATCCTGGCCAACATGGTGA
AACCCGGTCTCTACTAAAAATACAAAAATTAGCTGGGCATGGTGGCGTGCACCTGTAGTC
TCTGCTACTCGGGAGGCTGAGGCAGGAGAATCACTTGAACCCAGGTGGCAGAGGTTGCAG

FIG. 10
*(continued)*

TGAGCCGAGATCACGCCACTGCATTCCAGCCTGGCGACAGAGCAAGACTCCGTCTCAAAA
AAAAAAAAAAGAGAGAAAGATCTTCAAGTTGTAGTATGTGAAAAAATCAGGGTGTAAAAC
AAGAGAATCCCATTTGTGTGTGTGTCGAGTGTGTTTCACACAGGCTCAGAGGGAGTAGTG
TGTATATGCACATGAACATACGTGTCAGTGTATATATGTATATATACAAGGTTGTGGGTT
TGTTTGTTTTTTTTGAGACAGAGTCTTACTCTGTTGCCCAGGCTGGGGTGCAGTGGTGCA
ATCTTGACCCACTGCAACCTTCACCTCCCAGGTTCAAGTGATTCTTGTGCCTCAGCCTCC
CAAGTAGCTGAGACTACAGGCACGCACCACCATGCCCAGTTAATTTTTGTATTTTTAGTA
GAGATGGGGTTTCATCATGTTGCCCAGGCTGGTCTGGAACTCCTGGCCTCAAGTGCTCTG
CCCGCCTTGGCCTCCGAAAGTGCTGTTGCCCAGGCTGGAGCTCAGTGGCACAATCGCAGC
TCACTGCAACCCCGACGTCCCAGGCTCAGGCAATCTTTCCGTCTTAGCTTCCCAAGTAAC
TGGGACTACAGGTGTGTGCCATCAATGCCCCACCAATTTTTTAATTTTTTGTAGAGATGG
GGTTTCCCTACGTTGCCCAGGCTGATCTTGAACTCCTGGTCTCAAGCAATCCTCCCACCT
CAGCCTCCCAAAGTGCTGCGATTACAGGTGTGAGCCACCTTGCCCTGCCCTGTACAAAGA
TCTGCATAAAAGCAGTTAATAATACTATGTTTGAGGCTGCCATCACAGGGGTGAGGTCAA
GGACAAGTGTGAGAAATTCTTTTAGAATCTATTTTAAAAAAAGAAGAGATGACAGTGGTG
ACAGTCAGGGAACAGATAAGCAGGTAGATTGTGGGGGTCTAGGCTGTCTAACTGGTGTTT
AAAATGAAGCAACCGCTGAGCCTGCTGTATTTCATTTAATGGAGACTAGTAAAACAACAG
CCAGAAATTCTTCACTTTCCATCTAAGAGAGGCAAAAGTTATTTTCCCTTCAATAACCTG
GGACTGTAGGATTAAGGTTTTTTTTTTTTTTTTTTAAATACTACAATATGACTACCAGT
ATAATTTAAAAATGATTAGAATTCTATTTGAGTAAGAAATAGGTGTCTGCCTGAAGTAGA
CAGTCACTGAAGTCACTAAGTGGCAAAAGACAGAAAAAAAATTGAAAGTAGGAAACAATC
AGCAGATATGATACCAAACATGAGCTGTCAGTGATAATGGATTAAGTCCTTCAATAATGG
CTGAGCCAGATGGAATTAAAAGAAAAAATCCAGGCCGGGCATGGTGGCTCACACCTGTAA
TCCCAGCACTTTGGGAGGCTGAGGTGGGAGGATCACTTGAGTCCAGGAGTTTGAGACCAG
CCTGAACAACATAGTGGGACCCCATCTCTATTTTATAAAAATATTTTGAAAAAAGAAAAA
AAAATTCAGTTGTGTTCTGCTTTAAAAAGACAAATTGGCACAGAATGTCAAAGAATAAAT
AAAACAAACATGGGCAAAAGAGATTCAGGTGGTACCAATATCGGGCTAAGTAGCATTCAA
GATAAAGATTATTAAATAATAAGTTAGTTAATACTAGAGTAATTGCATATTAATGAAACA
TAATCTATGGTAGAGATATTATAGTCAATAATTGTTTTATGTATTCATTAAGGTAACAAC
AAGCAAACAAGCTTTAATAGTTTTAAATGCTTTATATGCTTTATAGTTCTTTTATGTGCA
TTAATTCATTAATTCTCATTTCCTATGAGGTAAACACTATTATTATCCACATTTTACAGA
TGTAAAAACCGAAGCAGAGAGATTAATTAGCTTGCCCAGGAGATGTGGCATTCTGGGATT
TGAGACAGTGGTTTGGCTCTGTAGGTTGCTTCAATAACCAAGAGATGCTTCAAATCAGAT
TTTTAAAATATGTTTTTCAGAAGCATTTTCCTGATACTTCTCCCCTTACATGGGTGTTAG
TCTTTTGGGTTGAAAAACATGAGTAAGTGCTAGAAGAGCAAAATATGCATCCAGATTTAA

FIG. 10 (continued)

TAGTATGTCTGTTTTTCTGAGCCTTGGCATTTCATTGCTTTTATAATAGAAATGAAGGCT
TTTTTTTTTTTTTGGCTGAGAATAGCACTGAACTCAGTGGGAGGGACTGTGGGTTGTAAG
TTGTCCGCCTCTGAATGGAGTTGAATTTAAGTTTCTTGGTTTCCAAAGAATGATTGATTT
AAAGACCCTCAAATTGCAAGTTAGAACTGACTTCAGTCCTTGAGGTTTTTTACCATTTAA
TGAATAATTAAATTTATGGTAATAAATGGTAATAAATGGTAAAAATGGTAATAAATTTTA
CCATTTAATGAATTTTTCTTAAAAAGCAATTGAATTGTTGATGAAAGGTGATGTTAAAAT
TATCCCAGATTTATCAATCTTTTTTTTATTGCCCCTGGATTTTGAGTCATAGAAAGCCTT
TCCTTATTCTAAGGTTAACAAGACATTCACCCATGTTTTCCTCTAGTATTGCATTGTTTC
ATCTTTTACGTTTATTATTTATTTTATTTTATTTTTTTGAGACAGGGTCTCACTGTGTCA
CTCAGGCTGGAGTGCAGTGGAATGATCTTGGCTCACTGCAGCCTCTGCCTCCCGCCTCCC
GGGTTCAAGCGATTCTGCTGCCTCGGCCTCCCAAGTAGCTGGGATTACAGGCACCTGCCA
CCGCGCCTGGCTAATTTTTGTATTTTTTTTTTAGTACAGATGGGGTTTTGCTGTTGGCCA
GGCTGGTCTCGAACTCCTGACCTTAAGTGATCCACCCGCCTTGGCCTCCCAAAGTGCTGG
GATTACAGGCATGAGCCACCGTGCCCGGCCTAAAATTTATTCTGATATGTGATATGATGT
ATGGTTCTAACTACTTTGTTACGGTGCATTATTTTCTAAATGTGGTATTGGATTCTTTTA
TATTTTGTTTAGAAGTTCTGCATCAATATTCATGAGTACCATTGGTCTCTGTTGTTTTTC
TTGTGCCATCTTTATTGGTATAGGTATCAGTGTTATATTTAGTTTGTAAAAGGAAGTTGG
AAGTTTTCCTTTCTTTTTAGTACTCAGGAATGATTTTAAGAATTGAGACTATTTGGTCTT
TGAAGGTTTGGTAGAAGTCCATTGGGAATCCATCTGGGCCTGGTGATTTTCTGTGCGGTA
GTTCCTTAATTGTTTTCCCTATTTTTTCTTATTTTTAATCAGGTAGCCTCTGAACCAGAA
TAGGTTCAGAGAGGCTCCCTCTATTTTTTTTAATACAAGTTGGTCTGCCTAAGTTTTCTT
ACTCTAATGGGTTAATTTTTGTAGACTGCATTTCCCTGAAAAATTACACGTTTGTTCTAG
GTTTTCTGACTTATTTCCACAACTTTTTAGTCTTTCCCCCTGGAATCATGCCCCTTTCCA
TAAACAGGACTCTGATGTACCTGAAGTATTTTCACACTTCGGGTGGACTTTCTGTTTCTG
GGGGTGGTTTTAGAGCAATTTTAGGCCTGCCACTAGCTACCCTGTTCTCTACACCATGCT
GTTTTTCTCAGAATGCTCTTCTTTTGCACAAAGGCTTGGAGTAGGAGGTTGAGCAGTCAC
TCACTGACGTTTGGTATATTTTCTTTTTTTTGCTTACAGGTAATCTGGAAGTTTGGGCAT
TCTCTTTAAGTTGAGGGTGTGGTTTTCATGTCATTTTATTTGTTTATTGTTTTCTTGTGT
GTGTTTCTTAGAGACAGGGTCCCACTCTTGCCCTGGCTGGAGTGCAGTGGCGTCTTGATC
ATAGCTTACTGCATCCTCAAGCTGCTGGGCTTAGATGAACCTCCCACCTCAGCCTCCTGA
GTAGCTGGGACTACAGGAGCACACCACCATACCTAATTTTTTTTTTTTTGAGACGAAGTC
TTGCTCTGTCCCCCAGATTGGAGTGTAGTGGTGCAATCTCGGCTCACTGCAACCTCTGCC
TCCCGGGTTCAAGCGATTCTCTCACCTCAGCCTCCCGAGTAGCTGAGACTGCAGGTGCAT
GCCACCATACCCGGCTAATTTTTGTATTTTTTAGTAGAAACAGGGTTTCACCATGTTGGC
TAGGCTGGTCTCAAACTCTTGACCTCAAGTGATCCACCCACCTTGGCCTCCCAAAGTGCT

FIG. 10
*(continued)*

GGGATTACAGGCTTGAGCCACTGTGCCTGGTCCCTGGCTAATTTTTAATTTTTTTGTAGA
GATGGGATCTTGCTATGTTGCCCAGGCTGGTCTTGAACACCTGGCCTTAAGCAATCCTCC
CACCCTAGCCTGCCAAAACACTGGGATTTACAGGCATGAACCATTGTGCCTGGCTTGTTT
TGTTTTTAATTCTATGTTGTTTTTGAAGGATGTATGGGGAGAGATGGATTTAGGCAATCA
TCGTTGTCCTTGGCTACCTGAAAGTCCAGGCACTCTTCTAGATACTTTATAAATATTAAC
TCATTTTATCCTCTCAACAACACTATGACATGGGTACTGTTACACCTTCCATTTTATAGG
ACTTAACAGAGAGGTTAAATATGTAGCCCAGGGTCACAGAGAGCTGGGCTTCAGACCAAG
ACAATCTGGCACCAGAGTCTATGTGGCTACCCCTAAGGCTTTGCCACCATGTGTTAGTGA
TTCTCAGCCTGTCATTTGGGGAGGGGATTGCCCTTTTTTTTAAACTTTTTAAAAAATTTA
TTCTTATTTTATTATATTTTTGAGACAGAGTCTCCCTCTTTTGCCGAGGCTGGAGTGGAG
TGGTGTGATTTCAGCTCACTGTAACCTCTGCCTCTGGGGTTCAAGTGATTCTCATGCCTC
AGCCTCCCAAGTAGCTGGGATTACAGTTGCCAGCCACCATGCCCAGCTAATTTTTGTATT
ATTATTATTATTATTTGAGACGGAGTCTCGCTCTTTTGTTCAGGCTGGAGTGCAGTGCTG
TGATCTCGGCTCTCTGTAACCTTCGTCTCCTGGGTTCAGGTGATTCTCCTGCCTCAGCCT
CCGGAGTAGCTGGGACTATAGGCGCGCACCACCATACTTGGCTAATTTTTTGTATTTTTA
GTAGAGACGGGGTTTCACTATGTTGGCCAGGCTGGTCTCGAACTCCTGACCTCAGGTGAT
CTACCTGCCTTGGCCTTCCAAAGTGCTGGGATTACAGGTGTGAGCCACCATGCATGGCTG
GATTGTCCTTTTTTTAAAAAAAAAAACAAAAACAAAAAAAAAAACCCAAACCATAAACCCA
ATATTCTGAAAGATTTGGTCTCCACACCTGTGTTATATAATAATTAGTTTTTCCATTTTT
TTCCTCTTGGTAGAAGGCACATATGCCACTCAGTTTCCAGTTGCCACACCCAATTAACAT
AATTGTTTTGCAGCCAAAAGCAAAAGAGAGTTGACATTTTAATTAGCTTATGTAGGTAGA
CAAATTGAGGCCTAATGTAAGAGTTTCATTATACCTTTTTGAAAAACTATAAATAGCTAG
AAGCCAGTTGTCATTACTTTTTGATTCCTTAGAATTCTGGGCATCTTTCATCTGGAACCA
CAGATGAAAGAAGCTGCAAGGAAGGATTTTTTTTCTTAACGGAATAGTTTAACCATTCTG
AATGCAAAAGTATTGGATGCTAGAATAATAGGTATCACATAAATTGAGGTTGACGTTTTC
CCGGGTGAAATTCTATTCTGTCTCAATTTCCTTTTTTTTTGAGACGGAATCTTGCTCTG
TCGCCCAGGCTGGAGTGCAGTGGCATGATCTCGGCTCACTGCAAGCTCCACCTCCTGGGT
TCATGCCATTTTCCTGCCTCAGCCTCCCGAGTAGCTGGGATTACAGGGGCCTGCCACAAC
ACCCAGCTAATTTTTTTGTATTTTTAGTAGAGACGGGGTTTCCCAGGATGGTCTCAATCT
CCTGACCTCGTGATCCGCCTGCCTCGGCCTCCCAAAGTGCCGGGATTACAGGCGTGAGCC
ACTGTGCCTGGCCTTTTTTTTTTTTTTTTTTTTTTTTTTTTTAAGACAGAGTCTCGCTTTG
TTGCCTAGGCTGGAGCGCAGTGGCATGATCTCAGCTTATTGCAACCTCCGCCTCCCGGGT
TCAAGTGATTCTCCTGCCTCAGCCTCCCGAGTATCTGAGATTACAGATGTGTGCCACCAT
GCCTGGCTAATTTTTGTATTTTTAGTACAGATGAGGTTTTGCCATGTTGCCCAGGCTGGC
CTCAAACTCCTGACCTCAGGTAATCCTCCTGCCTCAGCTCTTCCCAAAGTGCTGGGATTA

FIG. 10
*(continued)*

TAGGCATGAGTCACCGGGCCCAGACTCAATCTTCTGACAAGCTCTCAGAGAGAGTAAAAA
GCAAATGAATATTTCATTATTTTGATCTGAGCTTTACGATTTTTCTTTTCTTTTCTTTTT
TTTTTTTTTTTGAGATGGAGTTTTGCGTTGTTGCCCAGGCTAGAGTGCAGTGGTGGCGAT
CTTGGCTCACCGCACCCTCCGCTTCCCGGGTTCAAGCGATTCTTCTGCCTCAGCCTCCTG
AGTAACTGGGATTACAGGCATGCGCCACCATGCCCGGCTGATTTTGTATTTTTAGTAGGG
ACAGGGTTTCTCCATGTTGGTCAGGCTGGTCTTAAGCTCCCGACCTCAGGTGATCCACCT
GCCTCGGCCTCCCAAAGTGCTGGGATTACAAGCATGAGCCACCTTGCCCAGCCTTTTTTT
TTTAAATCTGAGAAGAGGTCTTGCTCGATTGCCTAGGCTGGAGTGCAGTGGTGCGATCTC
TGCTCACTGCATTCTCTGCCTCCCAGACTCAAGCAATCCTCCCACCTTAGCCTCCTGAGT
AGCTGGGACTACAGGCATATGCCACCACACCTGGCTAATGTTCGTATTTTTTTGTAGAGA
CAGGGTTTTGCCATTTTGCCCAGGCTGGTCTTGAACTCCTGACCTCAGGTGATCCTCCCA
CCTTGGCCTCCCAAAGTGCTGGGATTACAGGTGTGAGCCACTGTGCCTGGTCTCCTTCAC
TGTTGTAAGATACTTGAATTGGGTCAATATTTGTGGAGAAGTCTCTTAAAAGTTCACTTG
ATTGTCAGTACTAGAACTCTACATTTAATATTGACATATTCCTGGGAGCATTTCAGAGCA
TTCTATTAGCTTAGAAAGGTCCAGGATAATTTGACTTTAGAAGTTACTGTTACCATGAAT
CTCAATGACTTTTGAAATCCATGAAGAATATCTTTTTTTTTTTTTTGAGACGGAGTCTCA
CTCTGTCGCCCAGGCTGGAGTGCAGTGGTGATCTGGGCTCACTGCAAGCTCCGCCTACTG
GGTTCACGCCATTCTCCTGCCTCAGCCTCCCGAGTAGCTGGGATTACAGGCACATGCCAC
CACGCCTGGCTAATTTTTTTGCATTTTTAGTAGAGAGGGGGTTTCACTGTGTTAGCCAGG
ATGGTCTCGATCTCCTGACCTTGTGATCCGCCCGCCTCGGCCTCCCAAAGTGCTGGGATT
ACAGGCGTGAGCCACCGCGCCTGCCCAAGAATATCTTTTTGCTGGTAACTAGAGAGGACT
CCTCTGAAGCAGATGCCATTCATGATGGATTTCATCATTTATGGGTTTTAAAAAACATTT
TATTTTGAAATAATTTCAAATTTAAATAAGAGTTGCAAAATAGTACAAATAATTCGTGTT
AACTTTTCATCCAGATTTACAAGTCAACCTTATACAGGTTGAGTATCCCTTATCCAAAAT
GCTTGGGACCAGAAGTGTTTTGGATTTCAGATTTTTTCGAATTTTGGAATATTTTTATTA
TATACTTAAGCATCTCTAATCCCCAAATCTCAAATCTGAAATATCTGAAATGCTATGATG
AGCATTTCCTTTGAGTGTTATGTGGGCACTTTTTAAATTTATTTAATTAATTTATTTTTT
GAGATGGAGTATTGCTCCATCACCCAGGCTGGAGTGCAGTGAGCGATCTTGGCTTATTGC
AAACTTCACCTTCTGGGTTCAAGTGATTCTCCTGCCTCAGCCCCCTGAGTAGTTGGGACT
ATAGGCGCTTGCCACCACGGCCGGCTAATTTTTGTATTTTTAGTAGAGACAGGGTTTCAC
CGTGTTGGCCAGGCTGGTCTCGAACTCCTGACCTCAGGTGGTCCACCTGCCTCCGCCTCC
CAAAGTGCTGGGATTACAGGAGTGAACCACCGCGCCTGGCCATGGATTTTGCAGCATTTT
AGATTTGGATACTCAACCTGTACCATGTTTACTCTCTCTCCTCTCTCTCTCTCTCTTTT
TATATATATATATATATATATATATATATATATATATATATATATATAAATTATATATAC
ACTACACATATATGTATGTATATGTATGTATTTTATATATAAAATACATATCTACATATA

FIG. 10
*(continued)*

AAATACACATGTATATATACATGTGTACATATATGTGTCTCTATATTTAAGTTTTGTTGG
AACCACTTGAGGGTAAGTTGCAGACATGGCGTCTCATTGCTCCAAAATACTTCAGTGTGT
ATTTCTTAAATACAAGGACACTTGGTTACATAACCACAGTATATCACCAAATGTATATTA
TAACAAGACTACCATCAAATCCTTATATCTCTTTCAAATTGTTTTAGTAATATCCTTATA
GCAAAAGACAAAACAACAACAAAAACTGTTCCCTTTTATTTTGTTTGTTTTGGTCCATTA
TATGTCCAGGTTATGCATTAATGCATTGTGTTACTTGCTAAGTCTTGTTACTGGCCTTTA
ATTAGGATATTTCTTTGCATCCCGCCAAACTCCTCTTCATGGTTGTATCTTTTTTTTTTT
TTTTGGAGATGGAATTTTGCTTATGTTGCCCAGGCTGGAGTATAATGATGCGATCTTGGC
TCACTGCAACCTCCGTCTCCCGGGTTCAAGCGATTCTCCTGCCTCAGCCTCCCGAGTAAC
TGGGATTGCAGGCCTGCGCCACCTTGCCCAGCTAATTTTGGAATTTTGTGAGACGGGGTT
TTGCCATGTTGGTCAGACTAGTCTCGAACTCCTGACCTCATGATCCGCCCGCCTTGGCCT
CCCAAACTGTTGGGATTACAGGTGTGAGCCACTGTGCCCGGTCTTTTTTTTTTTTTTTTT
GAGACAGGGTCTTATTCTGTTGCCTGGCCTGGAGTGCAGTGGTATGATCTTGGCTCACTG
CAACCTGGACCTCCTGGGCTCAGGCGATCCTCCCACCTCAGCCTCCTTAGTAGCTGGGAC
TATAGGCACACACCACCATGCATGGCTAATTTTTATATTTTTTTGTAGAGACTGGGTTTC
GCCATGTTGCCCAAGCTGGTCTTGAACTCCTGGGCTCAAGTGATCCACCTGCCTTGGCCT
CCCAAAATGCTAGGATTACAGGTGTAAGCCACTGCGCCTGGCCCTAATTTTTGCATTTTT
TGTAGAGATGGGGTTTCACTATATTGCCCAGGCTGGTCTTGAACTCCTGGGCTCAAGTGA
TCTTCCCATCACAGCCCCCTAAAGTGCTGGGATTATAGGCGTGAACCACTGTGCCTGGCT
GAGGATTAAGTTTCAACCTCAGGGGAGCGGCATTCAAACTATAGCATTGTCCTTTAGTGA
CTGGCTTAGTTCACTTAGAATGTTTGTCTATTCATCCATCTATAGACACTGTTTTCTTTC
ACCTTTTGGCTTTGCAAATAATGCTGCTGTGAATATGAGTTATAGAAAAATACCAATTTG
AATCCGTGTTTTCAATTACTTTGAGTATATACCTGGAAGTGGAATTTCTGGATCATATGG
TACTTCCAAGTTTTTTTTTTTTCTTTTTTGAGACAAGGTCTCACTCTGTCACCCAGGCTG
GAGTGTAGTGGCACGATCTTGGCTCACTGCAACCTCCGCCTCCCGGGTTCAAGCGATTCT
CCTGCCTCAGCCTCTCAAGTAGCTGGGATTACAGGCACGCGCCACCACGCCCAACTAATT
TTGTATTTTTAGTAGAGATGGGTTTCTCCATGTTGGTCAGGCTGCTCCCGAACTCCCGAC
CTCAGGTGATCTGCCTGCCTCAGCCTCCCAAAATTCTGGGATTACAGGTGTGAGCCACCG
CACCTGGCCTCCATGTTTCAATTTTTAAACAAACAATTAGTTAAAAAAATAGGAAACTAA
GAGAATGAACTATTTCCTGTTTTATTCAGTGGGTTATAATCTGTTACTATCATTGTTTAT
TTTGAGGTACAAATTGTCCCTACTTTGGCCAGCAGAGGATCCTGCAGTTTGTCTCCTGTG
TCCTTTTCATAGCTCCTTGTTGGAACTCTTACTGGCCCACAATAGGATGTTCCAAGTTCA
TCTTCTTACTTTTACTGCCCCAACGCTGGGATCAGCCATTTCTTCAAGGAGGCCAGTTCC
TTTCATTGGAGAATGGAAAACCCAATATGTAGAAACCAAGATAGAGGTGTTAGGTGTGAT
TGCTACTGGAGTGTCATTGCTTCCAAACCCTTTCAGAAGAGACCTAGGAAATGTGTGTGT

FIG. 10
*(continued)*

GTGTGTATATATATATGTGTGTGTGTGTGTGTATTCATAAAAGCACATACACATACACAT
ACCCCGAAGCATGTATTTCTGTATTATTATTATTTTTTTGAGATGGAGTCTTGCTCTGTC
GCCCAGGCTGGAGTACAGTGGCACGATCATGGCTCACTGCAACCTCTGCCTCCTGGATTC
AAGCAATTCTCCTGTCTCAGCCTCCTGAGTAGCTGGGATTACAGGTGTCCACCACCACGC
CCACCTAATTTTTGTATTTTTAGTAGAGATGGGGTTTCACCACATTGGCCAGGATGGTCT
TGAACTCCTGACGTCAAGTGATCTGCCCGCCTCGGCCTCCCAAAGTGCTGGGATTATAGG
CGTGAGCCACTGTTCCCATCCAGAAGCATACATATCTATTTCTATATCTACATTTCTGTC
TTTACATGTATATATTAAAAATTACAGTTTGCACTAATACCTCCAATTACAATCTAACAT
CATGGGATTTATTCTGGCTTTCTCCCTTCTCATATTTGTGTCTCCCCAACAGTGAGAAAC
CTGGCTTGCTATCCTCAACATGGTAACTTATTTATTAAGAAACTTATTCTTTTTTTTTTT
TTTTTTCTGAGATTGAGTTTCGCTCTTGTTGCCCAAGCTGGAGTGCAGTGGTGTGATCTT
GGCTCACCGCAACCTCTGCCTCCTGGGTTCAAGCGATTCTCCTGCCTCAGCTTCTCAAGT
AGCTGGGATTACAGGCATGCACCACCATGCCCAGCTAATTTCGTATTTTTAGTAGAGATG
GGTTTCTCCATGTTGGTCAGGCTGCTCTGGAACTCCCGACCCCAGCTGATCTGCCTGCCT
CGGCCTCCCAAAGTCCTGGGATTACAGGCGTGAGCCACCGTGCCCTGCCTCTAGTTTATT
TATTTTTATTCCATGTGCTCAGTCTTGCGAGCACGTGGTCTGTTTTCTTGGGCCTGGCCC
CCTCAGTGCACTGTCTTAATACCCTAGCCCCCAGTCCCTCTGATCATATCCCCAGACACC
CCTACTGAATCCCAGGTCTCTACCAAGGGAAAGGCAGGGAGGAGGCATTGACCAAGGAGA
AGAGGGGGAAGGGACAGGGAAGGTCTTGATTTGTATTTTCTAAAATTTTCTACTCTGCTC
ATAATGCGTCTTAGCTGTGTTGTTGTGGAAAGTAGTGCTGACAGTGTCTTGTTTTTTTAT
TACTTACTTTGTCTTTCTTTTTAAGATGGTTTCACCCAAATATCACTGGTGTGGAGGCAG
AAAACCTACTGTTGACAAGAGGAGTTGATGGCAGTTTTTTGGCAAGGCCTAGTAAAAGTA
ACCCTGGAGACTTCACACTTTCCGTTAGGTAAGTTGGAATGAAAAGAGAGGATCCTGAGA
GTGTTTTCTAGGTAGGAAGTGGTAAAACCATGCTTGGATAGCTTGCTGCCTGCATTTCGA
GTTTGAAGGCCTTATCTGAGCCCTGGGCTGCCTTCAGGGTTTGGGGAGTGGCCTCCTGGA
CATTTAGCAGAAGAGGAGTAAGGAGGGCCCTTCTTCTCCCTCTGAGACCTCATGGAAGGT
GAGTTGGAGCAGGTCATAGAAGTTCTTAAGCCCTCCAGTGCTTGAGACTTGTTCCACACA
TCTTGAACCTGGTTTCTGCATTTTTCTTTTCCTTCCTGTTGATTTATTTAAAAATTTTAT
TTCTTTTCAATTTTTTTTTTTTTTTAAATAGAGGTGGGATCTTCCAATGTTGGCCAGGTT
GGCCTTGAACTTCTGGCCTCAAGCAATCCTGCCTCGGCCTCCCAAAGTGTTAGGATTACA
GGCGTGAGCCACTATGCCTGGCCTTCTTTTTTTGAGACAAGCTGTTGCTCTGTTGCCCAG
GCTGGAGTGCAGTGGTACGATCACAGCTTACAGCAGCCTTGAACTCCTGGGCTTAAGTGA
TCCTCCCGCCTCAGCCTCCCGGGTAGCTGGGACTCCAGGCTTGTGCCACCATGCTCAGCA
TTTTTAAAAAATATTTTTGTAGAGATGAGGTCTCACTGTATTACCAAGGCTGATCTTTA
ACTCTTAGCCTCAAGTGATCCTCCTGCCTCAGCCTCCCAAAGTGTTGGGATTACAGGCAT

FIG. 10
*(continued)*

GAGCCACCACACTCAGACTTTGTTGACTTCTTAATAAGAAAAATACTTGTTAAGAGTTTC
TTCAGATCACTTTCCTTTATCAACAAGTAAAACATGACTGAGGAAGTTGTGGTCCCCTTT
GCTTCCCTGCCCAGGCCCGTTTCCCTCCCTCTTTCCCCAGAGGAAACCACCAAGAGGTTG
GCATATATTCTTCCTGAACGTGTTTTTATAGTTGTACTGCACTTGTACTGTGTATGAACA
ATATAAAGTTGGTTTGTGTGTTTAAAAAATTCACATACATGGATTTATAATGTATGTATC
ATTTTGCAACTTAAAAATTTTTTTTGAGCTCCATGCTGATTGATAACGATCTATTTTTT
TTTTTTGAGATGGAGTTTCAGTCTTATTGCCCAGGCTGAAGTGCAATGGCGTGATCTCAG
CTCACTGCAACCTCAGCCTCCTGGGTTCAAGCTATTCTCCTGTCTCAGCCTCCGGAGTGG
CTGGGATTACAGGTGCATGCCACCATGCCCAGCTAATTTTTGTATTTTTAGTAGAGATGG
GGTTTCACCATGTCGACCAGGCTGGTCTCAAACTCCTGACCTCAGGTGATCTGCCTGCCT
TGGCCTCCCAAAGTGCTGGAATTACAGGCATGAGCTACCATGCCTGGCCTTTTTTTTTTT
TTTTTTTTGAGACAAAGTCTTGCTCTTTTTCCCAGGCTGGAGTGCAGTGGCCACAATCTT
GGCTCACTGCAACCTCTGCCTCCTGAGTTCAAGCAGTTCTCCTGCCTCAGCCTCCTGAGT
AGCTGGGATTACAGACATGTACCACCATGCCAAGTTAATTTTTGTATTTTTTGTAGAGAC
TAGGTTTTACCATGTTGGCCAGGCTGGTCCTGAACTCCTGACTTAAAGTGATCCATCTGC
CTTGGCTTCCCAAAGTGCTGGGGTTACAGGCATGAGCTATCGCGCCTGGCCTGAGAAATC
TCATTCTTACTCCTACTCCCTTGCACACTATCTCCATTCTGTAGGTAGCCATTTCTATTA
ATTTCTTGTTTACCCTTCTGTGTTTCTTTCATTCTTTTTCTTTTTTTCTTTTTTTTTTTT
GAGACAATCTTGCTCTGTTGCCCAGACTGGAGTGCAGTGGTGTGATCTTGGCTCACCGCA
ACCTCCACCTCCTGGGTTCAAGTGATTTTCATGACTCAGCCACCTAAGTAGTTGGGATTA
CAGCGCCTGGTGTACACTACCACACCCAGCTAATTTGTGTATTTTTAGTAGAGATGGGGT
TTCACCATGTTGTCCAGGCTAATCTCCAACTCTTGGCCTCAAGGGATCTGCCTGTCTCAG
CCTCCCAAAGTGCTGGGATTATAGGCATGAGCCACCATGCCTGGCCCTATGTTTCTTTTT
ATAAAAATAAGCAAATTAATATTTTTATTACTATTTTCCTTTTATTTTTACACATCAAGT
AGAACATTAAATATATTTCTCTGTAATTTTTTTCAGTTACCTAAATCTTTTAGTGATCTC
TCTCATCTTTTTAATCAGCTGGATCGCATTCTATCATGTGAATATTTTATAACTTCTATA
TACTGTCACCAGCAGGTAGCGATTTAGTTGTGTCTAATATTTTAAAATGATATATAATGC
CTCAATGAATATAGTAACCTTTTGCATATATTGTTTTGTGCTTTGGGATAACACTACCTC
GTATTGGAAACTGTGTCATTACATGTGTCTTTAAAATTACATGTGTCTTTTTATTTTTAT
TTTTATTTTTTTTGAGTGGGAGTTTCACTCTTGTTGCCCAGGCTGGAGTGCAGTGGTGAG
ATCTCGGCCGACTGCAACTTCCGCCTCCCGGGTTCAAGCGATTCTCCTGCCTCAGCCTCC
CCAGTAGGTGAGATTACAGGTGCCTGCCACCACGCCCAGCTAATTTTTGTATTTTTAGTA
GGGACGGGGTTTCACCATGTTGGCCAGGCTGGTATCGGTCTGCTGACCTCAGGTGATCCT
CCCACCTCAGCCTCCCAAAGTGCTGGGATTACAGACGTGAGCCACCATGCCTGGCCATCA
CTTTTTTTTTTTTCTTAATTGCTGCATAGTGGCCGGGCACAGTGGCTCACGCCTGTAATC

FIG. 10
*(continued)*

CCAGCACTTTGGGAGGCCAAGGCAGGCGGCGGATCATGAGGTCAGGAGACCAATACCATC
CTGGCTAACATGGTGAAACCCCGTCTCTACTAAAAATACAAAAAAATTTAGCTGGGCGTC
GTGGCGGGCGCCTGTAGTCCCAGCTACTTGGGAGGTTGAGGCAGGAGAATGGTGTGAACC
CGGGACGTGGAGCTTGCAGTGAGCCAAGATTGCACCACTGCACTCCAGCCTGGGTGATGG
AGTGAGACTCTGTCTCAAAAACAAACAAACAAACAAAAAAATTGCTGCATAGTATTCCAT
TGTATGAGTAGTAACACAACAATTTTTATAATGCATAGTATTCCATTGTATGAATAGTAA
TGTAGCACTATTTGTTTATACATTTTTATGATTAAAAAACAAAATGTTTTTCTATTATGA
ATAAAGTGGCAATGAATATTTTTGTACAAGTGTTTTGGTAGCTATACAGTTATTGTCACT
TAATATATGCAATTCGATAGGCCAGTCATTCAAAATAGAAGATATACAAGGTAGGCCGGG
CGTGGTGGCTCACGCCTGTAATCTCAGCACTTTGGGAGGCCGAGGTGGGTGGATCACCTG
TGGTTAGGAGTTTCAGACCAGCCTGACCAACATGGAGAAACCTCATCTCTACTAAAAATA
CAAAAGTAGCTGAGCGTGGTGGCGCATTCCTGTAATCCCAGCTTCTTGGGAGGCTGAGGT
AGGAGAATCACTTGAACCTGGATTTATAATGTATGTAAATCCACCGCGAAGGTTGCGGTG
AACCGAGATCACGTCATTGCACTCCAGCCTGGGCAATAAGAGCGAAACTCCATCTCAAAA
AAAAAAAAAAAAGATATGCAAGGTAAAGATACTAATAAAGACCTTTGTGTTGAGTTGGTT
GACATGTGGTTATTTCACCCATCGTATTTCTTATAGGGAATAGGTAAATTCGTTCCTTGG
GTTTCTTTCAACACTTAGGTAAAATCCGACGTGGAAGATGAGATCTGATTTTACTGGTGT
AACTCTTTATTTGTCCCCTTGCCTCCCTTTCCAATGGACTATTTTAGAAGAAATGGAGCT
GTCACCCACATCAAGATTCAGAACACTGGTGATTACTATGACCTGTATGGAGGGGAGAAA
TTTGCCACTTTGGCTGAGTTGGTCCAGTATTACATGGAACATCACGGGCAATTAAAAGAG
AAGAATGGAGATGTCATTGAGCTTAAATATCCTCTGAACTGTGCAGATCCTACCTCTGAA
AGGTCAGTAACATTTTAGTGACCACAAAGTCTGCTGCTCCCTTGTGCCCTGAGTGTCAGA
AATGCATGACGGTCTGTGTATGACTCTCTGACTCCAAAGGCTTGTGACTGTTTTTTGAGC
TGTAATCTTTAAAGAATTACTAAAGTGAGACTAATAGCATCAAATTATTTTCAGAGTACC
TTTTTCCTGCAAAAGTTTTAATCAGTGTTACTTACACTCATCCTATAGGGGTTGCATACC
ATTCCTGCATATACTTGGTACGTGTATTAGTTTTAAGACTTATTGAACTTCAGCAGATAA
TCTTTGAGAGTTATTAGAGGAAAACAAATGATAATGGAGACACCAAAATAGCAGCAGTTT
TCTATGGTGGCTCTCGACCAGTTATTCAGCAATGTCACCAACAGATGTCAGTTTAAGCTC
AGAAGTGGAAAAGCAGAGAGCTCAGAGGGTCAGCTTTTTCATCAGTTCTTTTAATGTTAT
CACCACAATTATGTGAGAATGACCTTGCTTAGAGAAAATTATGTTATTTTCGAGATCTTT
CCCCCTGTGTTGGAACTAGGCTGATGAAAGCATGGGCTTGACTTATTTATTGATTGTATT
CGTTTTGTACATTCCCAATCTCCTCTCTGACTTGGTGCAAATTCAGGATCTCTTAGTTAG
TTTGTATATTTTGTGTCTTCAGGTATGATTTTTTCAGCTTATACCTTTATGTCAGTGCTA
TTATGTGCTGATAATTTGTTTCTCTAGCTACCACCGTAGCTTCAGGCAAAAGGCTGTCAG
CCAACTCTGTACAGTTTATTTCTAAATTTTACTGTTTTCAGTTGAGTATGGATGAAGAAT

FIG. 10
*(continued)*

AACTCAAAGTTTATTCTTTTGATGATGAGCCCTTAACACCACCTGCCATGATAGTACTTG
CTTTCTGACCAAGATCCTGAGGGAAAAAGCCACTTTATTATTAGAACTATGTTAAGATGC
TTCCCAAAAAACATGGAGCAGTATTGTCTCAAAGTCTGTCCTTGGATGGCTTTGGATGCC
TACATCAGGACTGTCTGATGTGCTGGTTAAAATGCAGATTCCTGGGCCTCATTCAGACTT
ACATGTATTGATATTGCTGGTTGTGGAGCCTGGGAATTCATATTTTTAGCAAAATCCCTC
ATTTTTACTCCAAGTCTTATGTGCATTATACAGTTTGAGATGATCACCCAGGATATAGTC
CAAAGACACTGGAGGCTGTTGAAGTATAGGTTGTATATATGGAAAAGGTTGGAATGTTTG
AATTAATTTATAATGAAGATCCTTTTTAATTGAGTGTTCACATGCCAAGGCAAGGACAAA
CATTCAAAATGATTTTCTGTCTCTGTTACAACTTTTTCTTTCTTTTTTTTAATTTATTTA
TTTGAGATGGAGTCTCACTCTGTCACCCAGGCTGGAGTCAAGTGACGCGATCTCGGCTCA
CTACAACCTCCGCCTCCCAGATTCAAGTAATTCTCTTGCCTCAGCCTCCCGAGTAGCTGG
GACTACAGGCATGTGCCACCATGCCCAGTTAATTTTTGTATTTTTAGTAGAGACAGGGTT
TTGTCATGTTTGCCAGGCTGGTCTCAAACTCCTGAACTCAGGTGATCCGCCCACCTTGAC
CTCTCAAAGTGCTGGGATTATAGGCGTGAGCCACCGTGCCTGTCTCTATTACAACTTTTT
ATTACAACTTCTTTATTTTGACTTTATTTTTACAAATTATTTATTTATTTTTTTTGAGAT
GGAGTTTCGCTCGTCACCCAGGCTGGAGTGCAATGGTGCGATCTCAGCTCACTGCAACCT
CCGCCTCCCAGGTTCAAGTGATTCTCCTGCCTCAGCCTCCTGAGTAGCTGGGATTACAGG
CACTTGCCACCACACCCGGCCAATTTTGTATTTTTAGCAGAGACAGGGTTTCACCATGTT
GGTCAGGCTGGTCTCGAATTCTTGACCTCAGGTGATCCACCTGCCTCGGCCTCCCAAAGT
GTTGGGATTACAGGCATGAGCCACCACGTCCGGCCGACTTTTATTTTTTTTTCTTGAGAC
AGGGTCTTGCTCTGTCACCCAAGCTGGAGTGCGGTGGCATGATCATAGCGCACTGCAGCC
TCGACCTCCTGGACTCAAGTGATCCTCCTGCCTCGGCCTTGTGTATAGCTGGGATTACAG
GCAGTTGCCACCATGCCAGGCTAATTTTTAATTGTTTTGTGAAGATGGGGATTTCACTGT
GTTGCCCAGACTGGTCTTGAACTCCTGGCCTCAAGTGATCTTCCTGCCTTGGCCTTCCAA
AGTGTTGGGATTACAGGCATAAGCCACTATGCATGGCCTGTAACTTCTTTAAATGGCTAT
AATTAAACAGTTGGTCCTTTTAAGATTGGGCAATGGACGAATGGCAAATTGCATTTTTAA
AAGAGGAGGGATTTAAAAAAAAACAGGAAAGATTGGGGCATTTGTCTCTAAAGGACTGTG
GACTCATTTAAGAAGTTTAGTGGTCATTCTTACCATCTTTGTGGTTTTTCCTGCCTGCAT
GGGATGCAGATTTTCTGTCTCAGGTGGGATTGATCAATCCCTTGGAGGAATGTGTCTACT
TTTTAATTGTGTTTAGGAGAGCTGACTGTATACAGTAGTTTTGTGAAAGAACAACATGAA
CCCATAGTAGAGCTAAATTCTTTTTTATTTTTTAAAAACTTTAGGTGGTTTCATGGACAT
CTCTCTGGGAAAGAAGCAGAGAAATTATTAACTGAAAAAGGAAAACATGGTAGTTTTCTT
GTACGAGAGAGCCAGAGCCACCCTGGAGATTTTGTTCTTTCTGTGCGCACTGGTGATGAC
AAAGGGGAGAGCAATGACGGCAAGTCTAAAGTGACCCATGTTATGATTCGCTGTCAGGTA
AATCTCCAGTTGAAAAATGGGTCTGGCAAGATGTTACCTTTGGGTGATTTTTCTGCTGAC

FIG. 10
*(continued)*

AGAAGACAGACACCATTACATTCAAAGTCAGATTGTCTTTTATTTATTTATTTATTTATT
TATTTATTTGAGACAGGGTCTTGCTCTATCACCTACAGATGGGGTTTCACCACGTTGGGT
CTGGTGACCCAAATCTTTGGGTGATTTTTCTGCTGGAAGAGGACAAACACCATTACATTC
AAAGTCAGATTTTCTGTTTTTTTTTTTTTTTTGTTTTTGTTTTTTTAATATTCATTTGTT
TATTCATTTGAGACTGGGTCTTGCTCTGTCACGCAGGCTGGAGTGCAACCTCCCTGGGCT
CAGTTGATCTTCCCTCAGCCTCTTGAGTAGCTGGGACTACAGGTGTGTGCCACCATGCCC
AGCTAGTGTTTGTATTTTTTGTGGAGATGGTGTTTTGCCGCATTGCCCAGTGTGGTCTTG
AACTAGTGCTCAAGAGGCCTGCCTCCTTCAACCTCTCAAAGTGTTAGGATTACAGATGTG
AACTACTGTGCCTGATCCAAAGTCAGATTTTCTTTGCTTACTTAGTCAAGTTCGTCTATG
CTTTTATTATACTTAATATATTAGTATAGTTACTGTATTAGTATATTAGCATATTTAATA
TATTATTATACTTATCATACTTGAGTATATTGAGTATATTTACACTTTTAGTATATTTGT
ATACACACACCACATTTTTATTATTTATCTTTTTTTTGAGACAGAGTCTCCCTCTGTCTC
CCAGGCTGAAGCACAGTTGGCTCACTGCAACCTCTGCCTCTTGGGCTCAAGTGATTCTCG
TGCCTCACCCTCCTGAGTAGCAGGGATTACAGGTGTCCACCACCAAGCCTGGCTAATTTT
TGTATTTTTAGTGGATATGGGGTTTTACCATGTTGGCCAGGCTGGTCTCGAACTCCTGAC
CTCAAATGATCTGCCCGCCTTGGCCTCCCAAAGTGCTGGAATTACTGGCGTGAGCCACTG
CACCCAGCCTATTATCTGTCTTTTGATGGACATTTAAGTTGTCTCTATATACTAGCTATT
GTGAATAATGCTGCAGTGAACATGAGAGTGCTTGAAAACACTAATGTAACATAAAGGTAA
CAAATAATAAATGTCATGTGTTTATCTTGAAAGGAACTGAAAATACGACGTTGGTGGAGGA
GAACGGTTTGATTCTTTGACAGATCTTGTGGAACATTATAAGAAGAATCCTATGGTGGAA
ACATTGGGTACAGTACTACAACTCAAGCAGGTGAGCAGATTGGAAAGCTCAAGCTTTCTC
CTTAAAAACTTAAAACAAATCCTAATAGAGAATTTTGCAAACATACAGAGGTAGACAGAA
TAGTATCATCAGCCTCCATGTACCCATTGCAGCTTCAACTATCAAATCTTTTTTTTTTTT
TTTTTTTTTGAGACAGTCTTACTCTGTCACCCAGTCTGGAGTACAGTGTTGCAATCTTGG
CTCACTACAACCTCTGCTTCCTGGGTTCAAGCGATTCTCCTGCCTCAGCCTCCTGAGTAG
CTGGGACTACAGGTGCCCACCACCATGCCCGGCTAGTTTTTGTGTTTTTAATAGAGATGG
GGTTTCACCATGTTGGCCTGGCTGGTCTTGAATTCCCGACCTCAGGTTTTCTGCCCGCCT
TGGCCTCCCGAAGTTTTGGGATTACAGGCGTGAGCTACCACGCCCGGCCCTAAATCTTTT
CTTATTATGATTCCACTCACTGACTGCCGCTATAGTACTTGGAAACATATTCCAGATTTA
TATTATTCCCATATTTATCTGTAAAAGGCATTACAGAGGTTCTTTTTTTTTTTTTTTTTT
TTTGAGATGGAGTTTTGCTCTGTCGCCCAGGCTGGAGTGCAGTGGCGTGTTCTTGGCTCA
CTGCAACCTCTGCGTCCCGGGTTCAAGAGCTTCTCCTGCCTCAGCCTCCTGAGTAGCTGG
GATTATAGGTGGTGCCACTACACCCAGCTAATTTTTGTATTTTTAGTAGAGATGGGGTTT
CACCATGTTAGCCAGGCTGGTCTTGAACTCCTGACCTCAAGTGATCTGCCTGCCTCAGCC
TCTCAAAGTGCTGGGATTATAGGCATGAGCCACTGCATCTGGCCTAAGGCTGTACAGAGT

FIG. 10 *(continued)*

TTTAAAGCAAGTTTTCATTATAGATCCACTTCTGGTTACCTTTAGGTAACCTCACTTATT
CACTTTGGCATTGTTGCTATTTCAAATTTCACCTTTATGATAGTGGAAAATGATATAATC
TCTCTAAATAATGTGGTCTATTCATAAAGAAAAATAGGCTTGAATTTATATCAGCAGAGT
AAAGTGTATGTGAAGACTGAAGAAAGATACATTTTCTGGCTGAACAGAAAACACGGTGAA
ACGATTTGAAAACTTTTATTGTGAATTACAGGGTCCTATGAACCCTCTGTCCGTGCCTTT
ATGAATATCAACATAGACATGTTTTTTTTTTTTTTTTTTGCATTAACACCGTTTCTGTAA
TATTTTCTTTATTTTACATCAACTGCTGTACTCGATCAGCCCCTTAACACGACTCGTATA
AATGCTGCTGAAATAGAAAGCAGAGTTCGAGAACTAAGCAAATTAGCTGAGACCACAGAT
AAAGTCAAACAAGGCTTTTGGGAAGAATTTGAGGTAAGTTATTAAAAAACTGTTTTTACG
TGAGTTGTTATATCCTATTTTTAGTGGAGGAGAAGTTGCTCTTGTGTTTGGAATTGGACC
TGAGAGACTTGAAACTGACGTCCTTTTTTAATTCGGCCATTGATTGACACGGAGCAAGTT
GCTGAGAGGGCTTCTTCGAAACAGAAGAGCATTGTGTTCTGAGGGAAGGGAGTTGGCAGT
GAGTAGTCAATGGATGTGCTAGCCGCTCCATTTGGCTCTTTTGGTTTGGACTGGTGGCAA
AATCTCAGAGAAACAAAAGGATCTAATTTCTTCGAAAGATTTCCAGCATGCACTGGGGTC
TTTAGAAACAATCTATAGCCTTAGTGCAGCAAATGAGTATGAGTAAAAGAGAAACACCTT
GTGGTGGCTTTTTTTTTTTTTTTTTTGAGACAGGGTCTCGCTCTGTCGCCGAAGCTGGAG
TGTAGTGGCGTGATCTCGGTTTACTGCAGCCCCGTCCTCCCTGGGCTCAAGTGATCTTCC
CATCTCAGCCTACTGAGTAGCTGGGACTACAGGCACATGCCCCTATGCCTGGCTAATTTT
TGTATTTTTGGTAGAGATGAGGTTTTGCAGTGTTGCCCAGGCTGGTCTTGAACTCTTGGG
CTCAAGTGATCCTCCTACTTAAGCTTCCCGAGTAGCTGGGACTACAGGCACACGATACCA
TGCCCATCTAATTTTTGTATTTTTTTGTAGAGATGGGGTTTTGCAGTGTTGCCCAGGCTG
GTCTTGAACTCTTGGGCTCAAGTGATCCTCCAGCTTTGACGTGCCAAATGTGGTGGCTTT
AATTTCAGAGTTCAAATTGATAACTCTGGTAAGTTAAGTGAACTGATTTCTTTTTTTTTT
AAATTATTTTTGTTGATTATACTTTAAGTTCTGGGATATATGTGCAGAACGTGCAGGTTT
GTACATAGGTATACATGTGCCATCATGGTTTGCTGCACACATTAACCCATCATTTAGGTT
TTAAGTCCTGCATGCATTAGGTGTTTGTCCTAATGCTCTCCCTCCCCTTTAATGCATCAG
TGAAAAAGTGATGATAGGCTGGGCGTGGTGGCTCACTCCTGTAATCTCAGCACTTTGAGA
GGGTGAGGCAGGTGGACCACTTGAATCCAGGAGTTTGCCCCCATCCCCAGACAGTGTGTG
TGATGTTCCCCTCCCTGTGTCCATGTGTTCTCATTGTTTGGTTTTCTGTTCCTGTGTTAG
TTTGCTGAGAATGATGGTTTCCAGCTTCATCCATGACCCTGCAAAGGACATGAACTCATT
CTTTTTTTATGGCTGCATAGTATTCCATGGTGTGTATGTGCCACATTTTCTTTATCCGGT
CTATCATTGATGGGCATTTGGGTTGGTTCCAAGTCTTTGCTATTGTAAATAGTGCTGCAA
TAAACATATGTGTGCATATGTCTTTATAGTAGAATGTTTTATAATCCTTTGGGTATATAC
CCAGTAATGGGATTGCTGGGTCAAATGGTATTTCTGGTTCTAGATCCTTGAGGAGTCACC
ACACTGTCTTCCACAATGGTTCAACTAATTTACACTCCCACCAACAGTGTAAAAGCATTC

FIG. 10
*(continued)*

CTATTTCTCCACATCTTCTCCAGCATCTGTTGTTTCCTGACTTTAAGTGAACTGATCTCT
TTCCTGAAACTAACTTGGGTTGGAGAATGTCCCTGATGGGAATGTGCTGTGTTCCCATTG
CACTCTTCTATATCACTTACCCATTGACAATGTGATCTCTTTCATTTTCTCCTCATCCAT
TTGACAGAAAACTTCAAAAACAAGGATTCTGGCATATTTACCTTTGCAGTTGTCCCCAGC
ATGTAGCACGGTGCCTAGTACACAGAAGAAACTCCATAAATGTTTGTTGAATGAGATTTA
CATTTAACTCATGTTTACATCATTTTATTTTCCTGTTCTGTTTTATGGAATGATTATTC
TATGCTTTTTGAGGACTACAATTTATAAATATTTGTGGATTGAATGAATAAGTGAATACT
GGGCAAATAAAGTCCTTTTAGCCAGAGTATGTCTGAACAACTTGCTGAGATAGATATGAT
TTCCCATTTTCCAGCTGAGGGGCCTAAGGGAGGTTAAGTAAATTATTCAATCTTCATACC
ACAGTTTTTGTTTTGTTTTGTTTTGTTTTTTTTCCTCCTGAGACAGAGTCTCACTTTGCT
GCCATACTGGAGTACAGTGGTGCAATCATAGCTCACTGCAGCGTCCAACTTCTGGGCTCA
CGCCATCCTCCCACCTCAGCCTCCTGAGTAGCTGGTACTACAGGTGTGCACCACCATAGC
CGGCTAATTTTTCATTTTTTGTAGATATGGGGTCTCACTGTGTTACTCAGGTTGGTCTTG
AACTTCTGAGCTCAAACAATTCTCCTGTCTTGGCCTCTCAAAGTGTTGGGATTACAGGTG
TGAGCCACTGTGCCCGGCCCATACCACAGATATTGATTGAATTCCAGCAGTGGGGAGGAG
TGTGGAATAGAACATTCTCAGTCCTTGCTCAACATTACTGAACAGAGACTTGAATTTGAG
TTTATTCTCTCATCCCAGGCTTCGCGTTAGGCTCTGAAGACACTAGTGAACAAGACAGAC
AGGGTTACTGCCTTTAAAGGGAGCTTTTAGTTGAGAGAAGGAAAACAGTGATGAAAAGCA
TCAGTGAAAAAGTGATGATAGGCTGGGGCGTAGTGGCTACTCCTGTAATCTCAGCACTTT
TAGAGGGTGAGGCAGGCAGCTCACTTGATTCCAGGAGTTTGAGACCAGGCTGGGCAACAT
GGTAAAACCCCGTCTCTACAAAAAATACAAAAAGTAGCTGGGTGTGGGGGTGCGCACCCA
CAGTCCCAGCTACTCTGGGGGTTGAGGTGGGAGGATTGCTCGAGCCTGGGAGATTGAGGC
TGCAGTGAGCTGAGATCACGTCACTGCTCTCCAGCCTGAGCAACAGAGCCAGAACCTGTC
CCAAAAAAAAAAAAAATTGATGATAAACATAGTGAGACAGAATTTTGAAATCTCAGCCTC
ACTGTTGCCTTCCTTGTCCCCTGCCTGCCTAAATAATAAAAGGCAGCATTTCAGCAGTCA
TTCATTTCATTACTTTCACTTCATTTCACCTTCATAAAGCCTCATGAGGTAAGATGGGAA
GATACAGAAGTTTTAGAAACCGCTCATCAAAATTGAATGGAAAGCCGATTGTTCCAAAAC
TTTTTAGTGTGGAAAATTTCTATTATATGCAAAAGTAGAGAGAATGGGATAGTTATAGCA
GTATACCTGACACCCAGCATTAACAACTGTTGATAATATGGCCAATCTTTTTCGACTCTG
CCCCACTCACTTCCCCAGCCCTGACTTGTCTTGAAGCAAATACTTTTTTTTTTTTTTTGA
GATAGAGTTTTGTTTTGTTTTGTTTTTTGTTTTTGAGATGGAGTCTCACTCTGTCCCCCA
AGCTGGAGTGCTGTGGCTTGATCTTGGCTCACTACAACCTCCGCCTCCTGGGTTCAAGTG
ATTCTTGTGCCTCAGCCTCCTGAGTAACTGGGATTACAGGTGTGTACCACCATGCCCAGC
TAATTTTTGTATTTTTAGTAGGGACAGGGTTTTCACTATGTTGGCCACGCTGGTCTCAAA
CTCCTGACCTCAGGTGATCCGCCTGACTTGGCCTCCGAAAGTGCTGGGATTGTAGGTGTG

FIG. 10
*(continued)*

AGCCACTGCTCCCGGCCTTGAAGCAAATCTTAACACATCATTTCGTCTGTAACTATTTTA
TTTCAAAAAATTATAACCTGAATAGCATTATCATATCTAAAACTATTAACAGTATTTCCT
TAATATTAACACATATCAGTCACATTTTCCTGATTGCTACACACACACACACACACACAC
ACACACACACACTTGCAATTTGTGTTTTTTTCTTTTTAGATGGATCTCACTCTGTTGCCC
AGGCTGGAGTGCAATGGTGCATTCTCAGCTCACTGCAACCTCCACCTCCTGGGCTCAACT
GATTCTCTTGCCTCAGCCTCCTGAGTAGCTGGGACTACAGGTGCCCACCACCTCACCTGG
CTAGTTTTTGTATTTTTAGTAGAGGTGGGGTTTCACCATGTTGGCCAGGTTGGTCTCAAA
CTTCCGACCTCAGGTGATCCACCCACCTTGGCCTCCCAAAGTGCTGGGATTACAGGCATG
AGCCACTGTGCCCAGCAGCAATTTGTTTGAATTGGGAGTGCTTTCTTCCACCTTGATTAT
GAAAAAATTTCAAATGTGTATAAAACAGATTCATATAAAGGATCCTGATATGCCATTATC
AGCTTTATCAATTATCCCTGTCATCATATTTTTTATTTATAAATATTTCAATATTTGTGG
AATCCTTAAAAATGCATCACATAACCCAACATTGTTCATATTATACCAATTGTCTTATAA
TTTAAAAATATTTTGTTCAATCATTTTTCAGATAAGCTTCACACACTGTGGTTGGCTAAG
TCTCATAATATTTCTGTTGTAAAAATCTTAAGTCTGGGCGTGGTGGCACACGGCTGTCAT
TCCAGCACTTTGGGAGGCTGAGGTGGGCGGATCACGAGGTCAAGAGATCGAGACCATCCT
GGCCAACATGGTGAAACCCGGTCTCTACTAAAAATACAAAAATTAGCTGGGCGTGGTAGT
GCGTGCCTGTAGTCCCAGCTACTCGGGAGGCTGAGGCAGGAGAATCGCTTGAACCCAGAA
GGTGGCAGTTGCAGTGAGCCGAGATCGCGCCACTGCACTCCAGCCTAGAGACAGAGTGCG
GCTTCATCTCAAAACGAAACAAAACAAAACAATCTTAAGTCTCTTAGAATACTTTGATGC
CCCTTCCATCTCTCTTTTTCTGTCTTCCTTCCCCCTCTCCCTGTCTTTTCTGCTGTTGAA
GAAAGCAGATCATTTGTCCTGAGAGTTACTTATAGTCTGAATTTTGCTGAGTGCCTCTCT
GTGGTGGACTTAAGCATGTATCCATCCCTTATATTTCTTGTAAGTTGATATATCTAGAGA
CTTCATTGGATACAAGTTTTCTTTGGCAAGATAGCATGTATGGTGGTGTATCAGGAGGTG
TTTATGTCCTGTTGTTTCTTCTCTGATTTTCTTAGCAGCTCCTGATCATTATTACTTAGA
TCCATTAATTCATAAGGGACTATATGGTAGTGATATTGTAATTTTATCATTCTTCTTCAT
TTGTTAGGTTGGCATATTTCTATAAAAAGCTTTTCATCGCCGAGGGTTGATTTTTTCCTT
CTTACTAAGCAGTTTTCTTTTCTTTTTCTTTTTTTTTTTTTGAGGTAGGTCTCACTGTG
TTGCTCAGGCTGGTGTGCAGTGGCGCAAACACACAGTTGCGAACTCTTGGGCTGAGGTGA
TCCTCCTGCCTCAGTTTCCTGTGTAGTTGGGACCACAGGTGCATGCCACCATGCCTGGCT
AATTTTTTGATTCTTTTGTAGAGATGAGGTCTCACTTTATTTCCCAGGCTGGTCTTGAAT
GTCTGGGCTCAAGCAATCTTTCTACCTCAGCCTCCTGAGTAGCTGGGACTACAGGCACAT
ACCACCATGCCCAGCTAATTTTTTAATTTTTATTTTTAGTAGAGATGTGGTCGTATTATG
TTGCTCAGGATGGTCTCGAACTGCAGAGCTCAAGTGATCCTCCTGCCTCAGCCTCCCAGT
GTGCTGGGATTATAGGTGTACTACAGGCAAGAGCCAATGAGCCTGGTCAGATTTTTTTTT
CCTGATTTGAAATCTGTTATGGGTTCAATTGATACTTCCAAATCAAACTCAGGGTTTCAG

FIG. 10
*(continued)*

GATTTTTACTAACCTCATTGATCTTACCCATGTATCTCCTTTCTCTAATGCCAAAAATCC
TACTTCTTGAAGCCATAATAAGATTATTCATTTGTTTTATCCCACATTACACACAACAAT
CTTAGAATAATGACTTCCCAATAATATGATTACTGAAAACAGTTTAATTTTTTTTGCGCT
TTTCAAAAAAATCCTTCAGAGATGTGTAGTCAAGTTACTGTATTCTGCTGGGCACAGTGG
CTCACGCCTATAATCCCAGTACTTTGGGAGGACAAGAAGGGAGGATCGCTGGACCTCAGG
AGTTTGAGACCAGCCGGGGCAATATAGTGAGACCCTGTCTCTACAAAAGAAAATTAAAAA
TTAACCAGACATGGTGGCATGTCCCTATAGTCCCAGCTATTGAGAGGCTGTGGCGAGAGT
AGGCTTAAGCCCAGGAGTTTGAAGCTGCAGTGAGATACGATTGTGACACTGTACTCTAGG
GTGACAGAGCAGGGACCCTGTTTTTAAAAAAAAAAAATGAAAAAACTTCCTGTGCCTTAG
ACTCATTTGTAATCGTCCTTCTCTCTGTGTGGCTATATGCTAACTGGGTATATGGTTAGT
TTATTTGTTTCATTTAAAAAATCTCTTTCTGTTAAGTTTTATTTATAATTACACAAATAC
TGGCTTTGATAGTCAAATTGAAAAAACAAAGTGTATTCAAAGAAGTCTACCTTCTATCCT
TGTCCTTTCCTATGTTTTAGCCATAGTATAAAAAGTTATGGTTTATCATTATATTTCAAA
AATATAAGAAGATATTCCCATATCCCACTTTTTCTTAAACAGTAGCATAACTTTACATAC
TTTTTTCTAACCTTGCTTTTTTAAATATCCTGGACATCCTGGATATCCATAATAGTGTCT
AGAGATAGTCTTCATTCTTTTTTTACTGTATAGTAATCCACTGTGTACTTGTACCATAGT
TTATTCAACCTATTGATGGGCATTTGGGTAGTTTCCAAATGTATCACAGAGAGGATTACA
GTGAATAGCCTTGTGTATGCATCCTGCTTTACTTTTGCTGACTACTGGTAATATTAACAT
TTTTTATGTTCTGTATTTAAAAAATGGTGGTTATTATTCATCTATAACTTTTATTATACA
TGACTTTGGTTAGCATGCTTTAACCTTTTAGCATAACATTTGCAAGCTACTTGTTTTAAT
TAAAATTTTGGTTAAATGTAAAAAATAGTGAGCTATTTTGTAATCTAGATTCAATAGAAT
CTTATACTTCCTTTACAAATGATAGCTGAGTTGATCATTTGTGTAAATGACTGTGAACTT
AAAAATTACAGCATTTTTTAAAATAAATTTTTTTAACATTTTAAAATTATTTAAAATAAT
AGACACACAAAGTAAAAAGAGAAGAAAAAAAAAAGAGACAGGGTCTTGCTATGTTGCCCA
GGCTGGTCTCAAACTCCCAGGCTCAAATGATCCTCCTGCCTTGGCCTCCTAAAGTGTAAG
CCACCACACTTGGCAAAAATTAGTTTCTTTAAAACAAAAACATTACAGGTTATCTGGTAC
CATGGTAGCTTCTTTAACACTAGGTTCACTTAGAACAAAGCTTAGGAACAAAGTCAGACT
TTCACAAAGAGCTTGTGTGGCAATGGGGTATTTTTTGCAAATTCCATTGGTGGGGTCAAG
ATGTGAGTTTAGAAGGAACTCTTAGCCTGACTCTTCTGGCCATGGAAAAAGATGGTTGCT
TCTAAATGCTGACCTGGTGATTTTACACTGTCACATCTCAAATTGTGGTCATCTTTTATA
CATTATTAACAACAAAAGGGAAAAATTGAGTTGACTTTAAGAGGAAGTGGAAAATAACGA
GATCACATCTGTACTCTACAGGCTCTCCACAGAGGTCAGACTGAGGTGGTAAAATTGTTG
TGCACTAAATTAGGGCATTAACGTTTCATGGAAACTGAAGCTATATCTAAATAGCTGATG
GCCTGCTTTCTAGATCTCCTATATACCTGCTTCTCAAATTCAGTCTGTTTTAAAAAATTG
CCCTTTGAGGTTGGAACCAGCGAAATAAGGCTGAAAACAGAATAAGCCATTATTGAAAAA

FIG. 10 *(continued)*

ATTAGGAACTTGGAAGCAGATACTCATAATCTAAATCCTCTGAAGCTAAAGTTTGATCCA
CAATAGCAAAGCATTATCATTTTAGTGATTGTACCTTAGTTGTTTCCTGGCAGGTGATAA
ATTTGGGATCACTTTCTTCTTACAGTGTGCTCTGATAGTCTTTAAAACAAACCAGAGCTC
TAAATTGTAATGCCATTGGTAATTTAACTCTGATTTGTCTCTATGCCTGTCTCCTGGTGT
TCTGTAAAATTCTACACGTCATTTCAGGTATCACTATCCAGAAGACGTTACTTTTGCCTT
TGATGCACTTTAAAATGTGAAGTCTCTTGTGAAGCTCTTTGGTTATTTTCTCCTTTGCTG
CTGAAATAAATTCAGGTTGATGATTTTCTTGTAGGATATGTTGTGTGATCTAGACATTGC
AAACCCAAGTCTTTGATTTTTTTTTCCCTACAGATTGCCTGTTTCTTTTTTATTTTAATT
TTTATTAGTTATTATTATTTTTGAGATGGAGTCTCACTCTGTCACCCAGGCTGGAGTGCA
GAGGTGTGATAGCTCACTGCAACCTCCACCTCCCGGGTTCTTGTGCCTCAGCCACCCAGG
TAGCTGGGATTACAGGCACGTACCACCACTCTCAGCTAATTTTTTTGTATTTTTAGTAGG
GATGGGATTTCTCCATGTTGGCCAGGCTGATCTCAAACTCCTGACCTTAAGTGATCTTCC
TGCCTTGGTCTCTGAAAGTGTTGGGATTACAGGTGTGAGCCACTGTGCCTGGCCAGTTAT
TAATTTTTTTAAAGAGATGGGGTCTCACTATCTTGCCCAGGCTGGAGTGCAGTGGCTCTT
TACAGGCACTGTTGTAGTGCACTGCAGCCTTGAACTCCTGGGCTCAAGTGATCCTCCTGA
GAGGCTGGAATTACAGGCACACACCACTGTGTCCAACAGATTGCCCATTTGTGATCTGTG
TAAATATCTCTCACTTCCTGCAGTATCTCTGCTCAAGAATGTAAAGAGATGGATAATATT
TTTAGATTTGTTGAAACAAAGTAAAGTTCTGCTCAAATGAGAATGACACTAACTAAATGA
AAAGGCCGGTTATAATTCTGTAATTTTGTGCCTGCAATGTGTGTGTTATTGTACACTTGA
ATCGGCCCTGTGCATTGTGGCGAGGTGCATATTGCATGGTTGTATTGAAAAGGTGCTTGG
GCCGGGCGTGGTGGCTCACACCTGTAATCCCAGCAATTTGGGAGGCTGAGGCAGCTGGAT
TACCTGAGGTTAGGAGTTCAAGACCAGCCTGGCCAACATGGTGAAACCCTGTTTCTAGTA
AAAAATACAAAAAATTAGCTGGGTGTGGTGGTGGGTGCCTGTAATACCAGCTACTAGGGA
GGCTAAGGCAGGGAGAATTGCTTAAACCTGGGAGGCAGAGGTTGCAGTGAGCTGAGATTG
TGCCACTGCACTCCAGCCTGAGTGTATCACAAAAAAAAAAAAAAAAAGGTTTTTGCCCTCT
CTCTGTGCCTGCTGCTCCCTGTTGAGTCCTATAGGCCTGAGCTGCCAGGGGGTACTGTGG
GCTGAGACTGGACATTGCAACCGACTGCAAGGCACCGTGGGACCCAGGTTGTGGATGGAC
TGTCTCTCGGGCTTTCTTCTTTCCATTCATCTTCCTCCTCTAACTCCCCTCTGTATCCAG
TATCCTTGCTCTCCATACACCTGCTTCATTCTTTTTCCTTCAGTAGATTTTTCTGCTTCT
TGACTTACAAACCCTACTTCTAGCCCCTTTCAGATATTGAAACTAGCAACTTTCAGGCTT
TGTACCAAAGTCTCAGAGATTCTCATTGACTCGGATGCCATCCATCTCTAGTCCAAAGAA
CAATGTCAAGGACATGAACATGTGGAACAAAAGTGTCTGCTGTGGACACCTTTGGGGAGA
AATAGTTTTCAGTGATGAGGGTTGTAGTGAGTTGGGCAGATATCCCAAAAATATCTGCCA
AAAACTATAGACACTTCTGGTTGCAGTGACTTATTCCTTCCTTCATTCAGCAAATACTGA
TTGAACACCGACTGTATGTCTGGATCTATTCTAGGTTTTGGGGGTGGAGCAGTGAACAAA

FIG. 10
*(continued)*

TCAGTCTTTATCTTTATAGAGTGTACAGTCAAGTGGGAGAGACAGGCAGTAAACAAAGAA
ACAGTTCAATATTCAATCTGTGAGATGGTGATAAGTGCTACAGAGAAAACAAACTAGTGT
AAGATAAAAAGGGTGTTTTGATAGGCCTTTACTATTTAGGTCTCTTTGATAAGGTGGCAT
TTGAACAAAGCTCTGAAGGAAATAATGGAGCCAACCATGCATATAACCTCAGGGAGAACA
TTCTAGGTAGAGGGAACAGCAAGTGCAAAGGCCCTGAAGTGGGGGTTTGTTTACCTTGTT
GCACAATCTGCACACAGGCCAGTACAATTGGAATGGATGGGAAATGTAAAAGAGAGAAGT
TGAAAAGGCCAGGTGCAGTGGCTCATGCCTACAATCCCAGCATTTTGGGAGGCTGAAGTG
GGAGGAATTTGAGATCAGCCTGGGCAACAGAACCAGACCTCGGGCTAATTTTTGTATTTT
TAGTAGAGACAGGGTTTCACCATATTGGCCAGGCTGATCTCAAACTCCTGACCTCAGGTG
ATCCTCCTGCCTCAGCCTCCCAAAGTGCTAGGATTACAGGTGTGAGCCATGGCCCCCAGC
CGTATCTTTGTCTTAAAAAGTAATCTCTGTGCTTGGTAGGCCAAGAATTTAAAATATAAA
AAATTTAAGAAAGAAAAAAAATAAGTAAAGTAACTATACAGGTTGGTCTGGCCGTAATGG
TGAGTGTCATTATTTTTCTTCCCTAGGTATTTTGGCTCTGTTGCTCAGAGCAGTGCAGGC
GAAATGGTCATTAGGGCATCGTCATGGTGCCTGGGGATGCCTGGCTCAGCCAGTTTATTT
TCTGTCTGCCTCTCTCCTTGGTCCTTTTCCTCCACTTTCATTCATGAAATTCTAGTCAAG
AGCTGGGTCCAGTGGTTTTCAATCCAAGGGCTTTGGAAGCCTCTGGGGTCTATTTTGGTC
ATTGCAGTCACTGGGCTGCTGCTCCTGGCATTTAGGTTGGCAGGGGTCTGGGCTGGGAAG
CAGGAATGTTCAGTGGCCATAAATGTAAGGGTTGGTCTTACATTTACATAAGGGAGACAA
TGAAAACTTAACTCCTCCACAGTAGTGGAGTAGTGCCGTTGGGTACTCACAGTCAGTAGT
GCCGTTGGGTACTCACATGTACAACATGGATCAGGACATTGACTTTCTGTGGATACCTTT
TAATAGTTTATTAGATGTGTTAGGCTGTTTTGCACTGCTCTAAAGGAATATCTGAGTCTA
GGTAATTTATAAAGACAAGAGGTTTAATTGGCTCATGGTTCTGAAGGCTGTACAAGCATG
GCTCCAGCATCTGCTTCTGGTGAGGGCCTCAGGAAGCTTCCGGTCATAGTGGAAGGCAAA
AGGAGGGCAGACGATCACATGGCCGGAGTGGTGGCAAGGGTGGGGTGGGAGCCACGCTCT
TTTTTTAATTTTATTTTAATTTGAGACAGTGTCTCACTCTTTTGCCCAGCCTGGAGTGCA
GTGGCGTGATCTCAGCTCACTGCAGCCTCTGCCTCCCAGGTTCAAGCAATTCTCCTGCCT
CAGCCTCCTGAGTAGTTGGGACTACAGGCGCGCATCACAATGCCCAGCTGATTTTTGTAT
TTTTAGCAGAGACAGGGTTTCACCATGTTGGCCAGGCTGGTCTCGGACTCCTGATCTCAA
GTAATCCGCCTGCCTCGGCCTCCCAAAGTGCTGGGATTACAGGCATGAGCCACTGCGCAC
GGCCACCACACTGTTTTAAACAACCAGATTGCACGTGAACTTAGAGTGAGAACTCACTGT
GAGGATGGCACCAAAACATTCATGAAGGATCCACCACCTTCCTTTAGGCCCCACCTCCAA
CACTGGAGGTCATATTTCAACTTGAGATTTGGAGGGGACAGACATCCAAACCGTATCATT
AAATTTAATAGTTTTATGCAGTTTTTTTGGCTCTAGATCTGTTTAGACTCCTGCAGTCAG
GTGTCTGTAACTAGCCTCTGGTCCTTTTTGAGAGTTCACAGTTTGGTGCAAACCCTTTGG
ATGTATTATTTGGGAAAATGGGATATCTGGCAGCCTGTGTCCCTGCTTTACATTATCCTT

FIG. 10 *(continued)*

TTTGCTGCCTGCCCCAAGCCTCCTCATTAGCATCCCTGCCAAGGCCAGTGGAGAAGGATG
GAGATGCGGTGACATTCAGCTTGACAGGTCATTAGCAGCTTTTGTGCCCTAGGGACTGCT
GGTGGGAGGGAGGTTGTGGAAGATAAACCCTGACAGGAATGTATTCTCCTCGAGGGCAGG
GTTTATTTGATATTTTTCTGGAGCTTAGAACCATAAGCCTGGTGCTGGGGAGGAAGCGCC
CTTAGCATTTGGTAGCCTCTGTGGGCAGAGCATGGAAAGTCACAACTTCTGAATTGTTTG
TATTTTCAGTCTCACTCTAGATGGATGGCATCTTCTGCTATGGGAAATGAAATATGTTTA
GGCAACTTGAGTCCCAGGTGCAGATGAGGCTGGGCTAATTGGTGCACTAGGGAAGGAGCC
GGGGGAGAGATGTGCTGTTAGCTATTATCAATCTGTGACAACTGTCAGCTGCTGGCAGTT
AGCACCCACCTGAGCCTGGGATGCAGGGGTGCCTCTCCTGTCCTCTGTGGAAGCCTCTGG
ACCCAGCAGCCATCTTGACTGTGCACTGTTCAAGCCCCAAGTCCGCCTGGAAGAGGTGAT
TGAGAACTTACTGCAGGATAAGGAAAGCGCAGGACAGGTGCAGTGGCTCACGCCTGTAAT
CTCAGTGCTTTGGGAGGCTGAGGCCGGAGGAGGGCTGGAGTCCTTGAGTGCGAGACCAGC
CTGGGCAACATAGTGAGACCCTGTCTTTACAAAAAGGAAAAGAATTAGCCAGATGTGGTG
GTGCGTGCCTGTAGTCCCAGCCACTCAAGAGGCTGAGGTGCGAGGATCACTTGAGCCCAG
GAGTTTGAGGTTACAGTGAGCTATGATCATACCACTGCATTCCAGCCTGGGTGAGAGAGC
ATGACTCTGTCCCAACAACAAAAAAAAAGATTAAGGGAAGCCTCTGGCAGACCTGATGAT
GGGTGGCCCAGCCAAAATGAGTATTGATGAGGATTTCCCTGGTCTGGAACTCTGAATTTA
GTCTGGCAAAGTATTCCCTTTGTGTTGTGAGATGATTCTTGGTGTTACCCCATCACGGTA
GGTAAGATGAATTAGCAAATGAGAAAGGCTTTCTCTTTTTCATCCTTATCTAGTCCGTAG
ATGAAGCCTGAAGAAGGTCTCCATATGGTAGTAGTAAGTGTTTAACATCTACCTCTAACA
CTTGCCTGTGTCTTTTTTTTTTTGCAAAGCCTCAGGAATGCCCCAGTATCTAGGTAGAAT
TTGATAATATTTCATTTTTGTTATATTCCCTTTTCTGTTTACCTTCTATATACAGCAAAA
TGAAAAAATTTTTAAAATTTGTGCAAGTAAGGGCAATTTCTTTTTTCTTTTTCTTTTTTT
TTGAGACAGGGTCTTGCTCTGGCACCCAGGCTGGAGTGCAGTGACACAATCTCGGCTCAC
TGCAACCTCTGCTTCCTGGGTTTAAGCGATTCTCCTGCCTCAGGCTTCCAAGTAGCTGGG
ATTACAGGTGCCTGCCACCACTCCCAGCTAATTTTCATATTTTTAGTAGAGACCAGGTTT
TGCCATGTTGACTGGGCTGGTCTTGAACTCCTGACCTCAGGTGATCCATCCACCTTGGCC
TCCCAAAGTGCTGGGATTATAGGCTTGAGCCACTGGGCCTGGCTGAGGCAGTTTCTTTTT
GAAATATATTTTGTGAAGGAGAAAAAGAGGAGTTCAGTTTAAAGAAACAAATGACATAAG
AGGTGGTATGCAGAGATGCCAAAGCATCTTGAAGGTGCTTTTTTTTTTGGAAACAGAGTC
TTGCTTCATTGCCCAGTCTGGTCTGCAGTGGTGCAATCATGGTTCCCTGCAGCCTTGACC
TTCTGGGCTCAAGTAATCCTCCCACCTCAGCCTCTCAAGTAGCTGGGACTACAGATGCAT
GCCACTATGTCTGGCTAATCTTTAAATTTTTTGTAGAAGCCAGCTCTCACCATATTGCCC
AGGCTGGTCTTGACCTCCTGTCCTCGAGCAAAAATACCGATTTTGATTAAGTCTGGGGTA
GGACCTGGGGCTGGGATTCTAACCAGCTCCCAGGTGGTGCTAATGCTGCTGGTCTACAGA

FIG. 10
*(continued)*

CCACACGTGGAGTAGCCAGTGTAGAGTTCATGTAGCAATAGTGATGTCATAGAAATAGCC
AGTATCTGTATACTTGCTTTGTTGTATGTCACGCACTGTATAGTGATGTACATGCATCTC
ATTTGACCCTCACCCCGCCCCTTTGGGGGTAGAAAGGATTGTGCTCATTTCACACTCAAG
GAAACTGAGGCACAGACAGGCAAAGTAGCTTGGCGAAACAGAAAGGAACTTAGAGGCAGG
CCCTGATTAGCTCAGAGACTAGAAGGCCTTGTGCGTCATCCTGAACAGCTTGGACTTGAT
CTTGAAGGTGGAGGGAGAAATTGAAGGGTAATTAAACAGGAACTGTAGGAAATTCACCTT
GCATAGTGATTGCTTTGGCCACGTGTGCCCTGCCACCGCCCCCCCACCTCAGTGAAGTGT
CATGCGAAGTTGGGTTCGTAAATGAAGGCCCGAATGCTTTCCTGACAAGTTTGTTTTAAA
TCAAGCTGCTAATTAGTCCCAGTCCCCCTCCCCCGGTATGTATTTTTTTGTTGATGTCGT
TTCACTTCATTTAGTTGAAGTGATTGATTCAGTTCAGTGTTTGAACTTCTTTTTGAACCT
CACCTTAATAACCTGTCTAAACATCAAGGTTAAACCTTCTTGCTAACACAGCAGTATTGC
TTGGTAAGACTGGCTCACAGTCCAAGGAAATGCTTGCCCAGAGAGGGCAAACTGCCTTAA
CTCCTTAACCTGAGCTCATTAAAAAAAATTCAAATGACTGATTCCTTGTCACAGTTCTAC
CTACATTGTTTTTATTTTTGTCCAGGTTTCAGCTAGTTAAATGCTTTTGTGATGAGCTTA
TGTCCAGGCTGAAGGTTGCATTTTGAAACTGAGCGTCAAATACCAATTTAAAGTCCAGAC
CTTTACACTTGTGAAATTCAGATAAATGAAATGGAAATAAAACAGGGCTGCTGTGTTGTG
AAATATGACTGTGTTTTTCCTTGTAGGACTCTTTGAGGGTAGCCATTTTGGCATTTTATA
TATAAATTTTCTTTTCTTAGCCTACCTTTTACTTTCTTGATTTGCCTATTTGTGATTTCC
CATTAAACACTAGGCTTTTTGTAAACCAATTATCCCTTGAAATTGACTTTTTTTTTTTTT
GAGACAGGATCTTGTTTTGCCACACAGGCTGGAGTGCCGTGGCTCCATCATATGATAAAC
AGAAAGAGAGAGAGAGAGAGAGAGAGAGAGAGAGAGAGAGAGACCCTGTCTTATTTAAAACA
AAAAAAGAAGAAGAAAAAAAAGAATATAGATCACAGCTGTTATTTGTATATGCTACGCCAA
TCCTTGTTGGGTTTCATTCTTTATAATTGTTATTTTAAAGATTTTTCTTATGAATATTC
TATTGTTTCATTGTAGAAAATTTAAGGGAGAACACAGTGGGAAAAAAAAAACAAGAAAAG
GACTTCATAATCCTGCTACCCTGGGAGAAAAAAAAAATCACCATTACCTATTTGGTTCTT
CTCCCACTTTTTTTTTTTTCGAGATGGAGTCTCCCTTTGTTACCCAGGCTGGAGGGCAGG
GACGTGATCTTGGCTCTCTGCAACCTCTGCCTCCTGGGTTCAAGCGATTCTCGTGCCTCA
GCCTCCCGAGTATCTGGGATTACAGGGGTGTGCCATCACACCTGGCTAATTTTTGTATTT
TTAGTAGAGACGGGGTTTTGTCATGTTGGCCAGGCTGGTTTGTTGGCCATGTCTGGTTTT
TTGTCATATTGGCCAGTCTGTTTGTCATGTCAGGCTGACATGTTTTGTCATGTTGGCCAG
GCTGGTCTTTAACTCCTGACTTCAGGTAATCCTGAAGTGCTAGGATTATAGGCGTGAGCC
ATTGCACCTGGCCTTCTGCCTTTTTTTTAAAGAAAAAAAATTAAAACATTTTTTTCTTTT
TAAGATAGCGTCTCATTTTGTTGCCCAGGCTGGTCTTGAACTCCTGGGCTCAAGTGATCC
TCCAGCCTCAGCCTCTGGAGTAGCTGGGACTACAGATGCACATCATGGTGTCCTTATGCC
ATTTCTTTTGTACGTAGGTGAATGCAAGTGTATGATTACATCATATGCTATTTTGGAGGT

FIG. 10
*(continued)*

TTGACTTTCTTTTCACTTTCATCATCTTTCCAAGGTGTTATTTTCCTAGTACATCTTTTT
AAATGGACATAGAACATTCTTTTGTATGAACAAACAATAGTTTTATTTAGGCGGTCCTTT
CCTGTTGGACATTTATATTATTTTCAGCATTTCTCCACAGTTGTTGCAGCATTCAGATGA
ACCTTCTTTTTTTTTTTTTTGAGACGGAGTCTCGCTCTTTCGCCCAGGCTGGAGTGCAG
TGGCACAATCTCTCCTCAAGTGATTCCTGTGTCACCCTCCCACGTAGCTGGGATTACAGG
TGCCCATGTCTGGCTAATTTTTGTGTTTTTGGTAGAGCTGTGGTTTTACCATGTTGGCCA
GGCTGGTTTCGAACTCCTGCCCTGAAGTGATCTGCCCACCTCAGCCTCCCAAAGTGTGGG
GATTACAGGTGTAAGCCATCACGCCTGACCCAGATGAACATTCTTGTAGCTATCGCACAC
AATTCTGAACATTTCCTAGGATGAATTCCTTAAAGAAGTAATGCTGATCCAGGCTTTTTT
CTTTTTCTGTGACTCTTTGACACGTAATAATATTGACTTTTCTTTCTTTCCAGACACTAC
AACAACAGGAGTGCAAACTTCTCTACAGCCGAAAAGAGGGTCAAAGGCAAGAAAACAAAA
ACAAAAATAGATATAAAAACATCCTGCCCTGTAAGTATCAATATTCCGCTCAGTAATAGT
CACTCTTGGAGATTTTGATTCCTAGCACCTCTGTACCTTTCCTCAGGGTCGTGTGCTCTT
GTTAGCACATCGGAGGCCTTAGCTTCTTTAATTGCAAGCAGTTTCCAAAATAATCAACCA
TGGTGGGTGTTGATGACTTCATTCACTGAGCTCCCGTGATGCTGATTACTGAGTAAAGTT
GCCACTAGGTGGCTTTGTCTGTGGTTGGTTCCTTCTGTTAATTAATTTTCTGTCTGCCCA
AGATAGATCATCTCAAGGCTTGGGATCTCTCAGTGTCAGGGACCTTAGGGTGCCAGATTT
GTGTCTTGACTCCTCCTCACTGGGCCTGTGAGTCCTGGGTAAGGCCTGCCTCCTTTCTGG
GACTCAGTTCCCTTAAGTGGGAAACAGACAAACACCTCCTGAGGGCTCCTAGAACTGTTC
TGCTTGCTGATCCCCTGAGCTCAAGTTACTGGAGAAAGGGTATATACCTAAACTGCTCAG
AAGAAGACTTTGTGGGCCGGGCGCAGTGGCTCACACCTGTAATCCCAGCACTTTCGGAGG
CCGAGGCAAGCGGATCACCTCTGATCAGGAGTTCAAGACCAGCCTGGCCAACATGGTGAA
ACCCCATCTCTACTAAAAATACAAAAATTAGCCATATGTGGTGGTGTGCGCCTGTAATCC
CAGCTACTCGGGAGGCTGAGGCGGGAAATTGGTTGAACCCAGGAGATGGAGGTTGCAGTG
AGCCGAGATGTGCCATTGCACTCCAGCCTGGGTGACAAGAGCAAAACTCCGTCTCAAAAA
AAAAAAAGGAAGACTTTGTGAATATTCGCAAAGCTGTAAAGCTGTACCTTTCAATTTTTT
TTTGAGACATAGTCTCACTCTGTTGCTCAGGGTGCAGTCACAGCTCACTGTAGCCTCAAC
CTCCTGGGCTCAAGCGATTCTCCCACCTCAGCCTCCTGATTAGCTGGGACAATAGGCAGG
CACCAGTACACCTGGTTGATTTTACAGTTTTTCTGTAGGCCGGCGCAGTGGCTTACGCCT
GTAATCCCAGCACCCTGGGAGGCCGAGGTGGGCGGATCACCTGAGGTTAGGAGTTCGAGA
GTAGCCTGGCCAACATGGTGAAACCCCATCTCTATTAAAAATTACAAAAATTAGCTGGGC
GTGGTGGTGGATGCCTGTAATCCCAGCTACTTGGGAGGCTGAGGCTGAGGCAGGAGAATC
GCTTGAACCTGGGAGGCGGAGGTTGCAATGAGCCGGAGGTGCTATGTGCACCACTGCACT
CCAGGCTGGGCGACAGAGTGAGACTCTGTCTCAAAACAAAAAACGATTTAAAAAATAATA
AAATTTTTTCTAGGGCGGGGTCTCCCTATGTTGCCCAGGCTGGTCTTGAACTCCTGGGCT

FIG. 10
*(continued)*

CAAGTAGTCCTCCTGCCTCAGCCTCCCAAACTGTTGGGATTACCAGTGCAAGCCATTGTG
CCTGGCTGTACCTTCTGTAACACCCAAATGCCACCTGGCAAAGCCCAAGTTGAATCATGA
GGAAAAAAGGCCTGGAAGGATGTAGACCTTCCTTTTTTCTACTTATTTATTTATTTATTT
TTGAGATAGGGTCTTACTCTGTTGCCCAGGCTGGAGTGCAGTGGCATGATCATGGGTCAC
TGCAGCCTCAACCTCCCGGGCTCAAGTGGTCCTTCCCACCCCAGCCTGCAATGTAGCTGG
GACTACAGGCATGTGCTACCATGCCCAGCTAATTTTTGTATTTTTTGTAATTATTTTTTT
TGTAGAGACAGGGTTTCGTCATGTTGCCTAGGCTGGTCTCGAATTCCTGGGCTCAAACGA
TCTGCCTGCATCGGCCTCCCAAAGTGTTGGGATTACAGGTGTGAACCACTGTGTCTGGCT
ATATCTTCTGTAACACCCAAATGCCACCAGGCAAAGCCCAAGTTGAACCAGGAGGGAAAA
AGGCCTGGCAGGATGTAGGCCTTGCATGAGGATCTCAGAAACTGCACTAAACCAGTCACA
GTTCCTCTCTCCCGAGGTCTAACTCTATGCTGAACTCTTTGCATTTTTATCTCACTTAAT
CCATATCACATGCACAGGAAGGAAGCATTCGTAGTATCCTGGTTTCCTAGACCATTTTAG
CAAGGTTATAAGTGAAGGGGAGTGGGTGGGAGAACTGGCACTAGAGCCCCCAAAGTCACT
GTTCTTAGCACCACTCTAATGCATGGGGTTCTCCATTGATGTGCTATGCAAGGCAGTGCA
CTGAGGAGAAAGGAAGGAACATTTACAACTTCTCTTTATTTATATCCTGTCCCTAAAAAA
AAAAGAAAAAGAAAAATTTGTCTGAGGCCTAGATTGATTGCAGGGAGTGCATAATGTTTT
ATTGATTGATTGATTGATTGTATATAGAGATGGGGGGTCTCACTATATTGCCCAGGCTGA
TCTCGAACTCCTAGGCTCAAGCAATCCTCCTGCTTTGGCTTCCCAAAGTGCTGGGATTAC
AGGCATGAGCGACTGCACCTGGCTATGCATACTATATTTATCCAACTTACAAATAAGGCT
TGCTTGCCTGTAGTGCATATGTGTATACATTTCAGCATAGAAAAACTGTGTGATTGGGGG
TTGTGATCAAATTTGGAGAGCATTGCTCTCATGTCTTATCAGGTCAGAGTCATTTTGTCA
AATCTTGTAAACCATTCTTTGTGTGTGTCTATGCATGAAACATAGTCTTTCTCTTTCTGC
ATGCATATGTACATATACATGGTATATATGTATATCATATCTACATGGATATTGTAATGT
ATATGTATGAGGATGGGGGAAAGTGGAGACATTTGTAATACTGAGAAAAGGCAGTGAGGA
ATTTGCAGAGAAGCAGTTTGAGCTGTAGCATGGTACTAGTGACCTTGAGGAAGCCTTATC
CTTTTTTTTTGGAATTTATTTTTTCAATTTTAGAAATAGACAAGAGTTTCTCTATGTTG
CCCAGGCTGGTCTTGACCTCCTGGGCCCAAACTATCCTCCTGCCTTGGCTTCCCAAAGTG
CCAGGATTACAGGTGTGGACCACCATGCCTGGCCACCTTGTCCTTTCTATGTCTAAGTTG
TGACATCTGCTCAGGGGTCAGGTGGTATTAAATGGTATAAAATGTATGGGAAAGTGAAGG
GATCAATGGTATGCAGTATCTAAATAGAATATCGCTTTTTCCTCCCTTAAAGGTCTCATT
CAGATGTTTCCTCTGATGAACATCTCATTTCCTTAAAGATGAGGAGTCTGAAGCAAAAAA
GACATTATTCTTTTAAGACACATGGCTGTCTTACTAATTCCCATTGCAAAATATGTTGTT
TAGGTAGAGCACTCAGATTTTTATACGAATAATAGACTTTTGTACAGAATTTGGACAGTT
GATACTATCAGAGCCTTGTGATATTCCACTGCATTATGCTTCACTAAAAAATACCTGGCT
GGGTGCGGTGGCTCACAACTGTAATCCCAGCACTTTGGGAGGCTGAGGTGGGCAGATCAC

FIG. 10
*(continued)*

CTGAGGTCAGGAGTTCAAGATCAGCCTGGCTAACATGGCAAAACCCCATCTCTACTAAAA
ATACAAAAATTAGCCAGATGTGGTGGCACGCTCCTGTAATCCCAGTTACTCAGGAGGCTG
AGGTATGAGAATTGCTTGAGCCCAGGAGGCAGAGGTTGCAGAGAGCCGAGATAGTGCTAT
TGCACTCCAACCTGGGTGACAGAGGAAAACCCTGTCTCAAAAAATAAATTTAAAACAACA
ACAACAACAACAACAAAAACCCCTCTTTATTATGGAAATTTTCAAATATATTCAAGAGCA
TAAAGAACCCACATGTACCCATCACCCAGCTTCAACAATTATCAACTCATGCCCAGTCTT
GGTTTCATCTATACTCTGATCCACATCTCCTCTCTCCTTGAATTATTTTGAAGCCCATCT
CAGACATCATGTCATATATGTATACTTCAATCTTCTTTTTTTTTAAAACTCCCCCTCCCC
TTTTCTTTTTTCTTGAGACTGTGTCTCACTCTGTCATCCAGGCTGGAGTGATCTTGGCTC
ACTGCAATGTCCGCCTCTCGGGTTCAAGCGATTTTTGTACCTCAGCCTCCCTAGTAGCTA
GGATTACAGATGTGGACCAACATGCCTGGCTAATTTTTGTATTTTTAATAGAGACAGGGT
TTTGTCATGTTGGCCAGGCTGGTCTTGACCTCCTGACCTCATATGATCCACCTGCCTTGG
CCTCCCAAAGTGCTGAAATTATAGGCCACTGCGCCCAGCCCAAAATTTCTTGGTTTGAAA
TAATTTTGGAACTCATAAGAAGTTACACATATAGTAGAGAGAATTTTCTTGTACCTTCTC
TGAGCTTCCTATATACCCAATGATAACATCCTATATACCCATAGTATATGATCAAAACTA
GGAAATTGTGAAGATGGCATTTTGAGACATCAGGCAGTGTTCACGTTACTGTTTTGCTTA
CCTGGGCTTTAATTTTTATGTGTTTTTTTTTCAATCATTGAATGAACAAAACTTGGACTA
GGCTGGGGAGTAACTGATTTGAACTGTTTTTTCCTGAAGCAGTCCAGGACTTATGTGACC
GTGGTCTCTTTTTCTTCTAGTTGATCATACCAGGGTTGTCCTACACGATGGTGATCCCAA
TGAGCCTGTTTCAGATTACATCAATGCAAATATCATCATGGTAAGCTTTGCTTTTCACAG
TGTTTTCTGACCATACATTTCTAGCCTATTTTTGTATTTTAAATCCTTCCTCATGTCCTG
AAAGTAACTTTAAGGTGTTTGAAGGATTTTCTTCCTAAATTTCTAGCCTGAATTTGAAAC
CAAGTGCAACAATTCAAAGCCCAAAAAGAGTTACATTGCCACACAAGGCTGCCTGCAAAA
CACGGTGAATGACTTTTGGCGGATGGTGTTCCAAGAAAACTCCCGAGTGATTGTCATGAC
AACGAAAGAAGTGGAGAGAGGAAAGGTAAATCACAGAAACTTCTTTTCTGCTAAACTGTT
TTTAAAGTATCAGACATGTCAGATTGGCCATGTTTAGGAATTGAATAAATGAATTAAGCT
TACTGTAACTGATTCTCTGGAAAAAAGGGACTAGGAGAAATTTGATTATGTTATTCCTTG
GTGTAGTTTTCTTTATGTTTCTTCTGCTTGGGATTTGTTGAGCTTCTTGGCTCCATGGAT
TTGTAGTTTTCCTTAAATTTGGATAATGTTCAGTCTTAGTTTCTTCAGATACATATCCTG
GGCTGGGCATGGTGGCTCATGCCTGTAGTCCCAGCACTGTGGGGTGTTGAGGTGGGCGGA
TCACTTGAGGTCAGGAGTTTGAGACCAGCCTGGGCAATGTAGTAAGACCCCATCTCTTAA
AAAAAAAAAATGTACCCTGCACAACCTTGTCCTAGGACAGCAGTCATACGTGTATTAGAC
TACTTGAAGTTGTCTCATAGCCCACTGATACTTGGTTTATTTTATTCAGTTTTTTCTCCC
CGTGTTTCATTTCGAATAGCTTCTTTTGCTATGTCTCCAAGTTAATCTTCTGCAATATGT
CATCCGCTCTTAATCCTATCCAGAGTATTTTTCATCACAGACATTGTATTTTTCATCTCT

FIG. 10
*(continued)*

AGAAGTGTTAATGTCATCTATAGCTTTCCTTTTAACATGTGTAGCATTTTCCTTACCTTT
TGAATGTATGGAGTATTTCTGTTGTTGTTTTTTGTTTTGTAGAGACAGGGTCTCGGTCTG
TTGCCCAGGCCGGAGTGCAGTGGCATGATCTCAGCTCACTGCAGCCTCTGCCTCCCGGTT
CAAATGATTCTCATGCCTCAGCCTCCCAAGTAGCTGGGACTACAGGTGCGTGCCACCACG
CCTGGCTAATTTTTGTATTTTTAGTAGAGATGGGGTTTTGCCATGTTGGCCAGGCTGGTT
TTGGAACCCCTGAGCTTAGGTGATCCACCTTCCTTGACCTCCCAAAGTGTTGGGATTATA
GGTGTGAGCCACCATGCCTGGCCATGTTGTCTGTTTTAATTAACTCTGCCTAACTGTCCT
CCCAAATGGTTGCTGCAGTGCTCACTCCCACCAGCAGCACCTGCCTAGGACTCATTACTC
CATACTCTTCAAGACACTTCAGATTAAAAAAATAAATTGTAACACCCCACACCTACAGAA
GAGCGGACAGATCTTATTGAGTGACAGCCCTCTGTGTTATCTCAAAGTGAGCCCACCATG
GTGGTTTTTTTTTTAAATATGGAAAAGTTCTGTGTTTTTGTTTGTGTTCTAGTGAAAGTT
CTTTTTTAGATATCCTTTAATTGGTTTATATAAGATTTTATGTGGAATGTAGCAGTCATA
CCTATAAATTAAACCTAAGGCAGATGGAGAACTTTGGAGTTGAGCCTTCCTACTGTAATT
TTCATATTGGATGTGAAGGGCAGTGTGATTTTCATAAGACTTTCATTGTTGTACTCCTAG
TTGGTATACTTCTGAATACCTTTGAGGCCAGTTCTGGTCATCGTGAAACAAAGGTTTCCT
TCAGCAAATGCCTGTGGTAACATTAGGTGTTCTTGAATTAATGGACCAATGAAAACATCT
TTGTAGTTTCTGCTTCAGGCAAGGGTTTTTTGCCCTAAATGTGGATAGGAAGAATGAAGC
CCTTCATCCTCCTTTTTGCCTGATTATAGCTATAGGAGGTTCACCTGTTCTCAGAAGACA
TGAGGATTGTGAAGAGAGGGGTCTTGTGTTGCTTCAGAGGAATCAGTATCAGTCCCTTTC
AGAAGCTCTCCTGGATAGACAGGCATTAGGGCCAAATCACTCTGCCCCACCCCTCACCAC
CATGTCCTACTCTCTGCTCCCTGTCTCATTCTTCCTCTTTACTTTGGTGGTGCCGAGAGG
ATGACATGATGGGTATTGATTCTCTCCACAGACCTTTCTGACATCCTACTTTCAGTATCC
CCCCAGTGCACAGAAGACAAGCCAGACTGTGGACTGTGTTTGATTCCTGGGCTCTATTTT
AAAAGACAGTGTATTAGTTCTCACATTTTAGAATTTGTTTGCCAAGGTTTCCACGGGAGT
TTAGAAACTAGGGGGAGGGCTGATGTTTAAAGTTAGCTAAAATGTTCTTTTCAGGGTCAT
GATTTAATTTTATATTCTCTGGTGAGTTCCCTATAGTGACTGGGAGCAGTCCTCAGTCTT
GATTGGCCAGTGACAGCATAGAGTACAATTAATATTAGGAGTGCTCATTTGGGGAAACTA
AAATTTGCATCAAATCTGTCAGAGGTGTTTGGATCTACAAAATACCGGAGGGAAAGCTGA
ATTGAGAATCATAATAAATAAAAGACCACATCGTTCTTTTTTTTTTTTTTTTTTGGGACT
GTATCTTGCTCTGTCACTCAGGCTGCAGTGCAGTGGCACTATCTTGGATCACTGCAGGCT
CCGCCTCCCGGATTCAAGCGATTTTCCTGCCTCAGTGCCTGAGTAGCTGGGATTACAGGC
GTGTGCCACTACACCTGGCTAATTTTTGTAATTTTAGTAGAGACAGGTTTCACCATGTTG
GCCAGGCTGGTCTCAAACTCCTGGCCTCAAGTGATCCACCCGGCTTCCCAAAGTGCTGGG
ATTACAGGCGTGAGCCACTGCGCCCAACCAAGACCACATCCTTTTATTGAACGTTCCTCC
TACCATGTTTTCTTTTTTCTTTCAATTAATCATTGACTCATTGACTCTCACTGTTGATGT

FIG. 10
*(continued)*

CTGTAGCTGCTCTCTTATTTCCAGTTTTATAGCTGTAAATTTCTCTGTCTTCCTAAGATA
CAAGGTAAATTTCTCTTGCTGATATTGGTGGTTTTGGAAAGTGAGTGGTGTGGATGACTG
CCCAGAAAACAACAGAACACAAAAGCATTCTCTGCCCAGAACACATCACCAAATAGATAC
AAACTCATCTCTTACTGAGTGAAATAGCTTCCTTTTTGGCAGCAAGAATGATTTTCTTGG
TGCCATATTTTTCAATCCGCCTGCTCTTGAAGCCAGCAGCTATTGCAGACTTGGCATTCC
CAGGCACCCAGTTAAGGGAAAGTGACGTGTAGAGGAGGTATCAGATGGGTCTGGATATAG
AAAAAGCAGCTGGTTCAAAACCCCATGGGCTGCCTTTCTGTGATAGAGTTATTCACACTT
GGGTTAGATAAGGCACAGAGTCCTCCTACACTGGTGCGGAAATGAAACAGACAGTCTGGC
TCGTTGGGCAGCCTAGCCTCCTCCAGAATCTGTGCTTGCCTTCCCTATGGAGTGACTGGT
AGATCTTAGAATTCAGACCTCAGTGGTTGCTAGCCAGCACTCTCACATTGGTTGGTCCTT
CTCTCTGCATCTTTGATTCTTTAGAGATAGATAAACCAAGCACCGACTCTCCTTTGACAT
GTGCTTGGAACAGACACCTGCACGAGCTGCCTTTCTCCTCCCACTTCTGCCTGGTCTTCC
AAACACCTGCTTTTCTTGTTTGAACTCTTCCTTTTTTTTGAGACAGAACCTCTCTCTGT
CACCCAGGCTGGAGTGCAGTGGCATGATCTCAGCTCACTGCAACCTCTGCCTCCCAGGTT
CAAATAATTCTCCTGCCTCAGCCTCCCAAGTAGCTGGGATTACAGGTGCCTGCTATCACG
CCTGGCTAATTTTTGTATTTTTAGTAGAGACACGGTTTCACCATTTGGCCAGGTTGGTCT
CAAACCTCTGGTCTCAAGTGATCTGCCCGCCTCGGCCACCCGAACTGCTGGGATTACAGG
CATGAGCCACTGCGCCCCAGCTGATTCTTTACAGATAAACAAACATTGACTCTGCTTTGA
CATGTGCTTGGATCAGGTAACTGCACCAGCTGCCTTTCTCCTCCCACTTCTGCCTGGTCC
TCCGAATGCCTGCTTTTCTTATTTGAACTCTTCTGTCCTTTTCTGAAAACCTAACAGATG
CGAAACAGGCCATTTTCCATGTTGGTGGTTATTAAGCAAGACTTGAACATTTGTTTGTTG
CTTGTTTAGGCTTTTATTTCAGAGTTCACAGAATTAACTTTCTTTTTTTCTGATCTCTTC
CAGAGTAAATGTGTCAAATACTGGCCTGATGAGTATGCTCTAAAAGAATATGGCGTCATG
CGTGTTAGGAACGTCAAAGAAAGCGCCGCTCATGACTATACGCTAAGAGAACTTAAACTT
TCAAAGGTTGGACAAGTAAGTATATTGTCGTATTCTAGAGACTTTGGGAACTGTTGATGG
TGTGTAGGAATTCAGGGTCTTGCCGTTACTCATGTTTGCATACATGCATGCATTCGCTCA
CTCATTGATTCAGTAGCCATTTATTAGCTTCCTTCTATGTGCCAGGTACAGTTTAAGCAG
TACTGGTACATTGTGAACAAGGCAGGTAGTGTTCCTGCCCTCATCGAGCCTAGGGAGATA
GACAATTTAAAAACAAATAACTGGCCAGGCGCCGTGGCTCAGGCCTGTAATCCCAGCACT
TTGGGAGGCTGAGGTGGGTGGATCGCTTGAGCCGGGGAGTTCGAGACCAGCCCTGGGTGG
GAGACTGGGATAGGGTGACCTGAGTGGCTACAAGGTCTGTTAGGAGGCCTCCGCAGGGGC
CTATGTTGATGGCCTCCTCTCCAAGTATCCACAGACTTCAGCAGTTGTTCTTTTTTGTTC
CTTCCTTTGGAATGGAATATTATATAAAATGGCAGAATAAACTGGAAGAGAAGCAGTAGA
TGTGAGAGGTGCCGGGGGGTGAAGTCTGCAGGATGTGGGGATTGTTTGGCTTTTGGAGGA
GGAAGGAGGGATTCAAGACACATTGTAGAGGTTTGAGTCTGAGCGGACAGTGGTGCTGTG

FIG. 10
*(continued)*

GCAGACACCACAAAAGCTGGAAGGAGAACTGATGTGGGCAGTGATTTGTTTTCTTCTGGA
TGTGTTCAGCTGGGCATCTGAACAGTCATGTGGACATTCATCTATTCATTCAGAGATATT
TGTTCAATGACCTCTTGGTTCCTGGCACCATGCTGCTTGCTGGAGATAGAGCTGGGGAAC
AAAACAGATGGAATCCCTGCACTCCCAAGTGTACACTATACTGGCCAGTAATCTACCAGC
CCAGTAATTGCACATATAAATATATCATTATAAACTGTAATCAGGGCTAGAAAGAAAAAA
TGCAGGAGTTTAGGGTTCATTTGGAGGGGGAAGGGACTTTTTTTTTTTTTTTTTGAAAC
AGAATCTTGTTCTGTCACCCAGACTGGAGTGCACTGGTGCATTCACGGCTCACTGCAGCC
ACAACCTCCTAAGCTCAAGTGATCCTCTCACCTCAGCCTCCCATGTAGCTGGGGGCTACA
GGTGTGTGCCACCATGCCCACCCAATTGTTAAATTTTTTATAGAGACGGTTGTCTCATTA
TGTTGCCCAGGCTGGTCTTGAACTCCTGGGCTTAAGCGATCCTGCTGCCACATGCAGCCT
CCCAAGGTGCTGGAATTACAGGCGTGAGCCAGCGCACCCGGCCAAGGGAGGGGAGGTTCT
TAAGGCATAGGGAACAATGTGTTTGAGTCAGCAAAGGAGGTTGTGGGGGTTTGTCCTAAG
TGTGGTAAGCAGCCAGAGTTGGATTTAAGTTTTTAAGAGATTCCCCTCCACCCTGTAGAG
ACTGGAGGGGGCAGGAGTTGTTCTAGGGATTAGGACCAATTTGGAGGTAGTGCAGCCGTC
AGAGTAAAAAATAATAGGGATTGAACTAGGCCAGTGCCCAGGGTGCCTGAAAGAAGAGGA
CCCAGTAGAGCTGACTGGAGGCAGACATGCAGGGATTCAGTGAAGGAGTGTACCAAGGGC
GAGGGTGGTGTGCAGGGTGACTGGCAATTTTCTAGCTTGAGAAAGGTCCGGGGGGATGGC
AGTGGAGTTGAGGAAGCTGGGAGGATCAAGGACCTTTTTGTGAACACACAAAGTTTGAGA
TGCCTTGGACACATTGAAGTGGAGCGGTCAGGGAGGCAAGGGTGGAGGTGGGATGCGGAG
GGGAGGTGGGATGCAGAGCGTCGTGGATGGATCAGTTTTGCTCGATAGAGGGACATGTTT
TTCTGTGGCAACAGGAGGGCAAAAGGAGAAGGTGGCCACAGATGCCGGTAGATGAGCTGA
GAGTGATTGTATTCCCTATCCTCTCGGAAGCTTGAGGCAAGGCCATCAACAGACAATCAG
AGGGAATAAGAAGAGATAGAATATATGAAGAAAGGGAGAAAAGATGAAATCGTAATTGTG
TAGCAGGGCAAGAAGTCCAGAAATTTCTGTGCTGTGCCAAGTTCCCAGTTGAGGCGGTGA
ACATGAAAATATACTGATACCCATTGCCTGGTTTTTCTCCAAGGACACTTGGCTCCTAGG
GCACAAAACAGAAAGTACGTGGTTTGTCCAGGCCGAGGGCTTTGCATAGTTGCAGTGGAT
GGAGAGGAGGTCAAGGAATGGAGGCACATGGTAGAGAGAGACTGTCCCCAGAGCACGGGG
ACTCCTGGCCGGATGAGGGGGACAGGGGCAGGAGGAGGCAGGTGGAAAGTAGAGGGAGGG
CTCAGTGGTCTGGAGGCTACAGGAAGTGACGGGGGGACCAGAAGGAGCTGGAAACCAGTG
TGGTTGTGGCCCAGGGTGGGATGTTTGGATTTCTGATGTCAGAGAGGGTCCAGTCCTTCT
GATGATGGGGAGGGGTGGAGGCTGAATCTATGGTAGAGATAGTGAGAGGAACTGGAACAA
TGTAGCTGTCAAGTGGAAATGGGAGAAAGGGCTGGGCGTGGTGGCTCACGCCTGTAATCC
CAGCATATTGGGAGGCTGAGGCAAGAGGATCGTGTTAGCTCAGGAGTTCTGGGCTGCATT
GAGCTGTGATTGTGCCACTGCACTCCAGCCTTGGCAACAGAGTGCCCAGTTAAAAATAAA
AATAAAATAAAATAAAAAAATTAAAAAAAAAAGAAGAAGAAAAAAGAGAAAAGTGTCCTT

FIG. 10
*(continued)*

TTACATCCCTTTTAAAAATGTCACTTAAGGCTGGGCAAAGTGGCTCATGCCTGTAATCCC
TGCACTTTGGGAGGCTGAAGTGGGTGGATTACTTGAGGTCAGGAGTACAAGACCAGCCTG
GCCAACATGGCGAAACTCCTTCTCTACTAAAATTAGCTGGATGTGGTACATGCCTGTAGT
CCCAGCTACTCGGGAGTCGAGTCTGAGGCCCAAGAATTGCTTGAATCGGGGAGGCGTAGG
TTGCAGTGAGCTGTGATCAGGTCACTGTGCACCAGCCTGGATGACAGAGTGAGACTCTGT
CTCAAAAAAAAAAGTCACTTAGCTTAGATTGTCTCTACATATATAGGAAGAAGATGTAGG
AATGAATGGTGCTGCTACAATTACGTCATCTGGATAGACCCAGAAACATGATACTTTTTG
GTTTTCTGTAGCCTTGGTGCCATTGTTGATCTTTATTAATTATCATTATCCTCAAAATAG
CCATAATGTGCTGAGTCTCTTCCTATTTGCTGGGCAGAGGCTGAGTATTTCAGCGAGCTC
ACTGAGTCCTTAAAATTGCATTATGATAGAGAGAAAGAGATTATTATTTGCATTTTGCAA
AATGAAGAAATTGAGGTTTAGAGATACCCAAGGGCCACGTGAGTGTGAGTGCCTGGAATT
GGAGCCTAAATCTAGTCATCTGATAGCAAAGCCTGTTTTCTTATCTGCTTTGCATTAAAT
ATAAGTTTAAAATAGAACAATACTGGCCAGGCTGGGTGGCTCACGCCTGTAATCCCAGCA
CTTTGGGAGGTCGAGGCAGGCAGATCACCTGAGGTCAGGAGTTTGCAACCAGCCTGGCCA
ATATGGCGAAAGAAACCCCATCGCTACTAAAAATACAAAAATTAGCCAGGCATGGTGATG
TGTGCCTGTAATCCCAGCTACTTGGGAGGCTGAGGCAGGAGAATGGCTTGAACCCGGGAG
GCAGAGGTTGCAGTGAGCCAAGATCACGCCACTGCACTCCAGCCTGGGCAACAGAGTAAG
ACTCTGTCTTGGAAAAAAAAAAAAAAAAAGAATGATACTATAGTCTGTGTTTATATGGTGG
GGAAGGTTGAGTATCAAAAAAATAACAAAGAGGAATGAATGTCTTAAGTGAATGCCTGTT
TCCCCATCTGCTTCCTCTTCTGCTGGGAGGAGAGACCTGGATCCCTAGAGGTTTCAGTTG
CCTCCAGAGCTGAGTGCCACAGGGATGCAGGGGAATAGGGATGTTACCTGTCGCTGGTAA
TTCAGAGAGATGATTCAGGGTATAGTTACCTGAAAGAACAAATTGCCATGCCAGACGTCT
TGGTTCTTATGACAGAGGCAAAGAGTTGCCTCCAGGATTGCCCAAAAGGAGACGAGTTCT
GGGAACCTCACGAAGAGGACCTTTCAGTGGAACCTGGGGAGATTCTCTTCCTCTCCATTG
GATTTAGGAAAGCTTAGAACCGGGTGATTCCTCAACCTCTTGATTTATTTAATTCTTTTC
TGGTTTTTCTTGGCTCTACTCCAGGGGAATACGGAGAGAACGGTCTGGCAATACCACTTT
CGGACCTGGCCGGACCACGGCGTGCCCAGCGACCCTGGGGGCGTGCTGGACTTCCTGGAG
GAGGTGCACCATAAGCAGGAGAGCATCATGGATGCAGGCCCGGTCCGTGGTGCACTGCAGG
TGACAGCTCCTGCTGCCCCTCTAGGCCACAGCCTGTCCCTGTCTCCTAGCGCCCAGGGCT
TGCTTTTACCTACCCACTCCTAGCTCTTTAACTGTAGGAAGAATTTAATATCTGTTTGAG
GCATAGAGCAACTGCATTGAGGGACATTTTGATCCCAAGGCATATTTCTCCTAGACCCTA
CAGCACTGCCATTGGCCATGGCCATGGCAACATGCTCAGTTAAAACAGCAAAGACTAAGT
CAGCATTATCTCTGAGTCCACCAGAAGTTGTGCATTAAACAACTTCATCCTGGCTCTGCA
GTTTCTCCTTATTCTTCATGATGTTTGCTTTGTAGCTGTTGACTGCTTTGTAGGTATTGA
GGTGGTGGGGGTGTGGTGGAAATAGGCCTGACTCTTGAGGATCCCTTAAGTCATTTTTGC

FIG. 10
*(continued)*

TTGGTTCTCTTTTTCCTTCTTTTCTTCTACTCTTCTATGATTCATCTCTTTGATTGTGAT
TCTGTTCTCTCTCTCTCTCTCTTTTTTTTTTTTCGTTTTGAGACAGAGTCTTGTTTT
GTTGCCCAGGCTAGAGTGCAGTGGTGCCATCTTGGCTCACTGCAACCTCCGCCTCCCGGG
TTCAGGCCATTCTCCTGCCTCAGCCTCCCAAGTAGCTGGGATTACAGGCATCTGACACTA
CGCCCGGCTAATTTTTGTATTTTAATAGAGACAAGGTTTTGTCATGTTGGCCAGGCTGGT
CTCGAACCCTTGACCTCAGGTGATCCACCTGCCTTGTCCTTCCAAAGTGCTGGGATTACA
GGTATGAGCTACCATGCCCGGCCCATTCTGTTCTCTTCTACCATAAATATATTTCTCCCC
TAACACTATATTTGTTTGCTTCACAAGATTCCAGCTGCTTTTCCACCAAGGCCTTTGATG
GAAGCTGTGCTGTGACCTCTGTAATGAGTCTGTGGGCTGCTGATTCTCCAGTTTGGGCTT
CATGATTATACTGGGGAATATTGGGTTTCCTAAATCTCATTCATTTCTTGGGCAAGTAGA
TATATGTGAAAGTGTTTATTTGTCCAGTTGTTAAAGAAGCTACCATTTATTGAGCCAGCC
TCTGAGCACAATGTTTTTTGTTTTGTTTTGTTTTTAATTTTTAAAATTATTTACTTCTTC
TATTTCAATAACTTTATTATTATTATTTTTTGAGACAGAGTCTCACTCTGTCACCCAGGC
TAGAGTGCAATTGAGCGATCTTAGCTCACTGCAACCTCTGCTTTCTGGGTTCAAGCAATT
CTCATGTCTCAGCCTCCCGAGTAGCTGGGATTACTGGTACGTGACAACATGCCTGGCTAA
TTTTTGTGTTTTTAGTAGAGACGAGGTTTTGCTATGTTGGCCAGGCTGGTCTGGAACTCC
TGGCCCCAAGTGATCCTCCTGCCTCGGCCTCCCAAAGTGCTGGTATTATAGGTGAGAGCC
ACTGCGCCCGGCCCTCTTTCAGTAATTTTGATGTATTTTTTTGTATATGATTCCTGTTTC
ATTCTGTCCAACCAGCACTCTGTATGGTATGTGCTGTTGTCCCCATTTCACAGATGCAGA
AATTAAGGGTCAGAGAGGTTAAGGGACTTACCTCAGGCACGTTGTACTGGAGAAGCTGAA
CTCCAAGAGCAGGTTTGGGCTGACTCCAAAGCCCTATGCTTTTTGCCAACATATTTTCAA
ACATAAATAGACAATTTTATAAATAGCTCCAAAGAGTAGACATTGTTTCTGTTGATATTA
ATGGCTTGGTTTTGAGTCTGAAACCCCCATGAATGATTCTGTTGTCCCTGCTTTTTGTCC
TTCTGCCCGCAGTGCTGGAATTGGCCGGACAGGGACGTTCATTGTGATTGATATTCTTAT
TGACATCATCAGAGAGAAAGGTGGGTCATCTGGTGGGCAAGAAGCGACAGTTTCTGTTTT
TAGTTTATGGAAGGAAAGTGCTCACGAAAACAGTCTGGGGAAGAGAGGTTGAATGGGAAA
ATTCTTTCACAAAAATCTGGGCTGAAGACTTCAGTGTGTCTGCCTGAGAACAGAAGTGAC
ACTATTTGAGCTTTTGGCATAAAATGAAGTCTAGGAGCTGCAGAACCCACTGCCATGGCC
TTTTGTTGCATACACAGTGGTGGTCTCTATCCAGCCACCTGACCTTGTTTACAGTATGGG
GTGATTTGTTGGCAAGTGAGGGAATCCTGACTTCTGCCACTTCGTTATTTATGTAGTCTT
CTGGGATCATTGGTATTGGTCAGAAGTTCAACACTGTAGCCATTGCAACATGCTCAGTTA
AAACAGCAAAGACTAAATTAGCATTGTCTCTGAGTCCACTAAAAGTTGTGCATTAAACAA
CTTCATCCTGGCTCTGCAGTTTCTCTTTATTCTTCATGATGTTTCCTTCGTACGTGTTGA
CTGCGATATTGACGTTCCCAAAACCATCCAGATGGTGCGGTCTCAGAGGTCAGGGATGGT
CCAGACAGAAGCACAGTACCGATTTATCTATATGGCGGTCCAGCATTATATTGAAACACT

FIG. 10
*(continued)*

ACAGCGCAGGATTGAAGAAGAGCAGGTACCAGCCTGAGGGCTGGCATGCGGATTCTCATT
CTCTTGCTAGGCCTCTTGGATACGCTCTCCTTTTGAGCAGGAGGACAGGCTCTGATAGAC
AACTGTTTGATTTCGGAATGGGAAACAAACTCCCAACTAAAAGGGCCTCTGGAAACTGTC
AATTATTCTCCACTTCTCAGCTCTGATTTTTCACTGCAGAGGAGCTTAGGGAAGGGCACC
ATCCTATCAGCCTGGCCTGCCAGATTGAAGAACTGCCATGCAGAAAGGTTCTGATGTTCT
CAGGCTCATGTGGCAAGCGTAAAACTCAAAGCCTTGAAGTTTCTAGCCTGTTCCAGCCTT
GATCCAGGCCATGTTTATCCTGATTCCATCCTTTAAAACGAATGCCTCACTCTTAATAGC
GCACGGCAGTTTGAACCACTAATTTGGTCGAGTTGGAAACAGTGAAATTTCAATTTTAAT
AAGCTGTGCATAATGAAGAGGAATGTGGAATTGGAGCCTTTCCATCTGAAGCTATTCATA
ACAGGCACAAAGCTGAGTTAATTAGGAATATGCTGAGATGAAGGAAATGAGGAGAGCTGC
TCTTTTGGGGGCTGTGCTTCTCTCCCCAACCCCTCAACCCCATTGCCATGCTGCAGATGG
GGTGGTGTCTAAACATCAGTGGCGAGTGCCTGCATTACTCTGCTCGTTGCCTTCCAGAGA
ACTCAGCTTCTCCAAATGCTGAGCTCTTTTCAGAATGGGACCTGCCACCAGTATTTGAAA
GATTTCTAGCCTAGCAGAACAGCAGCCACGTTATCAAAGTTTGGTTGGCCAAAGGAAGGT
ACTTGCTAATTAGTTTAGTAGGTTTTCAGTCCGCACAGACATACGGGATTGTTTTATTGT
ACATAGACATCTTCAGAAACAGTGTATGTATAGAAATGTAAGGTCAAAATTTGAACCTCA
GTGCTTTAAATCTGAATTTGTATTAACTGATATGAAATATTTAGACGGTTACTTTATTTT
ATATCTGTCTTCCATTATACTTAATTTGGCTCAAGAATAGTTAGGCAAAAAGTTGCCCAA
AGAGAAGGATCTCCTAGTAAATACAAAGAGAATGTAACATAGTTGCTACAAGTTGGAGCA
TGTTCAGGGATGTCTTTTTTTTTTTTTTTTTTTGAGAGAGAGGTCTCTCTCTGTTGCCCA
GGCTGGAGTGCAGTGGTGTAATCATGGCTCACTGCAGCCTCAATCTCCCAGGCTTAAGCG
ATCCTCCCACCTCAGCCTCCCAAGTAGCTGGGACTATAGGCATGCGCCACCACACCTAGC
TAATTTTCGCATTTTTTGTAGTGTCACAGTTTCGCCATGTTGCCCAGGCTAGTCTCGAAT
TCCTAGGCTCAAGCAGTGCTTCTGCCTCAGCCTCTCTGAGTAGTTAGGACTACAAATTTG
TGGCTCCATGCCCGGCTAATTTTTTTATCTTTATTTTGTAGAGACAAGGTCTCACTGTGT
TGCCCAGGCTAGTCTTGAACTCCTGGGCTCAAACAACCCTCCCACTTTGGGTTTCCAAAG
TGCTGGGATTACAAGTGTGAGCCACTGAGCCCAGTGACCTCTGGGTTTTAAAAATGTGTA
GGCTTCAATTATTTATTTTAAAAAATGAAATCCTGCAATATATAGTTTTCTGCGTTGTGT
GGTTTGAATCAATCTGGGAACTGGCTTGCTGGCTGATTGTGGTAAAGTAAGAAGTACTTA
ATTTAGTAGAAAGTTTAAATGGCAGACATAACATTAAACCCAGCTGATTTATAAATGAAG
CAAAAGAACAAAACTCATTCAGGATAATTGGTTATTCTAAAATACAGTCATTTCTAAAAT
TATGAAGTGTTCAGGACCTTTGGGAGTGAAAGAATTTGCTAAAGAAGGATCAGTGAAAAA
AAGGAATGATGGGTGAAGAGCTGTGGAGAAGGAAGAGAAGAAACAGCACAAGGAAGGAAG
AATATAAAATCAGATGTGGGAATCCAGGGGAAAGTGCAAACGAAGCAAGATTGAGAAAAT
TCTCAAGTTTTTATAAACAGTTCTCACACTCTGCCAGTTCCTTGGAGGTAGACTTTTTTG

FIG. 10 *(continued)*

TTAACTTCCAACTACAGTAGTGAAAAAAAAAAAAAAACCCTCAAATTTGCAAAAGCAGTC
TGTGGAATTTTCTTTACCCAGCTTTCCTGACTGTTAACTTTTTAGCACACTTAACTTTAT
CATTCGTTTATTCTCTCTGTTTAAAATTAAAAATGTAAATTTTAAAAAGTAAAATGTTTG
TTGGTTACAAACATTTATACCCCTTTGTCTCTAAATATCATTTCATTTTAAAAAATGAAT
AATCTAAGCCTACACATTCTAAAATGTGTATATTTTCTAAAAATAAGGGCATTCTCTTAC
ATAACCAATGTCACAATTATTTGATACAGTGATCAAAATCAGGAAACTAACATTGATATA
ACACTATTATCTAACCTACAGACCATCTTCAAATTTTGTCCTGCTAGTATCTTTTATGGG
TCCAGGGTCACACAGTGCATTTGGCTATAATGTATCTTTTTTCTCTTTTTTTGAGACAGG
GTCTCACTTTGTTGCCCAGGTTGGAGTGCAGTGGTGCAATTATGGCTCACGGCAGCCTTG
ACCTCCTTGGGCTCAGGTGATCCTCCCACCTCAGCCTCTCGAGTAGCTGGAGACCACAGG
TGTGCACCACCATGCCTGGCTAAGTTTTGTATTTTTTGTAGAGATGGAGCTTCGCCGTGT
TGCCCCGGCTGGCCTTGAACTCCTGGGCTCAAGTGACCCTCCCGCCTTGGCCTCCCAAAG
TGCTGGGATTACAGGCGTGAGTCACCACACCTGGCCAGTTATTAGTATGTTTAGTCTCTT
TAATCTGGAACAGTTTCTCAGTCATTCTTTATTTTTCATGACCTGGATGTTTTTGAAGAG
TTTAGGCCAGCTATTTAGCAGAATGCCTTTCAGTTTGGATTTGTCCAGTGTTTTCTCTTG
ACTATATTCTAGTCATGCATTTTTGGCAGGACTGTCACAGAAATGTTGTTGTAGTCTTCT
TAGTACATCACATCAGGTACACACTGTTGATCTGATTCATTACTAGTGGTGTTAACTTTG
ATCACTTGAATAAGGTGGTGTCTGTCAAATTTGTCCACCGTAAAGTTACTTGAGCAAAAC
GTAGCTGGGACTACAGGCGTAGCAAAAAAATGTAGCAAAAAGTAGTATTTTTGCTACATTT
TTTTTTTAGGAACAAAGTATTTTTCCCTTTTAAGTTAATCTCTTGTCCATAAAGTTATTA
TTTTTCCCTTTTAAGTTAATATCTTGTGGGTAGATACTGGAGACTGCGTAAATTACCTAT
TTCTCATAATACTTTTTTTTTTTTTGAGATGGAGTCTCGCACCGTCTCCCAGGCTGGAGT
GCAGTGGTGCAATCTCGGGTCACTGCAAGCTCCACCTCCCGGGTTGACGCCATTCTCCTG
CCTCAGCCTCCCAAGTAGTTGGGACTACAGGCGCCCGCCATCACACCTGGCTAATTTTTT
GTATTTTTAGTAGAGACGGGGTCTCACCGTGTTAGCCAGGATGGTCTTGATCTCCTGACC
TTGTGATCTGCCCGCCTTGGCCTCCCAAAGTGCTGGGATTACAGATGTGAGTCACTGCGC
CCGGCTCTCATAATACTTTTTGCCTACTAATTTTATATTCATTGATTAAATTCTTGCCTG
AAAAAATTATTACTGTGGTATTTGCCAAATGGCAATTTTCTGTTTCCATCATTGCCTTTC
CCCCGCTTTTAAAAGTATAAGTGACAAAGAAAAACTGTATATAAAGTGTACACCATGATA
TTTTGATATATGTATACTTTGTGAAATGATTATCAAAATTGAGTTAAATAATGCATCCAA
CATCTCAGTTACTTTTTTTTTTTTTTGAGACAGAGTCTTGGTTTGTCACTAAGGCTGGAG
TGCAGTGCCACAATCTCGGCTCATTACAACCTCCACCTCCCAGGTTCAAGTGATTCTCCT
GCCTTGGCCTCCCCAGTAGCTGGGATTACAGGTGCCCACCATCACACCCGGCTAATTTTT
GTATTTTTAGTAGAGGTGGGGTTTCACTACGTTGGCCAGGCTGGTCTCGAACTCCTGACC
TCAAATGATCCTCCCGTCTCAGCTTTCCAAAGTGGTGGGATTACAGGCGTGAGCCACTGT

FIG. 10
*(continued)*

GCCCGGCCACTCTTAGTAAATTTTAAGTGTACATTTTTTTTTTTTTTTTTTTGAGATGGA
GTCTCACTTTGTCACCCTGGCTGGAGTGCAGTGGCATGATCTTGCCACACTGGAACCTCT
GCCTCCTGGGTTCATTCAGGTGCTTCTCCCACCTCAGCCTCCCAAGTAGCTGAGACTACA
GGTACCCGCCACCATGCCTGGCTAATTATTGTATTTTTAGTAGAGATGGGGGTTCACCAT
GTTAGCCAGGCTGGCCTCAAACTCCTGACCTCAGGTGATCTACCCACCTCGGCCTCCCAA
AGTACTGAGATTACAGGCATGAGCCACCACACCCAGCCACATTACGTTAGTATTAACTAT
AATCACCATGCTGTACATTAGATCTCCAAAATGTATTCATCTTATGTAACTTCAAGTTTG
TACCCTTTGACCAAAGTCTCCTTGTTTTCCCTACCCCCAACCCCTGGTAATCACTGCTTT
AATCTCAGTTTTTATGAGTTTGACTGGTTTAGATTCCACATACAAATGAGATCAGGCAGT
GATGGTTTATTTCACTTAGCATAATGTCATCCATGTTCTTGCAAATGACAGGATTTTCTT
CTTTTTAAAACTAATATCCATGCTGGACACGGTGGCTCATGCCTGTAATCCCAGCACTTT
GGAAGGCTGAGGAGGGTGGATCACTTGAGGTCAGGAGTTCGAGACCAGCCTGGCCAACAT
GGTGAAACCCCATCTCTACCAAAAATATAAAAAATTAGCTGGATGTGGTGGCGCACACCT
GTGATCCCAGCTACTTGGGACACTGAGGCAGGAGGATCGCTTGAACCCGGGAGGCGGAGG
TTGCAGTGAGCCAAGATGGTGCCACTGCACTTTAGCCTGGATGTTGATGTTGTTCCACTT
GTTTATTTTTATTTTGTTCCCTGTGCTTTTGGTATCAAATCCTAAAAACCATTGCCATGA
CCATTGTCATGTTACTTTCCCCATATGCTTTCTTCTAGAACTTTTAAGGTTCATCATTCC
CTTTTCTGTTTTTAGTTGCAAGCCTACTATAAGGAAGGGCTTTTCTTTCTTCCTTATTTA
TTTATTCATGTCTATCAGAATGGGCACCTTACTACTATTTTTGTTGTTATTGCTTGAATT
GACTTGAATTTGGCTAGTGGAAACCTTTTCAGATCGGGTACTCTGTCCTTTTGATCTCTT
TCCATTTTCAAGCACTTCTTTAGACTTAAGATGGTCTAGGCTCATCTTCTCCTTTCCCAG
CCATTTTTCAAAGGAACCTGATTCCTTTTAGTGAAGAGCAGTATTTTGAAACCAAGATCT
GGGCACTGGGTCTACTTGTTTGTACTGGTACAGTGTTCTTTGAATTGCTAATTAGCTGAT
CAATTACTGCTCTATTTGAGTTCCCTCTTTCTAAAACCTCACATATGTGTACAGACGGTC
CCTGACTTATGATGGTTCGACTTATGATTTTTGATTTTATGATGGTTTGAGAGCAATACA
TCCATTCTGTTTTTCACTTTTCATTCAACACTTTATTTTAAAATAGGGATTGTGAGATGA
TATTGCCCACGTGTAGGCTAATGTAAGTGTTCTGAGCACGTTTAAAGTAGGCTAGGCTAA
GCTGTGGTGTTTGGTAGGTTAGATATGTTAAATGCATTTTCGACTAGTGATATTTTCAAC
TTATGATGAGTTTATTGGGATGTATCCCCATAAAGTCGAGGAGCATTATACATATCTCTG
TATAACAGAGTGAGTTCCTTATACCTTTCATCCACTTTCCCCTGAAGTTAACATTTTACC
TAACCATGATACATTTATCAAAACTAAAACATTAACATCAATACATTGCTATTAACTAAA
CTAGAGTTTAATTGGATTTTGCCAGTTTTCCAATGAATATCCTTTTTCTGTTCCTTGATC
CAATTCATGGTCACACACTGAGTTTGGTCACTTGTCACTGTAGTCTTCTCCAATCTGCGA
CAGCTTCTTAGGCTTTCCTTGTTTTTCATGTACTCTTGACGATTTTTAAGAGTACTGGTC
AGATATCTTGTAGGATATCCCACAACTTGTGTTTAATCTTATGTTTTCTCATGATTAGAC

FIG. 10
*(continued)*

TTGAGTAATGGATTTTTGGGAAGAATACCACAGAGGTATATTGTTAAGTGTTCTCATCAC
TTGGAGGTAAATGTTATCAACATGGCCTGGTGATGTTAAACTTGTCAGTTTGTTTAGTTA
GTATCTGCCAGATTTTTCTCACTGCATAATTACAAATCCTCCTTAACTTATGATGGGGTT
ACAGCCTGATAAGCCCATCATAAATTGAAAATATCATAAGTCAAAAATGCATTTAATGCA
TCTAAACTACTAAACATCACAGCTTAGCCTAGCCTGCCTTGAACGTATTCAGGACACTTA
CATTAGCCTACAGTTGGGCAAAATCATCTCATGGGAAGCCTGTTTTATAATGTGTTGCAT
ATCTTATGTAATGTGTTGAGTACTGTACTCAGAATGAAAAACAGAAGGGTTGTATTGCTT
TTGCACCATCATAAAATCAAAAAAACCATAAGGCAAACCATCATGAAGTTGGGGACTGCC
TGTACTTTTTTCCTCTTTCCCTGTTCAATTCCTTGGAAGAAAGTCATTTAGTTCAGACCA
TACTCAAGAAAAGGGAAATAAAGCTCCATCTCTTGGAGCTTAATTGAAACTGGAATGACT
AGTTTCTATATACATTATTTAGAATCCTTTTGTAAGAAAGATTTGTTCCTTCTCTCCATT
TATTTATTCCATTATTTATATTGATAGAGACGCATGTACATTTATTTTATACTTTGGGTT
ATAATCTATTTTTCTTGCTCAAATTGTTACAGCTTTGGTCACTGGGAGGTTCTTCAGATT
GGCTCCTGTGTCATTTGACATGTCCCCACCCTCTCGTTTCTGAGTACTTCTCTACTTTGG
CATTACAAAAGATGTTCCAGGCTCCTCTTATATTTTTCCCTGCCGCAGCCCTAGAATCAT
CCATTTTTCTATGGTGCCCTGGTTCCTTTTACTTTAGATGGGGGTTTAGAAACCAATCTG
GGTGTTGGGTGTGCTCATTGCTACTGGAATCACTGCTTCTAGGCCCTCTCAGCAGATAGA
GCTAGAAAACATATGGCTGTATATGAATCCATGGATTCATATATATCTATAATTGTTTTC
TGTATCTGGCCATCTATATATATATTAAGCTAAACATGAATTCATACTGATGTCTCAGAC
TCGAATCCATTGCCGCAGGGCTCATTCTTGCCTTCCTCTTGCTTATTTGTGACTTCTTTC
TCTAACAGGGAGAAACCCCAGTCTCATTATCACCAACCTATCTACTCATTTGTTCAACCC
TGGTATAGGTGTAAAGTAGTTTCAGAATTACTAACCTATACCCATGTGAGAATTGTATTT
GCACTTCTTGTTTGAAGGAAATACATACAACACAGGTAGCGTCTCTACACTTCAGTATAC
AGAGATCTGAACAGTGTTCTCTCTGAGTGAATCATATTGCAGGACAGAAATTACTTTTAA
AAATTCTGTAATGGGTCAGGCCTATAATCCTAGCACTTTGGGAGGCTGAGGTGGGCAGAT
CACCTGAGGTCAGGAGTTCGAGACCAGCCTGGCCAAAATGGTAAAACCCCATCTCTACAA
AAAATACAAAAATTAGCCAGGCGTAGTGGTGTGTGCCTGTAATCCCAGCTACTCAGGAGG
CTGAGGCACGAGAATCACTTGAACCTGGGAGGCAGAGCTTGCAGTGAGCTGAGATTGAGC
CACTGCACTCCAGTCTGGGCGACAGAGCGAGACTCTGTCTCAAAAAAAAAAAAAAAAAAA
AATTCCATAATGATAGCAGAGCTGGAATAGAAATGGGATTGCACAGGCTGAATCTGAGTT
GTTGCAACAGTAAACGAGCAAGATTTAAACTGGCCTTGTGTAGCACTTGCTATTTGGCTC
CTCATATTTTATTAGACGCTTATTCTTTTTTGTTTGGTGTCATTCCTTTGAGAAATATTT
GAGTGCCTTTTCTGTTGCAGACATTGATTAGATGCTGAGGTTGTAACAATGAAGAAGATA
GCCATCGCTGTTGCCTCATGGAACTGAAGTTTTACTAGATGTAAAATTTGAGTTAACATG
AGGCCGTGCCCCTATGTGCCCTATTGTTTCTTCACACAGCTCCCTTCATCTCCTTGGTCC

FIG. 10 *(continued)*

AATGAAAAGGTTTTTTCATACTTGTTCATTCATTCCTGCATTAATTAAAGTAGGTTGTAC
TGTGCCAGGCACTGGGAATATTTAAGTAGTTGTGTTCCTGAATTGGAAATGAATCCAGCA
TGGTTGGAGTAGAAGGAGCTGGGGGGCAATGTGGAGTGTGATGGGGAGATTGGAAAAGTA
AGCTGAGACCAGATTTTTCAGTTTGGAGGGAGAGGTGGGCCTTGTAGGCCATATTACAGA
TTGTAGACTTTATTTGGAGGGACATGGAAGTCATTGAGGAGTCTGAAGCAGGGGAATGAC
ATAAAAAGATCCTCATTTTAGGCCGGATGTGGTGGCTCACGCCTGTAATCCCAGCACTTT
GGGAGGTTGAAGTGGGTGGATTGCTTGAGGCCAAGAGTTTGAGACTAGCCTGGGCAACAT
GGTGAAACCCTGTCTCTATCAAAAATACAAAAATTAGCTGGGCATGGTGGCTCACACCTG
TAGTCCCAGCTACTTGGGAGGCTGAGGCATGAGAATCGCTTGAACCCGGGAGGCAGAGAT
TGCAGTGAGCCGAGATTGTGCCACTGCATTCCAGCCTGGGTGACAGAGTGAGACTTCGTG
TCAAAAAAAAAACAAAAAACCCCTCATTTTGAAAGGGAACCCTGGCTTGAGGGTGAAGAA
TGGGTGGGCACTAGGCTAGAGCAGCTGCAGGGTCAGTGAGGAGCTGCCGCAGTGCTGCAC
GTGAGAACCCGTCATGGTTTGGTCAGGGTGGGCAGGACTGACAGTGAGCACAGAGCGAAG
TAAAACCAGCAAAATTTCATGATTGGATAGTGGAAGGAATCATGGTGTTTGTAGTCTTCA
AATGTGAACCCAGAGTGCACTGGACAAGTAGTCTAGGCTGCTCTGTAACCAAGGCAAGTG
TTTTCATTTTACCCTCTCTTCCTGCTCTTGGCCTTTGGATTTTTTGTAATTTAAGGTTTA
TGAATGTAATCAGTTACTTAACATGGAAAGATACTTAATACCAGATGATTTTGGAGTCTT
GTGATCAATACCTTCTCTCAATCTTGGGTGTGTGTCAGTTGGCAAGGCCATAAAATTTGT
TATAAACATTGCAGAAGGCTTGGTTACTGTGCTGTGACGTTGAATTTGGGTGGAGATAGA
TCAATTTCAGTTGATTTTCTAGGCTTCAGAAACACATTACCCTCTACTCCACAAACACAA
ATCAAAACAAAACAATCCCTATTCCCTGAGCATTTCTCTTGATCTATAACACAGCCTGGG
CTGTCACAGTACTAAGACAAGCCCATCTGATTTGTGAGTCAGTTTTATTTCTTGGTCTTC
TACATAAGCTAAAAAGTTTCAACATTTTAATGCTTTTCCTTGGATTCCTTTGAGTCATTG
AAGTAATTCCTGTTTCATTTGTACTAATTATTCCACACTAGAAAATTCTGTTGTAATCAC
TTTATGTATTAATAGAAATACTGATTTTTATTTTCAAGGAAGTATTGAGTAGGGAGGGGG
AAATAGGGATTTGCTGTTCAATGGGTATAGAGTTTCAGTAATACAAGACAAAAAACTTCA
GAGATCTTCTATACAGCAGTGGGTATATAGTTAACAATACTGCACATCTAACAGTTTGTT
AAGAGGGTAGATCTCATGTCATGTGTTTTTAAAAATTGCTTTTAAAAAAAGTATCGAGTA
AAAAAGCAGTTTTACTCCTCAGTTTCTATTTATATTTAAAATTTTTATTTAAAAAGTGAG
TTGAGATTTTTAAACCTCAGGATAAGTTTTATTTTTTAAAAAATTTATTTTTTATTATTT
TTTGAGATGGAGTCTCACTCCATCTCAAGTCACCCAGGCTGGAGTGCAGTGGTGTCTTGG
CTCACTGCGACCTCTATCTCCCAGGTTCAAGTGTTTCTGCTGCTTCAGCCTCCTGAGTAG
CTGGGATTACAGGTCTGCACCACCACGCCTGGCTAATTTTTGTATTTTTAGTAGAGATGG
GGTGTCACCATGTTGGCCAGGTTTGTCTTGAACTCCTAACCTCAAGTGACCACCTGCCTT
GGCCTCTCAAAGTGCTGGGATTACAGGTATGAGCCACAGTGCCCGGCGGGATAAGTTTTA

FIG. 10
*(continued)*

AAATAATATTCTCTGCTGGCTGGGCATGGTGGCTCATGCCTGTAAACCCAGCACTTTGGG
AGGCTGAGGCAGGAGCATCACTCGAGGCCAAGAGTTTGAGACCAGTCTGGGCAACATAAT
GAGACCCCCTCTCTACAAAAAATAAAAAAAATTTGGCTGAGTGTGGCATGTTCCTGTAGC
TATCGGGAGGCTGAGATGGGAGGATTGCTTGAGCCCAGGAGTTTGAGGCTGCAGTGAGCT
ATGATTGCACCACTGCGCTCTAGTCTGGGTGACAGTGTGAGACCCTGTCTCTTAAAAAAA
AAAAAAAAAAAGGCCAGGCACAGTGGCTCAGGCCTGTAACCCCAGCACTTTGGGAGGCCG
AGGCGGGTGGATCACTTGAGGCCAGGAATTTGAGACCAGGCTGGCCAACATGATGAAACC
CCGTCTCTACTAAAAATACAAAAATAAGCTGGGTGTTGTGGTGCACACCTGTAATCCCAG
CTACTTGGGAGGCTGAGGGAGAGAATTGCTTGAACCTGGGAGGCAGAGGCTACAGTGAGC
CGAGATCACACCACTGCACTCCAGCCTGGGTGACAGAGCAAGACTCCATCTCAAAAACAA
CAACAACAAAAAAACCAAATGTTCTTGCCAATTCTTCCATTTAATATTTAATTTTGAATT
ATATTGTATCTTTCTAAGGATTGTTTCTTATATAAGCAAAGATTTTTCAGTGCTAAACAT
TTACGACTGCTATTCAGAAATGGTTATTTACAAGTCTTTTTGTTTTAAGAAAATGGCTGT
TCAAAAAATTAAAATAGTATATAAACCAAACAAAATATTTTTGCTTTGGATGTCTGTTTT
GCAGCTTCTTCCCTACACTATAAGTTCTTACTGACTGCTTTATCACTTAATAAATTGGTT
TGGCTACTTTAACAGAGGCAAATAGTATCAGGCAAAAAATTATTTTTTATTTTTATTTTT
TGAGACAGTCTCACTCCATCACCCAGGCTGCAGTGCAGTGGCCTGATCTTGGCTCACTGC
AACCTCCACCTCCCAGGTTCAAGCGATTCTCATGCCTCAGCCTCCTGAGTAGCTGGAATT
ATAGGCATGCACCACCACACTCAGCTAATTTTTGTATTTTTAGTAGAGACAGGGTTTTGC
CATGTTGACCAGGCTAGTCTTGAACTCCTGACCTCAAGTGATCCATCTGCTTTGGCCTCC
CAAAGTGCTGGGATAACAGGCATGAGCCACCATGCCCAGCCCTATTTTTTATTTTTTAGA
GATGGGTCTCGCTTTTTTAGAGATGGGTCTTGTTGCCCAGGCCAGAGTGCAGTGGTGCGAT
CATAGCTTACTGCAGCCTTGAATTCCTGGGCTCAAGCAATTCTCCTGCCTCAGCCTCCCG
AGTAGCTGGGACTACAGGCCTGTGCCACCAGGCCTGGCTTGTACATTAGTATTTGATATG
GCTACCCTAAGGGCAATCCTATAGTGAAGTCAACATTAGATAATGATGCTCATCTGATGG
ATTAGATTTTCAGAGTTGGCTGTTTCCAGGTGCCTATAGGAGTAGAAAAGGGTGACAAAC
CTCCTAACTAGATGTCCTACCAAATATAGTTCACTCCACATCTGAGATGAGACTGCATGA
CTGCTGGTTTTCTTTGCCTTTTCCCCCCCAGGGTATCATCAGAACCAAAAATAAAGTTTT
AAAGGTGGGTCAGGTGTGTGTTGGCTCATGCCTGTAATCCTAGCACTTTGGGAGGCTGAG
GCAGGTGGATCATCTGAGCTCAGGAGTTCAAGACCAGCCTGGCTAATAACATGGTTAAGC
CCCATCTCTACTAAAATACAAAAAGTTAGCTGGGCATGGTGGTGGGCACCTGTAATCCCA
GCTACTCAGGAGGCTGAGGCATGAAAATCGCTTGAACCCCAGAGGCGGGGGTTGCAGTGA
GCCGAGATCATGCCACTGCACACTAGCCTGAACAACAGAGCAAGGCTCTGTCTCCAAACA
AACAAAAATGGTGCCAGAGTCTTTTCCAGGGCTGAGGGGAGATACAATGAAGTGTGTTAT
TTTTTCTGATAAGAGTGCTACCATCTTTCATTCTTGTGTGCCATTTCTAGTTGGGGTGAA

FIG. 10 *(continued)*

TTTGTTTTCGGAGTTCCTTTCCCAGCTGTTTGCCTGAAAAACCATGAAATGTGTTCCACA
TGAACTATGAAATGATTAGATGCTAATGTGGCAAAGAAAGTGTGAATTCTCTTGTAGAAA
CAGGGACATTTGGTTCGGTACAGTAAGTTGTTAATGCGTGACTCTGTGCTTTCAAATTCT
GTGGTTCAAAAGTACTTTTCACTCCTACTGTGTATTTACCTTGAGAAGGTGAATCCCCTA
ACAATTTGGTCAATGTATCAGTATTCTCAACCCGTCTATCAATTTTTTTTTCTTTCTCCC
TCTTTTTTCTTTTTTTGGGCAAAATACCTTTTTTGCTTTTTATCCCCTTAAAATAACCAT
TGTCCCTCACATGTGCACTCTTCCAAATTTCAGAAAAGCAAGAGGAAAGGGCACGAATAT
ACAAATATTAAGTATTCTCTAGCGGACCAGACGAGTGGAGATCAGAGCCCTCTCCCGCCT
TGTACTCCAACGCCACCCTGTGCAGAGTAAGTAGTGCTGAAGGAAATTCTTTTTACCTGG
TCATGGTGGTTTAAAAAGGTTTAAAAAACAAAAACAAAAACAAAACACAAGTTTGTAGCA
CATGCCTTTCACTGGTGCACGTTCCTGTTGCCCTACTGTTAGTGTATCTGTGACTGGTGA
TATCTATTGATTGTGTTAATGCTATCTCAACCACGTTTTAATTTTCCTAAGCTGGCCAGG
CACGGTGGCTAACGCCTGTAATCCCAGTGCTTTGGGAGGCCGAGGTTCATGGATTACTTT
GAAGTCAGGAGTTCGAGACCAGCCTGGCCAACATGGTGAAACCCTGTCTCTACTAAAAAT
ACAAAAATTAGCCGGGCATGGTGGCGCATGCCTGTAATCCCAGCTACTCAGGAGGCTGAG
GCAGGAGAATCGCTTGAACCCAGGAAACGGATGTTGCAGTGAGCCGAGATCATGCCACTG
CACTCCAGCCTGGGCGATAGAGTGAGCCTCTGTCTAAAAATAAAATAAAATAAAATAAAT
TCCTAAACTGAAGGCTGACTGCTATGCTAGCTAGGATTATATGGGATTTTAAGTATATCA
AGTGGTGGTTCTCCAAGAAGAATCTAATTTTTCTTTTGATGGGCTGGGGATTGTAACAAA
GGAAGGTCATATGTCTTAATGATGTGTTAAGGCTCTTTGCAAAATCAAAGTAAATAAATT
GACCACTAATGTGTCAGCCCAGCCATGTTCTGCTCATTTGCCACCAGTCAACAGAAATCT
ACTTTGGGTGTTTAAACCAGGAGTCAGCAAACTACAGCTCACAAGGCCAGATGTGGGCCA
TGGCCTGTTACTGTATGGCCTGTTAATGGTTTTAAAGGGTTGTAAAACAAAAGAACACAA
AACAAAGACCCAATAACAAAACAAAGCCCGAAGAATAATATGCGACAGAGACCATGTATG
GCATATAGAGCCTAAAATACTGACTCTCAAGCCCTTCCCAGAAATCCTTCCCGACTCCTT
GTTGAAAACACGGTAGGAAAGCATTTGTCAAATTGAGGATATGAATAGCAATTGTAAGTT
ATTATTTTTCTATATATTCGAAAGTCACTTGCTAGTATAACATTTACCTTTTATTTTTCC
CTAAGAATCTTCTCTCTGTTTGCTTTCGACATGGATTTTTAAACCCCTGCAGATTTTAAT
ATTCTATATAAATGTTTTAGGTGGCATATATGAGGTTTGTATTAACATTTGCTTTCTATT
TAACATTGAAATGAAATTATACAGCAGAGGTATTTTCTCGTCCAAGTTGCCACTTCTTTC
TATCTTTTTTCTTTTCTTTCCCAGTGGACTGCCTGGGAAAATTGATATTTTAAATTGCTC
TCTGCAATAATTTGCAATGGAACTGGAATGCCAGGGTTCTGAGTCCTTGCCAGACAGCTC
GTCCCTCCTGTTGGCATGACTGAGTCAGCTGTCATGATTCCCTCAGTACCAGTGGCATGC
CTGTGACAGACAGCCTGTCTGCCTTTCATTCCCGTCGTCTCCCTTGTAGGGTTCAGATCC
AGGATACACTGGTCCTGGAGCCCCTCTCAGCCTGGCACCCACAGCTGCTGGGTTCCTTAC

FIG. 10 *(continued)*

TCTCCTGGACTGCTCTGATGTCATCTCCCTGCTCAGCAGAAAGAAGTCTGGGATCTTGAT
GCTTTGGCCCTCTGTCCTAGGCCCTAAACCACCCATTGCCCTTCACATAACCTGAGCTGG
GGCTAAATAGATCTCTCATCACTGCCTGCCTGCTCCTGTATTTTCCCTTCTTGGAGCTTT
TGCCTGTTCAGATCCCTCTACTGGAAATTAATAGGATTTCATTCTATGTGTGCATTTCCA
ACCTTTCTTCACAGTGCGATCCAAATGCCTCATCCTACAGGCCTCCTTAAAACAACCTGC
TTTCTGCCAGACCCCAGGGAGCACCAGGACTTGAGGCTTTTATTGCACTTCTGTTGTTTT
TTTGAGATGGAGTCTCGCTCTGTCGCCCAGGCTGGAGTGCAGTGGCACGATCTCTGCTCA
CTGCAACCTCCATCTCCCGAGTTCAAGAGATTCTTCTGCCTCAGCCTCTCAAGCAGCTGG
GACTACAGGCATGTGCCATGACACCCGGATAATTTTTGTATTTTTAGTAGAGACGGGGTT
CACCATATTGGCCAGGCTGGTCTCAAACTCCTGACCTCGTGATCCACCCACCTGGGCCTC
CCAAAGTTCTGGGATTACAGGCGTGAGCCACCATGCCCAGCGTTATTTCACTTCTGCCTC
TGTAATTATATTGCTGTATGGCTATCTCTTCTCTCCCTGGGAATGTCAGGTCCTAGGCAC
AGGAACTGTGTCTGTACCATATCTGGTGCCCAAAGAATGTAGTATGTGTTTTATAGATAT
CATGTAAGCTTAAACAGCGTGGTCTACATTTTTGTAAATGTCTTTCTTTTTCTTTTCTCT
CCAGAATGAGAGAAGACAGTGCTAGAGTCTATGAAAACGTGGGCCTGATGCAACAGCAGA
AAAGTTTCAGATGAGAAAACCTGCCAAAACTTCAGCACAGAAATAGGTATTTAAATGCAA
GTGCTCTATTGGTTAATTGTTTATATAATTGGCAGTATTTTTAAGCAGGCAAGCAATTTG
GGAATGTTTTAGCAAAGTGTACCATAATTGAGTTTTACAAACCAGGCTCCTTTTTCCTCT
CCCTGTACTTCTTTTTCCAAGATGGTTTTAGTTTAGAGTTCATTAAACATTAAAATCAAA
CACAGAATTAATTCTGCATGAGGCAAGGCTAGCACTTATTCCAGAGAAATGGCTGATACT
GGTGGTAGAGTGCAGGTATCACTGTTCCTGCAATTTTTATTAGAGTTGGTTAGCCCAGGC
TGTGCTGGGGGATGATCTGTAGGGATCTGGGAAGCATCGGGACTCAGCACTGGGTGGTTG
GGAGTCAGGAAGCCTGAGTTCTCATTTCAGTCAGTCTCTGACCAACTGTGTGGCATGGGG
TGCTAGACCACTTGGCTGCCGACTGGGTCACCGACATCCCTTCCAGCTCTGCTGCTGGAA
ATTCATCTCTCCCATATGTTGCCTCCCCATCAATTACGTTTTTTAAGTGTGACCCAAGTA
TATGATGTATGTTTTCATGATAAATTAGAAACTTATCTGGGCATGGTGGCTCATACCTGT
AATCCCAGCACTTTGGGAGGCTGAGGTGGGCGGATCACCTGAGGTCAGGAGTTCGAGACC
AGCCTGACCAACTAAAATAGTAGAGACCAACCCGTCTCTACTAAAAATAGAAAATTAGCT
GAGCATGGTGGTGCATGCCTATAATCCCAGCTACTCAGGAGGCTGAGGCAGGAGAGGCAG
CGGTTGCAGTGTGCCAAGATCGCGCCATTGCACTCCACCTGGGCCACAAGAGTGAAACTC
CATCTCAAAAAAAAAAAAAAAAAAAAAAAAAACTCAGTGTCAGTATTTCATGTCGAAATTC
CACTTCAATGGGTAGTGTAGTTAAAAGCTCTAAGTCTACCTTAAAATCACCTAATGCTTT
GTTAAGCTTTTAGATATATGTTCCTTAAAAACTCTTAACTTATTTCTTCCCCAGATGTGG
ACTTTCACCCTCTCCCTAAAAAGATCAAGAACAGACGCAAGAAAGTTTATGTGAAGACAG
AATTTGGATTTGGAAGGCTTGCAATGTGCTTGACTACCTTTTGATAAGCAAAATTTGAAA

FIG. 10 *(continued)*

CCATTTAAAGACCACTGTATTTTAACTCAACAATACCTGCTTCCCAATTACTCATTTCCT
CAGATAAGAAGAAATCATCTCTACAATGTAGACAACATTATATTTTATAGAATTTGTTTG
AAATTGAGGAAGCAGTTAAATTGTGCGCTGTATTTTGCAGATTATGGGGATTCAAATTCT
AGTAATAGGCTTTTTTATTTTTATTTTTATACCCTTAACCAGTTTAATTTTTTTTTTCCT
CATTGTTGGGGATGATGAGAAGAAATGATTTGGGAAAATTAAGTAACAACGACCTAGAAA
AGTGAGAACAATCTCATTTACCATCATGTATCCAGTAGTGGATAATTCATTTTGATGGCT
TCTATTTTTGGCCAAATGAGAATTAAGCCAGTGCCTGAGACTGTCAGAAGTTGACCTTTG
CACTGGCATTAAAGAGTCATAGAAAAAGAATCATGGATATTTATGAATTAAGGTAAGAGG
TGTGGCTTTTTTTTTTTCTTTTTTCCAGCCGTTGACCAATTATAGTTCGGCTGTTGACT
GAGAAGTTTGTGGTGGGAAAACGTTTGCCATATTTTCTTTGCATTTGAATAATTGTCTTG
TACTTAGAAAAAGGCGTCTATGAATGACCAGTGTTTTTGGTCGCCAAATGTTGCTGACA
AACTTATCCCAAAACTTTAGTGGCTTAAAAAAACCTGCCCCCAACTGTTAGTCAATCTGA
GCTGGGCTCAGCTGGGCTGTTCTTCTGCCAGCCTGCAGGTGGCCACTCATGTGGTCAGCA
GGTCGGCGGAGAGACTGGGATGGCTGGGCTTCTCTCTCTGCCTGCAGTCCTGAGTCTCTC
CTTCTTCGTGTAGTCTCTTTCAGTGGCCTGGCTGGCAGGGTAGCTAGACCTCTCACATGC
AGCTCAGAGCTCCCAAGAGCTCAAAAGCAGAAATGGCCAGGCCTTCTGAAAACTTAAGTC
CAGAATTGTCACAGTGTCCCTTCTACTTCCCTCTATTGATGATGATGATGATGATGATGA
TGATGATGATGATGATGATGATGGTTTTTTCTAATCAGAAGAAAGCTGGGGTATGCCCTC
TACTTACTAAACAAGTCACAAGCCCAGCTCAGATTCAAGAAAAGGGTGTGAAGTAGAGGT
GCAGTTAAGTGGGGGGCCACTAGTCTAACAGACGGTCACAACCAGTGCCATGGAAAACCA
AGGATATTAGCAAAAGCAGAAGTTGCTAGTGACCTTGGGAAGCCGAAGCTGCTTACAGTA
GCTGGGACAAGCTGAAAGTCAGACTAAGAAATAAAGAGAGGGCCTTCAAGAAGCTTCCTG
AATGATTTCTGCTAGCCCTGAGCCTATTTTTGGAACCAGCACTTGGGGAAACTGATCTTG
TGAGGATGGATGTGTTTAGGGACACAGGGCTTTTGAGAGCAGCACCACCCCACTGGGGCA
TCCCCAGACTTGGGAAACGTGACTCTTTCTTAATGCCACTGGGTTTTAGTCAGGCCACAG
TGAGAAGGAACAGCCCTAACAGGCCTCCAGCCAGGTTGAATGAGCTCATTTTTGTTGTAG
CCAACCAGTAAGATTTGCTAATGTTCTACATTAAGTGCCTTCTCCAAAGACATCCCTCTT
TGCCTCATATGTTGAATCATCCAGTGCGGATATTTCAATGAAAATATCATTGCTTGACTT
TTGTGATGGTAATAATGCTATGGCATCTTTGCCATGAAGTTGTGGCCTCCTTGGATTCTT
CTGACTTTGGCTTCTGAAAGGAAGGCCTAGATCCAGCCCTGGTGGTAGTTCCTTTCTGAG
GTCTCTCAGTCCCTTGAGACTTTGGGGTAGTTTGGCTGCCATTCTCACTGACAAAATGTA
TATCAGCCCCCACCTCCACCCCCCAATATTCCTTGAACTTTGAATTGCTTCAGAACACAG
GTGTGGCCTGAAGGTATTCCCTTATTAGGGAAGTGTCACTGCTGTCTTCTAGTCAAACTT
GTAAAGAAAAAGATTCCAGTTCAGTATTTGCAGCAAGAAGCTTGAATGCTGTTCTTTTTA
TCGCATTGTTACATCGACTCATTCTCCATTTTGCTTTGGTTTTGTCTTGACTTGACTTGA

FIG. 10
*(continued)*

CTTTGGGGGTAAAGTCTTTCACCAGCACACAAGAGTTTGATTGTACAAATATATCTTCTG
CATTAACATCTCTGCCTGTTGCTTAAGATCAGTTGCTTTTATACTCAGAATGGAAATACC
TGATCTTGGCTAGTTTTGTTATAAGATATTGATTTCATTTAGATTTCCCTCCACGAGGTC
AGCAAACTATCATGTTCTTATGTAAACTTAGGCCAAGGCCAGAGTTATCATAGTCCCTAG
GTTGCTACGGCTTATCATGTGCTTGGTAAAAGGTGATCGCAGGTTCTCAGACGAGTTTAC
TTTACATGAGATGGAATCAGGCAGAGAGGCTGGGATGATGGAGAAAGCTCGAGGTGAAGT
TTTAAAAAAAAGTTGTGGAAAGGAAAGTTCCAAAGAGGTGGTTTCTGAGGAAGTCAGAG
CGCCCAGGGCCAGAGCAGTCAGTAATGGGTGAATGAGGTTGTTTGGAAAGTCGGTGTGAC
AGACACATGGATGCCATCTACTTCTAGGTTGCTGGTGGGTATTAAATATGCACAATATTC
CATAGCTCACTGAGGATTTTAAAATTATAAGCATAGGATTTTATATTTTGGGGTGAAAGA
ATTATCTGGCACATTAGGTATTGGAGTTTAAAAAAAAGCCAAATTTCACAGTCTTAATA
ACTTTTTTTAAAAAAACTAAAGGCGCTTCATGTCCAGTGTGTGGCCCTTCTGAAACTT
ATGGTCATCTCTCCCACTGAAACCAAGGTCTTTTCAAATGTGGCTAAATGGGGATGAGGA
GACACGGGTAGGACTTTCTTGGTGTGTGTGCATTCTTTAAAGAGCCAAGTTGCTTCGGGG
AAACAGCCAGGAAAATGGTCAAGATTATTTTTAGAGGTTATTTTATTGGGGATTTTAAGA
ACTAATAACATCTTGACTTATTTTTAATTCAGGGGGATGTGGAAAGGTTTGCAATTGTCA
AGTGTTTTGTTGTAGCTTAGTATCCATAAGGGAAACTTAGACTATAGACATAACTACAAA
GCCAGTGCAGCTTTTGTTTTCTGTATGTTGTTGGGGGATCAACTTTCACACATAGCAAGC
ACATGGCCTCCCTGATGTCAGGATGCCTTTGTTAGGATCTGTATTTGCCCTTAATTTTGT
TGAAATCTTTTTTCCTTCTTCCTCTTGAAAAGTTCCAAAATATAGTTTATTGTATCTTTC
ATCACTAAAAATTTGTTCCTTTTTCACTATGGGCAGTTCACACAAGGCAAAAACTATTGA
ACAGTTGGTTTTAGTGTGTTGTATAACTTTGCTGTATATCAAACTAATTTTGACAAGTTT
TCATCCTAAGCCTCAAATCATGTAATTAATAATTTGCCTGTTTATTTATGACCTAATTGT
GATTCTTTTATTAATAAAAGCTAATGGGAAAAGGATCCCTGATTAAGCTGATGACTAGAC
CTACAATTAATTTTCCTGCAGTATATGAAGTATTGTACCAGAGTATTAAAAGATATGTAA
TATTTTATTGATAAATCTATCCTTTAAAAGGAATACGTTTTAGGATGTCATCATTTTGAT
GTGAATCATGTAAATGTTGATAATATGCTGTTTATTATACATTTAGTGTTTCAAGAGATT
CACTTAATTGCCTTTTTGCCCACGTATATTATGTAGTCTATTTGCAACTGTTCTTAAAAA
AATGACATTAAAAGAATAGTTTATGTAGAGAAACATTAGTGGATGTTAATTGTCTCCCCA
CCTATATTTATGGGTGTTAGCGCAACTGCTTTGCTAGTTGCAAAGCTGTATTATCAGAGT
AAAAGTGTATTTGTAAACTGTATGGGAACTAAAAATTAGGAATAAAACCATTTTCTTATA
TGATGGCATTTGTCGTTTGCTTCATCAGAAATGTCCAGGAAAAAAATGGGATTATTGGTC
ACTCCACCTCTCACACTGGCAAAATACTGACATTTAGCAGCTCTTATCTAGAAGTGACTT
GGAACATAGAATAAAGGCATGAGTTCCTGAAGAATTCATTGAGTGTTTCCTGTAGAAATA
GCTTTAGGAGATAGGGAGTTCTATCTGGGAGAACATATGAGTAACTCAAGAGTAAAAAGT

FIG. 10
*(continued)*

```
ATAGTCTGTGTAAACTATAGAAGAAATGCTGGGCATGGTGGCGCGCCCCTGTAATCTCAG
CTACTTGGAGGCTGAGACGGGAGGATTCCTTGAACCCAGGAGCCCAGGAGTTTTAGACCA
GTCTGGGTAACATAGTGAGACCCTTTCTCACCTACTCTCACTGCATGCCCCCCAAAAATA
TATATGTGCGCGCACGCGCGCGCACACACACATACACACACACACACACACACACACACA
CAGAGGAAATTGTTAGAAAACACACAGAACTGAATGTAAATAGTATTAGGTGGGAATAAG
AAGTAAAGGGATGGTAAGGAGGCTTGGAGGAGGAGTAAATTATCTGCTATGGGACATCAG
CTC
```

FIG. 10
(continued)

MTSRRWFHPNITGVEAENLLLTRGVDGSFLARPSKSNPGDFTLSVRRNGAVTHIKIQNTG
DYYDLYGGEKFATLAELVQYYMEHHGQLKEKNGDVIELKYPLNCADPTSERWFHGHLSGK
EAEKLLTEKGKHGSFLVRESQSHPGDFVLSVRTGDDKGESNDGKSKVTHVMIRCQELKYD
VGGGERFDSLTDLVEHYKKNPMVETLGTVLQLKQPLNTTRINAAEIESRVRELSKLAETT
DKVKQGFWEEFETLQQQECKLLYSRKEGQRQENKNKNRYKNILPFDHTRVVLHDGDPNEP
VSDYINANIIMPEFETKCNNSKPKKSYIATQGCLQNTVNDFWRMVFQENSRVIVMTTKEV
ERGKSKCVKYWPDEYALKEYGVMRVRNVKESAAHDYTLRELKLSKVGQGNTERTVWQYHF
RTWPDHGVPSDPGGVLDFLEEVHHKQESIMDAGPVVVHCSAGIGRTGTFIVIDILIDIIR
EKGVDCDIDVPKTIQMVRSQRSGMVQTEAQYRFIYMAVQHYIETLQRRIEEEQKSKRKGH
EYTNIKYSLADQTSGDQSPLPPCTPTPPCAEMREDSARVYENVGLMQQQKSFR

SEQ ID NO: 61

FIG. 11

GENE EDITING THROUGH MICROFLUIDIC DELIVERY

RELATED APPLICATIONS

This application claims the benefit of priority under 35 U.S. C. § 371 to PCT Application No. PCT/US2016/013113, filed Jan. 12, 2016, which claims the benefit of priority under 35 U.S.C. § 119(e) to U.S. Provisional Application No. 62/102,347, filed Jan. 12, 2015, each of which are incorporated herein by reference in their entireties.

STATEMENT AS TO FEDERALLY-SPONSORED RESEARCH

This invention was made with Government support under Grant No. R01 GM101420 awarded by the National Institutes of Health, and Grant No. DE-FG02-02ER63445 awarded by the Department of Energy. The Government has certain rights in the invention.

TECHNICAL FIELD

The subject matter described herein relates to gene editing by introducing gene-editing components into a cell by mechanical cell disruption.

REFERENCE TO THE SEQUENCE LISTING

The contents of the text file submitted electronically herewith are incorporated herein by reference in their entirety and comprise a computer readable format copy of the Sequence Listing (filename: MITX 7635 01US SeqList ST25.TXT, date recorded Nov. 27, 2017, file size 517 kilobytes).

BACKGROUND

Genome editing technologies, such as clustered regularly interspaced short palindromic repeats (CRISPR)-CRISPR associated protein 9 (Cas9) and transcription activator-like effector nucleases (TALENs), have shown much potential in their ability to change the genetic code of cells. These technologies could thus enable novel insights in drug discovery and lead to the development of next generation gene therapies. Gene editing complexes, which include a protein component and a nucleic acid component, e.g., deoxyribonucleic acid (DNA) and/or ribonucleic acid (RNA) cannot readily cross the cellular membrane. Thus, delivery of such complexes has been a challenge.

SUMMARY

The methods and systems of the invention solve the problem of intracellular delivery of gene editing components and gene editing complexes to target cells. The results described herein indicate that delivery of gene editing components, e.g., protein, ribonucleic acid (RNA), and deoxyribonucleic acid (DNA), by mechanical disruption of cell membranes leads to successful gene editing. Because intracellular delivery of gene editing materials is a current challenge, the methods provide a robust mechanism to engineer target cells without the use of potentially harmful viral vectors or electric fields. Moreover, the scalability and relative simplicity of the process make it suitable for broad adoption. The strategy and methods are suitable for genome engineering applications in research and therapeutics.

Accordingly, a method for delivering a protein-nucleic acid complex into a cell is carried out by providing a cell in a suspension solution; passing the solution through a microfluidic channel that includes a cell-deforming constriction; passing the cell through the constriction such that a pressure is applied to the cell causing perturbations of the cell large enough for said protein-nucleic acid complex to pass through; and incubating the cell in a complex-containing solution for a predetermined time before or after the cell passes through the constriction. An exemplary protein-nucleic acid complex comprises gene editing components. For example, the protein-nucleic acid complex comprises a Cas protein (such as a Cas9 protein) and a guide RNA (gRNA) or donor DNA. In other examples, the protein-nucleic acid complex comprises a TALEN protein, Zinc-finger nuclease (ZFN), mega nuclease, or Cre recombinase.

The methods and system is generally applicable to cytosolic delivery of complexes, e.g., a protein-protein complex, small molecule+RNA complex, etc.

A variety of target cells types are processed in this manner. For example, the cell comprises a mammalian cell such as an immune cell (e.g., T cell) or a stem cell such as a hematopoetic stem cell.

The microfluidic system may include a plurality of microfluidic channels. Each of the microfluidic channels of the plurality defines a lumen and is configured such that a cell suspended in a buffer can pass through the lumen. In some embodiments, microfluidic channels include one or more cell-deforming constrictions. In some embodiments, the diameter of the constriction is a function of the diameter of the cell. Thus, there may be many microfluidic channels within a microfluidic system of the invention. For example, the microfluidic system may include a plurality of the microfluidic channels arranged in parallel, e.g., 2, 5, 10, 20, 40, 45, 50, 75, 100, 500, 1,000 or more.

Microfluidic systems having a plurality of parallel microfluidic channels allow for the high-throughput delivery of payloads to cells. Many cells can be passed through each parallel channel one after the other. It will be understood that, depending on context, a reference to a "cell" herein may refer to more than one cell.

The diameter of the constriction is chosen depending on the dimensions of the cell type to be treated. In some embodiments, the cell may be primarily compressed by the fluid flow. In some embodiments, the diameter is less than the diameter of the cell. For example, the diameter of the constriction may be substantially or about 20, 25, 30, 35, 40, 45, 50, 55, 60, 65, 70, 75, 80, 85, 90, 95, or 20-99% of the diameter of the cell. For example, the constriction is substantially 20-99% of the diameter of the cell, e.g., a diameter of the constriction is substantially 60% of the diameter of the cell. Non-limiting examples of the diameter of the constriction include substantially or about 2, 3, 4, 5, 6, 7, 8, 9, 10, 15, 20, 2-10 μm, or 10-20 μm. Different lengths of the constriction are also possible. Non-limiting examples of constriction lengths include substantially or about 10, 15, 20, 24, 30, 40, 50, 60, 70, 80, 90, 100, 10-40, 10-50, 10-60, or 10-100 μm.

The subject matter described herein provides many technical advantages over methods that deliver components (or nucleic acids encoding the components) of the complex piecemeal. Most gene editing systems require complex formation to occur inside the cell, which may be an inefficient process. Advantages of delivering the RNA and Cas (such as Cas9) in complex form (or other protein/nucleic acid gene editing composite assemblies) include better efficiency and specificity compared to other methods. By obviating the need for mRNA or DNA manipulation to express the Cas protein (such as a Cas9 protein), one can reduce how much time the cell spends exposed to the protein thus reducing the chance of off-target effects. Having the editing components delivered to the cell in complexed form also eliminates/minimizes the risk of the Cas (such as Cas9) complexing with other RNA strands in the cell and cleaving the wrong sites. For example, the RNA alone may be detected by intracellular and extracellular Toll-like receptor (TLR) and pattern recognition receptors, prompting an interferon response or other antiviral pathways. The complexed form does not interact with these pathways and can thus avoid undesirable side effects.

By complexing in vitro prior to delivery into a cell, one can precisely control the Cas (such as Cas9) and gRNA complexing reaction thus ensuring optimal functionality, while complexes forming in the cytosol may not be as efficient. For example, delivering the complex cytosolically ensures simultaneous interaction of Cas (such as Cas9) and gRNA with the target DNA. The complexes formed in vitro and delivered to the cell as described herein are fully functional and ready-to-go upon gaining access to the cytoplasm of the target cell.

The approach described here is relevant to any protein+RNA/DNA based system to guide the nuclease as the delivery process is independent of the exact size and composition of the complex and because complex formation of the editing materials occurs and is controlled in vitro under their optimal conditions.

Implementations of the invention may also provide one or more of the following features. Deforming the cell includes deforming the cell for substantially or about 1 μs to 10 ms, e.g., 10 μs, 50 μs, 100 μs, 500 μs, and 750 μs. Incubating occurs for 0.0001 seconds to 20 minutes or more, e.g., substantially or about 1 second, 30 seconds, 90 seconds, 270 seconds, and 900 seconds.

The pressure and speeds at which a cell is passed through a microfluidic channel may also vary. In some embodiments, a pressure of substantially or about 10-35 psi is used to pass the solution containing a cell through a microfluidic channel. The speed may be adjusted for a variety of reasons, including to improve viability of the treated cells while maintaining high payload delivery. In some embodiments, the cell passes through the microfluidic channel at a speed of substantially or about 300 mm/s, 400 mm/s, 500 mm/s, 600 mm/s, 700 mm/s, 800 mm/s, 900 mm/s, 100-300 mm/s, 200-700 mm/s, 250-400 mm/s, 1-1000 mm/s, 1 m/s, 2 m/s, 3 m/s, 4 m/s, 5 m/s, 6 m/s, 7 m/s, 8 m/s, 9 m/s, 10 m/s, 0.01-5 m/s, 5-10 m/s, or 0.01-10 m/s. Where the cell is a plurality of cells, substantially or about 5, 10, 20, 30, 40, 50, 60, 70, 75, 80, 85, 90, 91, 92, 93, 94, 95, 96, 97, 98, 99, 90-95, or 80-99% or more of the cells may be viable after passing through the constriction. In some embodiments, the cells are viable for at least about any of one hour, two hours, three hours, four hours, five hours, six hours, seven hours, eight hours, nine hours, ten hours, twelve hours, eighteen hours, twenty four hours, or forty eight hours after passing through the constriction.

In some examples, a device of the invention includes 2, 10, 20, 25, 45, 50, 75, 100 or more channels. In some embodiments, cells are moved, e.g., pushed, through the channels or conduits by application of pressure. In some embodiments, a cell driver can apply the pressure. A cell driver can include, for example, a pressure pump, a gas cylinder, a compressor, a vacuum pump, a syringe, a syringe pump, a peristaltic pump, a manual syringe, a pipette, a piston, a capillary actor, and gravity. As an alternative to channels, the cells may be passed through a constriction in the form of a net. In either case, the width of the constriction through which the cells traverse is 20-99% of the width or diameter of the cell to be treated in its unconstricted, i.e., suspended, state. Temperature can affect the uptake of compositions and affect viability.

In certain embodiments, a temperature of 0 to 45° C. is used during cell treatment, e.g., 0-25° C. In various embodiments, the methods are carried out at room temperature (e.g., 20° C.), physiological temperature (e.g., 39° C.), higher than physiological temperature, or reduced temperature (e.g., 0.1° C.), or temperatures between these exemplary temperatures (e.g., 0.1 to 40° C.).

In some embodiments relating to immune cells, treatment of unstimulated T cells, B cells and/or monocytes is carried out at temperature of 4-8° C., e.g., on ice. In another example, dendritic cells, activated T cells, and/or activated B cells are treated using the device at temperatures of 20-25° C., e.g., at typical ambient room temperature.

In some embodiments, following controlled injury (e.g., perturbations) to the cell by constriction, stretching, and/or a pulse of high shear rate, the cells are incubated in a delivery solution that contains the complex that one wishes to introduce into the cell. Controlled injury may be characterized as small, e.g., 200 nm in diameter, perturbation in the cell membrane. The recovery period for the cells is on the order of a few minutes to close the injury caused by passing through the constriction. The delivery period comprises 1-10 minutes or longer, e.g., 15, 20, 30, 60 minutes or more, with 2-5 minutes being optimal when operated at room temperature.

In some embodiments of the device and methods described herein, passage of stem cells or progenitor cells such as induced pluripotent stem cells (iPSCs) through a constriction channel does not induce differentiation, but does reliably induce uptake of compositions into the cell. For example, gene editing compounds are introduced into such cells without complications associated with the method by which the factor(s) was introduced into the cell.

The size and duration of temporary perturbations in cell membranes can be modified by adjusting various factors, such as the diameter of cell-deforming constrictions and the speed at which cells pass through the constrictions. Disclosures regarding the size and duration of perturbations provided herein should not be interpreted as limiting. Non-limiting descriptions of perturbations and recovery are provided in Sharei et al., (2014) Integr. Biol., 6, 470-475, the entire content of which is incorporated herein by reference. In some embodiments, the perturbations of the cell membrane may be characterized by a maximum diameter of substantially or about 1-20, 1-600, 4, 5, 6, 7, 8, 9, 10, 12, 14, 16, 18, 20, 25, 50, 75, 100, 150, 200, 250, 300, 350, 400, 450, 500, or 600 nm. In various embodiments, perturbations of the cell membrane having a maximum diameter of substantially or about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell membrane for at least substantially or about 1, 2, 3, 4, 5, 6, 7, 8, 9, 10, or 1-10 minutes or more (11, 13, 15, 18, 20 minutes or more).

In various embodiments, the diameter is less than the diameter of the cell. For example, the diameter of the constriction may be substantially or about 20, 25, 30, 35, 40, 45, 50, 55, 60, 65, 70, 75, 80, 85, 90, 95, or 20-99% of the diameter of the cell. Non-limiting examples of the diameter of the constriction include substantially or about 4, 5, 6, 7, 8, 9, 10, 15, 20 4-10 μm, or 10-20 μm. Different lengths of the constriction are also possible. Non-limiting examples of constriction lengths include substantially or about 10, 15, 20, 24, 30, 40, 50, 60, 70, 80, 90, 100 10-40, 10-50, 10-60, or 10-100 μm.

Many cells are between 5-20 μm in diameter, e.g. unstimulated T cells are 7-8 μm in diameter. For example, the diameter of the constriction portion is 4.5, 5, 5.5, 6, or 6.5 μm for processing of single cells. In another example, the size/diameter of the constricted portion for processing of a human egg is between 60 μm and 80 μm, although larger and smaller constrictions are possible (diameter of a human ovum is approximately 100 μm). In yet another example, embryos (e.g., clusters of 2-3 cells) are processed using a constriction diameter of between 12 μm and 17 μm. In a non-limiting example relating to unstimulated T and B cells, the device comprises a constriction having a length of about 10, 15, 20, 25, 30, or 10-30 μm, a width of about 3, 3.5, 4, or 3-4 μm, a depth of about 15, 20, 25, or 15-25 μm, and/or an about 5, 6, 7, 8, 9, 10, 11, 12, 13, 14, 15, or 5-15 degree angle. Examples of microfluidic devices useful for delivering payloads into immune cells are described in PCT International Patent Application No. PCT/US2015/058489, Delivery of Biomolecules to Immune Cells, filed Oct. 30, 2015, the entire contents of which are incorporated herein by reference.

In addition to single cells, even very large cells, e.g., eggs (approximately 200 μm in diameter), clusters of cells, e.g., 2-5 cell clusters such as an embryo comprising 2-3 cells, are treated to take up target compositions. The size of the aperture is adjusted accordingly, i.e., such that the width of the constriction is just below the size of the cluster. For example, the width of the channel is 20-99% of the width of the cell cluster.

Cells or cell clusters are purified/isolated or enriched for the desired cell type. Dendritic cells or other cells, e.g., immune cells such as macrophages, B cells, T cells, or stem cells such as embryonic stem cells or iPS, used in the methods are purified or enriched. For example, cells are isolated or enriched by virtue of their expression of cell surface markers or other identifying characteristics. Dendritic cells are identified and isolated by virtue of their expression of the β-intergrin, CD11c or other identifying cell surface markers. With regard to cells, the term “isolated” means that the cell is substantially free of other cell types or cellular material with which it naturally occurs. For example, a sample of cells of a particular tissue type or phenotype is “substantially pure” when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS).

Payload compositions such as polynucleotides, polypeptides, or other agents (e.g., Cas9 and gRNA) are purified and/or isolated. Specifically, as used herein, an “isolated” or “purified” nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Examples of a an isolated or purified nucleic acid molecule include: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

Complexes are prepared from purified modules or components, e.g., purified protein(s) and purified nucleic acids (RNA and/or DNA). Thus, the ratios of the components are controlled and tailored as desired to achieve a desired gene editing result. The present method is particularly suitable for delivery of sensitive payloads, e.g., protein-RNA/DNA complexes, e.g., complexes that are 40 kDa, 50 kDa, 75 kDa, 100 kDa, and up to 120, 130, 150, 200, 250, 300 kDa or more.

Surfactants (e.g., 0.1-10% w/w) are optionally used (e.g., poloxamer, animal derived serum, albumin protein) in the flow buffer. Delivery of molecules into cells is not affected by the presence of surfactants; however, surfactants are optionally used to reduce clogging of the device during operation.

In some aspects, the device is made from silicon, metal (e.g., stainless steel), plastic (e.g., polystyrene), ceramics, or any other material suitable for forming one or more appropriately sized channels or conduits. In some aspects, the device is formed of materials suitable for etching micron scaled features and includes one or more channels or conduits through which cells pass. Silicon is particularly well suited, because micro patterning methods are well established with this material, thus it is easier to fabricate new devices, change designs, etc. Additionally, the stiffness of silicon can provide advantages over more flexible substrates like Polydimethylsiloxane (PDMS), e.g., higher delivery rates. For example, the device includes 2, 10, 20, 25, 45, 50 75, 100 or more channels. The device is microfabricated by etching the silicon. Cells are moved, e.g., pushed, through the channels or conduits by application of pressure. A cell driver can apply the pressure. A cell driver can include, for example, a pressure pump, a gas cylinder, a compressor, a vacuum pump, a syringe, a syringe pump, a peristaltic pump, a manual syringe, a pipette, a piston, a capillary actor, and gravity. As an alternative to channels, the cells may be passed through a constriction in the form of a net. In either case, the width of the constriction through which the cells traverse is 20-99% of the width or diameter of the cell to be treated in its unconstricted, i.e., suspended state.

Various implementations of the invention may also provide one or more of the following clinical and research capabilities. Quantitative delivery of gene-editing complexes or components thereof to cell models for improved screening and dosage studies can be achieved. The method could be deployed as a high throughput method of screening protein activity in the cytosol to help identify protein therapeutics or understand disease mechanisms. The devices and techniques are useful for intracellular delivery of gene-editing complexes to a specific subset of circulating blood cells (e.g. lymphocytes) or even whole blood; high throughput delivery of complexes or components thereof into cells, especially oocytes and zygotes; targeted cell differentiation by introducing gene-editing (optionally together with genetic material such as donor DNA) to induce cell reprogramming to produce iPS cells; delivery of DNA and/or recombination enzymes into embryonic stem cells for the development of transgenic or mutant stem cell lines; delivery of DNA and/or recombination enzymes into zygotes for the development of transgenic or mutant organisms; dendritic cell (DC) cell activation; iPS cell generation; creating mutations in normal or diseased cells (such as cancer cells) to study the contribution of one or more genes to cellular function and/or disease; and stem cell differentiation. Skin cells used in connection with plastic surgery are also modified using the devices and method described herein. Methods of delivering gene-editing proteins disclosed herein may also be used to generate CAR-T cells or to genetically modify hematopoietic stem cells (HSCs) for treating genetic and other diseases. In embodiments relating to HSCs, a subject may receive an autologous, syngeneic, or an allogeneic edited HSC. In various embodiments, cells of a subject may be ablated before the subject receives a gene-edited cell. For example, bone marrow cells of a subject may be ablated with radiation or chemically before the subject receives a gene-edited HSC. In some embodiments, a gene associated with beta thalassemia or sickle cell anemia is edited using a method or composition disclosed herein. Cells processed ex vivo or in vitro, i.e., outside of the body of a subject, in accordance with the invention are useful for subsequent administration to a subject in need of treatment or diagnosis of a pathology. In alternative embodiments, in vivo cell processing is carried out.

In various embodiments, the SHP2 gene is edited/mutated to reduce the activity thereof or knock out or reduce SHP2 expression. In such embodiments relating to gene editing in T cells, the T cells become less responsive to immunosuppressive signals and have increased activity toward tumors. In such embodiments, the T cells may be more responsive to tumor antigens and more effective at treating cancer.

Aspects of the present subject matter relate to the rapid and transient delivery of protein-protein as well as protein-nucleic acid complexes, e.g., gene-editing complexes to cells. A nucleic acid component of the complex comprises a deoxynucleic acid (DNA), ribonucleic acid (RNA, e.g., mRNA, gRNA) or other double-stranded or single stranded nucleic acid compounds, respectively. For example, the delivery of a gene-editing complex (e.g., a ribonucleoprotein (RNP)) may achieve gene editing faster than if an expression vector encoding components of the gene editing complex (e.g. a Cas protein and a gRNA) was delivered to the cell. For example, the gene may be edited (e.g., mutated or replaced) in the cell 0.1, 0.5, 1, 1.5, 2, 2.5, 3, 3.5, 4, or 0.1-4 hours sooner than in a corresponding cell that has received microfluidic or electroporation-mediated delivery of an expression vector that encodes gene editing complex components.

Each embodiment disclosed herein is contemplated as being applicable to each of the other disclosed embodiments. Thus, all combinations of the various elements described herein are within the scope of the invention.

Related apparatus, systems, techniques, and articles are also described.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 6 shows a FoxP3 genomic sequence running from the first sheet of FIG. 6 to the last sheet of FIG. 6 (SEQ ID NO: 56). Exons belonging to FoxP3 are shown in underlined and highlighted letters. Other exons within this region that do not belong to FoxP3 are shown in non-underlined highlighted letters.

FIG. 7 shows a FoxP3 translated amino acid sequence (SEQ ID NO: 57). Alternating exons are underlined and non-underlined. Bold with italics indicate a residue overlap splice site.

FIG. 8 shows a SHP1 genomic sequence running from the first sheet of FIG. 8 to the last sheet of FIG. 8 (SEQ ID NO: 58). Exons belonging to SHP1 are shown in underlined and highlighted letters. Other exons within this region that do not belong to SHP1 are shown in non-underlined highlighted letters.

FIG. 9 shows a SHP1 translated amino acid sequence (SEQ ID NO: 59). Alternating exons are underlined and non-underlined. Bold with italics indicate a residue overlap splice site.

FIG. 10 shows a SHP2 genomic sequence running from the first sheet of FIG. 10 to the last sheet of FIG. 10 (SEQ ID NO: 60). Exons belonging to SHP2 are shown in underlined and highlighted letters. SEQ ID NO: 60 is also as follows:

AGGCTCAAGCAATCCTCTCACCTCAGCCTCCCGAGTAGCTGGGACTACAGGCGCGCGCCA

CCACGCCCGGCTAATTTTTGTATTTTTTGTAGAGATGGGATTTCACTATTTTGCCCGGGC

TGGTTCCCAACTCCTGGACTCAAGCGATTCGCCCGCCTCAGCCTCCCAAAGGGAAGTGCT

GGGATTTCAGGCGTGTGCCACCGCTCCCACCCCAAAGTAGTATTTATTGTAATTATTATT

ATTATTTTGAGACGGAGTCTCGCTCTATTGCCAGGCTGGAGTGCAGTGGCGCGATCTCGG

CTCAATGCAACCTCTGCCTCCCGGGTTCAAGCGATTCTCCTGCTTCAGACTCCCAAGCAG

CTGGGACTACAGGCGCCCCCCACCACGCCAGGCTAATTCTTGAATTTTTAGTGGAGACGG

GGTTTCACCATGTTGGCCAGGATGGTCTCGATCTCTTGACCTCGTGATCCGCCCACCTCG

GCCTCCCAAAGTGCTGGGATTACAGGCGTGAGCCACCGCGCCCAGCCTATTATTATTTTT

TTAGGCAGTGTCTTGCCCTGTCGCTCAGGGTGTAGTGCAGTGGCGTGATCACGACTCACT

GCAGCCCCGACTTCTCGGGCTTAAGTTATCTTCCCGCCGCAGCCTCCACGCCCGGTTAGT

TTTTTGCATTTTTTGTAGAGATGAGGTCTTGCTTTTTTGCCCAGGCTGGCCTCGAACTCC

TTGGCTTAAGCGAACCTCTTGCCGCAGCCTCCCAAAGTGTTGGGATTACGGGCGTGAACC

ACCGCGCCCAGCCTACTATCTTTATCTTACAGAAAGAAAAGAATGGAGGAAACCGAGGCT

CGGAGACAGTAGGTAATTTCCCCAAGGTTCCACAGCTAATGAGTGGAGCGGCGATTTGTG

GAACGAAATGAATGAAATCGATGTGGCAGCGGGCCCGGACGGGTCGGTGGCGTAGACGCG

GAGCGCGCAGCTCACACCTGGCGGCCGCGGTTTCCAGGAGGAAGCAAGGATGCTTTGGAC

ACTGTGCGTGGCGCCTCCGCGGAGCCCCCGCGCTGCCATTCCCGGCCGTCGCTTCGGTCCT

CCGCTGACGGGAAGCAGGAAGTGGCGGCGGGCGTCGCGAGCGGTGACATCACGGGGGCGA

CGGCGGCGAAGGGCGGGGGCGGAGGAGGAGCGAGCCGGGCCGGGGGGCAGCTGCACAGTC

TCCGGGATCCCCAGGCCTGGAGGGGGGTCTGTGCGCGGCCGGCTGGCTCTGCCCCGCGTC

CGGTCCCGAGCGGGCCTCCCTCGGGCCAGCCCGATGTGACCGAGCCCAGCGGAGCCTGAG

CAAGGAGCGGGTCCGTCGCGGAGCCGGAGGGCGGGAGGAACATGACATCGCGGAGGTGAG

GAGCCCCGAGGGGCCCGGCGCGGGCCTCGGCCCGGCCACCGCCGCGTTCGGTTAGCCCCG

TCCGGAAGGGGGCGCCCCGGCCGGGCTTCGGGCTCCCGCCCCGGGTCGGGGTTGGGGGCC

GGTTCCCTCCTCGTCCCCTCGCCCTCCAGGGGCCGGGGGCCGGCCCCACCGCGCCCCCAC

CCCTCGGGTCCCCATTCATTTCCTGCCTCCCCGAGTTCCGGCTGCGGCAGCCCCGGGGAT

GCCCGTCAGGCCCGGGGCAGGTAGAGCCGCCGAGGGAACCACGGGTGCCAGCGGCCAGGC

TCAGCGCCGCATTCCTGACCCATTGCCTCATGAGAATTGCCTCATGGTGATTCCGAAATA

ACCCTGCTCACTTGGGGAGGCTCCTTGGGACACGAGAGGGGAGTTGCGCGGGGCCGGGCC

CCCAGTGGTCTAGTCGTTCTGGCTCACTGTGCCACTTTCGTGCATTTGGGGACTTCACGC

AGGACCCCTGACCCTTTTATATGCCTCTTTGTGTCTTCTTTTCCTCCTACCCCTCACGTG

CCAGAAATGGAAAAACTGACTGTATCTGCAGCCACTAGAAGTATTTCCTTCCTCTGCGAT

CTTCGCTTTGGGAGATGGAAAGGAAGGGAGCCGCATCTCGTTATTTAATCCTTCACTGCA

ACCTTAACAGTCAGGTCACTTTACTGGTACCCGTTTTATGGATGAGGAAACCGAGGCCCA

GAAGCAACATGCTAGTAAATGACAAGATTTGAAACTTAGGAGGATTAGTGAGTTAATGAG

ATCCTTTGAAAGGTCAGGGTAATACTACTACTAATAGCTAACATTTGCTTAGTTCTGACC

ACAGCCCTATCAGATGGCTACTATTATCCCCATTGTAAAGATGAGTAAACCGAGTTTCAG

AGGTTAAGTAAATTGCCTAACCTCACAGCTAGTAGGTGGTGGAGACAGAATCCCTACTTT

-continued

TAATCACTATGTTGCTTCTATTATTTTGTAACTATTGCTAACCATTTGTAAGCCTTAATT

TTGTTGTCAAACAGTAGTGTGACCTGTTGTTTTCAGATAGTGATCCTGCTATTTTGTATA

GTCACTCTATATACCACTCACACTTAAGACCCATTGTCTATTCTTTTCCATGATTGTTCA

ATTATGGTCACTGTCTCAGACATTTAAAAAACGATTCAAGCTATTGAGGCTATTTGAATG

AGATTTTCTTTTCTTTTTTTCTTTTTTTTTTGGAGACGGAGGCTCACTCTGTTGCCCAG

GCTGGAGTGCAGTGGCGCAATCTCGGCTCACCACAATCTCCGCCTCCTAGGTTCAAGCGA

TTCTCCTGCCTCAGCCTCCCAAGTAACTAGGACTACAGGCGCACCACTATGCCCGGCTAA

TTTTTGTATTTTTAGTAGAGACAGGGTTTCACTATGTTGGCCAGGCTGGTCTCAAACTCC

TGACCTCGTGATCCGCCCGCCTTGGCCTCCCAAAGTGCTGGAATTACAGGCGTGAGCCAC

CGTACCCAGCCTGAATGAGATTTTTCAAAATATTAGGAATGTCTCCTCCAAACACACCTG

GCATGTTATTCATACATGGATCTGGAATTTAAAAAGGGGAGAAAAAGAAAACTGAGAACT

CGTAGGAAGTGAGTGACTTGGACAGGTCGGTTGGCAAGTGCTTACAGATCTGGGTAATAT

ATAACTGCATTTCAACAGAACAGTGTATAGCCTCAAATGTTCTAATTCTTTAGGGAGCTT

TTAAATAAACAGTTGTCTATTCTTTAATCTGTCAAATAGTCATTGAGCCTTTTGTTCCTG

GTGTCTGCTCTTCCAGACAAGTAAGGATCTGCTGCTTTAGGAGACATCAGACGGGGCTGG

GGGTTGGGAAAAGGTCTGGGTAGTAATAGACCCTACATTGTCCAGTTTGTTCATTTAGAA

GCATAGAAGTGTGGGCATAGTCAAAGTAGCAAGTGGTAAAGATGACAGTTTGAAATGGAG

TAATTCCTTCTCCCCTCCAGCCCTGGTATTATGCACCACCCAAAAAGCCGGGTTATGAAC

ATAATACACATAATTTTGAATGATTCATTATTTTTTGGATTATAAGCCTGTTTTATTTGT

TAACCAGCCTTAATGAGGTATAAATGACATGCAATTAATTGCATATATTTAAATGTACAA

TTTGATCAGTTTTGACATACATATACACTTGGGAAACCACCACCATAGTCAAGATAATGA

ACACATCTATCACCCCTGGTAATTTTGCCTTATGTTCTTTATAATCCTTCCTTTGTTCTT

AGGCAGCCACTATTCTGCTTTCTGTCACTATGTATTAGTTTGCATTTCCTAGAATTTTAT

TTTTAAAAATTTTAAAATTGTTTGAATAGAGATGGGGTCTCACTGTGTTGCCCAGGGCAG

TCTCAAACTCCTGGGTTCAAGTGATCCTCTCACCTTGGCCTCCTGAAGTGTTGGGATTAT

AGGCATGAGACACCCTGCCCAGCCCTAGAATTTTATTATTATTGTTATTATTGTGTTTTT

TTGAGATAGGGTCTCACTTTGTTGCCCAGGCTGGAGTGCAGTGGTGCAATCACTGCAGCC

TTGTTTTCCTAGGCTCAATCCATCCCCCCTCCTCAGCTTTCCGGTTACTGGGGCTACAGG

TGTGCACCACCACACCCGGCTAATTTTTGTATTTTTTTATAGAGACAGGGTTTTGCCATG

TTGGCCAGGCTGGTCTCAAACTCCCGGGCTCAAGCGATCTTCCTGCCTCGGCCTCCCAAA

GTGCTGGGATTACAGGCATGAGCTATTGCGTCCCGCCTTCAAATTACTTTAACCTAGTAT

TAATTCATTCAACAGGAAGTTAATGAGCCAGGCAGGATAAAGCAGTAAGATAGGAAAATA

TTGCTATTTTCATGGCTGAGAGAGAGCAGACAAACACATGACTAAATAGGGCAATTTCAG

GTAGTAATAAATTCTAGGAGGGAAAAAATCCCACAGAAATGTGAGGATGGGAGAATGCAG

TTAGTTTTGATAGGTGGTTTAGAGAAGGTGATCGTGTGAGCTGACACCTGAATGACAATT

AGTAGTCTGAATTTTGTTTTGCTTAATTATCAAAATAACTCCTCTTGGGTTCGGCTTTTA

TATGCATCCAGTAATTAAAATGTAAGTATATTCAATGTACTGATATCTCTCAGCATCATA

GGTAGGAAAACTAAGGCATTCAGCAATTAAGTGACTCCTCCCTTGATCATGTAGCAGTGA

TAGTACTGGATTTAGATTTTGAGGTTGCTTCTCTGCCCTTTTCTGCCTTTGTGAAACCAA

CAAAGCTGCCTGTATTTTCCAACTCTTCCTTCAGCATGTGGTACCTCCTTTACATCTGTT

TTTGTTGCTCTGAAATCCATACGCGACGATGAGCTGAGAGGGGCAGAAAATTGAGCTTGT

-continued

TCTGAGACTGGAGGCTTTTGGTTTATCTCTTGCAGGTCAAGTACATTTTGTCCTGGGCTC

TCCCTGGTGGCCACGTTTGTTTATCTCCTGCGGGAGTAAATAAACTTGCCTTGCTGAAAA

ATAACAGTTCTGTGTCTTTGCAGTGGAAACTGGGATGTCTTTATTAACGTTAGGTCCTGA

TGTAAGGCCAAGTTTTTGGTTAGAGTTGCTCAAGTGCAGAGGCCACTGCTAAGATGACTT

ACCCCTCGTGTCCATGGTCAATGTGGAGACTGTTATGAGTGGCACATGATGCTGGAAAAG

CAGAGCCAACTCATGTTTGTAATTGTCCTAGCAGGCCGTGGTGTACTTTGTTAGGCAGCC

ACAGAACAATAGAGAAACTCAGCTTATTCCCCTTCCCTCTGGGAAACACAGACAGTACTT

GCCATCCAACGCCAATGTTTTTAAGGAAGAAAGAGGCAAAAAGTGATGTTGGCAAGGTCT

CTGGGAGTTGTGGACCCCAACCAAGGATTGGAGACCCTGAAATGGATTCAGATGCCCTAA

AATGCAGCCCAGTTCATTACTATGAATTTTGGAGGACTTTGTGCCTTGAGCAAATGTGTA

TATGTGACGCTCTTTGACAACACTGAAATAGGAAAAATACTATCCATGTTCGCGAGGAGC

ACTGAATTTAGAGAGGGAGACAGACTTTTATGCCAGCATCAAATGAATTTGATAAAGCTA

GTACCAAAATGAAATTTGAAATTTTTTTTTTTTGAAATAGAGTCTTACTCAGTCACCCAG

GCTGGAGTGCAGTGATACAATATTGGCTCACTGCAACCTCCACCTCTTGGGTTCAAACAA

TTCTTGTGCCTCAGTCTCCTGAGTAGCTGGGATTACAGGTGCGTGCCACCATGTCTGGCT

AATTTTTATATTTTTAGTAGGGATGGGGTTTCACCATGTTGGCCAGGCCGGTCTTGAACT

CCTGGCCTCAAGTGATCTGCCCACCTTGGCCTTCCAAAGTGCTGGGATTATAGGCATGAG

CTACCACACAAGCCTGAAATTTGAAATGTATTGGTATAGAATATACTGTTTAGAATGTAT

GTGTATATATGTATATTTGTATACTCATATAAACACAAATACACATTGTATGTGTTTCTG

TAATATGTATATCTGTCTACACATACATGTATATACACACATACAATGTCTTTTTTTTTT

TTTTTTTTTTTTGAGACAGGGTCTTACCCTGTTGCCCAGGCTGGAGACTGCAGTGGCATA

ATCTTGGCTCACTGCAGCCTCGACCTCCTGGGCTCAAGTGATCCTCCCATCTCAGCCTCC

TGAGTAGCTGGGACTGACTACAGGCACGTGGCATCAAACTTGTCCAATTTTTCTATTTTT

TTGTAGAGTTAGGGTCTTGCTCTGTTGCCCAGGCTGGTCTCAAATTCCTGGGCTCAAGCT

GTCTGCCTGCCTCGGCCTTCCAAAGTACTAGGATTACAGATGTGAACCACTGTACCTGGC

CTTTACAATGTCTATTTTAAAGATAATGGTTCAAGTTTTTATCATCCCACTGGCCTACTC

TAATGAAACATCTATCCATTCATTGAAGAATTATTTATGGTGGGATAACTCTGTGCCAGG

TACCGTGCTAGGCATTGAGTATTCCAGGTTTTAGGAAACAGCACATGCAAAAGTGCTGAA

GTGGGAGAAGATCTCGGAGTGATTGAAGGCTAGGAGAGAGCAAGTGTGGGAGCTGTGAGG

CTGGGAAGGTGGGAGGTAGGTGGGAGCAGACCACATAGGGATTCTTAATGTCTTTAGTGT

CATGTGGACCATGGAGAGGAGTGTAGATTGTATTTTTAGAGCAATGCAAAATCATAGAAG

GATGTGATCGGGGGAGTGGCATGAGCTGATCTATTTAAAAATATTTCTCTGGCTGCTGTG

AAGGAAGGATTGTAGGAGGCAGGAGTAGATTCAGGGAGATGAGACAAGTGATGAGAGAGG

CTTTGAACTTGGGTAAAAGTAGTTTGTGGAAAGTCTTTTTTGGAGGTAGTTTTTGTTTAT

TGCCTTGTCATCAAAGCAGAGATGCTGACCAATGAAACTCCATGAGAAAATAGTGATTTA

TAAAGACATATCTATGCACTGCCATTAAAAAGCTGCTTGGAAAAAAAGGATAAAAAGCTG

CTTTAACAACTTTTTTTTTTGAGATGGGGTCTTACTCTGTCACCCAGGCTCACGACCTCA

GCTCACTGCAACCTCTGCCTCCCAGGCTCAAGCATTCTCCCACCTCAGCCTCCCGAGTGG

CTGGGACTGCAGGCACACGCCACCATGTCAGGCTAATTGTGTGTGTGTGTGTGTGTGTGT

ATGTGTGTGTGTGTGTGTGTGTGTGTGTGCTGGGACTGCAGGCACACACCACCATGTCAG

-continued

GCTAATTGTGTGTGTGTGTGTGTGTGTGTGTGTGTGTGTGTGTGTGTGTGTGTGTGTGTA

TGTAGAGATGGGGTTTTGCCATGTTGCCCAGGCTGGTCTCAAAATGTTGCCCAGGCTGGT

CTCAAACTCCTGAGCTCAGGTGATCCACCCGCCTCGGCCTCCAAAGTGCTGGAGATTACA

GACGTGAGCCACTGTGCCCACCTAACAACTTTAAAAAAATTTTGACATTTAGTAGGATAT

TTATTGCATTATTGTTGAGATGGCAAAATATTGGAGACAACTGAAATGTTCATCAGTGGG

GGGGGCTAGTTAAATGAAATACAGTGTAGCATGCATTAGAACACTTTTCAAGAATTTAAC

TTTTTTTGTAGCCTTTTACTTATAATGCTTGTCCCTATTGATGCCTTTTTTTTCAGCATG

ACTTACTCTTTTACTATAGGATATTAAAATTTAATTAGATTAGAAATGAGGAATATTCTT

GTAATCTGTAGAAAGTAACAAACTATAAACTTATTCCCCAAGAACAAATATAATAATTTT

TCTGGAGTAGCAGGTAAGAAAGATATAAATTTATATGTATACAAGAAACTGAAATTAGAC

TTTATACATTTAAAGGTTACAAGTGCAGTTTTATTACATGAATGTATTATCCAGCATTGA

AGTCTGGGCTTTTAGTGTAACCAGCACCTGAATAACATACATTGTACCCATTAAGTAATT

TCTCATCCCTCAAACCCCTCCCACCCTGAAATTAGACTTTGGATCCCTAGTTTAAATTCC

ACCCCTCTCTTTTTTTGAGACAAGGTCTCACTCTGTCACCCAGGCTGGAGGGCAATGTTG

CAATGATAGCTTACTGTAGCCTCAACCTCCTGGGCTCAAGGGATACACCCTCCTCAGCCT

CCTGAGTAGCTGGAACTGCAGGCGTGCACCACCACATTCAGCTAATTTTTTGATTTTTTT

ATAGAGATGAGGTCGGAACTCCTGGGCTCAAGCGATTCTCCCCAAGTGCTGGGGTTACAC

ACATGGGCCACTGCCCCCAGCCTAAACCTCCTTTCTCAGTATAGCAGCCTTGAGATGAAG

TTCCTGAAATTACTGGCCAGCTTGACTGTTTCCCCACATCACTGGAGGAGGGGGATGCAT

AGATAAAACAAAATATTCAGCATCATTGTATTTTCTTTTTGTTTCATCAGCATCTTTTTT

TAAAACTCACTTGACATAAGTCCCTAGCCTCAAAGAGTAAAGCCTTTGCAGAATCTGCAT

TCAGATTTCGGGTGTGATTTCCTGACAGATAGTTCAGGTTTGTAAACTCTTTTTTTTTTC

TTTGAGACAGAGTTTCACTCTTGTAGCGCAGGCTGGAGTGCAGTGGCACCATCTTGCCTC

ACTGCAACTTCTGCCCCCTTGATTCACGCGATTCTCCTGCCTCAGCCTCCTGAGTAGCTG

GGATTACAGGCATGCGCCACCACACCTGGGTAATTTTTGTATTTTTAGTAGAGATGGGGT

TTCACCATGTTGGCCAGGCTGGTTTTGAACTCCTGACTTCAGGTGATCTACCTGCCTCAG

CCTCCCAAAGTGATGGGATTACAGGTGTGAGCCACCGCAGCCGGCCAAAACTTTGTTTTT

TTTCCTCTTTTTGTTGCTGAGAAATGTAAACTCTTACAGACACAAATTATGTCTCCCATT

TTTTAAAACCCACTCAACACAGGGGTCATGTGTAATAGGCCCTGGAGCTTATTTTAGACA

TTGATTTGAGGCTCTTTTCCCCAAGTGCTGGTTTGTGTGTGTGTGTATGTGTGTGTAAGT

CTTTCTATGAGATGAGTGGTACCTACCTGGGCTGTGTGATCTTTTTTATTTTATTTATTT

TATTTTTGTAGATACGAGGTCTCACTATGTTGCTCAGGCTGGTCTTGAACTCTGGGGCTC

AACCTATCCTCCCTCCTTGGCCTCCTAGAGTGCTGAGATTACAGGTGTGAGCCACTGCAC

CTGGCCAGCGATCCTTAATAAATATAGATAATGGCCGGGCGTGGTGGCTCACACCTATAA

TACCAGTACTTTGAGGGGCCGAGGCTGGCAGGTCACCTGAGCTGAGGAGTTTGAGACCAG

CCTGGGTAACGTGGGTGAAACCCTGTCTCTACAGAAAATAGAAAAATTAGCCAGGTGTGG

TGGTGCATGCCTGTAGTCACAGCTACTTGGGAGGTTGAGACAGGAGAATTGCTTGAACCT

GGAAGGTGGAGGTTGCAGTGAGCCGAGATCGTGTCTTTGAACTCCAGCCTGGGTGACAGA

GTGAGACCTTGTCTCAAAAAAAAAATATAGATATAGGCTGGGCGTGGTGGCTCACACCTGT

AATCCCAGCACTTTGGGAGGCCGAGGCGGGTGGATCAGGAGGTCAGGAGATCGAGACCAT

CCTAGCTAACATGGTGAAACCCTGTCTCTACTAAAAATACAAACAATTAGCCAGGCCTGG

-continued

TGGTGGGTGCCTGTAGTCCCAGCTACTCGGGAGGCTGAGGCAGGAGAATGGCGTGAACCC

GGGAGGTGGAGGTTGCAGTGAGCCGAGACTGTGCCACTGCCCTCCAGCCTGGGCGACAGA

GCGAGACTCTGTCTCAAAAAAAAAAAAATCTATATATCTATATATCTATATCTATATAGAT

ATAGATATAGATAATGCCAGATGATGGCTGGTTAGAAGGGATTGTCAGGGGCTGGCAGGT

TTTGCAGGTGTTAGAATGAGCAAGATGAGGAGAAGGATGCTTACTTCCCTCTCCTTGTAA

CTCTCTACCCCCTCCCCTCAGTGTTTTTTTATTTTTATTTTTATTTATTTATTTTTTTTG

AGACAAGGTCTTGCTCTGTCACCCACACTGGATTGCAGTGATGCAATCATAGCTCATTGA

AGCCCAAACTCCTGGGCTCAAGTGATCCTCTTGCCTCAGCCTCCCAAGTAACTGGGACCA

CAGGTGCGTACAACTATGCCCAGTTAAGTTTTTCATTTTTTATACAGACGGGGTCTTGCT

ATGCTGTCCAGGCTGGACTTGCACTTCTGGCTTCAAGTGATTCTCTTGCCTCAGTTTCCC

AAAGTGCTGGCATTATGGGCATAAGCCACTGTGCCTAGCCCATCAGTGTCTTTTTATCCT

TTACTCCTATCAAAATTCATTCACTCAGCAGCCATTGATCAAGTGCCTACTATATACATG

TTGAGGACTGGAAATTTATTTGTCTCTTCTCATCTTATCTGGACCCTCTGTGTTAATTGT

AATTAACTGTAATCATTCTGTATTAATTGTAATAAACTTGTTGATAAACTCAAATGAGGC

CATACCGTTTTGCCACTTCCCCTCCTTCCAGGTTATATGGATGTACTTACATTGCAGGTT

TCATTTGTTGGTTCAGTTTTTAAACTAAGCCCTATTGTGTCAAATTATGCTAGGTGTGAG

ATGGGGAGTTCAAGCTGTGTGTTGTCTTTTTTTTTTTTTTTTTTTTTGCCTCACTTACTA

ATATACAAGCGCTTATAACCTTTGAGGCTGGCCCTATACATTAAGATTTTTATTAATTCC

ACTGTTCTTTATCTTCTCTTACTAAGTTCTCAGGGTCGAATGAACTCTAACTGCTCCTTG

CTAGTGATAAGCAAGTTGCAAATTACAGAATTGTCAGTGATTGAATACACGTATTAAACC

TGTAACTGGGAAGCATTTTTGGTAATTATGAATACTTTTGGAAAAAAAAAAAGCTATGGAA

GGAAAGTTTAAAATCTACGAAAGCTCAAGTAGATGGTCATGGAATAGCTATTTCAATTTC

TAACTATATATTACTTATTTATTTATTTATTTTTGAGACGGAGTTTAGCTCTTGTTGCCC

AGGCTGGAGTGTAATGGCGTGATCTCAGCTCACTGCAACCTCCACCTCCCGGGTTCAAGC

TATTCTCCTGCCTCAGCCTCCCGAGTAGCTGGGATTATAGACATGTGCCACCACGCCAGG

CTAATTTTGTATTTTTAGTAGAGACGGGGTTTCTCCACATTGGTCAGGCTGGTCTCGAAC

TCCCAACCTCAGCTGATCCGCCTGCCTCGGCCTCCCAAAGTGCTGGGATTACAGGCGTGA

GCCACCGCGTCCGGCCTCTTAACTATTGTTTGAAATAATGTAGAGACAGCTCCAGAGCCA

TGAAGAAGTGTATGAAGAAGCAGTGTTAGCTTAAATGACATACATGTCACAATTGCCTAT

GTGAAACTATCATAATTATGCATGAGAAGTATCTATCCTGCATAACCTCCACCAATAATA

ATAATGTTAATAATAGTGAAAACTAATGTTTATTAAGTCCTTACTGTCTCCAGCCTCTGT

GCTAAATACTGGTTACTAAGTTTCCCTGAAAATACTATTCTCATCTGTTTGTTCTTAATA

ACAGGATAGCATAATTGTAAGTTGTAAATGAAATAATACAGTTTATGTAATAAAAGGGTA

AAAGAGAAGACCACCTACCTTATCTTCTGTTGCTGATCTGGATGGATGTAGGTGGTGTTT

ACCTAGTTTCACCTTTGGCAGTTGAAACTACTTTTTTTTTTTTTTTTTTTTTTTTTAAGA

GACAGGGTGGGCCAGGCGCAGTGGCTCACGCCTGTAATCCCCGCACTTTGGGAGGCTGAG

GCGGACAGATCACTTGAGGTCAGAAGTTCGAGACCAGCCTGGCCAACATGGTGAAACCCT

GTCTCTACTAAAAATACAGAAAAATTAACTGGGTGTGGTGGTACACACCTGTAATTCCAG

CTACGTGGGAGGCTGAAGCAGGAGAATCGCTTGAACCCGGGAGTGGAGGTTGCAGTGAGC

TGAGATTGTGCCACTGCACTCCAGCCTGGGTGACAGAGCAGGACTCCGTCTCAAAAAAAA

-continued

AAACAACAACAAAAAAAGAAATTTTTAGAAATATGAGATGACAGCAAGAATGAGGGTATT

AAAAAGAAATTTTTAGAACTAAATAGCAGAATGTAATGGTGAAAAGTTTGATTTCTCAAG

TCTGCTTTGCACACAGGCATGTGGCAAACATTCAGTAAGTATAGCTGTAATTTTAACCAG

CTGTAATGTATAATAGCCAACATATCACATTTTTCTTTTTTCTTTTTTGAGACAGAGTCT

TGCTCTGTTGCCCAGGCTGGAGTGCAGTGGCACCATCTCGGCTCACTGCAACCTCTGCCT

CCTGAGTTCAAGTGATTCTTGTGCCTCAGCCTCTCAAGTAGCTGGGATTACAGGTGTGTG

CCACCACACTCGGCTATTTTTTGCATTTTTAGTAGAGATGGGGCTGGTCTTGAACTCCCA

GCCTCAGGTGATCTGCCTGCCTCAGCCTCCCAAAGTGCTGAGATTACAGGTGTGAGCCAC

AGCGCCTGGCCATATATTGCTTTTTTCTTATTATCAGAGCCAGTTCATAATTGTGGAAAA

ATAGTGTTTGTAACAATGTAAGTATGGATAAATCATCTTTTTAATTTTGTGATTCATATA

GGTTTGTTGTTGTTGTTGTTGTTTTGTTTTTATCTTGAGACAGAGTCTTGGTCTGTCACC

CAGGCTGGAGTGTAATGGCACAACCATGGCTCACTGCAGCCTCAGATGCCTGGGTTCAAG

CAATCCTCCCGTCTCAGCCTCTAGAGTAGATGGGACCACAGGTGTGGGCCACCATGCCTG

GGTAATTACAAAACTTTTTTTTTTTTTTCTAGAGATGAGGTCTCACTATGTTGCCCAGGC

TGGTCTCAAACCTTTGACCTCGCTTCAGCCTTTAGAGTAGCTATGACTATAGGCATGTGC

CATCACCCAGCTAATTAAAATTTTTTTTCTTTTTTTTTTTGGTGGAGATGCGGTCTTACT

TTGTTACCCAGACTGCAAGTTAGTTTCAGATATCAACATTTGGTGTTTCCAAATGCACGG

GGAGGCTTTGGAGCAAGTTTTTGGCTCATATGCATAGGTGTCCTAGACATTCACTTTGCA

AATTCTTATTAAAATGACTACAGTAGCATACAGATAGGGAAAAATATCCTTGTCAGTACC

ACCGATTGGGTGAGAAGAGACTGTATATTAAAAACAATGACCATCTTTTTGCCACATAAA

TTGCTGGTGGGGCCAGTTTGAAGAGGGCTTTGTCAGCTGCCTTCTGCCTCTTCCTCTTGA

GTACGTGGAGTTGGAGTCATCCTTGACAGCCTCCTGTTGACACCACCCGGGTCACAGATG

TGAAACTGTGTGGATGTAGGAGAGAGCAGTGATGGGGCTTACCCCAAGGTTGCTCTTCCT

TCCCTCTGGCCACAAATGTTTAGTAAGGAACTGCTCTGTATTAACCATTTGCTAGGGGCT

GCAGATACGGTGGTGAAGAAATAGACATGTTCCTACTCGGGATGCTGAGGTGGGAGGATT

GCTTGAGCCCAGGAGTTGGAGCTGCAGTGAGCCATGATCACACCACTGCACTCCAGCCTG

GGGGACAGAGCGAGACCCTATCTCTAAAAAACAATAAAAGAAATAGATGTGTCCTTCACC

CTCATGGAACTGCCAGTCTAGCCTTCAACCTGGTGACTGTAGAAATGTGTGATTAGATGC

TATATTGCCATGTTGAGTGTCACCCCTGAGAAGCAGGGTTTTTTTGAGAAGGTAGGATG

GGGGATCTGACTGTGGGACCACCAGAGGGAAAAGCACATGTAAAAGCTGCGTGTACCAAC

TGGAGGAAATCGGAGACGTGATCAGAGAACCAGAGTCAACCAGGGGCCATGCCGTACAGG

GTCCTGTTAAGATCTGTGACTTTTTTCTAAACGTTTTCTTCTGGATAACATCTAAATTTC

TAGTTCCAAATGTGAAACTCCAAGGGCGTTCTGTGCTAAACATTTTGCATGTATTAATTA

ATTTCCACCACACAACATTGCTGTGAATTAAGACAGTTTCTAAGCATGGCAAGAAACCCA

GAAATCATAATGGAAAAATCTGATAAATTTAACAATGCCAACATGAACCTCTGTAGGAAA

AAAAATACCACAGACTAAAAAGGGGGGAAAAAAACCAGAGACAAATATTTGCAACACATA

CAGTAAAGGGTAATTTTCTGGTTATATCAAGAGCTCCTACAAATCAGTAAGAAAAAAAAT

CTAATAGGAAATGAGCAACGACAAACTGACAACTCATAGAAAAGGAAACACAAGTGGTCT

GAAAACATGAAAAAGTGCTCAGTCTCACAAAGAAATGCAAACTAACATGGTACCATTTTC

CATTAATCAGATAGACAAAGATGAAAGAGTTTGGTAATGTATGTAGTATTGGCACAAGTG

AGGGAAAACAGGGGATTTCACACTCTATGCCCGTCCAAACCAGTACCTTATTTTGAGGGT

-continued

GGTTTGACAATATTTGTCAAAATAAAAAAATTATATATAGTCATTTGCCACATAATGATG

GTTCAGTTGATGATGGACGGCATACATAATGGTGGTCCCATAAGAATATAATGGGCTGGG

TGCAGTGGCTCTCACCTGCAATCCCAGCACTTTGGGAGGCCGAGGTGGGTGGATTGCCTG

AGGTCAGGAGTTTGAGACCAGCCTGGCCAACATGGTGAAACCCTGTCTCTGCTAAAAACA

TACAAACAATTAGCCAGGCATGGTGGCGGGTGCCTGTAATCCCAGCTACTCAGGAGGCAG

AGGCAGGAGAATCGCTTGAACCCGGAAGGCGGAGGTTGCAGTGAGGTGAGATTGGGCCAC

TGCACTCCCATCTAGATGACAAGGCAAAACTCCATCTCAAAAAAAAAAAAAAAAAAGAAT

ATTATGGGCCCAGCCACAGTGGCTCACACCTGTAATCCCAGTACTTTGGTAGGCCAAGGC

AGGAGAATCATTTGAACTCAGGAGTTTGAGACTAGTGGGGACAACATAGCAAGACCCCAT

CTCAAAAAAAAAAGATTATGGTGGAGCTGTCCTGTATAGACATACCATTTTTAACTTTTT

TTTTTTTTGAGATGGAGTCTTGCTGTGTCACCCAGGCTGATGTGTAGTGGCGTGATCTGG

GCTTACTGAAACCTCCACCTCCTGGGTTCAAGCGATTCTCCTGCCTCAGCTTCCTGAGTA

GCTGGGACTGCAGGCGCAGGACACCATATCTGGCTAATTTTTATATATTTAGTAGAGATG

GGGTTTCACCATGTTGGCCAGGCTGGTCTTGAACTCCTGACCTCAAGTGATCCGCCTGCC

TCAGCCTCCCAAAGTGCTGGGATTACAGGCATTAGCCACCATTTACAGGCACCTGGCCAC

CATTTTTAATCTTTTATATTGTATTTAAACTGTACCTTTTCTATGTATGGATGTGTTTAG

ATACACAAATACCATTGTGTTACAGTTACTTACAGTATTCAGTACAGTAGCATGCTGTAC

AGGTGTGTAGCCTAGGAGCAATAGGTTATACCATATAGCCCAGGTGTGTAGTAGGCTCTG

CCATCTAGGTTTGTGTAAGTACGCTCCATGATGTTACCACAGTGACGAAATCGCCTAATG

ATGCATTTCTCAGAACATATTCCTGTTGTTAAGCAATGCATGACCGTATCTTGACAAAGC

CATTTTATTTCTAAAACTTTAATTTTACAGATTTATTTGTAAAAGTATGTAAAAATGATT

GTAAAGGATATGTTCTGCTGCATTATTTGTAATAACAAAAAACCAGAGGATAACATAAAT

GTCCTATAAGAAGGGTTAGATTATGGATGGCACATTCATACAATGGGGTATTATGTAGCC

ATTGAATAAAAGGGTACTGGCTGGGCGCAGTGGCTCATGCCTATAATCTCAACACTTTGG

GTGGCCAAAGAAGGAGGATTGCTTGAAGCCAGGAGCTTGGGGCCAGCCTGGGCAACATAG

CAAGACCCTATCTCTACAAAGGAAAAATAAAACAATTAGCCAGGTTTGGTATTGGACACC

TTCATGGTCCCAGCTACTGAGGAGGCTGAGATTGGAGGGATCGCTTGTGCCTGGCAGGTT

GAGGCTGTAGTGAGCCATGATTGTGCCACTGCACTCCAGGCTGGGAGATAGAGTGGGACC

CTATCTCAAAAAAACAAAAACAAAAACAAAACCTCCTGTAAAATGTCAAGAAGTCCTAGA

TGTGGGCCAGGTGTGGTGGCTCACACTTGTAATCCCTGCACTTTGGGAGGCTGAGGCCAG

GAGTTTGAGACCAGGCAGAGCAAGATAGCAAGACTCCATTTCTACAAAAAAATAAAAAAAA

TTAGTTGGGCATAGTGGTGCATTCCTGTAGTCCCAGCTACTCAGGAGGCTGAGGTGGGAG

GATTGCTTGAGCCTGGGAGGTTGAGGCTGCAGTGAGCCATGATCACACCTCTGCACTCCA

ACCTGCGCAACAGAGTGAGACCCTGTCTCTAAAAACAACAACCAAAAAAACCCAGCAAAG

TACTGATAAAGATCTTTGGCTGGGCGCAGTGGCTCACACCTGTAATCCCAACACTTCAGG

AGGCTGAGGCGGGCAGGTCACAAGATCAAGAGATCAAGACCATCCTGGCCAACATGGTGA

AACCCGGTCTCTACTAAAAATACAAAAATTAGCTGGGCATGGTGGCGTGCACCTGTAGTC

TCTGCTACTCGGGAGGCTGAGGCAGGAGAATCACTTGAACCCAGGTGGCAGAGGTTGCAG

TGAGCCGAGATCACGCCACTGCATTCCAGCCTGGCGACAGAGCAAGACTCCGTCTCAAAA

AAAAAAAAAAGAGAGAAAGATCTTCAAGTTGTAGTATGTGAAAAAATCAGGGTGTAAAAC

-continued

AAGAGAATCCCATTTGTGTGTGTGTCGAGTGTGTTTCACACAGGCTCAGAGGGAGTAGTG

TGTATATGCACATGAACATACGTGTCAGTGTATATATGTATATATACAAGGTTGTGGGTT

TGTTTGTTTTTTTTGAGACAGAGTCTTACTCTGTTGCCCAGGCTGGGGTGCAGTGGTGCA

ATCTTGACCCACTGCAACCTTCACCTCCCAGGTTCAAGTGATTCTTGTGCCTCAGCCTCC

CAAGTAGCTGAGACTACAGGCACGCACCACCATGCCCAGTTAATTTTTGTATTTTTAGTA

GAGATGGGGTTTCATCATGTTGCCCAGGCTGGTCTGGAACTCCTGGCCTCAAGTGCTCTG

CCCGCCTTGGCCTCCGAAAGTGCTGTTGCCCAGGCTGGAGCTCAGTGGCACAATCGCAGC

TCACTGCAACCCCGACGTCCCAGGCTCAGGCAATCTTTCCGTCTTAGCTTCCCAAGTAAC

TGGGACTACAGGTGTGTGCCATCAATGCCCCACCAATTTTTTAATTTTTTGTAGAGATGG

GGTTTCCCTACGTTGCCCAGGCTGATCTTGAACTCCTGGTCTCAAGCAATCCTCCCACCT

CAGCCTCCCAAAGTGCTGCGATTACAGGTGTGAGCCACCTTGCCCTGCCCTGTACAAAGA

TCTGCATAAAAGCAGTTAATAATACTATGTTTGAGGCTGCCATCACAGGGGTGAGGTCAA

GGACAAGTGTGAGAAATTCTTTTAGAATCTATTTTAAAAAAAGAAGAGATGACAGTGGTG

ACAGTCAGGGAACAGATAAGCAGGTAGATTGTGGGGGTCTAGGCTGTCTAACTGGTGTTT

AAAATGAAGCAACCGCTGAGCCTGCTGTATTTCATTTAATGGAGACTAGTAAAACAACAG

CCAGAAATTCTTCACTTTCCATCTAAGAGAGGCAAAAGTTATTTTCCCTTCAATAACCTG

GGACTGTAGGATTAAGGTTTTTTTTTTTTTTTTTTTAAATACTACAATATGACTACCAGT

ATAATTTAAAAATGATTAGAATTCTATTTGAGTAAGAAATAGGTGTCTGCCTGAAGTAGA

CAGTCACTGAAGTCACTAAGTGGCAAAAGACAGAAAAAAAATTGAAAGTAGGAAACAATC

AGCAGATATGATACCAAACATGAGCTGTCAGTGATAATGGATTAAGTCCTTCAATAATGG

CTGAGCCAGATGGAATTAAAAGAAAAAATCCAGGCCGGGCATGGTGGCTCACACCTGTAA

TCCCAGCACTTTGGGAGGCTGAGGTGGGAGGATCACTTGAGTCCAGGAGTTTGAGACCAG

CCTGAACAACATAGTGGGACCCCATCTCTATTTTATAAAAATATTTTGAAAAAAGAAAAA

AAAATTCAGTTGTGTTCTGCTTTAAAAAGACAAATTGGCACAGAATGTCAAAGAATAAAT

AAAACAAACATGGGCAAAAGAGATTCAGGTGGTACCAATATCGGGCTAAGTAGCATTCAA

GATAAAGATTATTAAATAATAAGTTAGTTAATACTAGAGTAATTGCATATTAATGAAACA

TAATCTATGGTAGAGATATTATAGTCAATAATTGTTTTATGTATTCATTAAGGTAACAAC

AAGCAAACAAGCTTTAATAGTTTTAAATGCTTTATATGCTTTATAGTTCTTTTATGTGCA

TTAATTCATTAATTCTCATTTCCTATGAGGTAAACACTATTATTATCCACATTTTACAGA

TGTAAAAACCGAAGCAGAGAGATTAATTAGCTTGCCCAGGAGATGTGGCATTCTGGGATT

TGAGACAGTGGTTTGGCTCTGTAGGTTGCTTCAATAACCAAGAGATGCTTCAAATCAGAT

TTTTAAAATATGTTTTTCAGAAGCATTTTCCTGATACTTCTCCCCTTACATGGGTGTTAG

TCTTTTGGGTTGAAAAACATGAGTAAGTGCTAGAAGAGCAAAATATGCATCCAGATTTAA

TAGTATGTCTGTTTTTCTGAGCCTTGGCATTTCATTGCTTTTATAATAGAAATGAAGGCT

TTTTTTTTTTTTTGGCTGAGAATAGCACTGAACTCAGTGGGAGGGACTGTGGGTTGTAAG

TTGTCCGCCTCTGAATGGAGTTGAATTTAAGTTTCTTGGTTTCCAAAGAATGATTGATTT

AAAGACCCTCAAATTGCAAGTTAGAACTGACTTCAGTCCTTGAGGTTTTTTACCATTTAA

TGAATAATTAAATTTATGGTAATAAATGGTAATAAATGGTAAAAATGGTAATAAATTTTA

CCATTTAATGAATTTTTCTTAAAAAGCAATTGAATTGTTGATGAAAGGTGATGTTAAAAT

TATCCCAGATTTATCAATCTTTTTTTTATTGCCCCTGGATTTTGAGTCATAGAAAGCCTT

TCCTTATTCTAAGGTTAACAAGACATTCACCCATGTTTTCCTCTAGTATTGCATTGTTTC

-continued

Figure 1A:
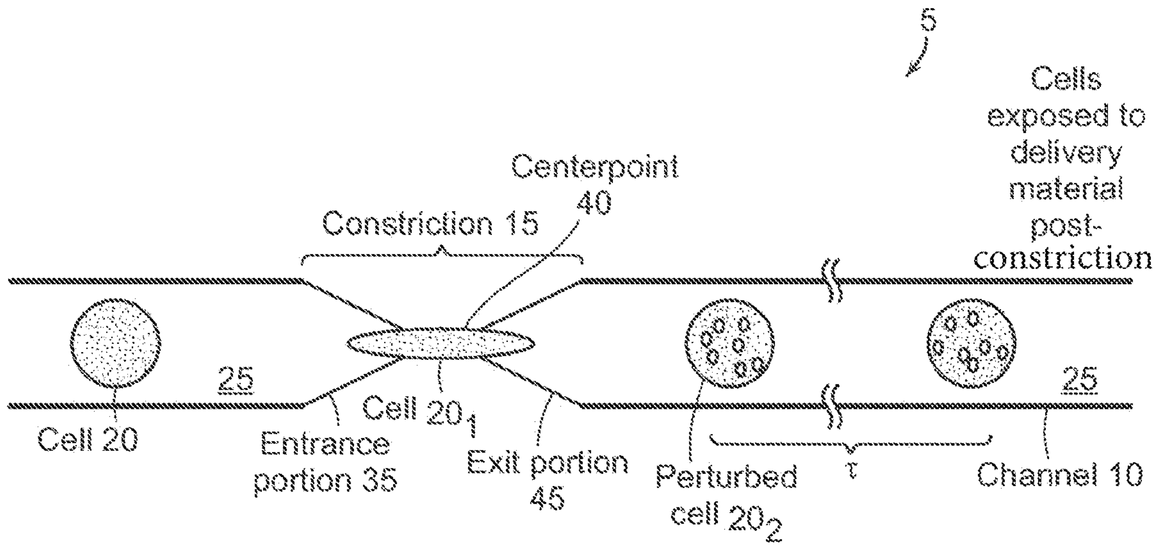
FIGS. 1A and 1B are schematic diagrams of a microfluidic system in which cells are exposed to the delivery material (payload) after passing through the constriction.

ATCTTTTACGTTTATTATTTATTTTATTTTATTTTTTTGAGACAGGGTCTCACTGTGTCA
CTCAGGCTGGAGTGCAGTGGAATGATCTTGGCTCACTGCAGCCTCTGCCTCCCGCCTCCC
GGGTTCAAGCGATTCTGCTGCCTCGGCCTCCCAAGTAGCTGGGATTACAGGCACCTGCCA
CCGCGCCTGGCTAATTTTTGTATTTTTTTTTTAGTACAGATGGGGTTTTGCTGTTGGCCA
GGCTGGTCTCGAACTCCTGACCTTAAGTGATCCACCCGCCTTGGCCTCCCAAAGTGCTGG
GATTACAGGCATGAGCCACCGTGCCCGGCCTAAAATTTATTCTGATATGTGATATGATGT
ATGGTTCTAACTACTTTGTTACGGTGCATTATTTTCTAAATGTGGTATTGGATTCTTTTA
TATTTTGTTTAGAAGTTCTGCATCAATATTCATGAGTACCATTGGTCTCTGTTGTTTTTC
TTGTGCCATCTTTATTGGTATAGGTATCAGTGTTATATTTAGTTTGTAAAAGGAAGTTGG
AAGTTTTCCTTTCTTTTTAGTACTCAGGAATGATTTTAAGAATTGAGACTATTTGGTCTT
TGAAGGTTTGGTAGAAGTCCATTGGGAATCCATCTGGGCCTGGTGATTTTCTGTGCGGTA
GTTCCTTAATTGTTTTCCCTATTTTTTCTTATTTTTAATCAGGTAGCCTCTGAACCAGAA
TAGGTTCAGAGAGGCTCCCTCTATTTTTTTTAATACAAGTTGGTCTGCCTAAGTTTTCTT
ACTCTAATGGGTTAATTTTTGTAGACTGCATTTCCCTGAAAAATTACACGTTTGTTCTAG
GTTTTCTGACTTATTTCCACAACTTTTTAGTCTTTCCCCCTGGAATCATGCCCCTTTCCA
TAAACAGGACTCTGATGTACCTGAAGTATTTTCACACTTCGGGTGGACTTTCTGTTTCTG
GGGGTGGTTTTAGAGCAATTTTAGGCCTGCCACTAGCTACCCTGTTCTCTACACCATGCT
GTTTTTCTCAGAATGCTCTTCTTTTGCACAAAGGCTTGGAGTAGGAGGTTGAGCAGTCAC
TCACTGACGTTTGGTATATTTTCTTTTTTTTGCTTACAGGTAATCTGGAAGTTTGGGCAT
TCTCTTTAAGTTGAGGGTGTGGTTTTCATGTCATTTTATTTGTTTATTGTTTTCTTGTGT
GTGTTTCTTAGAGACAGGGTCCCACTCTTGCCCTGGCTGGAGTGCAGTGGCGTCTTGATC
ATAGCTTACTGCATCCTCAAGCTGCTGGGCTTAGATGAACCTCCCACCTCAGCCTCCTGA
GTAGCTGGGACTACAGGAGCACACCACCATACCTAATTTTTTTTTTTTTGAGACGAAGTC
TTGCTCTGTCCCCCAGATTGGAGTGTAGTGGTGCAATCTCGGCTCACTGCAACCTCTGCC
TCCCGGGTTCAAGCGATTCTCTCACCTCAGCCTCCCGAGTAGCTGAGACTGCAGGTGCAT
GCCACCATACCCGGCTAATTTTTGTATTTTTTAGTAGAAACAGGGTTTCACCATGTTGGC
TAGGCTGGTCTCAAACTCTTGACCTCAAGTGATCCACCCACCTTGGCCTCCCAAAGTGCT
GGGATTACAGGCTTGAGCCACTGTGCCTGGTCCCTGGCTAATTTTTAATTTTTTTGTAGA
GATGGGATCTTGCTATGTTGCCCAGGCTGGTCTTGAACACCTGGCCTTAAGCAATCCTCC
CACCCTAGCCTGCCAAAACACTGGGATTTACAGGCATGAACCATTGTGCCTGGCTTGTTT
TGTTTTTAATTCTATGTTGTTTTTGAAGGATGTATGGGGAGAGATGGATTTAGGCAATCA
TCGTTGTCCTTGGCTACCTGAAAGTCCAGGCACTCTTCTAGATACTTTATAAATATTAAC
TCATTTTATCCTCTCAACAACACTATGACATGGGTACTGTTACACCTTCCATTTTATAGG
ACTTAACAGAGAGGTTAAATATGTAGCCCAGGGTCACAGAGAGCTGGGCTTCAGACCAAG
ACAATCTGGCACCAGAGTCTATGTGGCTACCCCTAAGGCTTTGCCACCATGTGTTAGTGA
TTCTCAGCCTGTCATTTGGGGAGGGGATTGCCCTTTTTTTTAAACTTTTTAAAAAATTTA
TTCTTATTTTATTATATTTTTGAGACAGAGTCTCCCTCTTTTGCCGAGGCTGGAGTGGAG
TGGTGTGATTTCAGCTCACTGTAACCTCTGCCTCTGGGGTTCAAGTGATTCTCATGCCTC
AGCCTCCCAAGTAGCTGGGATTACAGTTGCCAGCCACCATGCCCAGCTAATTTTTGTATT
ATTATTATTATTATTTGAGACGGAGTCTCGCTCTTTTGTTCAGGCTGGAGTGCAGTGCTG

-continued

TGATCTCGGCTCTCTGTAACCTTCGTCTCCTGGGTTCAGGTGATTCTCCTGCCTCAGCCT

CCGGAGTAGCTGGGACTATAGGCGCGCACCACCATACTTGGCTAATTTTTTGTATTTTTA

GTAGAGACGGGGTTTCACTATGTTGGCCAGGCTGGTCTCGAACTCCTGACCTCAGGTGAT

CTACCTGCCTTGGCCTTCCAAAGTGCTGGGATTACAGGTGTGAGCCACCATGCATGGCTG

GATTGTCCTTTTTTAAAAAAAAAAACAAAAACAAAAAAAAAAACCCAAACCATAAACCCA

ATATTCTGAAAGATTTGGTCTCCACACCTGTGTTATATAATAATTAGTTTTTCCATTTTT

TTCCTCTTGGTAGAAGGCACATATGCCACTCAGTTTCCAGTTGCCACACCCAATTAACAT

AATTGTTTTGCAGCCAAAAGCAAAAGAGAGTTGACATTTTAATTAGCTTATGTAGGTAGA

CAAATTGAGGCCTAATGTAAGAGTTTCATTATACCTTTTTGAAAAACTATAAATAGCTAG

AAGCCAGTTGTCATTACTTTTTGATTCCTTAGAATTCTGGGCATCTTTCATCTGGAACCA

CAGATGAAAGAAGCTGCAAGGAAGGATTTTTTTTCTTAACGGAATAGTTTAACCATTCTG

AATGCAAAAGTATTGGATGCTAGAATAATAGGTATCACATAAATTGAGGTTGACGTTTTC

CCGGGTGAAATTCTATTCTGTCTCAATTTTCCTTTTTTTTTGAGACGGAATCTTGCTCTG

TCGCCCAGGCTGGAGTGCAGTGGCATGATCTCGGCTCACTGCAAGCTCCACCTCCTGGGT

TCATGCCATTTTCCTGCCTCAGCCTCCCGAGTAGCTGGGATTACAGGGGCCTGCCACAAC

ACCCAGCTAATTTTTTTGTATTTTTAGTAGAGACGGGGTTTCCCAGGATGGTCTCAATCT

CCTGACCTCGTGATCCGCCTGCCTCGGCCTCCCAAAGTGCCGGGATTACAGGCGTGAGCC

ACTGTGCCTGGCCTTTTTTTTTTTTTTTTTTTTTTTTTTTTTAAGACAGAGTCTCGCTTTG

TTGCCTAGGCTGGAGCGCAGTGGCATGATCTCAGCTTATTGCAACCTCCGCCTCCCGGGT

TCAAGTGATTCTCCTGCCTCAGCCTCCCGAGTATCTGAGATTACAGATGTGTGCCACCAT

GCCTGGCTAATTTTTGTATTTTTAGTACAGATGAGGTTTTGCCATGTTGCCCAGGCTGGC

CTCAAACTCCTGACCTCAGGTAATCCTCCTGCCTCAGCTCTTCCCAAAGTGCTGGGATTA

TAGGCATGAGTCACCGGGCCCAGACTCAATCTTCTGACAAGCTCTCAGAGAGAGTAAAAA

GCAAATGAATATTTCATTATTTTGATCTGAGCTTTACGATTTTTCTTTTCTTTTCTTTTT

TTTTTTTTTTGAGATGGAGTTTTGCGTTGTTGCCCAGGCTAGAGTGCAGTGGTGGCGAT

CTTGGCTCACCGCACCCTCCGCTTCCCGGGTTCAAGCGATTCTTCTGCCTCAGCCTCCTG

AGTAACTGGGATTACAGGCATGCGCCACCATGCCCGGCTGATTTTGTATTTTTAGTAGGG

ACAGGGTTTCTCCATGTTGGTCAGGCTGGTCTTAAGCTCCCGACCTCAGGTGATCCACCT

GCCTCGGCCTCCCAAAGTGCTGGGATTACAAGCATGAGCCACCTTGCCCAGCCTTTTTTT

TTTAAATCTGAGAAGAGGTCTTGCTCGATTGCCTAGGCTGGAGTGCAGTGGTGCGATCTC

TGCTCACTGCATTCTCTGCCTCCCAGACTCAAGCAATCCTCCCACCTTAGCCTCCTGAGT

AGCTGGGACTACAGGCATATGCCACCACACCTGGCTAATGTTCGTATTTTTTTGTAGAGA

CAGGGTTTTGCCATTTTGCCCAGGCTGGTCTTGAACTCCTGACCTCAGGTGATCCTCCCA

CCTTGGCCTCCCAAAGTGCTGGGATTACAGGTGTGAGCCACTGTGCCTGGTCTCCTTCAC

TGTTGTAAGATACTTGAATTGGGTCAATATTTGTGGAGAAGTCTCTTAAAAGTTCACTTG

ATTGTCAGTACTAGAACTCTACATTTAATATTGACATATTCCTGGGAGCATTTCAGAGCA

TTCTATTAGCTTAGAAAGGTCCAGGATAATTTGACTTTAGAAGTTACTGTTACCATGAAT

CTCAATGACTTTTGAAATCCATGAAGAATATCTTTTTTTTTTTTTTGAGACGGAGTCTCA

CTCTGTCGCCCAGGCTGGAGTGCAGTGGTGATCTGGGCTCACTGCAAGCTCCGCCTACTG

GGTTCACGCCATTCTCCTGCCTCAGCCTCCCGAGTAGCTGGGATTACAGGCACATGCCAC

CACGCCTGGCTAATTTTTTTGCATTTTTAGTAGAGAGGGGGTTTCACTGTGTTAGCCAGG

-continued

ATGGTCTCGATCTCCTGACCTTGTGATCCGCCCGCCTCGGCCTCCCAAAGTGCTGGGATT
ACAGGCGTGAGCCACCGCGCCTGCCCAAGAATATCTTTTTGCTGGTAACTAGAGAGGACT
CCTCTGAAGCAGATGCCATTCATGATGGATTTCATCATTTATGGGTTTTAAAAAACATTT
TATTTTGAAATAATTTCAAATTTAAATAAGAGTTGCAAAATAGTACAAATAATTCGTGTT
AACTTTTCATCCAGATTTACAAGTCAACCTTATACAGGTTGAGTATCCCTTATCCAAAAT
GCTTGGGACCAGAAGTGTTTTGGATTTCAGATTTTTTCGAATTTTGGAATATTTTTATTA
TATACTTAAGCATCTCTAATCCCCAAATCTCAAATCTGAAATATCTGAAATGCTATGATG
AGCATTTCCTTTGAGTGTTATGTGGGCACTTTTTAAATTTATTTAATTAATTTATTTTTT
GAGATGGAGTATTGCTCCATCACCCAGGCTGGAGTGCAGTGAGCGATCTTGGCTTATTGC
AAACTTCACCTTCTGGGTTCAAGTGATTCTCCTGCCTCAGCCCCCTGAGTAGTTGGGACT
ATAGGCGCTTGCCACCACGGCCGGCTAATTTTTGTATTTTTAGTAGAGACAGGGTTTCAC
CGTGTTGGCCAGGCTGGTCTCGAACTCCTGACCTCAGGTGGTCCACCTGCCTCCGCCTCC
CAAAGTGCTGGGATTACAGGAGTGAACCACCGCGCCTGGCCATGGATTTTGCAGCATTTT
AGATTTGGGATACTCAACCTGTACCATGTTTACTCTCTCTCCTCTCTCTCTCTCTCTTTT
TATATATATATATATATATATATATATATATATATATATATATATATATAAATTATATATAC
ACTACACATATATGTATGTATATGTATGTATTTTATATATAAAATACATATCTACATATA
AAATACACATGTATATATACATGTGTACATATATGTGTCTCTATATTTAAGTTTTGTTGG
AACCACTTGAGGGTAAGTTGCAGACATGGCGTCTCATTGCTCCAAAATACTTCAGTGTGT
ATTTCTTAAATACAAGGACACTTGGTTACATAACCACAGTATATCACCAAATGTATATTA
TAACAAGACTACCATCAAATCCTTATATCTCTTTCAAATTGTTTTAGTAATATCCTTATA
GCAAAAGACAAAACAACAACAAAAACTGTTCCCTTTTATTTTGTTTGTTTTGGTCCATTA
TATGTCCAGGTTATGCATTAATGCATTGTGTTACTTGCTAAGTCTTGTTACTGGCCTTTA
ATTAGGATATTTCTTTGCATCCCGCCAAACTCCTCTTCATGGTTGTATCTTTTTTTTTTT
TTTTGGAGATGGAATTTTGCTTATGTTGCCCAGGCTGGAGTATAATGATGCGATCTTGGC
TCACTGCAACCTCCGTCTCCCGGGTTCAAGCGATTCTCCTGCCTCAGCCTCCCGAGTAAC
TGGGATTGCAGGCCTGCGCCACCTTGCCCAGCTAATTTTGGAATTTTGTGAGACGGGGTT
TTGCCATGTTGGTCAGACTAGTCTCGAACTCCTGACCTCATGATCCGCCCGCCTTGGCCT
CCCAAACTGTTGGGATTACAGGTGTGAGCCACTGTGCCCGGTCTTTTTTTTTTTTTTTTT
GAGACAGGGTCTTATTCTGTTGCCTGGCCTGGAGTGCAGTGGTATGATCTTGGCTCACTG
CAACCTGGACCTCCTGGGCTCAGGCGATCCTCCCACCTCAGCCTCCTTAGTAGCTGGGAC
TATAGGCACACACCACCATGCATGGCTAATTTTTATATTTTTTTGTAGAGACTGGGTTTC
GCCATGTTGCCCAAGCTGGTCTTGAACTCCTGGGCTCAAGTGATCCACCTGCCTTGGCCT
CCCAAAATGCTAGGATTACAGGTGTAAGCCACTGCGCCTGGCCCTAATTTTTGCATTTTT
TGTAGAGATGGGGTTTCACTATATTGCCCAGGCTGGTCTTGAACTCCTGGGCTCAAGTGA
TCTTCCCATCACAGCCCCCTAAAGTGCTGGGATTATAGGCGTGAACCACTGTGCCTGGCT
GAGGATTAAGTTTCAACCTCAGGGGAGCGGCATTCAAACTATAGCATTGTCCTTTAGTGA
CTGGCTTAGTTCACTTAGAATGTTTGTCTATTCATCCATCTATAGACACTGTTTTCTTTC
ACCTTTTGGCTTTGCAAATAATGCTGCTGTGAATATGAGTTATAGAAAAATACCAATTTG
AATCCGTGTTTTCAATTACTTTGAGTATATACCTGGAAGTGGAATTTCTGGATCATATGG
TACTTCCAAGTTTTTTTTTTTTTCTTTTTTGAGACAAGGTCTCACTCTGTCACCCAGGCTG

-continued

GAGTGTAGTGGCACGATCTTGGCTCACTGCAACCTCCGCCTCCCGGGTTCAAGCGATTCT

CCTGCCTCAGCCTCTCAAGTAGCTGGGATTACAGGCACGCGCCACCACGCCCAACTAATT

TTGTATTTTTAGTAGAGATGGGTTTCTCCATGTTGGTCAGGCTGCTCCCGAACTCCCGAC

CTCAGGTGATCTGCCTGCCTCAGCCTCCCAAAATTCTGGGATTACAGGTGTGAGCCACCG

CACCTGGCCTCCATGTTTCAATTTTTAAACAAACAATTAGTTAAAAAAATAGGAAACTAA

GAGAATGAACTATTTCCTGTTTTATTCAGTGGGTTATAATCTGTTACTATCATTGTTTAT

TTTGAGGTACAAATTGTCCCTACTTTGGCCAGCAGAGGATCCTGCAGTTTGTCTCCTGTG

TCCTTTTCATAGCTCCTTGTTGGAACTCTTACTGGCCCACAATAGGATGTTCCAAGTTCA

TCTTCTTACTTTTACTGCCCCAACGCTGGGATCAGCCATTTCTTCAAGGAGGCCAGTTCC

TTTCATTGGAGAATGGAAAACCCAATATGTAGAAACCAAGATAGAGGTGTTAGGTGTGAT

TGCTACTGGAGTGTCATTGCTTCCAAACCCTTTCAGAAGAGACCTAGGAAATGTGTGTGT

GTGTGTATATATATATGTGTGTGTGTGTGTGTATTCATAAAAGCACATACACATACACAT

ACCCCGAAGCATGTATTTCTGTATTATTATTATTTTTTTGAGATGGAGTCTTGCTCTGTC

GCCCAGGCTGGAGTACAGTGGCACGATCATGGCTCACTGCAACCTCTGCCTCCTGGATTC

AAGCAATTCTCCTGTCTCAGCCTCCTGAGTAGCTGGGATTACAGGTGTCCACCACCACGC

CCACCTAATTTTTGTATTTTTAGTAGAGATGGGGTTTCACCACATTGGCCAGGATGGTCT

TGAACTCCTGACGTCAAGTGATCTGCCCGCCTCGGCCTCCCAAAGTGCTGGGATTATAGG

CGTGAGCCACTGTTCCCATCCAGAAGCATACATATCTATTTCTATATCTACATTTCTGTC

TTTACATGTATATATTAAAAATTACAGTTTGCACTAATACCTCCAATTACAATCTAACAT

CATGGGATTTATTCTGGCTTTCTCCCTTCTCATATTTGTGTCTCCCCAACAGTGAGAAAC

CTGGCTTGCTATCCTCAACATGGTAACTTATTTATTAAGAAACTTATTCTTTTTTTTTTT

TTTTTTCTGAGATTGAGTTTCGCTCTTGTTGCCCAAGCTGGAGTGCAGTGGTGTGATCTT

GGCTCACCGCAACCTCTGCCTCCTGGGTTCAAGCGATTCTCCTGCCTCAGCTTCTCAAGT

AGCTGGGATTACAGGCATGCACCACCATGCCCAGCTAATTTCGTATTTTTAGTAGAGATG

GGTTTCTCCATGTTGGTCAGGCTGCTCTGGAACTCCCGACCCCAGCTGATCTGCCTGCCT

CGGCCTCCCAAAGTCCTGGGATTACAGGCGTGAGCCACCGTGCCCTGCCTCTAGTTTATT

TATTTTTATTCCATGTGCTCAGTCTTGCGAGCACGTGGTCTGTTTTCTTGGGCCTGGCCC

CCTCAGTGCACTGTCTTAATACCCTAGCCCCCAGTCCCTCTGATCATATCCCCAGACACC

CCTACTGAATCCCAGGTCTCTACCAAGGGAAAGGCAGGGAGGAGGCATTGACCAAGGAGA

AGAGGGGGAAGGGACAGGGAAGGTCTTGATTTGTATTTTCTAAAATTTTCTACTCTGCTC

ATAATGCGTCTTAGCTGTGTTGTTGTGGAAAGTAGTGCTGACAGTGTCTTGTTTTTTTAT

TACTTACTTTGTCTTTCTTTTTAAGATGGTTTCACCCAAATATCACTGGTGTGGAGGCAG

AAAACCTACTGTTGACAAGAGGAGTTGATGGCAGTTTTTTGGCAAGGCCTAGTAAAAGTA

ACCCTGGAGACTTCACACTTTCCGTTAGGTAAGTTGGAATGAAAAGAGAGGATCCTGAGA

GTGTTTTCTAGGTAGGAAGTGGTAAAACCATGCTTGGATAGCTTGCTGCCTGCATTTCGA

GTTTGAAGGCCTTATCTGAGCCCTGGGCTGCCTTCAGGGTTTGGGGAGTGGCCTCCTGGA

CATTTAGCAGAAGAGGAGTAAGGAGGGCCCTTCTTCTCCCTCTGAGACCTCATGGAAGGT

GAGTTGGAGCAGGTCATAGAAGTTCTTAAGCCCTCCAGTGCTTGAGACTTGTTCCACACA

TCTTGAACCTGGTTTCTGCATTTTTCTTTTCCTTCCTGTTGATTTATTTAAAAATTTTAT

TTCTTTTCAATTTTTTTTTTTTTTTTAAATAGAGGTGGGATCTTCCAATGTTGGCCAGGTT

-continued

GGCCTTGAACTTCTGGCCTCAAGCAATCCTGCCTCGGCCTCCCAAAGTGTTAGGATTACA

GGCGTGAGCCACTATGCCTGGCCTTCTTTTTTTGAGACAAGCTGTTGCTCTGTTGCCCAG

GCTGGAGTGCAGTGGTACGATCACAGCTTACAGCAGCCTTGAACTCCTGGGCTTAAGTGA

TCCTCCCGCCTCAGCCTCCCGGGTAGCTGGGACTCCAGGCTTGTGCCACCATGCTCAGCA

TTTTTAAAAAATATTTTTTGTAGAGATGAGGTCTCACTGTATTACCAAGGCTGATCTTTA

ACTCTTAGCCTCAAGTGATCCTCCTGCCTCAGCCTCCCAAAGTGTTGGGATTACAGGCAT

GAGCCACCACACTCAGACTTTGTTGACTTCTTAATAAGAAAAATACTTGTTAAGAGTTTC

TTCAGATCACTTTCCTTTATCAACAAGTAAAACATGACTGAGGAAGTTGTGGTCCCCTTT

GCTTCCCTGCCCAGGCCCGTTTCCCTCCCTCTTTCCCCAGAGGAAACCACCAAGAGGTTG

GCATATATTCTTCCTGAACGTGTTTTTATAGTTGTACTGCACTTGTACTGTGTATGAACA

ATATAAAGTTGGTTTGTGTGTTTAAAAAATTCACATACATGGATTTATAATGTATGTATC

ATTTTGCAACTTAAAAATTTTTTTTTGAGCTCCATGCTGATTGATAACGATCTATTTTTT

TTTTTTGAGATGGAGTTTCAGTCTTATTGCCCAGGCTGAAGTGCAATGGCGTGATCTCAG

CTCACTGCAACCTCAGCCTCCTGGGTTCAAGCTATTCTCCTGTCTCAGCCTCCGGAGTGG

CTGGGATTACAGGTGCATGCCACCATGCCCAGCTAATTTTTGTATTTTTAGTAGAGATGG

GGTTTCACCATGTCGACCAGGCTGGTCTCAAACTCCTGACCTCAGGTGATCTGCCTGCCT

TGGCCTCCCAAAGTGCTGGAATTACAGGCATGAGCTACCATGCCTGGCCTTTTTTTTTTT

TTTTTTTTGAGACAAAGTCTTGCTCTTTTTCCCAGGCTGGAGTGCAGTGGCCACAATCTT

GGCTCACTGCAACCTCTGCCTCCTGAGTTCAAGCAGTTCTCCTGCCTCAGCCTCCTGAGT

AGCTGGGATTACAGACATGTACCACCATGCCAAGTTAATTTTTGTATTTTTTGTAGAGAC

TAGGTTTTACCATGTTGGCCAGGCTGGTCCTGAACTCCTGACTTAAAGTGATCCATCTGC

CTTGGCTTCCCAAAGTGCTGGGGTTACAGGCATGAGCTATCGCGCCTGGCCTGAGAAATC

TCATTCTTACTCCTACTCCCTTGCACACTATCTCCATTCTGTAGGTAGCCATTTCTATTA

ATTTCTTGTTTACCCTTCTGTGTTTCTTTCATTCTTTTTCTTTTTTTCTTTTTTTTTTTT

GAGACAATCTTGCTCTGTTGCCCAGACTGGAGTGCAGTGGTGTGATCTTGGCTCACCGCA

ACCTCCACCTCCTGGGTTCAAGTGATTTTCATGACTCAGCCACCTAAGTAGTTGGGATTA

CAGCGCCTGGTGTACACTACCACACCCAGCTAATTTGTGTATTTTTAGTAGAGATGGGGT

TTCACCATGTTGTCCAGGCTAATCTCCAACTCTTGGCCTCAAGGGATCTGCCTGTCTCAG

CCTCCCAAAGTGCTGGGATTATAGGCATGAGCCACCATGCCTGGCCCTATGTTTCTTTTT

ATAAAAATAAGCAAATTAATATTTTTATTACTATTTTCCTTTTATTTTTACACATCAAGT

AGAACATTAAATATATTTCTCTGTAATTTTTTTCAGTTACCTAAATCTTTTAGTGATCTC

TCTCATCTTTTTAATCAGCTGGATCGCATTCTATCATGTGAATATTTTATAACTTCTATA

TACTGTCACCAGCAGGTAGCGATTTAGTTGTGTCTAATATTTTAAAATGATATATAATGC

CTCAATGAATATAGTAACCTTTTGCATATATTGTTTTGTGCTTTGGGATAACACTACCTC

GTATTGGAAACTGTGTCATTACATGTGTCTTTAAAATTACATGTGTCTTTTTATTTTTAT

TTTTATTTTTTTTGAGTGGGAGTTTCACTCTTGTTGCCCAGGCTGGAGTGCAGTGGTGAG

ATCTCGGCCGACTGCAACTTCCGCCTCCCGGGTTCAAGCGATTCTCCTGCCTCAGCCTCC

CCAGTAGGTGAGATTACAGGTGCCTGCCACCACGCCCAGCTAATTTTTGTATTTTTAGTA

GGGACGGGGTTTCACCATGTTGGCCAGGCTGGTATCGGTCTGCTGACCTCAGGTGATCCT

CCCACCTCAGCCTCCCAAAGTGCTGGGATTACAGACGTGAGCCACCATGCCTGGCCATCA

CTTTTTTTTTTTTCTTAATTGCTGCATAGTGGCCGGGCACAGTGGCTCACGCCTGTAATC

-continued

CCAGCACTTTGGGAGGCCAAGGCAGGCGGCGGATCATGAGGTCAGGAGACCAATACCATC

CTGGCTAACATGGTGAAACCCCGTCTCTACTAAAAATACAAAAAAATTTAGCTGGGCGTC

GTGGCGGGCGCCTGTAGTCCCAGCTACTTGGGAGGTTGAGGCAGGAGAATGGTGTGAACC

CGGGACGTGGAGCTTGCAGTGAGCCAAGATTGCACCACTGCACTCCAGCCTGGGTGATGG

AGTGAGACTCTGTCTCAAAAACAAACAAACAAACAAAAAAATTGCTGCATAGTATTCCAT

TGTATGAGTAGTAACACAACAATTTTTATAATGCATAGTATTCCATTGTATGAATAGTAA

TGTAGCACTATTTGTTTATACATTTTTATGATTAAAAAACAAAATGTTTTTCTATTATGA

ATAAAGTGGCAATGAATATTTTTGTACAAGTGTTTTGGTAGCTATACAGTTATTGTCACT

TAATATATGCAATTCGATAGGCCAGTCATTCAAAATAGAAGATATACAAGGTAGGCCGGG

CGTGGTGGCTCACGCCTGTAATCTCAGCACTTTGGGAGGCCGAGGTGGGTGGATCACCTG

TGGTTAGGAGTTTCAGACCAGCCTGACCAACATGGAGAAACCTCATCTCTACTAAAAATA

CAAAAGTAGCTGAGCGTGGTGGCGCATTCCTGTAATCCCAGCTTCTTGGGAGGCTGAGGT

AGGAGAATCACTTGAACCTGGATTTATAATGTATGTAAATCCACCGCGAAGGTTGCGGTG

AACCGAGATCACGTCATTGCACTCCAGCCTGGGCAATAAGAGCGAAACTCCATCTCAAAA

AAAAAAAAAAAAGATATGCAAGGTAAAGATACTAATAAAGACCTTTGTGTTGAGTTGGTT

GACATGTGGTTATTTCACCCATCGTATTTCTTATAGGGAATAGGTAAATTCGTTCCTTGG

GTTTCTTTCAACACTTAGGTAAAATCCGACGTGGAAGATGAGATCTGATTTTACTGGTGT

AACTCTTTATTTGTCCCCTTGCCTCCCTTTCCAATGGACTATTTTAGAAGAAATGGAGCT

GTCACCCACATCAAGATTCAGAACACTGGTGATTACTATGACCTGTATGGAGGGGAGAAA

TTTGCCACTTTGGCTGAGTTGGTCCAGTATTACATGGAACATCACGGGCAATTAAAAGAG

AAGAATGGAGATGTCATTGAGCTTAAATATCCTCTGAACTGTGCAGATCCTACCTCTGAA

AGGTCAGTAACATTTTAGTGACCACAAAGTCTGCTGCTCCCTTGTGCCCTGAGTGTCAGA

AATGCATGACGGTCTGTGTATGACTCTCTGACTCCAAAGGCTTGTGACTGTTTTTTGAGC

TGTAATCTTTAAAGAATTACTAAAGTGAGACTAATAGCATCAAATTATTTTCAGAGTACC

TTTTTCCTGCAAAAGTTTTAATCAGTGTTACTTACACTCATCCTATAGGGGTTGCATACC

ATTCCTGCATATACTTGGTACGTGTATTAGTTTTAAGACTTATTGAACTTCAGCAGATAA

TCTTTGAGAGTTATTAGAGGAAAACAAATGATAATGGAGACACCAAAATAGCAGCAGTTT

TCTATGGTGGCTCTCGACCAGTTATTCAGCAATGTCACCAACAGATGTCAGTTTAAGCTC

AGAAGTGGAAAAGCAGAGAGCTCAGAGGGTCAGCTTTTTCATCAGTTCTTTTAATGTTAT

CACCACAATTATGTGAGAATGACCTTGCTTAGAGAAAATTATGTTATTTTCGAGATCTTT

CCCCCTGTGTTGGAACTAGGCTGATGAAAGCATGGGCTTGACTTATTTATTGATTGTATT

CGTTTTGTACATTCCCAATCTCCTCTCTGACTTGGTGCAAATTCAGGATCTCTTAGTTAG

TTTGTATATTTTGTGTCTTCAGGTATGATTTTTTCAGCTTATACCTTTATGTCAGTGCTA

TTATGTGCTGATAATTTGTTTCTCTAGCTACCACCGTAGCTTCAGGCAAAAGGCTGTCAG

CCAACTCTGTACAGTTTATTTCTAAATTTTACTGTTTTCAGTTGAGTATGGATGAAGAAT

AACTCAAAGTTTATTCTTTTGATGATGAGCCCTTAACACCACCTGCCATGATAGTACTTG

CTTTCTGACCAAGATCCTGAGGGAAAAAGCCACTTTATTATTAGAACTATGTTAAGATGC

TTCCCAAAAAACATGGAGCAGTATTGTCTCAAAGTCTGTCCTTGGATGGCTTTGGATGCC

TACATCAGGACTGTCTGATGTGCTGGTTAAAATGCAGATTCCTGGGCCTCATTCAGACTT

-continued

ACATGTATTGATATTGCTGGTTGTGGAGCCTGGGAATTCATATTTTTAGCAAAATCCCTC

ATTTTTACTCCAAGTCTTATGTGCATTATACAGTTTGAGATGATCACCCAGGATATAGTC

CAAAGACACTGGAGGCTGTTGAAGTATAGGTTGTATATATGGAAAAGGTTGGAATGTTTG

AATTAATTTATAATGAAGATCCTTTTTAATTGAGTGTTCACATGCCAAGGCAAGGACAAA

CATTCAAAATGATTTTCTGTCTCTGTTACAACTTTTTCTTTCTTTTTTTTAATTTATTTA

TTTGAGATGGAGTCTCACTCTGTCACCCAGGCTGGAGTCAAGTGACGCGATCTCGGCTCA

CTACAACCTCCGCCTCCCAGATTCAAGTAATTCTCTTGCCTCAGCCTCCCGAGTAGCTGG

GACTACAGGCATGTGCCACCATGCCCAGTTAATTTTTGTATTTTTAGTAGAGACAGGGTT

TTGTCATGTTTGCCAGGCTGGTCTCAAACTCCTGAACTCAGGTGATCCGCCCACCTTGAC

CTCTCAAAGTGCTGGGATTATAGGCGTGAGCCACCGTGCCTGTCTCTATTACAACTTTTT

ATTACAACTTCTTTATTTTGACTTTATTTTTACAAATTATTTATTTATTTTTTTTGAGAT

GGAGTTTCGCTCGTCACCCAGGCTGGAGTGCAATGGTGCGATCTCAGCTCACTGCAACCT

CCGCCTCCCAGGTTCAAGTGATTCTCCTGCCTCAGCCTCCTGAGTAGCTGGGATTACAGG

CACTTGCCACCACACCCGGCCAATTTTGTATTTTTAGCAGAGACAGGGTTTCACCATGTT

GGTCAGGCTGGTCTCGAATTCTTGACCTCAGGTGATCCACCTGCCTCGGCCTCCCAAAGT

GTTGGGATTACAGGCATGAGCCACCACGTCCGGCCGACTTTTATTTTTTTTTCTTGAGAC

AGGGTCTTGCTCTGTCACCCAAGCTGGAGTGCGGTGGCATGATCATAGCGCACTGCAGCC

TCGACCTCCTGGACTCAAGTGATCCTCCTGCCTCGGCCTTGTGTATAGCTGGGATTACAG

GCAGTTGCCACCATGCCAGGCTAATTTTTAATTGTTTTGTGAAGATGGGGATTTCACTGT

GTTGCCCAGACTGGTCTTGAACTCCTGGCCTCAAGTGATCTTCCTGCCTTGGCCTTCCAA

AGTGTTGGGATTACAGGCATAAGCCACTATGCATGGCCTGTAACTTCTTTAAATGGCTAT

AATTAAACAGTTGGTCCTTTTAAGATTGGGCAATGGACGAATGGCAAATTGCATTTTTAA

AAGAGGAGGGATTTAAAAAAAAACAGGAAAGATTGGGGCATTTGTCTCTAAAGGACTGTG

GACTCATTTAAGAAGTTTAGTGGTCATTCTTACCATCTTTGTGGTTTTTCCTGCCTGCAT

GGGATGCAGATTTTCTGTCTCAGGTGGGATTGATCAATCCCTTGGAGGAATGTGTCTACT

TTTTAATTGTGTTTAGGAGAGCTGACTGTATACAGTAGTTTTGTGAAAGAACAACATGAA

CCCATAGTAGAGCTAAATTCTTTTTTATTTTTTAAAAACTTTAGGTGGTTTCATGGACAT

CTCTCTGGGAAAGAAGCAGAGAAATTATTAACTGAAAAAGGAAAACATGGTAGTTTTCTT

GTACGAGAGAGCCAGAGCCACCCTGGAGATTTTGTTCTTTCTGTGCGCACTGGTGATGAC

AAAGGGGAGAGCAATGACGGCAAGTCTAAAGTGACCCATGTTATGATTCGCTGTCAGGTA

AATCTCCAGTTGAAAAATGGGTCTGGCAAGATGTTACCTTTGGGTGATTTTTCTGCTGAC

AGAAGACAGACACCATTACATTCAAAGTCAGATTGTCTTTTATTTATTTATTTATTTATT

TATTTATTTGAGACAGGGTCTTGCTCTATCACCTACAGATGGGGTTTCACCACGTTGGGT

CTGGTGACCCAAATCTTTGGGTGATTTTTCTGCTGGAAGAGGACAAACACCATTACATTC

AAAGTCAGATTTTCTGTTTTTTTTTTTTTTTTTGTTTTTGTTTTTTTAATATTCATTTGTT

TATTCATTTGAGACTGGGTCTTGCTCTGTCACGCAGGCTGGAGTGCAACCTCCCTGGGCT

CAGTTGATCTTCCCTCAGCCTCTTGAGTAGCTGGGACTACAGGTGTGTGCCACCATGCCC

AGCTAGTGTTTGTATTTTTTGTGGAGATGGTGTTTTGCCGCATTGCCCAGTGTGGTCTTG

AACTAGTGCTCAAGAGGCCTGCCTCCTTCAACCTCTCAAAGTGTTAGGATTACAGATGTG

AACTACTGTGCCTGATCCAAAGTCAGATTTTCTTTGCTTACTTAGTCAAGTTCGTCTATG

-continued

CTTTTATTATACTTAATATATTAGTATAGTTACTGTATTAGTATATTAGCATATTTAATA

TATTATTATACTTATCATACTTGAGTATATTGAGTATATTTACACTTTTAGTATATTTGT

ATACACACACCACATTTTTATTATTTATCTTTTTTTTGAGACAGAGTCTCCCTCTGTCTC

CCAGGCTGAAGCACAGTTGGCTCACTGCAACCTCTGCCTCTTGGGCTCAAGTGATTCTCG

TGCCTCACCCTCCTGAGTAGCAGGGATTACAGGTGTCCACCACCAAGCCTGGCTAATTTT

TGTATTTTTAGTGGATATGGGGTTTTACCATGTTGGCCAGGCTGGTCTCGAACTCCTGAC

CTCAAATGATCTGCCCGCCTTGGCCTCCCAAAGTGCTGGAATTACTGGCGTGAGCCACTG

CACCCAGCCTATTATCTGTCTTTTGATGGACATTTAAGTTGTCTCTATATACTAGCTATT

GTGAATAATGCTGCAGTGAACATGAGAGTGCTTGAAAACACTAATGTAACATAAAGGTAA

CAAATAATAAATGTCATGTGTTTATCTTGAAAGGAACTGAAATACGACGTTGGTGGAGGA

GAACGGTTTGATTCTTTGACAGATCTTGTGGAACATTATAAGAAGAATCCTATGGTGGAA

ACATTGGGTACAGTACTACAACTCAAGCAGGTGAGCAGATTGGAAAGCTCAAGCTTTCTC

CTTAAAAACTTAAAACAAATCCTAATAGAGAATTTTGCAAACATACAGAGGTAGACAGAA

TAGTATCATCAGCCTCCATGTACCCATTGCAGCTTCAACTATCAAATCTTTTTTTTTTTT

TTTTTTTTTGAGACAGTCTTACTCTGTCACCCAGTCTGGAGTACAGTGTTGCAATCTTGG

CTCACTACAACCTCTGCTTCCTGGGTTCAAGCGATTCTCCTGCCTCAGCCTCCTGAGTAG

CTGGGACTACAGGTGCCCACCACCATGCCCGGCTAGTTTTTGTGTTTTTAATAGAGATGG

GGTTTCACCATGTTGGCCTGGCTGGTCTTGAATTCCCGACCTCAGGTTTTCTGCCCGCCT

TGGCCTCCCGAAGTTTTGGGATTACAGGCGTGAGCTACCACGCCCGGCCCTAAATCTTTT

CTTATTATGATTCCACTCACTGACTGCCGCTATAGTACTTGGAAACATATTCCAGATTTA

TATTATTCCCATATTTATCTGTAAAAGGCATTACAGAGGTTCTTTTTTTTTTTTTTTTTT

TTTGAGATGGAGTTTTGCTCTGTCGCCCAGGCTGGAGTGCAGTGGCGTGTTCTTGGCTCA

CTGCAACCTCTGCGTCCCGGGTTCAAGAGCTTCTCCTGCCTCAGCCTCCTGAGTAGCTGG

GATTATAGGTGGTGCCACTACACCCAGCTAATTTTTGTATTTTTAGTAGAGATGGGGTTT

CACCATGTTAGCCAGGCTGGTCTTGAACTCCTGACCTCAAGTGATCTGCCTGCCTCAGCC

TCTCAAAGTGCTGGGATTATAGGCATGAGCCACTGCATCTGGCCTAAGGCTGTACAGAGT

TTTAAAGCAAGTTTTCATTATAGATCCACTTCTGGTTACCTTTAGGTAACCTCACTTATT

CACTTTGGCATTGTTGCTATTTCAAATTTCACCTTTATGATAGTGGAAAATGATATAATC

TCTCTAAATAATGTGGTCTATTCATAAAGAAAAATAGGCTTGAATTTATATCAGCAGAGT

AAAGTGTATGTGAAGACTGAAGAAAGATACATTTTCTGGCTGAACAGAAAACACGGTGAA

ACGATTTGAAAACTTTTATTGTGAATTACAGGGTCCTATGAACCCTCTGTCCGTGCCTTT

ATGAATATCAACATAGACATGTTTTTTTTTTTTTTTTTGCATTAACACCGTTTTCTGTAA

TATTTTCTTTATTTTACATCAACTGCTGTACTCGATCAGCCCCTTAACACGACTCGTATA

AATGCTGCTGAAATAGAAAGCAGAGTTCGAGAACTAAGCAAATTAGCTGAGACCACAGAT

AAAGTCAAACAAGGCTTTTGGGAAGAATTTGAGGTAAGTTATTAAAAAACTGTTTTTACG

TGAGTTGTTATATCCTATTTTTAGTGGAGGAGAAGTTGCTCTTGTGTTTGGAATTGGACC

TGAGAGACTTGAAACTGACGTCCTTTTTTAATTCGGCCATTGATTGACACGGAGCAAGTT

GCTGAGAGGGCTTCTTCGAAACAGAAGAGCATTGTGTTCTGAGGGAAGGGAGTTGGCAGT

GAGTAGTCAATGGATGTGCTAGCCGCTCCATTTGGCTCTTTTGGTTTGGACTGGTGGCAA

AATCTCAGAGAAACAAAAGGATCTAATTTCTTCGAAAGATTTCCAGCATGCACTGGGGTC

-continued

TTTAGAAACAATCTATAGCCTTAGTGCAGCAAATGAGTATGAGTAAAAGAGAAACACCTT

GTGGTGGCTTTTTTTTTTTTTTTTTTGAGACAGGGTCTCGCTCTGTCGCCGAAGCTGGAG

TGTAGTGGCGTGATCTCGGTTTACTGCAGCCCCGTCCTCCCTGGGCTCAAGTGATCTTCC

CATCTCAGCCTACTGAGTAGCTGGGACTACAGGCACATGCCCCTATGCCTGGCTAATTTT

TGTATTTTTGGTAGAGATGAGGTTTTGCAGTGTTGCCCAGGCTGGTCTTGAACTCTTGGG

CTCAAGTGATCCTCCTACTTAAGCTTCCCGAGTAGCTGGGACTACAGGCACACGATACCA

TGCCCATCTAATTTTTGTATTTTTTTGTAGAGATGGGGTTTTGCAGTGTTGCCCAGGCTG

GTCTTGAACTCTTGGGCTCAAGTGATCCTCCAGCTTTGACGTGCCAAATGTGGTGGCTTT

AATTTCAGAGTTCAAATTGATAACTCTGGTAAGTTAAGTGAACTGATTTCTTTTTTTTTT

AAATTATTTTTGTTGATTATACTTTAAGTTCTGGGATATATGTGCAGAACGTGCAGGTTT

GTACATAGGTATACATGTGCCATCATGGTTTGCTGCACACATTAACCCATCATTTAGGTT

TTAAGTCCTGCATGCATTAGGTGTTTGTCCTAATGCTCTCCCTCCCCTTTAATGCATCAG

TGAAAAAGTGATGATAGGCTGGGCGTGGTGGCTCACTCCTGTAATCTCAGCACTTTGAGA

GGGTGAGGCAGGTGGACCACTTGAATCCAGGAGTTTGCCCCCATCCCCAGACAGTGTGTG

TGATGTTCCCCTCCCTGTGTCCATGTGTTCTCATTGTTTGGTTTTCTGTTCCTGTGTTAG

TTTGCTGAGAATGATGGTTTCCAGCTTCATCCATGACCCTGCAAAGGACATGAACTCATT

CTTTTTTTATGGCTGCATAGTATTCCATGGTGTGTATGTGCCACATTTTCTTTATCCGGT

CTATCATTGATGGGCATTTGGGTTGGTTCCAAGTCTTTGCTATTGTAAATAGTGCTGCAA

TAAACATATGTGTGCATATGTCTTTATAGTAGAATGTTTTATAATCCTTTGGGTATATAC

CCAGTAATGGGATTGCTGGGTCAAATGGTATTTCTGGTTCTAGATCCTTGAGGAGTCACC

ACACTGTCTTCCACAATGGTTCAACTAATTTACACTCCCACCAACAGTGTAAAAGCATTC

CTATTTCTCCACATCTTCTCCAGCATCTGTTGTTTCCTGACTTTAAGTGAACTGATCTCT

TTCCTGAAACTAACTTGGGTTGGAGAATGTCCCTGATGGGAATGTGCTGTGTTCCCATTG

CACTCTTCTATATCACTTACCCATTGACAATGTGATCTCTTTCATTTTCTCCTCATCCAT

TTGACAGAAAACTTCAAAAACAAGGATTCTGGCATATTTACCTTTGCAGTTGTCCCCAGC

ATGTAGCACGGTGCCTAGTACACAGAAGAAACTCCATAAATGTTTGTTGAATGAGATTTA

CATTTAACTCATGTTTACATCATTTTATTTTCCTGTTCTGTTTTATGGGAATGATTATTC

TATGCTTTTTGAGGACTACAATTTATAAATATTTGTGGATTGAATGAATAAGTGAATACT

GGGCAAATAAAGTCCTTTTAGCCAGAGTATGTCTGAACAACTTGCTGAGATAGATATGAT

TTCCCATTTTCCAGCTGAGGGGCCTAAGGGAGGTTAAGTAAATTATTCAATCTTCATACC

ACAGTTTTTGTTTTGTTTTGTTTTGTTTTTTTTCCTCCTGAGACAGAGTCTCACTTTGCT

GCCATACTGGAGTACAGTGGTGCAATCATAGCTCACTGCAGCGTCCAACTTCTGGGCTCA

CGCCATCCTCCCACCTCAGCCTCCTGAGTAGCTGGTACTACAGGTGTGCACCACCATAGC

CGGCTAATTTTTCATTTTTTGTAGATATGGGGTCTCACTGTGTTACTCAGGTTGGTCTTG

AACTTCTGAGCTCAAACAATTCTCCTGTCTTGGCCTCTCAAAGTGTTGGGATTACAGGTG

TGAGCCACTGTGCCCGGCCCATACCACAGATATTGATTGAATTCCAGCAGTGGGGAGGAG

TGTGGAATAGAACATTCTCAGTCCTTGCTCAACATTACTGAACAGAGACTTGAATTTGAG

TTTATTCTCTCATCCCAGGCTTCGCGTTAGGCTCTGAAGACACTAGTGAACAAGACAGAC

AGGGTTACTGCCTTTAAAGGGAGCTTTTAGTTGAGAGAAGGAAAACAGTGATGAAAAGCA

TCAGTGAAAAAGTGATGATAGGCTGGGGCGTAGTGGCTACTCCTGTAATCTCAGCACTTT

-continued

TAGAGGGTGAGGCAGGCAGCTCACTTGATTCCAGGAGTTTGAGACCAGGCTGGGCAACAT

GGTAAAACCCCGTCTCTACAAAAAATACAAAAAGTAGCTGGGTGTGGGGGTGCGCACCCA

CAGTCCCAGCTACTCTGGGGGTTGAGGTGGGAGGATTGCTCGAGCCTGGGAGATTGAGGC

TGCAGTGAGCTGAGATCACGTCACTGCTCTCCAGCCTGAGCAACAGAGCCAGAACCTGTC

CCAAAAAAAAAAAAAATTGATGATAAACATAGTGAGACAGAATTTTGAAATCTCAGCCTC

ACTGTTGCCTTCCTTGTCCCCTGCCTGCCTAAATAATAAAAGGCAGCATTTCAGCAGTCA

TTCATTTCATTACTTTCACTTCATTTCACCTTCATAAAGCCTCATGAGGTAAGATGGGAA

GATACAGAAGTTTTAGAAACCGCTCATCAAAATTGAATGGAAAGCCGATTGTTCCAAAAC

TTTTTAGTGTGGAAAATTTCTATTATATGCAAAAGTAGAGAGAATGGGATAGTTATAGCA

GTATACCTGACACCCAGCATTAACAACTGTTGATAATATGGCCAATCTTTTTCGACTCTG

CCCCACTCACTTCCCCAGCCCTGACTTGTCTTGAAGCAAATACTTTTTTTTTTTTTTTGA

GATAGAGTTTTGTTTTGTTTTGTTTTTTGTTTTTGAGATGGAGTCTCACTCTGTCCCCCA

AGCTGGAGTGCTGTGGCTTGATCTTGGCTCACTACAACCTCCGCCTCCTGGGTTCAAGTG

ATTCTTGTGCCTCAGCCTCCTGAGTAACTGGGATTACAGGTGTGTACCACCATGCCCAGC

TAATTTTTGTATTTTTAGTAGGGACAGGGTTTTCACTATGTTGGCCACGCTGGTCTCAAA

CTCCTGACCTCAGGTGATCCGCCTGACTTGGCCTCCGAAAGTGCTGGGATTGTAGGTGTG

AGCCACTGCTCCCGGCCTTGAAGCAAATCTTAACACATCATTTCGTCTGTAACTATTTTA

TTTCAAAAAATTATAACCTGAATAGCATTATCATATCTAAAACTATTAACAGTATTTCCT

TAATATTAACACATATCAGTCACATTTTCCTGATTGCTACACACACACACACACACACAC

ACACACACACACTTGCAATTTGTGTTTTTTTCTTTTTAGATGGATCTCACTCTGTTGCCC

AGGCTGGAGTGCAATGGTGCATTCTCAGCTCACTGCAACCTCCACCTCCTGGGCTCAACT

GATTCTCTTGCCTCAGCCTCCTGAGTAGCTGGGACTACAGGTGCCCACCACCTCACCTGG

CTAGTTTTTGTATTTTTAGTAGAGGTGGGGTTTCACCATGTTGGCCAGGTTGGTCTCAAA

CTTCCGACCTCAGGTGATCCACCCACCTTGGCCTCCCAAAGTGCTGGGATTACAGGCATG

AGCCACTGTGCCCAGCAGCAATTTGTTTGAATTGGGAGTGCTTTCTTCCACCTTGATTAT

GAAAAAATTTCAAATGTGTATAAAACAGATTCATATAAAGGATCCTGATATGCCATTATC

AGCTTTATCAATTATCCCTGTCATCATATTTTTTATTTATAAATATTTCAATATTTGTGG

AATCCTTAAAAATGCATCACATAACCCAACATTGTTCATATTATACCAATTGTCTTATAA

TTTAAAAATATTTTGTTCAATCATTTTTCAGATAAGCTTCACACACTGTGGTTGGCTAAG

TCTCATAATATTTCTGTTGTAAAAATCTTAAGTCTGGGCGTGGTGGCACACGGCTGTCAT

TCCAGCACTTTGGGAGGCTGAGGTGGGCGGATCACGAGGTCAAGAGATCGAGACCATCCT

GGCCAACATGGTGAAACCCGGTCTCTACTAAAAATACAAAAATTAGCTGGGCGTGGTAGT

GCGTGCCTGTAGTCCCAGCTACTCGGGAGGCTGAGGCAGGAGAATCGCTTGAACCCAGAA

GGTGGCAGTTGCAGTGAGCCGAGATCGCGCCACTGCACTCCAGCCTAGAGACAGAGTGCG

GCTTCATCTCAAAACGAAACAAAACAAAACAATCTTAAGTCTCTTAGAATACTTTGATGC

CCCTTCCATCTCTCTTTTTCTGTCTTCCTTCCCCCTCTCCCTGTCTTTTCTGCTGTTGAA

GAAAGCAGATCATTTGTCCTGAGAGTTACTTATAGTCTGAATTTTGCTGAGTGCCTCTCT

GTGGTGGACTTAAGCATGTATCCATCCCTTATATTTCTTGTAAGTTGATATATCTAGAGA

CTTCATTGGATACAAGTTTTCTTTGGCAAGATAGCATGTATGGTGGTGTATCAGGAGGTG

TTTATGTCCTGTTGTTTCTTCTCTGATTTTCTTAGCAGCTCCTGATCATTATTACTTAGA

-continued

TCCATTAATTCATAAGGGACTATATGGTAGTGATATTGTAATTTTATCATTCTTCTTCAT

TTGTTAGGTTGGCATATTTCTATAAAAAGCTTTTCATCGCCGAGGGTTGATTTTTTCCTT

CTTACTAAGCAGTTTTCTTTTCTTTTTCTTTTTTTTTTTTTTGAGGTAGGTCTCACTGTG

TTGCTCAGGCTGGTGTGCAGTGGCGCAAACACACAGTTGCGAACTCTTGGGCTGAGGTGA

TCCTCCTGCCTCAGTTTCCTGTGTAGTTGGGACCACAGGTGCATGCCACCATGCCTGGCT

AATTTTTTGATTCTTTTGTAGAGATGAGGTCTCACTTTATTTCCCAGGCTGGTCTTGAAT

GTCTGGGCTCAAGCAATCTTTCTACCTCAGCCTCCTGAGTAGCTGGGACTACAGGCACAT

ACCACCATGCCCAGCTAATTTTTTAATTTTTATTTTTAGTAGAGATGTGGTCGTATTATG

TTGCTCAGGATGGTCTCGAACTGCAGAGCTCAAGTGATCCTCCTGCCTCAGCCTCCCAGT

GTGCTGGGATTATAGGTGTACTACAGGCAAGAGCCAATGAGCCTGGTCAGATTTTTTTTT

CCTGATTTGAAATCTGTTATGGGTTCAATTGATACTTCCAAATCAAACTCAGGGTTTCAG

GATTTTTACTAACCTCATTGATCTTACCCATGTATCTCCTTTCTCTAATGCCAAAAATCC

TACTTCTTGAAGCCATAATAAGATTATTCATTTGTTTTATCCCACATTACACACAACAAT

CTTAGAATAATGACTTCCCAATAATATGATTACTGAAAACAGTTTAATTTTTTTTGCGCT

TTTCAAAAAAATCCTTCAGAGATGTGTAGTCAAGTTACTGTATTCTGCTGGGCACAGTGG

CTCACGCCTATAATCCCAGTACTTTGGGAGGACAAGAAGGGAGGATCGCTGGACCTCAGG

AGTTTGAGACCAGCCGGGGCAATATAGTGAGACCCTGTCTCTACAAAAGAAAATTAAAAA

TTAACCAGACATGGTGGCATGTCCCTATAGTCCCAGCTATTGAGAGGCTGTGGCGAGAGT

AGGCTTAAGCCCAGGAGTTTGAAGCTGCAGTGAGATACGATTGTGACACTGTACTCTAGG

GTGACAGAGCAGGGACCCTGTTTTTAAAAAAAAAAAAATGAAAAAACTTCCTGTGCCTTAG

ACTCATTTGTAATCGTCCTTCTCTCTGTGTGGCTATATGCTAACTGGGTATATGGTTAGT

TTATTTGTTTCATTTAAAAAATCTCTTTCTGTTAAGTTTTATTTATAATTACACAAATAC

TGGCTTTGATAGTCAAATTGAAAAAACAAAGTGTATTCAAAGAAGTCTACCTTCTATCCT

TGTCCTTTCCTATGTTTTAGCCATAGTATAAAAAGTTATGGTTTATCATTATATTTCAAA

AATATAAGAAGATATTCCCATATCCCACTTTTTCTTAAACAGTAGCATAACTTTACATAC

TTTTTTCTAACCTTGCTTTTTTAAATATCCTGGACATCCTGGATATCCATAATAGTGTCT

AGAGATAGTCTTCATTCTTTTTTTACTGTATAGTAATCCACTGTGTACTTGTACCATAGT

TTATTCAACCTATTGATGGGCATTTGGGTAGTTTCCAAATGTATCACAGAGAGGATTACA

GTGAATAGCCTTGTGTATGCATCCTGCTTTACTTTTGCTGACTACTGGTAATATTAACAT

TTTTTATGTTCTGTATTTAAAAAATGGTGGTTATTATTCATCTATAACTTTTATTATACA

TGACTTTGGTTAGCATGCTTTAACCTTTTAGCATAACATTTGCAAGCTACTTGTTTTAAT

TAAAATTTTGGTTAAATGTAAAAAATAGTGAGCTATTTTGTAATCTAGATTCAATAGAAT

CTTATACTTCCTTTACAAATGATAGCTGAGTTGATCATTTGTGTAAATGACTGTGAACTT

AAAAATTACAGCATTTTTTAAAATAAATTTTTTTAACATTTTAAAATTATTTAAAATAAT

AGACACACAAAGTAAAAAGAGAAGAAAAAAAAAAGAGACAGGGTCTTGCTATGTTGCCCA

GGCTGGTCTCAAACTCCCAGGCTCAAATGATCCTCCTGCCTTGGCCTCCTAAAGTGTAAG

CCACCACACTTGGCAAAAATTAGTTTCTTTAAAACAAAAACATTACAGGTTATCTGGTAC

CATGGTAGCTTCTTTAACACTAGGTTCACTTAGAACAAAGCTTAGGAACAAAGTCAGACT

TTCACAAAGAGCTTGTGTGGCAATGGGGTATTTTTTGCAAATTCCATTGGTGGGGTCAAG

ATGTGAGTTTAGAAGGAACTCTTAGCCTGACTCTTCTGGCCATGGAAAAAGATGGTTGCT

TCTAAATGCTGACCTGGTGATTTTACACTGTCACATCTCAAATTGTGGTCATCTTTTATA

-continued

CATTATTAACAACAAAAGGGAAAAATTGAGTTGACTTTAAGAGGAAGTGGAAAATAACGA
GATCACATCTGTACTCTACAGGCTCTCCACAGAGGTCAGACTGAGGTGGTAAAATTGTTG
TGCACTAAATTAGGGCATTAACGTTTCATGGAAACTGAAGCTATATCTAAATAGCTGATG
GCCTGCTTTCTAGATCTCCTATATACCTGCTTCTCAAATTCAGTCTGTTTTAAAAAATTG
CCCTTTGAGGTTGGAACCAGCGAAATAAGGCTGAAAACAGAATAAGCCATTATTGAAAAA
ATTAGGAACTTGGAAGCAGATACTCATAATCTAAATCCTCTGAAGCTAAAGTTTGATCCA
CAATAGCAAAGCATTATCATTTTAGTGATTGTACCTTAGTTGTTTCCTGGCAGGTGATAA
ATTTGGGATCACTTTCTTCTTACAGTGTGCTCTGATAGTCTTTAAAACAAACCAGAGCTC
TAAATTGTAATGCCATTGGTAATTTAACTCTGATTTGTCTCTATGCCTGTCTCCTGGTGT
TCTGTAAAATTCTACACGTCATTTCAGGTATCACTATCCAGAAGACGTTACTTTTGCCTT
TGATGCACTTTAAAATGTGAAGTCTCTTGTGAAGCTCTTTGGTTATTTTCTCCTTTGCTG
CTGAAATAAATTCAGGTTGATGATTTTCTTGTAGGATATGTTGTGTGATCTAGACATTGC
AAACCCAAGTCTTTGATTTTTTTTTCCCTACAGATTGCCTGTTTCTTTTTTATTTTAATT
TTTATTAGTTATTATTATTTTTGAGATGGAGTCTCACTCTGTCACCCAGGCTGGAGTGCA
GAGGTGTGATAGCTCACTGCAACCTCCACCTCCCGGGTTCTTGTGCCTCAGCCACCCAGG
TAGCTGGGATTACAGGCACGTACCACCACTCTCAGCTAATTTTTTTGTATTTTTAGTAGG
GATGGGATTTCTCCATGTTGGCCAGGCTGATCTCAAACTCCTGACCTTAAGTGATCTTCC
TGCCTTGGTCTCTGAAAGTGTTGGGATTACAGGTGTGAGCCACTGTGCCTGGCCAGTTAT
TAATTTTTTTAAAGAGATGGGGTCTCACTATCTTGCCCAGGCTGGAGTGCAGTGGCTCTT
TACAGGCACTGTTGTAGTGCACTGCAGCCTTGAACTCCTGGGCTCAAGTGATCCTCCTGA
GAGGCTGGAATTACAGGCACACACCACTGTGTCCAACAGATTGCCCATTTGTGATCTGTG
TAAATATCTCTCACTTCCTGCAGTATCTCTGCTCAAGAATGTAAAGAGATGGATAATATT
TTTAGATTTGTTGAAACAAAGTAAAGTTCTGCTCAAATGAGAATGACACTAACTAAATGA
AAAGGCCGGTTATAATTCTGTAATTTTGTGCCTGCAATGTGTGTGTTATTGTACACTTGA
ATCGGCCCTGTGCATTGTGGCGAGGTGCATATTGCATGGTTGTATTGAAAAGGTGCTTGG
GCCGGGCGTGGTGGCTCACACCTGTAATCCCAGCAATTTGGGAGGCTGAGGCAGCTGGAT
TACCTGAGGTTAGGAGTTCAAGACCAGCCTGGCCAACATGGTGAAACCCTGTTTCTAGTA
AAAAATACAAAAAATTAGCTGGGTGTGGTGGTGGGTGCCTGTAATACCAGCTACTAGGGA
GGCTAAGGCAGGGAGAATTGCTTAAACCTGGGAGGCAGAGGTTGCAGTGAGCTGAGATTG
TGCCACTGCACTCCAGCCTGAGTGTATCACAAAAAAAAAAAAAAAAAGGTTTTTGCCCTCT
CTCTGTGCCTGCTGCTCCCTGTTGAGTCCTATAGGCCTGAGCTGCCAGGGGGTACTGTGG
GCTGAGACTGGACATTGCAACCGACTGCAAGGCACCGTGGGACCCAGGTTGTGGATGGAC
TGTCTCTCGGGCTTTCTTCTTTCCATTCATCTTCCTCCTCTAACTCCCCTCTGTATCCAG
TATCCTTGCTCTCCATACACCTGCTTCATTCTTTTTCCTTCAGTAGATTTTTCTGCTTCT
TGACTTACAAACCCTACTTCTAGCCCCTTTCAGATATTGAAACTAGCAACTTTCAGGCTT
TGTACCAAAGTCTCAGAGATTCTCATTGACTCGGATGCCATCCATCTCTAGTCCAAAGAA
CAATGTCAAGGACATGAACATGTGGAACAAAAGTGTCTGCTGTGGACACCTTTGGGGAGA
AATAGTTTTCAGTGATGAGGGTTGTAGTGAGTTGGGCAGATATCCCAAAAATATCTGCCA
AAAACTATAGACACTTCTGGTTGCAGTGACTTATTCCTTCCTTCATTCAGCAAATACTGA
TTGAACACCGACTGTATGTCTGGATCTATTCTAGGTTTTGGGGGTGGAGCAGTGAACAAA

-continued

TCAGTCTTTATCTTTATAGAGTGTACAGTCAAGTGGGAGAGACAGGCAGTAAACAAAGAA

ACAGTTCAATATTCAATCTGTGAGATGGTGATAAGTGCTACAGAGAAAACAAACTAGTGT

AAGATAAAAAGGGTGTTTTGATAGGCCTTTACTATTTAGGTCTCTTTGATAAGGTGGCAT

TTGAACAAAGCTCTGAAGGAAATAATGGAGCCAACCATGCATATAACCTCAGGGAGAACA

TTCTAGGTAGAGGGAACAGCAAGTGCAAAGGCCCTGAAGTGGGGGTTTGTTTACCTTGTT

GCACAATCTGCACACAGGCCAGTACAATTGGAATGGATGGGAAATGTAAAAGAGAGAAGT

TGAAAAGGCCAGGTGCAGTGGCTCATGCCTACAATCCCAGCATTTTGGGAGGCTGAAGTG

GGAGGAATTTGAGATCAGCCTGGGCAACAGAACCAGACCTCGGGCTAATTTTTGTATTTT

TAGTAGAGACAGGGTTTCACCATATTGGCCAGGCTGATCTCAAACTCCTGACCTCAGGTG

ATCCTCCTGCCTCAGCCTCCCAAAGTGCTAGGATTACAGGTGTGAGCCATGGCCCCCAGC

CGTATCTTTGTCTTAAAAAGTAATCTCTGTGCTTGGTAGGCCAAGAATTTAAAATATAAA

AAATTTAAGAAAGAAAAAAAATAAGTAAAGTAACTATACAGGTTGGTCTGGCCGTAATGG

TGAGTGTCATTATTTTTCTTCCCTAGGTATTTTGGCTCTGTTGCTCAGAGCAGTGCAGGC

GAAATGGTCATTAGGGCATCGTCATGGTGCCTGGGGATGCCTGGCTCAGCCAGTTTATTT

TCTGTCTGCCTCTCTCCTTGGTCCTTTTCCTCCACTTTCATTCATGAAATTCTAGTCAAG

AGCTGGGTCCAGTGGTTTTCAATCCAAGGGCTTTGGAAGCCTCTGGGGTCTATTTTGGTC

ATTGCAGTCACTGGGCTGCTGCTCCTGGCATTTAGGTTGGCAGGGGTCTGGGCTGGGAAG

CAGGAATGTTCAGTGGCCATAAATGTAAGGGTTGGTCTTACATTTACATAAGGGAGACAA

TGAAAACTTAACTCCTCCACAGTAGTGGAGTAGTGCCGTTGGGTACTCACAGTCAGTAGT

GCCGTTGGGTACTCACATGTACAACATGGATCAGGACATTGACTTTCTGTGGATACCTTT

TAATAGTTTATTAGATGTGTTAGGCTGTTTTGCACTGCTCTAAAGGAATATCTGAGTCTA

GGTAATTTATAAAGACAAGAGGTTTAATTGGCTCATGGTTCTGAAGGCTGTACAAGCATG

GCTCCAGCATCTGCTTCTGGTGAGGGCCTCAGGAAGCTTCCGGTCATAGTGGAAGGCAAA

AGGAGGGCAGACGATCACATGGCCGGAGTGGTGGCAAGGGTGGGGTGGGAGCCACGCTCT

TTTTTTAATTTTATTTTAATTTGAGACAGTGTCTCACTCTTTTGCCCAGCCTGGAGTGCA

GTGGCGTGATCTCAGCTCACTGCAGCCTCTGCCTCCCAGGTTCAAGCAATTCTCCTGCCT

CAGCCTCCTGAGTAGTTGGGACTACAGGCGCGCATCACAATGCCCAGCTGATTTTTGTAT

TTTTAGCAGAGACAGGGTTTCACCATGTTGGCCAGGCTGGTCTCGGACTCCTGATCTCAA

GTAATCCGCCTGCCTCGGCCTCCCAAAGTGCTGGGATTACAGGCATGAGCCACTGCGCAC

GGCCACCACACTGTTTTAAACAACCAGATTGCACGTGAACTTAGAGTGAGAACTCACTGT

GAGGATGGCACCAAAACATTCATGAAGGATCCACCACCTTCCTTTAGGCCCCACCTCCAA

CACTGGAGGTCATATTTCAACTTGAGATTTGGAGGGGACAGACATCCAAACCGTATCATT

AAATTTAATAGTTTTATGCAGTTTTTTTGGCTCTAGATCTGTTTAGACTCCTGCAGTCAG

GTGTCTGTAACTAGCCTCTGGTCCTTTTTGAGAGTTCACAGTTTGGTGCAAACCCTTTGG

ATGTATTATTTGGGAAAATGGGATATCTGGCAGCCTGTGTCCCTGCTTTACATTATCCTT

TTTGCTGCCTGCCCCAAGCCTCCTCATTAGCATCCCTGCCAAGGCCAGTGGAGAAGGATG

GAGATGCGGTGACATTCAGCTTGACAGGTCATTAGCAGCTTTTGTGCCCTAGGGACTGCT

GGTGGGAGGGAGGTTGTGGAAGATAAACCCTGACAGGAATGTATTCTCCTCGAGGGCAGG

GTTTATTTGATATTTTTCTGGAGCTTAGAACCATAAGCCTGGTGCTGGGGAGGAAGCGCC

CTTAGCATTTGGTAGCCTCTGTGGGCAGAGCATGGAAAGTCACAACTTCTGAATTGTTTG

TATTTTCAGTCTCACTCTAGATGGATGGCATCTTCTGCTATGGGAAATGAAATATGTTTA

-continued

GGCAACTTGAGTCCCAGGTGCAGATGAGGCTGGGCTAATTGGTGCACTAGGGAAGGAGCC
GGGGGAGAGATGTGCTGTTAGCTATTATCAATCTGTGACAACTGTCAGCTGCTGGCAGTT
AGCACCCACCTGAGCCTGGGATGCAGGGGTGCCTCTCCTGTCCTCTGTGGAAGCCTCTGG
ACCCAGCAGCCATCTTGACTGTGCACTGTTCAAGCCCCAAGTCCGCCTGGAAGAGGTGAT
TGAGAACTTACTGCAGGATAAGGAAAGCGCAGGACAGGTGCAGTGGCTCACGCCTGTAAT
CTCAGTGCTTTGGGAGGCTGAGGCCGGAGGAGGGCTGGAGTCCTTGAGTGCGAGACCAGC
CTGGGCAACATAGTGAGACCCTGTCTTTACAAAAAGGAAAAGAATTAGCCAGATGTGGTG
GTGCGTGCCTGTAGTCCCAGCCACTCAAGAGGCTGAGGTGCGAGGATCACTTGAGCCCAG
GAGTTTGAGGTTACAGTGAGCTATGATCATACCACTGCATTCCAGCCTGGGTGAGAGAGC
ATAGCTCTGTCCCAACAACAAAAAAAAAGATTAAGGGAAGCCTCTGGCAGACCTGATGAT
GGGTGGCCCAGCCAAAATGAGTATTGATGAGGATTTCCCTGGTCTGGAACTCTGAATTTA
GTCTGGCAAAGTATTCCCTTTGTGTTGTGAGATGATTCTTGGTGTTACCCCATCACGGTA
GGTAAGATGAATTAGCAAATGAGAAAGGCTTTCTCTTTTTCATCCTTATCTAGTCCGTAG
ATGAAGCCTGAAGAAGGTCTCCATATGGTAGTAGTAAGTGTTTAACATCTACCTCTAACA
CTTGCCTGTGTCTTTTTTTTTTTGCAAAGCCTCAGGAATGCCCCAGTATCTAGGTAGAAT
TTGATAATATTTCATTTTTGTTATATTCCCTTTTCTGTTTACCTTCTATATACAGCAAAA
TGAAAAAATTTTTAAAATTTGTGCAAGTAAGGGCAATTTCTTTTTTCTTTTTCTTTTTTT
TTGAGACAGGGTCTTGCTCTGGCACCCAGGCTGGAGTGCAGTGACACAATCTCGGCTCAC
TGCAACCTCTGCTTCCTGGGTTTAAGCGATTCTCCTGCCTCAGGCTTCCAAGTAGCTGGG
ATTACAGGTGCCTGCCACCACTCCCAGCTAATTTTCATATTTTTAGTAGAGACCAGGTTT
TGCCATGTTGACTGGGCTGGTCTTGAACTCCTGACCTCAGGTGATCCATCCACCTTGGCC
TCCCAAAGTGCTGGGATTATAGGCTTGAGCCACTGGGCCTGGCTGAGGCAGTTTCTTTTT
GAAATATATTTTGTGAAGGAGAAAAAGAGGAGTTCAGTTTAAAGAAACAAATGACATAAG
AGGTGGTATGCAGAGATGCCAAAGCATCTTGAAGGTGCTTTTTTTTTTGGAAACAGAGTC
TTGCTTCATTGCCCAGTCTGGTCTGCAGTGGTGCAATCATGGTTCCCTGCAGCCTTGACC
TTCTGGGCTCAAGTAATCCTCCCACCTCAGCCTCTCAAGTAGCTGGGACTACAGATGCAT
GCCACTATGTCTGGCTAATCTTTAAATTTTTTGTAGAAGCCAGCTCTCACCATATTGCCC
AGGCTGGTCTTGACCTCCTGTCCTCGAGCAAAAATACCGATTTTGATTAAGTCTGGGGTA
GGACCTGGGGCTGGGATTCTAACCAGCTCCCAGGTGGTGCTAATGCTGCTGGTCTACAGA
CCACACGTGGAGTAGCCAGTGTAGAGTTCATGTAGCAATAGTGATGTCATAGAAATAGCC
AGTATCTGTATACTTGCTTTGTTGTATGTCACGCACTGTATAGTGATGTACATGCATCTC
ATTTGACCCTCACCCCGCCCCTTTGGGGGTAGAAAGGATTGTGCTCATTTCACACTCAAG
GAAACTGAGGCACAGACAGGCAAAGTAGCTTGGCGAAACAGAAAGGAACTTAGAGGCAGG
CCCTGATTAGCTCAGAGACTAGAAGGCCTTGTGCGTCATCCTGAACAGCTTGGACTTGAT
CTTGAAGGTGGAGGGAGAAATTGAAGGGTAATTAAACAGGAACTGTAGGAAATTCACCTT
GCATAGTGATTGCTTTGGCCACGTGTGCCCTGCCACCGCCCCCCCACCTCAGTGAAGTGT
CATGCGAAGTTGGGTTCGTAAATGAAGGCCCGAATGCTTTCCTGACAAGTTTGTTTTAAA
TCAAGCTGCTAATTAGTCCCAGTCCCCCTCCCCCGGTATGTATTTTTTTGTTGATGTCGT
TTCACTTCATTTAGTTGAAGTGATTGATTCAGTTCAGTGTTTGAACTTCTTTTTGAACCT
CACCTTAATAACCTGTCTAAACATCAAGGTTAAACCTTCTTGCTAACACAGCAGTATTGC

-continued

TTGGTAAGACTGGCTCACAGTCCAAGGAAATGCTTGCCCAGAGAGGGCAAACTGCCTTAA

CTCCTTAACCTGAGCTCATTAAAAAAAATTCAAATGACTGATTCCTTGTCACAGTTCTAC

CTACATTGTTTTTATTTTTGTCCAGGTTTCAGCTAGTTAAATGCTTTTGTGATGAGCTTA

TGTCCAGGCTGAAGGTTGCATTTTGAAACTGAGCGTCAAATACCAATTTAAAGTCCAGAC

CTTTACACTTGTGAAATTCAGATAAATGAAATGGAAATAAAACAGGGCTGCTGTGTTGTG

AAATATGACTGTGTTTTTCCTTGTAGGACTCTTTGAGGGTAGCCATTTTGGCATTTTATA

TATAAATTTTCTTTTCTTAGCCTACCTTTTACTTTCTTGATTTGCCTATTTGTGATTTCC

CATTAAACACTAGGCTTTTTGTAAACCAATTATCCCTTGAAATTGACTTTTTTTTTTTTT

GAGACAGGATCTTGTTTTGCCACACAGGCTGGAGTGCCGTGGCTCCATCATATGATAAAC

AGAAAGAGAGAGAGAGAGAGAGAGAGAGAGAGAGAGAGAGAGACCCTGTCTTATTTAAAACA

AAAAAAGAAGAAGAAAAAAAGAATATAGATCACAGCTGTTATTTGTATATGCTACGCCAA

TCCTTGTTGGGTTTCATTCTTTATAATTGTTATTTTTAAAGATTTTTCTTATGAATATTC

TATTGTTTCATTGTAGAAAATTTAAGGGAGAACACAGTGGGAAAAAAAAAAACAAGAAAAG

GACTTCATAATCCTGCTACCCTGGGAGAAAAAAAAAAATCACCATTACCTATTTGGTTCTT

CTCCCACTTTTTTTTTTTTCGAGATGGAGTCTCCCTTTGTTACCCAGGCTGGAGGGCAGG

GACGTGATCTTGGCTCTCTGCAACCTCTGCCTCCTGGGTTCAAGCGATTCTCGTGCCTCA

GCCTCCCGAGTATCTGGGATTACAGGGGTGTGCCATCACACCTGGCTAATTTTTGTATTT

TTAGTAGAGACGGGGTTTTGTCATGTTGGCCAGGCTGGTTTGTTGGCCATGTCTGGTTTT

TTGTCATATTGGCCAGTCTGTTTGTCATGTCAGGCTGACATGTTTTGTCATGTTGGCCAG

GCTGGTCTTTAACTCCTGACTTCAGGTAATCCTGAAGTGCTAGGATTATAGGCGTGAGCC

ATTGCACCTGGCCTTCTGCCTTTTTTTTAAAGAAAAAAAATTAAAACATTTTTTTCTTTT

TAAGATAGCGTCTCATTTTGTTGCCCAGGCTGGTCTTGAACTCCTGGGCTCAAGTGATCC

TCCAGCCTCAGCCTCTGGAGTAGCTGGGACTACAGATGCACATCATGGTGTCCTTATGCC

ATTTCTTTTGTACGTAGGTGAATGCAAGTGTATGATTACATCATATGCTATTTTGGAGGT

TTGACTTTCTTTTCACTTTCATCATCTTTCCAAGGTGTTATTTTCCTAGTACATCTTTTT

AAATGGACATAGAACATTCTTTTGTATGAACAAACAATAGTTTTATTTAGGCGGTCCTTT

CCTGTTGGACATTTATATTATTTTCAGCATTTCTCCACAGTTGTTGCAGCATTCAGATGA

ACCTTCTTTTTTTTTTTTTTTTGAGACGGAGTCTCGCTCTTTCGCCCAGGCTGGAGTGCAG

TGGCACAATCTCTCCTCAAGTGATTCCTGTGTCACCCTCCCACGTAGCTGGGATTACAGG

TGCCCATGTCTGGCTAATTTTTGTGTTTTTGGTAGAGCTGTGGTTTTACCATGTTGGCCA

GGCTGGTTTCGAACTCCTGCCCTGAAGTGATCTGCCCACCTCAGCCTCCCAAAGTGTGGG

GATTACAGGTGTAAGCCATCACGCCTGACCCAGATGAACATTCTTGTAGCTATCGCACAC

AATTCTGAACATTTCCTAGGATGAATTCCTTAAAGAAGTAATGCTGATCCAGGCTTTTTT

CTTTTTCTGTGACTCTTTGACACGTAATAATATTGACTTTTCTTTCTTTCCAGACACTAC

AACAACAGGAGTGCAAACTTCTCTACAGCCGAAAAGAGGGTCAAAGGCAAGAAAACAAAA

ACAAAAATAGATATAAAAACATCCTGCCCTGTAAGTATCAATATTCCGCTCAGTAATAGT

CACTCTTGGAGATTTTGATTCCTAGCACCTCTGTACCTTTCCTCAGGGTCGTGTGCTCTT

GTTAGCACATCGGAGGCCTTAGCTTCTTTAATTGCAAGCAGTTTCCAAAATAATCAACCA

TGGTGGGTGTTGATGACTTCATTCACTGAGCTCCCGTGATGCTGATTACTGAGTAAAGTT

GCCACTAGGTGGCTTTGTCTGTGGTTGGTTCCTTCTGTTAATTAATTTTCTGTCTGCCCA

-continued

AGATAGATCATCTCAAGGCTTGGGATCTCTCAGTGTCAGGGACCTTAGGGTGCCAGATTT

GTGTCTTGACTCCTCCTCACTGGGCCTGTGAGTCCTGGGTAAGGCCTGCCTCCTTTCTGG

GACTCAGTTCCCTTAAGTGGGAAACAGACAAACACCTCCTGAGGGCTCCTAGAACTGTTC

TGCTTGCTGATCCCCTGAGCTCAAGTTACTGGAGAAAGGGTATATACCTAAACTGCTCAG

AAGAAGACTTTGTGGGCCGGGCGCAGTGGCTCACACCTGTAATCCCAGCACTTTCGGAGG

CCGAGGCAAGCGGATCACCTCTGATCAGGAGTTCAAGACCAGCCTGGCCAACATGGTGAA

ACCCCATCTCTACTAAAAATACAAAAATTAGCCATATGTGGTGGTGTGCGCCTGTAATCC

CAGCTACTCGGGAGGCTGAGGCGGGAAATTGGTTGAACCCAGGAGATGGAGGTTGCAGTG

AGCCGAGATGTGCCATTGCACTCCAGCCTGGGTGACAAGAGCAAAACTCCGTCTCAAAAA

AAAAAAAGGAAGACTTTGTGAATATTCGCAAAGCTGTAAAGCTGTACCTTTCAATTTTTT

TTTGAGACATAGTCTCACTCTGTTGCTCAGGGTGCAGTCACAGCTCACTGTAGCCTCAAC

CTCCTGGGCTCAAGCGATTCTCCCACCTCAGCCTCCTGATTAGCTGGGACAATAGGCAGG

CACCAGTACACCTGGTTGATTTTACAGTTTTTCTGTAGGCCGGCGCAGTGGCTTACGCCT

GTAATCCCAGCACCCTGGGAGGCCGAGGTGGGCGGATCACCTGAGGTTAGGAGTTCGAGA

GTAGCCTGGCCAACATGGTGAAACCCCATCTCTATTAAAAATTACAAAAATTAGCTGGGC

GTGGTGGTGGATGCCTGTAATCCCAGCTACTTGGGAGGCTGAGGCTGAGGCAGGAGAATC

GCTTGAACCTGGGAGGCGGAGGTTGCAATGAGCCGGAGGTGCTATGTGCACCACTGCACT

CCAGGCTGGGCGACAGAGTGAGACTCTGTCTCAAAACAAAAAACGATTTAAAAAATAATA

AAATTTTTTCTAGGGCGGGGTCTCCCTATGTTGCCCAGGCTGGTCTTGAACTCCTGGGCT

CAAGTAGTCCTCCTGCCTCAGCCTCCCAAACTGTTGGGATTACCAGTGCAAGCCATTGTG

CCTGGCTGTACCTTCTGTAACACCCAAATGCCACCTGGCAAAGCCCAAGTTGAATCATGA

GGAAAAAAGGCCTGGAAGGATGTAGACCTTCCTTTTTTCTACTTATTTATTTATTTATTT

TTGAGATAGGGTCTTACTCTGTTGCCCAGGCTGGAGTGCAGTGGCATGATCATGGGTCAC

TGCAGCCTCAACCTCCCGGGCTCAAGTGGTCCTTCCCACCCCAGCCTGCAATGTAGCTGG

GACTACAGGCATGTGCTACCATGCCCAGCTAATTTTTGTATTTTTTGTAATTATTTTTTT

TGTAGAGACAGGGTTTCGTCATGTTGCCTAGGCTGGTCTCGAATTCCTGGGCTCAAACGA

TCTGCCTGCATCGGCCTCCCAAAGTGTTGGGATTACAGGTGTGAACCACTGTGTCTGGCT

ATATCTTCTGTAACACCCAAATGCCACCAGGCAAAGCCCAAGTTGAACCAGGAGGGAAAA

AGGCCTGGCAGGATGTAGGCCTTGCATGAGGATCTCAGAAACTGCACTAAACCAGTCACA

GTTCCTCTCTCCCGAGGTCTAACTCTATGCTGAACTCTTTGCATTTTTATCTCACTTAAT

CCATATCACATGCACAGGAAGGAAGCATTCGTAGTATCCTGGTTTCCTAGACCATTTTAG

CAAGGTTATAAGTGAAGGGGAGTGGGTGGGAGAACTGGCACTAGAGCCCCCAAAGTCACT

GTTCTTAGCACCACTCTAATGCATGGGGTTCTCCATTGATGTGCTATGCAAGGCAGTGCA

CTGAGGAGAAAGGAAGGAACATTTACAACTTCTCTTTATTTATATCCTGTCCCTAAAAAA

AAAAGAAAAAGAAAAATTTGTCTGAGGCCTAGATTGATTGCAGGGAGTGCATAATGTTTT

ATTGATTGATTGATTGATTGTATATAGAGATGGGGGGTCTCACTATATTGCCCAGGCTGA

TCTCGAACTCCTAGGCTCAAGCAATCCTCCTGCTTTGGCTTCCCAAAGTGCTGGGATTAC

AGGCATGAGCGACTGCACCTGGCTATGCATACTATATTTATCCAACTTACAAATAAGGCT

TGCTTGCCTGTAGTGCATATGTGTATACATTTCAGCATAGAAAAACTGTGTGATTGGGGG

TTGTGATCAAATTTGGAGAGCATTGCTCTCATGTCTTATCAGGTCAGAGTCATTTTGTCA

AATCTTGTAAACCATTCTTTGTGTGTGTCTATGCATGAAACATAGTCTTTCTCTTTCTGC

-continued

ATGCATATGTACATATACATGGTATATATGTATATCATATCTACATGGATATTGTAATGT

ATATGTATGAGGATGGGGGAAAGTGGAGACATTTGTAATACTGAGAAAAGGCAGTGAGGA

ATTTGCAGAGAAGCAGTTTGAGCTGTAGCATGGTACTAGTGACCTTGAGGAAGCCTTATC

CTTTTTTTTTGGAATTTATTTTTTCAATTTTTAGAAATAGACAAGAGTTTCTCTATGTTG

CCCAGGCTGGTCTTGACCTCCTGGGCCCAAACTATCCTCCTGCCTTGGCTTCCCAAAGTG

CCAGGATTACAGGTGTGGACCACCATGCCTGGCCACCTTGTCCTTTCTATGTCTAAGTTG

TGACATCTGCTCAGGGGTCAGGTGGTATTAAATGGTATAAAATGTATGGGAAAGTGAAGG

GATCAATGGTATGCAGTATCTAAATAGAATATCGCTTTTTCCTCCCTTAAAGGTCTCATT

CAGATGTTTCCTCTGATGAACATCTCATTTCCTTAAAGATGAGGAGTCTGAAGCAAAAAA

GACATTATTCTTTTAAGACACATGGCTGTCTTACTAATTCCCATTGCAAAATATGTTGTT

TAGGTAGAGCACTCAGATTTTTATACGAATAATAGACTTTTGTACAGAATTTGGACAGTT

GATACTATCAGAGCCTTGTGATATTCCACTGCATTATGCTTCACTAAAAAATACCTGGCT

GGGTGCGGTGGCTCACAACTGTAATCCCAGCACTTTGGGAGGCTGAGGTGGGCAGATCAC

CTGAGGTCAGGAGTTCAAGATCAGCCTGGCTAACATGGCAAAACCCCATCTCTACTAAAA

ATACAAAAATTAGCCAGATGTGGTGGCACGCTCCTGTAATCCCAGTTACTCAGGAGGCTG

AGGTATGAGAATTGCTTGAGCCCAGGAGGCAGAGGTTGCAGAGAGCCGAGATAGTGCTAT

TGCACTCCAACCTGGGTGACAGAGGAAAACCCTGTCTCAAAAAATAAATTTAAAACAACA

ACAACAACAACAACAAAAACCCCTCTTTATTATGGAAATTTTCAAATATATTCAAGAGCA

TAAAGAACCCACATGTACCCATCACCCAGCTTCAACAATTATCAACTCATGCCCAGTCTT

GGTTTCATCTATACTCTGATCCACATCTCCTCTCTCCTTGAATTATTTTGAAGCCCATCT

CAGACATCATGTCATATATGTATACTTCAATCTTCTTTTTTTTTAAAACTCCCCCTCCCC

TTTTCTTTTTTCTTGAGACTGTGTCTCACTCTGTCATCCAGGCTGGAGTGATCTTGGCTC

ACTGCAATGTCCGCCTCTCGGGTTCAAGCGATTTTTGTACCTCAGCCTCCCTAGTAGCTA

GGATTACAGATGTGGACCAACATGCCTGGCTAATTTTTGTATTTTTAATAGAGACAGGGT

TTTGTCATGTTGGCCAGGCTGGTCTTGACCTCCTGACCTCATATGATCCACCTGCCTTGG

CCTCCCAAAGTGCTGAAATTATAGGCCACTGCGCCCAGCCCAAAATTTCTTGGTTTGAAA

TAATTTTGGAACTCATAAGAAGTTACACATATAGTAGAGAGAATTTTCTTGTACCTTCTC

TGAGCTTCCTATATACCCAATGATAACATCCTATATACCCATAGTATATGATCAAAACTA

GGAAATTGTGAAGATGGCATTTTGAGACATCAGGCAGTGTTCACGTTACTGTTTTGCTTA

CCTGGGCTTTAATTTTTATGTGTTTTTTTTTCAATCATTGAATGAACAAAACTTGGACTA

GGCTGGGGAGTAACTGATTTGAACTGTTTTTTCCTGAAGCAGTCCAGGACTTATGTGACC

GTGGTCTCTTTTTCTTCTAGTTGATCATACCAGGGTTGTCCTACACGATGGTGATCCCAA

TGAGCCTGTTTCAGATTACATCAATGCAAATATCATCATGGTAAGCTTTGCTTTTCACAG

TGTTTTCTGACCATACATTTCTAGCCTATTTTTGTATTTTAAATCCTTCCTCATGTCCTG

AAAGTAACTTTAAGGTGTTTGAAGGATTTTCTTCCTAAATTTCTAGCCTGAATTTGAAAC

CAAGTGCAACAATTCAAAGCCCAAAAAGAGTTACATTGCCACACAAGGCTGCCTGCAAAA

CACGGTGAATGACTTTTGGCGGATGGTGTTCCAAGAAAACTCCCGAGTGATTGTCATGAC

AACGAAAGAAGTGGAGAGAGGAAAGGTAAATCACAGAAACTTCTTTTCTGCTAAACTGTT

TTTAAAGTATCAGACATGTCAGATTGGCCATGTTTAGGAATTGAATAAATGAATTAAGCT

-continued

TACTGTAACTGATTCTCTGGAAAAAAGGGACTAGGAGAAATTTGATTATGTTATTCCTTG

GTGTAGTTTTCTTTATGTTTCTTCTGCTTGGGATTTGTTGAGCTTCTTGGCTCCATGGAT

TTGTAGTTTTCCTTAAATTTGGATAATGTTCAGTCTTAGTTTCTTCAGATACATATCCTG

GGCTGGGCATGGTGGCTCATGCCTGTAGTCCCAGCACTGTGGGGTGTTGAGGTGGGCGGA

TCACTTGAGGTCAGGAGTTTGAGACCAGCCTGGGCAATGTAGTAAGACCCCATCTCTTAA

AAAAAAAAAATGTACCCTGCACAACCTTGTCCTAGGACAGCAGTCATACGTGTATTAGAC

TACTTGAAGTTGTCTCATAGCCCACTGATACTTGGTTTATTTTATTCAGTTTTTTCTCCC

CGTGTTTCATTTCGAATAGCTTCTTTTGCTATGTCTCCAAGTTAATCTTCTGCAATATGT

CATCCGCTCTTAATCCTATCCAGAGTATTTTTCATCACAGACATTGTATTTTTCATCTCT

AGAAGTGTTAATGTCATCTATAGCTTTCCTTTTAACATGTGTAGCATTTTCCTTACCTTT

TGAATGTATGGAGTATTTCTGTTGTTGTTTTTTGTTTTGTAGAGACAGGGTCTCGGTCTG

TTGCCCAGGCCGGAGTGCAGTGGCATGATCTCAGCTCACTGCAGCCTCTGCCTCCCGGTT

CAAATGATTCTCATGCCTCAGCCTCCCAAGTAGCTGGGACTACAGGTGCGTGCCACCACG

CCTGGCTAATTTTTGTATTTTTAGTAGAGATGGGGTTTTGCCATGTTGGCCAGGCTGGTT

TTGGAACCCCTGAGCTTAGGTGATCCACCTTCCTTGACCTCCCAAAGTGTTGGGATTATA

GGTGTGAGCCACCATGCCTGGCCATGTTGTCTGTTTTAATTAACTCTGCCTAACTGTCCT

CCCAAATGGTTGCTGCAGTGCTCACTCCCACCAGCAGCACCTGCCTAGGACTCATTACTC

CATACTCTTCAAGACACTTCAGATTAAAAAAATAAATTGTAACACCCCACACCTACAGAA

GAGCGGACAGATCTTATTGAGTGACAGCCCTCTGTGTTATCTCAAAGTGAGCCCACCATG

GTGGTTTTTTTTTTAAATATGGAAAAGTTCTGTGTTTTTGTTTGTGTTCTAGTGAAAGTT

CTTTTTTAGATATCCTTTAATTGGTTTATATAAGATTTTATGTGGAATGTAGCAGTCATA

CCTATAAATTAAACCTAAGGCAGATGGAGAACTTTGGAGTTGAGCCTTCCTACTGTAATT

TTCATATTGGATGTGAAGGGCAGTGTGATTTTCATAAGACTTTCATTGTTGTACTCCTAG

TTGGTATACTTCTGAATACCTTTGAGGCCAGTTCTGGTCATCGTGAAACAAAGGTTTCCT

TCAGCAAATGCCTGTGGTAACATTAGGTGTTCTTGAATTAATGGACCAATGAAAACATCT

TTGTAGTTTCTGCTTCAGGCAAGGGTTTTTTGCCCTAAATGTGGATAGGAAGAATGAAGC

CCTTCATCCTCCTTTTTGCCTGATTATAGCTATAGGAGGTTCACCTGTTCTCAGAAGACA

TGAGGATTGTGAAGAGAGGGGTCTTGTGTTGCTTCAGAGGAATCAGTATCAGTCCCTTTC

AGAAGCTCTCCTGGATAGACAGGCATTAGGGCCAAATCACTCTGCCCCACCCCTCACCAC

CATGTCCTACTCTCTGCTCCCTGTCTCATTCTTCCTCTTTACTTTGGTGGTGCCGAGAGG

ATGACATGATGGGTATTGATTCTCTCCACAGACCTTTCTGACATCCTACTTTCAGTATCC

CCCCAGTGCACAGAAGACAAGCCAGACTGTGGACTGTGTTTGATTCCTGGGCTCTATTTT

AAAAGACAGTGTATTAGTTCTCACATTTTAGAATTTGTTTGCCAAGGTTTCCACGGGAGT

TTAGAAACTAGGGGGGAGGGCTGATGTTTAAAGTTAGCTAAAATGTTCTTTTCAGGGTCAT

GATTTAATTTTATATTCTCTGGTGAGTTCCCTATAGTGACTGGGAGCAGTCCTCAGTCTT

GATTGGCCAGTGACAGCATAGAGTACAATTAATATTAGGAGTGCTCATTTGGGGAAACTA

AAATTTGCATCAAATCTGTCAGAGGTGTTTGGATCTACAAAATACCGGAGGGAAAGCTGA

ATTGAGAATCATAATAAATAAAAGACCACATCGTTCTTTTTTTTTTTTTTTTTTGGGACT

GTATCTTGCTCTGTCACTCAGGCTGCAGTGCAGTGGCACTATCTTGGATCACTGCAGGCT

CCGCCTCCCGGATTCAAGCGATTTTCCTGCCTCAGTGCCTGAGTAGCTGGGATTACAGGC

GTGTGCCACTACACCTGGCTAATTTTTGTAATTTTAGTAGAGACAGGTTTCACCATGTTG

-continued

GCCAGGCTGGTCTCAAACTCCTGGCCTCAAGTGATCCACCCGGCTTCCCAAAGTGCTGGG

ATTACAGGCGTGAGCCACTGCGCCCAACCAAGACCACATCCTTTTATTGAACGTTCCTCC

TACCATGTTTTCTTTTTTCTTTCAATTAATCATTGACTCATTGACTCTCACTGTTGATGT

CTGTAGCTGCTCTCTTATTTCCAGTTTTATAGCTGTAAATTTCTCTGTCTTCCTAAGATA

CAAGGTAAATTTCTCTTGCTGATATTGGTGGTTTTGGAAAGTGAGTGGTGTGGATGACTG

CCCAGAAAACAACAGAACACAAAAGCATTCTCTGCCCAGAACACATCACCAAATAGATAC

AAACTCATCTCTTACTGAGTGAAATAGCTTCCTTTTTGGCAGCAAGAATGATTTTCTTGG

TGCCATATTTTTCAATCCGCCTGCTCTTGAAGCCAGCAGCTATTGCAGACTTGGCATTCC

CAGGCACCCAGTTAAGGGAAAGTGACGTGTAGAGGAGGTATCAGATGGGTCTGGATATAG

AAAAAGCAGCTGGTTCAAAACCCCATGGGCTGCCTTTCTGTGATAGAGTTATTCACACTT

GGGTTAGATAAGGCACAGAGTCCTCCTACACTGGTGCGGAAATGAAACAGACAGTCTGGC

TCGTTGGGCAGCCTAGCCTCCTCCAGAATCTGTGCTTGCCTTCCCTATGGAGTGACTGGT

AGATCTTAGAATTCAGACCTCAGTGGTTGCTAGCCAGCACTCTCACATTGGTTGGTCCTT

CTCTCTGCATCTTTGATTCTTTAGAGATAGATAAACCAAGCACCGACTCTCCTTTGACAT

GTGCTTGGAACAGACACCTGCACGAGCTGCCTTTCTCCTCCCACTTCTGCCTGGTCTTCC

AAACACCTGCTTTTCTTGTTTGAACTCTTCCTTTTTTTTTGAGACAGAACCTCTCTCTGT

CACCCAGGCTGGAGTGCAGTGGCATGATCTCAGCTCACTGCAACCTCTGCCTCCCAGGTT

CAAATAATTCTCCTGCCTCAGCCTCCCAAGTAGCTGGGATTACAGGTGCCTGCTATCACG

CCTGGCTAATTTTTGTATTTTTAGTAGAGACACGGTTTCACCATTTGGCCAGGTTGGTCT

CAAACCTCTGGTCTCAAGTGATCTGCCCGCCTCGGCCACCCGAACTGCTGGGATTACAGG

CATGAGCCACTGCGCCCCAGCTGATTCTTTACAGATAAACAAACATTGACTCTGCTTTGA

CATGTGCTTGGATCAGGTAACTGCACCAGCTGCCTTTCTCCTCCCACTTCTGCCTGGTCC

TCCGAATGCCTGCTTTTCTTATTTGAACTCTTCTGTCCTTTTCTGAAAACCTAACAGATG

CGAAACAGGCCATTTTCCATGTTGGTGGTTATTAAGCAAGACTTGAACATTTGTTTGTTG

CTTGTTTAGGCTTTTATTTCAGAGTTCACAGAATTAACTTTCTTTTTTTCTGATCTCTTC

CAGAGTAAATGTGTCAAATACTGGCCTGATGAGTATGCTCTAAAAGAATATGGCGTCATG

CGTGTTAGGAACGTCAAAGAAAGCGCCGCTCATGACTATACGCTAAGAGAACTTAAACTT

TCAAAGGTTGGACAAGTAAGTATATTGTCGTATTCTAGAGACTTTGGGAACTGTTGATGG

TGTGTAGGAATTCAGGGTCTTGCCGTTACTCATGTTTGCATACATGCATGCATTCGCTCA

CTCATTGATTCAGTAGCCATTTATTAGCTTCCTTCTATGTGCCAGGTACAGTTTAAGCAG

TACTGGTACATTGTGAACAAGGCAGGTAGTGTTCCTGCCCTCATCGAGCCTAGGGAGATA

GACAATTTAAAAACAAATAACTGGCCAGGCGCCGTGGCTCAGGCCTGTAATCCCAGCACT

TTGGGAGGCTGAGGTGGGTGGATCGCTTGAGCCGGGGAGTTCGAGACCAGCCCTGGGTGG

GAGACTGGGATAGGGTGACCTGAGTGGCTACAAGGTCTGTTAGGAGGCCTCCGCAGGGGC

CTATGTTGATGGCCTCCTCTCCAAGTATCCACAGACTTCAGCAGTTGTTCTTTTTTGTTC

CTTCCTTTGGAATGGAATATTATATAAAATGGCAGAATAAACTGGAAGAGAAGCAGTAGA

TGTGAGAGGTGCCGGGGGGTGAAGTCTGCAGGATGTGGGGATTGTTTGGCTTTTGGAGGA

GGAAGGAGGGATTCAAGACACATTGTAGAGGTTTGAGTCTGAGCGGACAGTGGTGCTGTG

GCAGACACCACAAAAGCTGGAAGGAGAACTGATGTGGGCAGTGATTTGTTTTCTTCTGGA

TGTGTTCAGCTGGGCATCTGAACAGTCATGTGGACATTCATCTATTCATTCAGAGATATT

-continued

TGTTCAATGACCTCTTGGTTCCTGGCACCATGCTGCTTGCTGGAGATAGAGCTGGGGAAC

AAAACAGATGGAATCCCTGCACTCCCAAGTGTACACTATACTGGCCAGTAATCTACCAGC

CCAGTAATTGCACATATAAATATATCATTATAAACTGTAATCAGGGCTAGAAAGAAAAAA

TGCAGGAGTTTAGGGTTCATTTGGAGGGGGAAGGGACTTTTTTTTTTTTTTTTTGAAAC

AGAATCTTGTTCTGTCACCCAGACTGGAGTGCACTGGTGCATTCACGGCTCACTGCAGCC

ACAACCTCCTAAGCTCAAGTGATCCTCTCACCTCAGCCTCCCATGTAGCTGGGGGCTACA

GGTGTGTGCCACCATGCCCACCCAATTGTTAAATTTTTTATAGAGACGGTTGTCTCATTA

TGTTGCCCAGGCTGGTCTTGAACTCCTGGGCTTAAGCGATCCTGCTGCCACATGCAGCCT

CCCAAGGTGCTGGAATTACAGGCGTGAGCCAGCGCACCCGGCCAAGGGAGGGGAGGTTCT

TAAGGCATAGGGAACAATGTGTTTGAGTCAGCAAAGGAGGTTGTGGGGGTTTGTCCTAAG

TGTGGTAAGCAGCCAGAGTTGGATTTAAGTTTTTAAGAGATTCCCCTCCACCCTGTAGAG

ACTGGAGGGGGCAGGAGTTGTTCTAGGGATTAGGACCAATTTGGAGGTAGTGCAGCCGTC

AGAGTAAAAAATAATAGGGATTGAACTAGGCCAGTGCCCAGGGTGCCTGAAAGAAGAGGA

CCCAGTAGAGCTGACTGGAGGCAGACATGCAGGGATTCAGTGAAGGAGTGTACCAAGGGC

GAGGGTGGTGTGCAGGGTGACTGGCAATTTTCTAGCTTGAGAAAGGTCCGGGGGGATGGC

AGTGGAGTTGAGGAAGCTGGGAGGATCAAGGACCTTTTTGTGAACACACAAAGTTTGAGA

TGCCTTGGACACATTGAAGTGGAGCGGTCAGGGAGGCAAGGGTGGAGGTGGGATGCGGAG

GGGAGGTGGGATGCAGAGCGTCGTGGATGGATCAGTTTTGCTCGATAGAGGGACATGTTT

TTCTGTGGCAACAGGAGGGCAAAAGGAGAAGGTGGCCACAGATGCCGGTAGATGAGCTGA

GAGTGATTGTATTCCCTATCCTCTCGGAAGCTTGAGGCAAGGCCATCAACAGACAATCAG

AGGGAATAAGAAGAGATAGAATATATGAAGAAAGGGAGAAAAGATGAAATCGTAATTGTG

TAGCAGGGCAAGAAGTCCAGAAATTTCTGTGCTGTGCCAAGTTCCCAGTTGAGGCGGTGA

ACATGAAAATATACTGATACCCATTGCCTGGTTTTTCTCCAAGGACACTTGGCTCCTAGG

GCACAAAACAGAAAGTACGTGGTTTGTCCAGGCCGAGGGCTTTGCATAGTTGCAGTGGAT

GGAGAGGAGGTCAAGGAATGGAGGCACATGGTAGAGAGAGACTGTCCCCAGAGCACGGGG

ACTCCTGGCCGGATGAGGGGGACAGGGGCAGGAGGAGGCAGGTGGAAAGTAGAGGGAGGG

CTCAGTGGTCTGGAGGCTACAGGAAGTGACGGGGGGACCAGAAGGAGCTGGAAACCAGTG

TGGTTGTGGCCCAGGGTGGGATGTTTGGATTTCTGATGTCAGAGAGGGTCCAGTCCTTCT

GATGATGGGGAGGGGTGGAGGCTGAATCTATGGTAGAGATAGTGAGAGGAACTGGAACAA

TGTAGCTGTCAAGTGGAAATGGGAGAAAGGGCTGGGCGTGGTGGCTCACGCCTGTAATCC

CAGCATATTGGGAGGCTGAGGCAAGAGGATCGTGTTAGCTCAGGAGTTCTGGGCTGCATT

GAGCTGTGATTGTGCCACTGCACTCCAGCCTTGGCAACAGAGTGCCCAGTTAAAAATAAA

AATAAAATAAAATAAAAAAATTAAAAAAAAAAGAAGAAGAAAAAAGAGAAAAGTGTCCTT

TTACATCCCTTTTAAAAATGTCACTTAAGGCTGGGCAAAGTGGCTCATGCCTGTAATCCC

TGCACTTTGGGAGGCTGAAGTGGGTGGATTACTTGAGGTCAGGAGTACAAGACCAGCCTG

GCCAACATGGCGAAACTCCTTCTCTACTAAAATTAGCTGGATGTGGTACATGCCTGTAGT

CCCAGCTACTCGGGAGTCGAGTCTGAGGCCCAAGAATTGCTTGAATCGGGGAGGCGTAGG

TTGCAGTGAGCTGTGATCAGGTCACTGTGCACCAGCCTGGATGACAGAGTGAGACTCTGT

CTCAAAAAAAAAAGTCACTTAGCTTAGATTGTCTCTACATATATAGGAAGAAGATGTAGG

AATGAATGGTGCTGCTACAATTACGTCATCTGGATAGACCCAGAAACATGATACTTTTG

-continued

GTTTTCTGTAGCCTTGGTGCCATTGTTGATCTTTATTAATTATCATTATCCTCAAAATAG

CCATAATGTGCTGAGTCTCTTCCTATTTGCTGGGCAGAGGCTGAGTATTTCAGCGAGCTC

ACTGAGTCCTTAAAATTGCATTATGATAGAGAGAAAGAGATTATTATTTGCATTTTGCAA

AATGAAGAAATTGAGGTTTAGAGATACCCAAGGGCCACGTGAGTGTGAGTGCCTGGAATT

GGAGCCTAAATCTAGTCATCTGATAGCAAAGCCTGTTTTCTTATCTGCTTTGCATTAAAT

ATAAGTTTAAAATAGAACAATACTGGCCAGGCTGGGTGGCTCACGCCTGTAATCCCAGCA

CTTTGGGAGGTCGAGGCAGGCAGATCACCTGAGGTCAGGAGTTTGCAACCAGCCTGGCCA

ATATGGCGAAAGAAACCCCATCGCTACTAAAAATACAAAAATTAGCCAGGCATGGTGATG

TGTGCCTGTAATCCCAGCTACTTGGGAGGCTGAGGCAGGAGAATGGCTTGAACCCGGGAG

GCAGAGGTTGCAGTGAGCCAAGATCACGCCACTGCACTCCAGCCTGGGCAACAGAGTAAG

ACTCTGTCTTGGAAAAAAAAAAAAAAAAAGAATGATACTATAGTCTGTGTTTATATGGTGG

GGAAGGTTGAGTATCAAAAAAATAACAAAGAGGAATGAATGTCTTAAGTGAATGCCTGTT

TCCCCATCTGCTTCCTCTTCTGCTGGGAGGAGAGACCTGGATCCCTAGAGGTTTCAGTTG

CCTCCAGAGCTGAGTGCCACAGGGATGCAGGGGAATAGGGATGTTACCTGTCGCTGGTAA

TTCAGAGAGATGATTCAGGGTATAGTTACCTGAAAGAACAAATTGCCATGCCAGACGTCT

TGGTTCTTATGACAGAGGCAAAGAGTTGCCTCCAGGATTGCCCAAAAGGAGACGAGTTCT

GGGAACCTCACGAAGAGGACCTTTCAGTGGAACCTGGGGAGATTCTCTTCCTCTCCATTG

GATTTAGGAAAGCTTAGAACCGGGTGATTCCTCAACCTCTTGATTTATTTAATTCTTTTC

TGGTTTTTCTTGGCTCTACTCCAGGGGAATACGGAGAGAACGGTCTGGCAATACCACTTT

CGGACCTGGCCGGACCACGGCGTGCCCAGCGACCCTGGGGGCGTGCTGGACTTCCTGGAG

GAGGTGCACCATAAGCAGGAGAGCATCATGGATGCAGGGCCCGGTCGTGGTGCACTGCAGG

TGACAGCTCCTGCTGCCCCTCTAGGCCACAGCCTGTCCCTGTCTCCTAGCGCCCAGGGCT

TGCTTTTTACCTACCCACTCCTAGCTCTTTAACTGTAGGAAGAATTTAATATCTGTTTGAG

GCATAGAGCAACTGCATTGAGGGACATTTTGATCCCAAGGCATATTTCTCCTAGACCCTA

CAGCACTGCCATTGGCCATGGCCATGGCAACATGCTCAGTTAAAACAGCAAAGACTAAGT

CAGCATTATCTCTGAGTCCACCAGAAGTTGTGCATTAAACAACTTCATCCTGGCTCTGCA

GTTTCTCCTTATTCTTCATGATGTTTGCTTTGTAGCTGTTGACTGCTTTGTAGGTATTGA

GGTGGTGGGGGTGTGGTGGAAATAGGCCTGACTCTTGAGGATCCCTTAAGTCATTTTTGC

TTGGTTCTCTTTTTCCTTCTTTTCTTCTACTCTTCTATGATTCATCTCTTTGATTGTGAT

TCTGTTCTCTCTCTCTCTCTCTCTTTTTTTTTTTTCGTTTTTGAGACAGAGTCTTGTTTT

GTTGCCCAGGCTAGAGTGCAGTGGTGCCATCTTGGCTCACTGCAACCTCCGCCTCCCGGG

TTCAGGCCATTCTCCTGCCTCAGCCTCCCAAGTAGCTGGGATTACAGGCATCTGACACTA

CGCCCGGCTAATTTTTGTATTTTAATAGAGACAAGGTTTTGTCATGTTGGCCAGGCTGGT

CTCGAACCCTTGACCTCAGGTGATCCACCTGCCTTGTCCTTCCAAAGTGCTGGGATTACA

GGTATGAGCTACCATGCCCGGCCCATTCTGTTCTCTTCTACCATAAATATATTTCTCCCC

TAACACTATATTTGTTTGCTTCACAAGATTCCAGCTGCTTTTCCACCAAGGCCTTTGATG

GAAGCTGTGCTGTGACCTCTGTAATGAGTCTGTGGGCTGCTGATTCTCCAGTTTGGGCTT

CATGATTATACTGGGGAATATTGGGTTTCCTAAATCTCATTCATTTCTTGGGCAAGTAGA

TATATGTGAAAGTGTTTATTTGTCCAGTTGTTAAAGAAGCTACCATTTATTGAGCCAGCC

TCTGAGCACAATGTTTTTTGTTTTGTTTTGTTTTTAATTTTTAAAATTATTTACTTCTTC

-continued

TATTTCAATAACTTTATTATTATTATTTTTTGAGACAGAGTCTCACTCTGTCACCCAGGC

TAGAGTGCAATTGAGCGATCTTAGCTCACTGCAACCTCTGCTTTCTGGGTTCAAGCAATT

CTCATGTCTCAGCCTCCCGAGTAGCTGGGATTACTGGTACGTGACAACATGCCTGGCTAA

TTTTTGTGTTTTTAGTAGAGACGAGGTTTTGCTATGTTGGCCAGGCTGGTCTGGAACTCC

TGGCCCCAAGTGATCCTCCTGCCTCGGCCTCCCAAAGTGCTGGTATTATAGGTGAGAGCC

ACTGCGCCCGGCCCTCTTTCAGTAATTTTGATGTATTTTTTTGTATATGATTCCTGTTTC

ATTCTGTCCAACCAGCACTCTGTATGGTATGTGCTGTTGTCCCCATTTCACAGATGCAGA

AATTAAGGGTCAGAGAGGTTAAGGGACTTACCTCAGGCACGTTGTACTGGAGAAGCTGAA

CTCCAAGAGCAGGTTTGGGCTGACTCCAAAGCCCTATGCTTTTTGCCAACATATTTTCAA

ACATAAATAGACAATTTTATAAATAGCTCCAAAGAGTAGACATTGTTTCTGTTGATATTA

ATGGCTTGGTTTTGAGTCTGAAACCCCCATGAATGATTCTGTTGTCCCTGCTTTTTGTCC

TTCTGCCCGCAGTGCTGGAATTGGCCGGACAGGGACGTTCATTGTGATTGATATTCTTAT

TGACATCATCAGAGAGAAAGGTGGGTCATCTGGTGGGCAAGAAGCGACAGTTTCTGTTTT

TAGTTTATGGAAGGAAAGTGCTCACGAAAACAGTCTGGGGAAGAGAGGTTGAATGGGAAA

ATTCTTTCACAAAAATCTGGGCTGAAGACTTCAGTGTGTCTGCCTGAGAACAGAAGTGAC

ACTATTTGAGCTTTTGGCATAAAATGAAGTCTAGGAGCTGCAGAACCCACTGCCATGGCC

TTTTGTTGCATACACAGTGGTGGTCTCTATCCAGCCACCTGACCTTGTTTACAGTATGGG

GTGATTTGTTGGCAAGTGAGGGAATCCTGACTTCTGCCACTTCGTTATTTATGTAGTCTT

CTGGGATCATTGGTATTGGTCAGAAGTTCAACACTGTAGCCATTGCAACATGCTCAGTTA

AAACAGCAAAGACTAAATTAGCATTGTCTCTGAGTCCACTAAAAGTTGTGCATTAAACAA

CTTCATCCTGGCTCTGCAGTTTCTCTTTATTCTTCATGATGTTTCCTTCGTAGGTGTTGA

CTGCGATATTGACGTTCCCAAAACCATCCAGATGGTGCGGTCTCAGAGGTCAGGGATGGT

CCAGACAGAAGCACAGTACCGATTTATCTATATGGCGGTCCAGCATTATATTGAAACACT

ACAGCGCAGGATTGAAGAAGAGCAGGTACCAGCCTGAGGGCTGGCATGCGGATTCTCATT

CTCTTGCTAGGCCTCTTGGATACGCTCTCCTTTTGAGCAGGAGGACAGGCTCTGATAGAC

AACTGTTTGATTTCGGAATGGGAAACAAACTCCCAACTAAAAGGGCCTCTGGAAACTGTC

AATTATTCTCCACTTCTCAGCTCTGATTTTTCACTGCAGAGGAGCTTAGGGAAGGGCACC

ATCCTATCAGCCTGGCCTGCCAGATTGAAGAACTGCCATGCAGAAAGGTTCTGATGTTCT

CAGGCTCATGTGGCAAGCGTAAAACTCAAAGCCTTGAAGTTTCTAGCCTGTTCCAGCCTT

GATCCAGGCCATGTTTATCCTGATTCCATCCTTTAAAACGAATGCCTCACTCTTAATAGC

GCACGGCAGTTTGAACCACTAATTTGGTCGAGTTGGAAACAGTGAAATTTCAATTTTAAT

AAGCTGTGCATAATGAAGAGGAATGTGGAATTGGAGCCTTTCCATCTGAAGCTATTCATA

ACAGGCACAAAGCTGAGTTAATTAGGAATATGCTGAGATGAAGGAAATGAGGAGAGCTGC

TCTTTTGGGGGCTGTGCTTCTCTCCCCAACCCCTCAACCCCATTGCCATGCTGCAGATGG

GGTGGTGTCTAAACATCAGTGGCGAGTGCCTGCATTACTCTGCTCGTTGCCTTCCAGAGA

ACTCAGCTTCTCCAAATGCTGAGCTCTTTTCAGAATGGGACCTGCCACCAGTATTTGAAA

GATTTCTAGCCTAGCAGAACAGCAGCCACGTTATCAAAGTTTGGTTGGCCAAAGGAAGGT

ACTTGCTAATTAGTTTAGTAGGTTTTCAGTCCGCACAGACATACGGGATTGTTTTATTGT

ACATAGACATCTTCAGAAACAGTGTATGTATAGAAATGTAAGGTCAAAATTTGAACCTCA

-continued

GTGCTTTAAATCTGAATTTGTATTAACTGATATGAAATATTTAGACGGTTACTTTATTTT

ATATCTGTCTTCCATTATACTTAATTTGGCTCAAGAATAGTTAGGCAAAAAGTTGCCCAA

AGAGAAGGATCTCCTAGTAAATACAAAGAGAATGTAACATAGTTGCTACAAGTTGGAGCA

TGTTCAGGGATGTCTTTTTTTTTTTTTTTTTTTGAGAGAGAGGTCTCTCTCTGTTGCCCA

GGCTGGAGTGCAGTGGTGTAATCATGGCTCACTGCAGCCTCAATCTCCCAGGCTTAAGCG

ATCCTCCCACCTCAGCCTCCCAAGTAGCTGGGACTATAGGCATGCGCCACCACACCTAGC

TAATTTTCGCATTTTTTGTAGTGTCACAGTTTCGCCATGTTGCCCAGGCTAGTCTCGAAT

TCCTAGGCTCAAGCAGTGCTTCTGCCTCAGCCTCTCTGAGTAGTTAGGACTACAAATTTG

TGGCTCCATGCCCGGCTAATTTTTTTATCTTTATTTTGTAGAGACAAGGTCTCACTGTGT

TGCCCAGGCTAGTCTTGAACTCCTGGGCTCAAACAACCCTCCCACTTTGGGTTTCCAAAG

TGCTGGGATTACAAGTGTGAGCCACTGAGCCCAGTGACCTCTGGGTTTTAAAAATGTGTA

GGCTTCAATTATTTATTTTAAAAAATGAAATCCTGCAATATATAGTTTTCTGCGTTGTGT

GGTTTGAATCAATCTGGGAACTGGCTTGCTGGCTGATTGTGGTAAAGTAAGAAGTACTTA

ATTTAGTAGAAAGTTTAAATGGCAGACATAACATTAAACCCAGCTGATTTATAAATGAAG

CAAAAGAACAAAACTCATTCAGGATAATTGGTTATTCTAAAATACAGTCATTTCTAAAAT

TATGAAGTGTTCAGGACCTTTGGGAGTGAAAGAATTTGCTAAAGAAGGATCAGTGAAAAA

AAGGAATGATGGGTGAAGAGCTGTGGAGAAGGAAGAGAAGAAACAGCACAAGGAAGGAAG

AATATAAAATCAGATGTGGGAATCCAGGGGAAAGTGCAAACGAAGCAAGATTGAGAAAAT

TCTCAAGTTTTTATAAACAGTTCTCACACTCTGCCAGTTCCTTGGAGGTAGACTTTTTTG

TTAACTTCCAACTACAGTAGTGAAAAAAAAAAAAAAACCCTCAAATTTGCAAAAGCAGTC

TGTGGAATTTTCTTTACCCAGCTTTCCTGACTGTTAACTTTTTAGCACACTTAACTTTAT

CATTCGTTTATTCTCTCTGTTTAAAATTAAAAATGTAAATTTTAAAAAGTAAAATGTTTG

TTGGTTACAAACATTTATACCCCTTTGTCTCTAAATATCATTTCATTTTAAAAAATGAAT

AATCTAAGCCTACACATTCTAAAATGTGTATATTTTCTAAAAATAAGGGCATTCTCTTAC

ATAACCAATGTCACAATTATTTGATACAGTGATCAAAATCAGGAAACTAACATTGATATA

ACACTATTATCTAACCTACAGACCATCTTCAAATTTTGTCCTGCTAGTATCTTTTATGGG

TCCAGGGTCACACAGTGCATTTGGCTATAATGTATCTTTTTTCTCTTTTTTTGAGACAGG

GTCTCACTTTGTTGCCCAGGTTGGAGTGCAGTGGTGCAATTATGGCTCACGGCAGCCTTG

ACCTCCTTGGGCTCAGGTGATCCTCCCACCTCAGCCTCTCGAGTAGCTGGAGACCACAGG

TGTGCACCACCATGCCTGGCTAAGTTTTGTATTTTTTGTAGAGATGGAGCTTCGCCGTGT

TGCCCCGGCTGGCCTTGAACTCCTGGGCTCAAGTGACCCTCCCGCCTTGGCCTCCCAAAG

TGCTGGGATTACAGGCGTGAGTCACCACACCTGGCCAGTTATTAGTATGTTTAGTCTCTT

TAATCTGGAACAGTTTCTCAGTCATTCTTTATTTTTCATGACCTGGATGTTTTTGAAGAG

TTTAGGCCAGCTATTTAGCAGAATGCCTTTCAGTTTGGATTTGTCCAGTGTTTTCTCTTG

ACTATATTCTAGTCATGCATTTTTTGGCAGGACTGTCACAGAAATGTTGTTGTAGTCTTCT

TAGTACATCACATCAGGTACACACTGTTGATCTGATTCATTACTAGTGGTGTTAACTTTG

ATCACTTGAATAAGGTGGTGTCTGTCAAATTTGTCCACCGTAAAGTTACTTGAGCAAAAC

GTAGCTGGGACTACAGGCGTAGCAAAAAAATGTAGCAAAAAGTAGTATTTTTGCTACATTT

TTTTTTTAGGAACAAAGTATTTTTCCCTTTTAAGTTAATCTCTTGTCCATAAAGTTATTA

TTTTTCCCTTTTAAGTTAATATCTTGTGGGTAGATACTGGAGACTGCGTAAATTACCTAT

TTCTCATAATACTTTTTTTTTTTTTGAGATGGAGTCTCGCACCGTCTCCCAGGCTGGAGT

-continued

GCAGTGGTGCAATCTCGGGTCACTGCAAGCTCCACCTCCCGGGTTGACGCCATTCTCCTG

CCTCAGCCTCCCAAGTAGTTGGGACTACAGGCGCCCGCCATCACACCTGGCTAATTTTTT

GTATTTTTAGTAGAGACGGGGTCTCACCGTGTTAGCCAGGATGGTCTTGATCTCCTGACC

TTGTGATCTGCCCGCCTTGGCCTCCCAAAGTGCTGGGATTACAGATGTGAGTCACTGCGC

CCGGCTCTCATAATACTTTTTGCCTACTAATTTTATATTCATTGATTAAATTCTTGCCTG

AAAAAATTATTACTGTGGTATTTGCCAAATGGCAATTTTCTGTTTCCATCATTGCCTTTC

CCCCGCTTTTAAAAGTATAAGTGACAAAGAAAAACTGTATATAAAGTGTACACCATGATA

TTTTGATATATGTATACTTTGTGAAATGATTATCAAAATTGAGTTAAATAATGCATCCAA

CATCTCAGTTACTTTTTTTTTTTTTTGAGACAGAGTCTTGGTTTGTCACTAAGGCTGGAG

TGCAGTGCCACAATCTCGGCTCATTACAACCTCCACCTCCCAGGTTCAAGTGATTCTCCT

GCCTTGGCCTCCCCAGTAGCTGGGATTACAGGTGCCCACCATCACACCCGGCTAATTTTT

GTATTTTTAGTAGAGGTGGGGTTTCACTACGTTGGCCAGGCTGGTCTCGAACTCCTGACC

TCAAATGATCCTCCCGTCTCAGCTTTCCAAAGTGGTGGGATTACAGGCGTGAGCCACTGT

GCCCGGCCACTCTTAGTAAATTTTAAGTGTACATTTTTTTTTTTTTTTTTTTGAGATGGA

GTCTCACTTTGTCACCCTGGCTGGAGTGCAGTGGCATGATCTTGCCACACTGGAACCTCT

GCCTCCTGGGTTCATTCAGGTGCTTCTCCCACCTCAGCCTCCCAAGTAGCTGAGACTACA

GGTACCCGCCACCATGCCTGGCTAATTATTGTATTTTTAGTAGAGATGGGGGTTCACCAT

GTTAGCCAGGCTGGCCTCAAACTCCTGACCTCAGGTGATCTACCCACCTCGGCCTCCCAA

AGTACTGAGATTACAGGCATGAGCCACCACACCCAGCCACATTACGTTAGTATTAACTAT

AATCACCATGCTGTACATTAGATCTCCAAAATGTATTCATCTTATGTAACTTCAAGTTTG

TACCCTTTGACCAAAGTCTCCTTGTTTTCCCTACCCCCAACCCCTGGTAATCACTGCTTT

AATCTCAGTTTTTATGAGTTTGACTGGTTTAGATTCCACATACAAATGAGATCAGGCAGT

GATGGTTTATTTCACTTAGCATAATGTCATCCATGTTCTTGCAAATGACAGGATTTTCTT

CTTTTTAAAACTAATATCCATGCTGGACACGGTGGCTCATGCCTGTAATCCCAGCACTTT

GGAAGGCTGAGGAGGGTGGATCACTTGAGGTCAGGAGTTCGAGACCAGCCTGGCCAACAT

GGTGAAACCCCATCTCTACCAAAAATATAAAAAATTAGCTGGATGTGGTGGCGCACACCT

GTGATCCCAGCTACTTGGGACACTGAGGCAGGAGGATCGCTTGAACCCGGGAGGCGGAGG

TTGCAGTGAGCCAAGATGGTGCCACTGCACTTTAGCCTGGATGTTGATGTTGTTCCACTT

GTTTATTTTTATTTTGTTCCCTGTGCTTTTGGTATCAAATCCTAAAAACCATTGCCATGA

CCATTGTCATGTTACTTTCCCCATATGCTTTCTTCTAGAACTTTTAAGGTTCATCATTCC

CTTTTCTGTTTTTAGTTGCAAGCCTACTATAAGGAAGGGCTTTTCTTTCTTCCTTATTTA

TTTATTCATGTCTATCAGAATGGGCACCTTACTACTATTTTTGTTGTTATTGCTTGAATT

GACTTGAATTTGGCTAGTGGAAACCTTTTCAGATCGGGTACTCTGTCCTTTTGATCTCTT

TCCATTTTCAAGCACTTCTTTAGACTTAAGATGGTCTAGGCTCATCTTCTCCTTTCCCAG

CCATTTTTCAAAGGAACCTGATTCCTTTTAGTGAAGAGCAGTATTTTGAAACCAAGATCT

GGGCACTGGGTCTACTTGTTTGTACTGGTACAGTGTTCTTTGAATTGCTAATTAGCTGAT

CAATTACTGCTCTATTTGAGTTCCCTCTTTCTAAAACCTCACATATGTGTACAGACGGTC

CCTGACTTATGATGGTTCGACTTATGATTTTTGATTTTATGATGGTTTGAGAGCAATACA

TCCATTCTGTTTTTCACTTTTCATTCAACACTTTATTTTAAAATAGGGATTGTGAGATGA

TATTGCCCACGTGTAGGCTAATGTAAGTGTTCTGAGCACGTTTAAAGTAGGCTAGGCTAA

-continued

GCTGTGGTGTTTGGTAGGTTAGATATGTTAAATGCATTTTCGACTAGTGATATTTTCAAC

TTATGATGAGTTTATTGGGATGTATCCCCATAAAGTCGAGGAGCATTATACATATCTCTG

TATAACAGAGTGAGTTCCTTATACCTTTCATCCACTTTCCCCTGAAGTTAACATTTTACC

TAACCATGATACATTTATCAAAACTAAAACATTAACATCAATACATTGCTATTAACTAAA

CTAGAGTTTAATTGGATTTTGCCAGTTTTCCAATGAATATCCTTTTTCTGTTCCTTGATC

CAATTCATGGTCACACACTGAGTTTGGTCACTTGTCACTGTAGTCTTCTCCAATCTGCGA

CAGCTTCTTAGGCTTTCCTTGTTTTTCATGTACTCTTGACGATTTTTAAGAGTACTGGTC

AGATATCTTGTAGGATATCCCACAACTTGTGTTTAATCTTATGTTTTCTCATGATTAGAC

TTGAGTAATGGATTTTTGGGAAGAATACCACAGAGGTATATTGTTAAGTGTTCTCATCAC

TTGGAGGTAAATGTTATCAACATGGCCTGGTGATGTTAAACTTGTCAGTTTGTTTAGTTA

GTATCTGCCAGATTTTTCTCACTGCATAATTACAAATCCTCCTTAACTTATGATGGGGTT

ACAGCCTGATAAGCCCATCATAAATTGAAAATATCATAAGTCAAAAATGCATTTAAGCA

TCTAAACTACTAAACATCACAGCTTAGCCTAGCCTGCCTTGAACGTATTCAGGACACTTA

CATTAGCCTACAGTTGGGCAAAATCATCTCATGGGAAGCCTGTTTTATAATGTGTTGCAT

ATCTTATGTAATGTGTTGAGTACTGTACTCAGAATGAAAAACAGAAGGGTTGTATTGCTT

TTGCACCATCATAAAATCAAAAAAACCATAAGGCAAACCATCATGAAGTTGGGGACTGCC

TGTACTTTTTTCCTCTTTCCCTGTTCAATTCCTTGGAAGAAAGTCATTTAGTTCAGACCA

TACTCAAGAAAAGGGAAATAAAGCTCCATCTCTTGGAGCTTAATTGAAACTGGAATGACT

AGTTTCTATATACATTATTTAGAATCCTTTTGTAAGAAAGATTTGTTCCTTCTCTCCATT

TATTTATTCCATTATTTATATTGATAGAGACGCATGTACATTTATTTTATACTTTGGGTT

ATAATCTATTTTTCTTGCTCAAATTGTTACAGCTTTGGTCACTGGGAGGTTCTTCAGATT

GGCTCCTGTGTCATTTGACATGTCCCCACCCTCTCGTTTCTGAGTACTTCTCTACTTTGG

CATTACAAAAGATGTTCCAGGCTCCTCTTATATTTTTCCCTGCCGCAGCCCTAGAATCAT

CCATTTTTCTATGGTGCCCTGGTTCCTTTTACTTTAGATGGGGGTTTAGAAACCAATCTG

GGTGTTGGGTGTGCTCATTGCTACTGGAATCACTGCTTCTAGGCCCTCTCAGCAGATAGA

GCTAGAAAACATATGGCTGTATATGAATCCATGGATTCATATATATCTATAATTGTTTTC

TGTATCTGGCCATCTATATATATATTAAGCTAAACATGAATTCATACTGATGTCTCAGAC

TCGAATCCATTGCCGCAGGGCTCATTCTTGCCTTCCTCTTGCTTATTTGTGACTTCTTTC

TCTAACAGGGAGAAACCCCAGTCTCATTATCACCAACCTATCTACTCATTTGTTCAACCC

TGGTATAGGTGTAAAGTAGTTTCAGAATTACTAACCTATACCCATGTGAGAATTGTATTT

GCACTTCTTGTTTGAAGGAAATACATACAACACAGGTAGCGTCTCTACACTTCAGTATAC

AGAGATCTGAACAGTGTTCTCTCTGAGTGAATCATATTGCAGGACAGAAATTACTTTTAA

AAATTCTGTAATGGGTCAGGCCTATAATCCTAGCACTTTGGGAGGCTGAGGTGGGCAGAT

CACCTGAGGTCAGGAGTTCGAGACCAGCCTGGCCAAAATGGTAAAACCCCATCTCTACAA

AAAATACAAAAATTAGCCAGGCGTAGTGGTGTGTGCCTGTAATCCCAGCTACTCAGGAGG

CTGAGGCACGAGAATCACTTGAACCTGGGAGGCAGAGCTTGCAGTGAGCTGAGATTGAGC

CACTGCACTCCAGTCTGGGCGACAGAGCGAGACTCTGTCTCAAAAAAAAAAAAAAAAAAA

AATTCCATAATGATAGCAGAGCTGGAATAGAAATGGGATTGCACAGGCTGAATCTGAGTT

GTTGCAACAGTAAACGAGCAAGATTTAAACTGGCCTTGTGTAGCACTTGCTATTTGGCTC

CTCATATTTTATTAGACGCTTATTCTTTTTTGTTTGGTGTCATTCCTTTGAGAAATATTT

GAGTGCCTTTTCTGTTGCAGACATTGATTAGATGCTGAGGTTGTAACAATGAAGAAGATA

-continued

GCCATCGCTGTTGCCTCATGGAACTGAAGTTTTACTAGATGTAAAATTTGAGTTAACATG

AGGCCGTGCCCCTATGTGCCCTATTGTTTCTTCACACAGCTCCCTTCATCTCCTTGGTCC

AATGAAAAGGTTTTTTCATACTTGTTCATTCATTCCTGCATTAATTAAAGTAGGTTGTAC

TGTGCCAGGCACTGGGAATATTTAAGTAGTTGTGTTCCTGAATTGGAAATGAATCCAGCA

TGGTTGGAGTAGAAGGAGCTGGGGGGCAATGTGGAGTGTGATGGGGAGATTGGAAAAGTA

AGCTGAGACCAGATTTTTCAGTTTGGAGGGAGAGGTGGGCCTTGTAGGCCATATTACAGA

TTGTAGACTTTATTTGGAGGGACATGGAAGTCATTGAGGAGTCTGAAGCAGGGGAATGAC

ATAAAAAGATCCTCATTTTAGGCCGGATGTGGTGGCTCACGCCTGTAATCCCAGCACTTT

GGGAGGTTGAAGTGGGTGGATTGCTTGAGGCCAAGAGTTTGAGACTAGCCTGGGCAACAT

GGTGAAACCCTGTCTCTATCAAAAATACAAAAATTAGCTGGGCATGGTGGCTCACACCTG

TAGTCCCAGCTACTTGGGAGGCTGAGGCATGAGAATCGCTTGAACCCGGGAGGCAGAGAT

TGCAGTGAGCCGAGATTGTGCCACTGCATTCCAGCCTGGGTGACAGAGTGAGACTTCGTG

TCAAAAAAAAAACAAAAAACCCCTCATTTTGAAAGGGAACCCTGGCTTGAGGGTGAAGAA

TGGGTGGGCACTAGGCTAGAGCAGCTGCAGGGTCAGTGAGGAGCTGCCGCAGTGCTGCAC

GTGAGAACCCGTCATGGTTTGGTCAGGGTGGGCAGGACTGACAGTGAGCACAGAGCGAAG

TAAAACCAGCAAAATTTCATGATTGGATAGTGGAAGGAATCATGGTGTTTGTAGTCTTCA

AATGTGAACCCAGAGTGCACTGGACAAGTAGTCTAGGCTGCTCTGTAACCAAGGCAAGTG

TTTTCATTTTACCCTCTCTTCCTGCTCTTGGCCTTTGGATTTTTTGTAATTTAAGGTTTA

TGAATGTAATCAGTTACTTAACATGGAAAGATACTTAATACCAGATGATTTTGGAGTCTT

GTGATCAATACCTTCTCTCAATCTTGGGTGTGTGTCAGTTGGCAAGGCCATAAAATTTGT

TATAAACATTGCAGAAGGCTTGGTTACTGTGCTGTGACGTTGAATTTGGGTGGAGATAGA

TCAATTTCAGTTGATTTTCTAGGCTTCAGAAACACATTACCCTCTACTCCACAAACACAA

ATCAAAACAAAACAATCCCTATTCCCTGAGCATTTCTCTTGATCTATAACACAGCCTGGG

CTGTCACAGTACTAAGACAAGCCCATCTGATTTGTGAGTCAGTTTTATTTCTTGGTCTTC

TACATAAGCTAAAAAGTTTCAACATTTTAATGCTTTTCCTTGGATTCCTTTGAGTCATTG

AAGTAATTCCTGTTTCATTTGTACTAATTATTCCACACTAGAAAATTCTGTTGTAATCAC

TTTATGTATTAATAGAAATACTGATTTTTATTTTCAAGGAAGTATTGAGTAGGGAGGGGG

AAATAGGGATTTGCTGTTCAATGGGTATAGAGTTTCAGTAATACAAGACAAAAAACTTCA

GAGATCTTCTATACAGCAGTGGGTATATAGTTAACAATACTGCACATCTAACAGTTTGTT

AAGAGGGTAGATCTCATGTCATGTGTTTTTAAAAATTGCTTTTAAAAAAAGTATCGAGTA

AAAAAGCAGTTTTACTCCTCAGTTTCTATTTATATTTAAAATTTTTATTTAAAAAGTGAG

TTGAGATTTTTAAACCTCAGGATAAGTTTTATTTTTTAAAAAATTTATTTTTTTATTATTT

TTTGAGATGGAGTCTCACTCCATCTCAAGTCACCCAGGCTGGAGTGCAGTGGTGTCTTGG

CTCACTGCGACCTCTATCTCCCAGGTTCAAGTGTTTCTGCTGCTTCAGCCTCCTGAGTAG

CTGGGATTACAGGTCTGCACCACCACGCCTGGCTAATTTTTGTATTTTTAGTAGAGATGG

GGTGTCACCATGTTGGCCAGGTTTGTCTTGAACTCCTAACCTCAAGTGACCACCTGCCTT

GGCCTCTCAAAGTGCTGGGATTACAGGTATGAGCCACAGTGCCCGGCGGGATAAGTTTTA

AAATAATATTCTCTGCTGGCTGGGCATGGTGGCTCATGCCTGTAAACCCAGCACTTTGGG

AGGCTGAGGCAGGAGCATCACTCGAGGCCAAGAGTTTGAGACCAGTCTGGGCAACATAAT

GAGACCCCCTCTCTACAAAAAATAAAAAAAATTTGGCTGAGTGTGGCATGTTCCTGTAGC

-continued

```
TATCGGGAGGCTGAGATGGGAGGATTGCTTGAGCCCAGGAGTTTGAGGCTGCAGTGAGCT
ATGATTGCACCACTGCGCTCTAGTCTGGGTGACAGTGTGAGACCCTGTCTCTTAAAAAAA
AAAAAAAAAAAGGCCAGGCACAGTGGCTCAGGCCTGTAACCCCAGCACTTTGGGAGGCCG
AGGCGGGTGGATCACTTGAGGCCAGGAATTTGAGACCAGGCTGGCCAACATGATGAAACC
CCGTCTCTACTAAAAATACAAAAATAAGCTGGGTGTTGTGGTGCACACCTGTAATCCCAG
CTACTTGGGAGGCTGAGGGAGAGAATTGCTTGAACCTGGGAGGCAGAGGCTACAGTGAGC
CGAGATCACACCACTGCACTCCAGCCTGGGTGACAGAGCAAGACTCCATCTCAAAAACAA
CAACAACAAAAAAACCAAATGTTCTTGCCAATTCTTCCATTTAATATTTAATTTTGAATT
ATATTGTATCTTTCTAAGGATTGTTTCTTATATAAGCAAAGATTTTTCAGTGCTAAACAT
TTACGACTGCTATTCAGAAATGGTTATTTACAAGTCTTTTTGTTTTAAGAAAATGGCTGT
TCAAAAAATTAAAATAGTATATAAACCAAACAAAATATTTTTGCTTTGGATGTCTGTTTT
GCAGCTTCTTCCCTACACTATAAGTTCTTACTGACTGCTTTATCACTTAATAAATTGGTT
TGGCTACTTTAACAGAGGCAAATAGTATCAGGCAAAAAATTATTTTTTATTTTTATTTTT
TGAGACAGTCTCACTCCATCACCCAGGCTGCAGTGCAGTGGCCTGATCTTGGCTCACTGC
AACCTCCACCTCCCAGGTTCAAGCGATTCTCATGCCTCAGCCTCCTGAGTAGCTGGAATT
ATAGGCATGCACCACCACACTCAGCTAATTTTTGTATTTTTAGTAGAGACAGGGTTTTGC
CATGTTGACCAGGCTAGTCTTGAACTCCTGACCTCAAGTGATCCATCTGCTTTGGCCTCC
CAAAGTGCTGGGATAACAGGCATGAGCCACCATGCCCAGCCCTATTTTTTATTTTTTAGA
GATGGGTCTCGCTTTTTAGAGATGGGTCTTGTTGCCCAGGCCAGAGTGCAGTGGTGCGAT
CATAGCTTACTGCAGCCTTGAATTCCTGGGCTCAAGCAATTCTCCTGCCTCAGCCTCCCG
AGTAGCTGGGACTACAGGCCTGTGCCACCAGGCCTGGCTTGTACATTAGTATTTGATATG
GCTACCCTAAGGGCAATCCTATAGTGAAGTCAACATTAGATAATGATGCTCATCTGATGG
ATTAGATTTTCAGAGTTGGCTGTTTCCAGGTGCCTATAGGAGTAGAAAAGGGTGACAAAC
CTCCTAACTAGATGTCCTACCAAATATAGTTCACTCCACATCTGAGATGAGACTGCATGA
CTGCTGGTTTTCTTTGCCTTTTCCCCCCCAGGGTATCATCAGAACCAAAAATAAAGTTTT
AAAGGTGGGTCAGGTGTGTGTTGGCTCATGCCTGTAATCCTAGCACTTTGGGAGGCTGAG
GCAGGTGGATCATCTGAGCTCAGGAGTTCAAGACCAGCCTGGCTAATAACATGGTTAAGC
CCCATCTCTACTAAAATACAAAAAGTTAGCTGGGCATGGTGGTGGGCACCTGTAATCCCA
GCTACTCAGGAGGCTGAGGCATGAAAATCGCTTGAACCCCAGAGGCGGGGGTTGCAGTGA
GCCGAGATCATGCCACTGCACACTAGCCTGAACAACAGAGCAAGGCTCTGTCTCCAAACA
AACAAAAATGGTGCCAGAGTCTTTTCCAGGGCTGAGGGGAGATACAATGAAGTGTGTTAT
TTTTTCTGATAAGAGTGCTACCATCTTTCATTCTTGTGTGCCATTTCTAGTTGGGGTGAA
TTTGTTTTCGGAGTTCCTTTCCCAGCTGTTTGCCTGAAAAACCATGAAATGTGTTCCACA
TGAACTATGAAATGATTAGATGCTAATGTGGCAAAGAAAGTGTGAATTCTCTTGTAGAAA
CAGGGACATTTGGTTCGGTACAGTAAGTTGTTAATGCGTGACTCTGTGCTTTCAAATTCT
GTGGTTCAAAAGTACTTTTCACTCCTACTGTGTATTTACCTTGAGAAGGTGAATCCCCTA
ACAATTTGGTCAATGTATCAGTATTCTCAACCCGTCTATCAATTTTTTTTCTTTCTCCC
TCTTTTTTCTTTTTTTGGGCAAAATACCTTTTTTGCTTTTTATCCCCTTAAAATAACCAT
TGTCCCTCACATGTGCACTCTTCCAAATTTCAGAAAAGCAAGAGGAAAGGGCACGAATAT
ACAAATATTAAGTATTCTCTAGCGGACCAGACGAGTGGAGATCAGAGCCCTCTCCCGCCT
```

-continued

TGTACTCCAACGCCACCCTGTGCAGAGTAAGTAGTGCTGAAGGAAATTCTTTTTACCTGG

TCATGGTGGTTTAAAAAGGTTTAAAAAACAAAAACAAAAACAAAACACAAGTTTGTAGCA

CATGCCTTTCACTGGTGCACGTTCCTGTTGCCCTACTGTTAGTGTATCTGTGACTGGTGA

TATCTATTGATTGTGTTAATGCTATCTCAACCACGTTTTAATTTTCCTAAGCTGGCCAGG

CACGGTGGCTAACGCCTGTAATCCCAGTGCTTTGGGAGGCCGAGGTTCATGGATTACTTT

GAAGTCAGGAGTTCGAGACCAGCCTGGCCAACATGGTGAAACCCTGTCTCTACTAAAAAT

ACAAAAATTAGCCGGGCATGGTGGCGCATGCCTGTAATCCCAGCTACTCAGGAGGCTGAG

GCAGGAGAATCGCTTGAACCCAGGAAACGGATGTTGCAGTGAGCCGAGATCATGCCACTG

CACTCCAGCCTGGGCGATAGAGTGAGCCTCTGTCTAAAAATAAAATAAAATAAAATAAAT

TCCTAAACTGAAGGCTGACTGCTATGCTAGCTAGGATTATATGGGATTTTAAGTATATCA

AGTGGTGGTTCTCCAAGAAGAATCTAATTTTTCTTTTGATGGGCTGGGGATTGTAACAAA

GGAAGGTCATATGTCTTAATGATGTGTTAAGGCTCTTTGCAAAATCAAAGTAAATAAATT

GACCACTAATGTGTCAGCCCAGCCATGTTCTGCTCATTTGCCACCAGTCAACAGAAATCT

ACTTTGGGTGTTTAAACCAGGAGTCAGCAAACTACAGCTCACAAGGCCAGATGTGGGCCA

TGGCCTGTTACTGTATGGCCTGTTAATGGTTTTAAAGGGTTGTAAAACAAAAGAACACAA

AACAAAGACCCAATAACAAAACAAAGCCCGAAGAATAATATGCGACAGAGACCATGTATG

GCATATAGAGCCTAAAATACTGACTCTCAAGCCCTTCCCAGAAATCCTTCCCGACTCCTT

GTTGAAAACACGGTAGGAAAGCATTTGTCAAATTGAGGATATGAATAGCAATTGTAAGTT

ATTATTTTTCTATATATTCGAAAGTCACTTGCTAGTATAACATTTACCTTTTATTTTTCC

CTAAGAATCTTCTCTCTGTTTGCTTTCGACATGGATTTTTAAACCCCTGCAGATTTTAAT

ATTCTATATAAATGTTTTAGGTGGCATATATGAGGTTTGTATTAACATTTGCTTTCTATT

TAACATTGAAATGAAATTATACAGCAGAGGTATTTTCTCGTCCAAGTTGCCACTTCTTTC

TATCTTTTTTCTTTTCTTTCCCAGTGGACTGCCTGGGAAAATTGATATTTTAAATTGCTC

TCTGCAATAATTTGCAATGGAACTGGAATGCCAGGGTTCTGAGTCCTTGCCAGACAGCTC

GTCCCTCCTGTTGGCATGACTGAGTCAGCTGTCATGATTCCCTCAGTACCAGTGGCATGC

CTGTGACAGACAGCCTGTCTGCCTTTCATTCCCGTCGTCTCCCTTGTAGGGTTCAGATCC

AGGATACACTGGTCCTGGAGCCCCTCTCAGCCTGGCACCCACAGCTGCTGGGTTCCTTAC

TCTCCTGGACTGCTCTGATGTCATCTCCCTGCTCAGCAGAAAGAAGTCTGGGATCTTGAT

GCTTTGGCCCTCTGTCCTAGGCCCTAAACCACCCATTGCCCTTCACATAACCTGAGCTGG

GGCTAAATAGATCTCTCATCACTGCCTGCCTGCTCCTGTATTTTCCCTTCTTGGAGCTTT

TGCCTGTTCAGATCCCTCTACTGGAAATTAATAGGATTTCATTCTATGTGTGCATTTCCA

ACCTTTCTTCACAGTGCGATCCAAATGCCTCATCCTACAGGCCTCCTTAAAACAACCTGC

TTTCTGCCAGACCCCAGGGAGCACCAGGACTTGAGGCTTTTATTGCACTTCTGTTGTTTT

TTTGAGATGGAGTCTCGCTCTGTCGCCCAGGCTGGAGTGCAGTGGCACGATCTCTGCTCA

CTGCAACCTCCATCTCCCGAGTTCAAGAGATTCTTCTGCCTCAGCCTCTCAAGCAGCTGG

GACTACAGGCATGTGCCATGACACCCGGATAATTTTTGTATTTTTAGTAGAGACGGGGTT

CACCATATTGGCCAGGCTGGTCTCAAACTCCTGACCTCGTGATCCACCCACCTGGGCCTC

CCAAAGTTCTGGGATTACAGGCGTGAGCCACCATGCCCAGCGTTATTTCACTTCTGCCTC

TGTAATTATATTGCTGTATGGCTATCTCTTCTCTCCCTGGGAATGTCAGGTCCTAGGCAC

AGGAACTGTGTCTGTACCATATCTGGTGCCCAAAGAATGTAGTATGTGTTTTATAGATAT

-continued

CATGTAAGCTTAAACAGCGTGGTCTACATTTTTGTAAATGTCTTTCTTTTTCTTTTCTCT

CCAGAATGAGAGAAGACAGTGCTAGAGTCTATGAAAACGTGGGCCTGATGCAACAGCAGA

AAAGTTTCAGATGAGAAAACCTGCCAAAACTTCAGCACAGAAATAGGTATTTAAATGCAA

GTGCTCTATTGGTTAATTGTTTATATAATTGGCAGTATTTTTAAGCAGGCAAGCAATTTG

GGAATGTTTTAGCAAAGTGTACCATAATTGAGTTTTACAAACCAGGCTCCTTTTTCCTCT

CCCTGTACTTCTTTTTCCAAGATGGTTTTAGTTTAGAGTTCATTAAACATTAAAATCAAA

CACAGAATTAATTCTGCATGAGGCAAGGCTAGCACTTATTCCAGAGAAATGGCTGATACT

GGTGGTAGAGTGCAGGTATCACTGTTCCTGCAATTTTTATTAGAGTTGGTTAGCCCAGGC

TGTGCTGGGGGATGATCTGTAGGGATCTGGGAAGCATCGGGACTCAGCACTGGGTGGTTG

GGAGTCAGGAAGCCTGAGTTCTCATTTCAGTCAGTCTCTGACCAACTGTGTGGCATGGGG

TGCTAGACCACTTGGCTGCCGACTGGGTCACCGACATCCCTTCCAGCTCTGCTGCTGGAA

ATTCATCTCTCCCATATGTTGCCTCCCCATCAATTACGTTTTTTAAGTGTGACCCAAGTA

TATGATGTATGTTTTCATGATAAATTAGAAACTTATCTGGGCATGGTGGCTCATACCTGT

AATCCCAGCACTTTGGGAGGCTGAGGTGGGCGGATCACCTGAGGTCAGGAGTTCGAGACC

AGCCTGACCAACTAAAATAGTAGAGACCAACCCGTCTCTACTAAAAATAGAAAATTAGCT

GAGCATGGTGGTGCATGCCTATAATCCCAGCTACTCAGGAGGCTGAGGCAGGAGAGGCAG

CGGTTGCAGTGTGCCAAGATCGCGCCATTGCACTCCACCTGGGCCACAAGAGTGAAACTC

CATCTCAAAAAAAAAAAAAAAAAAAAAAAAAACTCAGTGTCAGTATTTCATGTCGAAATTC

CACTTCAATGGGTAGTGTAGTTAAAAGCTCTAAGTCTACCTTAAAATCACCTAATGCTTT

GTTAAGCTTTTAGATATATGTTCCTTAAAAACTCTTAACTTATTTCTTCCCCAGATGTGG

ACTTTCACCCTCTCCCTAAAAAGATCAAGAACAGACGCAAGAAAGTTTATGTGAAGACAG

AATTTGGATTTGGAAGGCTTGCAATGTGGTTGACTACCTTTTGATAAGCAAAATTTGAAA

CCATTTAAAGACCACTGTATTTTAACTCAACAATACCTGCTTCCCAATTACTCATTTCCT

CAGATAAGAAGAAATCATCTCTACAATGTAGACAACATTATATTTTATAGAATTTGTTTG

AAATTGAGGAAGCAGTTAAATTGTGCGCTGTATTTTGCAGATTATGGGGATTCAAATTCT

AGTAATAGGCTTTTTTATTTTTATTTTTATACCCTTAACCAGTTTAATTTTTTTTTTCCT

CATTGTTGGGGATGATGAGAAGAAATGATTTGGGAAAATTAAGTAACAACGACCTAGAAA

AGTGAGAACAATCTCATTTACCATCATGTATCCAGTAGTGGATAATTCATTTTGATGGCT

TCTATTTTTGGCCAATGAGAATTAAGCCAGTGCCTGAGACTGTCAGAAGTTGACCTTTG

CACTGGCATTAAAGAGTCATAGAAAAAGAATCATGGATATTTATGAATTAAGGTAAGAGG

TGTGGCTTTTTTTTTTTTTCTTTTTTTCCAGCCGTTGACCAATTATAGTTCGGCTGTTGACT

GAGAAGTTTGTGGTGGGAAAACGTTTGCCATATTTTCTTTGCATTTGAATAATTGTCTTG

TACTTAGAAAAAAGGCGTCTATGAATGACCAGTGTTTTTGGTCGCCAAATGTTGCTGACA

AACTTATCCCAAAACTTTAGTGGCTTAAAAAAACCTGCCCCCAACTGTTAGTCAATCTGA

GCTGGGCTCAGCTGGGCTGTTCTTCTGCCAGCCTGCAGGTGGCCACTCATGTGGTCAGCA

GGTCGGCGGAGAGACTGGGATGGCTGGGCTTCTCTCTCTGCCTGCAGTCCTGAGTCTCTC

CTTCTTCGTGTAGTCTCTTTCAGTGGCCTGGCTGGCAGGGTAGCTAGACCTCTCACATGC

-continued

AGCTCAGAGCTCCCAAGAGCTCAAAAGCAGAAATGGCCAGGCCTTCTGAAAACTTAAGTC

CAGAATTGTCACAGTGTCCCTTCTACTTCCCTCTATTGATGATGATGATGATGATGATGA

TGATGATGATGATGATGATGATGGTTTTTTCTAATCAGAAGAAAGCTGGGGTATGCCCTC

TACTTACTAAACAAGTCACAAGCCCAGCTCAGATTCAAGAAAAGGGTGTGAAGTAGAGGT

GCAGTTAAGTGGGGGGCCACTAGTCTAACAGACGGTCACAACCAGTGCCATGGAAAACCA

AGGATATTAGCAAAAGCAGAAGTTGCTAGTGACCTTGGGAAGCCGAAGCTGCTTACAGTA

GCTGGGACAAGCTGAAAGTCAGACTAAGAAATAAAGAGAGGGCCTTCAAGAAGCTTCCTG

AATGATTTCTGCTAGCCCTGAGCCTATTTTTGGAACCAGCACTTGGGGAAACTGATCTTG

TGAGGATGGATGTGTTTAGGGACACAGGGCTTTTGAGAGCAGCACCACCCCACTGGGGCA

TCCCCAGACTTGGGAAACGTGACTCTTTCTTAATGCCACTGGGTTTTAGTCAGGCCACAG

TGAGAAGGAACAGCCCTAACAGGCCTCCAGCCAGGTTGAATGAGCTCATTTTTGTTGTAG

CCAACCAGTAAGATTTGCTAATGTTCTACATTAAGTGCCTTCTCCAAAGACATCCCTCTT

TGCCTCATATGTTGAATCATCCAGTGCGGATATTTCAATGAAAATATCATTGGTTGACTT

TTGTGATGGTAATAATGCTATGGCATCTTTGCCATGAAGTTGTGGCCTCCTTGGATTCTT

CTGACTTTGGCTTCTGAAAGGAAGGCCTAGATCCAGCCCTGGTGGTAGTTCCTTTCTGAG

GTCTCTCAGTCCCTTGAGACTTTGGGGTAGTTTGGCTGCCATTCTCACTGACAAAATGTA

TATCAGCCCCCACCTCCACCCCCCAATATTCCTTGAACTTTGAATTGCTTCAGAACACAG

GTGTGGCCTGAAGGTATTCCCTTATTAGGGAAGTGTCACTGCTGTCTTCTAGTCAAACTT

GTAAAGAAAAAGATTCCAGTTCAGTATTTGCAGCAAGAAGCTTGAATGCTGTTCTTTTTA

TCGCATTGTTACATCGACTCATTCTCCATTTTGCTTTGGTTTTGTCTTGACTTGACTTGA

CTTTGGGGGTAAAGTCTTTCACCAGCACACAAGAGTTTGATTGTACAAATATATCTTCTG

CATTAACATCTCTGCCTGTTGCTTAAGATCAGTTGCTTTTATACTCAGAATGGAAATACC

TGATCTTGGCTAGTTTTGTTATAAGATATTGATTTCATTTAGATTTCCCTCCACGAGGTC

AGCAAACTATCATGTTCTTATGTAAACTTAGGCCAAGGCCAGAGTTATCATAGTCCCTAG

GTTGCTACGGCTTATCATGTGCTTGGTAAAAGGTGATCGCAGGTTCTCAGACGAGTTTAC

TTTACATGAGATGGAATCAGGCAGAGAGGCTGGGATGATGGAGAAAGCTCGAGGTGAAGT

TTTAAAAAAAAAGTTGTGGAAAGGAAAGTTCCAAAGAGGTGGTTTCTGAGGAAGTCAGAG

CGCCCAGGGCCAGAGCAGTCAGTAATGGGTGAATGAGGTTGTTTGGAAAGTCGGTGTGAC

AGACACATGGATGCCATCTACTTCTAGGTTGCTGGTGGGTATTAAATATGCACAATATTC

CATAGCTCACTGAGGATTTTAAAATTATAAGCATAGGATTTTATATTTTGGGGTGAAAGA

ATTATCTGGCACATTAGGTATTGGAGTTTAAAAAAAAAGCCAAATTTCACAGTCTTAATA

ACTTTTTTTTAAAAAAAACTAAAAGGCGCTTCATGTCCAGTGTGTGGCCCTTCTGAAACTT

ATGGTCATCTCTCCCACTGAAACCAAGGTCTTTTCAAATGTGGCTAAATGGGGATGAGGA

GACACGGGTAGGACTTTCTTGGTGTGTGTGCATTCTTTAAAGAGCCAAGTTGCTTCGGGG

AAACAGCCAGGAAAATGGTCAAGATTATTTTTAGAGGTTATTTTATTGGGGATTTTAAGA

ACTAATAACATCTTGAGTTATTTTTAATTCAGGGGGATGTGGAAAGGTTTGCAATTGTCA

-continued

```
AGTGTTTTGTTGTAGCTTAGTATCCATAAGGGAAACTTAGACTATAGACATAACTACAAA

GCCAGTGCAGCTTTTGTTTTCTGTATGTTGTTGGGGGATCAACTTTCACACATAGCAAGC

ACATGGCCTCCCTGATGTCAGGATGCCTTTGTTAGGATCTGTATTTGCCCTTAATTTTGT

TGAAATCTTTTTCCTTCTTCCTCTTGAAAAGTTCCAAAATATAGTTTATTGTATCTTTC

ACAGTTGGTTTTAGTGTGTTGTATAACTTTGCTGTATATCAAACTAATTTTGACAAGTTT

TCATCCTAAGCCTCAAATCATGTAATTAATAATTTGCCTGTTTATTTATGACCTAATTGT

GATTCTTTTATTAATAAAAGCTAATGGGAAAAGGATCCCTGATTAAGCTGATGACTAGAC

CTACAATTAATTTTCCTGCAGTATATGAAGTATTGTACCAGAGTATTAAAAGATATGTAA

TATTTTATTGATAAATCTATCCTTTAAAAGGAATACGTTTTAGGATGTCATCATTTTGAT

GTGAATCATGTAAATGTTGATAATATGCTGTTTATTATACATTTAGTGTTTCAAGAGATT

CACTTAATTGCCTTTTTGCCCACGTATATTATGTAGTCTATTTGCAACTGTTCTTAAAAA

AATGACATTAAAAGAATAGTTTATGTAGAGAAACATTAGTGGATGTTAATTGTCTCCCCA

CCTATATTTATGGGTGTTAGCGCAACTGCTTTGCTAGTTGCAAAGCTGTATTATCAGAGT

AAAAGTGTATTTGTAAACTGTATGGGAACTAAAAATTAGGAATAAAACCATTTTCTTATA

TGATGGCATTTGTCGTTTGCTTCATCAGAAATGTCCAGGAAAAAAATGGGATTATTGGTC

ACTCCACCTCTCACACTGGCAAAATACTGACATTTAGCAGCTCTTATCTAGAAGTGACTT

GGAACATAGAATAAAGGCATGAGTTCCTGAAGAATTCATTGAGTGTTTCCTGTAGAAATA

GCTTTAGGAGATAGGGAGTTCTATCTGGGAGAACATATGAGTAACTCAAGAGTAAAAGT

ATAGTCTGTGTAAACTATAGAAGAAATGCTGGGCATGGTGGCGCGCCCCTGTAATCTCAG

CTACTTGGAGGCTGAGACGGGAGGATTCCTTGAACCCAGGAGCCCAGGAGTTTTAGACCA

GTCTGGGTAACATAGTGAGACCCTTTCTCACCTACTCTCACTGCATGCCCCCCAAAAATA

TATATGTGCGCGCACGCGCGCGCACACACACATACACACACACACACACACACACACACA

CAGAGGAAATTGTTAGAAAACACACAGAACTGAATGTAAATAGTATTAGGTGGGAATAAG

AAGTAAAGGGATGGTAAGGAGGCTTGGAGGAGGAGTAAATTATCTGCTATGGGACATCAG

CTC
```

FIG. 11 shows a SHP2 translated amino acid sequence (SEQ ID NO: 61). Alternating exons are underlined and non-underlined. Bold with italics indicate a residue overlap splice site.

Like reference symbols in the various drawings indicate like elements.

DETAILED DESCRIPTION OF THE INVENTION

Protein/nucleic acid complexes or assemblies are difficult to manipulate due to their fragility and requirement for structural integrity (e.g., 3-dimensional conformation. Genome editing technologies, such as clustered regularly interspaced short palindromic repeats (CRISPR)-Cas9, transcription activator-like effector nucleases (TALENS), and others, have shown much potential in their ability to change the genetic code of cells. However, their activity is highly dependent on structural and conformational integrity.

Zinc-finger nucleases (ZFNs) and transcription activator-like effector nucleases (TALENs) are examples of a class of gene editing tools. These chimeric nucleases are composed of programmable, sequence-specific DNA-binding modules linked to a nonspecific DNA cleavage domain. ZFNs and TALENs enable a broad range of genetic modifications by inducing DNA double-strand breaks that stimulate error-prone nonhomologous end joining or homology-directed repair at specific genomic locations (Gaj et al., 2013, Trends Biotechnol. 31(7):397-405; hereby incorporated by reference).

Numerous publications describe the use of viruses, mRNA and plasmids to code for the Cas9 and/or gRNA and/or donor oligonucleotides (where relevant). Compared to these methods, the methods and systems described herein utilize a different strategy—delivery of the protein itself, complexed with the guide RNA. This process is fundamentally different, because it does not require the cell to translate/transcribe anything for the editing to work. For that reason, and because the protein/guide complex has a short half-life, the approach of the invention results in faster and more efficient editing with fewer off-target effects. Other Approaches Such as Liposome Mediated Protein Delivery, Microinjection, and Cell-Penetrating Peptides (CPP).

One example of liposome mediated protein delivery uses GFP fused to Cas-9, has also been used (Zuris et al., 2015, Nature Biotechnology 33:73-80). The GFP is capable of complexing with conventional lipofection agents (e.g. lipofectamine) due to charge interactions and appears to mediate a gene editing response. The main advantages of the invention relative to this approach are: 1) does not require a fusion protein 2) does not require lipofection agents which can have toxicity, endosome escape problems, and issues/problems translating to primary cells.

Microinjection mediated complex delivery is characterized by extremely low throughput and can be difficult to implement for most mammalian cell types. The latter drawback is highlighted by the fact that the work was done with embryos, i.e., cells that are much larger than a fibroblast or a T cell (cells which are desirable target cells for gene editing endeavors). By enabling high throughput and translatability to smaller primary cells, e.g., fibroblasts, T cells, stem cells, the methods described herein have a big advantage.

A CPP-based strategy does not involve a complex. One example of such as strategy is described in Ramakrishna et al., 2014, Genome Res. 24(6):1020-7. CPP mediated delivery of individual components is also associated with drawbacks. Conjugating a CPP to the guide and Cas9 requires extra modification that may inhibit function, limit scalability. CPP mediated delivery is known to go through endocytosis and is inefficient or ineffective in many primary cells (particularly immune cells).

Target Cells and Payload Compositions

Any gene can be manipulated using the gene editing strategies described. Some target genes/proteins are particularly relevant in clinical disease and thus gene editing of such target genes/proteins is useful for therapy. Examples include C—C chemokine receptor type 5 (CCR5): prevent human immunodeficiency virus (HIV) infection; major histocompatibility complex class I (MHC-I): reduce graft vs. host disease; cluster of differentiation 1 (CD1): reduce graft vs. host disease; programmed cell death protein 1 (PD-1), programmed death-ligand 1 (PDL-1), Cytotoxic T-Lymphocyte-Associated Protein 4 (CTLA-4), interferon-regulatory factor (IRF) protein family, TLR protein family, pattern recognition receptors (PRRs): modulate immunity to enhance or dampen effector/antiviral responses; forkhead box P3 (FoxP3): eliminate Treg mediated tolerance; cluster of differentiation 80 (CD80), cluster of differentiation 86 (CD86) and other costimulatory molecules: knockout costimulation abilities to promote tolerance; T cell receptor (TCR), B-cell receptor (BCR): eliminate endogenous TCR or BCR to allow for engineering of T cells and B cells with desired specificity; oncogenes (e.g., Kras, Myc, Tp53): cancer therapy. In another example, targeting transcription factors is used to change cell fate, e.g., delete FoxP3 to remove Treg type function. Delete nuclear factor-kappa B (NF-kB), t-bet, Eomesodermin (Eomes), etc. to alter T cell differentiation.

A protein coding sequence for forkhead box P3 (FoxP3) is as follows:

(SEQ ID NO: 62)
```
ATGCCCAACCCCAGGCCTGGCAAGCCCTCGGCCCCTTCCTTGGCCCTTGG

CCCATCCCCAGGAGCCTCGCCCAGCTGGAGGGCTGCACCCAAAGCCTCAG

ACCTGCTGGGGGCCCGGGGCCCAGGGGGAACCTTCCAGGGCCGAGATCTT
```

-continued
```
CGAGGCGGGGCCCATGCCTCCTCTTCTTCCTTGAACCCCATGCCACCATC

GCAGCTGCAGCTGCCCACACTGCCCCTAGTCATGGTGGCACCCTCCGGGG

CACGGCTGGGCCCCTTGCCCCACTTACAGGCACTCCTCCAGGACAGGCCA

CATTTCATGCACCAGCTCTCAACGGTGGATGCCCACGCCCGGACCCCTGT

GCTGCAGGTGCACCCCCTGGAGAGCCCAGCCATGATCAGCCTCACACCAC

CCACCACCGCCACTGGGGTCTTCTCCCTCAAGGCCCGGCCTGGCCTCCCA

CCTGGGATCAACGTGGCCAGCCTGGAATGGGTGTCCAGGGAGCCGGCACT

GCTCTGCACCTTCCCAAATCCCAGTGCACCCAGGAAGGACAGCACCCTTT

CGGCTGTGCCCCAGAGCTCCTACCCACTGCTGGCAAATGGTGTCTGCAAG

TGGCCCGGATGTGAGAAGGTCTTCGAAGAGCCAGAGGACTTCCTCAAGCA

CTGCCAGGCGGACCATCTTCTGGATGAGAAGGGCAGGGCACAATGTCTCC

TCCAGAGAGAGATGGTACAGTCTCTGGAGCAGCAGCTGGTGCTGGAGAAG

GAGAAGCTGAGTGCCATGCAGGCCCACCTGGCTGGGAAAATGGCACTGAC

CAAGGCTTCATCTGTGGCATCATCCGACAAGGGCTCCTGCTGCATCGTAG

CTGCTGGCAGCCAAGGCCCTGTCGTCCCAGCCTGGTCTGGCCCCCGGGAG

GCCCCTGACAGCCTGTTTGCTGTCCGGAGGCACCTGTGGGGTAGCCATGG

AAACAGCACATTCCCAGAGTTCCTCCACAACATGGACTACTTCAAGTTCC

ACAACATGCGACCCCCTTTCACCTACGCCACGCTCATCCGCTGGGCCATC

CTGGAGGCTCCAGAGAAGCAGCGGACACTCAATGAGATCTACCACTGGTT

CACACGCATGTTTGCCTTCTTCAGAAACCATCCTGCCACCTGGAAGAACG

CCATCCGCCACAACCTGAGTCTGCACAAGTGCTTTGTGCGGGTGGAGAGC

GAGAAGGGGGCTGTGTGGACCGTGGATGAGCTGGAGTTCCGCAAGAAACG

GAGCCAGAGGCCCAGCAGGTGTTCCAACCCTACACCTGGCCCCTGA
```

Src homology region 2 domain-containing phosphatase-1 (SHP1) is also known as tyrosine-protein phosphatase non-receptor type 6 (PTPN6). A protein coding sequence for SHP1 is as follows:

(SEQ ID NO: 63)
```
ATGGTGAGGTGGTTTCACCGAGACCTCAGTGGGCTGGATGCAGAGACCCT

GCTCAAGGGCCGAGGTGTCCACGGTAGCTTCCTGGCTCGGCCCAGTCGCA

AGAACCAGGGTGACTTCTCGCTCTCCGTCAGGGTGGGGGATCAGGTGACC

CATATTCGGATCCAGAACTCAGGGGATTTCTATGACCTGTATGGAGGGGA

GAAGTTTGCGACTCTGACAGAGCTGGTGGAGTACTACACTCAGCAGCAGG

GTGTCCTGCAGGACCGCGACGGCACCATCATCCACCTCAAGTACCCGCTG

AACTGCTCCGATCCCACTAGTGAGAGGTGGTACCATGGCCACATGTCTGG

CGGGCAGGCAGAGACGCTGCTGCAGGCCAAGGGCGAGCCCTGGACGTTTC

TTGTGCGTGAGAGCCTCAGCCAGCCTGGAGACTTCGTGCTTTCTGTGCTC

AGTGACCAGCCCAAGGCTGGCCCAGGCTCCCCGCTCAGGGTCACCCACAT

CAAGGTCATGTGCGAGGGTGGACGCTACACAGTGGGTGGTTTGGAGACCT

TCGACAGCCTCACGGACCTGGTGGAGCATTTCAAGAAGACGGGGATTGAG

GAGGCCTCAGGCGCCTTTGTCTACCTGCGGCAGCCGTACTATGCCACGAG

GGTGAATGCGGCTGACATTGAGAACCGAGTGTTGGAACTGAACAAGAAGC
```

-continued

AGGAGTCCGAGGATACAGCCAAGGCTGGCTTCTGGGAGGAGTTTGAGAGT

TTGCAGAAGCAGGAGGTGAAGAACTTGCACCAGCGTCTGGAAGGGCAGCG

GCCAGAGAACAAGGGCAAGAACCGCTACAAGAACATTCTCCCCTTTGACC

ACAGCCGAGTGATCCTGCAGGGACGGGACAGTAACATCCCCGGGTCCGAC

TACATCAATGCCAACTACATCAAGAACCAGCTGCTAGGCCCTGATGAGAA

CGCTAAGACCTACATCGCCAGCCAGGGTTGTCTGGAGGCCACGGTCAATG

ACTTCTGGCAGATGGCGTGGCAGGAGAACAGCCGTGTCATCGTCATGACC

ACCCGAGAGGTGGAGAAAGGCCGGAACAAATGCGTCCCATACTGGCCCGA

GGTGGGCATGCAGCGTGCTTATGGGCCCTACTCTGTGACCAACTGCGGGG

AGCATGACACAACCGAATACAAACTCCGTACCTTACAGGTCTCCCCGCTG

GACAATGGAGACCTGATTCGGGAGATCTGGCATTACCAGTACCTGAGCTG

GCCCGACCATGGGGTCCCCAGTGAGCCTGGGGGTGTCCTCAGCTTCCTGG

ACCAGATCAACCAGCGGCAGGAAAGTCTGCCTCACGCAGGGCCCATCATC

GTGCACTGCAGCGCCGGCATCGGCCGCACAGGCACCATCATTGTCATCGA

CATGCTCATGGAGAACATCTCCACCAAGGGCCTGGACTGTGACATTGACA

TCCAGAAGACCATCCAGATGGTGCGGGCGCAGCGCTCGGGCATGGTGCAG

ACGGAGGCGCAGTACAAGTTCATCTACGTGGCCATCGCCCAGTTCATTGA

AACCACTAAGAAGAAGCTGGAGGTCCTGCAGTCGCAGAAGGGCCAGGAGT

CGGAGTACGGGAACATCACCTATCCCCCAGCCATGAAGAATGCCCATGCC

AAGGCCTCCCGCACCTCGTCCAAGAGCTTGGAGTCTAGTGCAGGGACCGT

GGCTGCGTCACCTGTGAGACGGGGTGGCCAGAGGGGACTGCCAGTGCCGG

GTCCCCCTGTGCTGTCTCCTGACCTGCACCAACTGCCTGTACTTGCCCCC

CTGCACCCGGCTGCAGACACAAGGAGGATGTGTATGAGAACCTGCACACT

AAGAACAAGAGGGAGGAGAAAGTGA

Src homology region 2 domain-containing phosphatase-1 (SHP2) is also known as tyrosine-protein phosphatase non-receptor type 11 (PTPN11). A protein coding sequence for SHP2 is as follows:

(SEQ ID NO: 64)

ATGACATCGCGGAGATGGTTTCACCCAAATATCACTGGTGTGGAGGCAGA

AAACCTACTGTTGACAAGAGGAGTTGATGGCAGTTTTTTGGCAAGGCCTA

GTAAAAGTAACCCTGGAGACTTCACACTTTCCGTTAGAAGAAATGGAGCT

GTCACCCACATCAAGATTCAGAACACTGGTGATTACTATGACCTGTATGG

AGGGGAGAAATTTGCCACTTTGGCTGAGTTGGTCCAGTATTACATGGAAC

ATCACGGGCAATTAAAAGAGAAGAATGGAGATGTCATTGAGCTTAAATAT

CCTCTGAACTGTGCAGATCCTACCTCTGAAAGGTGGTTTCATGGACATCT

CTCTGGGAAAGAAGCAGAGAAATTATTAACTGAAAAAGGAAAACATGGTA

GTTTTCTTGTACGAGAGAGCCAGAGCCACCCTGGAGATTTTGTTCTTTCT

GTGCGCACTGGTGATGACAAAGGGGAGAGCAATGACGGCAAGTCTAAAGT

GACCCATGTTATGATTCGCTGTCAGGAACTGAAATACGACGTTGGTGGAG

GAGAACGGTTTGATTCTTTGACAGATCTTGTGGAACATTATAAGAAGAAT

-continued

CCTATGGTGGAAACATTGGGTACAGTACTACAACTCAAGCAGCCCCTTAA

CACGACTCGTATAAATGCTGCTGAAATAGAAAGCAGAGTTCGAGAACTAA

GCAAATTAGCTGAGACCACAGATAAAGTCAAACAAGGCTTTTGGGAAGAA

TTTGAGACACTACAACAACAGGAGTGCAAACTTCTCTACAGCCGAAAAGA

GGGTCAAAGGCAAGAAAACAAAAACAAAAATAGATATAAAAACATCCTGC

CCTTTGATCATACCAGGGTTGTCCTACACGATGGTGATCCCAATGAGCCT

GTTTCAGATTACATCAATGCAAATATCATCATGCCTGAATTTGAAACCAA

GTGCAACAATTCAAAGCCCAAAAAGAGTTACATTGCCACACAAGGCTGCC

TGCAAAACACGGTGAATGACTTTTGGCGGATGGTGTTCCAAGAAAACTCC

CGAGTGATTGTCATGACAACGAAAGAAGTGGAGAGAGGAAAGAGTAAATG

TGTCAAATACTGGCCTGATGAGTATGCTCTAAAAGAATATGGCGTCATGC

GTGTTAGGAACGTCAAAGAAAGCGCCGCTCATGACTATACGCTAAGAGAA

CTTAAACTTTCAAAGGTTGGACAAGGGAATACGGAGAGAACGGTCTGGCA

ATACCACTTTCGGACCTGGCCGGACCACGGCGTGCCCAGCGACCCTGGGG

GCGTGCTGGACTTCCTGGAGGAGGTGCACCATAAGCAGGAGAGCATCATG

GATGCAGGGGCCGGTCGTGGTGCACTGCAGTGCTGGAATTGGCCGGACAGG

GACGTTCATTGTGATTGATATTCTTATTGACATCATCAGAGAGAAAGGTG

TTGACTGCGATATTGACGTTCCCAAAACCATCCAGATGGTGCGGTCTCAG

AGGTCAGGGATGGTCCAGACAGAAGCACAGTACCGATTTATCTATATGGC

GGTCCAGCATTATATTGAAACACTACAGCGCAGGATTGAAGAAGAGCAGA

AAAGCAAGAGGAAAGGGCACGAATATACAAATATTAAGTATTCTCTAGCG

GACCAGACGAGTGGAGATCAGAGCCCTCTCCCGCCTTGTACTCCAACGCC

ACCCTGTGCAGAAATGAGAGAAGACAGTGCTAGAGTCTATGAAAACGTGG

GCCTGATGCAACAGCAGAAAAGTTTCAGATGA

Other targets include areas of the genome that can have a plasmid or donor DNA inserted into them so that the target cell can express a new gene, e.g. a recombinant TCR, a recombinant BCR, Chimerica Antigen Receptor, fluorescent protein, reprogramming factors.

In some embodiments, a genomic sequence is edited in a coding region. In certain embodiments, a genomic sequence is edited in a non-coding region.

In various embodiments relating to FoxP3, a genetic region upstream of FoxP3 may be edited. In such embodiments a region where a transcriptional repressor of Foxp3 might bind is edited. For example a site about 0.5, 1, 1.5, 2, 2.5, 3, 3.5, 4, 4.5, 5, 0.5-2.5, or 0.5-5 kb upstream of the FoxP3 transcriptional start site may be edited.

Treating Subjects

Aspects of the present invention relate to editing the genomes of a plurality of a subject's cells. In various embodiments, cells are removed from a subject, receive a gene-editing complex using a method of the present subject matter, and then are reintroduced back into the subject. For example, mutant cells may be produced in a process involving delivery of a gene-editing complex as described herein. The mutant cells may be heterozygous or homozygous for a mutated allele a gene involved in a disease. In certain embodiments, the mutant cells are null for the gene involved in a disease.

Cells, such as stem cells (e.g. hematopoietic stem cells) from bone marrow, or circulating immune cells in whole blood, may be treated using methods and devices described herein. Cells may be genetically modified to reduce the expression of a receptor for a pathogen (such as a viral or bacterial pathogen) or a toxin (such as a microbial pathogen toxin). Since a gene-editing protein complex or components thereof may be directly introduced into target cells without the need for expression, no transgene delivery is necessary. This approach has important advantages over traditional gene-therapy approaches, which suffer from aberrant expression, insertion, and silencing, as well as variable delivery of transgene copy number.

In one embodiment, a gene-editing complex that targets the C—C chemokine receptor type 5 (CCR5) gene is introduced into a blood (such as a CD4+ T cell) or bone marrow cell (such as a hematopoietic stem cell) of a subject who is infected with human immunodeficiency virus (HIV). The gene-editing complex may be designed to mutate the CCR5 gene such that cells receiving the gene-editing complex no longer express CCR5 or express CCR5 at a reduced level. In one example, hematopoietic stem cells expressing a version of CCR5 that binds HIV (or that produce progeny that express the CCR5) are removed from the subject, modified to no longer express a version of CCR5 that binds HIV, and then are transplanted into the subject. In another example, CCR5-expressing CD4+ T cells of the subject receive a gene-editing complex using methods and devices described herein such that the CD4+ T cells no longer express a version of CCR5 that binds HIV. The modified CD4+ T cells are then returned into the subject. Such treatment of the CD4+ T cell may be performed in whole blood from the subject. In these and other embodiments, bone marrow cells or blood cells are modified to no longer express a version of C—X—C chemokine receptor type 4 (CXCR4) to which HIV binds. Similarly, cells of a subject may be modified to have reduced CCR5 expression to treat or prevent an infection associates with *Yersinia pestis* (bubonic plague) or *Variola major* (small pox).

Subjects, other than humans, containing cells modified by methods and devices disclosed herein are also provided. Such subjects include non-human vertebrate, amphibian, mammalian, and primate subjects. Non-limiting examples include *Danio* sp., *Fugu* sp., *Xenopus* sp., *Mus* sp., *Rattus* sp., and others.

Introducing Gene-Editing Proteins and Complexes into Cells

The delivery of pre-formed protein complexes allows for the study of cellular processes without genetic modification of the cells being studied. The present subject matter is useful for delivering protein complexes and gene editing complexes to cells, including CRISPR.

The advantages of delivering protein complexes using the methods and devices described herein include the controlled and temporary introduction of test agents for the study of cell and protein complex function. Since transgene expression and cellular assembly of complex components is not needed, the timing and ratios (protein:RNA) of complex function can be controlled. Additionally, the transient nature of delivery enables the observation of changes due to temporary function, rather than prolonged expression which may result in off-target or secondary effects. From an in vivo homing perspective and a gene expression format, microfluidic delivery has far fewer side effects (10-fold) on treated cells rather than electroporation.

For example, microfluidic delivery results in fewer aberrant and non-specific gene expression changes compared to electroporation. Additionally, the structural and functional integrity of microfluidically squeezed cells is preserved compared to electroporation-mediated cargo delivery. As an example, an increased number of T cells exposed to microfluidic delivery ex vivo (and then introduced into a subject in vivo) home to lymph nodes compared to T cells that have undergone electroporation. Cells (e.g., T cells) treated by electroporation and then administered into a subject are more likely to be cleared from the subject compared to cells treated by microfluidic delivery. Such clearance is related to altered/aberrant gene expression following electroporation that marks such cells for destruction or clearance by the body.

Target Cells and Payload Compositions

Any eukaryotic, e.g., mammalian such as human, cell can be processed using the microfluidic device to alter the cell membrane for introduction of protein/nucleic acid complexes or assemblies into the cytosol of the target cell. Exemplary target cells include Lymphocytes/Immune cells: DCs, B cells, T cells, Natural killer cells (NK cells), neutrophils, basophils, eosinophils, innate lymphoid cells, monocytes, macrophages, hematopoietic stem cells, common lymphoid progenitor cells; Stem cells: Embryonic, mesenchymal, induced pluripotent; Other primary cells: Fibroblasts, hepatocytes, cardiomyocytes, neurons, epithelial, epidermal, endothelial, pancreatic islet cells; as well as Cell lines, e.g., cell lines for disease studies: T cell clones, Jurkat cells, HeLa cells, Human Embryonic Kidney 293 (HEK293) cells, U2OS cells, Chinese Hamster Ovary (CHO) cells. Prokaryotic cells can also be processed. The dimensions of the constriction of the device are tailored depending on the cell type to be processed.

In some embodiments, the cell is a prokaryotic cell. In other embodiments, the cell is a eukaryotic cell. Non-limiting examples of eukaryotic cells include protozoan, algal, fungi, yeast, plant, animal, vertebrate, invertebrate, arthropod, mammalian, rodent, primate, and human cells. The cell may be a cell, e.g., of a unicellular organism or a multicellular organism. The cell may be, e.g., a primary eukaryotic cell or an immortalized eukaryotic cell. In some embodiments, the cell is a cancer cell. In certain embodiments, the cell is other than a human cell. For example, a composition for treating cancer and/or a method of treating cancer or preparing a composition for treating cancer, comprises treating immune cells using the gene-editing methods described herein to reduce the expression/production of immune suppressing signals from tumor cells. An example includes reduction or SHP-2 knockout for increasing immune activity towards tumors.

In various embodiments, a cell may be in a mixture of two or more cell types or a plurality of cells may be a mixture of two or more cell types. A mixture of cell types may be a co-culture of multiple cell types (such as two or more of those disclosed herein) or a mixture of cell types that naturally occur together, such as in whole blood.

In some embodiments, the cell is a peripheral blood mononuclear cell. In various embodiments, the cell suspension comprises a purified cell population. In certain embodiments, the cell is a primary cell or a cell line cell.

In some embodiments, the cell is a blood cell. In some embodiments, the blood cell is an immune cell. In some embodiments, the immune cell is a lymphocyte. In some embodiments, the immune cell is a T cell, B cell, natural killer (NK) cell, dendritic cell (DC), Natural killer T (NKT) cell, mast cell, monocyte, macrophage, basophil, eosinophil, or neutrophil. In some embodiments, the immune cell is an adaptive immune cell such as a T cell and B cell. In some embodiments, the immune cell is an innate immune cell. Exemplary innate immune cells include innate lymphoid cells (ILCs; ILC1, ILC2, ILC3), basophils, eosinophils, mast cells, NK cells, neutrophils, and monocytes. In some embodiments, the immune cell is a memory cell. In some embodiments, the immune cell is a primary human T cell. In some embodiments, the cell is a mouse, dog, cat, horse, rat, goat, monkey, or rabbit cell.

In some embodiments, the cell is a human cell. In some embodiments, the cell suspension comprises a cell other than a human cell or a non-mammalian cell. In some embodiments, the cell is a chicken, frog, insect, or nematode cell.

Any physiologically-compatible or cell-compatible buffer system can be used as a solution to bathe/incubate the cells and process the cells through the device. For example, phosphate buffered saline (PBS), Opti-MEM®, Roswell Park Memorial Institute (RPMI), Dulbecco's Modified Eagle's Medium (DMEM). A reduced serum or serum-free media or buffer composition is preferable. The buffer or medium is chosen based to maintain and preserve the health or viability of the target cell and/or the effect on gene expression. For example, in some cases the presence of calcium in the buffer is desirable to promote or support mRNA expression.

Payload compositions include a protein-nucleic acid complex or assembly. Exemplary complexes include components or modules of a gene editing system as described above, e.g., nuclease/guide nucleic acid combination or assembly. For example, gRNA:Cas9 molar ratio ranges from 1:100,000 to 100,000:1, e.g., a preferred range, 1:10 to 10:1, e.g., 1:1 or 1:2, 2:1. Complex concentration in the buffer to facilitate delivery (molar concentrations) typically ranges from 100 mM to 1 nM, e.g., 10 uM to 100 nM. Complexes can be mixed with cells before going through constriction or afterwards.

Microfluidic Delivery of Gene Editing Complexes

In order to effect gene editing manipulations, Cas protein (such as Cas9 protein), guide RNA and donor DNA can be delivered to a cell through mechanical deformation using, for example, a microfluidic platform (e.g., as described in U.S. Application Publication No. 20140287509, filed Apr. 17, 2014; PCT International Application No. PCT/US2014/051343 filed Aug. 15, 2014; PCT International Application No. PCT/US2015/060689 filed Nov. 13, 2015; and PCT International Application No. PCT/US2015/058489 filed Oct. 30, 2015, each of which is hereby incorporated by reference).

Figure 1B:
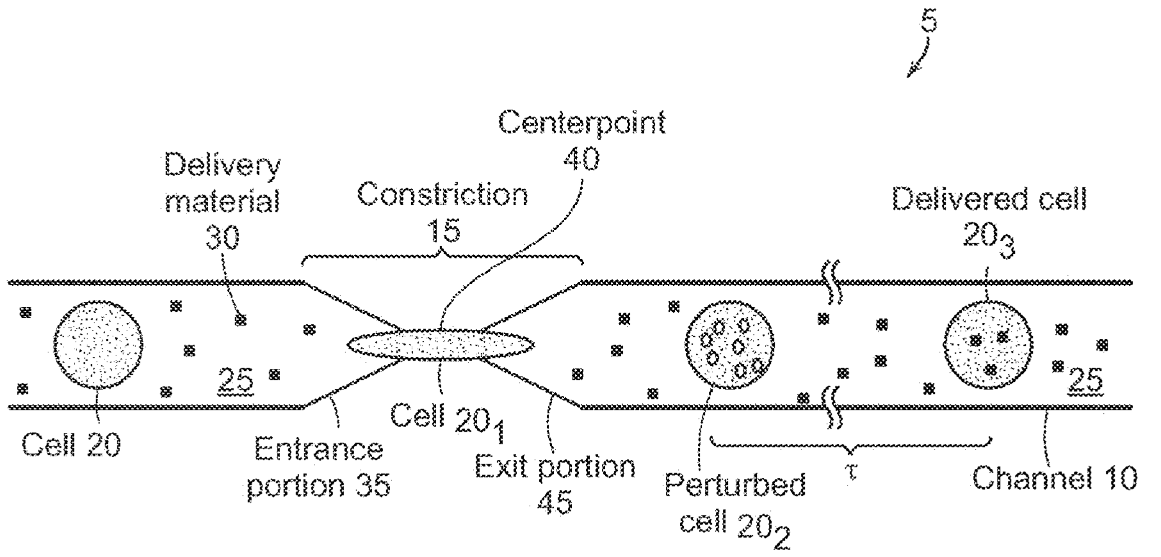
Figure 2A:
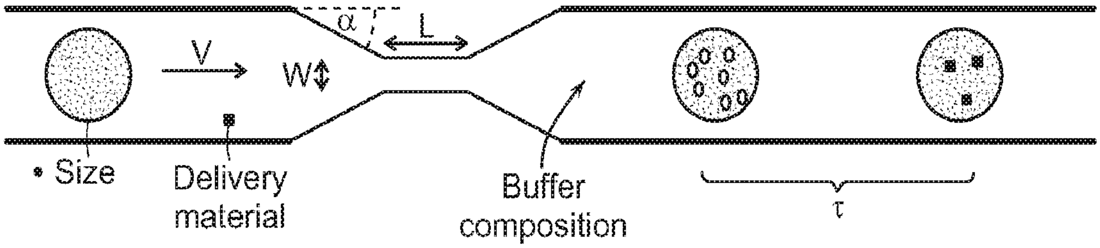
FIGS. 2A and 2B are schematic diagrams of an embodiment of a microfluidic system in depicting parameters such as channel depth, width, and length.
Figure 2B:
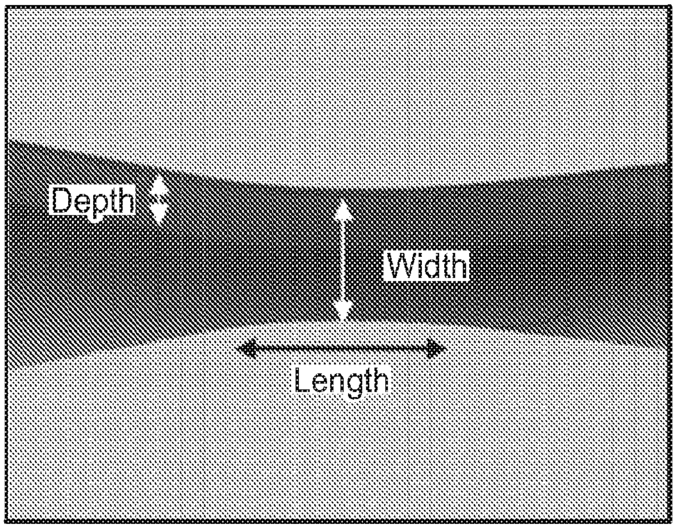

FIGS. 1-2 illustrate an example microfluidic system that can be used for the delivery of genome editing protein, RNA, and DNA. The microfluidic system 5 includes a channel 10 defining a tubular lumen. The microfluidic channel 10 includes a constriction 15 that is preferably configured such that only a single target cell 20 can pass through the constriction 15 at one time. Preferably, the cells 20 pass through the channel 10 suspended in a solution buffer 25 that also includes delivery materials 30, although the delivery materials can be added to the solution buffer 25 after the cells 20 pass through the constriction 15. As the cell 20 approaches and passes through the constriction 15, the constriction 15 applies pressure (e.g., mechanical compression) to the cell 20, squeezing the cell 20 (e.g., shown as cell $20_1$). The pressure applied to the cell by the constriction 15 causes perturbations (e.g., holes) in the cell membrane (e.g., cell $20_2$). Once the cell passes through the constriction 15, the cell 20 begins to uptake the material in the solution buffer 25 through the holes, including the delivery material 30 (e.g., cell $20_3$). The cell membrane recovers over time, and at least a portion of the delivery material 30 preferably remains trapped inside the cell.

In some embodiments, the device comprises a constriction length of about 5 μm to about 50 μm or any length or range of lengths therebetween. For example, the constriction length ranges from about 5 μm to about 40 μm, about 5 μm to about 30 μm, about 5 μm to about 20 μm, or about 5 μm to about 10 μm. In some embodiments, the constriction length ranges from about 10 μm to about 50 μm, about 20 μm to about 50 μm, about 30 μm to about 50 μm, or about 40 μm to about 50 μm. In some embodiments, the constriction depth ranges from about 2 μm to about 200 μm or any depth or range of depths there between. For example, the constriction depth ranges from about 2 μm to about 150 μm, about 2 μm to about 100 μm, about 2 μm to about 50 μm, about 2 μm to about 25 μm, about 2 μm to about 15 μm, or about 2 μm to about 10 μm. In some embodiments, the constriction depth ranges from about 10 μm to about 200 μm, about 25 μm to about 200 μm, about 50 μm to about 200 μm, about 100 μm to about 200 μm, or about 150 μm to about 200 μm. In some embodiments, the angle of the entrance or exit portion of the constriction ranges from about 0 degrees to about 90 degrees or any angle or range of angles therebetween. For example, the angle is about 5, about 10, about 15, about 20, about 30, about 40, about 50, about 60, about 70, about 80, or about 90 degrees or more. In some embodiments, the pressure ranges from about 50 psi to about 200 psi or any pressure or range of pressures there between. For example, the pressure ranges from about 50 psi to about 150 psi, about 50 psi to about 125 psi, about 50 psi to about 100 psi, or about 50 psi to about 75 psi. In some embodiments, the pressure ranges from about 75 psi to about 200 psi, about 100 psi to about 200 psi, about 125 psi to about 200 psi, about 150 psi to about 200 psi, or about 175 psi to about 200 psi. In some embodiments, the device comprises a constriction width of between about 2 μm and about 10 μm or any width or range of widths therebetween. For example, the constriction width can be any one of about 3 μm, about 4 μm, about 5 μm, about 6 μm, or about 7 μm.

The data described below was generated using the following materials and methods. Complexes were made as follows: Mix 10 μl of 1 mg/ml nuclear localization signal (NLS) tagged Cas9 protein with 5 μl of 1 mg/ml guide RNA. Incubate on ice for 20 min to allow complexes to form. For delivery, target cells are suspended at 10 million cells/ml in serum-free media. Cells and Cas9-gRNA complexes are mixed immediately before device treatment such that complex concentration is ~0.15 mg/ml. Cells are treated by the device using pressure, temperature, chip design and buffer conditions specific to the target cell type. For example, for primary human T cells, pressure is approximately 100 psi, on ice, through a 30 μm length, 4 μm width constriction. After a 2 min incubation post-treatment, cells are diluted in media and washed to remove undelivered complexes. Cells are then cultured to allow for gene editing to occur (e.g., 1, 2, 5, 12, 24 hours or more (for non-clinical applications, timeframe depends on assay readout, e.g., 24 hours or later). For clinical use, e.g., for patient therapy, the cells could be injected back into patient immediately after device treatment. Optionally, the cells are incubated in vitro for a time (e.g., 1, 2, 5, 12, 24 hours or more) prior to injecting the cells into a patient recipient. Temperatures, concentrations, iterations of the molecules vary depending on the target cell type.

Figure 3A:
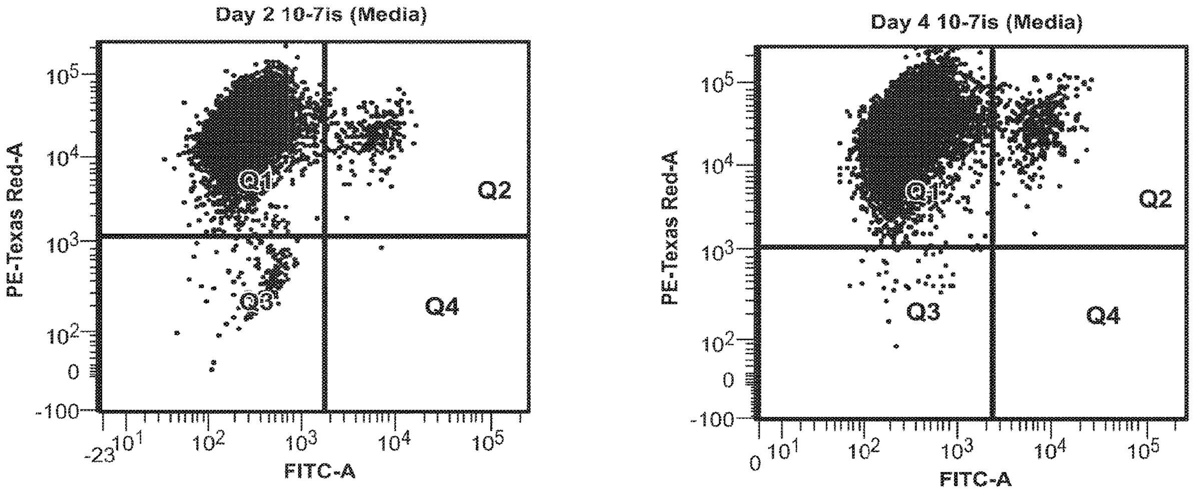
FIGS. 3A and 3B are a series of flow cytometry plots (FIG. 3A) and a bar graph (FIG. 3B) of the recombination efficiency for K562 reporter cells that had genetic editing material delivered to cell cytoplasm using the microfluidic device illustrated in FIGS. 1-2. For the reporter used, there is a frame-shifted GFP gene in the cell line. To perform the editing the Cas9 gRNA complex and a donor oligonucleotide would be delivered. The complex would cut near the GFP site and the oligonucleotide would insert itself into the cut site. Successful insertion of the oligo would correct the gene and result in GFP expression which is what is seen in this figure. Thus, in this assay something turned on upon gene editing as opposed to turned off. A gene would be expected to be turned off in instances where a gene (or depending on the context, a nucleotide or portion thereof) was being deleted in the absence of a donor oligonucleotide.
Figure 3B:
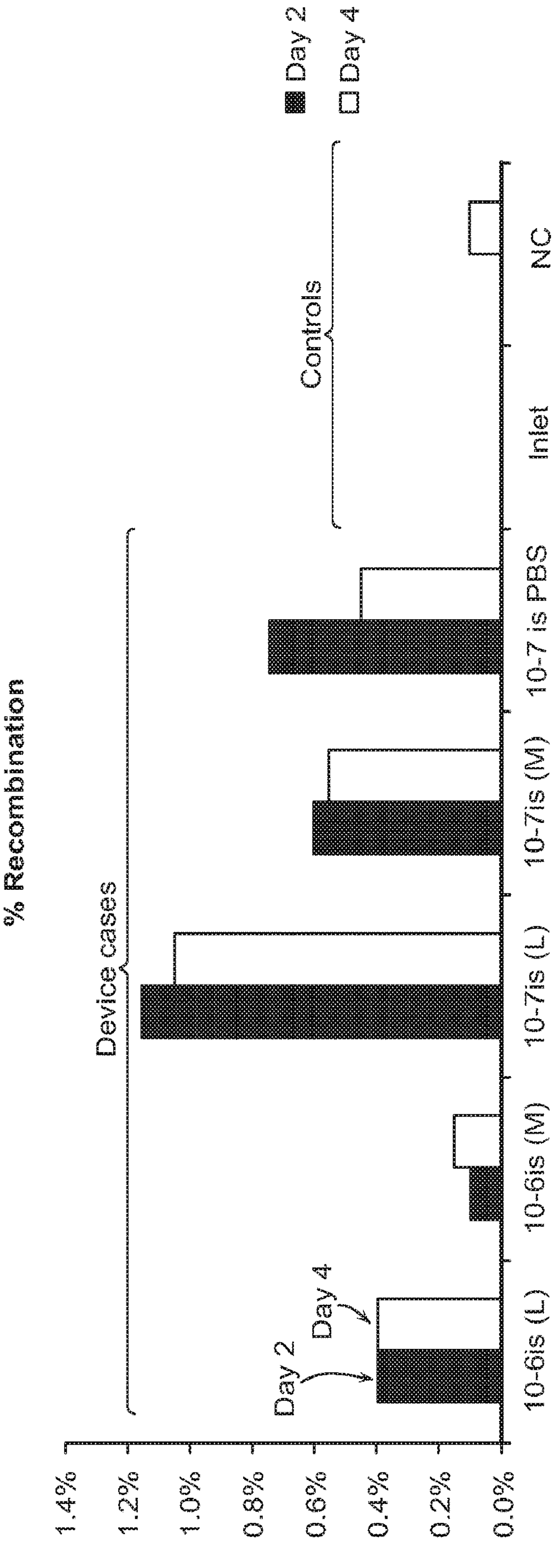

FIG. 3 is a series of flow cytometry plots and a bar graph of the recombination efficiency for K562 reporter cells (American Type Culture Collection (ATCC)® CCL-243™, bone marrow-derived cells derived from patient with chronic myelogenous leukemia; lymphoblast morphology) that had genetic editing material delivered to cell cytoplasm using the microfluidic device illustrated in FIGS. 1-2. At top are flow cytometry plots of K562 reporter cells that had a protein Cas9, site-specific gRNA, and donor oligonucleotide delivered. A CRISPR complex is ~150 kDa. These reporter cells had an mCherry gene and thus would normally appear in Q1 of the plots. If the site-specific DNA cleavage and insertion of donor oligonucleotide is successful it would lead to expression of green fluorescent protein (GFP), i.e., cells would appear in Q2. At bottom is a quantification of recombination efficiency based on flow cytometry for multiple device conditions as compared to endocytosis (inlet) and untreated (NC) controls. Delivery of Cas9 protein, guide RNA and donor DNA by cell squeezing led to successful changes in the genome of reporter cell lines. These data indicate that delivery of gene editing components (in the form of a complex or assembly) by mechanical cell disruption leads to effective changes in the genome.

Delivery of TALEN proteins or mRNA, zinc finger nucleases, mega nucleases, Cre recombinase or any other enzyme capable of cleaving DNA can also be delivered to the cytoplasm of a cell by mechanical disruption of the cell membrane. An exemplary TALEN genome-editing system, including exemplary TALEN proteins, is described in Ding et al., (2013) Cell Stem Cell, 12, 238-251, the entire content of which is incorporated herein by reference. Ding et al., (2013) Cell Stem Cell, 12, 238-251 describes non-limiting examples of generic TALEN amino acid sequences to recognize 15 base pair sequences. Non-limiting examples of generic TALEN amino acid sequences are:

(SEQ ID NO: 65)

MDYKDHDGDYKDHDIDYKDDDDKMAPKKKRKVGIHGVPSRVDLRTLGYSQ
QQQEKIKPKVRSTVAQHHEALVGHGFTHAHIVALSQHPAALGTVAVTYQN
IITALPEATHEDIVGVGKQWSGAPALEALLTDAGELRGPPLQLDTGQLVK
IAKRGGVTAMEAVHASRNALTGAPLNLTPEQVVAIASXXGGKQALETVQR
LLPVLCQAHGLTPEQVVAIASXXGGKQALETVQPLLPVLCQAHGLTPEQV
VAIASXXGGKQALETVQRLLPVLCQAHGLTPEQVVAIASXXGGKQALETV
QPLLPVLCQAHGLTPEQVVAIASXXGGKQALETVQRLLPVLCQAHGLTPE
QVVAIASXXGGKQALETVQPLLPVLCQAHGLTPEQVVAIASXXGGKQALE
TVQRLLPVLCQAHGLTPEQVVAIASXXGGKQALETVQPLLPVLCQAHGLT
PEQVVAIASXXGGKQALETVQRLLPVLCQAHGLTPEQVVAIASXXGGKQA
LETVQPLLPVLCQAHGLTPEQVVAIASXXGGKQALETVQRLLPVLCQAHG
LTPEQVVAIASXXGGKQALETVQPLLPVLCQAHGLTPEQVVAIASXXGGK
QALETVQRLLPVLCQAHGLTPEQVVAIASXXGGKQALETVQPLLPVLCQA
HGLTPEQVVAIASXXGGRPALESIVAQLSRPDPALAALTNDHLVALACLG
GRPAMDAVKKGLPHAPELIRRVNRRIGERTSHRVAGSQLVKSELEEKKSE
LRHKLKYVPHEYIELIEIARNPTQDRILEMKVMEFFMKVYGYPGEHLGGS
RKPDGAIYTVGSPIDYGVIVDTKAYSGGYNLPIGQADEMQRYVKENQTRN
KHINPNEWWKVYPSSVTEFKFLFVSGHFKGNYKAQLTRLNRKTNVNGAVL
SVEELLIGGEMTKAGTLTLEEVRRKFNNGEINF

-continued (SEQ ID NO: 66)

MDYKDHDGDYKDHDIDYKDDDKMAPKKKRKVGIHGVPARVDLRTLGYSQQ
QQEKIKPKVRSTVACHHEALVGHGFTHAHIVALSQHPAALGTVAVTYQHI
ITALPEATHEDIVGVGKQWSGARALEALLTDAGELRGPPLQLDTGQLVKI
AKRGGVTAMEAVHASRNALTGAPLNLTPEQVVAIASXXGGKQALETVQRL
LPVLCQAHGLTPEQVVAIASXXGGKQALETVQRLLPVLCQAHGLTPEQVV
AIASXXGGKQALETVQRLLPVLCQAHGLTPEQVVAIASXXGGKQALETVQ
RLLPVLCQAHGLTPEQVVAIASXXGGKQALETVQRLLPVLCQAHGLTPEQ
VVAIASXXGGKQALETVQRLLPVLCQAHGLTPEQVVAIASXXGGKQALET
VQRLLPVLCQAHGLTPEQVVAIASXXGGKQALETVQRLLPVLCQAHGLTP
EQVVAIASXXGGKQALETVQRLLPVLCQAHGLTPEQVVAIASXXGGKQAL
ETVQRLLPVLCQAHGLTPEQVVAIASXXGGKQALETVQRLLPVLCQAHGL
TPEQVVAIASXXGGKQALETVQRLLPVLCQAHGLTPEQVVAIASXXGGKQ
ALETVQRLLPVLCQAHGLTPEQVVAIASXXGGKQALETVQRLLPVLCQAH
GLTPEQVVAIASXXGGRPALESIVAQLSRPDPALAALTNDHLVALACLGG
RPAMDAVKKGLPHAPELIRRVNRRIGERTSHRVAGSQLVKSELEEKKSEL
RHKLKYVPHEYIELIEIARNPTQDRILEMKVMEFFMKVYGYPGEHLGGSR
KPDGAIYTVGSPIDYGVIVDTKAYSGGYNLPIGQADEMERYVEENQTRDK
HLNPNEWWKVYPSSVTEFKFLFVSGHFKGNYKAQLTRLNHITNCNGAVLS
VEELLIGGEMIKAGTLTLEEVRRKFNNGEINF

In SEQ ID NOS: 65 and 66, to recognize C: XX=HD; to recognize T: XX=NG; to recognize A: XX=NI; and to recognize G: XX=NN except in the last position where XX=NK. Underline indicates N-term and C-term of TAL effector.

Although a few variations have been described in detail above, other modifications or additions are possible. For example, genetic editing material can include TALEN proteins, TALEN mRNA, zinc finger nucleases, mega nucleases, Cre recombinase or any other enzyme capable of cleaving DNA delivered to the cytosol by mechanical disruption of the cell membrane.

Delivery of RNA and Cas9 in Complex Form

The results achieved were surprising in view of numerous factors that could potentially have impeded successful gene editing by microfluidic delivery of the gene complexes. For example, the Cas9-gRNA complex may have caused a Toll-like receptor (TLR) mediated or other PRR (pattern recognition receptor) mediated response that would have inhibited gene editing function and/or survival but this potential problem was not observed. Since the complex is not guaranteed to be stable once it enters the cytoplasm, it could have been degraded and rendered non-functional, but surprisingly, the delivered complexes were still able to edit.

The integrity of the gene editing complex was preserved using microfluidic based, cell-squeezing delivery to the cell. The complex does not have the same physical/chemical properties as a gRNA alone or protein alone and thus it was uncertain if the delivery process would behave the same in the context of delivering a complex vs. its individual components. Complexes are larger and less stable than their constituents. Complexes may fall apart due to, e.g., shear forces. Additionally, complexes may not survive membrane transit or in the cytosol because some other elements may break the complexes up before they are functional or have an opportunity to act on cellular targets. Complexes also have a different charge distribution which may affect the ability of a complex to be delivered. Shape and thus transport properties can also change compared to complex constituents. The delivery methods successfully preserved the structural and functional integrity of the complexes.

The shear forces involved with the delivery process could potentially have disrupted the Protein/gRNA complex and rendered it non-functional but surprisingly the delivery system was effective to introduce the complexes into the cell and the gene editing still worked. It was also not obvious that the complex would still have the appropriate nuclear localization behavior as compared to an uncomplexed Cas (such as Cas9) protein alone with NLS; however, the behavior and function was preserved throughout the process as demonstrated by the gene expression results described above.

The CRISPR-Cas system is known in the art. Non-limiting aspects of this system are described in U.S. Pat. No. 8,697,359, issued Apr. 15, 2014, the entire content of which is incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

Non-limiting examples of Cas9 amino acid and cDNA sequences are provided below.

The amino acid sequence of a *Streptococcus pyogenes* Cas9 protein may be found in the SwissProt database under accession number Q99ZW2. This amino acid sequence is:

```
                                           (SEQ ID NO: 1)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR
```

-continued

```
LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

SEQ ID NO: 1 may be encoded by the following nucleotide sequence found in the European Nucleotide Archive under accession number AAK33936.2:

```
                                           (SEQ ID NO: 2)
ATGGATAAGAAATACTCAATAGGCTTAGATATCGGCACAAATAGCGTCGG

ATGGGCGGTGATCACTGATGAATATAAGGTTCCGTCTAAAAAGTTCAAGG

TTCTGGGAAATACAGACCGCCACAGTATCAAAAAAAATCTTATAGGGGCT

CTTTTATTTGACAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGTAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC
```

-continued

TATTTATCCAGTTGGTACAAACCTACAATCAATTATTTGAAGAAAACCCT

ATTAACGCAAGTGGAGTAGATGCTAAAGCGATTCTTTCTGCACGATTGAG

TAAATCAAGACGATTAGAAAATCTCATTGCTCAGCTCCCCGGTGAGAAGA

AAAATGGCTTATTTGGGAATCTCATTGCTTTGTCATTGGGTTTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATACTGAAATAACTAAGGCTCCCCT

ATCAGCTTCAATGATTAAACGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAAGTACTACCAAAACATAGTTTGCTTTATGAGTA

TTTTACGGTTTATAACGAATTGACAAAGGTCAAATATGTTACTGAAGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGTACCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGAGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGACATTCAAAAAGCACAAGTGTCTGGACAAGG

CGATAGTTTACATGAACATATTGCAAATTTAGCTGGTAGCCCTGCTATTA

AAAAAGGTATTTTACAGACTGTAAAAGTTGTTGATGAATTGGTCAAAGTA

ATGGGGCGGCATAAGCCAGAAAATATCGTTATTGAAATGGCACGTGAAAA

TCAGACAACTCAAAAGGGCCAGAAAAATTCGCGAGAGCGTATGAAACGAA

TCGAAGAAGGTATCAAAGAATTAGGAAGTCAGATTCTTAAAGAGCATCCT

GTTGAAAATACTCAATTGCAAAATGAAAAGCTCTATCTCTATTATCTCCA

AAATGGAAGAGACATGTATGTGGACCAAGAATTAGATATTAATCGTTTAA

GTGATTATGATGTCGATCACATTGTTCCACAAAGTTTCCTTAAAGACGAT

TCAATAGACAATAAGGTCTTAACGCGTTCTGATAAAAATCGTGGTAAATC

-continued

GGATAACGTTCCAAGTGAAGAAGTAGTCAAAAAGATGAAAAACTATTGGA

GACAACTTCTAAACGCCAAGTTAATCACTCAACGTAAGTTTGATAATTTA

ACGAAAGCTGAACGTGGAGGTTTGAGTGAACTTGATAAAGCTGGTTTTAT

CAAACGCCAATTGGTTGAAACTCGCCAAATCACTAAGCATGTGGCACAAA

TTTTGGATAGTCGCATGAATACTAAATACGATGAAAATGATAAACTTATT

CGAGAGGTTAAAGTGATTACCTTAAAATCTAAATTAGTTTCTGACTTCCG

AAAAGATTTCCAATTCTATAAAGTACGTGAGATTAACAATTACCATCATG

CCCATGATGCGTATCTAAATGCCGTCGTTGGAACTGCTTTGATTAAGAAA

TATCCAAAACTTGAATCGGAGTTTGTCTATGGTGATTATAAAGTTTATGA

TGTTCGTAAAATGATTGCTAAGTCTGAGCAAGAAATAGGCAAAGCAACCG

CAAAATATTTCTTTTACTCTAATATCATGAACTTCTTCAAAACAGAAATT

ACACTTGCAAATGGAGAGATTCGCAAACGCCCTCTAATCGAAACTAATGG

GGAAACTGGAGAAATTGTCTGGGATAAAGGGCGAGATTTTGCCACAGTGC

GCAAAGTATTGTCCATGCCCCAAGTCAATATTGTCAAGAAAACAGAAGTA

CAGACAGGCGGATTCTCCAAGGAGTCAATTTTACCAAAAAGAAATTCGGA

CAAGCTTATTGCTCGTAAAAAAGACTGGGATCCAAAAAAATATGGTGGTT

TTGATAGTCCAACGGTAGCTTATTCAGTCCTAGTGGTTGCTAAGGTGGAA

AAAGGGAAATCGAAGAAGTTAAAATCCGTTAAAGAGTTACTAGGGATCAC

AATTATGGAAAGAAGTTCCTTTGAAAAAAATCCGATTGACTTTTTAGAAG

CTAAAGGATATAAGGAAGTTAAAAAAGACTTAATCATTAAACTACCTAAA

TATAGTCTTTTTGAGTTAGAAAACGGTCGTAAACGGATGCTGGCTAGTGC

CGGAGAATTACAAAAAGGAAATGAGCTGGCTCTGCCAAGCAAATATGTGA

ATTTTTTATATTTAGCTAGTCATTATGAAAAGTTGAAGGGTAGTCCAGAA

GATAACGAACAAAAACAATTGTTTGTGGAGCAGCATAAGCATTATTTAGA

TGAGATTATTGAGCAAATCAGTGAATTTTCTAAGCGTGTTATTTTAGCAG

ATGCCAATTTAGATAAAGTTCTTAGTGCATATAACAAACATAGAGACAAA

CCAATACGTGAACAAGCAGAAAATATTATTCATTTATTTACGTTGACGAA

TCTTGGAGCTCCCGCTGCTTTTAAATATTTTGATACAACAATTGATCGTA

AACGATATACGTCTACAAAAGAAGTTTTAGATGCCACTCTTATCCATCAA

TCCATCACTGGTCTTTATGAAACACGCATTGATTTGAGTCAGCTAGGAGG

TGACTGA

The amino acid sequence of a *Streptococcus thermophilus* Cas9 protein may be found in the UniProt database under accession number Q03J16.1. See also, Sapranauskas et al., (2011) Nucleic Acids Res. 39:9275-9282. This amino acid sequence is:

(SEQ ID NO: 3)

MTKPYSIGLDIGTNSVGWAVTTDNYKVPSKKMKVLGNTSKKYIKKNLLGV

LLFDSGITAEGRRLKRTARRRYTRRRNRILYLQEIFSTEMATLDDAFFQR

LDDSFLVPDDKRDSKYPIFGNLVEEKAYHDEFPTIYHLRKYLADSTKKAD

LRLVYLALAHMIKYRGHFLIEGEFNSKNNDIQKNFQDFLDTYNAIFESDL

-continued

SLENSKQLEEIVKDKISKLEKKDRILKLFPGEKNSGIFSEFLKLIVGNQA

DFRKCFNLDEKASLHFSKESYDEDLETLLGYIGDDYSDVFLKAKKLYDAI

LLSGFLTVTDNETEAPLSSAMIKRYNEHKEDLALLKEYIRNISLKTYNEV

FKDDTKNGYAGYIDGKTNQEDFYVYLKKLLAEFEGADYFLEKIDREDFLR

KQRTFDNGSIPYQIHLQEMRAILDKQAKFYPFLAKNKERIEKILTFRIPY

YVGPLARGNSDFAWSIRKRNEKITPWNFEDVIDKESSAEAFINRMTSFDL

YLPEEKVLPKHSLLYETFNVYNELTKVRFIAESMRDYQFLDSKQKKDIVR

LYFKDKRKVTDKDIIEYLHAIYGYDGIELKGIEKQFNSSLSTYHDLLNII

NDKEFLDDSSNEAIIEEIIHTLTIFEDREMIKQRLSKFENIFDKSVLKKL

SRRHYTGWGKLSAKLINGIRDEKSGNTILDYLIDDGISNRNFMQLIHDDA

LSFKKKIQKAQIIGDEDKGNIKEVVKSLPGSPAIKKGILQSIKIVDELVK

VMGGRKPESIVVEMARENQYTNQGKSNSQQRLKRLEKSLKELGSKILKEN

IPAKLSKIDNNALQNDRLYLYYLQNGKDMYTGDDLDIDRLSNYDIDHIIP

QAFLKDNSIDNKVLVSSASNRGKSDDVPSLEVVKKRKTFWYQLLKSKLIS

QRKFDNLTKAERGGLSPEDKAGFIQRQLVETRQITKHVARLLDEKFNNKK

DENNRAVRTVKIITLKSTLVSQFRKDFELYKVREINDFHHAHDAYLNAVV

ASALLKKYPKLEPEFVYGDYPKYNSFRERKSATEKVYFYSNIMNIFKKSI

SLADGRVIERPLIEVNEETGESVWNKESDLATVRRVLSYPQVNVVKKVEE

QNHGLDRGKPKGLFNANLSSKPKPNSNENLVGAKEYLDPKKYGGYAGISN

SFTVLVKGTIEKGAKKKITNVLEFQGISILDRINYRKDKLNFLLEKGYKD

IELIIELPKYSLFELSDGSRRMLASILSTNNKRGEIHKGNQIFLSQKFVK

LLYHAKRISNTINENHRKYVENHKKEFEELFYYILEFNENYVGAKKNGKL

LNSAFQSWQNHSIDELCSSFIGPTGSERKGLFELTSRGSAADFEFLGVKI

PRYRDYTPSSLLKDATLIHQSVTGLYETRIDLAKLGEG

SEQ ID NO: 3 may be encoded by the following nucleotide sequence found in the European Nucleotide Archive under accession number ABJ66636.1:

(SEQ ID NO: 4)

ATGACTAAGCCATACTCAATTGGACTTGATATTGGAACGAATAGTGTTGG

ATGGGCTGTAACAACTGATAATTACAAGGTTCCGTCTAAAAAAATGAAAG

TCTTAGGAAATACGAGTAAAAAGTATATCAAAAAGAACCTGTTAGGTGTA

TTACTCTTTGACTCTGGAATCACAGCAGAAGGAAGAAGATTGAAGCGTAC

TGCAAGAAGACGTTATACTAGACGCCGTAATCGTATCCTTTATTTGCAGG

AAATTTTTAGCACAGAGATGGCTACATTAGATGATGCTTTCTTTCAAAGA

CTTGACGATTCGTTTTTAGTTCCTGATGATAAACGTGATAGTAAGTATCC

GATATTTGGAAACTTAGTAGAAGAAAAAGCCTATCATGATGAATTTCCAA

CTATCTATCATTTAAGGAAATATTTAGCAGATAGTACTAAAAAAGCAGAT

TTGCGTCTAGTTTATCTTGCATTGGCTCATATGATTAAATATAGAGGTCA

CTTCTTAATTGAAGGAGAGTTTAATTCAAAAAATAATGATATTCAGAAGA

ATTTTCAAGACTTTTTGGACACTTATAATGCTATTTTTGAATCGGATTTA

TCACTTGAGAATAGTAAACAACTTGAGGAAATTGTTAAAGATAAGATTAG

-continued

TAAATTAGAAAAGAAAGATCGTATTTTAAAACTCTTCCCTGGGGAGAAGA

ATTCGGGGATTTTTTCAGAGTTTCTAAAGTTGATTGTAGGAAATCAAGCT

GATTTTAGGAAATGTTTTAATTTAGACGAAAAAGCCTCCTTACATTTTTC

CAAAGAAAGCTATGATGAAGATTTAGAGACTTTGTTAGGTTATATTGGAG

ATGATTACAGTGATGTCTTTCTCAAAGCAAAGAAACTTTATGATGCTATT

CTTTTATCGGGTTTTCTGACTGTAACTGATAATGAGACAGAAGCACCTCT

CTCTTCTGCTATGATAAAGCGATATAATGAACACAAAGAAGATTTAGCGT

TACTAAAGGAATATATAAGAAATATTTCACTAAAAACGTATAATGAAGTA

TTTAAAGATGACACCAAAAATGGTTATGCTGGTTATATTGATGGAAAAAC

AAATCAGGAAGATTTCTACGTATATCTAAAAAAACTATTGGCTGAATTTG

AAGGTGCGGATTATTTTCTTGAAAAAATTGATCGAGAAGATTTTTTGAGA

AAGCAACGTACATTTGACAATGGTTCGATACCATATCAGATTCATCTTCA

AGAAATGAGAGCAATTCTTGATAAGCAAGCTAAATTTTATCCTTTCTTGG

CTAAAAATAAAGAAAGAATCGAGAAGATTTTAACCTTCCGAATTCCTTAT

TATGTAGGTCCACTTGCGAGAGGGAATAGTGATTTTGCCTGGTCAATAAG

AAAACGAAATGAAAAAATTACACCTTGGAATTTTGAGGACGTTATTGACA

AAGAATCTTCGGCAGAGGCCTTCATTAATCGAATGACTAGTTTTGATTTG

TATTTGCCAGAAGAGAAGGTACTTCCAAAGCATAGTCTCTTATACGAAAC

TTTTAATGTATATAATGAATTAACAAAAGTTAGATTTATTGCCGAAAGTA

TGAGAGATTATCAATTTTTAGATAGTAAGCAGAAGAAAGATATTGTTAGA

CTTTATTTTAAAGATAAAAGGAAAGTTACTGATAAGGATATTATTGAATA

TTTACATGCAATTTATGGGTATGATGGAATTGAATTAAAAGGCATAGAGA

AACAGTTTAATTCTAGTTTATCTACTTATCACGATCTTTTAAATATTATT

AATGATAAAGAGTTTTTGGATGATAGTTCAAATGAAGCGATTATCGAAGA

AATTATCCATACTTTGACAATTTTTGAAGATAGAGAGATGATAAAACAAC

GTCTTTCAAAATTTGAGAATATATTCGATAAATCCGTTTTGAAAAAGTTA

TCTCGTAGACATTACACTGGCTGGGGTAAGTTATCTGCTAAGCTTATTAA

TGGTATTCGAGATGAAAAATCTGGTAATACTATTCTTGATTACTTAATTG

ATGATGGTATTTCTAACCGTAATTTCATGCAACTTATTCACGATGATGCT

CTTTCTTTTAAAAAGAAGATACAGAAAGCACAAATTATTGGTGACGAAGA

TAAAGGTAATATTAAAGAGGTCGTTAAGTCTTTGCCAGGTAGTCCTGCGA

TTAAAAAAGGTATTTTACAAAGCATAAAAATTGTAGATGAATTGGTCAAA

GTAATGGGAGGAAGAAAACCCGAGTCAATTGTTGTTGAGATGGCTCGTGA

AAATCAATATACCAATCAAGGTAAGTCTAATTCCCAACAACGCTTGAAAC

GTTTAGAAAAATCTCTCAAAGAGTTAGGTAGTAAGATACTTAAGGAAAAT

ATTCCTGCAAAACTTTCTAAAATAGACAATAACGCACTTCAAAATGATCG

ACTTTACTTATACTATCTTCAAAATGGAAAAGATATGTATACCGGAGATG

ATTTAGATATTGATAGATTAAGTAATTATGATATTGATCATATTATTCCT

CAAGCTTTTTTGAAAGATAATTCTATTGACAATAAAGTACTTGTTTCATC

TGCTAGTAACCGTGGTAAATCAGATGATGTTCCAAGTTTAGAGGTTGTCA

AAAAAAGAAAGACATTTTGGTATCAATTATTGAAATCAAAATTAATTTCT

-continued

```
CAACGAAAATTTGATAATCTGACAAAAGCTGAACGGGGAGGATTGTCACC

TGAGGACAAAGCTGGTTTTATTCAACGCCAGTTGGTTGAAACACGTCAAA

TAACAAAACATGTAGCTCGTTTACTTGATGAGAAATTTAATAATAAAAAA

GATGAAAATAATAGAGCGGTACGAACAGTAAAAATTATTACCTTGAAATC

TACCTTAGTTTCTCAATTTCGTAAGGATTTTGAACTTTATAAAGTTCGTG

AAATCAATGATTTTCATCATGCTCATGATGCTTACTTGAATGCCGTTGTA

GCAAGTGCTTTACTTAAGAAATACCCTAAACTAGAGCCAGAATTTGTGTA

CGGTGATTATCCAAAATACAATAGTTTTAGAGAAAGAAAGTCCGCTACAG

AAAAGGTATATTTCTATTCAAATATCATGAATATCTTTAAAAAATCTATT

TCTTTAGCTGATGGTAGAGTTATTGAAAGACCACTTATTGAGGTAAATGA

GGAGACCGGCGAATCCGTTTGGAATAAAGAATCTGATTTAGCAACTGTAA

GGAGAGTACTCTCTTATCCGCAAGTAAATGTTGTGAAAAAAGTTGAGGAA

CAGAATCACGGATTGGATAGAGGAAAACCAAAGGGATTGTTTAATGCAAA

TCTTTCCTCAAAGCCAAAACCAAATAGTAATGAAAATTTAGTAGGTGCTA

AAGAGTATCTTGACCCCAAAAAGTATGGGGGGTATGCTGGAATTTCTAAT

TCTTTTACTGTTCTTGTTAAAGGGACAATTGAAAAAGGTGCTAAGAAAAA

AATAACAAATGTACTAGAATTTCAAGGTATTTCTATTTTAGATAGGATTA

ATTATAGAAAAGATAAACTTAATTTTTTACTTGAAAAAGGTTATAAAGAT

ATTGAGTTAATTATTGAACTACCTAAATATAGTTTATTTGAACTTTCAGA

TGGTTCACGTCGTATGTTGGCTAGTATTTTGTCAACGAATAATAAGAGGG

GAGAGATTCACAAAGGAAATCAGATTTTTCTTTCACAGAAGTTTGTGAAA

TTACTTTATCATGCTAAGAGAATAAGTAACACAATTAATGAGAATCATAG

AAAATATGTTGAGAACCATAAAAAAGAGTTTGAAGAATTATTTTACTACA

TTCTTGAGTTTAATGAGAATTATGTTGGAGCTAAAAAGAATGGTAAACTC

TTAAACTCTGCCTTTCAATCTTGGCAAAATCATAGTATAGATGAACTCTG

TAGTAGTTTTATAGGACCTACCGGAAGTGAAAGAAAGGGGCTATTTGAAT

TAACCTCTCGTGGAAGTGCTGCTGATTTTGAATTTTTAGGTGTTAAAATT

CCAAGGTATAGAGACTATACCCCATCATCCCTATTAAAAGATGCCACACT

TATTCATCAATCTGTTACAGGCCTCTATGAAACACGAATAGACCTTGCCA

AACTAGGAGAGGGTTAA
```

An example of a Cas9 protein comprising a nuclear localization signal (GGSGPPKKKRKV; SEQ ID NO: 5) at the C-terminus thereof has the following amino acid sequence:

```
                                        (SEQ ID NO: 6)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI
```

-continued

```
LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGDGGSGPPKKKRKV
```

In some embodiments, a Cas9 nickase may be used in combination with guide sequence(s), e.g., two guide sequences, which target respectively sense and antisense strands of the DNA target. This combination allows both strands to be nicked and used to induce non-homologous end joining (NHEJ).

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity (where the amino acid numbering is as in SEQ ID NO: 1). In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme corresponds to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNXGG MMMMMMMMNNNNNNNNNNNNXXAGAAW where NNNNNNNNNNNNXGG (N is A, G, T, or C; and X can be a deoxynucleotide) has a single occurrence in the genome. A unique target sequence in a genome may include an *S. pyogenes* Cas9 target site of the form MMMMMMMMMNNNNNNNNNNNXGG where NNNNNNNNNNNNXGG (N is A, G, T, or C; and X can be a deoxynucleotide) has a single occurrence in the genome. For the *S. thermophilus* CRISPR1 Cas9, a unique target sequence in a genome may include a Cas9 target site of the form MMMMMMMMNNNNNNNNNNNNXXAGAAW (SEQ ID NO: 7) where NNNNNNNNNNNNXXAGAAW (SEQ ID NO: 8) (N is A, G, T, or C; X can be a deoxynucleotide; and W is A or T) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 9) where NNNNNNNNNNNXXAGAAW (SEQ ID NO: 10) (N is A, G, T, or C; X can be a deoxynucleotide; and W is A or T) has a single occurrence in the genome. For the *S. pyogenes* Cas9, a unique target sequence in a genome may include a Cas9 target site of the form MMMMMMMMNNNNNNNNNNNNXGGXG where NNNNNNNNNNNNXGGXG (N is A, G, T, or C; and X can be a deoxynucleotide) has a single occurrence in the genome. A unique target sequence in a genome may include an *S. pyogenes* Cas9 target site of the form MMMMMMMMMNNNNNNNNNNNXGGXG where NNNNNNNNNNNXGGXG (N is A, G, T, or C; and X can be a deoxynucleotide) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62). Further algorithms may be found in U.S. application Ser. No. 61/836,080; incorporated herein by reference.

Aspects of the present subject matter relate to delivery of CRISPR/CRISPR/CRISPR from *Prevotella* and *Francisella* 1 (Cpf1) gene editing complexes or components thereof (e.g., CPf1 proteins). Examples of human codon optimized Cpf1-family proteins are provided below.

Human Codon Optimized Cpf1-Family Proteins

Non-limiting examples of Cpf1-family protein sequences, and aspects of CRISPR/Cpf1 gene-editing, are described in Zetsche et al., Cell 163, 759-771, Oct. 22, 2015, the entire content of which is incorporated herein by reference.

*Francisella tularensis* subsp. *Novicida* U112 (FnCpf1; pY004)), including NLS and HA tag:

(SEQ ID NO: 11)

```
MSIYQEFVNKYSLSKTLRFELIPQGKTLENIKARGLILDDEKRAKDYKKA

KQIIDKYHQFFIEEILSSVCISEDLLQNYSDVYFKLKKSDDDNLQKDFKS

AKDTIKKQISEYIKDSEKFKNLFNQNLIDAKKGQESDLILWLKQSKDNGI

ELFKANSDITDIDEALEIIKSFKGWTTYFKGFHENRKNVYSSNDIPTSII

YRIVDDNLPKFLENKAKYESLKDKAPEAINYEQIKKDLAEELTFDIDYKT

SEVNQRVFSLDEVFEIANFNNYLNQSGITKFNTIIGGKFVNGENTKRKGI

NEYINLYSQQINDKTLKKYKMSVLFKQILSDTESKSFVIDKLEDDSDVVT

TMQSFYEQIAAFKTVEEKSIKETLSLLFDDLKAQKLDLSKIYFKNDKSLT

DLSQQVFDDYSVIGTAVLEYITQQIAPKNLDNPSKKEQELIAKKTEKAKY

LSLETIKLALEEFNKHRDIDKQCRFEEILANFAAIPMIFDEIAQNKDNLA

QISIKYQNQGKKDLLQASAEDDVKAIKDLLDQTNNLLHKLKIFHISQSED

KANILDKDEHFYLVFEECYFELANIVPLYNKIRNYITQKPYSDEKFKLNF

ENSTLANGWDKNKEPDNTAILFIKDDKYYLGVMNKKNNKIFDDKAIKENK

GEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSI

DEFYREVENQGYKLTFENISESYIDSVVNQGKLYLFQIYNKDFSAYSKGR

PNLHTLYWKALFDERNLQDVVYKLNGEAELFYRKQSIPKKITHPAKEAIA

NKNKDNPKKESVFEYDLIKDKRFTEDKFFFHCPITINFKSSGANKFNDEI

NLLLKEKANDVHILSIDRGERHLAYYTLVDGKGNIIKQDTFNIIGNDRMK

TNYHDKLAAIEKDRDSARKDWKKINNIKEMKEGYLSQVVHEIAKLVIEYN

AIVVFEDLNFGFKRGRFKVEKQVYQKLEKMLIEKLNYLVFKDNEFDKTGG

VLRAYQLTAPFETFKKMGKQTGIIYYVPAGFTSKICPVTGFVNQLYPKYE

SVSKSQEFFSKFDKICYNLDKGYFEFSFDYKNFGDKAAKGKWTIASFGSR

LINFRNSDKNHNWDTREVYPTKELEKLLKDYSIEYGHGECIKAAICGESD

KKFFAKLTSVLNTILQMRNSKTGTELDYLISPVADVNGNFFDSRQAPKNM

PQDADANGAYHIGLKGLMLLGRIKNNQEGKKLNLVIKNEEYFEFVQNRNN

KRPAATKKAGQAKKKKGSYPYDVPDYAYPYDVPDYAYPYDVPDYA
```

SEQ ID NO: 11 includes a nuclear localization signal (KRPAATKKAGQAKKKK) (SEQ ID NO: 12), followed by a glycine-serine linker (GS), followed by a Human influenza hemagglutinin (HA) tag (SEQ ID NO: 13)
(YPYDVPDYAYPYDVPDYAYPYDVPDYA).

SEQ ID NO: 11 may be encoded by the following nucleotide sequence:

(SEQ ID NO: 14)

```
ATGAGCATCTACCAGGAGTTCGTCAACAAGTATTCACTGAGTAAGACACT

GCGGTTCGAGCTGATCCCACAGGGCAAGACACTGGAGAACATCAAGGCCC
```

-continued

```
GAGGCCTGATTCTGGACGATGAGAAGCGGGCAAAAGACTATAAGAAAGCC

AAGCAGATCATTGATAAATACCACCAGTTCTTTATCGAGGAAATTCTGAG

CTCCGTGTGCATCAGTGAGGATCTGCTGCAGAATTACTCAGACGTGTACT

TCAAGCTGAAGAAGAGCGACGATGACAACCTGCAGAAGGACTTCAAGTCC

GCCAAGGACACCATCAAGAAACAGATTAGCGAGTACATCAAGGACTCCGA

AAAGTTTAAAAATCTGTTCAACCAGAATCTGATCGATGCTAAGAAAGGCC

AGGAGTCCGACCTGATCCTGTGGCTGAAACAGTCTAAGGACAATGGGATT

GAACTGTTCAAGGCTAACTCCGATATCACTGATATTGACGAGGCACTGGA

AATCATCAAGAGCTTCAAGGGATGGACCACATACTTTAAAGGCTTCCACG

AGAACCGCAAGAACGTGTACTCCAGCAACGACATTCCTACCTCCATCATC

TACCGAATCGTCGATGACAATCTGCCAAAGTTCCTGGAGAACAAGGCCAA

ATATGAATCTCTGAAGGACAAAGCTCCCGAGGCAATTAATTACGAACAGA

TCAAGAAAGATCTGGCTGAGGAACTGACATTCGATATCGACTATAAGACT

AGCGAGGTGAACCAGAGGGTCTTTTCCCTGGACGAGGTGTTTGAAATCGC

CAATTTCAACAATTACCTGAACCAGTCCGGCATTACTAAATTCAATACCA

TCATTGGCGGGAAGTTTGTGAACGGGGAGAATACCAAGCGCAAGGGAATT

AACGAATACATCAATCTGTATAGCCAGCAGATCAACGACAAAACTCTGAA

GAAATACAAGATGTCTGTGCTGTTCAAACAGATCCTGAGTGATACCGAGT

CCAAGTCTTTTGTCATTGATAAACTGGAAGATGACTCAGACGTGGTCACT

ACCATGCAGAGCTTTTATGAGCAGATCGCCGCTTTCAAGACAGTGGAGGA

AAAATCTATTAAGGAAACTCTGAGTCTGCTGTTCGATGACCTGAAAGCCC

AGAAGCTGGACCTGAGTAAGATCTACTTCAAAAACGATAAGAGTCTGACA

GACCTGTCACAGCAGGTGTTTGATGACTATTCCGTGATTGGGACCGCCGT

CCTGGAGTACATTACACAGCAGATCGCTCCAAAGAACCTGGATAATCCCT

CTAAGAAAGAGCAGGAACTGATCGCTAAGAAAACCGAGAAGGCAAAATAT

CTGAGTCTGGAAACAATTAAGCTGGCACTGGAGGAGTTCAACAAGCACAG

GGATATTGACAAACAGTGCCGCTTTGAGGAAATCCTGGCCAACTTCGCAG

CCATCCCCATGATTTTTGATGAGATCGCCCAGAACAAAGACAATCTGGCT

CAGATCAGTATTAAGTACCAGAACCAGGGCAAGAAAGACCTGCTGCAGGC

TTCAGCAGAAGATGACGTGAAAGCCATCAAGGATCTGCTGGACCAGACCA

ACAATCTGCTGCACAAGCTGAAAATCTTCCATATTAGTCAGTCAGAGGAT

AAGGCTAATATCCTGGATAAAGACGAACACTTCTACCTGGTGTTCGAGGA

ATGTTACTTCGAGCTGGCAAACATTGTCCCCCTGTATAACAAGATTAGGA

ACTACATCACACAGAAGCCTTACTCTGACGAGAAGTTTAAACTGAACTTC

GAAAATAGTACCCTGGCCAACGGGTGGGATAAGAACAAGGAGCCTGACAA

CACAGCTATCCTGTTCATCAAGGATGACAAGTACTATCTGGGAGTGATGA

ATAAGAAAAACAATAAGATCTTCGATGACAAAGCCATTAAGGAGAACAAA

GGGGAAGGATACAAGAAAATCGTGTATAAGCTGCTGCCCGGCGCAAATAA

GATGCTGCCTAAGGTGTTCTTCAGCGCCAAGAGTATCAAATTCTACAACC

CATCCGAGGACATCCTGCGGATTAGAAATCACTCAACACATACTAAGAAC

GGGAGCCCCCAGAAGGGATATGAGAAATTTGAGTTCAACATCGAGGATTG
```

-continued

CAGGAAGTTTATTGACTTCTACAAGCAGAGCATCTCCAAACACCCTGAAT
GGAAGGATTTTGGCTTCCGGTTTTCCGACACACAGAGATATAACTCTATC
GACGAGTTCTACCGCGAGGTGGAAAATCAGGGGTATAAGCTGACTTTTGA
GAACATTTCTGAAAGTTACATCGACAGCGTGGTCAATCAGGGAAAGCTGT
ACCTGTTCCAGATCTATAACAAAGATTTTTCAGCATACAGCAAGGGCAGA
CCAAACCTGCATACACTGTACTGGAAGGCCCTGTTCGATGAGAGGAATCT
GCAGGACGTGGTCTATAAACTGAACGGAGAGGCCGAACTGTTTTACCGGA
AGCAGTCTATTCCTAAGAAAATCACTCACCCAGCTAAGGAGGCCATCGCT
AACAAGAACAAGGACAATCCTAAGAAAGAGAGCGTGTTCGAATACGATCT
GATTAAGGACAAGCGGTTCACCGAAGATAAGTTCTTTTTCCATTGTCCAA
TCACCATTAACTTCAAGTCAAGCGGCGCTAACAAGTTCAACGACGAGATC
AATCTGCTGCTGAAGGAAAAAGCAAACGATGTGCACATCCTGAGCATTGA
CCGAGGAGAGCGGCATCTGGCCTACTATACCCTGGTGGATGGCAAAGGGA
ATATCATTAAGCAGGATACATTCAACATCATTGGCAATGACCGGATGAAA
ACCAACTACCACGATAAACTGGCTGCAATCGAGAAGGATAGAGACTCAGC
TAGGAAGGACTGGAAGAAAATCAACAACATTAAGGAGATGAAGGAAGGCT
ATCTGAGCCAGGTGGTCCATGAGATTGCAAAGCTGGTCATCGAATACAAT
GCCATTGTGGTGTTCGAGGATCTGAACTTCGGCTTTAAGAGGGGGCGCTT
TAAGGTGGAAAAACAGGTCTATCAGAAGCTGGAGAAAATGCTGATCGAAA
AGCTGAATTACCTGGTGTTTAAAGATAACGAGTTCGACAAGACCGGAGGC
GTCCTGAGAGCCTACCAGCTGACAGCTCCCTTTGAAACTTTCAAGAAAAT
GGGAAAACAGACAGGCATCATCTACTATGTGCCAGCCGGATTCACTTCCA
AGATCTGCCCCGTGACCGGCTTTGTCAACCAGCTGTACCCTAAATATGAG
TCAGTGAGCAAGTCCCAGGAATTTTTCAGCAAGTTCGATAAGATCTGTTA
TAATCTGGACAAGGGGTACTTCGAGTTTTCCTTCGATTACAAGAACTTCG
GCGACAAGGCCGCTAAGGGGAAATGGACCATTGCCTCCTTCGGATCTCGC
CTGATCAACTTTCGAAATTCCGATAAAAACCACAATTGGGACACTAGGGA
GGTGTACCCAACCAAGGAGCTGGAAAAGCTGCTGAAAGACTACTCTATCG
AGTATGGACATGGCGAATGCATCAAGGCAGCCATCTGTGGCGAGAGTGAT
AAGAAATTTTTCGCCAAGCTGACCTCAGTGCTGAATACAATCCTGCAGAT
GCGGAACTCAAAGACCGGGACAGAACTGGACTATCTGATTAGCCCCGTGG
CTGATGTCAACGGAAACTTCTTCGACAGCAGACAGGCACCCAAAAATATG
CCTCAGGATGCAGACGCCAACGGGGCCTACCACATCGGGCTGAAGGGACT
GATGCTGCTGGGCCGGATCAAGAACAATCAGGAGGGGAAGAAGCTGAACC
TGGTCATTAAGAACGAGGAATACTTCGAGTTTGTCCAGAATAGAAATAAC
AAAAGGCCGGCGGCCACGAAAAAGGCCGGCCAGGCAAAAAAGAAAAAGGG
ATCCTACCCATACGATGTTCCAGATTACGCTTATCCCTACGACGTGCCTG
ATTATGCATACCCATATGATGTCCCCGACTATGCCTAA

*Lachnospiraceae bacterium* MC2017 (Lb3Cpf1; pY005), including NLS and HA tag:

(SEQ ID NO: 15)

MDYGNGQFERRAPLTKTITLRLKPIGETRETIREQKLLEQDAAFRKLVET
VTPIVDDCIRKIADNALCHFGTEYDFSCLGNAISKNDSKAIKKETEKVEK
LLAKVLTENLPDGLRKVNDINSAAFIQDTLTSFVQDDADKRVLIQELKGK
TVLMQRFLTTRITALTVWLPDRVFENFNIFIENAEKMRILLDSPLNEKIM
KFDPDAEQYASLEFYGQCLSQKDIDSYNLIISGIYADDEVKNPGINEIVK
EYNQQIRGDKDESPLPKLKKLHKQILMPVEKAFFVRVLSNDSDARSILEK
ILKDTEMLPSKIIEAMKEADAGDIAVYGSRLHELSHVIYGDHGKLSQIIY
DKESKRISELMETLSPKERKESKKRLEGLEEHIRKSTYTFDELNRYAEKN
VMAAYIAAVEESCAEIMRKEKDLRTLLSKEDVKIRGNRHNTLIVKNYFNA
WTVFRNLIRILRRKSEAEIDSDFYDVLDDSVEVLSLTYKGENLCRSYITK
KIGSDLKPEIATYGSALRPNSRWWSPGEKFNVKFHTIVRRDGRLYYFILP
KGAKPVELEDMDGDIECLQMRKIPNPTIFLPKLVFKDPEAFFRDNPEADE
FVFLSGMKAPVTITRETYEAYRYKLYTVGKLRDGEVSEEEYKRALLQVLT
AYKEFLENRMIYADLNFGFKDLEEYKDSSEFIKQVETHNTFMCWAKVSSS
QLDDLVKSGNGLLFEIWSERLESYYKYGNEKVLRGYEGVLLSILKDENLV
SMRTLLNSRPMLVYRPKESSKPMVVHRDGSRVVDRFDKDGKYIPPEVHDE
LYRFFNNLLIKEKLGEKARKILDNKKVKVKVLESERVKWSKFYDEQFAVT
FSVKKNADCLDTTKDLNAEVMEQYSESNRLILIRNTTDILYYLVLDKNGK
VLKQRSLNIINDGARDVDWKERFRQVTKDRNEGYNEWDYSRTSNDLKEVY
LNYALKEIAEAVIEYNAILIIEKMSNAFKDKYSFLDDVTFKGFETKLLAK
LSDLHFRGIKDGEPCSFTNPLQLCQNDSNKILQDGVIFMVPNSMTRSLDP
DTGFIFAINDHNIRTKKAKLNFLSKFDQLKVSSEGCLIMKYSGDSLPTHN
TDNRVWNCCCNHPITNYDRETKKVEFIEEPVEELSRVLEENGIETDTELN
KLNERENVPGKVVDAIYSLVLNYLRGTVSGVAGQRAVYYSPVTGKKYDIS
FIQAMNLNRKCDYYRIGSKERGEWTDFVAQLINKRPAATKKAGQAKKKKG
SYPYDVPDYAYPYDVPDYAYPYDVPDYA

SEQ ID NO: 15 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 15 may be encoded by the following nucleotide sequence:

ATGGATTACGGCAACGGCCAGTTTGAGCGGAGAGCCCCCCTGACCAAGAC
AATCACCCTGCGCCTGAAGCCTATCGGCGAGACACGGGAGACAATCCGCG
AGCAGAAGCTGCTGGAGCAGGACGCCGCCTTCAGAAAGCTGGTGGAGACA
GTGACCCCTATCGTGGACGATTGTATCAGGAAGATCGCCGATAACGCCCT
GTGCCACTTTGGCACCGAGTATGACTTCAGCTGTCTGGGCAACGCCATCT
CTAAGAATGACAGCAAGGCCATCAAGAAGGAGACAGAGAAGGTGGAGAAG
CTGCTGGCCAAGGTGCTGACCGAGAATCTGCCAGATGGCCTGCGCAAGGT
GAACGACATCAATTCCGCCGCCTTTATCCAGGATACACTGACCTCTTTCG
TGCAGGACGATGCCGACAAGCGGGTGCTGATCCAGGAGCTGAAGGGCAAG

-continued

ACCGTGCTGATGCAGCGGTTCCTGACCACACGGATCACAGCCCTGACCGT
GTGGCTGCCCGACAGAGTGTTCGAGAACTTTAATATCTTCATCGAGAACG
CCGAGAAGATGAGAATCCTGCTGGACTCCCCTCTGAATGAGAAGATCATG
AAGTTTGACCCAGATGCCGAGCAGTACGCCTCTCTGGAGTTCTATGGCCA
GTGCCTGTCTCAGAAGGACATCGATAGCTACAACCTGATCATCTCCGGCA
TCTATGCCGACGATGAGGTGAAGAACCCTGGCATCAATGAGATCGTGAAG
GAGTACAATCAGCAGATCCGGGGCGACAAGGATGAGTCCCCACTGCCCAA
GCTGAAGAAGCTGCACAAGCAGATCCTGATGCCAGTGGAGAAGGCCTTCT
TTGTGCGCGTGCTGTCTAACGACAGCGATGCCCGGAGCATCCTGGAGAAG
ATCCTGAAGGACACAGAGATGCTGCCCTCCAAGATCATCGAGGCCATGAA
GGAGGCAGATGCAGGCGACATCGCCGTGTACGGCAGCCGGCTGCACGAGC
TGAGCCACGTGATCTACGGCGATCACGGCAAGCTGTCCCAGATCATCTAT
GACAAGGAGTCCAAGAGGATCTCTGAGCTGATGGAGACACTGTCTCCAAA
GGAGCGCAAGGAGAGCAAGAAGCGGCTGGAGGGCCTGGAGGAGCACATCA
GAAAGTCTACATACACCTTCGACGAGCTGAACAGGTATGCCGAGAAGAAT
GTGATGGCAGCATACATCGCAGCAGTGGAGGAGTCTTGTGCCGAGATCAT
GAGAAAGGAGAAGGATCTGAGGACCCTGCTGAGCAAGGAGGACGTGAAGA
TCCGGGGCAACAGACACAATACACTGATCGTGAAGAACTACTTTAATGCC
TGGACCGTGTTCCGGAACCTGATCAGAATCCTGAGGCGCAAGTCCGAGGC
CGAGATCGACTCTGACTTCTACGATGTGCTGGACGATTCCGTGGAGGTGC
TGTCTCTGACATACAAGGGCGAGAATCTGTGCCGCAGCTATATCACCAAG
AAGATCGGCTCCGACCTGAAGCCCGAGATCGCCACATACGGCAGCGCCCT
GAGGCCTAACAGCCGCTGGTGGTCCCCAGGAGAGAAGTTTAATGTGAAGT
TCCACACCATCGTGCGGAGAGATGGCCGGCTGTACTATTTCATCCTGCCC
AAGGGCGCCAAGCCTGTGGAGCTGGAGGACATGGATGGCGACATCGAGTG
TCTGCAGATGAGAAAGATCCCTAACCCAACAATCTTTCTGCCCAAGCTGG
TGTTCAAGGACCCTGAGGCCTTCTTTAGGGATAATCCAGAGGCCGACGAG
TTCGTGTTTCTGAGCGGCATGAAGGCCCCCGTGACAATCACCAGAGAGAC
ATACGAGGCCTACAGGTATAAGCTGTATACCGTGGGCAAGCTGCGCGATG
GCGAGGTGTCCGAAGAGGAGTACAAGCGGGCCCTGCTGCAGGTGCTGACC
GCCTACAAGGAGTTTCTGGAGAACAGAATGATCTATGCCGACCTGAATTT
CGGCTTTAAGGATCTGGAGGAGTATAAGGACAGCTCCGAGTTTATCAAGC
AGGTGGAGACACACAACACCTTCATGTGCTGGGCCAAGGTGTCTAGCTCC
CAGCTGGACGATCTGGTGAAGTCTGGCAACGGCCTGCTGTTCGAGATCTG
GAGCGAGCGCCTGGAGTCCTACTATAAGTACGGCAATGAGAAGGTGCTGC
GGGGCTATGAGGGCGTGCTGCTGAGCATCCTGAAGGATGAGAACCTGGTG
TCCATGCGGACCCTGCTGAACAGCCGGCCCATGCTGGTGTACCGGCCAAA
GGAGTCTAGCAAGCCTATGGTGGTGCACCGGGATGGCAGCAGAGTGGTGG
ACAGGTTTGATAAGGACGGCAAGTACATCCCCCCTGAGGTGCACGACGAG
CTGTATCGCTTCTTTAACAATCTGCTGATCAAGGAGAAGCTGGGCGAGAA
GGCCCGGAAGATCCTGGACAACAAGAAGGTGAAGGTGAAGGTGCTGGAGA
GCGAGAGAGTGAAGTGGTCCAAGTTCTACGATGAGCAGTTTGCCGTGACC
TTCAGCGTGAAGAAGAACGCCGATTGTCTGGACACCACAAAGGACCTGAA
TGCCGAAGTGATGGAGCAGTATAGCGAGTCCAACAGACTGATCCTGATCA
GGAATACCACAGATATCCTGTACTATCTGGTGCTGGACAAGAATGGCAAG
GTGCTGAAGCAGAGATCCCTGAACATCATCAATGACGGCGCCAGGGATGT
GGACTGGAAGGAGAGGTTCCGCCAGGTGACAAAGGATAGAAACGAGGGCT
ACAATGAGTGGGATTATTCCAGGACCTCTAACGACCTGAAGGAGGTGTAC
CTGAATTATGCCCTGAAGGAGATCGCCGAGGCCGTGATCGAGTACAACGC
CATCCTGATCATCGAGAAGATGTCTAATGCCTTTAAGGACAAGTATAGCT
TCCTGGACGACGTGACCTTCAAGGGCTTCGAGACAAAGCTGCTGGCCAAG
CTGAGCGATCTGCACTTTAGGGGCATCAAGGACGGCGAGCCATGTTCCTT
CACAAACCCCCTGCAGCTGTGCCAGAACGATTCTAATAAGATCCTGCAGG
ACGGCGTGATCTTTATGGTGCCAAATTCTATGACACGGAGCCTGGACCCC
GACACCGGCTTCATCTTTGCCATCAACGACCACAATATCAGGACCAAGAA
GGCCAAGCTGAACTTTCTGAGCAAGTTCGATCAGCTGAAGGTGTCCTCTG
AGGGCTGCCTGATCATGAAGTACAGCGGCGATTCCCTGCCTACACACAAC
ACCGACAATCGCGTGTGGAACTGCTGTTGCAATCACCCAATCACAAACTA
TGACCGGGAGACAAAGAAGGTGGAGTTCATCGAGGAGCCCGTGGAGGAGC
TGTCCCGCGTGCTGGAGGAGAATGGCATCGAGACAGACACCGAGCTGAAC
AAGCTGAATGAGCGGGAGAACGTGCCTGGCAAGGTGGTGGATGCCATCTA
CTCTCTGGTGCTGAATTATCTGCGCGGCACAGTGAGCGGAGTGGCAGGAC
AGAGGGCCGTGTACTATAGCCCTGTGACCGGCAAGAAGTACGATATCTCC
TTTATCCAGGCCATGAACCTGAATAGGAAGTGTGACTACTATAGGATCGG
CTCCAAGGAGAGGGGAGAGTGGACCGATTTCGTGGCCCAGCTGATCAACA
AAAGGCCGGCGGCCACGAAAAAGGCCGGCCAGGCAAAAAAGAAAAAGGGA
TCCTACCCATACGATGTTCCAGATTACGCTTATCCCTACGACGTGCCTGA
TTATGCATACCCATATGATGTCCCCGACTATGCCTAA

*Butyrivibrio proteoclasticus* (BpCpf1; pY006), including NLS and HA tag:

(SEQ ID NO: 17)

MSIYQEFVNKYSLSKTLRFELIPQGKTLENIKARGLILDDEKRAKDYKKA
KQIIDKYHQFFIEEILSSVCISEDLLQNYSDVYFKLKKSDDDNLQKDFKS
AKDTIKKQISEYIKDSEKFKNLFNQNLIDAKKGQESDLILWLKQSKDNGI
ELFKANSDITDIDEALEIIKSFKGWTTYFKGFHENRKNVYSSNDIPTSII
YRIVDDNLPKFLENKAKYESLKDKAPEAINYEQIKKDLAEELTFDIDYKT
SEVNQRVFSLDEVFEIANFNNYLNQSGITKFNTIIGGKFVNGENTKRKGI
NEYINLYSQQINDKTLKKYKMSVLFKQILSDTESKSFVIDKLEDDSDVVT
TMQSFYEQIAAFKTVEEKSIKETLSLLFDDLKAQKLDLSKIYFKNDKSLT
DLSQQVFDDYSVIGTAVLEYITQQIAPKNLDNPSKKEQELIAKKTEKAKY
LSLETIKLALEEFNKHRDIDKQCRFEEILANFAAIPMIFDEIAQNKDNLA

QISIKYQNQGKKDLLQASAEDDVKAIKDLLDQTNNLLHKLKIFHISQSED

KANILDKDEHFYLVFEECYFELANIVPLYNKIRNYITQKPYSDEKFKLNF

ENSTLANGWDKNKEPDNTAILFIKDDKYYLGVMNKKNNKIFDDKAIKENK

GEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSI

DEFYREVENQGYKLTFENISESYIDSVVNQGKLYLFQIYNKDFSAYSKGR

PNLHTLYWKALFDERNLQDVVYKLNGEAELFYRKQSIPKKITHPAKEAIA

NKNKDNPKKESVFEYDLIKDKRFTEDKFFFHCPITINFKSSGANKFNDEI

NLLLKEKANDVHILSIDRGERHLAYYTLVDGKGNIIKQDTFNIIGNDRMK

TNYHDKLAAIEKDRDSARKDWKKINNIKEMKEGYLSQVVHEIAKLVIEYN

AIVVFEDLNFGFKRGRFKVEKQVYQKLEKMLIEKLNYLVFKDNEFDKTGG

VLRAYQLTAPFETFKKMGKQTGIIYYVPAGFTSKICPVTGFVNQLYPKYE

SVSKSQEFFSKFDKICYNLDKGYFEFSFDYKNFGDKAAKGKWTIASFGSR

LINFRNSDKNHNWDTREVYPTKELEKLLKDYSIEYGHGECIKAAICGESD

KKFFAKLTSVLNTILQMRNSKTGTELDYLISPVADVNGNFFDSRQAPKNM

PQDADANGAYHIGLKGLMLLGRIKNNQEGKKLNLVIKNEEYFEFVQNRNN

KRPAATKKAGQAKKKKGSYPYDVPDYAYPYDVPDYAYPYDVPDYA

SEQ ID NO: 17 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 17 may be encoded by the following nucleotide sequence:

```
                                     (SEQ ID NO: 18)
ATGAGCATCTACCAGGAGTTCGTCAACAAGTATTCACTGAGTAAGACACT

GCGGTTCGAGCTGATCCCACAGGGCAAGACACTGGAGAACATCAAGGCCC

GAGGCCTGATTCTGGACGATGAGAAGCGGGCAAAAGACTATAAGAAAGCC

AAGCAGATCATTGATAAATACCACCAGTTCTTTATCGAGGAAATTCTGAG

CTCCGTGTGCATCAGTGAGGATCTGCTGCAGAATTACTCAGACGTGTACT

TCAAGCTGAAGAAGAGCGACGATGACAACCTGCAGAAGGACTTCAAGTCC

GCCAAGGACACCATCAAGAAACAGATTAGCGAGTACATCAAGGACTCCGA

AAAGTTTAAAAATCTGTTCAACCAGAATCTGATCGATGCTAAGAAAGGCC

AGGAGTCCGACCTGATCCTGTGGCTGAAACAGTCTAAGGACAATGGGATT

GAACTGTTCAAGGCTAACTCCGATATCACTGATATTGACGAGGCACTGGA

AATCATCAAGAGCTTCAAGGGATGGACCACATACTTTAAAGGCTTCCACG

AGAACCGCAAGAACGTGTACTCCAGCAACGACATTCCTACCTCCATCATC

TACCGAATCGTCGATGACAATCTGCCAAAGTTCCTGGAGAACAAGGCCAA

ATATGAATCTCTGAAGGACAAAGCTCCCGAGGCAATTAATTACGAACAGA

TCAAGAAAGATCTGGCTGAGGAACTGACATTCGATATCGACTATAAGACT

AGCGAGGTGAACCAGAGGGTCTTTTCCCTGGACGAGGTGTTTGAAATCGC

CAATTTCAACAATTACCTGAACCAGTCCGGCATTACTAAATTCAATACCA

TCATTGGCGGGAAGTTTGTGAACGGGGAGAATACCAAGCGCAAGGGAATT

AACGAATACATCAATCTGTATAGCCAGCAGATCAACGACAAAACTCTGAA

GAAATACAAGATGTCTGTGCTGTTCAAACAGATCCTGAGTGATACCGAGT

CCAAGTCTTTTGTCATTGATAAACTGGAAGATGACTCAGACGTGGTCACT

ACCATGCAGAGCTTTTATGAGCAGATCGCCGCTTTCAAGACAGTGGAGGA

AAAATCTATTAAGGAAACTCTGAGTCTGCTGTTCGATGACCTGAAAGCCC

AGAAGCTGGACCTGAGTAAGATCTACTTCAAAAACGATAAGAGTCTGACA

GACCTGTCACAGCAGGTGTTTGATGACTATTCCGTGATTGGGACCGCCGT

CCTGGAGTACATTACACAGCAGATCGCTCCAAAGAACCTGGATAATCCCT

CTAAGAAAGAGCAGGAACTGATCGCTAAGAAAACCGAGAAGGCAAAATAT

CTGAGTCTGGAAACAATTAAGCTGGCACTGGAGGAGTTCAACAAGCACAG

GGATATTGACAAACAGTGCCGCTTTGAGGAAATCCTGGCCAACTTCGCAG

CCATCCCCATGATTTTTGATGAGATCGCCCAGAACAAAGACAATCTGGCT

CAGATCAGTATTAAGTACCAGAACCAGGGCAAGAAAGACCTGCTGCAGGC

TTCAGCAGAAGATGACGTGAAAGCCATCAAGGATCTGCTGGACCAGACCA

ACAATCTGCTGCACAAGCTGAAAATCTTCCATATTAGTCAGTCAGAGGAT

AAGGCTAATATCCTGGATAAAGACGAACACTTCTACCTGGTGTTCGAGGA

ATGTTACTTCGAGCTGGCAAACATTGTCCCCCTGTATAACAAGATTAGGA

ACTACATCACACAGAAGCCTTACTCTGACGAGAAGTTTAAACTGAACTTC

GAAAATAGTACCCTGGCCAACGGGTGGGATAAGAACAAGGAGCCTGACAA

CACAGCTATCCTGTTCATCAAGGATGACAAGTACTATCTGGGAGTGATGA

ATAAGAAAAACAATAAGATCTTCGATGACAAAGCCATTAAGGAGAACAAA

GGGGAAGGATACAAGAAAATCGTGTATAAGCTGCTGCCCGGCGCAAATAA

GATGCTGCCTAAGGTGTTCTTCAGCGCCAAGAGTATCAAATTCTACAACC

CATCCGAGGACATCCTGCGGATTAGAAATCACTCAACACATACTAAGAAC

GGGAGCCCCCAGAAGGGATATGAGAAATTTGAGTTCAACATCGAGGATTG

CAGGAAGTTTATTGACTTCTACAAGCAGAGCATCTCCAAACACCCTGAAT

GGAAGGATTTTGGCTTCCGGTTTTCCGACACACAGAGATATAACTCTATC

GACGAGTTCTACCGCGAGGTGGAAAATCAGGGGTATAAGCTGACTTTTGA

GAACATTTCTGAAAGTTACATCGACAGCGTGGTCAATCAGGGAAAGCTGT

ACCTGTTCCAGATCTATAACAAAGATTTTTCAGCATACAGCAAGGGCAGA

CCAAACCTGCATACACTGTACTGGAAGGCCCTGTTCGATGAGAGGAATCT

GCAGGACGTGGTCTATAAACTGAACGGAGAGGCCGAACTGTTTTACCGGA

AGCAGTCTATTCCTAAGAAAATCACTCACCCAGCTAAGGAGGCCATCGCT

AACAAGAACAAGGACAATCCTAAGAAAGAGAGCGTGTTCGAATACGATCT

GATTAAGGACAAGCGGTTCACCGAAGATAAGTTCTTTTTCCATTGTCCAA

TCACCATTAACTTCAAGTCAAGCGGCGCTAACAAGTTCAACGACGAGATC

AATCTGCTGCTGAAGGAAAAAGCAAACGATGTGCACATCCTGAGCATTGA

CCGAGGAGAGCGGCATCTGGCCTACTATACCCTGGTGGATGGCAAAGGGA

ATATCATTAAGCAGGATACATTCAACATCATTGGCAATGACCGGATGAAA

ACCAACTACCACGATAAACTGGCTGCAATCGAGAAGGATAGAGACTCAGC
```

-continued

TAGGAAGGACTGGAAGAAAATCAACAACATTAAGGAGATGAAGGAAGGCT

ATCTGAGCCAGGTGGTCCATGAGATTGCAAAGCTGGTCATCGAATACAAT

GCCATTGTGGTGTTCGAGGATCTGAACTTCGGCTTTAAGAGGGGGCGCTT

TAAGGTGGAAAAACAGGTCTATCAGAAGCTGGAGAAAATGCTGATCGAAA

AGCTGAATTACCTGGTGTTTAAAGATAACGAGTTCGACAAGACCGGAGGC

GTCCTGAGAGCCTACCAGCTGACAGCTCCCTTTGAAACTTTCAAGAAAAT

GGGAAAACAGACAGGCATCATCTACTATGTGCCAGCCGGATTCACTTCCA

AGATCTGCCCCGTGACCGGCTTTGTCAACCAGCTGTACCCTAAATATGAG

TCAGTGAGCAAGTCCCAGGAATTTTTCAGCAAGTTCGATAAGATCTGTTA

TAATCTGGACAAGGGGTACTTCGAGTTTTCCTTCGATTACAAGAACTTCG

GCGACAAGGCCGCTAAGGGGAAATGGACCATTGCCTCCTTCGGATCTCGC

CTGATCAACTTTCGAAATTCCGATAAAAACCACAATTGGGACACTAGGGA

GGTGTACCCAACCAAGGAGCTGGAAAAGCTGCTGAAAGACTACTCTATCG

AGTATGGACATGGCGAATGCATCAAGGCAGCCATCTGTGGCGAGAGTGAT

AAGAAATTTTTCGCCAAGCTGACCTCAGTGCTGAATACAATCCTGCAGAT

GCGGAACTCAAAGACCGGGACAGAACTGGACTATCTGATTAGCCCCGTGG

CTGATGTCAACGGAAACTTCTTCGACAGCAGACAGGCACCCAAAAATATG

CCTCAGGATGCAGACGCCAACGGGGCCTACCACATCGGGCTGAAGGGACT

GATGCTGCTGGGCCGGATCAAGAACAATCAGGAGGGGAAGAAGCTGAACC

TGGTCATTAAGAACGAGGAATACTTCGAGTTTGTCCAGAATAGAAATAAC

AAAAGGCCGGCGGCCACGAAAAAGGCCGGCCAGGCAAAAAAGAAAAAGGG

ATCCTACCCATACGATGTTCCAGATTACGCTTATCCCTACGACGTGCCTG

ATTATGCATACCCATATGATGTCCCCGACTATGCCTAA

*Peregrinibacteria bacterium* GW2011_GWA_33_10 (PeCpf1; pY007), including NLS and HA tag:

(SEQ ID NO: 19)

MSNFFKNFTNLYELSKTLRFELKPVGDTLTNMKDHLEYDEKLQTFLKDQN

IDDAYQALKPQFDEIHEEFITDSLESKKAKEIDFSEYLDLFQEKKELNDS

EKKLRNKIGETFNKAGEKWKKEKYPQYEWKKGSKIANGADILSCQDMLQF

IKYKNPEDEKIKNYIDDTLKGFFTYFGGFNQNRANYYETKKEASTAVATR

IVHENLPKFCDNVIQFKHIIKRKKDGTVEKTERKTEYLNAYQYLKNNNKI

TQIKDAETEKMIESTPIAEKIFDVYYFSSCLSQKQIEEYNRIIGHYNLLI

NLYNQAKRSEGKHLSANEKKYKDLPKFKTLYKQIGCGKKKDLFYTIKCDT

EEEANKSRNEGKESHSVEEIINKAQEAINKYFKSNNDCENINTVPDFINY

ILTKENYEGVYWSKAAMNTISDKYFANYHDLQDRLKEAKVFQKADKKSED

DIKIPEAIELSGLFGVLDSLADWQTTLFKSSILSNEDKLKIITDSQTPSE

ALLKMIFNDIEKNMESFLKETNDIITLKKYKGNKEGTEKIKQWFDYTLAI

NRMLKYFLVKENKIKGNSLDTNISEALKTLIYSDDAEWFKWYDALRNYLT

QKPQDEAKENKLKLNFDNPSLAGGWDVNKECSNFCVILKDKNEKKYLAIM

KKGENTLFQKEWTEGRGKNLTKKSNPLFEINNCEILSKMEYDFWADVSKM

-continued

IPKCSTQLKAVVNHFKQSDNEFIFPIGYKVTSGEKFREECKISKQDFELN

NKVFNKNELSVTAMRYDLSSTQEKQYIKAFQKEYWELLFKQEKRDTKLTN

NEIFNEWINFCNKKYSELLSWERKYKDALTNWINFCKYFLSKYPKTTLFN

YSFKESENYNSLDEFYRDVDICSYKLNINTTINKSILDRLVEEGKLYLFE

IKNQDSNDGKSIGHKNNLHTIYWNAIFENFDNRPKLNGEAEIFYRKAISK

DKLGIVKGKKTKNGTEIIKNYRFSKEKFILHVPITLNFCSNNEYVNDIVN

TKFYNFSNLHFLGIDRGEKHLAYYSLVNKNGEIVDQGTLNLPFTDKDGNQ

RSIKKEKYFYNKQEDKWEAKEVDCWNYNDLLDAMASNRDMARKNWQRIGT

IKEAKNGYVSLVIRKIADLAVNNERPAFIVLEDLNTGFKRSRQKIDKSVY

QKFELALAKKLNFLVDKNAKRDEIGSPTKALQLTPPVNNYGDIENKKQAG

IMLYTRANYTSQTDPATGWRKTIYLKAGPEETTYKKDGKIKNKSVKDQII

ETFTDIGFDGKDYYFEYDKGEFVDEKTGEIKPKKWRLYSGENGKSLDRFR

GEREKDKYEWKIDKIDIVKILDDLFVNFDKNISLLKQLKEGVELTRNNEH

GTGESLRFAINLIQQIRNTGNNERDNDFILSPVRDENGKHFDSREYWDKE

TKGEKISMPSSGDANGAFNIARKGIIMNAHILANSDSKDLSLFVSDEEWD

LHLNNKTEWKKQLNIFSSRKAMAKRKKKRPAATKKAGQAKKKKGSYPYDV

PDYAYPYDVPDYAYPYDVPDYA

SEQ ID NO: 19 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 19 may be encoded by the following nucleotide sequence:

(SEQ ID NO: 20)

ATGTCCAACTTCTTTAAGAATTTCACCAACCTGTATGAGCTGTCCAAGAC

ACTGAGGTTTGAGCTGAAGCCCGTGGGCGACACCCTGACAAACATGAAGG

ACCACCTGGAGTACGATGAGAAGCTGCAGACCTTCCTGAAGGATCAGAAT

ATCGACGATGCCTATCAGGCCCTGAAGCCTCAGTTCGACGAGATCCACGA

GGAGTTTATCACAGATTCTCTGGAGAGCAAGAAGGCCAAGGAGATCGACT

TCTCCGAGTACCTGGATCTGTTTCAGGAGAAGAAGGAGCTGAACGACTCT

GAGAAGAAGCTGCGCAACAAGATCGGCGAGACATTCAACAAGGCCGGCGA

GAAGTGGAAGAAGGAGAAGTACCCTCAGTATGAGTGGAAGAAGGGCTCCA

AGATCGCCAATGGCGCCGACATCCTGTCTTGCCAGGATATGCTGCAGTTT

ATCAAGTATAAGAACCCAGAGGATGAGAAGATCAAGAATTACATCGACGA

TACACTGAAGGGCTTCTTTACCTATTTCGGCGGCTTTAATCAGAACAGGG

CCAACTACTATGAGACAAAGAAGGAGGCCTCCACCGCAGTGGCAACAAGG

ATCGTGCACGAGAACCTGCCAAAGTTCTGTGACAATGTGATCCAGTTTAA

GCACATCATCAAGCGGAAGAAGGATGGCACCGTGGAGAAAACCGAGAGAA

AGACCGAGTACCTGAACGCCTACCAGTATCTGAAGAACAATAACAAGATC

ACACAGATCAAGGACGCCGAGACAGAGAAGATGATCGAGTCTACACCCAT

CGCCGAGAAGATCTTCGACGTGTACTACTTCAGCAGCTGCCTGAGCCAGA

AGCAGATCGAGGAGTACAACCGGATCATCGGCCACTATAATCTGCTGATC

-continued

AACCTGTATAACCAGGCCAAGAGATCTGAGGGCAAGCACCTGAGCGCCAA

CGAGAAGAAGTATAAGGACCTGCCTAAGTTCAAGACCCTGTATAAGCAGA

TCGGCTGCGGCAAGAAGAAGGACCTGTTTTACACAATCAAGTGTGATACC

GAGGAGGAGGCCAATAAGTCCCGGAACGAGGGCAAGGAGTCCCACTCTGT

GGAGGAGATCATCAACAAGGCCCAGGAGGCCATCAATAAGTACTTCAAGT

CTAATAACGACTGTGAGAATATCAACACCGTGCCCGACTTCATCAACTAT

ATCCTGACAAAGGAGAATTACGAGGGCGTGTATTGGAGCAAGGCCGCCAT

GAACACCATCTCCGACAAGTACTTCGCCAATTATCACGACCTGCAGGATA

GACTGAAGGAGGCCAAGGTGTTTCAGAAGGCCGATAAGAAGTCCGAGGAC

GATATCAAGATCCCAGAGGCCATCGAGCTGTCTGGCCTGTTCGGCGTGCT

GGACAGCCTGGCCGATTGGCAGACCACACTGTTTAAGTCTAGCATCCTGA

GCAACGAGGACAAGCTGAAGATCATCACAGATTCCCAGACCCCCTCTGAG

GCCCTGCTGAAGATGATCTTCAATGACATCGAGAAGAACATGGAGTCCTT

TCTGAAGGAGACAAACGATATCATCACCCTGAAGAAGTATAAGGGCAATA

AGGAGGGCACCGAGAAGATCAAGCAGTGGTTCGACTATACACTGGCCATC

AACCGGATGCTGAAGTACTTTCTGGTGAAGGAGAATAAGATCAAGGGCAA

CTCCCTGGATACCAATATCTCTGAGGCCCTGAAAACCCTGATCTACAGCG

ACGATGCCGAGTGGTTCAAGTGGTACGACGCCCTGAGAAACTATCTGACC

CAGAAGCCTCAGGATGAGGCCAAGGAGAATAAGCTGAAGCTGAATTTCGA

CAACCCATCTCTGGCCGGCGGCTGGGATGTGAACAAGGAGTGCAGCAATT

TTTGCGTGATCCTGAAGGACAAGAACGAGAAGAAGTACCTGGCCATCATG

AAGAAGGGCGAGAATACCCTGTTCCAGAAGGAGTGGACAGAGGGCCGGGG

CAAGAACCTGACAAAGAAGTCTAATCCACTGTTCGAGATCAATAACTGCG

AGATCCTGAGCAAGATGGAGTATGACTTTTGGGCCGACGTGAGCAAGATG

ATCCCCAAGTGTAGCACCCAGCTGAAGGCCGTGGTGAACCACTTCAAGCA

GTCCGACAATGAGTTCATCTTTCCTATCGGCTACAAGGTGACAAGCGGCG

AGAAGTTTAGGGAGGAGTGCAAGATCTCCAAGCAGGACTTCGAGCTGAAT

AACAAGGTGTTTAATAAGAACGAGCTGAGCGTGACCGCCATGCGCTACGA

TCTGTCCTCTACACAGGAGAAGCAGTATATCAAGGCCTTCCAGAAGGAGT

ACTGGGAGCTGCTGTTTAAGCAGGAGAAGCGGGACACCAAGCTGACAAAT

AACGAGATCTTCAACGAGTGGATCAATTTTTGCAACAAGAAGTATAGCGA

GCTGCTGTCCTGGGAGAGAAAGTACAAGGATGCCCTGACCAATTGGATCA

ACTTCTGTAAGTACTTTCTGAGCAAGTATCCCAAGACCACACTGTTCAAC

TACTCTTTTAAGGAGAGCGAGAATTATAACTCCCTGGACGAGTTCTACCG

GGACGTGGATATCTGTTCTTACAAGCTGAATATCAACACCACAATCAATA

AGAGCATCCTGGATAGACTGGTGGAGGAGGGCAAGCTGTACCTGTTTGAG

ATCAAGAATCAGGACAGCAACGATGGCAAGTCCATCGGCCACAAGAATAA

CCTGCACACCATCTACTGGAACGCCATCTTCGAGAATTTTGACAACAGGC

CTAAGCTGAATGGCGAGGCCGAGATCTTCTATCGCAAGGCCATCTCCAAG

GATAAGCTGGGCATCGTGAAGGGCAAGAAAACCAAGAACGGCACCGAGAT

-continued

CATCAAGAATTACAGATTCAGCAAGGAGAAGTTTATCCTGCACGTGCCAA

TCACCCTGAACTTCTGCTCCAATAACGAGTATGTGAATGACATCGTGAAC

ACAAAGTTCTACAATTTTTCCAACCTGCACTTTCTGGGCATCGATAGGGG

CGAGAAGCACCTGGCCTACTATTCTCTGGTGAATAAGAACGGCGAGATCG

TGGACCAGGGCACACTGAACCTGCCTTTCACCGACAAGGATGGCAATCAG

CGCAGCATCAAGAAGGAGAAGTACTTTTATAACAAGCAGGAGGACAAGTG

GGAGGCCAAGGAGGTGGATTGTTGGAATTATAACGACCTGCTGGATGCCA

TGGCCTCTAACCGGGACATGGCCAGAAAGAATTGGCAGAGGATCGGCACC

ATCAAGGAGGCCAAGAACGGCTACGTGAGCCTGGTCATCAGGAAGATCGC

CGATCTGGCCGTGAATAACGAGCGCCCCGCCTTCATCGTGCTGGAGGACC

TGAATACAGGCTTTAAGCGGTCCAGACAGAAGATCGATAAGAGCGTGTAC

CAGAAGTTCGAGCTGGCCCTGGCCAAGAAGCTGAACTTTCTGGTGGACAA

GAATGCCAAGCGCGATGAGATCGGCTCCCCTACAAAGGCCCTGCAGCTGA

CCCCCCCTGTGAATAACTACGGCGACATTGAGAACAAGAAGCAGGCCGGC

ATCATGCTGTATACCCGGGCCAATTATACCTCTCAGACAGATCCAGCCAC

AGGCTGGAGAAAGACCATCTATCTGAAGGCCGGCCCCGAGGAGACAACAT

ACAAGAAGGACGGCAAGATCAAGAACAAGAGCGTGAAGGACCAGATCATC

GAGACATTCACCGATATCGGCTTTGACGGCAAGGATTACTATTTCGAGTA

CGACAAGGGCGAGTTTGTGGATGAGAAAACCGGCGAGATCAAGCCCAAGA

AGTGGCGGCTGTACTCCGGCGAGAATGGCAAGTCCCTGGACAGGTTCCGC

GGAGAGAGGGAGAAGGATAAGTATGAGTGGAAGATCGACAAGATCGATAT

CGTGAAGATCCTGGACGATCTGTTCGTGAATTTTGACAAGAACATCAGCC

TGCTGAAGCAGCTGAAGGAGGGCGTGGAGCTGACCCGGAATAACGAGCAC

GGCACAGGCGAGTCCCTGAGATTCGCCATCAACCTGATCCAGCAGATCCG

GAATACCGGCAATAACGAGAGAGACAACGATTTCATCCTGTCCCCAGTGA

GGGACGAGAATGGCAAGCACTTTGACTCTCGCGAGTACTGGGATAAGGAG

ACAAAGGGCGAGAAGATCAGCATGCCCAGCTCCGGCGATGCCAATGGCGC

CTTCAACATCGCCCGGAAGGGCATCATCATGAACGCCCACATCCTGGCCA

ATAGCGACTCCAAGGATCTGTCCCTGTTCGTGTCTGACGAGGAGTGGGAT

CTGCACCTGAATAACAAGACCGAGTGGAAGAAGCAGCTGAACATCTTTTC

TAGCAGGAAGGCCATGGCCAAGCGCAAGAAGAAAAGGCCGGCGGCCACGA

AAAAGGCCGGCCAGGCAAAAAAGAAAAAGGGATCCTACCCATACGATGTT

CCAGATTACGCTTATCCCTACGACGTGCCTGATTATGCATACCCATATGA

TGTCCCCGACTATGCCTAA

*Parcubacteria bacterium* GWC2011_GWC2_44_17 (PbCpf1; pY008), including NLS and HA tag:

(SEQ ID NO: 21)

MENIFDQFIGKYSLSKTLRFELKPVGKTEDFLKINKVFEKDQTIDDSYNQ

AKFYFDSLHQKFIDAALASDKTSELSFQNFADVLEKQNKIILDKKREMGA

LRKRDKNAVGIDRLQKEINDAEDIIQKEKEKIYKDVRTLFDNEAESWKTY

YQEREVDGKKITFSKADLKQKGADFLTAAGILKVLKYEFPEEKEKEFQAK

-continued

NQPSLFVEEKENPGQKRYIFDSFDKFAGYLTKFQQTKKNLYAADGTSTAV
ATRIADNFIIFHQNTKVFRDKYKNNHTDLGFDEENIFEIERYKNCLLQRE
IEHIKNENSYNKIIGRINKKIKEYRDQKAKDTKLTKSDFPFFKNLDKQIL
GEVEKEKQLIEKTREKTEEDVLIERFKEFIENNEERFTAAKKLMNAFCNG
EFESEYEGIYLKNKAINTISRRWFVSDRDFELKLPQQKSKNKSEKNEPKV
KKFISIAEIKNAVEELDGDIFKAVFYDKKIIAQGGSKLEQFLVIWKYEFE
YLFRDIERENGEKLLGYDSCLKIAKQLGIFPQEKEAREKATAVIKNYADA
GLGIFQMMKYFSLDDKDRKNTPGQLSTNFYAEYDGYYKDFEFIKYYNEFR
NFITKKPFDEDKIKLNFENGALLKGWDENKEYDFMGVILKKEGRLYLGIM
HKNHRKLFQSMGNAKGDNANRYQKMIYKQIADASKDVPRLLLTSKKAMEK
FKPSQEILRIKKEKTFKRESKNFSLRDLHALIEYYRNCIPQYSNWSFYDF
QFQDTGKYQNIKEFTDDVQKYGYKISFRDIDDEYINQALNEGKMYLFEVV
NKDIYNTKNGSKNLHTLYFEHILSAENLNDPVFKLSGMAEIFQRQPSVNE
REKITTQKNQCILDKGDRAYKYRRYTEKKIMFHMSLVLNTGKGEIKQVQF
NKIINQRISSSDNEMRVNVIGIDRGEKNLLYYSVVKQNGEIIEQASLNEI
NGVNYRDKLIEREKERLKNRQSWKPVVKIKDLKKGYISHVIHKICQLIEK
YSAIVVLEDLNMRFKQIRGGIERSVYQQFEKALIDKLGYLVFKDNRDLRA
PGGVLNGYQLSAPFVSFEKMRKQTGILFYTQAEYTSKTDPITGFRKNVYI
SNSASLDKIKEAVKKFDAIGWDGKEQSYFFKYNPYNLADEKYKNSTVSKE
WAIFASAPRIRRQKGEDGYWKYDRVKVNEEFEKLLKVWNFVNPKATDIKQ
EIIKKEKAGDLQGEKELDGRLRNFWHSFIYLFNLVLELRNSFSLQIKIKA
GEVIAVDEGVDFIASPVKPFFTTPNPYIPSNLCWLAVENADANGAYNIAR
KGVMILKKIREHAKKDPEFKKLPNLFISNAEWDEAARDWGKYAGTTALNL
DHKRPAATKKAGQAKKKKGSYPYDVPDYAYPYDVPDYAYPYDVPDYA

SEQ ID NO: 21 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 21 may be encoded by the following nucleotide sequence:

(SEQ ID NO: 22)

ATGGAGAACATCTTCGACCAGTTTATCGGCAAGTACAGCCTGTCCAAGAC
CCTGAGATTCGAGCTGAAGCCCGTGGGCAAGACAGAGGACTTCCTGAAGA
TCAACAAGGTGTTTGAGAAGGATCAGACCATCGACGATAGCTACAATCAG
GCCAAGTTCTATTTTGATTCCCTGCACCAGAAGTTTATCGACGCCGCCCT
GGCCTCCGATAAGACATCCGAGCTGTCTTTCCAGAACTTTGCCGACGTGC
TGGAGAAGCAGAATAAGATCATCCTGGATAAGAAGAGAGAGATGGGCGCC
CTGAGGAAGCGCGACAAGAACGCCGTGGGCATCGATAGGCTGCAGAAGGA
GATCAATGACGCCGAGGATATCATCCAGAAGGAGAAGGAGAAGATCTACA
AGGACGTGCGCACCCTGTTCGATAACGAGGCCGAGTCTTGGAAAACCTAC
TATCAGGAGCGGGAGGTGGACGGCAAGAAGATCACCTTCAGCAAGGCCGA

-continued

CCTGAAGCAGAAGGGCGCCGATTTTCTGACAGCCGCCGGCATCCTGAAGG
TGCTGAAGTATGAGTTCCCCGAGGAGAAGGAGAAGGAGTTTCAGGCCAAG
AACCAGCCCTCCCTGTTCGTGGAGGAGAAGGAGAATCCTGGCCAGAAGAG
GTACATCTTCGACTCTTTTGATAAGTTCGCCGGCTATCTGACCAAGTTTC
AGCAGACAAAGAAGAATCTGTACGCAGCAGACGGCACCAGCACAGCAGTG
GCCACCCGCATCGCCGATAACTTTATCATCTTCCACCAGAATACCAAGGT
GTTCCGGGACAAGTACAAGAACAATCACACAGACCTGGGCTTCGATGAGG
AGAACATCTTTGAGATCGAGAGGTATAAGAATTGCCTGCTGCAGCGCGAG
ATCGAGCACATCAAGAATGAGAATAGCTACAACAAGATCATCGGCCGGAT
CAATAAGAAGATCAAGGAGTATCGGGACCAGAAGGCCAAGGATACCAAGC
TGACAAAGTCCGACTTCCCTTTCTTTAAGAACCTGGATAAGCAGATCCTG
GGCGAGGTGGAGAAGGAGAAGCAGCTGATCGAGAAAACCCGGGAGAAAAC
CGAGGAGGACGTGCTGATCGAGCGGTTCAAGGAGTTCATCGAGAACAATG
AGGAGAGGTTCACCGCCGCCAAGAAGCTGATGAATGCCTTCTGTAACGGC
GAGTTTGAGTCCGAGTACGAGGGCATCTATCTGAAGAATAAGGCCATCAA
CACAATCTCCCGGAGATGGTTCGTGTCTGACAGAGATTTTGAGCTGAAGC
TGCCTCAGCAGAAGTCCAAGAACAAGTCTGAGAAGAATGAGCCAAAGGTG
AAGAAGTTCATCTCCATCGCCGAGATCAAGAACGCCGTGGAGGAGCTGGA
CGGCGATATCTTTAAGGCCGTGTTCTACGACAAGAAGATCATCGCCCAGG
GCGGCTCTAAGCTGGAGCAGTTCCTGGTCATCTGGAAGTACGAGTTTGAG
TATCTGTTCCGGGACATCGAGAGAGAGAACGGCGAGAAGCTGCTGGGCTA
TGATAGCTGCCTGAAGATCGCCAAGCAGCTGGGCATCTTCCCACAGGAGA
AGGAGGCCCGCGAGAAGGCAACCGCCGTGATCAAGAATTACGCCGACGCC
GGCCTGGGCATCTTCCAGATGATGAAGTATTTTTCTCTGGACGATAAGGA
TCGGAAGAACACCCCCGGCCAGCTGAGCACAAATTTCTACGCCGAGTATG
ACGGCTACTACAAGGATTTCGAGTTTATCAAGTACTACAACGAGTTTAGG
AACTTCATCACCAAGAAGCCTTTCGACGAGGATAAGATCAAGCTGAACTT
TGAGAATGGCGCCCTGCTGAAGGGCTGGGACGAGAACAAGGAGTACGATT
TCATGGGCGTGATCCTGAAGAAGGAGGGCCGCCTGTATCTGGGCATCATG
CACAAGAACCACCGGAAGCTGTTTCAGTCCATGGGCAATGCCAAGGGCGA
CAACGCCAATAGATACCAGAAGATGATCTATAAGCAGATCGCCGACGCCT
CTAAGGATGTGCCCAGGCTGCTGCTGACCAGCAAGAAGGCCATGGAGAAG
TTCAAGCCTTCCCAGGAGATCCTGAGAATCAAGAAGGAGAAAACCTTCAA
GCGGGAGAGCAAGAACTTTTCCCTGAGAGATCTGCACGCCCTGATCGAGT
ACTATAGGAACTGCATCCCTCAGTACAGCAATTGGTCCTTTTATGACTTC
CAGTTTCAGGATACCGGCAAGTACCAGAATATCAAGGAGTTCACAGACGA
TGTGCAGAAGTACGGCTATAAGATCTCCTTTCGCGACATCGACGATGAGT
ATATCAATCAGGCCCTGAACGAGGGCAAGATGTACCTGTTCGAGGTGGTG
AACAAGGATATCTATAACACCAAGAATGGCTCCAAGAATCTGCACACACT
GTACTTTGAGCACATCCTGTCTGCCGAGAACCTGAATGACCCAGTGTTCA
AGCTGTCTGGCATGGCCGAGATCTTTCAGCGGCAGCCCAGCGTGAACGAA

-continued

AGAGAGAAGATCACCACACAGAAGAATCAGTGTATCCTGGACAAGGGCGA

TAGAGCCTACAAGTATAGGCGCTACACCGAGAAGAAGATCATGTTCCACA

TGAGCCTGGTGCTGAACACAGGCAAGGGCGAGATCAAGCAGGTGCAGTTT

AATAAGATCATCAACCAGAGGATCAGCTCCTCTGACAACGAGATGAGGGT

GAATGTGATCGGCATCGATCGCGGCGAGAAGAACCTGCTGTACTATAGCG

TGGTGAAGCAGAATGGCGAGATCATCGAGCAGGCCTCCCTGAACGAGATC

AATGGCGTGAACTACCGGGACAAGCTGATCGAGAGGGAGAAGGAGCGCCT

GAAGAACCGGCAGAGCTGGAAGCCTGTGGTGAAGATCAAGGATCTGAAGA

AGGGCTACATCTCCCACGTGATCCACAAGATCTGCCAGCTGATCGAGAAG

TATTCTGCCATCGTGGTGCTGGAGGACCTGAATATGAGATTCAAGCAGAT

CAGGGGAGGAATCGAGCGGAGCGTGTACCAGCAGTTCGAGAAGGCCCTGA

TCGATAAGCTGGGCTATCTGGTGTTTAAGGACAACAGGGATCTGAGGGCA

CCAGGAGGCGTGCTGAATGGCTACCAGCTGTCTGCCCCCTTTGTGAGCTT

CGAGAAGATGCGCAAGCAGACCGGCATCCTGTTCTACACACAGGCCGAGT

ATACCAGCAAGACAGACCCAATCACCGGCTTTCGGAAGAACGTGTATATC

TCTAATAGCGCCTCCCTGGATAAGATCAAGGAGGCCGTGAAGAAGTTCGA

CGCCATCGGCTGGGATGGCAAGGAGCAGTCTTACTTCTTTAAGTACAACC

CTTACAACCTGGCCGACGAGAAGTATAAGAACTCTACCGTGAGCAAGGAG

TGGGCCATCTTTGCCAGCGCCCCAAGAATCCGGAGACAGAAGGGCGAGGA

CGGCTACTGGAAGTATGATAGGGTGAAAGTGAATGAGGAGTTCGAGAAGC

TGCTGAAGGTCTGGAATTTTGTGAACCCAAAGGCCACAGATATCAAGCAG

GAGATCATCAAGAAGGAGAAGGCAGGCGACCTGCAGGGAGAGAAGGAGCT

GGATGGCCGGCTGAGAAACTTTTGGCACTCTTTCATCTACCTGTTTAACC

TGGTGCTGGAGCTGCGCAATTCTTTCAGCCTGCAGATCAAGATCAAGGCA

GGAGAAGTGATCGCAGTGGACGAGGGCGTGGACTTCATCGCCAGCCCAGT

GAAGCCCTTCTTTACCACACCCAACCCTTACATCCCCTCCAACCTGTGCT

GGCTGGCCGTGGAGAATGCAGACGCAAACGGAGCCTATAATATCGCCAGG

AAGGGCGTGATGATCCTGAAGAAGATCCGCGAGCACGCCAAGAAGGACCC

CGAGTTCAAGAAGCTGCCAAACCTGTTTATCAGCAATGCAGAGTGGGACG

AGGCAGCCCGGGATTGGGGCAAGTACGCAGGCACCACAGCCCTGAACCTG

GACCACAAAAGGCCGGCGGCCACGAAAAAGGCCGGCCAGGCAAAAAAGAA

AAAGGGATCCTACCCATACGATGTTCCAGATTACGCTTATCCCTACGACG

TGCCTGATTATGCATACCCATATGATGTCCCCGACTATGCCTAA

*Smithella* sp. SC_K08D17 (SsCpf1; pY009), including NLS and HA tag:

(SEQ ID NO: 23)

MQTLFENFTNQYPVSKTLRFELIPQGKTKDFIEQKGLLKKDEDRAEKYKK

VKNIIDEYHKDFIEKSLNGLKLDGLEKYKTLYLKQEKDDKDKKAFDKEKE

NLRKQIANAFRNNEKFKTLFAKELIKNDLMSFACEEDKKNVKEFEAFTTY

FTGFHQNRANMYVADEKRTAIASRLIHENLPKFIDNIKIFEKMKKEAPEL

-continued

LSPFNQTLKDMKDVIKGTTLEEIFSLDYFNKTLTQSGIDIYNSVIGGRTP

EEGKTKIKGLNEYINTDFNQKQTDKKKRQPKFKQLYKQILSDRQSLSFIA

EAFKNDTEILEAIEKFYVNELLHFSNEGKSTNVLDAIKNAVSNLESFNLT

KMYFRSGASLTDVSRKVFGEWSIINRALDNYYATTYPIKPREKSEKYEER

KEKWLKQDFNVSLIQTAIDEYDNETVKGKNSGKVIADYFAKFCDDKETDL

IQKVNEGYIAVKDLLNTPCPENEKLGSNKDQVKQIKAFMDSIMDIMHFVR

PLSLKDTDKEKDETFYSLFTPLYDHLTQTIALYNKVRNYLTQKPYSTEKI

KLNFENSTLLGGWDLNKETDNTAIILRKDNLYYLGIMDKRHNRIFRNVPK

ADKKDFCYEKMVYKLLPGANKMLPKVFFSQSRIQEFTPSAKLLENYANET

HKKGDNFNLNHCHKLIDFFKDSINKHEDWKNFDFRFSATSTYADLSGFYH

EVEHQGYKISFQSVADSFIDDLVNEGKLYLFQIYNKDFSPFSKGKPNLHT

LYWKMLFDENNLKDVVYKLNGEAEVFYRKKSIAEKNTTIHKANESIINKN

PDNPKATSTFNYDIVKDKRYTIDKFQFHIPITMNFKAEGIFNMNQRVNQF

LKANPDINIIGIDRGERHLLYYALINQKGKILKQDTLNVIANEKQKVDYH

NLLDKKEGDRATARQEWGVIETIKELKEGYLSQVIHKLTDLMIENNAIIV

MEDLNFGFKRGRQKVEKQVYQKFEKMLIDKLNYLVDKNKKANELGGLLNA

FQLANKFESFQKMGKQNGFIFYVPAWNTSKTDPATGFIDFLKPRYENLNQ

AKDFFEKFDSIRLNSKADYFEFAFDFKNFTEKADGGRTKWTVCTTNEDRY

AWNRALNNNRGSQEKYDITAELKSLFDGKVDYKSGKDLKQQIASQESADF

FKALMKNLSITLSLRHNNGEKGDNEQDYILSPVADSKGRFFDSRKADDDM

PKNADANGAYHIALKGLWCLEQISKTDDLKKVKLAISNKEWLEFVQTLKG

KRPAATKKAGQAKKKKGSYPYDVPDYAYPYDVPDYAYPYDVPDYA

SEQ ID NO: 23 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 23 may be encoded by the following nucleotide sequence:

(SEQ ID NO: 24)

ATGCAGACCCTGTTTGAGAACTTCACAAATCAGTACCCAGTGTCCAAGAC

CCTGCGCTTTGAGCTGATCCCCCAGGGCAAGACAAAGGACTTCATCGAGC

AGAAGGGCCTGCTGAAGAAGGATGAGGACCGGGCCGAGAAGTATAAGAAG

GTGAAGAACATCATCGATGAGTACCACAAGGACTTCATCGAGAAGTCTCT

GAATGGCCTGAAGCTGGACGGCCTGGAGAAGTACAAGACCCTGTATCTGA

AGCAGGAGAAGGACGATAAGGATAAGAAGGCCTTTGACAAGGAGAAGGAG

AACCTGCGCAAGCAGATCGCCAATGCCTTCCGGAACAATGAGAAGTTTAA

GACACTGTTCGCCAAGGAGCTGATCAAGAACGATCTGATGTCTTTCGCCT

GCGAGGAGGACAAGAAGAATGTGAAGGAGTTTGAGGCCTTCACCACATAC

TTCACCGGCTTCCACCAGAACCGCGCCAATATGTACGTGGCCGATGAGAA

GAGAACAGCCATCGCCAGCAGGCTGATCCACGAGAACCTGCCAAAGTTTA

TCGACAATATCAAGATCTTCGAGAAGATGAAGAAGGAGGCCCCCGAGCTG

CTGTCTCCTTTCAACCAGACCCTGAAGGATATGAAGGACGTGATCAAGGG

-continued

CACCACACTGGAGGAGATCTTTAGCCTGGATTATTTCAACAAGACCCTGA
CACAGAGCGGCATCGACATCTACAATTCCGTGATCGGCGGCAGAACCCCT
GAGGAGGGCAAGACAAAGATCAAGGGCCTGAACGAGTACATCAATACCGA
CTTCAACCAGAAGCAGACAGACAAGAAGAAGCGGCAGCCAAAGTTCAAGC
AGCTGTATAAGCAGATCCTGAGCGATAGGCAGAGCCTGTCCTTTATCGCC
GAGGCCTTCAAGAACGACACCGAGATCCTGGAGGCCATCGAGAAGTTTTA
CGTGAATGAGCTGCTGCACTTCAGCAATGAGGGCAAGTCCACAAACGTGC
TGGACGCCATCAAGAATGCCGTGTCTAACCTGGAGAGCTTTAACCTGACC
AAGATGTATTTCCGCTCCGGCGCCTCTCTGACAGACGTGAGCCGGAAGGT
GTTTGGCGAGTGGAGCATCATCAATAGAGCCCTGGACAACTACTATGCCA
CCACATATCCAATCAAGCCCAGAGAGAAGTCTGAGAAGTACGAGGAGAGG
AAGGAGAAGTGGCTGAAGCAGGACTTCAACGTGAGCCTGATCCAGACCGC
CATCGATGAGTACGACAACGAGACAGTGAAGGGCAAGAACAGCGGCAAAG
TGATCGCCGATTATTTTGCCAAGTTCTGCGACGATAAGGAGACAGACCTG
ATCCAGAAGGTGAACGAGGGCTACATCGCCGTGAAGGATCTGCTGAATAC
ACCCTGTCCTGAGAACGAGAAGCTGGGCAGCAATAAGGACCAGGTGAAGC
AGATCAAGGCCTTTATGGATTCTATCATGGACATCATGCACTTCGTGCGC
CCCCTGAGCCTGAAGGATACCGACAAGGAGAAGGATGAGACATTCTACTC
CCTGTTCACACCTCTGTACGACCACCTGACCCAGACAATCGCCCTGTATA
ACAAGGTGCGGAACTATCTGACCCAGAAGCCTTACAGCACAGAGAAGATC
AAGCTGAACTTCGAGAACAGCACCCTGCTGGGCGGCTGGGATCTGAATAA
GGAGACAGACAACACAGCCATCATCCTGAGGAAGGATAACCTGTACTATC
TGGGCATCATGGACAAGAGGCACAATCGCATCTTTCGGAACGTGCCCAAG
GCCGATAAGAAGGACTTCTGCTACGAGAAGATGGTGTATAAGCTGCTGCC
TGGCGCCAACAAGATGCTGCCAAAGGTGTTCTTTTCTCAGAGCAGAATCC
AGGAGTTTACCCCTTCCGCCAAGCTGCTGGAGAACTACGCCAATGAGACA
CACAAGAAGGGCGATAATTTCAACCTGAATCACTGTCACAAGCTGATCGA
TTTCTTTAAGGACTCTATCAACAAGCACGAGGATTGGAAGAATTTCGACT
TTAGGTTCAGCGCCACCTCCACCTACGCCGACCTGAGCGGCTTTTACCAC
GAGGTGGAGCACCAGGGCTACAAGATCTCTTTTCAGAGCGTGGCCGATTC
CTTCATCGACGATCTGGTGAACGAGGGCAAGCTGTACCTGTTCCAGATCT
ATAATAAGGACTTTTCCCCATTCTCTAAGGGCAAGCCCAACCTGCACACC
CTGTACTGGAAGATGCTGTTTGATGAGAACAATCTGAAGGACGTGGTGTA
TAAGCTGAATGGCGAGGCCGAGGTGTTCTACCGCAAGAAGAGCATTGCCG
AGAAGAACACCACAATCCACAAGGCCAATGAGTCCATCATCAACAAGAAT
CCTGATAACCCAAAGGCCACCAGCACCTTCAACTATGATATCGTGAAGGA
CAAGAGATACACCATCGACAAGTTTCAGTTCCACATCCCAATCACAATGA
ACTTTAAGGCCGAGGGCATCTTCAACATGAATCAGAGGGTGAATCAGTTC
CTGAAGGCCAATCCCGATATCAACATCATCGGCATCGACAGAGGCGAGAG
GCACCTGCTGTACTATGCCCTGATCAACCAGAAGGGCAAGATCCTGAAGC

-continued

AGGATACCCTGAATGTGATCGCCAACGAGAAGCAGAAGGTGGACTACCAC
AATCTGCTGGATAAGAAGGAGGGCGACCGCGCAACCGCAAGGCAGGAGTG
GGGCGTGATCGAGACAATCAAGGAGCTGAAGGAGGGCTATCTGTCCCAGG
TCATCCACAAGCTGACCGATCTGATGATCGAGAACAATGCCATCATCGTG
ATGGAGGACCTGAACTTTGGCTTCAAGCGGGGCAGACAGAAGGTGGAGAA
GCAGGTGTATCAGAAGTTTGAGAAGATGCTGATCGATAAGCTGAATTACC
TGGTGGACAAGAATAAGAAGGCAAACGAGCTGGGAGGCCTGCTGAACGCA
TTCCAGCTGGCCAATAAGTTTGAGTCCTTCCAGAAGATGGGCAAGCAGAA
CGGCTTTATCTTCTACGTGCCCGCCTGGAATACCTCTAAGACAGATCCTG
CCACCGGCTTTATCGACTTCCTGAAGCCCCGCTATGAGAACCTGAATCAG
GCCAAGGATTTCTTTGAGAAGTTTGACTCTATCCGGCTGAACAGCAAGGC
CGATTACTTTGAGTTCGCCTTTGACTTCAAGAATTTCACCGAGAAGGCCG
ATGGCGGCAGAACCAAGTGGACAGTGTGCACCACAAACGAGGACAGATAT
GCCTGGAATAGGGCCCTGAACAATAACAGGGGCAGCCAGGAGAAGTACGA
CATCACAGCCGAGCTGAAGTCCCTGTTCGATGGCAAGGTGGACTATAAGT
CTGGCAAGGATCTGAAGCAGCAGATCGCCAGCCAGGAGTCCGCCGACTTC
TTTAAGGCCCTGATGAAGAACCTGTCCATCACCCTGTCTCTGAGACACAA
TAACGGCGAGAAGGGCGATAATGAGCAGGACTACATCCTGTCCCCTGTGG
CCGATTCTAAGGGCCGCTTCTTTGACTCCCGGAAGGCCGACGATGACATG
CCAAAGAATGCCGACGCCAACGGCGCCTATCACATCGCCCTGAAGGGCCT
GTGGTGTCTGGAGCAGATCAGCAAGACCGATGACCTGAAGAAGGTGAAGC
TGGCCATCTCCAACAAGGAGTGGCTGGAGTTCGTGCAGACACTGAAGGGC
AAAAGGCCGGCGGCCACGAAAAAGGCCGGCCAGGCAAAAAAGAAAAAGGG
ATCCTACCCATACGATGTTCCAGATTACGCTTATCCCTACGACGTGCCTG
ATTATGCATACCCATATGATGTCCCCGACTATGCCTAA

*Acidaminococcus* sp. BV3L6 (AsCpf1; pY010), including NLS and HA tag:

(SEQ ID NO: 25)
MTQFEGFTNLYQVSKTLRFELIPQGKTLKHIQEQGFIEEDKARNDHYKEL
KPIIDRIYKTYADQCLQLVQLDWENLSAAIDSYRKEKTEETRNALIEEQA
TYRNAIHDYFIGRTDNLTDAINKRHAEIYKGLFKAELFNGKVLKQLGTVT
TTEHENALLRSFDKFTTYFSGFYENRKNVFSAEDISTAIPHRIVQDNFPK
FKENCHIFTRLITAVPSLREHFENVKKAIGIFVSTSIEEVFSFPFYNQLL
TQTQIDLYNQLLGGISREAGTEKIKGLNEVLNLAIQKNDETAHIIASLPH
RFIPLFKQILSDRNTLSFILEEFKSDEEVIQSFCKYKTLLRNENVLETAE
ALFNELNSIDLTHIFISHKKLETISSALCDHWDTLRNALYERRISELTGK
ITKSAKEKVQRSLKHEDINLQEIISAAGKELSEAFKQKTSEILSHAHAAL
DQPLPTTLKKQEEKEILKSQLDSLLGLYHLLDWFAVDESNEVDPEFSARL
TGIKLEMEPSLSFYNKARNYATKKPYSVEKFKLNFQMPTLASGWDVNKEK
NNGAILFVKNGLYYLGIMPKQKGRYKALSFEPTEKTSEGFDKMYYDYFPD
AAKMIPKCSTQLKAVTAHFQTHTTPILLSNNFIEPLEITKEIYDLNNPEK

-continued

EPKKFQTAYAKKTGDQKGYREALCKWIDFTRDFLSKYTKTTSIDLSSLRP

SSQYKDLGEYYAELNPLLYHISFQRIAEKEIMDAVETGKLYLFQIYNKDF

AKGHHGKPNLHTLYWTGLFSPENLAKTSIKLNGQAELFYRPKSRMKRMAH

RLGEKMLNKKLKDQKTPIPDTLYQELYDYVNHRLSHDLSDEARALLPNVI

TKEVSHEIIKDRRFTSDKFFFHVPITLNYQAANSPSKFNQRVNAYLKEHP

ETPIIGIDRGERNLIYITVIDSTGKILEQRSLNTIQQFDYQKKLDNREKE

RVAARQAWSVVGTIKDLKQGYLSQVIHEIVDLMIHYQAVVVLENLNFGFK

SKRTGIAEKAVYQQFEKMLIDKLNCLVLKDYPAEKVGGVLNPYQLTDQFT

SFAKMGTQSGFLFYVPAPYTSKIDPLTGFVDPFVWKTIKNHESRKHFLEG

FDFLHYDVKTGDFILHFKMNRNLSFQRGLPGFMPAWDIVFEKNETQFDAK

GTPFIAGKRIVPVIENHRFTGRYRDLYPANELIALLEEKGIVFRDGSNIL

PKLLENDDSHAIDTMVALIRSVLQMRNSNAATGEDYINSPVRDLNGVCFD

SRFQNPEWPMDADANGAYHIALKGQLLLNHLKESKDLKLQNGISNQDWLA

YIQELRNKRPAATKKAGQAKKKKGSYPYDVPDYAYPYDVPDYAYPYDVPD

YA

SEQ ID NO: 25 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 25 may be encoded by the following nucleotide sequence:

(SEQ ID NO: 26)

ATGACACAGTTCGAGGGCTTTACCAACCTGTATCAGGTGAGCAAGACACT

GCGGTTTGAGCTGATCCCACAGGGCAAGACCCTGAAGCACATCCAGGAGC

AGGGCTTCATCGAGGAGGACAAGGCCCGCAATGATCACTACAAGGAGCTG

AAGCCCATCATCGATCGGATCTACAAGACCTATGCCGACCAGTGCCTGCA

GCTGGTGCAGCTGGATTGGGAGAACCTGAGCGCCGCCATCGACTCCTATA

GAAAGGAGAAAACCGAGGAGACAAGGAACGCCCTGATCGAGGAGCAGGCC

ACATATCGCAATGCCATCCACGACTACTTCATCGGCCGGACAGACAACCT

GACCGATGCCATCAATAAGAGACACGCCGAGATCTACAAGGGCCTGTTCA

AGGCCGAGCTGTTTAATGGCAAGGTGCTGAAGCAGCTGGGCACCGTGACC

ACAACCGAGCACGAGAACGCCCTGCTGCGGAGCTTCGACAAGTTTACAAC

CTACTTCTCCGGCTTTTATGAGAACAGGAAGAACGTGTTCAGCGCCGAGG

ATATCAGCACAGCCATCCCACACCGCATCGTGCAGGACAACTTCCCCAAG

TTTAAGGAGAATTGTCACATCTTCACACGCCTGATCACCGCCGTGCCCAG

CCTGCGGGAGCACTTTGAGAACGTGAAGAAGGCCATCGGCATCTTCGTGA

GCACCTCCATCGAGGAGGTGTTTTCCTTCCCTTTTTATAACCAGCTGCTG

ACACAGACCCAGATCGACCTGTATAACCAGCTGCTGGGAGGAATCTCTCG

GGAGGCAGGCACCGAGAAGATCAAGGGCCTGAACGAGGTGCTGAATCTGG

CCATCCAGAAGAATGATGAGACAGCCCACATCATCGCCTCCCTGCCACAC

AGATTCATCCCCCTGTTTAAGCAGATCCTGTCCGATAGGAACACCCTGTC

-continued

TTTCATCCTGGAGGAGTTTAAGAGCGACGAGGAAGTGATCCAGTCCTTCT

GCAAGTACAAGACACTGCTGAGAAACGAGAACGTGCTGGAGACAGCCGAG

GCCCTGTTTAACGAGCTGAACAGCATCGACCTGACACACATCTTCATCAG

CCACAAGAAGCTGGAGACAATCAGCAGCGCCCTGTGCGACCACTGGGATA

CACTGAGGAATGCCCTGTATGAGCGGAGAATCTCCGAGCTGACAGGCAAG

ATCACCAAGTCTGCCAAGGAGAAGGTGCAGCGCAGCCTGAAGCACGAGGA

TATCAACCTGCAGGAGATCATCTCTGCCGCAGGCAAGGAGCTGAGCGAGG

CCTTCAAGCAGAAAACCAGCGAGATCCTGTCCCACGCACACGCCGCCCTG

GATCAGCCACTGCCTACAACCCTGAAGAAGCAGGAGGAGAAGGAGATCCT

GAAGTCTCAGCTGGACAGCCTGCTGGGCCTGTACCACCTGCTGGACTGGT

TTGCCGTGGATGAGTCCAACGAGGTGGACCCCGAGTTCTCTGCCCGGCTG

ACCGGCATCAAGCTGGAGATGGAGCCTTCTCTGAGCTTCTACAACAAGGC

CAGAAATTATGCCACCAAGAAGCCCTACTCCGTGGAGAAGTTCAAGCTGA

ACTTTCAGATGCCTACACTGGCCTCTGGCTGGGACGTGAATAAGGAGAAG

AACAATGGCGCCATCCTGTTTGTGAAGAACGGCCTGTACTATCTGGGCAT

CATGCCAAAGCAGAAGGGCAGGTATAAGGCCCTGAGCTTCGAGCCCACAG

AGAAAACCAGCGAGGGCTTTGATAAGATGTACTATGACTACTTCCCTGAT

GCCGCCAAGATGATCCCAAAGTGCAGCACCCAGCTGAAGGCCGTGACAGC

CCACTTTCAGACCCACACAACCCCCATCCTGCTGTCCAACAATTTCATCG

AGCCTCTGGAGATCACAAAGGAGATCTACGACCTGAACAATCCTGAGAAG

GAGCCAAAGAAGTTTCAGACAGCCTACGCCAAGAAAACCGGCGACCAGAA

GGGCTACAGAGAGGCCCTGTGCAAGTGGATCGACTTCACAAGGGATTTTC

TGTCCAAGTATACCAAGACAACCTCTATCGATCTGTCTAGCCTGCGGCCA

TCCTCTCAGTATAAGGACCTGGGCGAGTACTATGCCGAGCTGAATCCCCT

GCTGTACCACATCAGCTTCCAGAGAATCGCCGAGAAGGAGATCATGGATG

CCGTGGAGACAGGCAAGCTGTACCTGTTCCAGATCTATAACAAGGACTTT

GCCAAGGGCCACCACGGCAAGCCTAATCTGCACACACTGTATTGGACCGG

CCTGTTTTCTCCAGAGAACCTGGCCAAGACAAGCATCAAGCTGAATGGCC

AGGCCGAGCTGTTCTACCGCCCTAAGTCCAGGATGAAGAGGATGGCACAC

CGGCTGGGAGAGAAGATGCTGAACAAGAAGCTGAAGGATCAGAAAACCCC

AATCCCCGACACCCTGTACCAGGAGCTGTACGACTATGTGAATCACAGAC

TGTCCCACGACCTGTCTGATGAGGCCAGGGCCCTGCTGCCCAACGTGATC

ACCAAGGAGGTGTCTCACGAGATCATCAAGGATAGGCGCTTTACCAGCGA

CAAGTTCTTTTTCCACGTGCCTATCACACTGAACTATCAGGCCGCCAATT

CCCCATCTAAGTTCAACCAGAGGGTGAATGCCTACCTGAAGGAGCACCCC

GAGACACCTATCATCGGCATCGATCGGGGCGAGAGAAACCTGATCTATAT

CACAGTGATCGACTCCACCGGCAAGATCCTGGAGCAGCGGAGCCTGAACA

CCATCCAGCAGTTTGATTACCAGAAGAAGCTGGACAACAGGGAGAAGGAG

AGGGTGGCAGCAAGGCAGGCCTGGTCTGTGGTGGGCACAATCAAGGATCT

GAAGCAGGGCTATCTGAGCCAGGTCATCCACGAGATCGTGGACCTGATGA

TCCACTACCAGGCCGTGGTGGTGCTGGAGAACCTGAATTTCGGCTTTAAG

-continued

```
AGCAAGAGGACCGGCATCGCCGAGAAGGCCGTGTACCAGCAGTTCGAGAA
GATGCTGATCGATAAGCTGAATTGCCTGGTGCTGAAGGACTATCCAGCAG
AGAAAGTGGGAGGCGTGCTGAACCCATACCAGCTGACAGACCAGTTCACC
TCCTTTGCCAAGATGGGCACCCAGTCTGGCTTCCTGTTTTACGTGCCTGC
CCCATATACATCTAAGATCGATCCCCTGACCGGCTTCGTGGACCCCTTCG
TGTGGAAAACCATCAAGAATCACGAGAGCCGCAAGCACTTCCTGGAGGGC
TTCGACTTTCTGCACTACGACGTGAAAACCGGCGACTTCATCCTGCACTT
TAAGATGAACAGAAATCTGTCCTTCCAGAGGGGCCTGCCCGGCTTTATGC
CTGCATGGGATATCGTGTTCGAGAAGAACGAGACACAGTTTGACGCCAAG
GGCACCCCTTTCATCGCCGGCAAGAGAATCGTGCCAGTGATCGAGAATCA
CAGATTCACCGGCAGATACCGGGACCTGTATCCTGCCAACGAGCTGATCG
CCCTGCTGGAGGAGAAGGGCATCGTGTTCAGGGATGGCTCCAACATCCTG
CCAAAGCTGCTGGAGAATGACGATTCTCACGCCATCGACACCATGGTGGC
CCTGATCCGCAGCGTGCTGCAGATGCGGAACTCCAATGCCGCCACAGGCG
AGGACTATATCAACAGCCCCGTGCGCGATCTGAATGGCGTGTGCTTCGAC
TCCCGGTTTCAGAACCCAGAGTGGCCCATGGACGCCGATGCCAATGGCGC
CTACCACATCGCCCTGAAGGGCCAGCTGCTGCTGAATCACCTGAAGGAGA
GCAAGGATCTGAAGCTGCAGAACGGCATCTCCAATCAGGACTGGCTGGCC
TACATCCAGGAGCTGCGCAACAAAAGGCCGGCGGCCACGAAAAAGGCCGG
CCAGGCAAAAAAGAAAAAGGGATCCTACCCATACGATGTTCCAGATTACG
CTTATCCCTACGACGTGCCTGATTATGCATACCCATATGATGTCCCCGAC
TATGCCTAA
```

*Lachnospiraceae bacterium* MA2020 (Lb2Cpf1; pY011), including NLS and HA tag:

```
                                          (SEQ ID NO: 27)
MYYESLTKQYPVSKTIRNELIPIGKTLDNIRQNNILESDVKRKQNYEHVK
GILDEYHKQLINEALDNCTLPSLKIAAEIYLKNQKEVSDREDFNKTQDLL
RKEVVEKLKAHENFTKIGKKDILDLLEKLPSISEDDYNALESFRNFYTYF
TSYNKVRENLYSDKEKSSTVAYRLINENFPKFLDNVKSYRFVKTAGILAD
GLGEEEQDSLFIVETFNKTLTQDGIDTYNSQVGKINSSINLYNQKNQKAN
GFRKIPKMKMLYKQILSDREESFIDEFQSDEVLIDNVESYGSVLIESLKS
SKVSAFFDALRESKGKNVYVKNDLAKTAMSNIVFENWRTFDDLLNQEYDL
ANENKKKDDKYFEKRQKELKKNKSYSLEHLCNLSEDSCNLIENYIHQISD
DIENIIINNETFLRIVINEHDRSRKLAKNRKAVKAIKDFLDSIKVLEREL
KLINSSGQELEKDLIVYSAHEELLVELKQVDSLYNMTRNYLTKKPFSTEK
VKLNFNRSTLLNGWDRNKETDNLGVLLLKDGKYYLGIMNTSANKAFVNPP
VAKTEKVFKKVDYKLLPVPNQMLPKVFFAKSNIDFYNPSSEIYSNYKKGT
HKKGNMFSLEDCHNLIDFFKESISKHEDWSKFGFKFSDTASYNDISEFYR
EVEKQGYKLTYTDIDETYINDLIERNELYLFQIYNKDFSMYSKGKLNLHT
LYFMMLFDQRNIDDVVYKLNGEAEVFYRPASISEDELIIHKAGEEIKNKN
```

-continued

```
PNRARTKETSTFSYDIVKDKRYSKDKFTLHIPITMNFGVDEVKRFNDAVN
SAIRIDENVNVIGIDRGERNLLYVVVIDSKGNILEQISLNSIINKEYDIE
TDYHALLDEREGGRDKARKDWNTVENIRDLKAGYLSQVVNVVAKLVLKYN
AIICLEDLNFGFKRGRQKVEKQVYQKFEKMLIDKLNYLVIDKSREQTSPK
ELGGALNALQLTSKFKSFKELGKQSGVIYYVPAYLTSKIDPTTGFANLFY
MKCENVEKSKRFFDGFDFIRFNALENVFEFGFDYRSFTQRACGINSKWTV
CTNGERIIKYRNPDKNNMFDEKVVVVTDEMKNLFEQYKIPYEDGRNVKDM
IISNEEAEFYRRLYRLLQQTLQMRNSTSDGTRDYIISPVKNKREAYFNSE
LSDGSVPKDADANGAYNIARKGLWVLEQIRQKSEGEKINLAMTNAEWLEY
AQTHLLKRPAATKKAGQAKKKKGSYPYDVPDYAYPYDVPDYAYPYDVPDY
A
```

SEQ ID NO: 27 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 27 may be encoded by the following nucleotide sequence:

```
                                          (SEQ ID NO: 28)
ATGTACTATGAGTCCCTGACCAAGCAGTACCCCGTGTCTAAGACAATCCG
GAATGAGCTGATCCCTATCGGCAAGACACTGGATAACATCCGCCAGAACA
ATATCCTGGAGAGCGACGTGAAGCGGAAGCAGAACTACGAGCACGTGAAG
GGCATCCTGGATGAGTATCACAAGCAGCTGATCAACGAGGCCCTGGACAA
TTGCACCCTGCCATCCCTGAAGATCGCCGCCGAGATCTACCTGAAGAATC
AGAAGGAGGTGTCTGACAGAGAGGATTTCAACAAGACACAGGACCTGCTG
AGGAAGGAGGTGGTGGAGAAGCTGAAGGCCCACGAGAACTTTACCAAGAT
CGGCAAGAAGGACATCCTGGATCTGCTGGAGAAGCTGCCTTCCATCTCTG
AGGACGATTACAATGCCCTGGAGAGCTTCCGCAACTTTTACACCTATTTC
ACATCCTACAACAAGGTGCGGGAGAATCTGTATTCTGATAAGGAGAAGAG
CTCCACAGTGGCCTACAGACTGATCAACGAGAATTTCCCAAAGTTTCTGG
ACAATGTGAAGAGCTATAGGTTTGTGAAAACCGCAGGCATCCTGGCAGAT
GGCCTGGGAGAGGAGGAGCAGGACTCCCTGTTCATCGTGGAGACATTCAA
CAAGACCCTGACACAGGACGGCATCGATACCTACAATTCTCAAGTGGGCA
AGATCAACTCTAGCATCAATCTGTATAACCAGAAGAATCAGAAGGCCAAT
GGCTTCAGAAAGATCCCCAAGATGAAGATGCTGTATAAGCAGATCCTGTC
CGATAGGGAGGAGTCTTTCATCGACGAGTTTCAGAGCGATGAGGTGCTGA
TCGACAACGTGGAGTCTTATGGCAGCGTGCTGATCGAGTCTCTGAAGTCC
TCTAAGGTGAGCGCCTTCTTTGATGCCCTGAGAGAGTCTAAGGGCAAGAA
CGTGTACGTGAAGAATGACCTGGCCAAGACAGCCATGAGCAACATCGTGT
TCGAGAATTGGAGGACCTTTGACGATCTGCTGAACCAGGAGTACGACCTG
GCCAACGAGAACAAGAAGAAGGACGATAAGTATTTCGAGAAGCGCCAGAA
GGAGCTGAAGAAGAATAAGAGCTACTCCCTGGAGCACCTGTGCAACCTGT
CCGAGGATTCTTGTAACCTGATCGAGAATTATATCCACCAGATCTCCGAC
```

-continued

GATATCGAGAATATCATCATCAACAATGAGACATTCCTGCGCATCGTGAT
CAATGAGCACGACAGGTCCCGCAAGCTGGCCAAGAACCGGAAGGCCGTGA
AGGCCATCAAGGACTTTCTGGATTCTATCAAGGTGCTGGAGCGGGAGCTG
AAGCTGATCAACAGCTCCGGCCAGGAGCTGGAGAAGGATCTGATCGTGTA
CTCTGCCCACGAGGAGCTGCTGGTGGAGCTGAAGCAGGTGGACAGCCTGT
ATAACATGACCAGAAATTATCTGACAAAGAAGCCTTTCTCTACCGAGAAG
GTGAAGCTGAACTTTAATCGCAGCACACTGCTGAACGGCTGGGATCGGAA
TAAGGAGACAGACAACCTGGGCGTGCTGCTGCTGAAGGACGGCAAGTACT
ATCTGGGCATCATGAACACAAGCGCCAATAAGGCCTTCGTGAATCCCCCT
GTGGCCAAGACCGAGAAGGTGTTTAAGAAGGTGGATTACAAGCTGCTGCC
AGTGCCCAACCAGATGCTGCCAAAGGTGTTCTTTGCCAAGAGCAATATCG
ACTTCTATAACCCCTCTAGCGAGATCTACTCCAATTATAAGAAGGGCACC
CACAAGAAGGGCAATATGTTTTCCCTGGAGGATTGTCACAACCTGATCGA
CTTCTTTAAGGAGTCTATCAGCAAGCACGAGGACTGGAGCAAGTTCGGCT
TTAAGTTCAGCGATACAGCCTCCTACAACGACATCTCCGAGTTCTATCGC
GAGGTGGAGAAGCAGGGCTACAAGCTGACCTATACAGACATCGATGAGAC
ATACATCAATGATCTGATCGAGCGGAACGAGCTGTACCTGTTCCAGATCT
ATAATAAGGACTTTAGCATGTACTCCAAGGGCAAGCTGAACCTGCACACA
CTGTATTTCATGATGCTGTTTGATCAGCGCAATATCGACGACGTGGTGTA
TAAGCTGAACGGAGAGGCAGAGGTGTTCTATAGGCCAGCCTCCATCTCTG
AGGACGAGCTGATCATCCACAAGGCCGGCGAGGAGATCAAGAACAAGAAT
CCTAACCGGGCCAGAACCAAGGAGACAAGCACCTTCAGCTACGACATCGT
GAAGGATAAGCGGTATAGCAAGGATAAGTTTACCCTGCACATCCCCATCA
CAATGAACTTCGGCGTGGATGAGGTGAAGCGGTTCAACGACGCCGTGAAC
AGCGCCATCCGGATCGATGAGAATGTGAACGTGATCGGCATCGACCGGGG
CGAGAGAAATCTGCTGTACGTGGTGGTCATCGACTCTAAGGGCAACATCC
TGGAGCAGATCTCCCTGAACTCTATCATCAATAAGGAGTACGACATCGAG
ACAGATTATCACGCACTGCTGGATGAGAGGGAGGGCGGCAGAGATAAGGC
CCGGAAGGACTGGAACACCGTGGAGAATATCAGGGACCTGAAGGCCGGCT
ACCTGAGCCAGGTGGTGAACGTGGTGGCCAAGCTGGTGCTGAAGTATAAT
GCCATCATCTGCCTGGAGGACCTGAACTTTGGCTTCAAGAGGGGCCGCCA
GAAGGTGGAGAAGCAGGTGTACCAGAAGTTCGAGAAGATGCTGATCGATA
AGCTGAATTACCTGGTCATCGACAAGAGCCGCGAGCAGACATCCCCTAAG
GAGCTGGGAGGCGCCCTGAACGCACTGCAGCTGACCTCTAAGTTCAAGAG
CTTTAAGGAGCTGGGCAAGCAGTCCGGCGTGATCTACTATGTGCCTGCCT
ACCTGACCTCTAAGATCGATCCAACCACAGGCTTCGCCAATCTGTTTTAT
ATGAAGTGTGAGAACGTGGAGAAGTCCAAGAGATTCTTTGACGGCTTTGA
TTTCATCAGGTTCAACGCCCTGGAGAACGTGTTCGAGTTCGGCTTTGACT
ACCGGAGCTTCACCCAGAGGGCCTGCGGCATCAATTCCAAGTGGACCGTG
TGCACCAACGGCGAGCGCATCATCAAGTATCGGAATCCAGATAAGAACAA

-continued

TATGTTCGACGAGAAGGTGGTGGTGGTGACCGATGAGATGAAGAACCTGT
TTGAGCAGTACAAGATCCCCTATGAGGATGGCAGAAATGTGAAGGACATG
ATCATCAGCAACGAGGAGGCCGAGTTCTACCGGAGACTGTATAGGCTGCT
GCAGCAGACCCTGCAGATGAGAAACAGCACCTCCGACGGCACAAGGGATT
ACATCATCTCCCCTGTGAAGAATAAGAGAGAGGCCTACTTCAACAGCGAG
CTGTCCGACGGCTCTGTGCCAAAGGACGCCGATGCCAACGGCGCCTACAA
TATCGCCAGAAAGGGCCTGTGGGTGCTGGAGCAGATCAGGCAGAAGAGCG
AGGGCGAGAAGATCAATCTGGCCATGACCAACGCCGAGTGGCTGGAGTAT
GCCCAGACACACCTGCTGAAAAGGCCGGCGGCCACGAAAAAGGCCGGCCA
GGCAAAAAAGAAAAAGGGATCCTACCCATACGATGTTCCAGATTACGCTT
ATCCCTACGACGTGCCTGATTATGCATACCCATATGATGTCCCCGACTAT
GCCTAA

*Candidatus Methanoplasma termitum* (CMtCpf1; pY012), including NLS and HA tag:

(SEQ ID NO: 29)
MNNYDEFTKLYPIQKTIRFELKPQGRTMEHLETFNFFEEDRDRAEKYKIL
KEAIDEYHKKFIDEHLTNMSLDWNSLKQISEKYYKSREEKDKKVFLSEQK
RMRQEIVSEFKKDDRFKDLFSKKLFSELLKEEIYKKGNHQEIDALKSFDK
FSGYFIGLHENRKNMYSDGDEITAISNRIVNENFPKFLDNLQKYQEARKK
YPEWIIKAESALVAHNIKMDEVFSLEYFNKVLNQEGIQRYNLALGGYVTK
SGEKMMGLNDALNLAHQSEKSSKGRIHMTPLFKQILSEKESFSYIPDVFT
EDSQLLPSIGGFFAQIENDKDGNIFDRALELISSYAEYDTERIYIRQADI
NRVSNVIFGEWGTLGGLMREYKADSINDINLERTCKKVDKWLDSKEFALS
DVLEAIKRTGNNDAFNEYISKMRTAREKIDAARKEMKFISEKISGDEESI
HIIKTLLDSVQQFLHFFNLFKARQDIPLDGAFYAEFDEVHSKLFAIVPLY
NKVRNYLTKNNLNTKKIKLNFKNPTLANGWDQNKVYDYASLIFLRDGNYY
LGIINPKRKKNIKFEQGSGNGPFYRKMVYKQIPGPNKNLPRVFLTSTKGK
KEYKPSKEIIEGYEADKHIRGDKFDLDFCHKLIDFFKESIEKHKDWSKFN
FYFSPTESYGDISEFYLDVEKQGYRMHFENISAETIDEYVEKGDLFLFQI
YNKDFVKAATGKKDMHTIYWNAAFSPENLQDVVVKLNGEAELFYRDKSDI
KEIVHREGEILVNRTYNGRTPVPDKIHKKLTDYHNGRTKDLGEAKEYLDK
VRYFKAHYDITKDRRYLNDKIYFHVPLTLNFKANGKKNLNKMVIEKFLSD
EKAHIIGIDRGERNLLYYSIIDRSGKIIDQQSLNVIDGFDYREKLNQREI
EMKDARQSWNAIGKIKDLKEGYLSKAVHEITKMAIQYNAIVVMEELNYGF
KRGRFKVEKQIYQKFENMLIDKMNYLVFKDAPDESPGGVLNAYQLTNPLE
SFAKLGKQTGILFYVPAAYTSKIDPTTGFVNLFNTSSKTNAQERKEFLQK
FESISYSAKDGGIFAFAFDYRKFGTSKTDHKNVWTAYTNGERMRYIKEKK
RNELFDPSKEIKEALTSSGIKYDGGQNILPDILRSNNNGLIYTMYSSFIA
AIQMRVYDGKEDYIISPIKNSKGEFFRTDPKRRELPIDADANGAYNIALR
GELTMRAIAEKFDPDSEKMAKLELKHKDWFEFMQTRGDKRPAATKKAGQA
KKKKGSYPYDVPDYAYPYDVPDYAYPYDVPDYA

SEQ ID NO: 29 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 29 may be encoded by the following nucleotide sequence:

(SEQ ID NO: 30)

ATGAACAATTACGACGAGTTCACCAAGCTGTATCCTATCCAGAAAACCAT
CCGGTTTGAGCTGAAGCCACAGGGCAGAACCATGGAGCACCTGGAGACAT
TCAACTTCTTTGAGGAGGACCGGGATAGAGCCGAGAAGTATAAGATCCTG
AAGGAGGCCATCGACGAGTACCACAAGAAGTTTATCGATGAGCACCTGAC
CAATATGTCCCTGGATTGGAACTCTCTGAAGCAGATCAGCGAGAAGTACT
ATAAGAGCAGGGAGGAGAAGGACAAGAAGGTGTTCCTGTCCGAGCAGAAG
AGGATGCGCCAGGAGATCGTGTCTGAGTTTAAGAAGGACGATCGCTTCAA
GGACCTGTTTTCCAAGAAGCTGTTCTCTGAGCTGCTGAAGGAGGAGATCT
ACAAGAAGGGCAACCACCAGGAGATCGACGCCCTGAAGAGCTTCGATAAG
TTTTCCGGCTATTTCATCGGCCTGCACGAGAATAGGAAGAACATGTACTC
CGACGGCGATGAGATCACCGCCATCTCCAATCGCATCGTGAATGAGAACT
TCCCCAAGTTTCTGGATAACCTGCAGAAGTACCAGGAGGCCAGGAAGAAG
TATCCTGAGTGGATCATCAAGGCCGAGAGCGCCCTGGTGGCCCACAATAT
CAAGATGGACGAGGTGTTCTCCCTGGAGTACTTTAATAAGGTGCTGAACC
AGGAGGGCATCCAGCGGTACAACCTGGCCCTGGGCGGCTATGTGACCAAG
AGCGGCGAGAAGATGATGGGCCTGAATGATGCCCTGAACCTGGCCCACCA
GTCCGAGAAGAGCTCCAAGGGCAGAATCCACATGACCCCCCTGTTCAAGC
AGATCCTGTCCGAGAAGGAGTCCTTCTCTTACATCCCCGACGTGTTTACA
GAGGATTCTCAGCTGCTGCCTAGCATCGGCGGCTTCTTTGCCCAGATCGA
GAATGACAAGGATGGCAACATCTTCGACCGGGCCCTGGAGCTGATCTCTA
GCTACGCCGAGTATGATACCGAGCGGATCTATATCAGACAGGCCGACATC
AATAGAGTGTCCAACGTGATCTTTGGAGAGTGGGGCACCCTGGGAGGCCT
GATGAGGGAGTACAAGGCCGACTCTATCAATGATATCAACCTGGAGCGCA
CATGCAAGAAGGTGGACAAGTGGCTGGATTCTAAGGAGTTTGCCCTGAGC
GATGTGCTGGAGGCCATCAAGAGGACCGGCAACAATGACGCCTTCAACGA
GTATATCTCCAAGATGCGGACAGCCAGAGAGAAGATCGATGCCGCCCGCA
AGGAGATGAAGTTCATCAGCGAGAAGATCTCCGGCGATGAGGAGTCTATC
CACATCATCAAGACCCTGCTGGACAGCGTGCAGCAGTTCCTGCACTTCTT
TAATCTGTTTAAGGCAAGGCAGGACATCCCACTGGATGGAGCCTTCTACG
CCGAGTTTGACGAGGTGCACAGCAAGCTGTTTGCCATCGTGCCCCTGTAT
AACAAGGTGCGGAACTATCTGACCAAGAACAATCTGAACACAAAGAAGAT
CAAGCTGAATTTCAAGAACCCTACACTGGCCAATGGCTGGGACCAGAACA
AGGTGTACGATTATGCCTCCCTGATCTTTCTGCGGGACGGCAATTACTAT
CTGGGCATCATCAATCCTAAGAGAAAGAAGAACATCAAGTTCGAGCAGGG
CTCTGGCAACGGCCCCTTCTACCGGAAGATGGTGTATAAGCAGATCCCCG

-continued

GCCCTAATAAGAACCTGCCAAGAGTGTTCCTGACCTCCACAAAGGGCAAG
AAGGAGTATAAGCCCTCTAAGGAGATCATCGAGGGCTACGAGGCCGACAA
GCACATCAGGGGCGATAAGTTCGACCTGGATTTTTGTCACAAGCTGATCG
ATTTCTTTAAGGAGTCCATCGAGAAGCACAAGGACTGGTCTAAGTTCAAC
TTCTACTTCAGCCCAACCGAGAGCTATGGCGACATCTCTGAGTTCTACCT
GGATGTGGAGAAGCAGGGCTATCGCATGCACTTTGAGAATATCAGCGCCG
AGACAATCGACGAGTATGTGGAGAAGGGCGATCTGTTTCTGTTCCAGATC
TACAACAAGGATTTTGTGAAGGCCGCCACCGGCAAGAAGGACATGCACAC
AATCTACTGGAATGCCGCCTTCAGCCCCGAGAACCTGCAGGACGTGGTGG
TGAAGCTGAACGGCGAGGCCGAGCTGTTTTATAGGGACAAGTCCGATATC
AAGGAGATCGTGCACCGCGAGGGCGAGATCCTGGTGAATAGGACCTACAA
CGGCCGCACACCAGTGCCCGACAAGATCCACAAGAAGCTGACCGATTATC
ACAATGGCCGGACAAAGGACCTGGGCGAGGCCAAGGAGTACCTGGATAAG
GTGAGATACTTCAAGGCCCACTATGACATCACCAAGGATCGGAGATACCT
GAACGACAAGATCTATTTCCACGTGCCTCTGACCCTGAACTTCAAGGCCA
ACGGCAAGAAGAATCTGAACAAGATGGTCATCGAGAAGTTCCTGTCCGAT
GAGAAGGCCCACATCATCGGCATCGACAGGGGCGAGCGCAATCTGCTGTA
CTATTCCATCATCGACAGGTCTGGCAAGATCATCGATCAGCAGAGCCTGA
ATGTGATCGACGGCTTTGATTATCGGGAGAAGCTGAACCAGAGAGAGATC
GAGATGAAGGATGCCCGCCAGTCTTGGAACGCCATCGGCAAGATCAAGGA
CCTGAAGGAGGGCTACCTGAGCAAGGCCGTGCACGAGATCACCAAGATGG
CCATCCAGTATAATGCCATCGTGGTCATGGAGGAGCTGAACTACGGCTTC
AAGCGGGGCCGGTTCAAGGTGGAGAAGCAGATCTATCAGAAGTTCGAGAA
TATGCTGATCGATAAGATGAACTACCTGGTGTTTAAGGACGCACCTGATG
AGTCCCCAGGAGGCGTGCTGAATGCCTACCAGCTGACAAACCCACTGGAG
TCTTTCGCCAAGCTGGGCAAGCAGACCGGCATCCTGTTTTACGTGCCAGC
CGCCTATACATCCAAGATCGACCCCACCACAGGCTTCGTGAATCTGTTTA
ACACCTCCTCTAAGACAAACGCCCAGGAGCGGAAGGAGTTCCTGCAGAAG
TTTGAGAGCATCTCCTATTCTGCCAAGGATGGCGGCATCTTTGCCTTCGC
CTTTGACTACAGAAAGTTCGGCACCAGCAAGACAGATCACAAGAACGTGT
GGACCGCCTATACAAACGGCGAGAGGATGCGCTACATCAAGGAGAAGAAG
CGGAATGAGCTGTTTGACCCTTCTAAGGAGATCAAGGAGGCCCTGACCAG
CTCCGGCATCAAGTACGATGGCGGCCAGAACATCCTGCCAGACATCCTGA
GGAGCAACAATAACGGCCTGATCTACACAATGTATTCTAGCTTCATCGCC
GCCATCCAGATGCGCGTGTACGACGGCAAGGAGGATTATATCATCAGCCC
CATCAAGAACTCCAAGGGCGAGTTCTTTAGGACCGACCCCAAGAGGCGCG
AGCTGCCTATCGACGCCGATGCCAATGGCGCCTACAACATCGCCCTGAGG
GGAGAGCTGACAATGAGGGCAATCGCAGAGAAGTTCGACCCTGATAGCGA
GAAGATGGCCAAGCTGGAGCTGAAGCACAAGGATTGGTTCGAGTTTATGC

-continued

AGACCAGAGGCGACAAAAGGCCGGCGGCCACGAAAAAGGCCGGCCAGGCA

AAAAAGAAAAAGGGATCCTACCCATACGATGTTCCAGATTACGCTTATCC

CTACGACGTGCCTGATTATGCATACCCATATGATGTCCCCGACTATGCCT

AA

*Eubacterium eligens* (EeCpf1; pY013), including NLS and HA tag:

(SEQ ID NO: 31)

MNGNRSIVYREFVGVIPVAKTLRNELRPVGHTQEHIIQNGLIQEDELRQE

KSTELKNIMDDYYREYIDKSLSGVTDLDFTLLFELMNLVQSSPSKDNKKA

LEKEQSKMREQICTHLQSDSNYKNIFNAKLLKEILPDFIKNYNQYDVKDK

AGKLETLALFNGFSTYFTDFFEKRKNVFTKEAVSTSIAYRIVHENSLIFL

ANMTSYKKISEKALDEIEVIEKNNQDKMGDWELNQIFNPDFYNMVLIQSG

IDFYNEICGVVNAHMNLYCQQTKNNYNLFKMRKLHKQILAYTSTSFEVPK

MFEDDMSVYNAVNAFIDETEKGNIIGKLKDIVNKYDELDEKRIYISKDFY

ETLSCFMSGNWNLITGCVENFYDENIHAKGKSKEEKVKKAVKEDKYKSIN

DVNDLVEKYIDEKERNEFKNSNAKQYIREISNIITDTETAHLEYDDHISL

IESEEKADEMKKRLDMYMNMYHWAKAFIVDEVLDRDEMFYSDIDDIYNIL

ENIVPLYNRVRNYVTQKPYNSKKIKLNFQSPTLANGWSQSKEFDNNAIIL

IRDNKYYLAIFNAKNKPDKKIIQGNSDKKNDNDYKKMVYNLLPGANKMLP

KVFLSKKGIETFKPSDYIISGYNAHKHIKTSENFDISFCRDLIDYFKNSI

EKHAEWRKYEFKFSATDSYSDISEFYREVEMQGYRIDWTYISEADINKLD

EEGKIYLFQIYNKDFAENSTGKENLHTMYFKNIFSEENLKDIIIKLNGQA

ELFYRRASVKNPVKHKKDSVLVNKTYKNQLDNGDVVRIPIPDDIYNEIYK

MYNGYIKESDLSEAAKEYLDKVEVRTAQKDIVKDYRYTVDKYFIHTPITI

NYKVTARNNVNDMVVKYIAQNDDIHVIGIDRGERNLIYISVIDSHGNIVK

QKSYNILNNYDYKKKLVEKEKTREYARKNWKSIGNIKELKEGYISGVVHE

IAMLIVEYNAIIAMEDLNYGFKRGRFKVERQVYQKFESMLINKLNYFASK

EKSVDEPGGLLKGYQLTYVPDNIKNLGKQCGVIFYVPAAFTSKIDPSTGF

ISAFNFKSISTNASRKQFFMQFDEIRYCAEKDMFSFGFDYNNFDTYNITM

GKTQWTVYTNGERLQSEFNNARRTGKTKSINLTETIKLLLEDNEINYADG

HDIRIDMEKMDEDKKSEFFAQLLSLYKLTVQMRNSYTEAEEQENGISYDK

IISPVINDEGEFFDSDNYKESDDKECKMPKDADANGAYCIALKGLYEVLK

IKSEWTEDGFDRNCLKLPHAEWLDFIQNKRYEKRPAATKKAGQAKKKKGS

YPYDVPDYAYPYDVPDYAYPYDVPDYA

SEQ ID NO: 31 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 31 may be encoded by the following nucleotide sequence:

(SEQ ID NO: 32)

ATGAACGGCAATAGGTCCATCGTGTACCGCGAGTTCGTGGGCGTGATCCC

CGTGGCCAAGACCCTGAGGAATGAGCTGCGCCCTGTGGGCCACACACAGG

AGCACATCATCCAGAACGGCCTGATCCAGGAGGACGAGCTGCGGCAGGAG

AAGAGCACCGAGCTGAAGAACATCATGGACGATTACTATAGAGAGTACAT

CGATAAGTCTCTGAGCGGCGTGACCGACCTGGACTTCACCCTGCTGTTCG

AGCTGATGAACCTGGTGCAGAGCTCCCCCTCCAAGGACAATAAGAAGGCC

CTGGAGAAGGAGCAGTCTAAGATGAGGGAGCAGATCTGCACCCACCTGCA

GTCCGACTCTAACTACAAGAATATCTTTAACGCCAAGCTGCTGAAGGAGA

TCCTGCCTGATTTCATCAAGAACTACAATCAGTATGACGTGAAGGATAAG

GCCGGCAAGCTGGAGACACTGGCCCTGTTTAATGGCTTCAGCACATACTT

TACCGACTTCTTTGAGAAGAGGAAGAACGTGTTCACCAAGGAGGCCGTGA

GCACATCCATCGCCTACCGCATCGTGCACGAGAACTCCCTGATCTTCCTG

GCCAATATGACCTCTTATAAGAAGATCAGCGAGAAGGCCCTGGATGAGAT

CGAAGTGATCGAGAAGAACAATCAGGACAAGATGGGCGATTGGGAGCTGA

ATCAGATCTTTAACCCTGACTTCTACAATATGGTGCTGATCCAGTCCGGC

ATCGACTTCTACAACGAGATCTGCGGCGTGGTGAATGCCCACATGAACCT

GTACTGTCAGCAGACCAAGAACAATTATAACCTGTTCAAGATGCGGAAGC

TGCACAAGCAGATCCTGGCCTACACCAGCACCAGCTTCGAGGTGCCCAAG

ATGTTCGAGGACGATATGAGCGTGTATAACGCCGTGAACGCCTTCATCGA

CGAGACAGAGAAGGGCAACATCATCGGCAAGCTGAAGGATATCGTGAATA

AGTACGACGAGCTGGATGAGAAGAGAATCTATATCAGCAAGGACTTTTAC

GAGACACTGAGCTGCTTCATGTCCGGCAACTGGAATCTGATCACAGGCTG

CGTGGAGAACTTCTACGATGAGAACATCCACGCCAAGGGCAAGTCCAAGG

AGGAGAAGGTGAAGAAGGCCGTGAAGGAGGACAAGTACAAGTCTATCAAT

GACGTGAACGATCTGGTGGAGAAGTATATCGATGAGAAGGAGAGGAATGA

GTTCAAGAACAGCAATGCCAAGCAGTACATCCGCGAGATCTCCAACATCA

TCACCGACACAGAGACAGCCCACCTGGAGTATGACGATCACATCTCTCTG

ATCGAGAGCGAGGAGAAGGCCGACGAGATGAAGAAGCGGCTGGATATGTA

TATGAACATGTACCACTGGGCCAAGGCCTTTATCGTGGACGAGGTGCTGG

ACAGAGATGAGATGTTCTACAGCGATATCGACGATATCTATAATATCCTG

GAGAACATCGTGCCACTGTATAATCGGGTGAGAAACTACGTGACCCAGAA

GCCCTACAACTCTAAGAAGATCAAGCTGAATTTCCAGAGCCCTACACTGG

CCAATGGCTGGTCCCAGTCTAAGGAGTTCGACAACAATGCCATCATCCTG

ATCAGAGATAACAAGTACTATCTGGCCATCTTCAATGCCAAGAACAAGCC

AGACAAGAAGATCATCCAGGGCAACTCCGATAAGAAGAACGACAACGATT

ACAAGAAGATGGTGTATAACCTGCTGCCAGGCGCCAACAAGATGCTGCCC

AAGGTGTTTCTGTCTAAGAAGGGCATCGAGACATTCAAGCCCTCCGACTA

TATCATCTCTGGCTACAACGCCCACAAGCACATCAAGACAAGCGAGAATT

TTGATATCTCCTTCTGTCGGGACCTGATCGATTACTTCAAGAACAGCATC

GAGAAGCACGCCGAGTGGAGAAAGTATGAGTTCAAGTTTTCCGCCACCGA

-continued

CAGCTACTCCGATATCTCTGAGTTCTATCGGGAGGTGGAGATGCAGGGCT

ACAGAATCGACTGGACATATATCAGCGAGGCCGACATCAACAAGCTGGAT

GAGGAGGGCAAGATCTATCTGTTTCAGATCTACAATAAGGATTTCGCCGA

GAACAGCACCGGCAAGGAGAATCTGCACACAATGTACTTTAAGAACATCT

TCTCCGAGGAGAATCTGAAGGACATCATCATCAAGCTGAACGGCCAGGCC

GAGCTGTTTTATCGGAGAGCCTCTGTGAAGAATCCCGTGAAGCACAAGAA

GGATAGCGTGCTGGTGAACAAGACCTACAAGAATCAGCTGGACAACGGCG

ACGTGGTGAGAATCCCCATCCCTGACGATATCTATAACGAGATCTACAAG

ATGTATAATGGCTACATCAAGGAGTCCGACCTGTCTGAGGCCGCCAAGGA

GTACCTGGATAAGGTGGAGGTGAGGACCGCCCAGAAGGACATCGTGAAGG

ATTACCGCTATACAGTGGACAAGTACTTCATCCACACACCTATCACCATC

AACTATAAGGTGACCGCCCGCAACAATGTGAATGATATGGTGGTGAAGTA

CATCGCCCAGAACGACGATATCCACGTGATCGGCATCGACCGGGGCGAGA

GAAACCTGATCTACATCTCCGTGATCGATTCTCACGGCAACATCGTGAAG

CAGAAATCCTACAACATCCTGAACAACTACGACTACAAGAAGAAGCTGGT

GGAGAAGGAGAAAACCCGGGAGTACGCCAGAAAGAACTGGAAGAGCATCG

GCAATATCAAGGAGCTGAAGGAGGGCTATATCTCCGGCGTGGTGCACGAG

ATCGCCATGCTGATCGTGGAGTACAACGCCATCATCGCCATGGAGGACCT

GAATTATGGCTTTAAGAGGGGCCGCTTCAAGGTGGAGCGGCAGGTGTACC

AGAAGTTTGAGAGCATGCTGATCAATAAGCTGAACTATTTCGCCAGCAAG

GAGAAGTCCGTGGACGAGCCAGGAGGCCTGCTGAAGGGCTATCAGCTGAC

CTACGTGCCCGATAATATCAAGAACCTGGGCAAGCAGTGCGGCGTGATCT

TTTACGTGCCTGCCGCCTTCACCAGCAAGATCGACCCATCCACAGGCTTT

ATCTCTGCCTTCAACTTTAAGTCTATCAGCACAAATGCCTCTCGGAAGCA

GTTCTTTATGCAGTTTGACGAGATCAGATACTGTGCCGAGAAGGATATGT

TCAGCTTTGGCTTCGACTACAACAACTTCGATACCTACAACATCACAATG

GGCAAGACACAGTGGACCGTGTATACAAACGGCGAGAGACTGCAGTCTGA

GTTCAACAATGCCAGGCGCACCGGCAAGACAAAGAGCATCAATCTGACAG

AGACAATCAAGCTGCTGCTGGAGGACAATGAGATCAACTACGCCGACGGC

CACGATATCAGGATCGATATGGAGAAGATGGACGAGGATAAGAAGAGCGA

GTTCTTTGCCCAGCTGCTGAGCCTGTATAAGCTGACCGTGCAGATGCGCA

ATTCCTATACAGAGGCCGAGGAGCAGGAGAACGGCATCTCTTACGACAAG

ATCATCAGCCCTGTGATCAATGATGAGGGCGAGTTCTTTGACTCCGATAA

CTATAAGGAGTCTGACGATAAGGAGTGCAAGATGCCAAAGGACGCCGATG

CCAACGGCGCCTACTGTATCGCCCTGAAGGGCCTGTATGAGGTGCTGAAG

ATCAAGAGCGAGTGGACCGAGGACGGCTTTGATAGGAATTGCCTGAAGCT

GCCACACGCAGAGTGGCTGGACTTCATCCAGAACAAGCGGTACGAGAAAA

GGCCGGCGGCCACGAAAAAGGCCGGCCAGGCAAAAAAGAAAAAGGGATCC

TACCCATACGATGTTCCAGATTACGCTTATCCCTACGACGTGCCTGATTA

TGCATACCCATATGATGTCCCCGACTATGCCTAA

*Moraxella bovoculi* 237 (MbCpf1; pY014), including NLS and HA tag:

(SEQ ID NO: 33)

MLFQDFTHLYPLSKTVRFELKPIDRTLEHIHAKNFLSQDETMADMHQKVK

VILDDYHRDFIADMMGEVKLTKLAEFYDVYLKFRKNPKDDELQKQLKDLQ

AVLRKEIVKPIGNGGKYKAGYDRLFGAKLFKDGKELGDLAKFVIAQEGES

SPKLAHLAHFEKFSTYFTGFHDNRKNMYSDEDKHTAIAYRLIHENLPRFI

DNLQILTTIKQKHSALYDQIINELTASGLDVSLASHLDGYHKLLTQEGIT

AYNTLLGGISGEAGSPKIQGINELINSHHNQHCHKSERIAKLRPLHKQIL

SDGMSVSFLPSKFADDSEMCQAVNEFYRHYADVFAKVQSLFDGFDDHQKD

GIYVEHKNLNELSKQAFGDFALLGRVLDGYYVDVVNPEFNERFAKAKTDN

AKAKLTKEKDKFIKGVHSLASLEQAIEHYTARHDDESVQAGKLGQYFKHG

LAGVDNPIQKIHNNHSTIKGFLERERPAGERALPKIKSGKNPEMTQLRQL

KELLDNALNVAHFAKLLTTKTTLDNQDGNFYGEFGVLYDELAKIPTLYNK

VRDYLSQKPFSTEKYKLNFGNPTLLNGWDLNKEKDNFGVILQKDGCYYLA

LLDKAHKKVFDNAPNTGKSIYQKMIYKYLEVRKQFPKVFFSKEAIAINYH

PSKELVEIKDKGRQRSDDERLKLYRFILECLKIHPKYDKKFEGAIGDIQL

FKKDKKGREVPISEKDLFDKINGIFSSKPKLEMEDFFIGEFKRYNPSQDL

VDQYNIYKKIDSNDNRKKENFYNNHPKFKKDLVRYYYESMCKHEEWEESF

EFSKKLQDIGCYVDVNELFTEIETRRLNYKISFCNINADYIDELVEQGQL

YLFQIYNKDFSPKAHGKPNLHTLYFKALFSEDNLADPIYKLNGEAQIFYR

KASLDMNETTIHRAGEVLENKNPDNPKKRQFVYDIIKDKRYTQDKFMLHV

PITMNFGVQGMTIKEFNKKVNQSIQQYDEVNVIGIDRGERHLLYLTVINS

KGEILEQCSLNDITTASANGTQMTTPYHKILDKREIERLNARVGWGEIET

IKELKSGYLSHVVHQISQLMLKYNAIVVLEDLNFGFKRGRFKVEKQIYQN

FENALIKKLNHLVLKDKADDEIGSYKNALQLTNNFTDLKSIGKQTGFLFY

VPAWNTSKIDPETGFVDLLKPRYENIAQSQAFFGKFDKICYNADKDYFEF

HIDYAKFTDKAKNSRQIWTICSHGDKRYVYDKTANQNKGAAKGINVNDEL

KSLFARHHINEKQPNLVMDICQNNDKEFHKSLMYLLKTLLALRYSNASSD

EDFILSPVANDEGVFFNSALADDTQPQNADANGAYHIALKGLWLLNELKN

SDDLNKVKLAIDNQTWLNFAQNRKRPAATKKAGQAKKKKGSYPYDVPDYA

YPYDVPDYAYPYDVPDYA

SEQ ID NO: 33 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 33 may be encoded by the following nucleotide sequence:

(SEQ ID NO: 34)

ATGCTGTTCCAGGACTTTACCCACCTGTATCCACTGTCCAAGACAGTGAG

ATTTGAGCTGAAGCCCATCGATAGGACCCTGGAGCACATCCACGCCAAGA

ACTTCCTGTCTCAGGACGAGACAATGGCCGATATGCACCAGAAGGTGAAA

GTGATCCTGGACGATTACCACCGCGACTTCATCGCCGATATGATGGGCGA

GGTGAAGCTGACCAAGCTGGCCGAGTTCTATGACGTGTACCTGAAGTTTC

-continued

GGAAGAACCCAAAGGACGATGAGCTGCAGAAGCAGCTGAAGGATCTGCAG

GCCGTGCTGAGAAAGGAGATCGTGAAGCCCATCGGCAATGGCGGCAAGTA

TAAGGCCGGCTACGACAGGCTGTTCGGCGCCAAGCTGTTTAAGGACGGCA

AGGAGCTGGGCGATCTGGCCAAGTTCGTGATCGCACAGGAGGGAGAGAGC

TCCCCAAAGCTGGCCCACCTGGCCCACTTCGAGAAGTTTTCCACCTATTT

CACAGGCTTTCACGATAACCGGAAGAATATGTATTCTGACGAGGATAAGC

ACACCGCCATCGCCTACCGCCTGATCCACGAGAACCTGCCCCGGTTTATC

GACAATCTGCAGATCCTGACCACAATCAAGCAGAAGCACTCTGCCCTGTA

CGATCAGATCATCAACGAGCTGACCGCCAGCGGCCTGGACGTGTCTCTGG

CCAGCCACCTGGATGGCTATCACAAGCTGCTGACACAGGAGGGCATCACC

GCCTACAATACACTGCTGGGAGGAATCTCCGGAGAGGCAGGCTCTCCTAA

GATCCAGGGCATCAACGAGCTGATCAATTCTCACCACAACCAGCACTGCC

ACAAGAGCGAGAGAATCGCCAAGCTGAGGCCACTGCACAAGCAGATCCTG

TCCGACGGCATGAGCGTGTCCTTCCTGCCCTCTAAGTTTGCCGACGATAG

CGAGATGTGCCAGGCCGTGAACGAGTTCTATCGCCACTACGCCGACGTGT

TCGCCAAGGTGCAGAGCCTGTTCGACGGCTTTGACGATCACCAGAAGGAT

GGCATCTACGTGGAGCACAAGAACCTGAATGAGCTGTCCAAGCAGGCCTT

CGGCGACTTTGCACTGCTGGGACGCGTGCTGGACGGATACTATGTGGATG

TGGTGAATCCAGAGTTCAACGAGCGGTTTGCCAAGGCCAAGACCGACAAT

GCCAAGGCCAAGCTGACAAAGGAGAAGGATAAGTTCATCAAGGGCGTGCA

CTCCCTGGCCTCTCTGGAGCAGGCCATCGAGCACTATACCGCAAGGCACG

ACGATGAGAGCGTGCAGGCAGGCAAGCTGGGACAGTACTTCAAGCACGGC

CTGGCCGGAGTGGACAACCCCATCCAGAAGATCCACAACAATCACAGCAC

CATCAAGGGCTTTCTGGAGAGGGAGCGCCCTGCAGGAGAGAGAGCCCTGC

CAAAGATCAAGTCCGGCAAGAATCCTGAGATGACACAGCTGAGGCAGCTG

AAGGAGCTGCTGGATAACGCCCTGAATGTGGCCCACTTCGCCAAGCTGCT

GACCACAAAGACCACACTGGACAATCAGGATGGCAACTTCTATGGCGAGT

TTGGCGTGCTGTACGACGAGCTGGCCAAGATCCCCACCCTGTATAACAAG

GTGAGAGATTACCTGAGCCAGAAGCCTTTCTCCACCGAGAAGTACAAGCT

GAACTTTGGCAATCCAACACTGCTGAATGGCTGGGACCTGAACAAGGAGA

AGGATAATTTCGGCGTGATCCTGCAGAAGGACGGCTGCTACTATCTGGCC

CTGCTGGACAAGGCCCACAAGAAGGTGTTTGATAACGCCCCTAATACAGG

CAAGAGCATCTATCAGAAGATGATCTATAAGTACCTGGAGGTGAGGAAGC

AGTTCCCCAAGGTGTTCTTTTCCAAGGAGGCCATCGCCATCAACTACCAC

CCTTCTAAGGAGCTGGTGGAGATCAAGGACAAGGGCCGGCAGAGATCCGA

CGATGAGCGCCTGAAGCTGTATCGGTTTATCCTGGAGTGTCTGAAGATCC

ACCCTAAGTACGATAAGAAGTTCGAGGGCGCCATCGGCGACATCCAGCTG

TTTAAGAAGGATAAGAAGGGCAGAGAGGTGCCAATCAGCGAGAAGGACCT

GTTCGATAAGATCAACGGCATCTTTTCTAGCAAGCCTAAGCTGGAGATGG

AGGACTTCTTTATCGGCGAGTTCAAGAGGTATAACCCAAGCCAGGACCTG

GTGGATCAGTATAATATCTACAAGAAGATCGACTCCAACGATAATCGCAA

-continued

GAAGGAGAATTTCTACAACAATCACCCCAAGTTTAAGAAGGATCTGGTGC

GGTACTATTACGAGTCTATGTGCAAGCACGAGGAGTGGGAGGAGAGCTTC

GAGTTTTCCAAGAAGCTGCAGGACATCGGCTGTTACGTGGATGTGAACGA

GCTGTTTACCGAGATCGAGACACGGAGACTGAATTATAAGATCTCCTTCT

GCAACATCAATGCCGACTACATCGATGAGCTGGTGGAGCAGGGCCAGCTG

TATCTGTTCCAGATCTACAACAAGGACTTTTCCCCAAAGGCCCACGGCAA

GCCCAATCTGCACACCCTGTACTTCAAGGCCCTGTTTTCTGAGGACAACC

TGGCCGATCCTATCTATAAGCTGAATGGCGAGGCCCAGATCTTCTACAGA

AAGGCCTCCCTGGACATGAACGAGACAACAATCCACAGGGCCGGCGAGGT

GCTGGAGAACAAGAATCCCGATAATCCTAAGAAGAGACAGTTCGTGTACG

ACATCATCAAGGATAAGAGGTACACACAGGACAAGTTCATGCTGCACGTG

CCAATCACCATGAACTTTGGCGTGCAGGGCATGACAATCAAGGAGTTCAA

TAAGAAGGTGAACCAGTCTATCCAGCAGTATGACGAGGTGAACGTGATCG

GCATCGATCGGGGCGAGAGACACCTGCTGTACCTGACCGTGATCAATAGC

AAGGGCGAGATCCTGGAGCAGTGTTCCCTGAACGACATCACCACAGCCTC

TGCCAATGGCACACAGATGACCACACCTTACCACAAGATCCTGGATAAGA

GGGAGATCGAGCGCCTGAACGCCCGGGTGGGATGGGGCGAGATCGAGACA

ATCAAGGAGCTGAAGTCTGGCTATCTGAGCCACGTGGTGCACCAGATCAG

CCAGCTGATGCTGAAGTACAACGCCATCGTGGTGCTGGAGGACCTGAATT

TCGGCTTTAAGAGGGGCCGCTTTAAGGTGGAGAAGCAGATCTATCAGAAC

TTCGAGAATGCCCTGATCAAGAAGCTGAACCACCTGGTGCTGAAGGACAA

GGCCGACGATGAGATCGGCTCTTACAAGAATGCCCTGCAGCTGACCAACA

ATTTCACAGATCTGAAGAGCATCGGCAAGCAGACCGGCTTCCTGTTTTAT

GTGCCCGCCTGGAACACCTCTAAGATCGACCCTGAGACAGGCTTTGTGGA

TCTGCTGAAGCCAAGATACGAGAACATCGCCCAGAGCCAGGCCTTCTTTG

GCAAGTTCGACAAGATCTGCTATAATGCCGACAAGGATTACTTCGAGTTT

CACATCGACTACGCCAAGTTTACCGATAAGGCCAAGAATAGCCGCCAGAT

CTGGACAATCTGTTCCCACGGCGACAAGCGGTACGTGTACGATAAGACAG

CCAACCAGAATAAGGGCGCCGCCAAGGGCATCAACGTGAATGATGAGCTG

AAGTCCCTGTTCGCCCGCCACCACATCAACGAGAAGCAGCCCAACCTGGT

CATGGACATCTGCCAGAACAATGATAAGGAGTTTCACAAGTCTCTGATGT

ACCTGCTGAAAACCCTGCTGGCCCTGCGGTACAGCAACGCCTCCTCTGAC

GAGGATTTCATCCTGTCCCCCGTGGCAAACGACGAGGGCGTGTTCTTTAA

TAGCGCCCTGGCCGACGATACACAGCCTCAGAATGCCGATGCCAACGGCG

CCTACCACATCGCCCTGAAGGGCCTGTGGCTGCTGAATGAGCTGAAGAAC

TCCGACGATCTGAACAAGGTGAAGCTGGCCATCGACAATCAGACCTGGCT

GAATTTCGCCCAGAACAGGAAAAGGCCGGCGGCCACGAAAAAGGCCGGCC

AGGCAAAAAAGAAAAAGGGATCCTACCCATACGATGTTCCAGATTACGCT

TATCCCTACGACGTGCCTGATTATGCATACCCATATGATGTCCCCGACTA

TGCCTAA

*Leptospira inadai* (LiCpf1; pY015), including NLS and HA tag:

(SEQ ID NO: 35)
MEDYSGFVNIYSIQKTLRFELKPVGKTLEHIEKKGFLKKDKIRAEDYKAV
KKIIDKYHRAYIEEVFDSVLHQKKKKDKTRFSTQFIKEIKEFSELYYKTE
KNIPDKERLEALSEKLRKMLVGAFKGEFSEEVAEKYKNLFSKELIRNEIE
KFCETDEERKQVSNFKSFTTYFTGFHSNRQNIYSDEKKSTAIGYRIIHQN
LPKFLDNLKIIESIQRRFKDFPWSDLKKNLKKIDKNIKLTEYFSIDGFVN
VLNQKGIDAYNTILGGKSEESGEKIQGLNEYINLYRQKNNIDRKNLPNVK
ILFKQILGDRETKSFIPEAFPDDQSVLNSITEFAKYLKLDKKKKSIIAEL
KKFLSSFNRYELDGIYLANDNSLASISTFLFDDWSFIKKSVSFKYDESVG
DPKKKIKSPLKYEKEKEKWLKQKYYTISFLNDAIESYSKSQDEKRVKIRL
EAYFAEFKSKDDAKKQFDLLERIEEAYAIVEPLLGAEYPRDRNLKADKKE
VGKIKDFLDSIKSLQFFLKPLLSAEIFDEKDLGFYNQLEGYYEEIDSIGH
LYNKVRNYLTGKIYSKEKFKLNFENSTLLKGWDENREVANLCVIFREDQK
YYLGVMDKENNTILSDIPKVKPNELFYEKMVYKLIPTPHMQLPRIIFSSD
NLSIYNPSKSILKIREAKSFKEGKNFKLKDCHKFIDFYKESISKNEDWSR
FDFKFSKTSSYENISEFYREVERQGYNLDFKKVSKFYIDSLVEDGKLYLF
QIYNKDFSIFSKGKPNLHTIYFRSLFSKENLKDVCLKLNGEAEMFFRKKS
INYDEKKKREGHHPELFEKLKYPILKDKRYSEDKFQFHLPISLNFKSKER
LNFNLKVNEFLKRNKDINIIGIDRGERNLLYLVMINQKGEILKQTLLDSM
QSGKGRPEINYKEKLQEKEIERDKARKSWGTVENIKELKEGYLSIVIHQI
SKLMVENNAIVVLEDLNIGFKRGRQKVERQVYQKFEKMLIDKLNFLVFKE
NKPTEPGGVLKAYQLTDEFQSFEKLSKQTGFLFYVPSWNTSKIDPRTGFI
DFLHPAYENIEKAKQWINKFDSIRFNSKMDWFEFTADTRKFSENLMLGKN
RVWVICTTNVERYFTSKTANSSIQYNSIQITEKLKELFVDIPFSNGQDLK
PEILRKNDAVFFKSLLFYIKTTLSLRQNNGKKGEEEKDFILSPVVDSKGR
FFNSLEASDDEPKDADANGAYHIALKGLMNLLVLNETKEENLSRPKWKIK
NKDWLEFVWERNRKRPAATKKAGQAKKKKGSYPYDVPDYAYPYDVPDYAY
PYDVPDYA

SEQ ID NO: 35 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 35 may be encoded by the following nucleotide sequence:

(SEQ ID NO: 36)
ATGGAGGACTATTCCGGCTTTGTGAACATCTACTCTATCCAGAAAACCCT
GAGGTTCGAGCTGAAGCCAGTGGGCAAGACACTGGAGCACATCGAGAAGA
AGGGCTTCCTGAAGAAGGACAAGATCCGGGCCGAGGATTACAAGGCCGTG
AAGAAGATCATCGATAAGTACCACAGAGCCTATATCGAGGAGGTGTTTGA
TTCCGTGCTGCACCAGAAGAAGAAGAAGGACAAGACCCGCTTTTCTACAC

-continued
AGTTCATCAAGGAGATCAAGGAGTTCAGCGAGCTGTACTATAAGACCGAG
AAGAACATCCCCGACAAGGAGAGGCTGGAGGCCCTGAGCGAGAAGCTGCG
CAAGATGCTGGTGGGCGCCTTTAAGGGCGAGTTCTCCGAGGAGGTGGCCG
AGAAGTATAAGAACCTGTTTTCTAAGGAGCTGATCAGGAATGAGATCGAG
AAGTTCTGCGAGACAGACGAGGAGCGCAAGCAGGTGTCTAACTTCAAGAG
CTTCACCACATACTTTACCGGCTTCCACTCCAACAGGCAGAATATCTATT
CCGACGAGAAGAAGTCTACAGCCATCGGCTACCGCATCATCCACCAGAAC
CTGCCTAAGTTCCTGGATAATCTGAAGATCATCGAGTCCATCCAGCGGCG
GTTCAAGGACTTCCCATGGTCTGATCTGAAGAAGAACCTGAAGAAGATCG
ATAAGAATATCAAGCTGACCGAGTACTTCAGCATCGACGGCTTCGTGAAC
GTGCTGAATCAGAAGGGCATCGATGCCTACAACACAATCCTGGGCGGCAA
GTCCGAGGAGTCTGGCGAGAAGATCCAGGGCCTGAACGAGTACATCAATC
TGTATCGGCAGAAGAACAATATCGACAGAAAGAACCTGCCCAATGTGAAG
ATCCTGTTTAAGCAGATCCTGGGCGATAGGGAGACAAAGAGCTTTATCCC
TGAGGCCTTCCCAGACGATCAGTCCGTGCTGAACTCTATCACAGAGTTCG
CCAAGTACCTGAAGCTGGATAAGAAGAAGAAGAGCATCATCGCCGAGCTG
AAGAAGTTTCTGAGCTCCTTCAATCGCTACGAGCTGGACGGCATCTATCT
GGCCAACGATAATAGCCTGGCCTCTATCAGCACCTTCCTGTTTGACGATT
GGTCCTTTATCAAGAAGTCCGTGTCTTTCAAGTATGACGAGTCCGTGGGC
GACCCCAAGAAGAAGATCAAGTCTCCCCTGAAGTACGAGAAGGAGAAGGA
GAAGTGGCTGAAGCAGAAGTACTATACAATCTCTTTCCTGAACGATGCCA
TCGAGAGCTATTCCAAGTCTCAGGACGAGAAGAGGGTGAAGATCCGCCTG
GAGGCCTACTTTGCCGAGTTCAAGAGCAAGGACGATGCCAAGAAGCAGTT
CGACCTGCTGGAGAGGATCGAGGAGGCCTATGCCATCGTGGAGCCTCTGC
TGGGAGCAGAGTACCCAAGGGACCGCAACCTGAAGGCCGATAAGAAGGAA
GTGGGCAAGATCAAGGACTTCCTGGATAGCATCAAGTCCCTGCAGTTCTT
TCTGAAGCCTCTGCTGTCCGCCGAGATCTTTGACGAGAAGGATCTGGGCT
TCTACAATCAGCTGGAGGGCTACTATGAGGAGATCGATTCTATCGGCCAC
CTGTATAACAAGGTGCGGAATTATCTGACCGGCAAGATCTACAGCAAGGA
GAAGTTTAAGCTGAACTTCGAGAACAGCACCCTGCTGAAGGGCTGGGACG
AGAACCGGGAGGTGGCCAATCTGTGCGTGATCTTCAGAGAGGACCAGAAG
TACTATCTGGGCGTGATGGATAAGGAGAACAATACCATCCTGTCCGACAT
CCCCAAGGTGAAGCCTAACGAGCTGTTTTACGAGAAGATGGTGTATAAGC
TGATCCCCACACCTCACATGCAGCTGCCCCGGATCATCTTCTCTAGCGAC
AACCTGTCTATCTATAATCCTAGCAAGTCCATCCTGAAGATCAGAGAGGC
CAAGAGCTTTAAGGAGGGCAAGAACTTCAAGCTGAAGGACTGTCACAAGT
TTATCGATTTCTACAAGGAGTCTATCAGCAAGAATGAGGACTGGAGCAGA
TTCGACTTCAAGTTCAGCAAGACCAGCAGCTACGAGAACATCAGCGAGTT
TTACCGGGAGGTGGAGAGACAGGGCTATAACCTGGACTTCAAGAAGGTGT
CTAAGTTCTACATCGACAGCCTGGTGGAGGATGGCAAGCTGTACCTGTTC
CAGATCTATAACAAGGACTTTTCTATCTTCAGCAAGGGCAAGCCCAATCT -continued

```
GCACACCATCTATTTTCGGTCCCTGTTCTCTAAGGAGAACCTGAAGGACG
TGTGCCTGAAGCTGAATGGCGAGGCCGAGATGTTCTTTCGGAAGAAGTCC
ATCAACTACGATGAGAAGAAGAAGCGGGAGGGCCACCACCCCGAGCTGTT
TGAGAAGCTGAAGTATCCTATCCTGAAGGACAAGAGATACAGCGAGGATA
AGTTTCAGTTCCACCTGCCCATCAGCCTGAACTTCAAGTCCAAGGAGCGG
CTGAACTTTAATCTGAAAGTGAATGAGTTCCTGAAGAGAAACAAGGACAT
CAATATCATCGGCATCGATCGGGGCGAGAGAAACCTGCTGTACCTGGTCA
TGATCAATCAGAAGGGCGAGATCCTGAAGCAGACCCTGCTGGACAGCATG
CAGTCCGGCAAGGGCCGGCCTGAGATCAACTACAAGGAGAAGCTGCAGGA
GAAGGAGATCGAGAGGGATAAGGCCCGCAAGAGCTGGGGCACAGTGGAGA
ATATCAAGGAGCTGAAGGAGGGCTATCTGTCTATCGTGATCCACCAGATC
AGCAAGCTGATGGTGGAGAACAATGCCATCGTGGTGCTGGAGGACCTGAA
CATCGGCTTTAAGCGGGGCAGACAGAAGGTGGAGCGGCAGGTGTACCAGA
AGTTCGAGAAGATGCTGATCGATAAGCTGAACTTTCTGGTGTTCAAGGAG
AATAAGCCAACCGAGCCAGGAGGCGTGCTGAAGGCCTATCAGCTGACAGA
CGAGTTTCAGTCTTTCGAGAAGCTGAGCAAGCAGACCGGCTTTCTGTTCT
ACGTGCCAAGCTGGAACACCTCCAAGATCGACCCCAGAACAGGCTTTATC
GATTTCCTGCACCCTGCCTACGAGAATATCGAGAAGGCCAAGCAGTGGAT
CAACAAGTTTGATTCCATCAGGTTCAATTCTAAGATGGACTGGTTTGAGT
TCACCGCCGATACACGCAAGTTTTCCGAGAACCTGATGCTGGGCAAGAAT
CGGGTGTGGGTCATCTGCACCACAAATGTGGAGCGGTACTTCACCAGCAA
GACCGCCAACAGCTCCATCCAGTACAATAGCATCCAGATCACCGAGAAGC
TGAAGGAGCTGTTTGTGGACATCCCTTTCAGCAACGGCCAGGATCTGAAG
CCAGAGATCCTGAGGAAGAATGACGCCGTGTTCTTTAAGAGCCTGCTGTT
TTACATCAAGACCACACTGTCCCTGCGCCAGAACAATGGCAAGAAGGGCG
AGGAGGAGAAGGACTTCATCCTGAGCCCAGTGGTGGATTCCAAGGGCCGG
TTCTTTAACTCTCTGGAGGCCAGCGACGATGAGCCCAAGGACGCCGATGC
CAATGGCGCCTACCACATCGCCCTGAAGGGCCTGATGAACCTGCTGGTGC
TGAATGAGACAAAGGAGGAGAACCTGAGCAGACCAAAGTGGAAGATCAAG
AATAAGGACTGGCTGGAGTTCGTGTGGGAGAGGAACCGCAAAAGGCCGGC
GGCCACGAAAAAGGCCGGCCAGGCAAAAAAGAAAAAGGGATCCTACCCAT
ACGATGTTCCAGATTACGCTTATCCCTACGACGTGCCTGATTATGCATAC
CCATATGATGTCCCCGACTATGCCTAA
```

*Lachnospiraceae bacterium* ND2006 (LbCpf1; pY016), including NLS and HA tag:

(SEQ ID NO: 37)

```
MSKLEKFTNCYSLSKTLRFKAIPVGKTQENIDNKRLLVEDEKRAEDYKGV
KKLLDRYYLSFINDVLHSIKLKNLNNYISLFRKKTRTEKENKELENLEIN
LRKEIAKAFKGNEGYKSLFKKDIIETILPEFLDDKDEIALVNSFNGFTTA
FTGFFDNRENMFSEEAKSTSIAFRCINENLTRYISNMDIFEKVDAIFDKH
```

-continued

```
EVQEIKEKILNSDYDVEDFFEGEFFNFVLTQEGIDVYNAIIGGFVTESGE
KIKGLNEYINLYNQKTKQKLPKFKPLYKQVLSDRESLSFYGEGYTSDEEV
LEVFRNTLNKNSEIFSSIKKLEKLFKNFDEYSSAGIFVKNGPAISTISKD
IFGEWNVIRDKWNAEYDDIHLKKKAVVTEKYEDDRRKSFKKIGSFSLEQL
QEYADADLSVVEKLKEIIIQKVDEIYKVYGSSEKLFDADFVLEKSLKKND
AVVAIMKDLLDSVKSFENYIKAFFGEGKETNRDESFYGDFVLAYDILLKV
DHIYDAIRNYVTQKPYSKDKFKLYFQNPQFMGGWDKDKETDYRATILRYG
SKYYLAIMDKKYAKCLQKIDKDDVNGNYEKINYKLLPGPNKMLPKVFFSK
KWMAYYNPSEDIQKIYKNGTFKKGDMFNLNDCHKLIDFFKDSISRYPKWS
NAYDFNFSETEKYKDIAGFYREVEEQGYKVSFESASKKEVDKLVEEGKLY
MFQIYNKDFSDKSHGTPNLHTMYFKLLFDENNHGQIRLSGGAELFMRRAS
LKKEELVVHPANSPIANKNPDNPKKTTTLSYDVYKDKRFSEDQYELHIPI
AINKCPKNIFKINTEVRVLLKHDDNPYVIGIDRGERNLLYIVVVDGKGNI
VEQYSLNEIINNFNGIRIKTDYHSLLDKKEKERFEARQNWTSIENIKELK
AGYISQVVHKICELVEKYDAVIALEDLNSGFKNSRVKVEKQVYQKFEKML
IDKLNYMVDKKSNPCATGGALKGYQITNKFESFKSMSTQNGFIFYIPAWL
TSKIDPSTGFVNLLKTKYTSIADSKKFISSFDRIMYVPEEDLFEFALDYK
NFSRTDADYIKKWKLYSYGNRIRIFRNPKKNNVFDWEEVCLTSAYKELFN
KYGINYQQGDIRALLCEQSDKAFYSSFMALMSLMLQMRNSITGRTDVDFL
ISPVKNSDGIFYDSRNYEAQENAILPKNADANGAYNIARKVLWAIGQFKK
AEDEKLDKVKIAISNKEWLEYAQTSVKHKRPAATKKAGQAKKKKGSYPYD
VPDYAYPYDVPDYAYPYDVPDYA
```

SEQ ID NO: 37 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 37 may be encoded by the following nucleotide sequence:

(SEQ ID NO: 38)

```
ATGAGCAAGCTGGAGAAGTTTACAAACTGCTACTCCCTGTCTAAGACCCT
GAGGTTCAAGGCCATCCCTGTGGGCAAGACCCAGGAGAACATCGACAATA
AGCGGCTGCTGGTGGAGGACGAGAAGAGAGCCGAGGATTATAAGGGCGTG
AAGAAGCTGCTGGATCGCTACTATCTGTCTTTTATCAACGACGTGCTGCA
CAGCATCAAGCTGAAGAATCTGAACAATTACATCAGCCTGTTCCGGAAGA
AAACCAGAACCGAGAAGGAGAATAAGGAGCTGGAGAACCTGGAGATCAAT
CTGCGGAAGGAGATCGCCAAGGCCTTCAAGGGCAACGAGGGCTACAAGTC
CCTGTTTAAGAAGGATATCATCGAGACAATCCTGCCAGAGTTCCTGGACG
ATAAGGACGAGATCGCCCTGGTGAACAGCTTCAATGGCTTTACCACAGCC
TTCACCGGCTTCTTTGATAACAGAGAGAATATGTTTTCCGAGGAGGCCAA
GAGCACATCCATCGCCTTCAGGTGTATCAACGAGAATCTGACCCGCTACA
TCTCTAATATGGACATCTTCGAGAAGGTGGACGCCATCTTTGATAAGCAC
GAGGTGCAGGAGATCAAGGAGAAGATCCTGAACAGCGACTATGATGTGGA
```

-continued

GGATTTCTTTGAGGGCGAGTTCTTTAACTTTGTGCTGACACAGGAGGGCA
TCGACGTGTATAACGCCATCATCGGCGGCTTCGTGACCGAGAGCGGCGAG
AAGATCAAGGGCCTGAACGAGTACATCAACCTGTATAATCAGAAAACCAA
GCAGAAGCTGCCTAAGTTTAAGCCACTGTATAAGCAGGTGCTGAGCGATC
GGGAGTCTCTGAGCTTCTACGGCGAGGGCTATACATCCGATGAGGAGGTG
CTGGAGGTGTTTAGAAACACCCTGAACAAGAACAGCGAGATCTTCAGCTC
CATCAAGAAGCTGGAGAAGCTGTTCAAGAATTTTGACGAGTACTCTAGCG
CCGGCATCTTTGTGAAGAACGGCCCCGCCATCAGCACAATCTCCAAGGAT
ATCTTCGGCGAGTGGAACGTGATCCGGGACAAGTGGAATGCCGAGTATGA
CGATATCCACCTGAAGAAGAAGGCCGTGGTGACCGAGAAGTACGAGGACG
ATCGGAGAAAGTCCTTCAAGAAGATCGGCTCCTTTTCTCTGGAGCAGCTG
CAGGAGTACGCCGACGCCGATCTGTCTGTGGTGGAGAAGCTGAAGGAGAT
CATCATCCAGAAGGTGGATGAGATCTACAAGGTGTATGGCTCCTCTGAGA
AGCTGTTCGACGCCGATTTTGTGCTGGAGAAGAGCCTGAAGAAGAACGAC
GCCGTGGTGGCCATCATGAAGGACCTGCTGGATTCTGTGAAGAGCTTCGA
GAATTACATCAAGGCCTTCTTTGGCGAGGGCAAGGAGACAAACAGGGACG
AGTCCTTCTATGGCGATTTTGTGCTGGCCTACGACATCCTGCTGAAGGTG
GACCACATCTACGATGCCATCCGCAATTATGTGACCCAGAAGCCCTACTC
TAAGGATAAGTTCAAGCTGTATTTTCAGAACCCTCAGTTCATGGGCGGCT
GGGACAAGGATAAGGAGACAGACTATCGGGCCACCATCCTGAGATACGGC
TCCAAGTACTATCTGGCCATCATGGATAAGAAGTACGCCAAGTGCCTGCA
GAAGATCGACAAGGACGATGTGAACGGCAATTACGAGAAGATCAACTATA
AGCTGCTGCCCGGCCCTAATAAGATGCTGCCAAAGGTGTTCTTTTCTAAG
AAGTGGATGGCCTACTATAACCCCAGCGAGGACATCCAGAAGATCTACAA
GAATGGCACATTCAAGAAGGGCGATATGTTTAACCTGAATGACTGTCACA
AGCTGATCGACTTCTTTAAGGATAGCATCTCCCGGTATCCAAAGTGGTCC
AATGCCTACGATTTCAACTTTTCTGAGACAGAGAAGTATAAGGACATCGC
CGGCTTTTACAGAGAGGTGGAGGAGCAGGGCTATAAGGTGAGCTTCGAGT
CTGCCAGCAAGAAGGAGGTGGATAAGCTGGTGGAGGAGGGCAAGCTGTAT
ATGTTCCAGATCTATAACAAGGACTTTTCCGATAAGTCTCACGGCACACC
CAATCTGCACACCATGTACTTCAAGCTGCTGTTTGACGAGAACAATCACG
GACAGATCAGGCTGAGCGGAGGAGCAGAGCTGTTCATGAGGCGCGCCTCC
CTGAAGAAGGAGGAGCTGGTGGTGCACCCAGCCAACTCCCCTATCGCCAA
CAAGAATCCAGATAATCCCAAGAAAACCACAACCCTGTCCTACGACGTGT
ATAAGGATAAGAGGTTTTCTGAGGACCAGTACGAGCTGCACATCCCAATC
GCCATCAATAAGTGCCCCAAGAACATCTTCAAGATCAATACAGAGGTGCG
CGTGCTGCTGAAGCACGACGATAACCCCTATGTGATCGGCATCGATAGGG
GCGAGCGCAATCTGCTGTATATCGTGGTGGTGGACGGCAAGGGCAACATC
GTGGAGCAGTATTCCCTGAACGAGATCATCAACAACTTCAACGGCATCAG
GATCAAGACAGATTACCACTCTCTGCTGGACAAGAAGGAGAAGGAGAGGT

-continued

TCGAGGCCCGCCAGAACTGGACCTCCATCGAGAATATCAAGGAGCTGAAG
GCCGGCTATATCTCTCAGGTGGTGCACAAGATCTGCGAGCTGGTGGAGAA
GTACGATGCCGTGATCGCCCTGGAGGACCTGAACTCTGGCTTTAAGAATA
GCCGCGTGAAGGTGGAGAAGCAGGTGTATCAGAAGTTCGAGAAGATGCTG
ATCGATAAGCTGAACTACATGGTGGACAAGAAGTCTAATCCTTGTGCAAC
AGGCGGCGCCCTGAAGGGCTATCAGATCACCAATAAGTTCGAGAGCTTTA
AGTCCATGTCTACCCAGAACGGCTTCATCTTTTACATCCCTGCCTGGCTG
ACATCCAAGATCGATCCATCTACCGGCTTTGTGAACCTGCTGAAAACCAA
GTATACCAGCATCGCCGATTCCAAGAAGTTCATCAGCTCCTTTGACAGGA
TCATGTACGTGCCCGAGGAGGATCTGTTCGAGTTTGCCCTGGACTATAAG
AACTTCTCTCGCACAGACGCCGATTACATCAAGAAGTGGAAGCTGTACTC
CTACGGCAACCGGATCAGAATCTTCCGGAATCCTAAGAAGAACAACGTGT
TCGACTGGGAGGAGGTGTGCCTGACCAGCGCCTATAAGGAGCTGTTCAAC
AAGTACGGCATCAATTATCAGCAGGGCGATATCAGAGCCCTGCTGTGCGA
GCAGTCCGACAAGGCCTTCTACTCTAGCTTTATGGCCCTGATGAGCCTGA
TGCTGCAGATGCGGAACAGCATCACAGGCCGCACCGACGTGGATTTTCTG
ATCAGCCCTGTGAAGAACTCCGACGGCATCTTCTACGATAGCCGGAACTA
TGAGGCCCAGGAGAATGCCATCCTGCCAAAGAACGCCGACGCCAATGGCG
CCTATAACATCGCCAGAAAGGTGCTGTGGGCCATCGGCCAGTTCAAGAAG
GCCGAGGACGAGAAGCTGGATAAGGTGAAGATCGCCATCTCTAACAAGGA
GTGGCTGGAGTACGCCCAGACCAGCGTGAAGCACAAAAGGCCGGCGGCCA
CGAAAAAGGCCGGCCAGGCAAAAAAGAAAAAGGGATCCTACCCATACGAT
GTTCCAGATTACGCTTATCCCTACGACGTGCCTGATTATGCATACCCATA
TGATGTCCCCGACTATGCCTAA

*Porphyromonas crevioricanis* (PcCpf1; pY017), including NLS and HA tag:

(SEQ ID NO: 39)
MDSLKDFTNLYPVSKTLRFELKPVGKTLENIEKAGILKEDEHRAESYRRV
KKIIDTYHKVFIDSSLENMAKMGIENEIKAMLQSFCELYKKDHRTEGEDK
ALDKIRAVLRGLIVGAFTGVCGRRENTVQNEKYESLFKEKLIKEILPDFV
LSTEAESLPFSVEEATRSLKEFDSFTSYFAGFYENRKNIYSTKPQSTAIA
YRLIHENLPKFIDNILVFQKIKEPIAKELEHIRADFSAGGYIKKDERLED
IFSLNYYIHVLSQAGIEKYNALIGKIVTEGDGEMKGLNEHINLYNQQRGR
EDRLPLFRPLYKQILSDREQLSYLPESFEKDEELLRALKEFYDHIAEDIL
GRTQQLMTSISEYDLSRIYVRNDSQLTDISKKMLGDWNAIYMARERAYDH
EQAPKRITAKYERDRIKALKGEESISLANLNSCIAFLDNVRDCRVDTYLS
TLGQKEGPHGLSNLVENVFASYHEAEQLLSFPYPEENNLIQDKDNVVLIK
NLLDNISDLQRFLKPLWGMGDEPDKDERFYGEYNYIRGALDQVIPLYNKV
RNYLTRKPYSTRKVKLNFGNSQLLSGWDRNKEKDNSCVILRKGQNFYLAI
MNNRHKRSFENKMLPEYKEGEPYFEKMDYKFLPDPNKMLPKVFLSKKGIE
IYKPSPKLLEQYGHGTHKKGDTFSMDDLHELIDFFKHSIEAHEDWKQFGF

-continued

KFSDTATYENVSSFYREVEDQGYKLSFRKVSESYVYSLIDQGKLYLFQIY

NKDFSPCSKGTPNLHTLYWRMLFDERNLADVIYKLDGKAEIFFREKSLKN

DHPTHPAGKPIKKKSRQKKGEESLFEYDLVKDRRYTMDKFQFHVPITMNF

KCSAGSKVNDMVNAHIREAKDMHVIGIDRGERNLLYICVIDSRGTILDQI

SLNTINDIDYHDLLESRDKDRQQEHRNWQTIEGIKELKQGYLSQAVHRIA

ELMVAYKAVVALEDLNMGFKRGRQKVESSVYQQFEKQLIDKLNYLVDKKK

RPEDIGGLLRAYQFTAPFKSFKEMGKQNGFLFYIPAWNTSNIDPTTGFVN

LFHVQYENVDKAKSFFQKFDSISYNPKKDWFEFAFDYKNFTKKAEGSRSM

WILCTHGSRIKNFRNSQKNGQWDSEEFALTEAFKSLFVRYEIDYTADLKT

AIVDEKQKDFFVDLLKLFKLTVQMRNSWKEKDLDYLISPVAGADGRFFDT

REGNKSLPKDADANGAYNIALKGLWALRQIRQTSEGGKLKLAISNKEWLQ

FVQERSYEKDKRPAATKKAGQAKKKKGSYPYDVPDYAYPYDVPDYAYPYD

VPDYA

SEQ ID NO: 39 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 39 may be encoded by the following nucleotide sequence:

(SEQ ID NO: 40)

ATGGACAGCCTGAAGGATTTCACCAACCTGTACCCCGTGTCCAAGACACT

GCGGTTTGAGCTGAAGCCTGTGGGCAAGACCCTGGAGAATATCGAGAAGG

CCGGCATCCTGAAGGAGGATGAGCACAGAGCCGAGAGCTACCGGAGAGTG

AAGAAGATCATCGATACATATCACAAGGTGTTCATCGACAGCTCCCTGGA

GAACATGGCCAAGATGGGCATCGAGAATGAGATCAAGGCCATGCTGCAGT

CCTTTTGCGAGCTGTATAAGAAGGACCACAGGACCGAGGGAGAGGACAAG

GCCCTGGATAAGATCAGGGCCGTGCTGAGGGGCCTGATCGTGGGAGCCTT

CACCGGCGTGTGCGGCCGGCGGGAGAACACAGTGCAGAATGAGAAGTATG

AGAGCCTGTTTAAGGAGAAGCTGATCAAGGAGATCCTGCCAGATTTCGTG

CTGTCTACAGAGGCCGAGTCCCTGCCCTTTTCTGTGGAGGAGGCCACCAG

AAGCCTGAAGGAGTTCGACTCCTTTACATCTTACTTCGCCGGCTTTTATG

AGAACCGGAAGAATATCTACTCTACCAAGCCCCAGAGCACAGCCATCGCC

TATAGACTGATCCACGAGAACCTGCCTAAGTTCATCGATAATATCCTGGT

GTTTCAGAAGATCAAGGAGCCAATCGCCAAGGAGCTGGAGCACATCAGGG

CAGACTTCAGCGCCGGCGGCTACATCAAGAAGGATGAGCGCCTGGAGGAC

ATCTTTTCCCTGAACTACTATATCCACGTGCTGTCTCAGGCCGGCATCGA

GAAGTACAATGCCCTGATCGGCAAGATCGTGACCGAGGGCGATGGCGAGA

TGAAGGGCCTGAACGAGCACATCAACCTGTATAATCAGCAGAGGGGCCGC

GAGGACCGGCTGCCACTGTTCAGACCCCTGTATAAGCAGATCCTGTCTGA

TAGGGAGCAGCTGTCCTATCTGCCAGAGTCTTTCGAGAAGGACGAGGAGC

TGCTGAGGGCCCTGAAGGAGTTTTACGATCACATCGCAGAGGACATCCTG

-continued

GGAAGGACCCAGCAGCTGATGACAAGCATCTCCGAGTACGATCTGTCCCG

GATCTATGTGAGAAACGATAGCCAGCTGACCGACATCTCCAAGAAGATGC

TGGGCGATTGGAATGCCATCTACATGGCCCGGGAGAGAGCCTATGACCAC

GAGCAGGCCCCCAAGCGCATCACAGCCAAGTACGAGAGGGACCGCATCAA

GGCCCTGAAGGGCGAGGAGTCTATCAGCCTGGCCAACCTGAACAGCTGCA

TCGCCTTCCTGGACAACGTGAGGGATTGTCGCGTGGACACCTATCTGTCT

ACACTGGGACAGAAGGAGGGACCTCACGGCCTGAGCAACCTGGTGGAGAA

CGTGTTCGCCTCCTACCACGAGGCCGAGCAGCTGCTGTCTTTTCCCTATC

CTGAGGAGAACAATCTGATCCAGGACAAGGATAACGTGGTGCTGATCAAG

AACCTGCTGGATAATATCAGCGACCTGCAGAGGTTCCTGAAGCCACTGTG

GGGCATGGGCGATGAGCCCGACAAGGATGAGAGGTTTTACGGCGAGTACA

ATTATATCAGGGGCGCCCTGGACCAGGTCATCCCTCTGTATAACAAGGTG

CGGAATTATCTGACCCGCAAGCCATACTCCACACGCAAGGTGAAGCTGAA

CTTCGGCAATAGCCAGCTGCTGTCCGGCTGGGATAGGAACAAGGAGAAGG

ACAATTCTTGCGTGATCCTGCGCAAGGGCCAGAACTTCTACCTGGCCATC

ATGAACAATCGGCACAAGCGGAGCTTCGAGAATAAGATGCTGCCCGAGTA

TAAGGAGGGCGAGCCTTACTTCGAGAAGATGGATTATAAGTTTCTGCCAG

ACCCCAACAAGATGCTGCCCAAGGTGTTCCTGTCTAAGAAGGGCATCGAG

ATCTACAAGCCTAGCCCAAAGCTGCTGGAGCAGTATGGCCACGGCACCCA

CAAGAAGGGCGATACCTTCAGCATGGACGATCTGCACGAGCTGATCGACT

TCTTTAAGCACTCCATCGAGGCCCACGAGGATTGGAAGCAGTTCGGCTTT

AAGTTCAGCGACACCGCCACATACGAGAACGTGAGCAGCTTCTACCGGGA

GGTGGAGGACCAGGGCTACAAGCTGTCTTTTAGAAAGGTGTCCGAGTCTT

ACGTGTATAGCCTGATCGATCAGGGCAAGCTGTACCTGTTCCAGATCTAT

AACAAGGACTTTAGCCCTTGTTCCAAGGGCACCCCAAATCTGCACACACT

GTACTGGCGGATGCTGTTCGATGAGAGAAACCTGGCCGACGTGATCTATA

AGCTGGATGGCAAGGCCGAGATCTTCTTTCGGGAGAAGTCCCTGAAGAAT

GACCACCCAACCCACCCTGCAGGCAAGCCCATCAAGAAGAAGAGCCGGCA

GAAGAAGGGCGAGGAGAGCCTGTTCGAGTACGATCTGGTGAAGGACCGGA

GATATACCATGGATAAGTTTCAGTTCCACGTGCCAATCACAATGAACTTT

AAGTGCTCTGCCGGCAGCAAGGTGAACGACATGGTGAATGCCCACATCAG

GGAGGCCAAGGACATGCACGTGATCGGCATCGATAGGGGCGAGCGCAATC

TGCTGTATATCTGCGTGATCGACAGCCGCGGCACCATCCTGGATCAGATC

TCCCTGAACACAATCAATGACATCGATTATCACGATCTGCTGGAGTCCAG

GGACAAGGATCGCCAGCAGGAGCACAGGAACTGGCAGACCATCGAGGGCA

TCAAGGAGCTGAAGCAGGGCTACCTGTCTCAGGCCGTGCACCGCATCGCC

GAGCTGATGGTGGCCTATAAGGCCGTGGTGGCCCTGGAGGACCTGAACAT

GGGCTTCAAGCGGGGCAGACAGAAGGTGGAGAGCAGCGTGTACCAGCAGT

TTGAGAAGCAGCTGATCGACAAGCTGAATTATCTGGTGGATAAGAAGAAG

CGGCCCGAGGACATCGGAGGCCTGCTGAGAGCCTACCAGTTCACCGCCCC

TTTCAAGAGCTTTAAGGAGATGGGCAAGCAGAACGGCTTTCTGTTCTATA

-continued

TCCCTGCCTGGAACACATCCAATATCGACCCAACCACAGGCTTCGTGAAC

CTGTTTCACGTGCAGTACGAGAATGTGGATAAGGCCAAGAGCTTCTTTCA

GAAGTTCGACAGCATCTCCTACAACCCTAAGAAGGATTGGTTTGAGTTCG

CCTTTGACTATAAGAACTTCACCAAGAAGGCCGAGGGCTCTAGGAGCATG

TGGATTCTGTGCACCCACGGCTCCCGGATCAAGAACTTCAGAAATTCTCA

GAAGAATGGCCAGTGGGATAGCGAGGAGTTTGCCCTGACCGAGGCCTTCA

AGTCCCTGTTTGTGCGGTACGAGATCGATTATACCGCCGACCTGAAAACC

GCCATCGTGGACGAGAAGCAGAAGGATTTCTTTGTGGACCTGCTGAAGCT

GTTCAAGCTGACCGTGCAGATGAGAAACTCCTGGAAGGAGAAGGACCTGG

ATTACCTGATCTCTCCAGTGGCCGGCGCCGATGGCAGGTTCTTTGACACA

CGCGAGGGCAATAAGAGCCTGCCCAAGGACGCAGATGCAAACGGAGCCTA

TAATATCGCCCTGAAGGGCCTGTGGGCACTGAGGCAGATCAGACAGACCT

CCGAGGGCGGCAAGCTGAAGCTGGCCATCTCTAACAAGGAGTGGCTGCAG

TTTGTGCAGGAGAGATCCTACGAGAAGGACAAAAGGCCGGCGGCCACGAA

AAAGGCCGGCCAGGCAAAAAAGAAAAAGGGATCCTACCCATACGATGTTC

CAGATTACGCTTATCCCTACGACGTGCCTGATTATGCATACCCATATGAT

GTCCCCGACTATGCCTAA

*Prevotella disiens* (PdCpf1; pY018), including NLS and HA tag:

(SEQ ID NO: 41)

MENYQEFTNLFQLNKTLRFELKPIGKTCELLEEGKIFASGSFLEKDKVRA

DNVSYVKKEIDKKHKIFIEETLSSFSISNDLLKQYFDCYNELKAFKKDCK

SDEEEVKKTALRNKCTSIQRAMREAISQAFLKSPQKKLLAIKNLIENVFK

ADENVQHFSEFTSYFSGFETNRENFYSDEEKSTSIAYRLVHDNLPIFIKN

IYIFEKLKEQFDAKTLSEIFENYKLYVAGSSLDEVFSLEYFNNTLTQKGI

DNYNAVIGKIVKEDKQEIQGLNEHINLYNQKHKDRRLPFFISLKKQILSD

REALSWLPDMFKNDSEVIKALKGFYIEDGFENNVLTPLATLLSSLDKYNL

NGIFIRNNEALSSLSQNVYRNFSIDEAIDANAELQTFNNYELIANALRAK

IKKETKQGRKSFEKYEEYIDKKVKAIDSLSIQEINELVENYVSEFNSNSG

NMPRKVEDYFSLMRKGDFGSNDLIENIKTKLSAAEKLLGTKYQETAKDIF

KKDENSKLIKELLDATKQFQHFIKPLLGTGEEADRDLVFYGDFLPLYEKF

EELTLLYNKVRNRLTQKPYSKDKIRLCFNKPKLMTGWVDSKTEKSDNGTQ

YGGYLFRKKNEIGEYDYFLGISSKAQLFRKNEAVIGDYERLDYYQPKANT

IYGSAYEGENSYKEDKKRLNKVIIAYIEQIKQTNIKKSIIESISKYPNIS

DDDKVTPSSLLEKIKKVSIDSYNGILSFKSFQSVNKEVIDNLLKTISPLK

NKAEFLDLINKDYQIFTEVQAVIDEICKQKTFIYFPISNVELEKEMGDKD

KPLCLFQISNKDLSFAKTFSANLRKKRGAENLHTMLFKALMEGNQDNLDL

GSGAIFYRAKSLDGNKPTHPANEAIKCRNVANKDKVSLFTYDIYKNRRYM

ENKFLFHLSIVQNYKAANDSAQLNSSATEYIRKADDLHIIGIDRGERNLL

YYSVIDMKGNIVEQDSLNIIRNNDLETDYHDLLDKREKERKANRQNWEAV

-continued

EGIKDLKKGYLSQAVHQIAQLMLKYNAIIALEDLGQMFVTRGQKIEKAVY

QQFEKSLVDKLSYLVDKKRPYNELGGILKAYQLASSITKNNSDKQNGFLF

YVPAWNTSKIDPVTGFTDLLRPKAMTIKEAQDFFGAFDNISYNDKGYFEF

ETNYDKFKIRMKSAQTRWTICTFGNRIKRKKDKNYWNYEEVELTEEFKKL

FKDSNIDYENCNLKEEIQNKDNRKFFDDLIKLLQLTLQMRNSDDKGNDYI

ISPVANAEGQFFDSRNGDKKLPLDADANGAYNIARKGLWNIRQIKQTKND

KKLNLSISSTEWLDFVREKPYLKKRPAATKKAGQAKKKKGSYPYDVPDYA

YPYDVPDYAYPYDVPDYA

SEQ ID NO: 41 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 41 may be encoded by the following nucleotide sequence:

(SEQ ID NO: 42)

ATGGAGAACTATCAGGAGTTCACCAACCTGTTTCAGCTGAATAAGACACT

GAGATTCGAGCTGAAGCCCATCGGCAAGACCTGCGAGCTGCTGGAGGAGG

GCAAGATCTTCGCCAGCGGCTCCTTTCTGGAGAAGGACAAGGTGAGGGCC

GATAACGTGAGCTACGTGAAGAAGGAGATCGACAAGAAGCACAAGATCTT

TATCGAGGAGACACTGAGCTCCTTCTCTATCAGCAACGATCTGCTGAAGC

AGTACTTTGACTGCTATAATGAGCTGAAGGCCTTCAAGAAGGACTGTAAG

AGCGATGAGGAGGAGGTGAAGAAAACCGCCCTGCGCAACAAGTGTACCTC

CATCCAGAGGGCCATGCGCGAGGCCATCTCTCAGGCCTTTCTGAAGAGCC

CCCAGAAGAAGCTGCTGGCCATCAAGAACCTGATCGAGAACGTGTTCAAG

GCCGACGAGAATGTGCAGCACTTCTCCGAGTTTACCAGCTATTTCTCCGG

CTTTGAGACAAACAGAGAGAATTTCTACTCTGACGAGGAGAAGTCCACAT

CTATCGCCTATAGGCTGGTGCACGATAACCTGCCTATCTTCATCAAGAAC

ATCTACATCTTCGAGAAGCTGAAGGAGCAGTTCGACGCCAAGACCCTGAG

CGAGATCTTCGAGAACTACAAGCTGTATGTGGCCGGCTCTAGCCTGGATG

AGGTGTTCTCCCTGGAGTACTTTAACAATACCCTGACACAGAAGGGCATC

GACAACTATAATGCCGTGATCGGCAAGATCGTGAAGGAGGATAAGCAGGA

GATCCAGGGCCTGAACGAGCACATCAACCTGTATAATCAGAAGCACAAGG

ACCGGAGACTGCCCTTCTTTATCTCCCTGAAGAAGCAGATCCTGTCCGAT

CGGGAGGCCCTGTCTTGGCTGCCTGACATGTTCAAGAATGATTCTGAAGT

GATCAAGGCCCTGAAGGGCTTCTACATCGAGGACGGCTTTGAGAACAATG

TGCTGACACCTCTGGCCACCCTGCTGTCCTCTCTGGATAAGTACAACCTG

AATGGCATCTTTATCCGCAACAATGAGGCCCTGAGCTCCCTGTCCCAGAA

CGTGTATCGGAATTTTTCTATCGACGAGGCCATCGATGCCAACGCCGAGC

TGCAGACCTTCAACAATTACGAGCTGATCGCCAATGCCCTGCGCGCCAAG

ATCAAGAAGGAGACAAAGCAGGGCCGGAAGTCTTTCGAGAAGTACGAGGA

GTATATCGATAAGAAGGTGAAGGCCATCGACAGCCTGTCCATCCAGGAGA

TCAACGAGCTGGTGGAGAATTACGTGAGCGAGTTTAACTCTAATAGCGGC

-continued

AACATGCCAAGAAAGGTGGAGGACTACTTCAGCCTGATGAGGAAGGGCGA

CTTCGGCTCCAACGATCTGATCGAAAATATCAAGACCAAGCTGAGCGCCG

CAGAGAAGCTGCTGGGCACAAAGTACCAGGAGACAGCCAAGGACATCTTC

AAGAAGGATGAGAACTCCAAGCTGATCAAGGAGCTGCTGGACGCCACCAA

GCAGTTCCAGCACTTTATCAAGCCACTGCTGGGCACAGGCGAGGAGGCAG

ATCGGGACCTGGTGTTCTACGGCGATTTTCTGCCCCTGTATGAGAAGTTT

GAGGAGCTGACCCTGCTGTATAACAAGGTGCGGAATAGACTGACACAGAA

GCCCTATTCCAAGGACAAGATCCGCCTGTGCTTCAACAAGCCTAAGCTGA

TGACAGGCTGGGTGGATTCCAAGACCGAGAAGTCTGACAACGGCACACAG

TACGGCGGCTATCTGTTTCGGAAGAAGAATGAGATCGGCGAGTACGATTA

TTTTCTGGGCATCTCTAGCAAGGCCCAGCTGTTCAGAAAGAACGAGGCCG

TGATCGGCGACTACGAGAGGCTGGATTACTATCAGCCAAAGGCCAATACC

ATCTACGGCTCTGCCTATGAGGGCGAGAACAGCTACAAGGAGGACAAGAA

GCGGCTGAACAAAGTGATCATCGCCTATATCGAGCAGATCAAGCAGACAA

ACATCAAGAAGTCTATCATCGAGTCCATCTCTAAGTATCCTAATATCAGC

GACGATGACAAGGTGACCCCATCCTCTCTGCTGGAGAAGATCAAGAAGGT

GTCTATCGACAGCTACAACGGCATCCTGTCCTTCAAGTCTTTTCAGAGCG

TGAACAAGGAAGTGATCGATAACCTGCTGAAAACCATCAGCCCCCTGAAG

AACAAGGCCGAGTTTCTGGACCTGATCAATAAGGATTATCAGATCTTCAC

CGAGGTGCAGGCCGTGATCGACGAGATCTGCAAGCAGAAAACCTTCATCT

ACTTTCCAATCTCCAACGTGGAGCTGGAGAAGGAGATGGGCGATAAGGAC

AAGCCCCTGTGCCTGTTCCAGATCAGCAATAAGGATCTGTCCTTCGCCAA

GACCTTTAGCGCCAACCTGCGGAAGAAGAGAGGCGCCGAGAATCTGCACA

CAATGCTGTTTAAGGCCCTGATGGAGGGCAACCAGGATAATCTGGACCTG

GGCTCTGGCGCCATCTTCTACAGAGCCAAGAGCCTGGACGGCAACAAGCC

CACACACCCTGCCAATGAGGCCATCAAGTGTAGGAACGTGGCCAATAAGG

ATAAGGTGTCCCTGTTCACCTACGACATCTATAAGAACAGGCGCTACATG

GAGAATAAGTTCCTGTTTCACCTGAGCATCGTGCAGAACTATAAGGCCGC

CAATGACTCCGCCCAGCTGAACAGCTCCGCCACCGAGTATATCAGAAAGG

CCGATGACCTGCACATCATCGGCATCGATAGGGGCGAGCGCAATCTGCTG

TACTATTCCGTGATCGATATGAAGGGCAACATCGTGGAGCAGGACTCTCT

GAATATCATCAGGAACAATGACCTGGAGACAGATTACCACGACCTGCTGG

ATAAGAGGGAGAAGGAGCGCAAGGCCAACCGGCAGAATTGGGAGGCCGTG

GAGGGCATCAAGGACCTGAAGAAGGGCTACCTGAGCCAGGCCGTGCACCA

GATCGCCCAGCTGATGCTGAAGTATAACGCCATCATCGCCCTGGAGGATC

TGGGCCAGATGTTTGTGACCCGCGGCCAGAAGATCGAGAAGGCCGTGTAC

CAGCAGTTCGAGAAGAGCCTGGTGGATAAGCTGTCCTACCTGGTGGACAA

GAAGCGGCCTTATAATGAGCTGGGCGGCATCCTGAAGGCCTACCAGCTGG

CCTCTAGCATCACCAAGAACAATTCTGACAAGCAGAACGGCTTCCTGTTT

TATGTGCCAGCCTGGAATACAAGCAAGATCGATCCCGTGACCGGCTTTAC

-continued

AGACCTGCTGCGGCCCAAGGCCATGACCATCAAGGAGGCCCAGGACTTCT

TTGGCGCCTTCGATAACATCTCTTACAATGACAAGGGCTATTTCGAGTTT

GAGACAAACTACGACAAGTTTAAGATCAGAATGAAGAGCGCCCAGACCAG

GTGGACAATCTGCACCTTCGGCAATCGGATCAAGAGAAAGAAGGATAAGA

ACTACTGGAATTATGAGGAGGTGGAGCTGACCGAGGAGTTCAAGAAGCTG

TTTAAGGACAGCAACATCGATTACGAGAACTGTAATCTGAAGGAGGAGAT

CCAGAACAAGGACAATCGCAAGTTCTTTGATGACCTGATCAAGCTGCTGC

AGCTGACACTGCAGATGCGGAACTCCGATGACAAGGGCAATGATTATATC

ATCTCTCCTGTGGCCAACGCCGAGGGCCAGTTCTTTGACTCCCGCAATGG

CGATAAGAAGCTGCCACTGGATGCAGACGCAAACGGAGCCTACAATATCG

CCCGCAAGGGCCTGTGGAACATCCGGCAGATCAAGCAGACCAAGAACGAC

AAGAAGCTGAATCTGAGCATCTCCTCTACAGAGTGGCTGGATTTCGTGCG

GGAGAAGCCTTACCTGAAGAAAAGGCCGGCGGCCACGAAAAAGGCCGGCC

AGGCAAAAAAGAAAAAGGGATCCTACCCATACGATGTTCCAGATTACGCT

TATCCCTACGACGTGCCTGATTATGCATACCCATATGATGTCCCCGACTA

TGCCTAA

*Porphyromonas macacae* (PmCpf1; pY09), including NLS and HA tag:

(SEQ ID NO: 43)

MKTQHFFEDFTSLYSLSKTIRFELKPIGKTLENIKKNGLIRRDEQRLDDY

EKLKKVIDEYHEDFIANILSSFSFSEEILQSYIQNLSESEARAKIEKTMR

DTLAKAFSEDERYKSIFKKELVKKDIPVWCPAYKSLCKKFDNFTTSLVPF

HENRKNLYTSNEITASIPYRIVHVNLPKFIQNIEALCELQKKMGADLYLE

MMENLRNVWPSFVKTPDDLCNLKTYNHLMVQSSISEYNRFVGGYSTEDGT

KHQGINEWINIYRQRNKEMRLPGLVFLHKQILAKVDSSSFISDTLENDDQ

VFCVLRQFRKLFWNTVSSKEDDAASLKDLFCGLSGYDPEAIYVSDAHLAT

ISKNIFDRWNYISDAIRRKTEVLMPRKKESVERYAEKISKQIKKRQSYSL

AELDDLLAHYSEESLPAGFSLLSYFTSLGGQKYLVSDGEVILYEEGSNIW

DEVLIAFRDLQVILDKDFTEKKLGKDEEAVSVIKKALDSALRLRKFFDLL

SGTGAEIRRDSSFYALYTDRMDKLKGLLKMYDKVRNYLTKKPYSIEKFKL

HFDNPSLLSGWDKNKELNNLSVIFRQNGYYYLGIMTPKGKNLFKTLPKLG

AEEMFYEKMEYKQIAEPMLMLPKVFFPKKTKPAFAPDQSVVDIYNKKTFK

TGQKGFNKKDLYRLIDFYKEALTVHEWKLFNFSFSPTEQYRNIGEFFDEV

REQAYKVSMVNVPASYIDEAVENGKLYLFQIYNKDFSPYSKGIPNLHTLY

WKALFSEQNQSRVYKLCGGGELFYRKASLHMQDTTVHPKGISIHKKNLNK

KGETSLFNYDLVKDKRFTEDKFFFHVPISINYKNKKITNVNQMVRDYIAQ

NDDLQIIGIDRGERNLLYISRIDTRGNLLEQFSLNVIESDKGDLRTDYQK

ILGDREQERLRRRQEWKSIESIKDLKDGYMSQVVHKICNMVVEHKAIVVL

ENLNLSFMKGRKKVEKSVYEKFERMLVDKLNYLVVDKKNLSNEPGGLYAA

YQLTNPLFSFEELHRYPQSGILFFVDPWNTSLTDPSTGFVNLLGRINYTN

VGDARKFFDRFNAIRYDGKGNILFDLDLSRFDVRVETQRKLWTLTTFGSR

-continued

```
IAKSKKSGKWMVERIENLSLCFLELFEQFNIGYRVEKDLKKAILSQDRKE

FYVRLIYLFNLMMQIRNSDGEEDYILSPALNEKNLQFDSRLIEAKDLPVD

ADANGAYNVARKGLMVVQRIKRGDHESIHRIGRAQWLRYVQEGIVEKRPA

ATKKAGQAKKKKGSYPYDVPDYAYPYDVPDYAYPYDVPDYA
```

SEQ ID NO: 43 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 43 may be encoded by the following nucleotide sequence:

```
                                            (SEQ ID NO: 44)
ATGAAAACCCAGCACTTCTTTGAGGACTTCACAAGCCTGTACTCTCTGAG

CAAGACCATCCGGTTTGAGCTGAAGCCAATCGGCAAGACCCTGGAGAACA

TCAAGAAGAATGGCCTGATCCGGAGAGATGAGCAGAGACTGGACGATTAC

GAGAAGCTGAAGAAAGTGATCGACGAGTATCACGAGGATTTCATCGCCAA

CATCCTGAGCTCCTTTTCCTTCTCTGAGGAGATCCTGCAGTCCTACATCC

AGAATCTGAGCGAGTCCGAGGCCAGGGCCAAGATCGAGAAAACCATGCGC

GACACACTGGCCAAGGCCTTCTCTGAGGATGAGAGGTACAAGAGCATCTT

TAAGAAGGAGCTGGTGAAGAAGGACATCCCCGTGTGGTGCCCTGCCTATA

AGAGCCTGTGCAAGAAGTTCGATAACTTTACCACATCTCTGGTGCCCTTC

CACGAGAACAGGAAGAACCTGTATACCAGCAATGAGATCACAGCCTCTAT

CCCTTATCGCATCGTGCACGTGAACCTGCCAAAGTTTATCCAGAATATCG

AGGCCCTGTGCGAGCTGCAGAAGAAGATGGGCGCCGACCTGTACCTGGAG

ATGATGGAGAACCTGCGCAACGTGTGGCCCAGCTTCGTGAAAACCCCAGA

CGACCTGTGCAACCTGAAAACCTATAATCACCTGATGGTGCAGTCTAGCA

TCAGCGAGTACAACAGGTTTGTGGGCGGCTATTCCACCGAGGACGGCACA

AAGCACCAGGGCATCAACGAGTGGATCAATATCTACAGACAGAGGAATAA

GGAGATGCGCCTGCCTGGCCTGGTGTTCCTGCACAAGCAGATCCTGGCCA

AGGTGGACTCCTCTAGCTTCATCAGCGATACACTGGAGAACGACGATCAG

GTGTTTTGCGTGCTGAGACAGTTCAGGAAGCTGTTTTGGAATACCGTGTC

CTCTAAGGAGGACGATGCCGCCTCCCTGAAGGACCTGTTCTGTGGCCTGT

CTGGCTATGACCCTGAGGCCATCTACGTGAGCGATGCCCACCTGGCCACA

ATCTCCAAGAACATCTTTGACAGATGGAATTACATCTCCGATGCCATCAG

GCGCAAGACCGAGGTGCTGATGCCACGGAAGAAGGAGAGCGTGGAGAGAT

ATGCCGAGAAGATCTCCAAGCAGATCAAGAAGAGACAGTCTTACAGCCTG

GCCGAGCTGGACGATCTGCTGGCCCACTATAGCGAGGAGTCCCTGCCCGC

AGGCTTCTCTCTGCTGAGCTACTTTACATCTCTGGGCGGCCAGAAGTATC

TGGTGAGCGACGGCGAAGTGATCCTGTACGAGGAGGGCAGCAACATCTGG

GACGAGGTGCTGATCGCCTTCAGGGATCTGCAGGTCATCCTGGACAAGGA

CTTCACCGAGAAGAAGCTGGGCAAGGATGAGGAGGCCGTGTCTGTGATCA

AGAAGGCCCTGGACAGCGCCCTGCGCCTGCGGAAGTTCTTTGATCTGCTG
```

-continued

```
TCCGGCACAGGCGCAGAGATCAGGAGAGACAGCTCCTTCTATGCCCTGTA

TACCGACCGGATGGATAAGCTGAAGGGCCTGCTGAAGATGTATGATAAGG

TGAGAAACTACCTGACCAAGAAGCCTTATTCCATCGAGAAGTTCAAGCTG

CACTTTGACAACCCATCCCTGCTGTCTGGCTGGGATAAGAATAAGGAGCT

GAACAATCTGTCTGTGATCTTCCGGCAGAACGGCTACTATTACCTGGGCA

TCATGACACCCAAGGGCAAGAATCTGTTCAAGACCCTGCCTAAGCTGGGC

GCCGAGGAGATGTTTTATGAGAAGATGGAGTACAAGCAGATCGCCGAGCC

TATGCTGATGCTGCCAAAGGTGTTCTTTCCCAAGAAAACCAAGCCAGCCT

TCGCCCCAGACCAGAGCGTGGTGGATATCTACAACAAGAAAACCTTCAAG

ACAGGCCAGAAGGGCTTTAATAAGAAGGACCTGTACCGGCTGATCGACTT

CTACAAGGAGGCCCTGACAGTGCACGAGTGGAAGCTGTTTAACTTCTCCT

TTTCTCCAACCGAGCAGTATCGGAATATCGGCGAGTTCTTTGACGAGGTG

AGAGAGCAGGCCTACAAGGTGTCCATGGTGAACGTGCCCGCCTCTTATAT

CGACGAGGCCGTGGAGAACGGCAAGCTGTATCTGTTCCAGATCTACAATA

AGGACTTCAGCCCCTACTCCAAGGGCATCCCTAACCTGCACACACTGTAT

TGGAAGGCCCTGTTCAGCGAGCAGAATCAGAGCCGGGTGTATAAGCTGTG

CGGAGGAGGAGAGCTGTTTTATAGAAAGGCCAGCCTGCACATGCAGGACA

CCACAGTGCACCCCAAGGGCATCTCTATCCACAAGAAGAACCTGAATAAG

AAGGGCGAGACAAGCCTGTTCAACTACGACCTGGTGAAGGATAAGAGGTT

TACCGAGGACAAGTTCTTTTTCCACGTGCCTATCTCTATCAACTACAAGA

ATAAGAAGATCACCAACGTGAATCAGATGGTGCGCGATTATATCGCCCAG

AACGACGATCTGCAGATCATCGGCATCGACCGCGGCGAGCGGAATCTGCT

GTATATCAGCCGGATCGATACAAGGGGCAACCTGCTGGAGCAGTTCAGCC

TGAATGTGATCGAGTCCGACAAGGGCGATCTGAGAACCGACTATCAGAAG

ATCCTGGGCGATCGCGAGCAGGAGCGGCTGAGGCGCCGGCAGGAGTGGAA

GTCTATCGAGAGCATCAAGGACCTGAAGGATGGCTACATGAGCCAGGTGG

TGCACAAGATCTGTAACATGGTGGTGGAGCACAAGGCCATCGTGGTGCTG

GAGAACCTGAATCTGAGCTTCATGAAGGGCAGGAAGAAGGTGGAGAAGTC

CGTGTACGAGAAGTTTGAGCGCATGCTGGTGGACAAGCTGAACTATCTGG

TGGTGGATAAGAAGAACCTGTCCAATGAGCCAGGAGGCCTGTATGCAGCA

TACCAGCTGACCAATCCACTGTTCTCTTTTGAGGAGCTGCACAGATACCC

CCAGAGCGGCATCCTGTTTTTCGTGGACCCATGGAACACCTCTCTGACAG

ATCCCAGCACAGGCTTCGTGAATCTGCTGGGCAGAATCAACTACACCAAT

GTGGGCGACGCCCGCAAGTTTTTCGATCGGTTTAACGCCATCAGATATGA

CGGCAAGGGCAATATCCTGTTCGACCTGGATCTGTCCAGATTTGATGTGA

GGGTGGAGACACAGAGGAAGCTGTGGACACTGACCACATTCGGCTCTCGC

ATCGCCAAATCCAAGAAGTCTGGCAAGTGGATGGTGGAGCGGATCGAGAA

CCTGAGCCTGTGCTTTCTGGAGCTGTTCGAGCAGTTTAATATCGGCTACA

GAGTGGAGAAGGACCTGAAGAAGGCCATCCTGAGCCAGGATAGGAAGGAG

TTCTATGTGCGCCTGATCTACCTGTTTAACCTGATGATGCAGATCCGGAA

CAGCGACGGCGAGGAGGATTATATCCTGTCTCCCGCCCTGAACGAGAAGA
```

-continued

```
ATCTGCAGTTCGACAGCAGGCTGATCGAGGCCAAGGATCTGCCTGTGGAC

GCAGATGCAAACGGAGCATACAATGTGGCCCGCAAGGGCCTGATGGTGGT

GCAGAGAATCAAGAGGGGCGACCACGAGTCCATCCACAGGATCGGAAGGG

CACAGTGGCTGAGATATGTGCAGGAGGGCATCGTGGAGAAAAGGCCGGCG

GCCACGAAAAAGGCCGGCCAGGCAAAAAAGAAAAAGGGATCCTACCCATA

CGATGTTCCAGATTACGCTTATCCCTACGACGTGCCTGATTATGCATACC

CATATGATGTCCCCGACTATGCCTAA
```

Some of the non-limiting sequences shown above include a sequence such as a nuclear localization signal and/or a tag sequence (such as a HA tags). In various embodiments, a different nuclear localization signal may be present. In some embodiments, no nuclear localization signal is used. In certain embodiments no tag (e.g., no HA tag) is used.

In various embodiments relating to a protein (such as a protein within a gene-editing complex) the protein may include a nuclear localization signal. For example, the protein (e.g., a Cas protein) may comprise a nuclear localization signal (NLS). Such signals are known in the art, and non-limiting examples are described in Kalderon et al., (1984) Cell 39 (3 Pt 2): 499-509; Makkerh et al., (1996) *Curr Biol.* 6 (8): 1025-7; and Dingwall et al., (1991) *Trends in Biochemical Sciences* 16 (12): 478-81, the contents of each of which are hereby incorporated herein by reference. Specific non-limiting examples of nuclear localization signals include GGSGPPKKKRKV (SEQ ID NO: 5), KRPAATKKAGQAKKKK (SEQ ID NO: 12), PKKKRKV (SEQ ID NO: 45), KR[PAATKKAGQA]KKKK (SEQ ID NO: 46), KR[XXXXXXXXXX]KKKK (SEQ ID NO: 47), KKXK (SEQ ID NO: 48), KRXK (SEQ ID NO: 49), KKXR (SEQ ID NO: 50), KRXR (SEQ ID NO: 51), AVKRPAATKKAGQAKKKKLD (SEQ ID NO: 52), MSRRRKANPTKLSENAKKLAKEVEN (SEQ ID NO: 53), PAAKRVKLD (SEQ ID NO: 54), and KLKIKRPVK (SEQ ID NO: 55).

General Definitions and General Techniques

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The terms "plasma membrane" and "cell membrane" are used interchangeably herein, and refer to the semipermeable membrane that separates the interior of a cell from the environment outside the cell.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically plasmids. Expression vectors of the present invention include any vectors that function (i.e., direct gene expression) in host cells of the present invention, including in one of the prokaryotic or eukaryotic cells described herein, e.g., protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art. In preferred embodiments, the methods do not comprise the use of viral vectors such as adenoviruses to deliver nucleic acid molecules or constructs.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to 5.0 mg.

Unless otherwise implicitly or explicitly contradicted by the context in which it is used, references to cell "squeeze" "squeezing" "deformation" and the like refer to a process used to deliver macromolecules directly into the cytosol of cells with minimal cytotoxicity. The principle underlying this approach is temporary membrane disruption by rapid mechanical deformation, or squeezing, of the target cell, which permits the uptake by diffusion of macromolecules in the fluid medium and is followed by cell membrane repair (see, e.g., U.S. Patent Application Publication No. 2014/0287509, published Sep. 25, 2014; PCT International Patent Application No. PCT/US2015/058489, filed Oct. 30, 2015; and PCT International Patent Application No. PCT/2015/060689, filed Nov. 13, 2015, the entire contents of each of which are incorporated herein by reference).

As used herein, "gRNA" refers to a CRISPR-Cas system guide RNA.

As used herein the term "protein complex" refers to a composite unit arising from the specific binding of a protein with a binding partner, wherein said binding partner can be one or more proteins, one or more nucleic acids, or a combination of one or more proteins and one or more nucleic acids, and the like, to form said protein complex. Protein complexes may be protein-protein complexes, protein-nucleic acid complexes, and the like. In certain embodiments, a protein complex may comprise protein-protein interactions, e.g. interactions between different proteins, or dimers, trimers, tetramers or higher oligomers of the same protein. Interactions between subunits of protein complexes (e.g., in protein-protein complexes or protein-nucleic acid complexes that comprise more than one protein) or between proteins and nucleic acids (e.g., in protein-nucleic acid complexes) are usually non-binding interactions, such as those interactions caused by hydrogen bridges, pi electron systems such as (optionally conjugated) C—C double bonds or aromatic rings, e.g. phenyl, and heteroaromatic rings, e.g. pyrrole, imidazole, indole, pyrimidine or purine rings, and interactions between metal atoms and oxygen, nitrogen or sulfur atoms, but may also be weak, and in particular reversible, covalent binding interactions, e.g. sulfur-sulfur bridges.

A "protein-protein complex" means a composite unit that is a combination of two or more proteins formed by interaction between the proteins. Typically but not necessarily, a "protein complex" is formed by the binding of two or more proteins together through specific non-covalent binding affinities. However, covalent bonds may also be present between the interacting partners. For instance, the two interacting partners can be covalently crosslinked so that the protein complex becomes more stable.

Similarly, a "protein-nucleic acid complex" means a composite unit that is a combination of at least one protein and at least one nucleic acid formed by interactions that include an interaction between a protein and a nucleic acid. Typically but not necessarily, a "protein-nucleic acid complex" is formed by the binding of a protein and a nucleic acid through non-covalent binding affinities.

In various embodiments, a gene-editing complex is a protein-nucleic acid complex, such as a RNP. A non-limiting example of an RNP is a CRISPR-Cas RNP comprising a Cas protein and a gRNA.

Methods and devices described herein deliver an intact and functional gene-editing complex into cells. The components of the gene-editing complex do not disassociate during delivery and remain functional after delivery into the cell.

Various assays are available to determine whether an intact and functional gene-editing complex has been delivered to a cell. For example, the detection of gene editing by the gene-editing complex may be used to indicate that an intact and functional gene-editing complex was delivered into a cell. Alternatively or in addition, cells to which the gene-editing complex has been delivered may be lysed using non-denaturing conditions (such as a non-denaturing buffer or a French press), and the lysate may be analyzed using a non-denaturing gel to determine whether the gene-editing complex was intact within the cells. Alternatively or in addition, the cells may be lysed using non-denaturing conditions and then immunoprecipitation may be used to isolate the gene-editing complex from the lysate (i.e., to verify that one component of the complex can be co-isolated with another using immunoprecipitation). The isolated gene-editing complex can be assayed before or after delivery to a cell using a non-denaturing gel or a denaturing assay (such as sodium dodecyl sulfate polyacrylamide gel electrophoresis) to determine whether the gene-editing complex was present in a pre-delivery/pre-cell squeeze buffer as well as whether the complex is present after microfluidic/squeeze processing and found intact and/or functional in the treated cells. In some embodiments relating to CRISPR-Cas9 RNPs, a band on a non-denaturing gel of about 145, 150, 155, or 145-160 kDa may indicate that the RNP was delivered as a complete and functional gene-editing complex into the cell.

As used herein, device dimensions are denoted by a series of numbers indicating length, width, and optionally number of constrictions (e.g., 30 μm-6 m×5 denotes a device with a 30 μm length, 6 μm width, and 5 constrictions).

Exemplary Embodiments

Aspects of the present subject matter provide a method for delivering a protein and a nucleic acid into a cell, the method comprising: providing a cell in a solution; passing the solution through a microfluidic channel that includes a cell-deforming constriction; passing the cell through the constriction such that a pressure is applied to the cell causing perturbations of the cell large enough for the protein and the nucleic acid to pass through; and contacting the cell with the protein and the nucleic acid before, during, and/or after the cell passes through the constriction.

In some embodiments, said solution comprises the protein and the nucleic acid before, during, and/or after the cell passes through the constriction.

In some embodiments, the protein and the nucleic acid form a protein-nucleic acid complex.

In some embodiments, the protein and the nucleic acid are the components of the protein-nucleic acid complex but are not complexed when delivered to the cell.

In some embodiments, the protein and the nucleic acid form a protein-nucleic acid complex after delivery into the cell.

In some embodiments, the protein and the nucleic acid form a protein-nucleic acid complex before delivery into the cell.

In some embodiments, the protein and the nucleic acid comprise gene editing components.

In some embodiments, said protein-nucleic acid complex comprises a ribonucleoprotein (RNP).

In some embodiments, (a) the protein is a Cas protein or a Cpf1 protein; and (b) the nucleic acid is a single guide RNA (sgRNA) or a CRISPR RNA (crRNA) and a trans-activating crRNA (tracrRNA).

In some embodiments, the complex is a RNP comprising a Cas protein or a Cpf1 protein and a sgRNA, wherein the Cas protein or the Cpf1 protein and the sgRNA were complexed using about a 0.5, 2.0, 2.5, or 3.0 molar excess of the Cas protein or Cpf1 protein.

In some embodiments, the Cas protein comprises a Cas9 protein.

In some embodiments, said protein-nucleic acid complex comprises a first RNP and a second RNP.

In some embodiments, the first RNP and the second RNP are both nickases.

In some embodiments, the first RNP nicks a target sequence different from the target sequence of the second RNP.

In some embodiments, said protein-nucleic acid complex comprises a TALEN protein, Zinc finger nuclease, mega nuclease, or Cre recombinase.

In some embodiments, the nucleic acid comprises an mRNA encoding a TALEN protein, a Zinc finger nuclease, a mega nuclease, or a Cre recombinase In some embodiments, said protein-nucleic acid complex comprises (a) a nucleic acid molecule that is complexed with a protein via electrostatic attraction; (b) a nucleic acid molecule wrapped around a protein; (c) DNA and a histone; (d) a ribonucleoprotein (RNP); (e) a ribosome, an enzyme telomerase, a vault ribonucleoprotein, RNase P, hnRNP, or a small nuclear RNP (snRNP); or (f) a chromosome comprising a protein.

In some embodiments, the solution further comprises donor DNA.

In some embodiments, the solution further comprises donor DNA before, during, and/or after the cell passes through the constriction.

In some embodiments, said cell comprises a mammalian cell.

In some embodiments, said cell comprises a human cell.

In some embodiments, the diameter of the constriction is selected to induce temporary perturbations of the cell membrane large enough for the protein and the nucleic acid to pass through.

In some embodiments, a diameter of the constriction is about 20-99% of the diameter of the cell.

In some embodiments, a diameter of the constriction is about 60% of the diameter of the cell.

In some embodiments, the microfluidic channel is one of a plurality of parallel microfluidic channels in the microfluidic system.

In some embodiments, the plurality of parallel microfluidic channels comprises at least about 2, 5, 10, 20, 25, 30, 40, 45, 50, 75, 100, 500, 1,000, or 2-1,000 microfluidic channels.

In some embodiments, the cell is a plurality of cells, and each cell is passed through one of a plurality of parallel microfluidic channels, and wherein each microfluidic channel of the plurality of parallel microfluidic channels includes a cell-deforming constriction.

In some embodiments, (a) the diameter of the constriction is about 2, 3, 4, 5, 6, 7, 8, 9, 10, 15, 20, 2-10 μm, or 10-20 μm; (b) the length of the constriction is about 10, 15, 20, 24, 30, 40, 50, 60, 70, 80, 90, 100, 10-40, 10-50, 10-60, or 10-100 μm; (c) a pressure of about 10, 20, 30, 40, 50, 60, 70, 80, 90, 100 or 10-100 psi is used to pass the solution through the microfluidic channel; (d) the cell passes through the microfluidic channel at a speed of about 300, 400, 500, 600, 700, 800, 900, 100-300, 200-700, 250-400, 100-1000 mm/s, 1-1000 mm/s, 1 m/s, 2 m/s, 3 m/s, 4 m/s, 5 m/s, 6 m/s, 7 m/s, 8 m/s, 9 m/s, 10 m/s, 0.01-5 m/s, 5-10 m/s, or 0.01-10 m/s; (e) said microfluidic channel comprises multiple cell-deforming constrictions in series; (f) said microfluidic channel comprises a single cell-deforming constriction; (g) the perturbations of the cell membrane include a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm; and/or (h) perturbations of the cell membrane having a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell membrane for at least about 1, 2, 3, 4, 5, 6, 7, 8, 9, 10, or 1-10 minutes.

In some embodiments, (a) the expression of a target gene in the cell is reduced by at least about 5, 10, 15, 20, 25, 30, 35, 40, 45, 50, 55, 60, 75, 80, 85, 90, 95, or 99% or more; or (b) the cell is a plurality of cells and the expression of a target gene in the plurality of cells is reduced by at least about 5, 10, 15, 20, 25, 30, 35, 40, 45, 50, 55, 60, 75, 80, 85, 90, 95, or 99% or more, after the protein and the nucleic acid are delivered to the cell.

In some embodiments, (a) the expression of a target gene in the cell is reduced by at least about 5, 10, 15, 20, 25, 30, 35, 40, 45, 50, 55, 60, 75, 80, 85, 90, 95, or 99% or more; or (b) the cell is a plurality of cells and the expression of a target gene in the plurality of cells is reduced by at least about 5, 10, 15, 20, 25, 30, 35, 40, 45, 50, 55, 60, 75, 80, 85, 90, 95, or 99% or more, about 1, 2, 5, 12, 24, 1-12, 6-12, 6-18, 12-24, or 1-24 hours after the protein and the nucleic acid are delivered to the cell.

In some embodiments, (a) the expression of a target gene in the cell is increased by at least about 5, 10, 25, 50, 75, 100, 250, 500% or more; or (b) the cell is a plurality of cells and the expression of a target gene in the plurality of cells is increased by at least about 5, 10, 25, 50, 75, 100, 250, 500% or more, after the protein and the nucleic acid are delivered to the cell.

In some embodiments, (a) the expression of a target gene in the cell is increased by at least about 5, 10, 25, 50, 75, 100, 250, 500% or more; or (b) the cell is a plurality of cells and the expression of a target gene in the plurality of cells is increased by at least about 5, 10, 25, 50, 75, 100, 250, 500% or more, about 1, 2, 5, 12, 24, 1-12, 6-12, 6-18, 12-24, or 1-24 hours after the protein and the nucleic acid are delivered to the cell.

Aspects of the present subject matter provide a device for delivering a protein-nucleic acid complex to a cell, comprising at least one microfluidic channel, wherein said channel comprises a constriction length of about 30 μm and a constriction width of about 4 μm.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Editing of the B2M Locus in Primary Human T Cells Using CellSqueeze (SQZ) to Deliver CRISPR/Cas9 Gene Editing Complex A series of experiments have been undertaken in unstimulated human T cells to demonstrate the ability of the SQZ platform to deliver Cas9 ribonucleoproteins (RNPs; recombinant Cas9 protein complexed with a single-guide RNA) and accomplish efficient genome editing of a model locus, the $\beta_2$ microglobulin component of MHC class 1 (B2M).

Delivery of Cas9 RNP to Unstimulated Human T Cells

Fresh PBMCs were isolated from human blood using a standard Ficoll gradient. Next, T cells were negatively selected (Human T cell enrichment kit (StemCell Technologies)) counted, washed and resuspended at 10-20×$10^6$ cells/mL in OptiMEM for delivery. Ten μg of recombinant CAS9 (PNA Bio) was pre-complexed with a 2.5 molar excess of unmodified gRNA (PNA Bio) designed to specifically target the B2M locus. Recombinant CAS9 is reconstituted to a solution with a final concentration of 20 mM Hepes, 150 mM KCl, 1% sucrose. gRNA is added directly to the CAS9 solution and incubated on ice for 20 minutes to form the complex. The complex is added directly to resuspended cells. RNP complexes were incubated on ice 20 minutes prior to SQZ-mediated delivery. The RNP (2.2 uM) was co-delivered with a 3 kD-Cascade Blue Dextran (0.15 mg/mL) used as a proxy for delivery efficiency. Two different chips, 10-4 and 30-4 were used to deliver the complex at a pressures of 60 and 90 psi. The chips have constrictions of the same width (4 microns) but have two different constriction lengths (30 vs. 10 microns).

Figure 4:
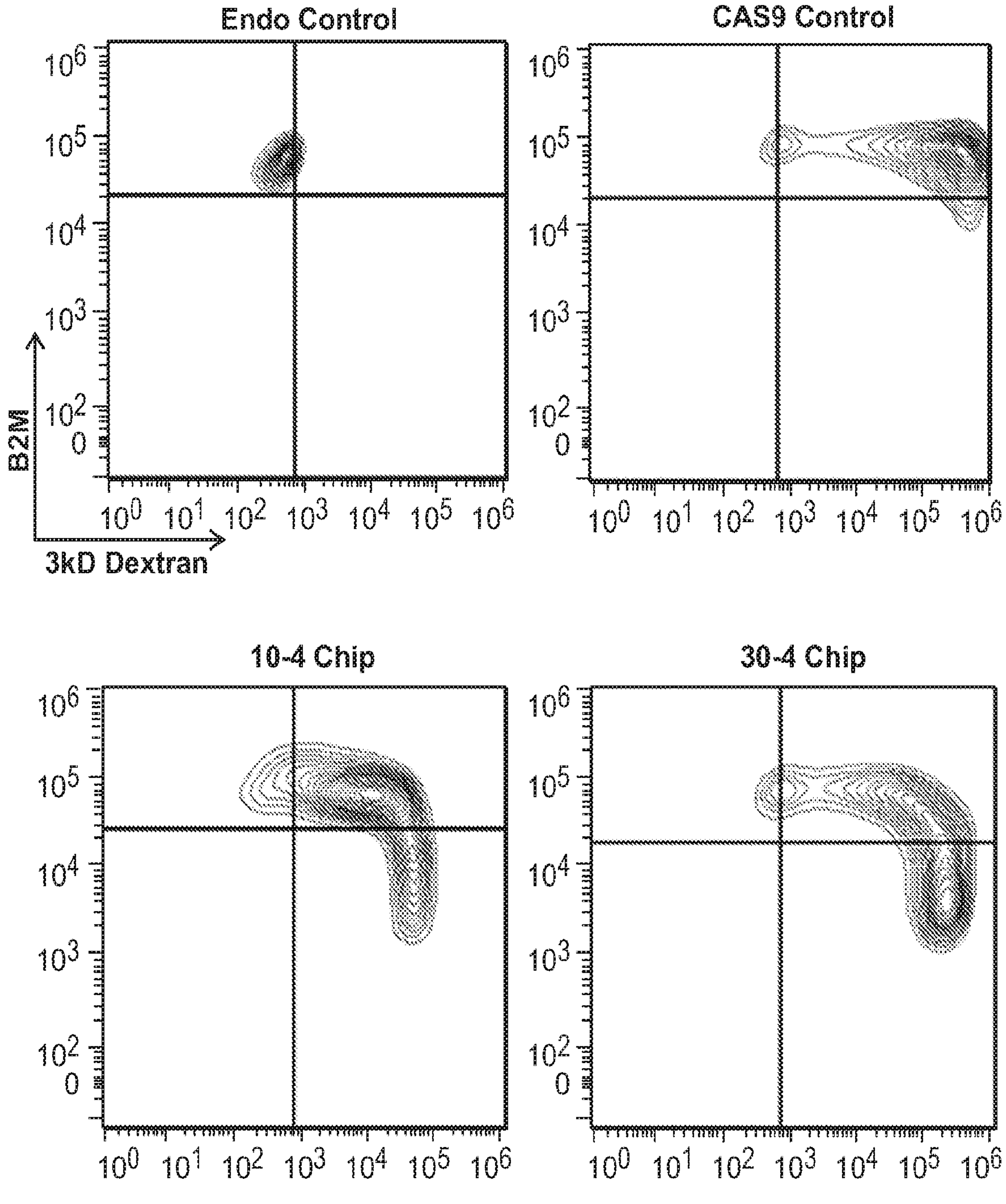
FIG. 4 is a series of FACs plots showing $\beta_2$ microglobulin component of MHC class 1 (B2M) expression vs. delivered dextran for four different cell populations obtained using FACS. The delivery of the RNP using the 30-4 chip at 90 psi results in a 54.4% reduction in B2M expression as compared to the endocytosis control whereas the 10-4 chip at 90 psi results in a 25.2% reduction in B2M expression. B2M expression on the CAS9 control is not significantly different than the endocytosis control. The longer constriction chip results in more delivery of the RNP complex and a larger reduction in B2M expression.

At 48 hours post-delivery, a FACS based readout was used to determine B2M protein levels. Reduced B2M expression was used as a measure of functional editing. Two controls were used; 1) T cells incubated with the RNP complex at room temperature for the same time as the delivery process using the Cell Squeeze process (endocytosis control; "endo control"), and 2) T cells squeezed with Cas9 protein but no gRNA. Plots of B2M expression vs. delivered dextran are shown (FIG. 4) for the four different cell populations. B2M expression on the Cas9 control was not significantly different than the endocytosis control. The delivery of the RNP using the 30-4 chip at 90 psi resulted in a 54.4% reduction in B2M expression as compared to the endo control whereas the 10-4 chip at 90 psi resulted in a 25.2% reduction in B2M expression. The longer constriction chip resulted in more delivery of the RNP complex and a larger reduction in B2M expression.

Dextran delivery was used to define low, mid and high delivered populations. The differences in efficiency of B2M knockdown for these specific populations was then determined using the mean fluorescence intensity (MFI) of B2M staining. For the 10-4 chip, the MFI of the highly delivered population was 18,637 versus 71,173 for the mid delivered populations and 83,676 for the low or non-delivered populations. This nearly 5-fold intensity drop in B2M staining for the high delivered populations demonstrates the degree to which delivery influences RNP activity. Similarly, for the 30-4 chip, the MFI of the highly delivered population was 16,460 versus 44,207 for the mid delivered populations and 54,159 for the low delivered population. These data demonstrated the importance that the cell squeezing delivery system of gene editing complexes to the cytosol of a cell has on editing efficiency, even within a single population.

To confirm the FACS readout, a second, sequence based analysis, was also employed in which DNA was extracted and amplified using primers flanking the target region thereby generating an amplicon of the edited region for Next Generation Sequencing (NGS). Sequencing results were analyzed using a simple algorithm designed to detect CRISPR variants from NGS reads. As expected, the sequence-based readout showed higher editing efficiencies. Indeed, some of the indels identified in sequencing still resulted in a functional, full length protein (i.e. single base substitutions that did not change the resultant amino acid).

TABLE

Comparison of FACS- and Sequence-based readouts from 10-4 editing experiment.

| | Endo | Cas9 | RNP |
|---|---|---|---|
| FACS | 0.3 | 8.15 | 20.4 |
| Sequencing | 3.87 | 3.04 | 27.18 |

These data demonstrated successful editing ability of the RNP complex when delivered by the Cell Squeeze platform.

Effect of RNP Complex Amount on Editing Efficiency

Figure 5:
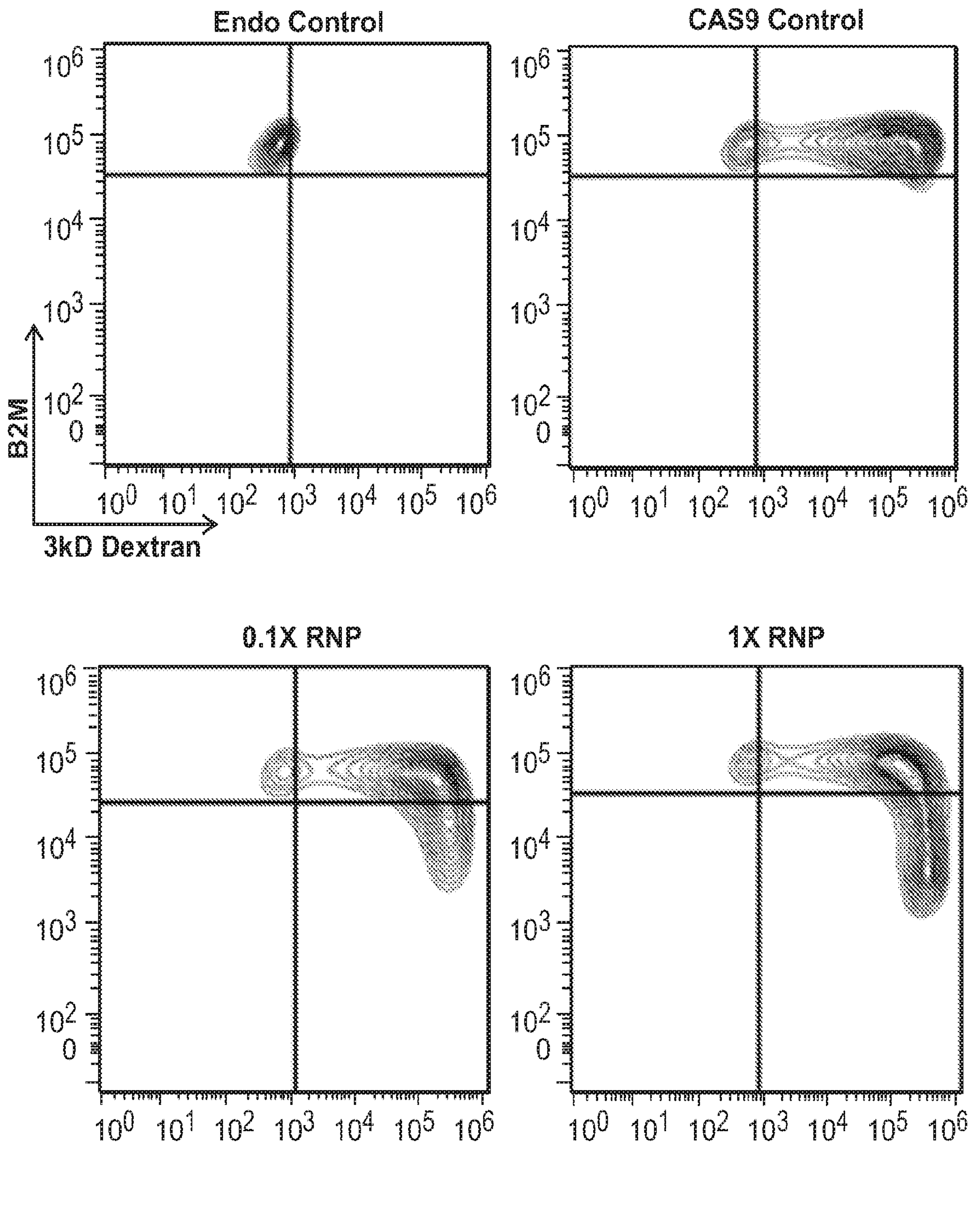
FIG. 5 is a series of FACs plots showing reduced B2M expression in a dose dependent manner determined by FACS as a measure of functional editing with the indicated conditions.

RNP complex was delivered to unstimulated human T cells using the 30-4 chip and at two different RNP amounts: 1) the standard 1×RNP complex (10 ug Cas9, 2.5 molar excess of gRNA) and, 2) 0.1× the standard RNP complex amount. At 48 hours post-delivery, a FACS based readout was used to determine B2M protein levels. Reduced B2M expression was used as a measure of functional editing. Plots of B2M expression vs. delivered dextran are shown below for the four different cell populations. Two controls were used; 1) T cells incubated in 1×RNP complex at room temperature for the same time as the delivery process using the Cell Squeeze process (endocytosis control), and 2) T cells squeezed with Cas9 protein but no gRNA (FIG. 5).

B2M expression on the Cas9 control (Cas9 protein with no gRNA) is not significantly different than the endocytosis control. The lower amount of the RNP complex (0.1×RNP) resulted in a 20.7% reduction of B2M positive cells as compared to the 55.4% reduction in B2M positive cells at the higher amount of RNP complex (1×RNP complex (10 ug CAS9, 2.5 molar excess of gRNA)). This experiment demonstrates a dose-dependent response directly related to the delivery of the RNP.

Other Embodiments

Cited references are incorporated herein by reference. To the extent that any of the incorporated material is inconsistent with the present disclosure, the present disclosure shall control. Furthermore, to the extent necessary, material incorporated by reference herein should be disregarded if necessary to preserve the validity of the claims.

Further, while the description above refers to the invention, the description may include more than one invention.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for delivering a protein-nucleic acid complex into a cell comprising:
   - providing a cell in a suspension;
   - passing the suspension through a microfluidic channel that includes a cell-deforming constriction;
   - wherein a diameter of the constriction is 20-99% of a diameter of the cell and passage of the cell through the constriction induces perturbations of the cell membrane large enough for the protein-nucleic acid complex to pass through the perturbations in the membrane; and
   - contacting the cell with the protein-nucleic acid complex;
   - wherein the protein-nucleic acid complex passes through the perturbations in the membrane, thereby delivering the protein-nucleic acid complex into the cell, wherein a pressure of at least 10 psi is used to pass the suspension through the microfluidic channel.

2. The method of claim 1, comprising contacting the cell with the protein-nucleic acid complex before the cell passes through the constriction.

3. The method of claim 2, comprising contacting the cell with the protein-nucleic acid complex during passage of the cell through the constriction.

4. The method of claim 1, comprising contacting the cell with the protein-nucleic acid complex after the cell passes through the constriction.

5. The method of claim 1, wherein the protein-nucleic acid complex comprises gene editing components.

6. The method of claim 1, wherein the protein-nucleic acid complex comprises a ribonucleoprotein (RNP).

7. The method of claim 5, wherein the protein-nucleic acid complex comprises:
   - (a) a Cas protein; and
   - (b) a single guide RNA (sgRNA), or a CRISPR RNA (crRNA) and a trans-activating crRNA (tracrRNA).

8. The method of claim 7, wherein the protein-nucleic acid complex comprises a ribonucleoprotein (RNP) comprising a Cas protein and an sgRNA and wherein the Cas protein and the sgRNA are complexed at a molar ratio between about 1:10 and about 10:1, respectively.

9. The method of claim 7, wherein the Cas protein comprises a Cas9 protein.

10. The method of claim 1, wherein said protein-nucleic acid complex comprises a first ribonucleoprotein (RNP) and a second RNP.

11. The method of claim 10, wherein the first RNP and the second RNP both comprise nickase proteins.

12. The method of claim 11, wherein the first RNP nicks a target sequence different from the target sequence of the second RNP.

13. The method of claim 1, wherein said protein-nucleic acid complex comprises a TALEN protein, Zinc finger nuclease, mega nuclease, or Cre recombinase.

14. The method of claim 1, wherein the protein-nucleic acid complex comprises:
   - (a) the nucleic acid molecule complexed with the protein via electrostatic attraction;
   - (b) the nucleic acid molecule wrapped around the protein;
   - (c) a DNA nucleic acid molecule and a histone protein;

(d) a ribonucleoprotein (RNP);

(e) a ribosome, an enzyme telomerase, a vault ribonucleoprotein, RNase P, hnRNP, or a small nuclear RNP (snRNP); or (f) a chromosome comprising a protein.

15. The method of claim 1, wherein the suspension further comprises a donor DNA.

16. The method of claim 15, wherein the donor DNA is present in the suspension before the cell passes through the constriction.

17. The method of claim 1, wherein the cell is a mammalian cell.

18. The method of claim 17, wherein the cell is a human cell.

19. The method of claim 1, wherein the diameter of the constriction is substantially about 20% to about 60% of the diameter of the cell.

20. The method of claim 1, wherein the microfluidic channel is one of a plurality of parallel microfluidic channels in a microfluidic system.

21. The method of claim 20, wherein the plurality of parallel microfluidic channels comprises at least about 2, 5, 10, 20, 25, 30, 40, 45, 50, 75, 100, 500, or 1,000 microfluidic channels.

22. The method of claim 1, wherein the cell is a plurality of cells, wherein each cell is passed through one of a plurality of parallel microfluidic channels, and wherein each microfluidic channel of the plurality of parallel microfluidic channels includes a cell-deforming constriction.

23. The method of claim 1, wherein the diameter of the constriction is about 2, 3, 4, 5, 6, 7, 8, 9, 10, 15, 20, 2-10 μm, or 10-20 μm.

24. The method of claim 5, wherein after the protein-nucleic acid complex is delivered to the cell, (a) an expression of a target gene in the cell is reduced by at least about 5, 10, 15, 20, 25, 30, 35, 40, 45, 50, 55, 60, 75, 80, 85, 90, 95, or 99% or more; or (b) the cell is a plurality of cells and an expression of the target gene in the plurality of cells is reduced by at least about 5, 10, 15, 20, 25, 30, 35, 40, 45, 50, 55, 60, 75, 80, 85, 90, 95, or 99% or more.

25. The method of claim 24, wherein the expression of the target gene is reduced about 1, 2, 5, 12, 24, 48, 1-12, 6-12, 6-18, 12-24, or 1-24 hours after the protein-nucleic acid complex is delivered to the cell.

26. The method of claim 5, wherein after the protein-nucleic acid complex is delivered to the cell, (a) an expression of a target gene in the cell is increased by at least about 5, 10, 25, 50, 75, 100, 250, 500% or more; or (b) the cell is a plurality of cells and an expression of the target gene in the plurality of cells is increased by at least about 5, 10, 25, 50, 75, 100, 250, 500% or more.

27. The method of claim 26, wherein the expression of the target gene is increased about 1, 2, 5, 12, 24, 48, 1-12, 6-12, 6-18, 12-24, or 1-24 hours after the protein-nucleic acid complex is delivered to the cell.

28. The method of claim 1, wherein said microfluidic channel comprises multiple cell-deforming constrictions.

29. The method of claim 1, wherein the cell is contacted with the protein-nucleic acid complex for 0.0001 seconds to 20 minutes before, during, and/or after the cell passes through the constriction.

30. The method of claim 15, wherein the cell is contacted with the protein-nucleic acid complex in the suspension comprising the donor DNA for 0.0001 seconds to 20 minutes before, during, and/or after the cell passes through the constriction.

31. The method of claim 1, wherein a length of the constriction is about 10, 15, 20, 24, 30, 40, 50, 60, 70, 80, 90, 100, 10-40, 10-50, 10-60, or 10-100 μm.

32. The method of claim 1, wherein a pressure of about 10, 20, 30, 40, 50, 60, 70, 80, 90, 100 or 10-100 psi is used to pass the suspension through the microfluidic channel.

33. The method of claim 1, wherein the cell passes through the microfluidic channel at a speed of about 300, 400, 500, 600, 700, 800, 900, 100-300, 200-700, 250-400, 100-1000 mm/s, 1-1000 mm/s, 1 m/s, 2 m/s, 3 m/s, 4 m/s, 5 m/s, 6 m/s, 7 m/s, 8 m/s, 9 m/s, 10 m/s, 0.01-5 m/s, 5-10 m/s, or 0.01-10 m/s.

34. The method of claim 1, wherein said microfluidic channel comprises a single cell-deforming constriction.

35. The method of claim 1, wherein the perturbations of the cell include a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm.

36. The method of claim 1, wherein perturbations of the cell having a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell for at least about 1, 2, 3, 4, 5, 6, 7, 8, 9, or 10, or 1-10 minutes.

37. The method of claim 1, wherein said microfluidic channel comprises multiple cell-deforming constrictions in parallel or in series.

38. The method of claim 15, wherein the donor DNA is present in the suspension during passage of the cell through the constriction.

39. The method of claim 15, wherein the donor DNA is present in the suspension after the cell passes through the constriction.

40. The method of claim 5, wherein the protein-nucleic acid complex comprises:

(a) a Cpf1 protein; and (b) a single guide RNA (sgRNA), or a CRISPR RNA (crRNA) and a trans-activating crRNA (tracrRNA).

41. The method of claim 40, wherein the protein-nucleic acid complex comprises a ribonucleoprotein (RNP) comprising a Cpf1 protein and an sgRNA, and wherein the Cpf1 protein and the sgRNA are complexed at a molar ratio between about 1:10 and about 10:1, respectively.

* * * * *

SEQUENCE LISTING

```
<160> NUMBER OF SEQ ID NOS: 66

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
```

-continued

```
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430
```

-continued

```
Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845
```

-continued

```
Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
```

-continued

```
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 2
<211> LENGTH: 4107
<212> TYPE: DNA
<213> ORGANISM: Streptococcus pyogenes

<400> SEQUENCE: 2

atggataaga aatactcaat aggcttagat atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agattttttc aaatgagatg gcgaaagtag atgatagttt ctttcatcga    300

cttgaagagt cttttttggt ggaagaagac aagaagcatg aacgtcatcc tatttttgga    360

aatatagtag atgaagttgc ttatcatgag aaatatccaa ctatctatca tctgcgaaaa    420

aaattggtag attctactga taaagcggat ttgcgcttaa tctatttggc cttagcgcat    480

atgattaagt ttcgtggtca tttttttgatt gagggagatt taaatcctga taatagtgat    540

gtggacaaac tatttatcca gttggtacaa acctacaatc aattatttga agaaaaccct    600

attaacgcaa gtggagtaga tgctaaagcg attctttctg cacgattgag taaatcaaga    660

cgattagaaa atctcattgc tcagctcccc ggtgagaaga aaaatggctt atttgggaat    720

ctcattgctt tgtcattggg tttgacccct aattttaaat caaattttga tttggcagaa    780

gatgctaaat tacagctttc aaaagatact tacgatgatg atttagataa tttattggcg    840

caaattggag atcaatatgc tgatttgttt ttggcagcta agaatttatc agatgctatt    900

ttactttcag atatcctaag agtaaatact gaaataacta aggctcccct atcagcttca    960

atgattaaac gctacgatga acatcatcaa gacttgactc ttttaaaagc tttagttcga   1020

caacaacttc cagaaaagta taaagaaatc ttttttgatc aatcaaaaaa cggatatgca   1080

ggttatattg atgggggagc tagccaagaa gaattttata aatttatcaa accaatttta   1140

gaaaaaatgg atggtactga ggaattattg gtgaaactaa atcgtgaaga tttgctgcgc   1200

aagcaacgga cctttgacaa cggctctatt ccccatcaaa ttcacttggg tgagctgcat   1260

gctattttga gaagacaaga agacttttat ccatttttaa aagacaatcg tgagaagatt   1320

gaaaaaatct tgacttttcg aattccttat tatgttggtc cattggcgcg tggcaatagt   1380

cgttttgcat ggatgactcg gaagtctgaa gaaacaatta ccccatggaa ttttgaagaa   1440
```

-continued

```
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540
tttttagaag ctaaaggata taaggaagtt aaaaaagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga atttttata tttagctagt   3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
```

```
attttagcag atgccaattt agataaagtt cttagtgcat ataacaaaca tagagacaaa   3900

ccaatacgtg aacaagcaga aaatattatt catttattta cgttgacgaa tcttggagct   3960

cccgctgctt ttaaatattt tgatacaaca attgatcgta aacgatatac gtctacaaaa   4020

gaagttttag atgccactct tatccatcaa tccatcactg gtctttatga aacacgcatt   4080

gatttgagtc agctaggagg tgactga                                       4107


<210> SEQ ID NO 3
<211> LENGTH: 1388
<212> TYPE: PRT
<213> ORGANISM: Streptococcus thermophilus

<400> SEQUENCE: 3

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320
```

-continued

```
Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
    530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
    610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
    690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
```

```
            740                 745                 750

Gly Gly Arg Lys Pro Glu Ser Ile Val Val Glu Met Ala Arg Glu Asn
        755                 760                 765

Gln Tyr Thr Asn Gln Gly Lys Ser Asn Ser Gln Gln Arg Leu Lys Arg
    770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
        835                 840                 845

Ile Pro Gln Ala Phe Leu Lys Asp Asn Ser Ile Asp Asn Lys Val Leu
    850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Ser Pro Glu Asp Lys Ala Gly Phe Ile Gln Arg Gln Leu
        915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Val  Ala Ser Ala Leu Leu  Lys Lys Tyr
        995                 1000                1005

Pro Lys  Leu Glu Pro Glu Phe  Val Tyr Gly Asp Tyr  Pro Lys Tyr
    1010                1015                1020

Asn Ser  Phe Arg Glu Arg Lys  Ser Ala Thr Glu Lys  Val Tyr Phe
    1025                1030                1035

Tyr Ser  Asn Ile Met Asn Ile  Phe Lys Lys Ser Ile  Ser Leu Ala
    1040                1045                1050

Asp Gly  Arg Val Ile Glu Arg  Pro Leu Ile Glu Val  Asn Glu Glu
    1055                1060                1065

Thr Gly  Glu Ser Val Trp Asn  Lys Glu Ser Asp Leu  Ala Thr Val
    1070                1075                1080

Arg Arg  Val Leu Ser Tyr Pro  Gln Val Asn Val Val  Lys Lys Val
    1085                1090                1095

Glu Glu  Gln Asn His Gly Leu  Asp Arg Gly Lys Pro  Lys Gly Leu
    1100                1105                1110

Phe Asn  Ala Asn Leu Ser Ser  Lys Pro Lys Pro Asn  Ser Asn Glu
    1115                1120                1125

Asn Leu  Val Gly Ala Lys Glu  Tyr Leu Asp Pro Lys  Lys Tyr Gly
    1130                1135                1140

Gly Tyr  Ala Gly Ile Ser Asn  Ser Phe Thr Val Leu  Val Lys Gly
    1145                1150                1155
```

Thr Ile Glu Lys Gly Ala Lys Lys Lys Ile Thr Asn Val Leu Glu
1160 1165 1170

Phe Gln Gly Ile Ser Ile Leu Asp Arg Ile Asn Tyr Arg Lys Asp
1175 1180 1185

Lys Leu Asn Phe Leu Leu Glu Lys Gly Tyr Lys Asp Ile Glu Leu
1190 1195 1200

Ile Ile Glu Leu Pro Lys Tyr Ser Leu Phe Glu Leu Ser Asp Gly
1205 1210 1215

Ser Arg Arg Met Leu Ala Ser Ile Leu Ser Thr Asn Asn Lys Arg
1220 1225 1230

Gly Glu Ile His Lys Gly Asn Gln Ile Phe Leu Ser Gln Lys Phe
1235 1240 1245

Val Lys Leu Leu Tyr His Ala Lys Arg Ile Ser Asn Thr Ile Asn
1250 1255 1260

Glu Asn His Arg Lys Tyr Val Glu Asn His Lys Lys Glu Phe Glu
1265 1270 1275

Glu Leu Phe Tyr Tyr Ile Leu Glu Phe Asn Glu Asn Tyr Val Gly
1280 1285 1290

Ala Lys Lys Asn Gly Lys Leu Leu Asn Ser Ala Phe Gln Ser Trp
1295 1300 1305

Gln Asn His Ser Ile Asp Glu Leu Cys Ser Ser Phe Ile Gly Pro
1310 1315 1320

Thr Gly Ser Glu Arg Lys Gly Leu Phe Glu Leu Thr Ser Arg Gly
1325 1330 1335

Ser Ala Ala Asp Phe Glu Phe Leu Gly Val Lys Ile Pro Arg Tyr
1340 1345 1350

Arg Asp Tyr Thr Pro Ser Ser Leu Leu Lys Asp Ala Thr Leu Ile
1355 1360 1365

His Gln Ser Val Thr Gly Leu Tyr Glu Thr Arg Ile Asp Leu Ala
1370 1375 1380

Lys Leu Gly Glu Gly
1385

<210> SEQ ID NO 4
<211> LENGTH: 4167
<212> TYPE: DNA
<213> ORGANISM: Streptococcus thermophilus

<400> SEQUENCE: 4
atgactaagc catactcaat tggacttgat attggaacga atagtgttgg atgggctgta 60
acaactgata attacaaggt tccgtctaaa aaaatgaaag tcttaggaaa tacgagtaaa 120
aagtatatca aaaagaacct gttaggtgta ttactctttg actctggaat cacagcagaa 180
ggaagaagat tgaagcgtac tgcaagaaga cgttatacta gacgccgtaa tcgtatcctt 240
tatttgcagg aaatttttag cacagagatg gctacattag atgatgcttt ctttcaaaga 300
cttgacgatt cgtttttagt tcctgatgat aaacgtgata gtaagtatcc gatatttgga 360
aacttagtag aagaaaaagc ctatcatgat gaatttccaa ctatctatca tttaaggaaa 420
tatttagcag atagtactaa aaaagcagat ttgcgtctag tttatcttgc attggctcat 480
atgattaaat atagaggtca cttcttaatt gaaggagagt ttaattcaaa aaataatgat 540
attcagaaga attttcaaga ctttttggac acttataatg ctatttttga atcggattta 600
tcacttgaga atagtaaaca acttgaggaa attgttaaag ataagattag taaattagaa 660

-continued

```
aagaaagatc gtattttaaa actcttccct ggggagaaga attcggggat tttttcagag    720
tttctaaagt tgattgtagg aaatcaagct gattttagga aatgttttaa tttagacgaa    780
aaagcctcct tacatttttc caaagaaagc tatgatgaag atttagagac tttgttaggt    840
tatattggag atgattacag tgatgtcttt ctcaaagcaa agaaacttta tgatgctatt    900
cttttatcgg gttttctgac tgtaactgat aatgagacag aagcacctct ctcttctgct    960
atgataaagc gatataatga acacaaagaa gatttagcgt tactaaagga atatataaga   1020
aatatttcac taaaaacgta taatgaagta tttaaagatg acaccaaaaa tggttatgct   1080
ggttatattg atggaaaaac aaatcaggaa gatttctacg tatatctaaa aaaactattg   1140
gctgaatttg aaggtgcgga ttattttctt gaaaaaattg atcgagaaga tttttttgaga   1200
aagcaacgta catttgacaa tggttcgata ccatatcaga ttcatcttca agaaatgaga   1260
gcaattcttg ataagcaagc taaattttat cctttcttgg ctaaaaataa agaaagaatc   1320
gagaagattt taaccttccg aattccttat tatgtaggtc cacttgcgag agggaatagt   1380
gattttgcct ggtcaataag aaaacgaaat gaaaaaatta caccttggaa ttttgaggac   1440
gttattgaca aagaatcttc ggcagaggcc ttcattaatc gaatgactag ttttgatttg   1500
tatttgccag aagagaaggt acttccaaag catagtctct tatacgaaac ttttaatgta   1560
tataatgaat taacaaaagt tagatttatt gccgaaagta tgagagatta tcaatttta   1620
gatagtaagc agaagaaaga tattgttaga ctttatttta aagataaaag gaaagttact   1680
gataaggata ttattgaata tttacatgca atttatgggt atgatggaat tgaattaaaa   1740
ggcatagaga aacagtttaa ttctagttta tctacttatc acgatctttt aaatattatt   1800
aatgataaag agtttttgga tgatagttca aatgaagcga ttatcgaaga aattatccat   1860
actttgacaa tttttgaaga tagagagatg ataaaacaac gtctttcaaa atttgagaat   1920
atattcgata aatccgtttt gaaaaagtta tctcgtagac attacactgg ctggggtaag   1980
ttatctgcta agcttattaa tggtattcga gatgaaaaat ctggtaatac tattcttgat   2040
tacttaattg atgatggtat ttctaaccgt aatttcatgc aacttattca cgatgatgct   2100
ctttctttta aaaagaagat acagaaagca caaattattg gtgacgaaga taaaggtaat   2160
attaaagagg tcgttaagtc tttgccaggt agtcctgcga ttaaaaaagg tattttacaa   2220
agcataaaaa ttgtagatga attggtcaaa gtaatgggag gaagaaaacc cgagtcaatt   2280
gttgttgaga tggctcgtga aaatcaatat accaatcaag gtaagtctaa ttcccaacaa   2340
cgcttgaaac gtttagaaaa atctctcaaa gagttaggta gtaagatact taaggaaaat   2400
attcctgcaa aactttctaa aatagacaat aacgcacttc aaaatgatcg actttactta   2460
tactatcttc aaaatggaaa agatatgtat accggagatg atttagatat tgatagatta   2520
agtaattatg atattgatca tattattcct caagcttttt tgaaagataa ttctattgac   2580
aataaagtac ttgtttcatc tgctagtaac cgtggtaaat cagatgatgt tccaagttta   2640
gaggttgtca aaaaaagaaa gacattttgg tatcaattat tgaaatcaaa attaatttct   2700
caacgaaaat ttgataatct gacaaaagct gaacggggag gattgtcacc tgaggacaaa   2760
gctggtttta ttcaacgcca gttggttgaa acacgtcaaa taacaaaaca tgtagctcgt   2820
ttacttgatg agaaatttaa taataaaaaa gatgaaaata atagagcggt acgaacagta   2880
aaaattatta ccttgaaatc taccttagtt tctcaatttc gtaaggattt tgaactttat   2940
aaagttcgtg aaatcaatga ttttcatcat gctcatgatg cttacttgaa tgccgttgta   3000
gcaagtgctt tacttaagaa ataccctaaa ctagagccag aatttgtgta cggtgattat   3060
```

```
ccaaaataca atagttttag agaaagaaag tccgctacag aaaaggtata tttctattca   3120

aatatcatga atatctttaa aaaatctatt tctttagctg atggtagagt tattgaaaga   3180

ccacttattg aggtaaatga ggagaccggc gaatccgttt ggaataaaga atctgattta   3240

gcaactgtaa ggagagtact ctcttatccg caagtaaatg ttgtgaaaaa agttgaggaa   3300

cagaatcacg gattggatag aggaaaacca aagggattgt ttaatgcaaa tctttcctca   3360

aagccaaaac caaatagtaa tgaaaattta gtaggtgcta aagagtatct tgaccccaaa   3420

aagtatgggg ggtatgctgg aatttctaat tcttttactg ttcttgttaa agggacaatt   3480

gaaaaaggtg ctaagaaaaa aataacaaat gtactagaat ttcaaggtat ttctatttta   3540

gataggatta attatagaaa agataaactt aatttttttac ttgaaaaagg ttataaagat   3600

attgagttaa ttattgaact acctaaatat agtttatttg aactttcaga tggttcacgt   3660

cgtatgttgg ctagtatttt gtcaacgaat aataagaggg gagagattca caaaggaaat   3720

cagatttttc tttcacagaa gtttgtgaaa ttactttatc atgctaagag aataagtaac   3780

acaattaatg agaatcatag aaaatatgtt gagaaccata aaaaagagtt tgaagaatta   3840

ttttactaca ttcttgagtt taatgagaat tatgttggag ctaaaaagaa tggtaaactc   3900

ttaaactctg cctttcaatc ttggcaaaat catagtatag atgaactctg tagtagtttt   3960

ataggaccta ccggaagtga aagaaagggg ctatttgaat taacctctcg tggaagtgct   4020

gctgattttg aatttttagg tgttaaaatt ccaaggtata gagactatac cccatcatcc   4080

ctattaaaag atgccacact tattcatcaa tctgttacag gcctctatga aacacgaata   4140

gaccttgcca aactaggaga gggttaa                                       4167
```

<210> SEQ ID NO 5
<211> LENGTH: 12
<212> TYPE: PRT
<213> ORGANISM: Artificial Sequence
<220> FEATURE:
<223> OTHER INFORMATION: Nuclear Localization Signal

<400> SEQUENCE: 5

```
Gly Gly Ser Gly Pro Pro Lys Lys Lys Arg Lys Val
1               5                   10
```

<210> SEQ ID NO 6
<211> LENGTH: 1380
<212> TYPE: PRT
<213> ORGANISM: Artificial Sequence
<220> FEATURE:
<223> OTHER INFORMATION: Cas9 protein comprising a C-terminal nuclear localization signal.

<400> SEQUENCE: 6

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
```

-continued

```
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510
```

-continued

Leu Leu Tyr Glu Tyr Phe Thr Val Tyr Asn Glu Leu Thr Lys Val Lys
515 520 525

Tyr Val Thr Glu Gly Met Arg Lys Pro Ala Phe Leu Ser Gly Glu Gln
530 535 540

Lys Lys Ala Ile Val Asp Leu Leu Phe Lys Thr Asn Arg Lys Val Thr
545 550 555 560

Val Lys Gln Leu Lys Glu Asp Tyr Phe Lys Lys Ile Glu Cys Phe Asp
565 570 575

Ser Val Glu Ile Ser Gly Val Glu Asp Arg Phe Asn Ala Ser Leu Gly
580 585 590

Thr Tyr His Asp Leu Leu Lys Ile Ile Lys Asp Lys Asp Phe Leu Asp
595 600 605

Asn Glu Glu Asn Glu Asp Ile Leu Glu Asp Ile Val Leu Thr Leu Thr
610 615 620

Leu Phe Glu Asp Arg Glu Met Ile Glu Glu Arg Leu Lys Thr Tyr Ala
625 630 635 640

His Leu Phe Asp Asp Lys Val Met Lys Gln Leu Lys Arg Arg Arg Tyr
645 650 655

Thr Gly Trp Gly Arg Leu Ser Arg Lys Leu Ile Asn Gly Ile Arg Asp
660 665 670

Lys Gln Ser Gly Lys Thr Ile Leu Asp Phe Leu Lys Ser Asp Gly Phe
675 680 685

Ala Asn Arg Asn Phe Met Gln Leu Ile His Asp Asp Ser Leu Thr Phe
690 695 700

Lys Glu Asp Ile Gln Lys Ala Gln Val Ser Gly Gln Gly Asp Ser Leu
705 710 715 720

His Glu His Ile Ala Asn Leu Ala Gly Ser Pro Ala Ile Lys Lys Gly
725 730 735

Ile Leu Gln Thr Val Lys Val Val Asp Glu Leu Val Lys Val Met Gly
740 745 750

Arg His Lys Pro Glu Asn Ile Val Ile Glu Met Ala Arg Glu Asn Gln
755 760 765

Thr Thr Gln Lys Gly Gln Lys Asn Ser Arg Glu Arg Met Lys Arg Ile
770 775 780

Glu Glu Gly Ile Lys Glu Leu Gly Ser Gln Ile Leu Lys Glu His Pro
785 790 795 800

Val Glu Asn Thr Gln Leu Gln Asn Glu Lys Leu Tyr Leu Tyr Tyr Leu
805 810 815

Gln Asn Gly Arg Asp Met Tyr Val Asp Gln Glu Leu Asp Ile Asn Arg
820 825 830

Leu Ser Asp Tyr Asp Val Asp His Ile Val Pro Gln Ser Phe Leu Lys
835 840 845

Asp Asp Ser Ile Asp Asn Lys Val Leu Thr Arg Ser Asp Lys Asn Arg
850 855 860

Gly Lys Ser Asp Asn Val Pro Ser Glu Glu Val Val Lys Lys Met Lys
865 870 875 880

Asn Tyr Trp Arg Gln Leu Leu Asn Ala Lys Leu Ile Thr Gln Arg Lys
885 890 895

Phe Asp Asn Leu Thr Lys Ala Glu Arg Gly Gly Leu Ser Glu Leu Asp
900 905 910

Lys Ala Gly Phe Ile Lys Arg Gln Leu Val Glu Thr Arg Gln Ile Thr
915 920 925

```
Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
```

```
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

Gly Gly  Ser Gly Pro Pro Lys  Lys Lys Arg Lys Val
    1370                1375                1380


<210> SEQ ID NO 7
<211> LENGTH: 27
<212> TYPE: DNA
<213> ORGANISM: Artificial Sequence
<220> FEATURE:
<223> OTHER INFORMATION: Cas9 target sequence
<220> FEATURE:
<221> NAME/KEY: misc_feature
<222> LOCATION: (1)..(20)
<223> OTHER INFORMATION: n is a, g, t, or c
<220> FEATURE:
<221> NAME/KEY: misc_feature
<222> LOCATION: (21)..(22)
<223> OTHER INFORMATION: n is a deoxynucleotide
<220> FEATURE:
<221> NAME/KEY: misc_feature
<222> LOCATION: (27)..(27)
<223> OTHER INFORMATION: n is a or t

<400> SEQUENCE: 7

nnnnnnnnnn nnnnnnnnnn nnagaan                                        27


<210> SEQ ID NO 8
<211> LENGTH: 19
<212> TYPE: DNA
<213> ORGANISM: Artificial Sequence
<220> FEATURE:
<223> OTHER INFORMATION: Cas9 target sequence
<220> FEATURE:
<221> NAME/KEY: misc_feature
<222> LOCATION: (1)..(12)
<223> OTHER INFORMATION: n is a, g, t, or c
<220> FEATURE:
<221> NAME/KEY: misc_feature
<222> LOCATION: (13)..(14)
<223> OTHER INFORMATION: n is a deoxynucleotide
<220> FEATURE:
<221> NAME/KEY: misc_feature
<222> LOCATION: (19)..(19)
<223> OTHER INFORMATION: n is a or t

<400> SEQUENCE: 8

nnnnnnnnnn nnnnagaan                                                 19


<210> SEQ ID NO 9
<211> LENGTH: 27
<212> TYPE: DNA
<213> ORGANISM: Artificial Sequence
<220> FEATURE:
<223> OTHER INFORMATION: Cas9 target sequence
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (20)..(21)
<223> OTHER INFORMATION: n is a, g, t, or c
<220> FEATURE:
<221> NAME/KEY: misc_feature
<222> LOCATION: (22)..(23)
<223> OTHER INFORMATION: n is a deoxynucleotide
<220> FEATURE:
```

<221> NAME/KEY: misc_feature
<222> LOCATION: (27)..(27)
<223> OTHER INFORMATION: n is a or t

<400> SEQUENCE: 9
nnnnnnnnnn nnnnnnnnnn nnagaan 27

<210> SEQ ID NO 10
<211> LENGTH: 18
<212> TYPE: DNA
<213> ORGANISM: Artificial Sequence
<220> FEATURE:
<223> OTHER INFORMATION: Cas9 target sequence
<220> FEATURE:
<221> NAME/KEY: misc_feature
<222> LOCATION: (1)..(11)
<223> OTHER INFORMATION: n is a, g, t, or c
<220> FEATURE:
<221> NAME/KEY: misc_feature
<222> LOCATION: (12)..(13)
<223> OTHER INFORMATION: n is a deoxynucleotide
<220> FEATURE:
<221> NAME/KEY: misc_feature
<222> LOCATION: (18)..(18)
<223> OTHER INFORMATION: n is a or t

<400> SEQUENCE: 10
nnnnnnnnnn nnnnagaan 18

<210> SEQ ID NO 11
<211> LENGTH: 1345
<212> TYPE: PRT
<213> ORGANISM: Artificial Sequence
<220> FEATURE:
<223> OTHER INFORMATION: Francisella tularensis subsp. Novicida U112
(FnCpf1; pY004)), including NLS and HA tag

<400> SEQUENCE: 11

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Glu Tyr
100 105 110

Ile Lys Asp Ser Glu Lys Phe Lys Asn Leu Phe Asn Gln Asn Leu Ile
115 120 125

Asp Ala Lys Lys Gly Gln Glu Ser Asp Leu Ile Leu Trp Leu Lys Gln
130 135 140

Ser Lys Asp Asn Gly Ile Glu Leu Phe Lys Ala Asn Ser Asp Ile Thr
145 150 155 160

Asp Ile Asp Glu Ala Leu Glu Ile Ile Lys Ser Phe Lys Gly Trp Thr
165 170 175

Thr Tyr Phe Lys Gly Phe His Glu Asn Arg Lys Asn Val Tyr Ser Ser
180 185 190

-continued

```
Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
```

-continued

```
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035
```

```
Val Phe  Lys Asp Asn Glu Phe  Asp Lys Thr Gly Gly  Val Leu Arg
    1040                 1045                 1050

Ala Tyr  Gln Leu Thr Ala Pro  Phe Glu Thr Phe Lys  Lys Met Gly
    1055                 1060                 1065

Lys Gln  Thr Gly Ile Ile Tyr  Tyr Val Pro Ala Gly  Phe Thr Ser
    1070                 1075                 1080

Lys Ile  Cys Pro Val Thr Gly  Phe Val Asn Gln Leu  Tyr Pro Lys
    1085                 1090                 1095

Tyr Glu  Ser Val Ser Lys Ser  Gln Glu Phe Phe Ser  Lys Phe Asp
    1100                 1105                 1110

Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
    1130                 1135                 1140

Ile Ala  Ser Phe Gly Ser Arg  Leu Ile Asn Phe Arg  Asn Ser Asp
    1145                 1150                 1155

Lys Asn  His Asn Trp Asp Thr  Arg Glu Val Tyr Pro  Thr Lys Glu
    1160                 1165                 1170

Leu Glu  Lys Leu Leu Lys Asp  Tyr Ser Ile Glu Tyr  Gly His Gly
    1175                 1180                 1185

Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
    1250                 1255                 1260

Leu Lys  Gly Leu Met Leu Leu  Gly Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn  Lys Arg Pro Ala Ala  Thr Lys Lys
    1295                 1300                 1305

Ala Gly  Gln Ala Lys Lys Lys  Lys Gly Ser Tyr Pro  Tyr Asp Val
    1310                 1315                 1320

Pro Asp  Tyr Ala Tyr Pro Tyr  Asp Val Pro Asp Tyr  Ala Tyr Pro
    1325                 1330                 1335

Tyr Asp  Val Pro Asp Tyr Ala
    1340                 1345
```

<210> SEQ ID NO 12
<211> LENGTH: 16
<212> TYPE: PRT
<213> ORGANISM: Artificial Sequence
<220> FEATURE:
<223> OTHER INFORMATION: Nuclear Localization Signal

<400> SEQUENCE: 12

```
Lys Arg Pro Ala Ala Thr Lys Lys Ala Gly Gln Ala Lys Lys Lys Lys
1               5                   10                  15
```

<210> SEQ ID NO 13

<211> LENGTH: 27
<212> TYPE: PRT
<213> ORGANISM: Artificial Sequence
<220> FEATURE:
<223> OTHER INFORMATION: HA Tag

<400> SEQUENCE: 13

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25

<210> SEQ ID NO 14
<211> LENGTH: 4038
<212> TYPE: DNA
<213> ORGANISM: Artificial Sequence
<220> FEATURE:
<223> OTHER INFORMATION: Francisella tularensis subsp. Novicida U112
(FnCpf1; pY004)), including NLS and HA tag

<400> SEQUENCE: 14
atgagcatct accaggagtt cgtcaacaag tattcactga gtaagacact gcggttcgag 60
ctgatcccac agggcaagac actggagaac atcaaggccc gaggcctgat tctggacgat 120
gagaagcggg caaaagacta taagaaagcc aagcagatca ttgataaata ccaccagttc 180
tttatcgagg aaattctgag ctccgtgtgc atcagtgagg atctgctgca gaattactca 240
gacgtgtact tcaagctgaa gaagagcgac gatgacaacc tgcagaagga cttcaagtcc 300
gccaaggaca ccatcaagaa acagattagc gagtacatca aggactccga aaagtttaaa 360
aatctgttca accagaatct gatcgatgct aagaaaggcc aggagtccga cctgatcctg 420
tggctgaaac agtctaagga caatgggatt gaactgttca aggctaactc cgatatcact 480
gatattgacg aggcactgga aatcatcaag agcttcaagg gatggaccac atactttaaa 540
ggcttccacg agaaccgcaa gaacgtgtac tccagcaacg acattcctac ctccatcatc 600
taccgaatcg tcgatgacaa tctgccaaag ttcctggaga acaaggccaa atatgaatct 660
ctgaaggaca aagctcccga ggcaattaat tacgaacaga tcaagaaaga tctggctgag 720
gaactgacat tcgatatcga ctataagact agcgaggtga accagagggt cttttccctg 780
gacgaggtgt ttgaaatcgc caatttcaac aattacctga accagtccgg cattactaaa 840
ttcaatacca tcattggcgg gaagtttgtg aacggggaga ataccaagcg caagggaatt 900
aacgaataca tcaatctgta tagccagcag atcaacgaca aaactctgaa gaaatacaag 960
atgtctgtgc tgttcaaaca gatcctgagt gataccgagt ccaagtcttt tgtcattgat 1020
aaactggaag atgactcaga cgtggtcact accatgcaga gcttttatga gcagatcgcc 1080
gctttcaaga cagtggagga aaaatctatt aaggaaactc tgagtctgct gttcgatgac 1140
ctgaaagccc agaagctgga cctgagtaag atctacttca aaaacgataa gagtctgaca 1200
gacctgtcac agcaggtgtt tgatgactat tccgtgattg ggaccgccgt cctggagtac 1260
attacacagc agatcgctcc aaagaacctg gataatccct ctaagaaaga gcaggaactg 1320
atcgctaaga aaaccgagaa ggcaaaatat ctgagtctgg aaacaattaa gctggcactg 1380
gaggagttca acaagcacag ggatattgac aaacagtgcc gctttgagga aatcctggcc 1440
aacttcgcag ccatccccat gatttttgat gagatcgccc agaacaaaga caatctggct 1500
cagatcagta ttaagtacca gaaccagggc aagaaagacc tgctgcaggc ttcagcagaa 1560
gatgacgtga aagccatcaa ggatctgctg gaccagacca acaatctgct gcacaagctg 1620

-continued

```
aaaatcttcc atattagtca gtcagaggat aaggctaata tcctggataa agacgaacac   1680
ttctacctgg tgttcgagga atgttacttc gagctggcaa acattgtccc cctgtataac   1740
aagattagga actacatcac acagaagcct tactctgacg agaagtttaa actgaacttc   1800
gaaaatagta ccctggccaa cgggtgggat aagaacaagg agcctgacaa cacagctatc   1860
ctgttcatca aggatgacaa gtactatctg ggagtgatga ataagaaaaa caataagatc   1920
ttcgatgaca aagccattaa ggagaacaaa ggggaaggat acaagaaaat cgtgtataag   1980
ctgctgcccg gcgcaaataa gatgctgcct aaggtgttct tcagcgccaa gagtatcaaa   2040
ttctacaacc catccgagga catcctgcgg attagaaatc actcaacaca tactaagaac   2100
gggagccccc agaagggata tgagaaattt gagttcaaca tcgaggattg caggaagttt   2160
attgacttct acaagcagag catctccaaa caccctgaat ggaaggattt tggcttccgg   2220
ttttccgaca cacagagata taactctatc gacgagttct accgcgaggt ggaaaatcag   2280
gggtataagc tgacttttga gaacatttct gaaagttaca tcgacagcgt ggtcaatcag   2340
ggaaagctgt acctgttcca gatctataac aaagattttt cagcatacag caagggcaga   2400
ccaaacctgc atacactgta ctggaaggcc ctgttcgatg agaggaatct gcaggacgtg   2460
gtctataaac tgaacggaga ggccgaactg ttttaccgga agcagtctat tcctaagaaa   2520
atcactcacc cagctaagga ggccatcgct aacaagaaca aggacaatcc taagaaagag   2580
agcgtgttcg aatacgatct gattaaggac aagcggttca ccgaagataa gttctttttc   2640
cattgtccaa tcaccattaa cttcaagtca agcggcgcta acaagttcaa cgacgagatc   2700
aatctgctgc tgaaggaaaa agcaaacgat gtgcacatcc tgagcattga ccgaggagag   2760
cggcatctgg cctactatac cctggtggat ggcaaaggga atatcattaa gcaggataca   2820
ttcaacatca ttggcaatga ccggatgaaa accaactacc acgataaact ggctgcaatc   2880
gagaaggata gagactcagc taggaaggac tggaagaaaa tcaacaacat taaggagatg   2940
aaggaaggct atctgagcca ggtggtccat gagattgcaa agctggtcat cgaatacaat   3000
gccattgtgg tgttcgagga tctgaacttc ggctttaaga gggggcgctt taaggtggaa   3060
aaacaggtct atcagaagct ggagaaaatg ctgatcgaaa agctgaatta cctggtgttt   3120
aaagataacg agttcgacaa gaccggaggc gtcctgagag cctaccagct gacagctccc   3180
tttgaaactt tcaagaaaat gggaaaacag acaggcatca tctactatgt gccagccgga   3240
ttcacttcca agatctgccc cgtgaccggc tttgtcaacc agctgtaccc taaatatgag   3300
tcagtgagca agtcccagga atttttcagc aagttcgata agatctgtta taatctggac   3360
aaggggtact tcgagttttc cttcgattac aagaacttcg gcgacaaggc cgctaagggg   3420
aaatggacca ttgcctcctt cggatctcgc ctgatcaact ttcgaaattc cgataaaaac   3480
cacaattggg acactaggga ggtgtaccca accaaggagc tggaaaagct gctgaaagac   3540
tactctatcg agtatggaca tggcgaatgc atcaaggcag ccatctgtgg cgagagtgat   3600
aagaaatttt tcgccaagct gacctcagtg ctgaatacaa tcctgcagat gcggaactca   3660
aagaccggga cagaactgga ctatctgatt agccccgtgg ctgatgtcaa cggaaacttc   3720
ttcgacagca gacaggcacc caaaaatatg cctcaggatg cagacgccaa cggggcctac   3780
cacatcgggc tgaagggact gatgctgctg ggccggatca agaacaatca ggaggggaag   3840
aagctgaacc tggtcattaa gaacgaggaa tacttcgagt ttgtccagaa tagaaataac   3900
aaaaggccgg cggccacgaa aaaggccggc caggcaaaaa agaaaaaggg atcctaccca   3960
tacgatgttc cagattacgc ttatccctac gacgtgcctg attatgcata cccatatgat   4020
```

gtccccgact atgcctaa 4038

<210> SEQ ID NO 15
<211> LENGTH: 1278
<212> TYPE: PRT
<213> ORGANISM: Artificial Sequence
<220> FEATURE:
<223> OTHER INFORMATION: Lachnospiraceae bacterium MC2017 (Lb3Cpf1; pY005), including NLS and HA tag

<400> SEQUENCE: 15

```
Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

Ser Asn Asp Ser Asp Ala Arg Ser Ile Leu Glu Lys Ile Leu Lys Asp
    290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350
```

-continued

```
Glu Ser Lys Arg Ile Ser Glu Leu Met Glu Thr Leu Ser Pro Lys Glu
        355                 360                 365

Arg Lys Glu Ser Lys Lys Arg Leu Glu Gly Leu Glu Glu His Ile Arg
    370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
        435                 440                 445

Asn Ala Trp Thr Val Phe Arg Asn Leu Ile Arg Ile Leu Arg Arg Lys
    450                 455                 460

Ser Glu Ala Glu Ile Asp Ser Asp Phe Tyr Asp Val Leu Asp Asp Ser
465                 470                 475                 480

Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
        515                 520                 525

Lys Phe Asn Val Lys Phe His Thr Ile Val Arg Arg Asp Gly Arg Leu
    530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
        595                 600                 605

Ala Pro Val Thr Ile Thr Arg Glu Thr Tyr Glu Ala Tyr Arg Tyr Lys
    610                 615                 620

Leu Tyr Thr Val Gly Lys Leu Arg Asp Gly Glu Val Ser Glu Glu Glu
625                 630                 635                 640

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
            660                 665                 670

Glu Glu Tyr Lys Asp Ser Ser Glu Phe Ile Lys Gln Val Glu Thr His
        675                 680                 685

Asn Thr Phe Met Cys Trp Ala Lys Val Ser Ser Ser Gln Leu Asp Asp
    690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
        755                 760                 765
```

```
Ser Ser Lys Pro Met Val Val His Arg Asp Gly Ser Arg Val Val Asp
    770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
            820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
    850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
    930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Leu Leu Ala Lys  Leu Ser Asp Leu His  Phe Arg Gly
        995                 1000                1005

Ile Lys  Asp Gly Glu Pro Cys  Ser Phe Thr Asn Pro  Leu Gln Leu
    1010                1015                1020

Cys Gln  Asn Asp Ser Asn Lys  Ile Leu Gln Asp Gly  Val Ile Phe
    1025                1030                1035

Met Val  Pro Asn Ser Met Thr  Arg Ser Leu Asp Pro  Asp Thr Gly
    1040                1045                1050

Phe Ile  Phe Ala Ile Asn Asp  His Asn Ile Arg Thr  Lys Lys Ala
    1055                1060                1065

Lys Leu  Asn Phe Leu Ser Lys  Phe Asp Gln Leu Lys  Val Ser Ser
    1070                1075                1080

Glu Gly  Cys Leu Ile Met Lys  Tyr Ser Gly Asp Ser  Leu Pro Thr
    1085                1090                1095

His Asn  Thr Asp Asn Arg Val  Trp Asn Cys Cys Cys  Asn His Pro
    1100                1105                1110

Ile Thr  Asn Tyr Asp Arg Glu  Thr Lys Lys Val Glu  Phe Ile Glu
    1115                1120                1125

Glu Pro  Val Glu Glu Leu Ser  Arg Val Leu Glu Glu  Asn Gly Ile
    1130                1135                1140

Glu Thr  Asp Thr Glu Leu Asn  Lys Leu Asn Glu Arg  Glu Asn Val
    1145                1150                1155

Pro Gly  Lys Val Val Asp Ala  Ile Tyr Ser Leu Val  Leu Asn Tyr
    1160                1165                1170

Leu Arg  Gly Thr Val Ser Gly  Val Ala Gly Gln Arg  Ala Val Tyr
```

1175 1180 1185

Tyr Ser Pro Val Thr Gly Lys Lys Tyr Asp Ile Ser Phe Ile Gln
1190 1195 1200

Ala Met Asn Leu Asn Arg Lys Cys Asp Tyr Tyr Arg Ile Gly Ser
1205 1210 1215

Lys Glu Arg Gly Glu Trp Thr Asp Phe Val Ala Gln Leu Ile Asn
1220 1225 1230

Lys Arg Pro Ala Ala Thr Lys Lys Ala Gly Gln Ala Lys Lys Lys
1235 1240 1245

Lys Gly Ser Tyr Pro Tyr Asp Val Pro Asp Tyr Ala Tyr Pro Tyr
1250 1255 1260

Asp Val Pro Asp Tyr Ala Tyr Pro Tyr Asp Val Pro Asp Tyr Ala
1265 1270 1275

<210> SEQ ID NO 16
<211> LENGTH: 3837
<212> TYPE: DNA
<213> ORGANISM: Artificial Sequence
<220> FEATURE:
<223> OTHER INFORMATION: Lachnospiraceae bacterium MC2017 (Lb3Cpf1; pY005), including NLS and HA tag

<400> SEQUENCE: 16
atggattacg gcaacggcca gtttgagcgg agagcccccc tgaccaagac aatcaccctg 60
cgcctgaagc ctatcggcga gacacgggag acaatccgcg agcagaagct gctggagcag 120
gacgccgcct tcagaaagct ggtggagaca gtgaccccta tcgtggacga ttgtatcagg 180
aagatcgccg ataacgccct gtgccacttt ggcaccgagt atgacttcag ctgtctgggc 240
aacgccatct ctaagaatga cagcaaggcc atcaagaagg agacagagaa ggtggagaag 300
ctgctggcca aggtgctgac cgagaatctg ccagatggcc tgcgcaaggt gaacgacatc 360
aattccgccg cctttatcca ggatacactg acctctttcg tgcaggacga tgccgacaag 420
cgggtgctga tccaggagct gaagggcaag accgtgctga tgcagcggtt cctgaccaca 480
cggatcacag ccctgaccgt gtggctgccc gacagagtgt tcgagaactt taatatcttc 540
atcgagaacg ccgagaagat gagaatcctg ctggactccc ctctgaatga gaagatcatg 600
aagtttgacc cagatgccga gcagtacgcc tctctggagt tctatggcca gtgcctgtct 660
cagaaggaca tcgatagcta caacctgatc atctccggca tctatgccga cgatgaggtg 720
aagaaccctg gcatcaatga gatcgtgaag gagtacaatc agcagatccg gggcgacaag 780
gatgagtccc cactgcccaa gctgaagaag ctgcacaagc agatcctgat gccagtggag 840
aaggccttct ttgtgcgcgt gctgtctaac gacagcgatg cccggagcat cctggagaag 900
atcctgaagg acacagagat gctgccctcc aagatcatcg aggccatgaa ggaggcagat 960
gcaggcgaca tcgccgtgta cggcagccgg ctgcacgagc tgagccacgt gatctacggc 1020
gatcacggca agctgtccca gatcatctat gacaaggagt ccaagaggat ctctgagctg 1080
atggagacac tgtctccaaa ggagcgcaag gagagcaaga agcggctgga gggcctggag 1140
gagcacatca gaaagtctac atacaccttc gacgagctga acaggtatgc cgagaagaat 1200
gtgatggcag catacatcgc agcagtggag gagtcttgtg ccgagatcat gagaaaggag 1260
aaggatctga ggaccctgct gagcaaggag gacgtgaaga tccggggcaa cagacacaat 1320
acactgatcg tgaagaacta ctttaatgcc tggaccgtgt tccggaacct gatcagaatc 1380
ctgaggcgca agtccgaggc cgagatcgac tctgacttct acgatgtgct ggacgattcc 1440

-continued

```
gtggaggtgc tgtctctgac atacaagggc gagaatctgt gccgcagcta tatcaccaag   1500
aagatcggct ccgacctgaa gcccgagatc gccacatacg gcagcgccct gaggcctaac   1560
agccgctggt ggtccccagg agagaagttt aatgtgaagt tccacaccat cgtgcggaga   1620
gatggccggc tgtactattt catcctgccc aagggcgcca agcctgtgga gctggaggac   1680
atggatggcg acatcgagtg tctgcagatg agaaagatcc ctaacccaac aatctttctg   1740
cccaagctgg tgttcaagga ccctgaggcc ttctttaggg ataatccaga ggccgacgag   1800
ttcgtgtttc tgagcggcat gaaggccccc gtgacaatca ccagagagac atacgaggcc   1860
tacaggtata agctgtatac cgtgggcaag ctgcgcgatg gcgaggtgtc cgaagaggag   1920
tacaagcggg ccctgctgca ggtgctgacc gcctacaagg agtttctgga gaacagaatg   1980
atctatgccg acctgaattt cggctttaag gatctggagg agtataagga cagctccgag   2040
tttatcaagc aggtggagac acacaacacc ttcatgtgct gggccaaggt gtctagctcc   2100
cagctggacg atctggtgaa gtctggcaac ggcctgctgt tcgagatctg gagcgagcgc   2160
ctggagtcct actataagta cggcaatgag aaggtgctgc ggggctatga gggcgtgctg   2220
ctgagcatcc tgaaggatga gaacctggtg tccatgcgga ccctgctgaa cagccggccc   2280
atgctggtgt accggccaaa ggagtctagc aagcctatgg tggtgcaccg ggatggcagc   2340
agagtggtgg acaggtttga taaggacggc aagtacatcc cccctgaggt gcacgacgag   2400
ctgtatcgct tctttaacaa tctgctgatc aaggagaagc tgggcgagaa ggcccggaag   2460
atcctggaca acaagaaggt gaaggtgaag gtgctggaga gcgagagagt gaagtggtcc   2520
aagttctacg atgagcagtt tgccgtgacc ttcagcgtga agaagaacgc cgattgtctg   2580
gacaccacaa aggacctgaa tgccgaagtg atggagcagt atagcgagtc caacagactg   2640
atcctgatca ggaataccac agatatcctg tactatctgg tgctggacaa gaatggcaag   2700
gtgctgaagc agagatccct gaacatcatc aatgacggcg ccagggatgt ggactggaag   2760
gagaggttcc gccaggtgac aaaggataga aacgagggct acaatgagtg ggattattcc   2820
aggacctcta acgacctgaa ggaggtgtac ctgaattatg ccctgaagga gatcgccgag   2880
gccgtgatcg agtacaacgc catcctgatc atcgagaaga tgtctaatgc ctttaaggac   2940
aagtatagct tcctggacga cgtgaccttc aagggcttcg agacaaagct gctggccaag   3000
ctgagcgatc tgcactttag ggcatcaag gacggcgagc catgttcctt cacaaacccc   3060
ctgcagctgt gccagaacga ttctaataag atcctgcagg acggcgtgat ctttatggtg   3120
ccaaattcta tgacacggag cctggacccc gacaccggct tcatctttgc catcaacgac   3180
cacaatatca ggaccaagaa ggccaagctg aactttctga gcaagttcga tcagctgaag   3240
gtgtcctctg agggctgcct gatcatgaag tacagcggcg attccctgcc tacacacaac   3300
accgacaatc gcgtgtggaa ctgctgttgc aatcacccaa tcacaaacta tgaccgggag   3360
acaaagaagg tggagttcat cgaggagccc gtggaggagc tgtcccgcgt gctggaggag   3420
aatggcatcg agacagacac cgagctgaac aagctgaatg agcgggagaa cgtgcctggc   3480
aaggtggtgg atgccatcta ctctctggtg ctgaattatc tgcgcggcac agtgagcgga   3540
gtggcaggac agagggccgt gtactatagc cctgtgaccg gcaagaagta cgatatctcc   3600
tttatccagg ccatgaacct gaataggaag tgtgactact ataggatcgg ctccaaggag   3660
aggggagagt ggaccgattt cgtggcccag ctgatcaaca aaaggccggc ggccacgaaa   3720
aaggccggcc aggcaaaaaa gaaaaaggga tcctacccat acgatgttcc agattacgct   3780
tatccctacg acgtgcctga ttatgcatac ccatatgatg tccccgacta tgcctaa      3837
```

<210> SEQ ID NO 17
<211> LENGTH: 1345
<212> TYPE: PRT
<213> ORGANISM: Artificial Sequence
<220> FEATURE:
<223> OTHER INFORMATION: Butyrivibrio proteoclasticus (BpCpf1; pY006), including NLS and HA tag

<400> SEQUENCE: 17

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys

```
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780
```

```
Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185
```

```
Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
    1250                 1255                 1260

Leu Lys  Gly Leu Met Leu Leu  Gly Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn  Lys Arg Pro Ala Ala  Thr Lys Lys
    1295                 1300                 1305

Ala Gly  Gln Ala Lys Lys Lys  Lys Gly Ser Tyr Pro  Tyr Asp Val
    1310                 1315                 1320

Pro Asp  Tyr Ala Tyr Pro Tyr  Asp Val Pro Asp Tyr  Ala Tyr Pro
    1325                 1330                 1335

Tyr Asp  Val Pro Asp Tyr Ala
    1340                 1345


<210> SEQ ID NO 18
<211> LENGTH: 4038
<212> TYPE: DNA
<213> ORGANISM: Artificial Sequence
<220> FEATURE:
<223> OTHER INFORMATION: Butyrivibrio proteoclasticus (BpCpf1; pY006),
      including NLS and HA tag

<400> SEQUENCE: 18

atgagcatct accaggagtt cgtcaacaag tattcactga gtaagacact gcggttcgag     60

ctgatcccac agggcaagac actggagaac atcaaggccc gaggcctgat tctggacgat    120

gagaagcggg caaaagacta taagaaagcc aagcagatca ttgataaata ccaccagttc    180

tttatcgagg aaattctgag ctccgtgtgc atcagtgagg atctgctgca gaattactca    240

gacgtgtact tcaagctgaa gaagagcgac gatgacaacc tgcagaagga cttcaagtcc    300

gccaaggaca ccatcaagaa acagattagc gagtacatca aggactccga aaagtttaaa    360

aatctgttca accagaatct gatcgatgct aagaaaggcc aggagtccga cctgatcctg    420

tggctgaaac agtctaagga caatgggatt gaactgttca aggctaactc cgatatcact    480

gatattgacg aggcactgga aatcatcaag agcttcaagg gatggaccac atactttaaa    540

ggcttccacg agaaccgcaa gaacgtgtac tccagcaacg acattcctac ctccatcatc    600

taccgaatcg tcgatgacaa tctgccaaag ttcctggaga acaaggccaa atatgaatct    660

ctgaaggaca aagctcccga ggcaattaat tacgaacaga tcaagaaaga tctggctgag    720

gaactgacat tcgatatcga ctataagact agcgaggtga accagagggt cttttccctg    780

gacgaggtgt ttgaaatcgc caatttcaac aattacctga accagtccgg cattactaaa    840

ttcaatacca tcattggcgg gaagtttgtg aacggggaga ataccaagcg caagggaatt    900

aacgaataca tcaatctgta tagccagcag atcaacgaca aaactctgaa gaaatacaag    960

atgtctgtgc tgttcaaaca gatcctgagt gataccgagt ccaagtcttt tgtcattgat   1020

aaactggaag atgactcaga cgtggtcact accatgcaga gcttttatga gcagatcgcc   1080
```

-continued

```
gctttcaaga cagtggagga aaaatctatt aaggaaactc tgagtctgct gttcgatgac   1140
ctgaaagccc agaagctgga cctgagtaag atctacttca aaaacgataa gagtctgaca   1200
gacctgtcac agcaggtgtt tgatgactat tccgtgattg ggaccgccgt cctggagtac   1260
attacacagc agatcgctcc aaagaacctg gataatccct ctaagaaaga gcaggaactg   1320
atcgctaaga aaaccgagaa ggcaaaatat ctgagtctgg aaacaattaa gctggcactg   1380
gaggagttca acaagcacag ggatattgac aaacagtgcc gctttgagga aatcctggcc   1440
aacttcgcag ccatccccat gatttttgat gagatcgccc agaacaaaga caatctggct   1500
cagatcagta ttaagtacca gaaccagggc aagaaagacc tgctgcaggc ttcagcagaa   1560
gatgacgtga aagccatcaa ggatctgctg gaccagacca acaatctgct gcacaagctg   1620
aaaatcttcc atattagtca gtcagaggat aaggctaata tcctggataa agacgaacac   1680
ttctacctgg tgttcgagga atgttacttc gagctggcaa acattgtccc cctgtataac   1740
aagattagga actacatcac acagaagcct tactctgacg agaagtttaa actgaacttc   1800
gaaaatagta ccctggccaa cgggtgggat aagaacaagg agcctgacaa cacagctatc   1860
ctgttcatca aggatgacaa gtactatctg ggagtgatga ataagaaaaa caataagatc   1920
ttcgatgaca aagccattaa ggagaacaaa ggggaaggat acaagaaaat cgtgtataag   1980
ctgctgcccg gcgcaaataa gatgctgcct aaggtgttct tcagcgccaa gagtatcaaa   2040
ttctacaacc catccgagga catcctgcgg attagaaatc actcaacaca tactaagaac   2100
gggagccccc agaagggata tgagaaattt gagttcaaca tcgaggattg caggaagttt   2160
attgacttct acaagcagag catctccaaa caccctgaat ggaaggattt tggcttccgg   2220
ttttccgaca cacagagata taactctatc gacgagttct accgcgaggt ggaaaatcag   2280
gggtataagc tgacttttga gaacatttct gaaagttaca tcgacagcgt ggtcaatcag   2340
ggaaagctgt acctgttcca gatctataac aaagattttt cagcatacag caagggcaga   2400
ccaaacctgc atacactgta ctggaaggcc ctgttcgatg agaggaatct gcaggacgtg   2460
gtctataaac tgaacggaga ggccgaactg ttttaccgga agcagtctat tcctaagaaa   2520
atcactcacc cagctaagga ggccatcgct aacaagaaca aggacaatcc taagaaagag   2580
agcgtgttcg aatacgatct gattaaggac aagcggttca ccgaagataa gttcttttc    2640
cattgtccaa tcaccattaa cttcaagtca agcggcgcta acaagttcaa cgacgagatc   2700
aatctgctgc tgaaggaaaa agcaaacgat gtgcacatcc tgagcattga ccgaggagag   2760
cggcatctgg cctactatac cctggtggat ggcaaaggga atatcattaa gcaggataca   2820
ttcaacatca ttggcaatga ccggatgaaa accaactacc acgataaact ggctgcaatc   2880
gagaaggata gagactcagc taggaaggac tggaagaaaa tcaacaacat taaggagatg   2940
aaggaaggct atctgagcca ggtggtccat gagattgcaa agctggtcat cgaatacaat   3000
gccattgtgg tgttcgagga tctgaacttc ggctttaaga gggggcgctt taaggtggaa   3060
aaacaggtct atcagaagct ggagaaaatg ctgatcgaaa agctgaatta cctggtgttt   3120
aaagataacg agttcgacaa gaccggaggc gtcctgagag cctaccagct gacagctccc   3180
tttgaaactt tcaagaaaat gggaaaacag acaggcatca tctactatgt gccagccgga   3240
ttcacttcca agatctgccc cgtgaccggc tttgtcaacc agctgtaccc taaatatgag   3300
tcagtgagca agtcccagga atttttcagc aagttcgata agatctgtta taatctggac   3360
aaggggtact tcgagttttc cttcgattac aagaacttcg gcgacaaggc cgctaagggg   3420
```

-continued

```
aaatggacca ttgcctcctt cggatctcgc ctgatcaact ttcgaaattc cgataaaaac   3480

cacaattggg acactaggga ggtgtaccca accaaggagc tggaaaagct gctgaaagac   3540

tactctatcg agtatggaca tggcgaatgc atcaaggcag ccatctgtgg cgagagtgat   3600

aagaaatttt tcgccaagct gacctcagtg ctgaatacaa tcctgcagat gcggaactca   3660

aagaccggga cagaactgga ctatctgatt agccccgtgg ctgatgtcaa cggaaacttc   3720

ttcgacagca gacaggcacc caaaaatatg cctcaggatg cagacgccaa cggggcctac   3780

cacatcgggc tgaagggact gatgctgctg ggccggatca agaacaatca ggaggggaag   3840

aagctgaacc tggtcattaa gaacgaggaa tacttcgagt ttgtccagaa tagaaataac   3900

aaaaggccgg cggccacgaa aaaggccggc caggcaaaaa agaaaaaggg atcctaccca   3960

tacgatgttc cagattacgc ttatccctac gacgtgcctg attatgcata cccatatgat   4020

gtccccgact atgcctaa                                                 4038
```

```
<210> SEQ ID NO 19
<211> LENGTH: 1522
<212> TYPE: PRT
<213> ORGANISM: Artificial Sequence
<220> FEATURE:
<223> OTHER INFORMATION: Peregrinibacteria bacterium GW2011_GWA_33_10
      (PeCpf1; pY007), including NLS and HA tag

<400> SEQUENCE: 19

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
```

```
                245                 250                 255

Glu Thr Glu Lys Met Ile Glu Ser Thr Pro Ile Ala Glu Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
    290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu
        355                 360                 365

Glu Ile Ile Asn Lys Ala Gln Glu Ala Ile Asn Lys Tyr Phe Lys Ser
    370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
            420                 425                 430

Asp Arg Leu Lys Glu Ala Lys Val Phe Gln Lys Ala Asp Lys Lys Ser
        435                 440                 445

Glu Asp Asp Ile Lys Ile Pro Glu Ala Ile Glu Leu Ser Gly Leu Phe
    450                 455                 460

Gly Val Leu Asp Ser Leu Ala Asp Trp Gln Thr Thr Leu Phe Lys Ser
465                 470                 475                 480

Ser Ile Leu Ser Asn Glu Asp Lys Leu Lys Ile Ile Thr Asp Ser Gln
                485                 490                 495

Thr Pro Ser Glu Ala Leu Leu Lys Met Ile Phe Asn Asp Ile Glu Lys
            500                 505                 510

Asn Met Glu Ser Phe Leu Lys Glu Thr Asn Asp Ile Ile Thr Leu Lys
        515                 520                 525

Lys Tyr Lys Gly Asn Lys Glu Gly Thr Glu Lys Ile Lys Gln Trp Phe
    530                 535                 540

Asp Tyr Thr Leu Ala Ile Asn Arg Met Leu Lys Tyr Phe Leu Val Lys
545                 550                 555                 560

Glu Asn Lys Ile Lys Gly Asn Ser Leu Asp Thr Asn Ile Ser Glu Ala
                565                 570                 575

Leu Lys Thr Leu Ile Tyr Ser Asp Asp Ala Glu Trp Phe Lys Trp Tyr
            580                 585                 590

Asp Ala Leu Arg Asn Tyr Leu Thr Gln Lys Pro Gln Asp Glu Ala Lys
        595                 600                 605

Glu Asn Lys Leu Lys Leu Asn Phe Asp Asn Pro Ser Leu Ala Gly Gly
    610                 615                 620

Trp Asp Val Asn Lys Glu Cys Ser Asn Phe Cys Val Ile Leu Lys Asp
625                 630                 635                 640

Lys Asn Glu Lys Lys Tyr Leu Ala Ile Met Lys Lys Gly Glu Asn Thr
                645                 650                 655

Leu Phe Gln Lys Glu Trp Thr Glu Gly Arg Gly Lys Asn Leu Thr Lys
            660                 665                 670
```

-continued

```
Lys Ser Asn Pro Leu Phe Glu Ile Asn Asn Cys Glu Ile Leu Ser Lys
    675                 680                 685

Met Glu Tyr Asp Phe Trp Ala Asp Val Ser Lys Met Ile Pro Lys Cys
    690                 695                 700

Ser Thr Gln Leu Lys Ala Val Val Asn His Phe Lys Gln Ser Asp Asn
705                 710                 715                 720

Glu Phe Ile Phe Pro Ile Gly Tyr Lys Val Thr Ser Gly Glu Lys Phe
                725                 730                 735

Arg Glu Glu Cys Lys Ile Ser Lys Gln Asp Phe Glu Leu Asn Asn Lys
            740                 745                 750

Val Phe Asn Lys Asn Glu Leu Ser Val Thr Ala Met Arg Tyr Asp Leu
        755                 760                 765

Ser Ser Thr Gln Glu Lys Gln Tyr Ile Lys Ala Phe Gln Lys Glu Tyr
    770                 775                 780

Trp Glu Leu Leu Phe Lys Gln Glu Lys Arg Asp Thr Lys Leu Thr Asn
785                 790                 795                 800

Asn Glu Ile Phe Asn Glu Trp Ile Asn Phe Cys Asn Lys Lys Tyr Ser
                805                 810                 815

Glu Leu Leu Ser Trp Glu Arg Lys Tyr Lys Asp Ala Leu Thr Asn Trp
            820                 825                 830

Ile Asn Phe Cys Lys Tyr Phe Leu Ser Lys Tyr Pro Lys Thr Thr Leu
        835                 840                 845

Phe Asn Tyr Ser Phe Lys Glu Ser Glu Asn Tyr Asn Ser Leu Asp Glu
    850                 855                 860

Phe Tyr Arg Asp Val Asp Ile Cys Ser Tyr Lys Leu Asn Ile Asn Thr
865                 870                 875                 880

Thr Ile Asn Lys Ser Ile Leu Asp Arg Leu Val Glu Glu Gly Lys Leu
                885                 890                 895

Tyr Leu Phe Glu Ile Lys Asn Gln Asp Ser Asn Asp Gly Lys Ser Ile
            900                 905                 910

Gly His Lys Asn Asn Leu His Thr Ile Tyr Trp Asn Ala Ile Phe Glu
        915                 920                 925

Asn Phe Asp Asn Arg Pro Lys Leu Asn Gly Glu Ala Glu Ile Phe Tyr
    930                 935                 940

Arg Lys Ala Ile Ser Lys Asp Lys Leu Gly Ile Val Lys Gly Lys Lys
945                 950                 955                 960

Thr Lys Asn Gly Thr Glu Ile Ile Lys Asn Tyr Arg Phe Ser Lys Glu
                965                 970                 975

Lys Phe Ile Leu His Val Pro Ile Thr Leu Asn Phe Cys Ser Asn Asn
            980                 985                 990

Glu Tyr Val Asn Asp Ile Val Asn  Thr Lys Phe Tyr Asn  Phe Ser Asn
        995                 1000                1005

Leu His  Phe Leu Gly Ile Asp  Arg Gly Glu Lys His  Leu Ala Tyr
    1010                1015                1020

Tyr Ser  Leu Val Asn Lys Asn  Gly Glu Ile Val Asp  Gln Gly Thr
    1025                1030                1035

Leu Asn  Leu Pro Phe Thr Asp  Lys Asp Gly Asn Gln  Arg Ser Ile
    1040                1045                1050

Lys Lys  Glu Lys Tyr Phe Tyr  Asn Lys Gln Glu Asp  Lys Trp Glu
    1055                1060                1065

Ala Lys  Glu Val Asp Cys Trp  Asn Tyr Asn Asp Leu  Leu Asp Ala
    1070                1075                1080
```

```
Met Ala  Ser Asn Arg Asp Met  Ala Arg Lys Asn Trp  Gln Arg Ile
    1085                 1090                 1095

Gly Thr  Ile Lys Glu Ala Lys  Asn Gly Tyr Val Ser  Leu Val Ile
    1100                 1105                 1110

Arg Lys  Ile Ala Asp Leu Ala  Val Asn Asn Glu Arg  Pro Ala Phe
    1115                 1120                 1125

Ile Val  Leu Glu Asp Leu Asn  Thr Gly Phe Lys Arg  Ser Arg Gln
    1130                 1135                 1140

Lys Ile  Asp Lys Ser Val Tyr  Gln Lys Phe Glu Leu  Ala Leu Ala
    1145                 1150                 1155

Lys Lys  Leu Asn Phe Leu Val  Asp Lys Asn Ala Lys  Arg Asp Glu
    1160                 1165                 1170

Ile Gly  Ser Pro Thr Lys Ala  Leu Gln Leu Thr Pro  Pro Val Asn
    1175                 1180                 1185

Asn Tyr  Gly Asp Ile Glu Asn  Lys Lys Gln Ala Gly  Ile Met Leu
    1190                 1195                 1200

Tyr Thr  Arg Ala Asn Tyr Thr  Ser Gln Thr Asp Pro  Ala Thr Gly
    1205                 1210                 1215

Trp Arg  Lys Thr Ile Tyr Leu  Lys Ala Gly Pro Glu  Glu Thr Thr
    1220                 1225                 1230

Tyr Lys  Lys Asp Gly Lys Ile  Lys Asn Lys Ser Val  Lys Asp Gln
    1235                 1240                 1245

Ile Ile  Glu Thr Phe Thr Asp  Ile Gly Phe Asp Gly  Lys Asp Tyr
    1250                 1255                 1260

Tyr Phe  Glu Tyr Asp Lys Gly  Glu Phe Val Asp Glu  Lys Thr Gly
    1265                 1270                 1275

Glu Ile  Lys Pro Lys Lys Trp  Arg Leu Tyr Ser Gly  Glu Asn Gly
    1280                 1285                 1290

Lys Ser  Leu Asp Arg Phe Arg  Gly Glu Arg Glu Lys  Asp Lys Tyr
    1295                 1300                 1305

Glu Trp  Lys Ile Asp Lys Ile  Asp Ile Val Lys Ile  Leu Asp Asp
    1310                 1315                 1320

Leu Phe  Val Asn Phe Asp Lys  Asn Ile Ser Leu Leu  Lys Gln Leu
    1325                 1330                 1335

Lys Glu  Gly Val Glu Leu Thr  Arg Asn Asn Glu His  Gly Thr Gly
    1340                 1345                 1350

Glu Ser  Leu Arg Phe Ala Ile  Asn Leu Ile Gln Gln  Ile Arg Asn
    1355                 1360                 1365

Thr Gly  Asn Asn Glu Arg Asp  Asn Asp Phe Ile Leu  Ser Pro Val
    1370                 1375                 1380

Arg Asp  Glu Asn Gly Lys His  Phe Asp Ser Arg Glu  Tyr Trp Asp
    1385                 1390                 1395

Lys Glu  Thr Lys Gly Glu Lys  Ile Ser Met Pro Ser  Ser Gly Asp
    1400                 1405                 1410

Ala Asn  Gly Ala Phe Asn Ile  Ala Arg Lys Gly Ile  Ile Met Asn
    1415                 1420                 1425

Ala His  Ile Leu Ala Asn Ser  Asp Ser Lys Asp Leu  Ser Leu Phe
    1430                 1435                 1440

Val Ser  Asp Glu Glu Trp Asp  Leu His Leu Asn Asn  Lys Thr Glu
    1445                 1450                 1455

Trp Lys  Lys Gln Leu Asn Ile  Phe Ser Ser Arg Lys  Ala Met Ala
    1460                 1465                 1470

Lys Arg  Lys Lys Lys Arg Pro  Ala Ala Thr Lys Lys  Ala Gly Gln
```

```
    1475                1480                1485

Ala Lys  Lys Lys Lys Gly Ser  Tyr Pro Tyr Asp Val  Pro Asp Tyr
    1490                1495                1500

Ala Tyr  Pro Tyr Asp Val Pro  Asp Tyr Ala Tyr Pro  Tyr Asp Val
    1505                1510                1515

Pro Asp  Tyr Ala
    1520


<210> SEQ ID NO 20
<211> LENGTH: 4569
<212> TYPE: DNA
<213> ORGANISM: Artificial Sequence
<220> FEATURE:
<223> OTHER INFORMATION: Peregrinibacteria bacterium GW2011_GWA_33_10
      (PeCpf1; pY007), including NLS and HA tag

<400> SEQUENCE: 20

atgtccaact tctttaagaa tttcaccaac ctgtatgagc tgtccaagac actgaggttt     60

gagctgaagc ccgtgggcga caccctgaca aacatgaagg accacctgga gtacgatgag    120

aagctgcaga ccttcctgaa ggatcagaat atcgacgatg cctatcaggc cctgaagcct    180

cagttcgacg agatccacga ggagtttatc acagattctc tggagagcaa gaaggccaag    240

gagatcgact tctccgagta cctggatctg tttcaggaga agaaggagct gaacgactct    300

gagaagaagc tgcgcaacaa gatcggcgag acattcaaca aggccggcga gaagtggaag    360

aaggagaagt accctcagta tgagtggaag aagggctcca agatcgccaa tggcgccgac    420

atcctgtctt gccaggatat gctgcagttt atcaagtata agaacccaga ggatgagaag    480

atcaagaatt acatcgacga tacactgaag ggcttcttta cctatttcgg cggctttaat    540

cagaacaggg ccaactacta tgagacaaag aaggaggcct ccaccgcagt ggcaacaagg    600

atcgtgcacg agaacctgcc aaagttctgt gacaatgtga tccagtttaa gcacatcatc    660

aagcggaaga aggatggcac cgtggagaaa accgagagaa agaccgagta cctgaacgcc    720

taccagtatc tgaagaacaa taacaagatc acacagatca aggacgccga gacagagaag    780

atgatcgagt ctacacccat cgccgagaag atcttcgacg tgtactactt cagcagctgc    840

ctgagccaga agcagatcga ggagtacaac cggatcatcg gccactataa tctgctgatc    900

aacctgtata accaggccaa gagatctgag ggcaagcacc tgagcgccaa cgagaagaag    960

tataaggacc tgcctaagtt caagaccctg tataagcaga tcggctgcgg caagaagaag   1020

gacctgtttt acacaatcaa gtgtgatacc gaggaggagg ccaataagtc ccggaacgag   1080

ggcaaggagt cccactctgt ggaggagatc atcaacaagg cccaggaggc catcaataag   1140

tacttcaagt ctaataacga ctgtgagaat atcaacaccg tgcccgactt catcaactat   1200

atcctgacaa aggagaatta cgagggcgtg tattggagca aggccgccat gaacaccatc   1260

tccgacaagt acttcgccaa ttatcacgac ctgcaggata gactgaagga ggccaaggtg   1320

tttcagaagg ccgataagaa gtccgaggac gatatcaaga tcccagaggc catcgagctg   1380

tctggcctgt tcggcgtgct ggacagcctg gccgattggc agaccacact gtttaagtct   1440

agcatcctga gcaacgagga caagctgaag atcatcacag attcccagac cccctctgag   1500

gccctgctga agatgatctt caatgacatc gagaagaaca tggagtcctt tctgaaggag   1560

acaaacgata tcatcaccct gaagaagtat aagggcaata aggagggcac cgagaagatc   1620

aagcagtggt tcgactatac actggccatc aaccggatgc tgaagtactt tctggtgaag   1680

gagaataaga tcaagggcaa ctccctggat accaatatct ctgaggccct gaaaaccctg   1740
```

atctacagcg acgatgccga gtggttcaag tggtacgacg ccctgagaaa ctatctgacc 1800
cagaagcctc aggatgaggc caaggagaat aagctgaagc tgaatttcga caacccatct 1860
ctggccggcg gctgggatgt gaacaaggag tgcagcaatt tttgcgtgat cctgaaggac 1920
aagaacgaga agaagtacct ggccatcatg aagaagggcg agaataccct gttccagaag 1980
gagtggacag agggccgggg caagaacctg acaaagaagt ctaatccact gttcgagatc 2040
aataactgcg agatcctgag caagatggag tatgactttt gggccgacgt gagcaagatg 2100
atccccaagt gtagcaccca gctgaaggcc gtggtgaacc acttcaagca gtccgacaat 2160
gagttcatct ttcctatcgg ctacaaggtg acaagcggcg agaagtttag ggaggagtgc 2220
aagatctcca agcaggactt cgagctgaat aacaaggtgt ttaataagaa cgagctgagc 2280
gtgaccgcca tgcgctacga tctgtcctct acacaggaga agcagtatat caaggccttc 2340
cagaaggagt actgggagct gctgtttaag caggagaagc gggacaccaa gctgacaaat 2400
aacgagatct tcaacgagtg gatcaatttt tgcaacaaga agtatagcga gctgctgtcc 2460
tgggagagaa agtacaagga tgccctgacc aattggatca acttctgtaa gtactttctg 2520
agcaagtatc ccaagaccac actgttcaac tactctttta aggagagcga gaattataac 2580
tccctggacg agttctaccg ggacgtggat atctgttctt acaagctgaa tatcaacacc 2640
acaatcaata agagcatcct ggatagactg gtggaggagg gcaagctgta cctgtttgag 2700
atcaagaatc aggacagcaa cgatggcaag tccatcggcc acaagaataa cctgcacacc 2760
atctactgga acgccatctt cgagaatttt gacaacaggc ctaagctgaa tggcgaggcc 2820
gagatcttct atcgcaaggc catctccaag gataagctgg gcatcgtgaa gggcaagaaa 2880
accaagaacg gcaccgagat catcaagaat tacagattca gcaaggagaa gtttatcctg 2940
cacgtgccaa tcaccctgaa cttctgctcc aataacgagt atgtgaatga catcgtgaac 3000
acaaagttct acaatttttc caacctgcac tttctgggca tcgatagggg cgagaagcac 3060
ctggcctact attctctggt gaataagaac ggcgagatcg tggaccaggg cacactgaac 3120
ctgcctttca ccgacaagga tggcaatcag cgcagcatca agaaggagaa gtacttttat 3180
aacaagcagg aggacaagtg ggaggccaag gaggtggatt gttggaatta taacgacctg 3240
ctggatgcca tggcctctaa ccgggacatg gccagaaaga attggcagag gatcggcacc 3300
atcaaggagg ccaagaacgg ctacgtgagc ctggtcatca ggaagatcgc cgatctggcc 3360
gtgaataacg agcgccccgc cttcatcgtg ctggaggacc tgaatacagg ctttaagcgg 3420
tccagacaga agatcgataa gagcgtgtac cagaagttcg agctggccct ggccaagaag 3480
ctgaactttc tggtggacaa gaatgccaag cgcgatgaga tcggctcccc tacaaaggcc 3540
ctgcagctga cccccccctgt gaataactac ggcgacattg agaacaagaa gcaggccggc 3600
atcatgctgt atacccgggc caattatacc tctcagacag atccagccac aggctggaga 3660
aagaccatct atctgaaggc cggcccccgag gagacaacat acaagaagga cggcaagatc 3720
aagaacaaga gcgtgaagga ccagatcatc gagacattca ccgatatcgg ctttgacggc 3780
aaggattact atttcgagta cgacaagggc gagtttgtgg atgagaaaac cggcgagatc 3840
aagcccaaga agtggcggct gtactccggc gagaatggca agtccctgga caggttccgc 3900
ggagagaggg agaaggataa gtatgagtgg aagatcgaca agatcgatat cgtgaagatc 3960
ctggacgatc tgttcgtgaa ttttgacaag aacatcagcc tgctgaagca gctgaaggag 4020
ggcgtggagc tgacccggaa taacgagcac ggcacaggcg agtccctgag attcgccatc 4080

```
aacctgatcc agcagatccg gaataccggc aataacgaga gagacaacga tttcatcctg   4140

tccccagtga gggacgagaa tggcaagcac tttgactctc gcgagtactg ggataaggag   4200

acaaagggcg agaagatcag catgcccagc tccggcgatg ccaatggcgc cttcaacatc   4260

gcccggaagg gcatcatcat gaacgcccac atcctggcca atagcgactc caaggatctg   4320

tccctgttcg tgtctgacga ggagtgggat ctgcacctga ataacaagac cgagtggaag   4380

aagcagctga acatcttttc tagcaggaag gccatggcca agcgcaagaa gaaaaggccg   4440

gcggccacga aaaaggccgg ccaggcaaaa aagaaaaagg gatcctaccc atacgatgtt   4500

ccagattacg cttatcccta cgacgtgcct gattatgcat acccatatga tgtccccgac   4560

tatgcctaa                                                           4569


<210> SEQ ID NO 21
<211> LENGTH: 1397
<212> TYPE: PRT
<213> ORGANISM: Artificial Sequence
<220> FEATURE:
<223> OTHER INFORMATION: Parcubacteria bacterium GWC2011_GWC2_44_17
      (PbCpf1; pY008), including NLS and HA tag

<400> SEQUENCE: 21

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30

Lys Ile Asn Lys Val Phe Glu Lys Asp Gln Thr Ile Asp Asp Ser Tyr
        35                  40                  45

Asn Gln Ala Lys Phe Tyr Phe Asp Ser Leu His Gln Lys Phe Ile Asp
    50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
    130                 135                 140

Glu Ser Trp Lys Thr Tyr Tyr Gln Glu Arg Glu Val Asp Gly Lys Lys
145                 150                 155                 160

Ile Thr Phe Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270
```

```
Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685
```

-continued

```
Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Asp Val
        755                 760                 765

Gln Lys Tyr Gly Tyr Lys Ile Ser Phe Arg Asp Ile Asp Asp Glu Tyr
    770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
            820                 825                 830

Phe Lys Leu Ser Gly Met Ala Glu Ile Phe Gln Arg Gln Pro Ser Val
        835                 840                 845

Asn Glu Arg Glu Lys Ile Thr Thr Gln Lys Asn Gln Cys Ile Leu Asp
    850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
        915                 920                 925

Leu Leu Tyr Tyr Ser Val Val Lys Gln Asn Gly Glu Ile Ile Glu Gln
    930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
            980                 985                 990

Lys Ile Cys Gln Leu Ile Glu Lys  Tyr Ser Ala Ile Val  Val Leu Glu
        995                 1000                 1005

Asp Leu  Asn Met Arg Phe Lys  Gln Ile Arg Gly Gly  Ile Glu Arg
    1010                 1015                 1020

Ser Val  Tyr Gln Gln Phe Glu  Lys Ala Leu Ile Asp  Lys Leu Gly
    1025                 1030                 1035

Tyr Leu  Val Phe Lys Asp Asn  Arg Asp Leu Arg Ala  Pro Gly Gly
    1040                 1045                 1050

Val Leu  Asn Gly Tyr Gln Leu  Ser Ala Pro Phe Val  Ser Phe Glu
    1055                 1060                 1065

Lys Met  Arg Lys Gln Thr Gly  Ile Leu Phe Tyr Thr  Gln Ala Glu
    1070                 1075                 1080

Tyr Thr  Ser Lys Thr Asp Pro  Ile Thr Gly Phe Arg  Lys Asn Val
    1085                 1090                 1095

Tyr Ile  Ser Asn Ser Ala Ser  Leu Asp Lys Ile Lys  Glu Ala Val
```

-continued

```
    1100                1105                1110

Lys Lys  Phe Asp Ala Ile Gly  Trp Asp Gly Lys Glu  Gln Ser Tyr
    1115                1120                1125

Phe Phe  Lys Tyr Asn Pro Tyr  Asn Leu Ala Asp Glu  Lys Tyr Lys
    1130                1135                1140

Asn Ser  Thr Val Ser Lys Glu  Trp Ala Ile Phe Ala  Ser Ala Pro
    1145                1150                1155

Arg Ile  Arg Arg Gln Lys Gly  Glu Asp Gly Tyr Trp  Lys Tyr Asp
    1160                1165                1170

Arg Val  Lys Val Asn Glu Glu  Phe Glu Lys Leu Leu  Lys Val Trp
    1175                1180                1185

Asn Phe  Val Asn Pro Lys Ala  Thr Asp Ile Lys Gln  Glu Ile Ile
    1190                1195                1200

Lys Lys  Glu Lys Ala Gly Asp  Leu Gln Gly Glu Lys  Glu Leu Asp
    1205                1210                1215

Gly Arg  Leu Arg Asn Phe Trp  His Ser Phe Ile Tyr  Leu Phe Asn
    1220                1225                1230

Leu Val  Leu Glu Leu Arg Asn  Ser Phe Ser Leu Gln  Ile Lys Ile
    1235                1240                1245

Lys Ala  Gly Glu Val Ile Ala  Val Asp Glu Gly Val  Asp Phe Ile
    1250                1255                1260

Ala Ser  Pro Val Lys Pro Phe  Phe Thr Thr Pro Asn  Pro Tyr Ile
    1265                1270                1275

Pro Ser  Asn Leu Cys Trp Leu  Ala Val Glu Asn Ala  Asp Ala Asn
    1280                1285                1290

Gly Ala  Tyr Asn Ile Ala Arg  Lys Gly Val Met Ile  Leu Lys Lys
    1295                1300                1305

Ile Arg  Glu His Ala Lys Lys  Asp Pro Glu Phe Lys  Lys Leu Pro
    1310                1315                1320

Asn Leu  Phe Ile Ser Asn Ala  Glu Trp Asp Glu Ala  Ala Arg Asp
    1325                1330                1335

Trp Gly  Lys Tyr Ala Gly Thr  Thr Ala Leu Asn Leu  Asp His Lys
    1340                1345                1350

Arg Pro  Ala Ala Thr Lys Lys  Ala Gly Gln Ala Lys  Lys Lys Lys
    1355                1360                1365

Gly Ser  Tyr Pro Tyr Asp Val  Pro Asp Tyr Ala Tyr  Pro Tyr Asp
    1370                1375                1380

Val Pro  Asp Tyr Ala Tyr Pro  Tyr Asp Val Pro Asp  Tyr Ala
    1385                1390                1395
```

<210> SEQ ID NO 22
<211> LENGTH: 4194
<212> TYPE: DNA
<213> ORGANISM: Artificial Sequence
<220> FEATURE:
<223> OTHER INFORMATION: Parcubacteria bacterium GWC2011_GWC2_44_17
      (PbCpf1; pY008), including NLS and HA tag

<400> SEQUENCE: 22

```
atggagaaca tcttcgacca gtttatcggc aagtacagcc tgtccaagac cctgagattc      60

gagctgaagc ccgtgggcaa gacagaggac ttcctgaaga tcaacaaggt gtttgagaag     120

gatcagacca tcgacgatag ctacaatcag gccaagttct attttgattc cctgcaccag     180

aagtttatcg acgccgccct ggcctccgat aagacatccg agctgtcttt ccagaacttt     240

gccgacgtgc tggagaagca gaataagatc atcctggata agaagagaga gatgggcgcc     300
```

```
ctgaggaagc gcgacaagaa cgccgtgggc atcgataggc tgcagaagga gatcaatgac    360
gccgaggata tcatccagaa ggagaaggag aagatctaca aggacgtgcg caccctgttc    420
gataacgagg ccgagtcttg gaaaacctac tatcaggagc gggaggtgga cggcaagaag    480
atcaccttca gcaaggccga cctgaagcag aagggcgccg attttctgac agccgccggc    540
atcctgaagg tgctgaagta tgagttcccc gaggagaagg agaaggagtt tcaggccaag    600
aaccagccct ccctgttcgt ggaggagaag gagaatcctg gccagaagag gtacatcttc    660
gactcttttg ataagttcgc cggctatctg accaagtttc agcagacaaa gaagaatctg    720
tacgcagcag acggcaccag cacagcagtg gccacccgca tcgccgataa ctttatcatc    780
ttccaccaga ataccaaggt gttccgggac aagtacaaga acaatcacac agacctgggc    840
ttcgatgagg agaacatctt tgagatcgag aggtataaga attgcctgct gcagcgcgag    900
atcgagcaca tcaagaatga gaatagctac aacaagatca tcggccggat caataagaag    960
atcaaggagt atcgggacca gaaggccaag gataccaagc tgacaaagtc cgacttccct   1020
ttctttaaga acctggataa gcagatcctg ggcgaggtgg agaaggagaa gcagctgatc   1080
gagaaaaccc gggagaaaac cgaggaggac gtgctgatcg agcggttcaa ggagttcatc   1140
gagaacaatg aggagaggtt caccgccgcc aagaagctga tgaatgcctt ctgtaacggc   1200
gagtttgagt ccgagtacga gggcatctat ctgaagaata aggccatcaa cacaatctcc   1260
cggagatggt tcgtgtctga cagagatttt gagctgaagc tgcctcagca gaagtccaag   1320
aacaagtctg agaagaatga gccaaaggtg aagaagttca tctccatcgc cgagatcaag   1380
aacgccgtgg aggagctgga cggcgatatc tttaaggccg tgttctacga caagaagatc   1440
atcgcccagg gcggctctaa gctggagcag ttcctggtca tctggaagta cgagtttgag   1500
tatctgttcc gggacatcga gagagagaac ggcgagaagc tgctgggcta tgatagctgc   1560
ctgaagatcg ccaagcagct gggcatcttc ccacaggaga aggaggcccg cgagaaggca   1620
accgccgtga tcaagaatta cgccgacgcc ggcctgggca tcttccagat gatgaagtat   1680
ttttctctgg acgataagga tcggaagaac acccccggcc agctgagcac aaatttctac   1740
gccgagtatg acggctacta caaggatttc gagtttatca agtactacaa cgagtttagg   1800
aacttcatca ccaagaagcc tttcgacgag gataagatca agctgaactt tgagaatggc   1860
gccctgctga agggctggga cgagaacaag gagtacgatt tcatgggcgt gatcctgaag   1920
aaggagggcc gcctgtatct gggcatcatg cacaagaacc accggaagct gtttcagtcc   1980
atgggcaatg ccaagggcga caacgccaat agataccaga agatgatcta taagcagatc   2040
gccgacgcct ctaaggatgt gcccaggctg ctgctgacca gcaagaaggc catggagaag   2100
ttcaagcctt cccaggagat cctgagaatc aagaaggaga aaaccttcaa gcgggagagc   2160
aagaactttt ccctgagaga tctgcacgcc ctgatcgagt actataggaa ctgcatccct   2220
cagtacagca attggtcctt ttatgacttc cagtttcagg ataccggcaa gtaccagaat   2280
atcaaggagt tcacagacga tgtgcagaag tacggctata agatctcctt tcgcgacatc   2340
gacgatgagt atatcaatca ggccctgaac gagggcaaga tgtacctgtt cgaggtggtg   2400
aacaaggata tctataacac caagaatggc tccaagaatc tgcacacact gtactttgag   2460
cacatcctgt ctgccgagaa cctgaatgac ccagtgttca agctgtctgg catggccgag   2520
atctttcagc ggcagcccag cgtgaacgaa agagagaaga tcaccacaca gaagaatcag   2580
tgtatcctgg acaagggcga tagagcctac aagtataggc gctacaccga gaagaagatc   2640
```

atgttccaca tgagcctggt gctgaacaca ggcaagggcg agatcaagca ggtgcagttt 2700
aataagatca tcaaccagag gatcagctcc tctgacaacg agatgagggt gaatgtgatc 2760
ggcatcgatc gcggcgagaa gaacctgctg tactatagcg tggtgaagca gaatggcgag 2820
atcatcgagc aggcctccct gaacgagatc aatggcgtga actaccggga caagctgatc 2880
gagagggaga aggagcgcct gaagaaccgg cagagctgga agcctgtggt gaagatcaag 2940
gatctgaaga agggctacat ctcccacgtg atccacaaga tctgccagct gatcgagaag 3000
tattctgcca tcgtggtgct ggaggacctg aatatgagat tcaagcagat caggggagga 3060
atcgagcgga gcgtgtacca gcagttcgag aaggccctga tcgataagct gggctatctg 3120
gtgtttaagg acaacaggga tctgagggca ccaggaggcg tgctgaatgg ctaccagctg 3180
tctgccccct ttgtgagctt cgagaagatg cgcaagcaga ccggcatcct gttctacaca 3240
caggccgagt ataccagcaa gacagaccca atcaccggct ttcggaagaa cgtgtatatc 3300
tctaatagcg cctccctgga taagatcaag gaggccgtga agaagttcga cgccatcggc 3360
tgggatggca aggagcagtc ttacttcttt aagtacaacc cttacaacct ggccgacgag 3420
aagtataaga actctaccgt gagcaaggag tgggccatct ttgccagcgc cccaagaatc 3480
cggagacaga agggcgagga cggctactgg aagtatgata gggtgaaagt gaatgaggag 3540
ttcgagaagc tgctgaaggt ctggaatttt gtgaacccaa aggccacaga tatcaagcag 3600
gagatcatca agaaggagaa ggcaggcgac ctgcagggag agaaggagct ggatggccgg 3660
ctgagaaact tttggcactc tttcatctac ctgtttaacc tggtgctgga gctgcgcaat 3720
tctttcagcc tgcagatcaa gatcaaggca ggagaagtga tcgcagtgga cgagggcgtg 3780
gacttcatcg ccagcccagt gaagcccttc tttaccacac ccaaccctta catccccctcc 3840 aacctgtgct ggctggccgt ggagaatgca gacgcaaacg gagcctataa tatcgccagg 3900
aagggcgtga tgatcctgaa gaagatccgc gagcacgcca agaaggaccc cgagttcaag 3960
aagctgccaa acctgtttat cagcaatgca gagtgggacg aggcagcccg ggattggggc 4020
aagtacgcag gcaccacagc cctgaacctg gaccacaaaa ggccggcggc cacgaaaaag 4080
gccggccagg caaaaaagaa aaagggatcc tacccatacg atgttccaga ttacgcttat 4140
ccctacgacg tgcctgatta tgcataccca tatgatgtcc ccgactatgc ctaa 4194

<210> SEQ ID NO 23
<211> LENGTH: 1295
<212> TYPE: PRT
<213> ORGANISM: Artificial Sequence
<220> FEATURE:
<223> OTHER INFORMATION: Smithella sp. SC_K08D17 (SsCpf1; pY009), including NLS and HA tag

<400> SEQUENCE: 23

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
    50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp

-continued

```
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
        195                 200                 205

Lys Asp Met Lys Asp Val Ile Lys Gly Thr Thr Leu Glu Glu Ile Phe
    210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
        275                 280                 285

Ile Leu Ser Asp Arg Gln Ser Leu Ser Phe Ile Ala Glu Ala Phe Lys
    290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
            340                 345                 350

Tyr Phe Arg Ser Gly Ala Ser Leu Thr Asp Val Ser Arg Lys Val Phe
        355                 360                 365

Gly Glu Trp Ser Ile Ile Asn Arg Ala Leu Asp Asn Tyr Tyr Ala Thr
    370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
            420                 425                 430

Lys Val Ile Ala Asp Tyr Phe Ala Lys Phe Cys Asp Asp Lys Glu Thr
        435                 440                 445

Asp Leu Ile Gln Lys Val Asn Glu Gly Tyr Ile Ala Val Lys Asp Leu
    450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
            500                 505                 510
```

```
Glu Thr Phe Tyr Ser Leu Phe Thr Pro Leu Tyr Asp His Leu Thr Gln
        515                 520                 525

Thr Ile Ala Leu Tyr Asn Lys Val Arg Asn Tyr Leu Thr Gln Lys Pro
    530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
            580                 585                 590

Arg Ile Phe Arg Asn Val Pro Lys Ala Asp Lys Lys Asp Phe Cys Tyr
        595                 600                 605

Glu Lys Met Val Tyr Lys Leu Leu Pro Gly Ala Asn Lys Met Leu Pro
    610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
            660                 665                 670

Ile Asn Lys His Glu Asp Trp Lys Asn Phe Asp Phe Arg Phe Ser Ala
        675                 680                 685

Thr Ser Thr Tyr Ala Asp Leu Ser Gly Phe Tyr His Glu Val Glu His
    690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
        755                 760                 765

Leu Asn Gly Glu Ala Glu Val Phe Tyr Arg Lys Lys Ser Ile Ala Glu
    770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
        835                 840                 845

Gln Phe Leu Lys Ala Asn Pro Asp Ile Asn Ile Ile Gly Ile Asp Arg
    850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
            900                 905                 910

Ala Arg Gln Glu Trp Gly Val Ile Glu Thr Ile Lys Glu Leu Lys Glu
        915                 920                 925
```

-continued

```
Gly Tyr Leu Ser Gln Val Ile His Lys Leu Thr Asp Leu Met Ile Glu
    930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
                965                 970                 975

Leu Ile Asp Lys Leu Asn Tyr Leu Val Asp Lys Asn Lys Lys Ala Asn
            980                 985                 990

Glu Leu Gly Gly Leu Leu Asn Ala  Phe Gln Leu Ala Asn  Lys Phe Glu
        995                 1000                1005

Ser Phe  Gln Lys Met Gly Lys  Gln Asn Gly Phe Ile  Phe Tyr Val
    1010                1015                1020

Pro Ala  Trp Asn Thr Ser Lys  Thr Asp Pro Ala Thr  Gly Phe Ile
    1025                1030                1035

Asp Phe  Leu Lys Pro Arg Tyr  Glu Asn Leu Asn Gln  Ala Lys Asp
    1040                1045                1050

Phe Phe  Glu Lys Phe Asp Ser  Ile Arg Leu Asn Ser  Lys Ala Asp
    1055                1060                1065

Tyr Phe  Glu Phe Ala Phe Asp  Phe Lys Asn Phe Thr  Glu Lys Ala
    1070                1075                1080

Asp Gly  Gly Arg Thr Lys Trp  Thr Val Cys Thr Thr  Asn Glu Asp
    1085                1090                1095

Arg Tyr  Ala Trp Asn Arg Ala  Leu Asn Asn Asn Arg  Gly Ser Gln
    1100                1105                1110

Glu Lys  Tyr Asp Ile Thr Ala  Glu Leu Lys Ser Leu  Phe Asp Gly
    1115                1120                1125

Lys Val  Asp Tyr Lys Ser Gly  Lys Asp Leu Lys Gln  Gln Ile Ala
    1130                1135                1140

Ser Gln  Glu Ser Ala Asp Phe  Phe Lys Ala Leu Met  Lys Asn Leu
    1145                1150                1155

Ser Ile  Thr Leu Ser Leu Arg  His Asn Asn Gly Glu  Lys Gly Asp
    1160                1165                1170

Asn Glu  Gln Asp Tyr Ile Leu  Ser Pro Val Ala Asp  Ser Lys Gly
    1175                1180                1185

Arg Phe  Phe Asp Ser Arg Lys  Ala Asp Asp Asp Met  Pro Lys Asn
    1190                1195                1200

Ala Asp  Ala Asn Gly Ala Tyr  His Ile Ala Leu Lys  Gly Leu Trp
    1205                1210                1215

Cys Leu  Glu Gln Ile Ser Lys  Thr Asp Asp Leu Lys  Lys Val Lys
    1220                1225                1230

Leu Ala  Ile Ser Asn Lys Glu  Trp Leu Glu Phe Val  Gln Thr Leu
    1235                1240                1245

Lys Gly  Lys Arg Pro Ala Ala  Thr Lys Lys Ala Gly  Gln Ala Lys
    1250                1255                1260

Lys Lys  Lys Gly Ser Tyr Pro  Tyr Asp Val Pro Asp  Tyr Ala Tyr
    1265                1270                1275

Pro Tyr  Asp Val Pro Asp Tyr  Ala Tyr Pro Tyr Asp  Val Pro Asp
    1280                1285                1290

Tyr Ala
    1295
```

<210> SEQ ID NO 24
<211> LENGTH: 3888
<212> TYPE: DNA

<213> ORGANISM: Artificial Sequence
<220> FEATURE:
<223> OTHER INFORMATION: Smithella sp. SC_K08D17 (SsCpf1; pY009), including NLS and HA tag

<400> SEQUENCE: 24

```
atgcagaccc tgtttgagaa cttcacaaat cagtacccag tgtccaagac cctgcgcttt     60
gagctgatcc cccagggcaa gacaaaggac ttcatcgagc agaagggcct gctgaagaag    120
gatgaggacc gggccgagaa gtataagaag gtgaagaaca tcatcgatga gtaccacaag    180
gacttcatcg agaagtctct gaatggcctg aagctggacg gcctggagaa gtacaagacc    240
ctgtatctga agcaggagaa ggacgataag gataagaagg cctttgacaa ggagaaggag    300
aacctgcgca agcagatcgc caatgccttc cggaacaatg agaagtttaa gacactgttc    360
gccaaggagc tgatcaagaa cgatctgatg tctttcgcct gcgaggagga caagaagaat    420
gtgaaggagt ttgaggcctt caccacatac ttcaccggct tccaccagaa ccgcgccaat    480
atgtacgtgg ccgatgagaa gagaacagcc atcgccagca ggctgatcca cgagaacctg    540
ccaaagttta tcgacaatat caagatcttc gagaagatga agaaggaggc ccccgagctg    600
ctgtctcctt tcaaccagac cctgaaggat atgaaggacg tgatcaaggg caccacactg    660
gaggagatct ttagcctgga ttatttcaac aagaccctga cacagagcgg catcgacatc    720
tacaattccg tgatcggcgg cagaacccct gaggagggca agacaaagat caagggcctg    780
aacgagtaca tcaataccga cttcaaccag aagcagacag acaagaagaa gcggcagcca    840
aagttcaagc agctgtataa gcagatcctg agcgataggc agagcctgtc ctttatcgcc    900
gaggccttca agaacgacac cgagatcctg gaggccatcg agaagtttta cgtgaatgag    960
ctgctgcact tcagcaatga gggcaagtcc acaaacgtgc tggacgccat caagaatgcc   1020
gtgtctaacc tggagagctt taacctgacc aagatgtatt tccgctccgg cgcctctctg   1080
acagacgtga gccggaaggt gtttggcgag tggagcatca tcaatagagc cctggacaac   1140
tactatgcca ccacatatcc aatcaagccc agagagaagt ctgagaagta cgaggagagg   1200
aaggagaagt ggctgaagca ggacttcaac gtgagcctga tccagaccgc catcgatgag   1260
tacgacaacg agacagtgaa gggcaagaac agcggcaaag tgatcgccga ttattttgcc   1320
aagttctgcg acgataagga gacagacctg atccagaagg tgaacgaggg ctacatcgcc   1380
gtgaaggatc tgctgaatac accctgtcct gagaacgaga agctgggcag caataaggac   1440
caggtgaagc agatcaaggc ctttatggat tctatcatgg acatcatgca cttcgtgcgc   1500
cccctgagcc tgaaggatac cgacaaggag aaggatgaga cattctactc cctgttcaca   1560
cctctgtacg accacctgac ccagacaatc gccctgtata acaaggtgcg gaactatctg   1620
acccagaagc cttacagcac agagaagatc aagctgaact tcgagaacag caccctgctg   1680
ggcggctggg atctgaataa ggagacagac aacacagcca tcatcctgag gaaggataac   1740
ctgtactatc tgggcatcat ggacaagagg cacaatcgca tctttcggaa cgtgcccaag   1800
gccgataaga aggacttctg ctacgagaag atggtgtata agctgctgcc tggcgccaac   1860
aagatgctgc caaaggtgtt cttttctcag agcagaatcc aggagtttac cccttccgcc   1920
aagctgctgg agaactacgc caatgagaca cacaagaagg gcgataattt caacctgaat   1980
cactgtcaca agctgatcga tttctttaag gactctatca acaagcacga ggattggaag   2040
aatttcgact ttaggttcag cgccacctcc acctacgccg acctgagcgg cttttaccac   2100
gaggtggagc accagggcta caagatctct tttcagagcg tggccgattc cttcatcgac   2160
```

-continued

```
gatctggtga acgagggcaa gctgtacctg ttccagatct ataataagga cttttcccca   2220

ttctctaagg gcaagcccaa cctgcacacc ctgtactgga agatgctgtt tgatgagaac   2280

aatctgaagg acgtggtgta taagctgaat ggcgaggccg aggtgttcta ccgcaagaag   2340

agcattgccg agaagaacac cacaatccac aaggccaatg agtccatcat caacaagaat   2400

cctgataacc caaaggccac cagcaccttc aactatgata tcgtgaagga caagagatac   2460

accatcgaca agtttcagtt ccacatccca atcacaatga actttaaggc cgagggcatc   2520

ttcaacatga atcagagggt gaatcagttc ctgaaggcca atcccgatat caacatcatc   2580

ggcatcgaca gaggcgagag gcacctgctg tactatgccc tgatcaacca gaagggcaag   2640

atcctgaagc aggataccct gaatgtgatc gccaacgaga agcagaaggt ggactaccac   2700

aatctgctgg ataagaagga gggcgaccgc gcaaccgcaa ggcaggagtg gggcgtgatc   2760

gagacaatca aggagctgaa ggagggctat ctgtcccagg tcatccacaa gctgaccgat   2820

ctgatgatcg agaacaatgc catcatcgtg atggaggacc tgaactttgg cttcaagcgg   2880

ggcagacaga aggtggagaa gcaggtgtat cagaagtttg agaagatgct gatcgataag   2940

ctgaattacc tggtggacaa gaataagaag gcaaacgagc tgggaggcct gctgaacgca   3000

ttccagctgg ccaataagtt tgagtccttc cagaagatgg gcaagcagaa cggctttatc   3060

ttctacgtgc ccgcctggaa tacctctaag acagatcctg ccaccggctt tatcgacttc   3120

ctgaagcccc gctatgagaa cctgaatcag gccaaggatt tctttgagaa gtttgactct   3180

atccggctga acagcaaggc cgattacttt gagttcgcct ttgacttcaa gaatttcacc   3240

gagaaggccg atggcggcag aaccaagtgg acagtgtgca ccacaaacga ggacagatat   3300

gcctggaata gggccctgaa caataacagg ggcagccagg agaagtacga catcacagcc   3360

gagctgaagt ccctgttcga tggcaaggtg gactataagt ctggcaagga tctgaagcag   3420

cagatcgcca gccaggagtc cgccgacttc tttaaggccc tgatgaagaa cctgtccatc   3480

accctgtctc tgagacacaa taacggcgag aagggcgata atgagcagga ctacatcctg   3540

tcccctgtgg ccgattctaa gggccgcttc tttgactccc ggaaggccga cgatgacatg   3600

ccaaagaatg ccgacgccaa cggcgcctat cacatcgccc tgaagggcct gtggtgtctg   3660

gagcagatca gcaagaccga tgacctgaag aaggtgaagc tggccatctc caacaaggag   3720

tggctggagt tcgtgcagac actgaagggc aaaaggccgg cggccacgaa aaaggccggc   3780

caggcaaaaa agaaaaaggg atcctaccca tacgatgttc cagattacgc ttatccctac   3840

gacgtgcctg attatgcata cccatatgat gtccccgact atgcctaa                3888
```

<210> SEQ ID NO 25
<211> LENGTH: 1352
<212> TYPE: PRT
<213> ORGANISM: Artificial Sequence
<220> FEATURE:
<223> OTHER INFORMATION: Acidaminococcus sp. BV3L6 (AsCpf1; pY010), including NLS and HA tag

<400> SEQUENCE: 25

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
```

```
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480
```

```
Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
        610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
        690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895
```

-continued

```
Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn Lys
```

-continued

```
    1295                1300                1305

Arg Pro  Ala Ala Thr Lys Lys  Ala Gly Gln Ala Lys  Lys Lys Lys
    1310                1315                1320

Gly Ser  Tyr Pro Tyr Asp Val  Pro Asp Tyr Ala Tyr  Pro Tyr Asp
    1325                1330                1335

Val Pro  Asp Tyr Ala Tyr Pro  Tyr Asp Val Pro Asp  Tyr Ala
    1340                1345                1350


<210> SEQ ID NO 26
<211> LENGTH: 4059
<212> TYPE: DNA
<213> ORGANISM: Artificial Sequence
<220> FEATURE:
<223> OTHER INFORMATION: Acidaminococcus sp. BV3L6 (AsCpf1; pY010),
      including NLS and HA tag

<400> SEQUENCE: 26

atgacacagt tcgagggctt taccaacctg tatcaggtga gcaagacact gcggtttgag     60

ctgatcccac agggcaagac cctgaagcac atccaggagc agggcttcat cgaggaggac    120

aaggcccgca atgatcacta caaggagctg aagcccatca tcgatcggat ctacaagacc    180

tatgccgacc agtgcctgca gctggtgcag ctggattggg agaacctgag cgccgccatc    240

gactcctata gaaaggagaa aaccgaggag acaaggaacg ccctgatcga ggagcaggcc    300

acatatcgca atgccatcca cgactacttc atcggccgga cagacaacct gaccgatgcc    360

atcaataaga gacacgccga gatctacaag ggcctgttca aggccgagct gtttaatggc    420

aaggtgctga agcagctggg caccgtgacc acaaccgagc acgagaacgc cctgctgcgg    480

agcttcgaca agtttacaac ctacttctcc ggcttttatg agaacaggaa gaacgtgttc    540

agcgccgagg atatcagcac agccatccca caccgcatcg tgcaggacaa cttccccaag    600

tttaaggaga attgtcacat cttcacacgc ctgatcaccg ccgtgcccag cctgcgggag    660

cactttgaga acgtgaagaa ggccatcggc atcttcgtga gcacctccat cgaggaggtg    720

ttttccttcc ctttttataa ccagctgctg acacagaccc agatcgacct gtataaccag    780

ctgctgggag gaatctctcg ggaggcaggc accgagaaga tcaagggcct gaacgaggtg    840

ctgaatctgg ccatccagaa gaatgatgag acagcccaca tcatcgcctc cctgccacac    900

agattcatcc ccctgtttaa gcagatcctg tccgatagga acaccctgtc tttcatcctg    960

gaggagttta agagcgacga ggaagtgatc cagtccttct gcaagtacaa gacactgctg   1020

agaaacgaga acgtgctgga gacagccgag gccctgttta acgagctgaa cagcatcgac   1080

ctgacacaca tcttcatcag ccacaagaag ctggagacaa tcagcagcgc cctgtgcgac   1140

cactgggata cactgaggaa tgccctgtat gagcggagaa tctccgagct gacaggcaag   1200

atcaccaagt ctgccaagga gaaggtgcag cgcagcctga agcacgagga tatcaacctg   1260

caggagatca tctctgccgc aggcaaggag ctgagcgagg ccttcaagca gaaaaccagc   1320

gagatcctgt cccacgcaca cgccgccctg gatcagccac tgcctacaac cctgaagaag   1380

caggaggaga aggagatcct gaagtctcag ctggacagcc tgctgggcct gtaccacctg   1440

ctggactggt ttgccgtgga tgagtccaac gaggtggacc ccgagttctc tgcccggctg   1500

accggcatca agctggagat ggagccttct ctgagcttct acaacaaggc cagaaattat   1560

gccaccaaga agccctactc cgtggagaag ttcaagctga actttcagat gcctacactg   1620

gcctctggct gggacgtgaa taaggagaag aacaatggcg ccatcctgtt tgtgaagaac   1680

ggcctgtact atctgggcat catgccaaag cagaagggca ggtataaggc cctgagcttc   1740
```

```
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgatcggggc gagagaaacc tgatctatat cacagtgatc   2760
gactccaccg gcaagatcct ggagcagcgg agcctgaaca ccatccagca gtttgattac   2820
cagaagaagc tggacaacag ggagaaggag agggtggcag caaggcaggc ctggtctgtg   2880
gtgggcacaa tcaaggatct gaagcagggc tatctgagcc aggtcatcca cgagatcgtg   2940
gacctgatga tccactacca ggccgtggtg gtgctggaga acctgaattt cggctttaag   3000
agcaagagga ccggcatcgc cgagaaggcc gtgtaccagc agttcgagaa gatgctgatc   3060
gataagctga attgcctggt gctgaaggac tatccagcag agaaagtggg aggcgtgctg   3120
aacccatacc agctgacaga ccagttcacc tcctttgcca agatgggcac ccagtctggc   3180
ttcctgtttt acgtgcctgc cccatataca tctaagatcg atcccctgac cggcttcgtg   3240
gacccctteg tgtggaaaac catcaagaat cacgagagcc gcaagcactt cctggagggc   3300
ttcgactttc tgcactacga cgtgaaaacc ggcgacttca tcctgcactt taagatgaac   3360
agaaatctgt ccttccagag gggcctgccc ggctttatgc ctgcatggga tatcgtgttc   3420
gagaagaacg agacacagtt tgacgccaag ggcacccctt tcatcgccgg caagagaatc   3480
gtgccagtga tcgagaatca cagattcacc ggcagatacc gggacctgta tcctgccaac   3540
gagctgatcg ccctgctgga ggagaagggc atcgtgttca gggatggctc caacatcctg   3600
ccaaagctgc tggagaatga cgattctcac gccatcgaca ccatggtggc cctgatccgc   3660
agcgtgctgc agatgcggaa ctccaatgcc gccacaggcg aggactatat caacagcccc   3720
gtgcgcgatc tgaatggcgt gtgcttcgac tcccggtttc agaacccaga gtggcccatg   3780
gacgccgatg ccaatggcgc ctaccacatc gccctgaagg gccagctgct gctgaatcac   3840
ctgaaggaga gcaaggatct gaagctgcag aacggcatct ccaatcagga ctggctggcc   3900
tacatccagg agctgcgcaa caaaaggccg gcggccacga aaaaggccgg ccaggcaaaa   3960
aagaaaaagg gatcctaccc atacgatgtt ccagattacg cttatcccta cgacgtgcct   4020
gattatgcat acccatatga tgtccccgac tatgcctaa                          4059
```

<210> SEQ ID NO 27
<211> LENGTH: 1251
<212> TYPE: PRT
<213> ORGANISM: Artificial Sequence
<220> FEATURE:
<223> OTHER INFORMATION: Lachnospiraceae bacterium MA2020 (Lb2Cpf1; pY011), including NLS and HA tag

<400> SEQUENCE: 27

```
Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
        275                 280                 285

Ser Tyr Gly Ser Val Leu Ile Glu Ser Leu Lys Ser Ser Lys Val Ser
    290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Asn Ile Val Phe Glu Asn
                325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
        355                 360                 365
```

-continued

```
Leu Lys Lys Asn Lys Ser Tyr Ser Leu Glu His Leu Cys Asn Leu Ser
    370                 375                 380

Glu Asp Ser Cys Asn Leu Ile Glu Asn Tyr Ile His Gln Ile Ser Asp
385                 390                 395                 400

Asp Ile Glu Asn Ile Ile Ile Asn Asn Glu Thr Phe Leu Arg Ile Val
                405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
        435                 440                 445

Glu Leu Lys Leu Ile Asn Ser Ser Gly Gln Glu Leu Glu Lys Asp Leu
    450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
    530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
                565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
        595                 600                 605

Leu Glu Asp Cys His Asn Leu Ile Asp Phe Phe Lys Glu Ser Ile Ser
    610                 615                 620

Lys His Glu Asp Trp Ser Lys Phe Gly Phe Lys Phe Ser Asp Thr Ala
625                 630                 635                 640

Ser Tyr Asn Asp Ile Ser Glu Phe Tyr Arg Glu Val Glu Lys Gln Gly
                645                 650                 655

Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
        675                 680                 685

Ser Met Tyr Ser Lys Gly Lys Leu Asn Leu His Thr Leu Tyr Phe Met
    690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
        755                 760                 765

Asp Lys Arg Tyr Ser Lys Asp Lys Phe Thr Leu His Ile Pro Ile Thr
    770                 775                 780
```

```
Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Val Ile Asp Ser Lys Gly Asn
            820                 825                 830

Ile Leu Glu Gln Ile Ser Leu Asn Ser Ile Ile Asn Lys Glu Tyr Asp
        835                 840                 845

Ile Glu Thr Asp Tyr His Ala Leu Leu Asp Glu Arg Glu Gly Gly Arg
    850                 855                 860

Asp Lys Ala Arg Lys Asp Trp Asn Thr Val Glu Asn Ile Arg Asp Leu
865                 870                 875                 880

Lys Ala Gly Tyr Leu Ser Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
        915                 920                 925

Lys Met Leu Ile Asp Lys Leu Asn Tyr Leu Val Ile Asp Lys Ser Arg
    930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr  Met Lys Cys Glu Asn  Val Glu Lys
        995                 1000                 1005

Ser Lys  Arg Phe Phe Asp Gly  Phe Asp Phe Ile Arg  Phe Asn Ala
    1010                 1015                 1020

Leu Glu  Asn Val Phe Glu Phe  Gly Phe Asp Tyr Arg  Ser Phe Thr
    1025                 1030                 1035

Gln Arg  Ala Cys Gly Ile Asn  Ser Lys Trp Thr Val  Cys Thr Asn
    1040                 1045                 1050

Gly Glu  Arg Ile Ile Lys Tyr  Arg Asn Pro Asp Lys  Asn Asn Met
    1055                 1060                 1065

Phe Asp  Glu Lys Val Val Val  Val Thr Asp Glu Met  Lys Asn Leu
    1070                 1075                 1080

Phe Glu  Gln Tyr Lys Ile Pro  Tyr Glu Asp Gly Arg  Asn Val Lys
    1085                 1090                 1095

Asp Met  Ile Ile Ser Asn Glu  Glu Ala Glu Phe Tyr  Arg Arg Leu
    1100                 1105                 1110

Tyr Arg  Leu Leu Gln Gln Thr  Leu Gln Met Arg Asn  Ser Thr Ser
    1115                 1120                 1125

Asp Gly  Thr Arg Asp Tyr Ile  Ile Ser Pro Val Lys  Asn Lys Arg
    1130                 1135                 1140

Glu Ala  Tyr Phe Asn Ser Glu  Leu Ser Asp Gly Ser  Val Pro Lys
    1145                 1150                 1155

Asp Ala  Asp Ala Asn Gly Ala  Tyr Asn Ile Ala Arg  Lys Gly Leu
    1160                 1165                 1170

Trp Val  Leu Glu Gln Ile Arg  Gln Lys Ser Glu Gly  Glu Lys Ile
    1175                 1180                 1185

Asn Leu  Ala Met Thr Asn Ala  Glu Trp Leu Glu Tyr  Ala Gln Thr
```

```
    1190                1195                1200

His Leu  Leu Lys Arg Pro Ala  Ala Thr Lys Lys Ala  Gly Gln Ala
    1205                1210                1215

Lys Lys  Lys Lys Gly Ser Tyr  Pro Tyr Asp Val Pro  Asp Tyr Ala
    1220                1225                1230

Tyr Pro  Tyr Asp Val Pro Asp  Tyr Ala Tyr Pro Tyr  Asp Val Pro
    1235                1240                1245

Asp Tyr  Ala
    1250


<210> SEQ ID NO 28
<211> LENGTH: 3756
<212> TYPE: DNA
<213> ORGANISM: Artificial Sequence
<220> FEATURE:
<223> OTHER INFORMATION: Lachnospiraceae bacterium MA2020 (Lb2Cpf1;
      pY011), including NLS and HA tag

<400> SEQUENCE: 28

atgtactatg agtccctgac caagcagtac cccgtgtcta agacaatccg gaatgagctg     60

atccctatcg gcaagacact ggataacatc cgccagaaca atatcctgga gagcgacgtg    120

aagcggaagc agaactacga gcacgtgaag ggcatcctgg atgagtatca caagcagctg    180

atcaacgagg ccctggacaa ttgcaccctg ccatccctga agatcgccgc cgagatctac    240

ctgaagaatc agaaggaggt gtctgacaga gaggatttca acaagacaca ggacctgctg    300

aggaaggagg tggtggagaa gctgaaggcc cacgagaact ttaccaagat cggcaagaag    360

gacatcctgg atctgctgga gaagctgcct tccatctctg aggacgatta caatgccctg    420

gagagcttcc gcaactttta cacctatttc acatcctaca acaaggtgcg ggagaatctg    480

tattctgata aggagaagag ctccacagtg gcctacagac tgatcaacga gaatttccca    540

aagtttctgg acaatgtgaa gagctatagg tttgtgaaaa ccgcaggcat cctggcagat    600

ggcctgggag aggaggagca ggactccctg ttcatcgtgg agacattcaa caagaccctg    660

acacaggacg gcatcgatac ctacaattct caagtgggca agatcaactc tagcatcaat    720

ctgtataacc agaagaatca gaaggccaat ggcttcagaa agatccccaa gatgaagatg    780

ctgtataagc agatcctgtc cgatagggag gagtctttca tcgacgagtt tcagagcgat    840

gaggtgctga tcgacaacgt ggagtcttat ggcagcgtgc tgatcgagtc tctgaagtcc    900

tctaaggtga gcgccttctt tgatgccctg agagagtcta agggcaagaa cgtgtacgtg    960

aagaatgacc tggccaagac agccatgagc aacatcgtgt tcgagaattg gaggaccttt   1020

gacgatctgc tgaaccagga gtacgacctg gccaacgaga acaagaagaa ggacgataag   1080

tatttcgaga agcgccagaa ggagctgaag aagaataaga gctactccct ggagcacctg   1140

tgcaacctgt ccgaggattc ttgtaacctg atcgagaatt atatccacca gatctccgac   1200

gatatcgaga atatcatcat caacaatgag acattcctgc gcatcgtgat caatgagcac   1260

gacaggtccc gcaagctggc caagaaccgg aaggccgtga aggccatcaa ggactttctg   1320

gattctatca aggtgctgga gcgggagctg aagctgatca acagctccgg ccaggagctg   1380

gagaaggatc tgatcgtgta ctctgcccac gaggagctgc tggtggagct gaagcaggtg   1440

gacagcctgt ataacatgac cagaaattat ctgacaaaga agcctttctc taccgagaag   1500

gtgaagctga actttaatcg cagcacactg ctgaacggct gggatcggaa taaggagaca   1560

gacaacctgg gcgtgctgct gctgaaggac ggcaagtact atctgggcat catgaacaca   1620
```

-continued

```
agcgccaata aggccttcgt gaatccccct gtggccaaga ccgagaaggt gtttaagaag   1680
gtggattaca agctgctgcc agtgcccaac cagatgctgc caaaggtgtt ctttgccaag   1740
agcaatatcg acttctataa cccctctagc gagatctact ccaattataa gaagggcacc   1800
cacaagaagg gcaatatgtt ttccctggag gattgtcaca acctgatcga cttctttaag   1860
gagtctatca gcaagcacga ggactggagc aagttcggct ttaagttcag cgatacagcc   1920
tcctacaacg acatctccga gttctatcgc gaggtggaga agcagggcta caagctgacc   1980
tatacagaca tcgatgagac atacatcaat gatctgatcg agcggaacga gctgtacctg   2040
ttccagatct ataataagga ctttagcatg tactccaagg gcaagctgaa cctgcacaca   2100
ctgtatttca tgatgctgtt tgatcagcgc aatatcgacg acgtggtgta taagctgaac   2160
ggagaggcag aggtgttcta taggccagcc tccatctctg aggacgagct gatcatccac   2220
aaggccggcg aggagatcaa gaacaagaat cctaaccggg ccagaaccaa ggagacaagc   2280
accttcagct acgacatcgt gaaggataag cggtatagca aggataagtt taccctgcac   2340
atccccatca caatgaactt cggcgtggat gaggtgaagc ggttcaacga cgccgtgaac   2400
agcgccatcc ggatcgatga gaatgtgaac gtgatcggca tcgaccgggg cgagagaaat   2460
ctgctgtacg tggtggtcat cgactctaag ggcaacatcc tggagcagat ctccctgaac   2520
tctatcatca ataaggagta cgacatcgag acagattatc acgcactgct ggatgagagg   2580
gagggcggca gagataaggc ccggaaggac tggaacaccg tggagaatat cagggacctg   2640
aaggccggct acctgagcca ggtggtgaac gtggtggcca agctggtgct gaagtataat   2700
gccatcatct gcctggagga cctgaacttt ggcttcaaga ggggccgcca gaaggtggag   2760
aagcaggtgt accagaagtt cgagaagatg ctgatcgata agctgaatta cctggtcatc   2820
gacaagagcc gcgagcagac atcccctaag gagctgggag gcgccctgaa cgcactgcag   2880
ctgacctcta agttcaagag ctttaaggag ctgggcaagc agtccggcgt gatctactat   2940
gtgcctgcct acctgacctc taagatcgat ccaaccacag gcttcgccaa tctgttttat   3000
atgaagtgtg agaacgtgga gaagtccaag agattctttg acggctttga tttcatcagg   3060
ttcaacgccc tggagaacgt gttcgagttc ggctttgact accggagctt cacccagagg   3120
gcctgcggca tcaattccaa gtggaccgtg tgcaccaacg gcgagcgcat catcaagtat   3180
cggaatccag ataagaacaa tatgttcgac gagaaggtgg tggtggtgac cgatgagatg   3240
aagaacctgt ttgagcagta caagatcccc tatgaggatg gcagaaatgt gaaggacatg   3300
atcatcagca acgaggaggc cgagttctac cggagactgt ataggctgct gcagcagacc   3360
ctgcagatga gaaacagcac ctccgacggc acaagggatt acatcatctc ccctgtgaag   3420
aataagagag aggcctactt caacagcgag ctgtccgacg gctctgtgcc aaaggacgcc   3480
gatgccaacg gcgcctacaa tatcgccaga aagggcctgt gggtgctgga gcagatcagg   3540
cagaagagcg agggcgagaa gatcaatctg gccatgacca acgccgagtg gctggagtat   3600
gcccagacac acctgctgaa aaggccggcg gccacgaaaa aggccggcca ggcaaaaaag   3660
aaaaagggat cctacccata cgatgttcca gattacgctt atccctacga cgtgcctgat   3720
tatgcatacc catatgatgt ccccgactat gcctaa                              3756
```

<210> SEQ ID NO 29
<211> LENGTH: 1283
<212> TYPE: PRT
<213> ORGANISM: Artificial Sequence
<220> FEATURE:
<223> OTHER INFORMATION: Candidatus Methanoplasma termitum (CMtCpf1;

pY012), including NLS and HA tag

<400> SEQUENCE: 29

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95

Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Glu Val Phe Ser
    210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Glu Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
    290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
        355                 360                 365

Arg Glu Tyr Lys Ala Asp Ser Ile Asn Asp Ile Asn Leu Glu Arg Thr
    370                 375                 380

Cys Lys Lys Val Asp Lys Trp Leu Asp Ser Lys Glu Phe Ala Leu Ser
385                 390                 395                 400

```
Asp Val Leu Glu Ala Ile Lys Arg Thr Gly Asn Asn Asp Ala Phe Asn
                405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
        435                 440                 445

Ser Ile His Ile Ile Lys Thr Leu Leu Asp Ser Val Gln Gln Phe Leu
    450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
        515                 520                 525

Gly Trp Asp Gln Asn Lys Val Tyr Asp Tyr Ala Ser Leu Ile Phe Leu
    530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Pro Arg Val
            580                 585                 590

Phe Leu Thr Ser Thr Lys Gly Lys Lys Glu Tyr Lys Pro Ser Lys Glu
        595                 600                 605

Ile Ile Glu Gly Tyr Glu Ala Asp Lys His Ile Arg Gly Asp Lys Phe
    610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
            660                 665                 670

Gly Tyr Arg Met His Phe Glu Asn Ile Ser Ala Glu Thr Ile Asp Glu
        675                 680                 685

Tyr Val Glu Lys Gly Asp Leu Phe Leu Phe Gln Ile Tyr Asn Lys Asp
    690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Val Lys Leu
                725                 730                 735

Asn Gly Glu Ala Glu Leu Phe Tyr Arg Asp Lys Ser Asp Ile Lys Glu
            740                 745                 750

Ile Val His Arg Glu Gly Glu Ile Leu Val Asn Arg Thr Tyr Asn Gly
        755                 760                 765

Arg Thr Pro Val Pro Asp Lys Ile His Lys Lys Leu Thr Asp Tyr His
    770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
```

```
            820                 825                 830

Ala Asn Gly Lys Lys Asn Leu Asn Lys Met Val Ile Glu Lys Phe Leu
        835                 840                 845

Ser Asp Glu Lys Ala His Ile Ile Gly Ile Asp Arg Gly Glu Arg Asn
    850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910

Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
    930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
            980                 985                 990

Tyr Gln Leu Thr Asn Pro Leu Glu  Ser Phe Ala Lys Leu  Gly Lys Gln
        995                 1000                1005

Thr Gly  Ile Leu Phe Tyr Val  Pro Ala Ala Tyr Thr  Ser Lys Ile
    1010                1015                1020

Asp Pro  Thr Thr Gly Phe Val  Asn Leu Phe Asn Thr  Ser Ser Lys
    1025                1030                1035

Thr Asn  Ala Gln Glu Arg Lys  Glu Phe Leu Gln Lys  Phe Glu Ser
    1040                1045                1050

Ile Ser  Tyr Ser Ala Lys Asp  Gly Gly Ile Phe Ala  Phe Ala Phe
    1055                1060                1065

Asp Tyr  Arg Lys Phe Gly Thr  Ser Lys Thr Asp His  Lys Asn Val
    1070                1075                1080

Trp Thr  Ala Tyr Thr Asn Gly  Glu Arg Met Arg Tyr  Ile Lys Glu
    1085                1090                1095

Lys Lys  Arg Asn Glu Leu Phe  Asp Pro Ser Lys Glu  Ile Lys Glu
    1100                1105                1110

Ala Leu  Thr Ser Ser Gly Ile  Lys Tyr Asp Gly Gly  Gln Asn Ile
    1115                1120                1125

Leu Pro  Asp Ile Leu Arg Ser  Asn Asn Asn Gly Leu  Ile Tyr Thr
    1130                1135                1140

Met Tyr  Ser Ser Phe Ile Ala  Ala Ile Gln Met Arg  Val Tyr Asp
    1145                1150                1155

Gly Lys  Glu Asp Tyr Ile Ile  Ser Pro Ile Lys Asn  Ser Lys Gly
    1160                1165                1170

Glu Phe  Phe Arg Thr Asp Pro  Lys Arg Arg Glu Leu  Pro Ile Asp
    1175                1180                1185

Ala Asp  Ala Asn Gly Ala Tyr  Asn Ile Ala Leu Arg  Gly Glu Leu
    1190                1195                1200

Thr Met  Arg Ala Ile Ala Glu  Lys Phe Asp Pro Asp  Ser Glu Lys
    1205                1210                1215

Met Ala  Lys Leu Glu Leu Lys  His Lys Asp Trp Phe  Glu Phe Met
    1220                1225                1230
```

```
Gln Thr  Arg Gly Asp Lys Arg  Pro Ala Ala Thr Lys  Lys Ala Gly
    1235                 1240                 1245

Gln Ala  Lys Lys Lys Lys Gly  Ser Tyr Pro Tyr Asp  Val Pro Asp
    1250                 1255                 1260

Tyr Ala  Tyr Pro Tyr Asp Val  Pro Asp Tyr Ala Tyr  Pro Tyr Asp
    1265                 1270                 1275

Val Pro  Asp Tyr Ala
    1280


<210> SEQ ID NO 30
<211> LENGTH: 3852
<212> TYPE: DNA
<213> ORGANISM: Artificial Sequence
<220> FEATURE:
<223> OTHER INFORMATION: Candidatus Methanoplasma termitum (CMtCpf1;
      pY012), including NLS and HA tag

<400> SEQUENCE: 30

atgaacaatt acgacgagtt caccaagctg tatcctatcc agaaaaccat ccggtttgag     60

ctgaagccac agggcagaac catggagcac ctggagacat tcaacttctt tgaggaggac    120

cgggatagag ccgagaagta taagatcctg aaggaggcca tcgacgagta ccacaagaag    180

tttatcgatg agcacctgac caatatgtcc ctggattgga actctctgaa gcagatcagc    240

gagaagtact ataagagcag ggaggagaag gacaagaagg tgttcctgtc cgagcagaag    300

aggatgcgcc aggagatcgt gtctgagttt aagaaggacg atcgcttcaa ggacctgttt    360

tccaagaagc tgttctctga gctgctgaag gaggagatct acaagaaggg caaccaccag    420

gagatcgacg ccctgaagag cttcgataag ttttccggct atttcatcgg cctgcacgag    480

aataggaaga acatgtactc cgacggcgat gagatcaccg ccatctccaa tcgcatcgtg    540

aatgagaact tccccaagtt tctggataac ctgcagaagt accaggaggc caggaagaag    600

tatcctgagt ggatcatcaa ggccgagagc gccctggtgg cccacaatat caagatggac    660

gaggtgttct ccctggagta ctttaataag gtgctgaacc aggagggcat ccagcggtac    720

aacctggccc tgggcggcta tgtgaccaag agcggcgaga agatgatggg cctgaatgat    780

gccctgaacc tggcccacca gtccgagaag agctccaagg gcagaatcca catgaccccc    840

ctgttcaagc agatcctgtc cgagaaggag tccttctctt acatccccga cgtgtttaca    900

gaggattctc agctgctgcc tagcatcggc ggcttctttg cccagatcga gaatgacaag    960

gatggcaaca tcttcgaccg ggccctggag ctgatctcta gctacgccga gtatgatacc   1020

gagcggatct atatcagaca ggccgacatc aatagagtgt ccaacgtgat ctttggagag   1080

tggggcaccc tgggaggcct gatgagggag tacaaggccg actctatcaa tgatatcaac   1140

ctggagcgca catgcaagaa ggtggacaag tggctggatt ctaaggagtt tgccctgagc   1200

gatgtgctgg aggccatcaa gaggaccggc aacaatgacg ccttcaacga gtatatctcc   1260

aagatgcgga cagccagaga gaagatcgat gccgcccgca aggagatgaa gttcatcagc   1320

gagaagatct ccggcgatga ggagtctatc cacatcatca agaccctgct ggacagcgtg   1380

cagcagttcc tgcacttctt taatctgttt aaggcaaggc aggacatccc actggatgga   1440

gccttctacg ccgagtttga cgaggtgcac agcaagctgt ttgccatcgt gcccctgtat   1500

aacaaggtgc ggaactatct gaccaagaac aatctgaaca caaagaagat caagctgaat   1560

ttcaagaacc ctacactggc caatggctgg gaccagaaca aggtgtacga ttatgcctcc   1620

ctgatctttc tgcgggacgg caattactat ctgggcatca tcaatcctaa gagaaagaag   1680
```

-continued

```
aacatcaagt tcgagcaggg ctctggcaac ggccccttct accggaagat ggtgtataag   1740
cagatccccg gccctaataa gaacctgcca agagtgttcc tgacctccac aaagggcaag   1800
aaggagtata agccctctaa ggagatcatc gagggctacg aggccgacaa gcacatcagg   1860
ggcgataagt tcgacctgga tttttgtcac aagctgatcg atttctttaa ggagtccatc   1920
gagaagcaca aggactggtc taagttcaac ttctacttca gcccaaccga gagctatggc   1980
gacatctctg agttctacct ggatgtggag aagcagggct atcgcatgca ctttgagaat   2040
atcagcgccg agacaatcga cgagtatgtg gagaagggcg atctgtttct gttccagatc   2100
tacaacaagg attttgtgaa ggccgccacc ggcaagaagg acatgcacac aatctactgg   2160
aatgccgcct tcagccccga gaacctgcag gacgtggtgg tgaagctgaa cggcgaggcc   2220
gagctgtttt atagggacaa gtccgatatc aaggagatcg tgcaccgcga gggcgagatc   2280
ctggtgaata ggacctacaa cggccgcaca ccagtgcccg acaagatcca caagaagctg   2340
accgattatc acaatggccg gacaaaggac ctgggcgagg ccaaggagta cctggataag   2400
gtgagatact tcaaggccca ctatgacatc accaaggatc ggagatacct gaacgacaag   2460
atctatttcc acgtgcctct gaccctgaac ttcaaggcca acggcaagaa gaatctgaac   2520
aagatggtca tcgagaagtt cctgtccgat gagaaggccc acatcatcgg catcgacagg   2580
ggcgagcgca atctgctgta ctattccatc atcgacaggt ctggcaagat catcgatcag   2640
cagagcctga atgtgatcga cggctttgat tatcgggaga agctgaacca gagagagatc   2700
gagatgaagg atgcccgcca gtcttggaac gccatcggca agatcaagga cctgaaggag   2760
ggctacctga gcaaggccgt gcacgagatc accaagatgg ccatccagta taatgccatc   2820
gtggtcatgg aggagctgaa ctacggcttc aagcggggcc ggttcaaggt ggagaagcag   2880
atctatcaga agttcgagaa tatgctgatc gataagatga actacctggt gtttaaggac   2940
gcacctgatg agtccccagg aggcgtgctg aatgcctacc agctgacaaa cccactggag   3000
tctttcgcca agctgggcaa gcagaccggc atcctgtttt acgtgccagc cgcctataca   3060
tccaagatcg accccaccac aggcttcgtg aatctgttta acacctcctc taagacaaac   3120
gcccaggagc ggaaggagtt cctgcagaag tttgagagca tctcctattc tgccaaggat   3180
ggcggcatct ttgccttcgc ctttgactac agaaagttcg gcaccagcaa gacagatcac   3240
aagaacgtgt ggaccgccta tacaaacggc gagaggatgc gctacatcaa ggagaagaag   3300
cggaatgagc tgtttgaccc ttctaaggag atcaaggagg ccctgaccag ctccggcatc   3360
aagtacgatg gcggccagaa catcctgcca gacatcctga ggagcaacaa taacggcctg   3420
atctacacaa tgtattctag cttcatcgcc gccatccaga tgcgcgtgta cgacggcaag   3480
gaggattata tcatcagccc catcaagaac tccaagggcg agttctttag gaccgacccc   3540
aagaggcgcg agctgcctat cgacgccgat gccaatggcg cctacaacat cgccctgagg   3600
ggagagctga caatgagggc aatcgcagag aagttcgacc ctgatagcga gaagatggcc   3660
aagctggagc tgaagcacaa ggattggttc gagtttatgc agaccagagg cgacaaaagg   3720
ccggcggcca cgaaaaaggc cggccaggca aaaaagaaaa agggatccta cccatacgat   3780
gttccagatt acgcttatcc ctacgacgtg cctgattatg catacccata tgatgtcccc   3840
gactatgcct aa                                                       3852
```

<210> SEQ ID NO 31
<211> LENGTH: 1327
<212> TYPE: PRT

<213> ORGANISM: Artificial Sequence
<220> FEATURE:
<223> OTHER INFORMATION: Eubacterium eligens (EeCpf1; pY013), including
NLS and HA tag

<400> SEQUENCE: 31

```
Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
        35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
        115                 120                 125

Lys Leu Leu Lys Glu Ile Leu Pro Asp Phe Ile Lys Asn Tyr Asn Gln
    130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
            180                 185                 190

His Glu Asn Ser Leu Ile Phe Leu Ala Asn Met Thr Ser Tyr Lys Lys
        195                 200                 205

Ile Ser Glu Lys Ala Leu Asp Glu Ile Glu Val Ile Glu Lys Asn Asn
    210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
        275                 280                 285

Leu Ala Tyr Thr Ser Thr Ser Phe Glu Val Pro Lys Met Phe Glu Asp
    290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                325                 330                 335

Glu Leu Asp Glu Lys Arg Ile Tyr Ile Ser Lys Asp Phe Tyr Glu Thr
            340                 345                 350

Leu Ser Cys Phe Met Ser Gly Asn Trp Asn Leu Ile Thr Gly Cys Val
        355                 360                 365

Glu Asn Phe Tyr Asp Glu Asn Ile His Ala Lys Gly Lys Ser Lys Glu
    370                 375                 380
```

```
Glu Lys Val Lys Lys Ala Val Lys Glu Asp Lys Tyr Lys Ser Ile Asn
385                 390                 395                 400

Asp Val Asn Asp Leu Val Glu Lys Tyr Ile Asp Glu Lys Glu Arg Asn
                405                 410                 415

Glu Phe Lys Asn Ser Asn Ala Lys Gln Tyr Ile Arg Glu Ile Ser Asn
            420                 425                 430

Ile Ile Thr Asp Thr Glu Thr Ala His Leu Glu Tyr Asp Asp His Ile
        435                 440                 445

Ser Leu Ile Glu Ser Glu Glu Lys Ala Asp Glu Met Lys Lys Arg Leu
    450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                485                 490                 495

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
        515                 520                 525

Gln Ser Pro Thr Leu Ala Asn Gly Trp Ser Gln Ser Lys Glu Phe Asp
    530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
            580                 585                 590

Pro Gly Ala Asn Lys Met Leu Pro Lys Val Phe Leu Ser Lys Lys Gly
        595                 600                 605

Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
        675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Lys Asp Ile Ile Ile Lys Leu Asn Gly Gln Ala Glu Leu
            740                 745                 750

Phe Tyr Arg Arg Ala Ser Val Lys Asn Pro Val Lys His Lys Lys Asp
        755                 760                 765

Ser Val Leu Val Asn Lys Thr Tyr Lys Asn Gln Leu Asp Asn Gly Asp
    770                 775                 780

Val Val Arg Ile Pro Ile Pro Asp Asp Ile Tyr Asn Glu Ile Tyr Lys
785                 790                 795                 800

Met Tyr Asn Gly Tyr Ile Lys Glu Ser Asp Leu Ser Glu Ala Ala Lys
```

```
                805                 810                 815

Glu Tyr Leu Asp Lys Val Glu Val Arg Thr Ala Gln Lys Asp Ile Val
            820                 825                 830

Lys Asp Tyr Arg Tyr Thr Val Asp Lys Tyr Phe Ile His Thr Pro Ile
        835                 840                 845

Thr Ile Asn Tyr Lys Val Thr Ala Arg Asn Asn Val Asn Asp Met Val
    850                 855                 860

Val Lys Tyr Ile Ala Gln Asn Asp Asp Ile His Val Ile Gly Ile Asp
865                 870                 875                 880

Arg Gly Glu Arg Asn Leu Ile Tyr Ile Ser Val Ile Asp Ser His Gly
                885                 890                 895

Asn Ile Val Lys Gln Lys Ser Tyr Asn Ile Leu Asn Asn Tyr Asp Tyr
            900                 905                 910

Lys Lys Lys Leu Val Glu Lys Glu Lys Thr Arg Glu Tyr Ala Arg Lys
        915                 920                 925

Asn Trp Lys Ser Ile Gly Asn Ile Lys Glu Leu Lys Glu Gly Tyr Ile
    930                 935                 940

Ser Gly Val Val His Glu Ile Ala Met Leu Ile Val Glu Tyr Asn Ala
945                 950                 955                 960

Ile Ile Ala Met Glu Asp Leu Asn Tyr Gly Phe Lys Arg Gly Arg Phe
                965                 970                 975

Lys Val Glu Arg Gln Val Tyr Gln Lys Phe Glu Ser Met Leu Ile Asn
            980                 985                 990

Lys Leu Asn Tyr Phe Ala Ser Lys  Glu Lys Ser Val Asp  Glu Pro Gly
        995                 1000                1005

Gly Leu  Leu Lys Gly Tyr Gln  Leu Thr Tyr Val Pro  Asp Asn Ile
    1010                 1015                 1020

Lys Asn  Leu Gly Lys Gln Cys  Gly Val Ile Phe Tyr  Val Pro Ala
    1025                 1030                 1035

Ala Phe  Thr Ser Lys Ile Asp  Pro Ser Thr Gly Phe  Ile Ser Ala
    1040                 1045                 1050

Phe Asn  Phe Lys Ser Ile Ser  Thr Asn Ala Ser Arg  Lys Gln Phe
    1055                 1060                 1065

Phe Met  Gln Phe Asp Glu Ile  Arg Tyr Cys Ala Glu  Lys Asp Met
    1070                 1075                 1080

Phe Ser  Phe Gly Phe Asp Tyr  Asn Asn Phe Asp Thr  Tyr Asn Ile
    1085                 1090                 1095

Thr Met  Gly Lys Thr Gln Trp  Thr Val Tyr Thr Asn  Gly Glu Arg
    1100                 1105                 1110

Leu Gln  Ser Glu Phe Asn Asn  Ala Arg Arg Thr Gly  Lys Thr Lys
    1115                 1120                 1125

Ser Ile  Asn Leu Thr Glu Thr  Ile Lys Leu Leu Leu  Glu Asp Asn
    1130                 1135                 1140

Glu Ile  Asn Tyr Ala Asp Gly  His Asp Ile Arg Ile  Asp Met Glu
    1145                 1150                 1155

Lys Met  Asp Glu Asp Lys Lys  Ser Glu Phe Phe Ala  Gln Leu Leu
    1160                 1165                 1170

Ser Leu  Tyr Lys Leu Thr Val  Gln Met Arg Asn Ser  Tyr Thr Glu
    1175                 1180                 1185

Ala Glu  Glu Gln Glu Asn Gly  Ile Ser Tyr Asp Lys  Ile Ile Ser
    1190                 1195                 1200

Pro Val  Ile Asn Asp Glu Gly  Glu Phe Phe Asp Ser  Asp Asn Tyr
    1205                 1210                 1215
```

```
Lys Glu  Ser Asp Asp Lys Glu  Cys Lys Met Pro Lys  Asp Ala Asp
    1220                 1225                 1230

Ala Asn  Gly Ala Tyr Cys Ile  Ala Leu Lys Gly Leu  Tyr Glu Val
    1235                 1240                 1245

Leu Lys  Ile Lys Ser Glu Trp  Thr Glu Asp Gly Phe  Asp Arg Asn
    1250                 1255                 1260

Cys Leu  Lys Leu Pro His Ala  Glu Trp Leu Asp Phe  Ile Gln Asn
    1265                 1270                 1275

Lys Arg  Tyr Glu Lys Arg Pro  Ala Ala Thr Lys Lys  Ala Gly Gln
    1280                 1285                 1290

Ala Lys  Lys Lys Lys Gly Ser  Tyr Pro Tyr Asp Val  Pro Asp Tyr
    1295                 1300                 1305

Ala Tyr  Pro Tyr Asp Val Pro  Asp Tyr Ala Tyr Pro  Tyr Asp Val
    1310                 1315                 1320

Pro Asp  Tyr Ala
    1325


<210> SEQ ID NO 32
<211> LENGTH: 3984
<212> TYPE: DNA
<213> ORGANISM: Artificial Sequence
<220> FEATURE:
<223> OTHER INFORMATION: Eubacterium eligens (EeCpf1; pY013), including
      NLS and HA tag

<400> SEQUENCE: 32

atgaacggca ataggtccat cgtgtaccgc gagttcgtgg gcgtgatccc cgtggccaag     60

accctgagga atgagctgcg ccctgtgggc cacacacagg agcacatcat ccagaacggc    120

ctgatccagg aggacgagct gcggcaggag aagagcaccg agctgaagaa catcatggac    180

gattactata gagagtacat cgataagtct ctgagcggcg tgaccgacct ggacttcacc    240

ctgctgttcg agctgatgaa cctggtgcag agctccccct ccaaggacaa taagaaggcc    300

ctggagaagg agcagtctaa gatgagggag cagatctgca cccacctgca gtccgactct    360

aactacaaga atatctttaa cgccaagctg ctgaaggaga tcctgcctga tttcatcaag    420

aactacaatc agtatgacgt gaaggataag gccggcaagc tggagacact ggccctgttt    480

aatggcttca gcacatactt taccgacttc tttgagaaga ggaagaacgt gttcaccaag    540

gaggccgtga gcacatccat cgcctaccgc atcgtgcacg agaactccct gatcttcctg    600

gccaatatga cctcttataa gaagatcagc gagaaggccc tggatgagat cgaagtgatc    660

gagaagaaca atcaggacaa gatgggcgat tgggagctga atcagatctt taaccctgac    720

ttctacaata tggtgctgat ccagtccggc atcgacttct acaacgagat ctgcggcgtg    780

gtgaatgccc acatgaacct gtactgtcag cagaccaaga acaattataa cctgttcaag    840

atgcggaagc tgcacaagca gatcctggcc tacaccagca ccagcttcga ggtgcccaag    900

atgttcgagg acgatatgag cgtgtataac gccgtgaacg ccttcatcga cgagacagag    960

aagggcaaca tcatcggcaa gctgaaggat atcgtgaata agtacgacga gctggatgag   1020

aagagaatct atatcagcaa ggacttttac gagacactga gctgcttcat gtccggcaac   1080

tggaatctga tcacaggctg cgtggagaac ttctacgatg agaacatcca cgccaagggc   1140

aagtccaagg aggagaaggt gaagaaggcc gtgaaggagg acaagtacaa gtctatcaat   1200

gacgtgaacg atctggtgga gaagtatatc gatgagaagg agaggaatga gttcaagaac   1260

agcaatgcca agcagtacat ccgcgagatc tccaacatca tcaccgacac agagacagcc   1320
```

cacctggagt atgacgatca catctctctg atcgagagcg aggagaaggc cgacgagatg 1380
aagaagcggc tggatatgta tatgaacatg taccactggg ccaaggcctt tatcgtggac 1440
gaggtgctgg acagagatga gatgttctac agcgatatcg acgatatcta taatatcctg 1500
gagaacatcg tgccactgta taatcgggtg agaaactacg tgacccagaa gccctacaac 1560
tctaagaaga tcaagctgaa tttccagagc cctacactgg ccaatggctg gtcccagtct 1620
aaggagttcg acaacaatgc catcatcctg atcagagata acaagtacta tctggccatc 1680
ttcaatgcca agaacaagcc agacaagaag atcatccagg gcaactccga taagaagaac 1740
gacaacgatt acaagaagat ggtgtataac ctgctgccag gcgccaacaa gatgctgccc 1800
aaggtgtttc tgtctaagaa gggcatcgag acattcaagc cctccgacta tatcatctct 1860
ggctacaacg cccacaagca catcaagaca agcgagaatt ttgatatctc cttctgtcgg 1920
gacctgatcg attacttcaa gaacagcatc gagaagcacg ccgagtggag aaagtatgag 1980
ttcaagtttt ccgccaccga cagctactcc gatatctctg agttctatcg ggaggtggag 2040
atgcagggct acagaatcga ctggacatat atcagcgagg ccgacatcaa caagctggat 2100
gaggagggca agatctatct gtttcagatc tacaataagg atttcgccga gaacagcacc 2160
ggcaaggaga atctgcacac aatgtacttt aagaacatct tctccgagga gaatctgaag 2220
gacatcatca tcaagctgaa cggccaggcc gagctgtttt atcggagagc ctctgtgaag 2280
aatcccgtga agcacaagaa ggatagcgtg ctggtgaaca agacctacaa gaatcagctg 2340
gacaacggcg acgtggtgag aatccccatc cctgacgata tctataacga gatctacaag 2400
atgtataatg gctacatcaa ggagtccgac ctgtctgagg ccgccaagga gtacctggat 2460
aaggtggagg tgaggaccgc ccagaaggac atcgtgaagg attaccgcta tacagtggac 2520
aagtacttca tccacacacc tatcaccatc aactataagg tgaccgcccg caacaatgtg 2580
aatgatatgg tggtgaagta catcgcccag aacgacgata tccacgtgat cggcatcgac 2640
cggggcgaga gaaacctgat ctacatctcc gtgatcgatt ctcacggcaa catcgtgaag 2700
cagaaatcct acaacatcct gaacaactac gactacaaga agaagctggt ggagaaggag 2760
aaaacccggg agtacgccag aaagaactgg aagagcatcg gcaatatcaa ggagctgaag 2820
gagggctata tctccggcgt ggtgcacgag atcgccatgc tgatcgtgga gtacaacgcc 2880
atcatcgcca tggaggacct gaattatggc tttaagaggg gccgcttcaa ggtggagcgg 2940
caggtgtacc agaagtttga gagcatgctg atcaataagc tgaactattt cgccagcaag 3000
gagaagtccg tggacgagcc aggaggcctg ctgaagggct atcagctgac ctacgtgccc 3060
gataatatca agaacctggg caagcagtgc ggcgtgatct tttacgtgcc tgccgccttc 3120
accagcaaga tcgacccatc cacaggcttt atctctgcct tcaactttaa gtctatcagc 3180
acaaatgcct ctcggaagca gttctttatg cagtttgacg agatcagata ctgtgccgag 3240
aaggatatgt tcagctttgg cttcgactac aacaacttcg atacctacaa catcacaatg 3300
ggcaagacac agtggaccgt gtatacaaac ggcgagagac tgcagtctga gttcaacaat 3360
gccaggcgca ccggcaagac aaagagcatc aatctgacag agacaatcaa gctgctgctg 3420
gaggacaatg agatcaacta cgccgacggc cacgatatca ggatcgatat ggagaagatg 3480
gacgaggata agaagagcga gttctttgcc cagctgctga gcctgtataa gctgaccgtg 3540
cagatgcgca attcctatac agaggccgag gagcaggaga acggcatctc ttacgacaag 3600
atcatcagcc ctgtgatcaa tgatgagggc gagttctttg actccgataa ctataaggag 3660

```
tctgacgata aggagtgcaa gatgccaaag gacgccgatg ccaacggcgc ctactgtatc   3720

gccctgaagg gcctgtatga ggtgctgaag atcaagagcg agtggaccga ggacggcttt   3780

gataggaatt gcctgaagct gccacacgca gagtggctgg acttcatcca gaacaagcgg   3840

tacgagaaaa ggccggcggc cacgaaaaag gccggccagg caaaaaagaa aaagggatcc   3900

tacccatacg atgttccaga ttacgcttat ccctacgacg tgcctgatta tgcataccca   3960

tatgatgtcc ccgactatgc ctaa                                          3984


<210> SEQ ID NO 33
<211> LENGTH: 1418
<212> TYPE: PRT
<213> ORGANISM: Artificial Sequence
<220> FEATURE:
<223> OTHER INFORMATION: Moraxella bovoculi 237 (MbCpf1; pY014),
      including NLS and HA tag

<400> SEQUENCE: 33

Met Leu Phe Gln Asp Phe Thr His Leu Tyr Pro Leu Ser Lys Thr Val
1               5                   10                  15

Arg Phe Glu Leu Lys Pro Ile Asp Arg Thr Leu Glu His Ile His Ala
            20                  25                  30

Lys Asn Phe Leu Ser Gln Asp Glu Thr Met Ala Asp Met His Gln Lys
        35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Glu Leu Gln Lys Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300
```

```
Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
        515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
    610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Asp Lys
705                 710                 715                 720
```

-continued

```
Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
    770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Asp
    930                 935                 940

Lys Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser  Lys Gly Glu Ile Leu  Glu Gln Cys
        995                 1000                1005

Ser Leu  Asn Asp Ile Thr Thr  Ala Ser Ala Asn Gly  Thr Gln Met
    1010                1015                1020

Thr Thr  Pro Tyr His Lys Ile  Leu Asp Lys Arg Glu  Ile Glu Arg
    1025                1030                1035

Leu Asn  Ala Arg Val Gly Trp  Gly Glu Ile Glu Thr  Ile Lys Glu
    1040                1045                1050

Leu Lys  Ser Gly Tyr Leu Ser  His Val Val His Gln  Ile Ser Gln
    1055                1060                1065

Leu Met  Leu Lys Tyr Asn Ala  Ile Val Val Leu Glu  Asp Leu Asn
    1070                1075                1080

Phe Gly  Phe Lys Arg Gly Arg  Phe Lys Val Glu Lys  Gln Ile Tyr
    1085                1090                1095

Gln Asn  Phe Glu Asn Ala Leu  Ile Lys Lys Leu Asn  His Leu Val
    1100                1105                1110

Leu Lys  Asp Lys Ala Asp Asp  Glu Ile Gly Ser Tyr  Lys Asn Ala
    1115                1120                1125

Leu Gln  Leu Thr Asn Asn Phe  Thr Asp Leu Lys Ser  Ile Gly Lys
```

```
    1130                1135                1140

Gln Thr  Gly Phe Leu Phe Tyr  Val Pro Ala Trp Asn  Thr Ser Lys
    1145                1150                1155

Ile Asp  Pro Glu Thr Gly Phe  Val Asp Leu Leu Lys  Pro Arg Tyr
    1160                1165                1170

Glu Asn  Ile Ala Gln Ser Gln  Ala Phe Phe Gly Lys  Phe Asp Lys
    1175                1180                1185

Ile Cys  Tyr Asn Ala Asp Lys  Asp Tyr Phe Glu Phe  His Ile Asp
    1190                1195                1200

Tyr Ala  Lys Phe Thr Asp Lys  Ala Lys Asn Ser Arg  Gln Ile Trp
    1205                1210                1215

Thr Ile  Cys Ser His Gly Asp  Lys Arg Tyr Val Tyr  Asp Lys Thr
    1220                1225                1230

Ala Asn  Gln Asn Lys Gly Ala  Ala Lys Gly Ile Asn  Val Asn Asp
    1235                1240                1245

Glu Leu  Lys Ser Leu Phe Ala  Arg His His Ile Asn  Glu Lys Gln
    1250                1255                1260

Pro Asn  Leu Val Met Asp Ile  Cys Gln Asn Asn Asp  Lys Glu Phe
    1265                1270                1275

His Lys  Ser Leu Met Tyr Leu  Leu Lys Thr Leu Leu  Ala Leu Arg
    1280                1285                1290

Tyr Ser  Asn Ala Ser Ser Asp  Glu Asp Phe Ile Leu  Ser Pro Val
    1295                1300                1305

Ala Asn  Asp Glu Gly Val Phe  Phe Asn Ser Ala Leu  Ala Asp Asp
    1310                1315                1320

Thr Gln  Pro Gln Asn Ala Asp  Ala Asn Gly Ala Tyr  His Ile Ala
    1325                1330                1335

Leu Lys  Gly Leu Trp Leu Leu  Asn Glu Leu Lys Asn  Ser Asp Asp
    1340                1345                1350

Leu Asn  Lys Val Lys Leu Ala  Ile Asp Asn Gln Thr  Trp Leu Asn
    1355                1360                1365

Phe Ala  Gln Asn Arg Lys Arg  Pro Ala Ala Thr Lys  Lys Ala Gly
    1370                1375                1380

Gln Ala  Lys Lys Lys Lys Gly  Ser Tyr Pro Tyr Asp  Val Pro Asp
    1385                1390                1395

Tyr Ala  Tyr Pro Tyr Asp Val  Pro Asp Tyr Ala Tyr  Pro Tyr Asp
    1400                1405                1410

Val Pro  Asp Tyr Ala
    1415
```

<210> SEQ ID NO 34
<211> LENGTH: 4257
<212> TYPE: DNA
<213> ORGANISM: Artificial Sequence
<220> FEATURE:
<223> OTHER INFORMATION: Moraxella bovoculi 237 (MbCpf1; pY014), including NLS and HA tag

<400> SEQUENCE: 34

```
atgctgttcc aggactttac ccacctgtat ccactgtcca agacagtgag atttgagctg     60

aagcccatcg ataggaccct ggagcacatc cacgccaaga acttcctgtc tcaggacgag    120

acaatggccg atatgcacca gaaggtgaaa gtgatcctgg acgattacca ccgcgacttc    180

atcgccgata tgatgggcga ggtgaagctg accaagctgg ccgagttcta tgacgtgtac    240

ctgaagtttc ggaagaaccc aaaggacgat gagctgcaga agcagctgaa ggatctgcag    300
```

gccgtgctga gaaaggagat cgtgaagccc atcggcaatg gcggcaagta taaggccggc 360
tacgacaggc tgttcggcgc caagctgttt aaggacggca aggagctggg cgatctggcc 420
aagttcgtga tcgcacagga gggagagagc tccccaaagc tggcccacct ggcccacttc 480
gagaagtttt ccacctattt cacaggcttt cacgataacc ggaagaatat gtattctgac 540
gaggataagc acaccgccat cgcctaccgc ctgatccacg agaacctgcc ccggtttatc 600
gacaatctgc agatcctgac cacaatcaag cagaagcact ctgccctgta cgatcagatc 660
atcaacgagc tgaccgccag cggcctggac gtgtctctgg ccagccacct ggatggctat 720
cacaagctgc tgacacagga gggcatcacc gcctacaata cactgctggg aggaatctcc 780
ggagaggcag gctctcctaa gatccagggc atcaacgagc tgatcaattc tcaccacaac 840
cagcactgcc acaagagcga gagaatcgcc aagctgaggc cactgcacaa gcagatcctg 900
tccgacggca tgagcgtgtc cttcctgccc tctaagtttg ccgacgatag cgagatgtgc 960
caggccgtga acgagttcta tcgccactac gccgacgtgt tcgccaaggt gcagagcctg 1020
ttcgacggct ttgacgatca ccagaaggat ggcatctacg tggagcacaa gaacctgaat 1080
gagctgtcca agcaggcctt cggcgacttt gcactgctgg gacgcgtgct ggacggatac 1140
tatgtggatg tggtgaatcc agagttcaac gagcggtttg ccaaggccaa gaccgacaat 1200
gccaaggcca agctgacaaa ggagaaggat aagttcatca agggcgtgca ctccctggcc 1260
tctctggagc aggccatcga gcactatacc gcaaggcacg acgatgagag cgtgcaggca 1320
ggcaagctgg gacagtactt caagcacggc ctggccggag tggacaaccc catccagaag 1380
atccacaaca atcacagcac catcaagggc tttctggaga gggagcgccc tgcaggagag 1440
agagccctgc caaagatcaa gtccggcaag aatcctgaga tgacacagct gaggcagctg 1500
aaggagctgc tggataacgc cctgaatgtg gcccacttcg ccaagctgct gaccacaaag 1560
accacactgg acaatcagga tggcaacttc tatggcgagt ttggcgtgct gtacgacgag 1620
ctggccaaga tccccaccct gtataacaag gtgagagatt acctgagcca gaagcctttc 1680
tccaccgaga agtacaagct gaactttggc aatccaacac tgctgaatgg ctgggacctg 1740
aacaaggaga aggataattt cggcgtgatc ctgcagaagg acggctgcta ctatctggcc 1800
ctgctggaca aggcccacaa gaaggtgttt gataacgccc ctaatacagg caagagcatc 1860
tatcagaaga tgatctataa gtacctggag gtgaggaagc agttccccaa ggtgttcttt 1920
tccaaggagg ccatcgccat caactaccac ccttctaagg agctggtgga gatcaaggac 1980
aagggccggc agagatccga cgatgagcgc ctgaagctgt atcggtttat cctggagtgt 2040
ctgaagatcc accctaagta cgataagaag ttcgagggcg ccatcggcga catccagctg 2100
tttaagaagg ataagaaggg cagagaggtg ccaatcagcg agaaggacct gttcgataag 2160
atcaacggca tcttttctag caagcctaag ctggagatgg aggacttctt tatcggcgag 2220
ttcaagaggt ataacccaag ccaggacctg gtggatcagt ataatatcta caagaagatc 2280
gactccaacg ataatcgcaa gaaggagaat ttctacaaca atcaccccaa gtttaagaag 2340
gatctggtgc ggtactatta cgagtctatg tgcaagcacg aggagtggga ggagagcttc 2400
gagttttcca agaagctgca ggacatcggc tgttacgtgg atgtgaacga gctgtttacc 2460
gagatcgaga cacggagact gaattataag atctccttct gcaacatcaa tgccgactac 2520
atcgatgagc tggtggagca gggccagctg tatctgttcc agatctacaa caaggacttt 2580
tccccaaagg cccacggcaa gcccaatctg cacaccctgt acttcaaggc cctgttttct 2640

```
gaggacaacc tggccgatcc tatctataag ctgaatggcg aggcccagat cttctacaga   2700

aaggcctccc tggacatgaa cgagacaaca atccacaggg ccggcgaggt gctggagaac   2760

aagaatcccg ataatcctaa gaagagacag ttcgtgtacg acatcatcaa ggataagagg   2820

tacacacagg acaagttcat gctgcacgtg ccaatcacca tgaactttgg cgtgcagggc   2880

atgacaatca aggagttcaa taagaaggtg aaccagtcta tccagcagta tgacgaggtg   2940

aacgtgatcg gcatcgatcg gggcgagaga cacctgctgt acctgaccgt gatcaatagc   3000

aagggcgaga tcctggagca gtgttccctg aacgacatca ccacagcctc tgccaatggc   3060

acacagatga ccacacctta ccacaagatc ctggataaga gggagatcga gcgcctgaac   3120

gcccgggtgg gatggggcga gatcgagaca atcaaggagc tgaagtctgg ctatctgagc   3180

cacgtggtgc accagatcag ccagctgatg ctgaagtaca acgccatcgt ggtgctggag   3240

gacctgaatt tcggctttaa gaggggccgc tttaaggtgg agaagcagat ctatcagaac   3300

ttcgagaatg ccctgatcaa gaagctgaac cacctggtgc tgaaggacaa ggccgacgat   3360

gagatcggct cttacaagaa tgccctgcag ctgaccaaca atttcacaga tctgaagagc   3420

atcggcaagc agaccggctt cctgttttat gtgcccgcct ggaacacctc taagatcgac   3480

cctgagacag gctttgtgga tctgctgaag ccaagatacg agaacatcgc ccagagccag   3540

gccttctttg gcaagttcga caagatctgc tataatgccg acaaggatta cttcgagttt   3600

cacatcgact acgccaagtt taccgataag gccaagaata gccgccagat ctggacaatc   3660

tgttcccacg gcgacaagcg gtacgtgtac gataagacag ccaaccagaa taagggcgcc   3720

gccaagggca tcaacgtgaa tgatgagctg aagtccctgt tcgcccgcca ccacatcaac   3780

gagaagcagc ccaacctggt catggacatc tgccagaaca atgataagga gtttcacaag   3840

tctctgatgt acctgctgaa aaccctgctg gccctgcggt acagcaacgc ctcctctgac   3900

gaggatttca tcctgtcccc cgtggcaaac gacgagggcg tgttctttaa tagcgccctg   3960

gccgacgata cacagcctca gaatgccgat gccaacggcg cctaccacat cgccctgaag   4020

ggcctgtggc tgctgaatga gctgaagaac tccgacgatc tgaacaaggt gaagctggcc   4080

atcgacaatc agacctggct gaatttcgcc cagaacagga aaaggccggc ggccacgaaa   4140

aaggccggcc aggcaaaaaa gaaaaaggga tcctacccat acgatgttcc agattacgct   4200

tatccctacg acgtgcctga ttatgcatac ccatatgatg tccccgacta tgcctaa      4257
```

```
<210> SEQ ID NO 35
<211> LENGTH: 1308
<212> TYPE: PRT
<213> ORGANISM: Artificial Sequence
<220> FEATURE:
<223> OTHER INFORMATION: Leptospira inadai (LiCpf1; pY015), including
      NLS and HA tag

<400> SEQUENCE: 35

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
        35                  40                  45

Ala Val Lys Lys Ile Ile Asp Lys Tyr His Arg Ala Tyr Ile Glu Glu
    50                  55                  60

Val Phe Asp Ser Val Leu His Gln Lys Lys Lys Lys Asp Lys Thr Arg
65                  70                  75                  80
```

-continued

```
Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
        115                 120                 125

Ser Glu Glu Val Ala Glu Lys Tyr Lys Asn Leu Phe Ser Lys Glu Leu
    130                 135                 140

Ile Arg Asn Glu Ile Glu Lys Phe Cys Glu Thr Asp Glu Glu Arg Lys
145                 150                 155                 160

Gln Val Ser Asn Phe Lys Ser Phe Thr Thr Tyr Phe Thr Gly Phe His
                165                 170                 175

Ser Asn Arg Gln Asn Ile Tyr Ser Asp Glu Lys Lys Ser Thr Ala Ile
            180                 185                 190

Gly Tyr Arg Ile Ile His Gln Asn Leu Pro Lys Phe Leu Asp Asn Leu
        195                 200                 205

Lys Ile Ile Glu Ser Ile Gln Arg Arg Phe Lys Asp Phe Pro Trp Ser
    210                 215                 220

Asp Leu Lys Lys Asn Leu Lys Lys Ile Asp Lys Asn Ile Lys Leu Thr
225                 230                 235                 240

Glu Tyr Phe Ser Ile Asp Gly Phe Val Asn Val Leu Asn Gln Lys Gly
                245                 250                 255

Ile Asp Ala Tyr Asn Thr Ile Leu Gly Gly Lys Ser Glu Glu Ser Gly
            260                 265                 270

Glu Lys Ile Gln Gly Leu Asn Glu Tyr Ile Asn Leu Tyr Arg Gln Lys
        275                 280                 285

Asn Asn Ile Asp Arg Lys Asn Leu Pro Asn Val Lys Ile Leu Phe Lys
    290                 295                 300

Gln Ile Leu Gly Asp Arg Glu Thr Lys Ser Phe Ile Pro Glu Ala Phe
305                 310                 315                 320

Pro Asp Asp Gln Ser Val Leu Asn Ser Ile Thr Glu Phe Ala Lys Tyr
                325                 330                 335

Leu Lys Leu Asp Lys Lys Lys Lys Ser Ile Ile Ala Glu Leu Lys Lys
            340                 345                 350

Phe Leu Ser Ser Phe Asn Arg Tyr Glu Leu Asp Gly Ile Tyr Leu Ala
        355                 360                 365

Asn Asp Asn Ser Leu Ala Ser Ile Ser Thr Phe Leu Phe Asp Asp Trp
    370                 375                 380

Ser Phe Ile Lys Lys Ser Val Ser Phe Lys Tyr Asp Glu Ser Val Gly
385                 390                 395                 400

Asp Pro Lys Lys Lys Ile Lys Ser Pro Leu Lys Tyr Glu Lys Glu Lys
                405                 410                 415

Glu Lys Trp Leu Lys Gln Lys Tyr Tyr Thr Ile Ser Phe Leu Asn Asp
            420                 425                 430

Ala Ile Glu Ser Tyr Ser Lys Ser Gln Asp Glu Lys Arg Val Lys Ile
        435                 440                 445

Arg Leu Glu Ala Tyr Phe Ala Glu Phe Lys Ser Lys Asp Asp Ala Lys
    450                 455                 460

Lys Gln Phe Asp Leu Leu Glu Arg Ile Glu Glu Ala Tyr Ala Ile Val
465                 470                 475                 480

Glu Pro Leu Leu Gly Ala Glu Tyr Pro Arg Asp Arg Asn Leu Lys Ala
                485                 490                 495
```

```
Asp Lys Lys Glu Val Gly Lys Ile Lys Asp Phe Leu Asp Ser Ile Lys
            500                 505                 510

Ser Leu Gln Phe Phe Leu Lys Pro Leu Leu Ser Ala Glu Ile Phe Asp
        515                 520                 525

Glu Lys Asp Leu Gly Phe Tyr Asn Gln Leu Glu Gly Tyr Tyr Glu Glu
    530                 535                 540

Ile Asp Ser Ile Gly His Leu Tyr Asn Lys Val Arg Asn Tyr Leu Thr
545                 550                 555                 560

Gly Lys Ile Tyr Ser Lys Glu Lys Phe Lys Leu Asn Phe Glu Asn Ser
                565                 570                 575

Thr Leu Leu Lys Gly Trp Asp Glu Asn Arg Glu Val Ala Asn Leu Cys
            580                 585                 590

Val Ile Phe Arg Glu Asp Gln Lys Tyr Tyr Leu Gly Val Met Asp Lys
        595                 600                 605

Glu Asn Asn Thr Ile Leu Ser Asp Ile Pro Lys Val Lys Pro Asn Glu
    610                 615                 620

Leu Phe Tyr Glu Lys Met Val Tyr Lys Leu Ile Pro Thr Pro His Met
625                 630                 635                 640

Gln Leu Pro Arg Ile Ile Phe Ser Ser Asp Asn Leu Ser Ile Tyr Asn
                645                 650                 655

Pro Ser Lys Ser Ile Leu Lys Ile Arg Glu Ala Lys Ser Phe Lys Glu
            660                 665                 670

Gly Lys Asn Phe Lys Leu Lys Asp Cys His Lys Phe Ile Asp Phe Tyr
        675                 680                 685

Lys Glu Ser Ile Ser Lys Asn Glu Asp Trp Ser Arg Phe Asp Phe Lys
    690                 695                 700

Phe Ser Lys Thr Ser Ser Tyr Glu Asn Ile Ser Glu Phe Tyr Arg Glu
705                 710                 715                 720

Val Glu Arg Gln Gly Tyr Asn Leu Asp Phe Lys Lys Val Ser Lys Phe
                725                 730                 735

Tyr Ile Asp Ser Leu Val Glu Asp Gly Lys Leu Tyr Leu Phe Gln Ile
            740                 745                 750

Tyr Asn Lys Asp Phe Ser Ile Phe Ser Lys Gly Lys Pro Asn Leu His
        755                 760                 765

Thr Ile Tyr Phe Arg Ser Leu Phe Ser Lys Glu Asn Leu Lys Asp Val
    770                 775                 780

Cys Leu Lys Leu Asn Gly Glu Ala Glu Met Phe Phe Arg Lys Lys Ser
785                 790                 795                 800

Ile Asn Tyr Asp Glu Lys Lys Lys Arg Glu Gly His His Pro Glu Leu
                805                 810                 815

Phe Glu Lys Leu Lys Tyr Pro Ile Leu Lys Asp Lys Arg Tyr Ser Glu
            820                 825                 830

Asp Lys Phe Gln Phe His Leu Pro Ile Ser Leu Asn Phe Lys Ser Lys
        835                 840                 845

Glu Arg Leu Asn Phe Asn Leu Lys Val Asn Glu Phe Leu Lys Arg Asn
    850                 855                 860

Lys Asp Ile Asn Ile Ile Gly Ile Asp Arg Gly Glu Arg Asn Leu Leu
865                 870                 875                 880

Tyr Leu Val Met Ile Asn Gln Lys Gly Glu Ile Leu Lys Gln Thr Leu
                885                 890                 895

Leu Asp Ser Met Gln Ser Gly Lys Gly Arg Pro Glu Ile Asn Tyr Lys
            900                 905                 910

Glu Lys Leu Gln Glu Lys Glu Ile Glu Arg Asp Lys Ala Arg Lys Ser
```

-continued

```
        915                 920                 925

Trp Gly Thr Val Glu Asn Ile Lys Glu Leu Lys Glu Gly Tyr Leu Ser
    930                 935                 940

Ile Val Ile His Gln Ile Ser Lys Leu Met Val Glu Asn Asn Ala Ile
945                 950                 955                 960

Val Val Leu Glu Asp Leu Asn Ile Gly Phe Lys Arg Gly Arg Gln Lys
                965                 970                 975

Val Glu Arg Gln Val Tyr Gln Lys Phe Glu Lys Met Leu Ile Asp Lys
            980                 985                 990

Leu Asn Phe Leu Val Phe Lys Glu  Asn Lys Pro Thr Glu  Pro Gly Gly
        995                 1000                1005

Val Leu  Lys Ala Tyr Gln Leu  Thr Asp Glu Phe Gln  Ser Phe Glu
    1010                1015                1020

Lys Leu  Ser Lys Gln Thr Gly  Phe Leu Phe Tyr Val  Pro Ser Trp
    1025                1030                1035

Asn Thr  Ser Lys Ile Asp Pro  Arg Thr Gly Phe Ile  Asp Phe Leu
    1040                1045                1050

His Pro  Ala Tyr Glu Asn Ile  Glu Lys Ala Lys Gln  Trp Ile Asn
    1055                1060                1065

Lys Phe  Asp Ser Ile Arg Phe  Asn Ser Lys Met Asp  Trp Phe Glu
    1070                1075                1080

Phe Thr  Ala Asp Thr Arg Lys  Phe Ser Glu Asn Leu  Met Leu Gly
    1085                1090                1095

Lys Asn  Arg Val Trp Val Ile  Cys Thr Thr Asn Val  Glu Arg Tyr
    1100                1105                1110

Phe Thr  Ser Lys Thr Ala Asn  Ser Ser Ile Gln Tyr  Asn Ser Ile
    1115                1120                1125

Gln Ile  Thr Glu Lys Leu Lys  Glu Leu Phe Val Asp  Ile Pro Phe
    1130                1135                1140

Ser Asn  Gly Gln Asp Leu Lys  Pro Glu Ile Leu Arg  Lys Asn Asp
    1145                1150                1155

Ala Val  Phe Phe Lys Ser Leu  Leu Phe Tyr Ile Lys  Thr Thr Leu
    1160                1165                1170

Ser Leu  Arg Gln Asn Asn Gly  Lys Lys Gly Glu Glu  Glu Lys Asp
    1175                1180                1185

Phe Ile  Leu Ser Pro Val Val  Asp Ser Lys Gly Arg  Phe Phe Asn
    1190                1195                1200

Ser Leu  Glu Ala Ser Asp Asp  Glu Pro Lys Asp Ala  Asp Ala Asn
    1205                1210                1215

Gly Ala  Tyr His Ile Ala Leu  Lys Gly Leu Met Asn  Leu Leu Val
    1220                1225                1230

Leu Asn  Glu Thr Lys Glu Glu  Asn Leu Ser Arg Pro  Lys Trp Lys
    1235                1240                1245

Ile Lys  Asn Lys Asp Trp Leu  Glu Phe Val Trp Glu  Arg Asn Arg
    1250                1255                1260

Lys Arg  Pro Ala Ala Thr Lys  Lys Ala Gly Gln Ala  Lys Lys Lys
    1265                1270                1275

Lys Gly  Ser Tyr Pro Tyr Asp  Val Pro Asp Tyr Ala  Tyr Pro Tyr
    1280                1285                1290

Asp Val  Pro Asp Tyr Ala Tyr  Pro Tyr Asp Val Pro  Asp Tyr Ala
    1295                1300                1305
```

<210> SEQ ID NO 36

```
<211> LENGTH: 3927
<212> TYPE: DNA
<213> ORGANISM: Artificial Sequence
<220> FEATURE:
<223> OTHER INFORMATION: Leptospira inadai (LiCpf1; pY015), including
      NLS and HA tag

<400> SEQUENCE: 36

atggaggact attccggctt tgtgaacatc tactctatcc agaaaaccct gaggttcgag     60

ctgaagccag tgggcaagac actggagcac atcgagaaga agggcttcct gaagaaggac    120

aagatccggg ccgaggatta caaggccgtg aagaagatca tcgataagta ccacagagcc    180

tatatcgagg aggtgtttga ttccgtgctg caccagaaga agaagaagga caagacccgc    240

ttttctacac agttcatcaa ggagatcaag gagttcagcg agctgtacta taagaccgag    300

aagaacatcc ccgacaagga gaggctggag gccctgagcg agaagctgcg caagatgctg    360

gtgggcgcct ttaagggcga gttctccgag gaggtggccg agaagtataa gaacctgttt    420

tctaaggagc tgatcaggaa tgagatcgag aagttctgcg agacagacga ggagcgcaag    480

caggtgtcta acttcaagag cttcaccaca tactttaccg gcttccactc caacaggcag    540

aatatctatt ccgacgagaa gaagtctaca gccatcggct accgcatcat ccaccagaac    600

ctgcctaagt tcctggataa tctgaagatc atcgagtcca tccagcggcg gttcaaggac    660

ttcccatggt ctgatctgaa gaagaacctg aagaagatcg ataagaatat caagctgacc    720

gagtacttca gcatcgacgg cttcgtgaac gtgctgaatc agaagggcat cgatgcctac    780

aacacaatcc tgggcggcaa gtccgaggag tctggcgaga agatccaggg cctgaacgag    840

tacatcaatc tgtatcggca gaagaacaat atcgacagaa agaacctgcc caatgtgaag    900

atcctgttta agcagatcct gggcgatagg gagacaaaga gctttatccc tgaggccttc    960

ccagacgatc agtccgtgct gaactctatc acagagttcg ccaagtacct gaagctggat   1020

aagaagaaga agagcatcat cgccgagctg aagaagtttc tgagctcctt caatcgctac   1080

gagctggacg gcatctatct ggccaacgat aatagcctgg cctctatcag caccttcctg   1140

tttgacgatt ggtcctttat caagaagtcc gtgtctttca agtatgacga gtccgtgggc   1200

gaccccaaga agaagatcaa gtctcccctg aagtacgaga aggagaagga gaagtggctg   1260

aagcagaagt actatacaat ctctttcctg aacgatgcca tcgagagcta ttccaagtct   1320

caggacgaga agagggtgaa gatccgcctg gaggcctact ttgccgagtt caagagcaag   1380

gacgatgcca agaagcagtt cgacctgctg gagaggatcg aggaggccta tgccatcgtg   1440

gagcctctgc tgggagcaga gtacccaagg gaccgcaacc tgaaggccga taagaaggaa   1500

gtgggcaaga tcaaggactt cctggatagc atcaagtccc tgcagttctt tctgaagcct   1560

ctgctgtccg ccgagatctt tgacgagaag gatctgggct tctacaatca gctggagggc   1620

tactatgagg agatcgattc tatcggccac ctgtataaca aggtgcggaa ttatctgacc   1680

ggcaagatct acagcaagga gaagtttaag ctgaacttcg agaacagcac cctgctgaag   1740

ggctgggacg agaaccggga ggtggccaat ctgtgcgtga tcttcagaga ggaccagaag   1800

tactatctgg gcgtgatgga taaggagaac aataccatcc tgtccgacat ccccaaggtg   1860

aagcctaacg agctgtttta cgagaagatg gtgtataagc tgatccccac acctcacatg   1920

cagctgcccc ggatcatctt ctctagcgac aacctgtcta tctataatcc tagcaagtcc   1980

atcctgaaga tcagagaggc caagagcttt aaggagggca agaacttcaa gctgaaggac   2040

tgtcacaagt ttatcgattt ctacaaggag tctatcagca agaatgagga ctggagcaga   2100
```

-continued ttcgacttca agttcagcaa gaccagcagc tacgagaaca tcagcgagtt ttaccgggag 2160
gtggagagac agggctataa cctggacttc aagaaggtgt ctaagttcta catcgacagc 2220
ctggtggagg atggcaagct gtacctgttc cagatctata acaaggactt ttctatcttc 2280
agcaagggca agcccaatct gcacaccatc tattttcggt ccctgttctc taaggagaac 2340
ctgaaggacg tgtgcctgaa gctgaatggc gaggccgaga tgttctttcg gaagaagtcc 2400
atcaactacg atgagaagaa gaagcgggag ggccaccacc ccgagctgtt tgagaagctg 2460
aagtatccta tcctgaagga caagagatac agcgaggata agtttcagtt ccacctgccc 2520
atcagcctga acttcaagtc caaggagcgg ctgaacttta atctgaaagt gaatgagttc 2580
ctgaagagaa acaaggacat caatatcatc ggcatcgatc ggggcgagag aaacctgctg 2640
tacctggtca tgatcaatca gaagggcgag atcctgaagc agaccctgct ggacagcatg 2700
cagtccggca agggccggcc tgagatcaac tacaaggaga agctgcagga gaaggagatc 2760
gagagggata aggcccgcaa gagctggggc acagtggaga atatcaagga gctgaaggag 2820
ggctatctgt ctatcgtgat ccaccagatc agcaagctga tggtggagaa caatgccatc 2880
gtggtgctgg aggacctgaa catcggcttt aagcggggca gacagaaggt ggagcggcag 2940
gtgtaccaga agttcgagaa gatgctgatc gataagctga actttctggt gttcaaggag 3000
aataagccaa ccgagccagg aggcgtgctg aaggcctatc agctgacaga cgagtttcag 3060
tctttcgaga agctgagcaa gcagaccggc tttctgttct acgtgccaag ctggaacacc 3120
tccaagatcg accccagaac aggctttatc gatttcctgc accctgccta cgagaatatc 3180
gagaaggcca agcagtggat caacaagttt gattccatca ggttcaattc taagatggac 3240
tggtttgagt tcaccgccga tacacgcaag ttttccgaga acctgatgct gggcaagaat 3300
cgggtgtggg tcatctgcac cacaaatgtg gagcggtact tcaccagcaa gaccgccaac 3360
agctccatcc agtacaatag catccagatc accgagaagc tgaaggagct gtttgtggac 3420
atccctttca gcaacggcca ggatctgaag ccagagatcc tgaggaagaa tgacgccgtg 3480
ttctttaaga gcctgctgtt ttacatcaag accacactgt ccctgcgcca gaacaatggc 3540
aagaagggcg aggaggagaa ggacttcatc ctgagcccag tggtggattc caagggccgg 3600
ttctttaact ctctggaggc cagcgacgat gagcccaagg acgccgatgc caatggcgcc 3660
taccacatcg ccctgaaggg cctgatgaac ctgctggtgc tgaatgagac aaaggaggag 3720
aacctgagca gaccaaagtg gaagatcaag aataaggact ggctggagtt cgtgtgggag 3780
aggaaccgca aaaggccggc ggccacgaaa aaggccggcc aggcaaaaaa gaaaaaggga 3840
tcctacccat acgatgttcc agattacgct tatccctacg acgtgcctga ttatgcatac 3900
ccatatgatg tccccgacta tgcctaa 3927

<210> SEQ ID NO 37
<211> LENGTH: 1273
<212> TYPE: PRT
<213> ORGANISM: Artificial Sequence
<220> FEATURE:
<223> OTHER INFORMATION: Lachnospiraceae bacterium ND2006 (LbCpf1; pY016), including NLS and HA tag

<400> SEQUENCE: 37

Met Ser Lys Leu Glu Lys Phe Thr Asn Cys Tyr Ser Leu Ser Lys Thr
1 5 10 15

Leu Arg Phe Lys Ala Ile Pro Val Gly Lys Thr Gln Glu Asn Ile Asp
20 25 30

Asn Lys Arg Leu Leu Val Glu Asp Glu Lys Arg Ala Glu Asp Tyr Lys
35 40 45

Gly Val Lys Lys Leu Leu Asp Arg Tyr Tyr Leu Ser Phe Ile Asn Asp
50 55 60

Val Leu His Ser Ile Lys Leu Lys Asn Leu Asn Asn Tyr Ile Ser Leu
65 70 75 80

Phe Arg Lys Lys Thr Arg Thr Glu Lys Glu Asn Lys Glu Leu Glu Asn
85 90 95

Leu Glu Ile Asn Leu Arg Lys Glu Ile Ala Lys Ala Phe Lys Gly Asn
100 105 110

Glu Gly Tyr Lys Ser Leu Phe Lys Lys Asp Ile Ile Glu Thr Ile Leu
115 120 125

Pro Glu Phe Leu Asp Asp Lys Asp Glu Ile Ala Leu Val Asn Ser Phe
130 135 140

Asn Gly Phe Thr Thr Ala Phe Thr Gly Phe Phe Asp Asn Arg Glu Asn
145 150 155 160

Met Phe Ser Glu Glu Ala Lys Ser Thr Ser Ile Ala Phe Arg Cys Ile
165 170 175

Asn Glu Asn Leu Thr Arg Tyr Ile Ser Asn Met Asp Ile Phe Glu Lys
180 185 190

Val Asp Ala Ile Phe Asp Lys His Glu Val Gln Glu Ile Lys Glu Lys
195 200 205

Ile Leu Asn Ser Asp Tyr Asp Val Glu Asp Phe Phe Glu Gly Glu Phe
210 215 220

Phe Asn Phe Val Leu Thr Gln Glu Gly Ile Asp Val Tyr Asn Ala Ile
225 230 235 240

Ile Gly Gly Phe Val Thr Glu Ser Gly Glu Lys Ile Lys Gly Leu Asn
245 250 255

Glu Tyr Ile Asn Leu Tyr Asn Gln Lys Thr Lys Gln Lys Leu Pro Lys
260 265 270

Phe Lys Pro Leu Tyr Lys Gln Val Leu Ser Asp Arg Glu Ser Leu Ser
275 280 285

Phe Tyr Gly Glu Gly Tyr Thr Ser Asp Glu Glu Val Leu Glu Val Phe
290 295 300

Arg Asn Thr Leu Asn Lys Asn Ser Glu Ile Phe Ser Ser Ile Lys Lys
305 310 315 320

Leu Glu Lys Leu Phe Lys Asn Phe Asp Glu Tyr Ser Ser Ala Gly Ile
325 330 335

Phe Val Lys Asn Gly Pro Ala Ile Ser Thr Ile Ser Lys Asp Ile Phe
340 345 350

Gly Glu Trp Asn Val Ile Arg Asp Lys Trp Asn Ala Glu Tyr Asp Asp
355 360 365

Ile His Leu Lys Lys Lys Ala Val Val Thr Glu Lys Tyr Glu Asp Asp
370 375 380

Arg Arg Lys Ser Phe Lys Lys Ile Gly Ser Phe Ser Leu Glu Gln Leu
385 390 395 400

Gln Glu Tyr Ala Asp Ala Asp Leu Ser Val Val Glu Lys Leu Lys Glu
405 410 415

Ile Ile Ile Gln Lys Val Asp Glu Ile Tyr Lys Val Tyr Gly Ser Ser
420 425 430

Glu Lys Leu Phe Asp Ala Asp Phe Val Leu Glu Lys Ser Leu Lys Lys
435 440 445

Asn Asp Ala Val Val Ala Ile Met Lys Asp Leu Leu Asp Ser Val Lys

```
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880
```

```
Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His Lys Arg  Pro Ala Ala
    1220                1225                1230

Thr Lys  Lys Ala Gly Gln Ala  Lys Lys Lys Lys Gly  Ser Tyr Pro
    1235                1240                1245

Tyr Asp  Val Pro Asp Tyr Ala  Tyr Pro Tyr Asp Val  Pro Asp Tyr
    1250                1255                1260

Ala Tyr  Pro Tyr Asp Val Pro  Asp Tyr Ala
    1265                1270
```

<210> SEQ ID NO 38
<211> LENGTH: 3822
<212> TYPE: DNA
<213> ORGANISM: Artificial Sequence
<220> FEATURE:
<223> OTHER INFORMATION: Lachnospiraceae bacterium ND2006 (LbCpf1; pY016), including NLS and HA tag

<400> SEQUENCE: 38

```
atgagcaagc tggagaagtt tacaaactgc tactccctgt ctaagaccct gaggttcaag     60
gccatccctg tgggcaagac ccaggagaac atcgacaata agcggctgct ggtggaggac    120
gagaagagag ccgaggatta taagggcgtg aagaagctgc tggatcgcta ctatctgtct    180
tttatcaacg acgtgctgca cagcatcaag ctgaagaatc tgaacaatta catcagcctg    240
ttccggaaga aaaccagaac cgagaaggag aataaggagc tggagaacct ggagatcaat    300
ctgcggaagg agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga gaagatcctg aacagcgact atgatgtgga ggatttcttt    660
gagggcgagt tctttaactt tgtgctgaca caggagggca tcgacgtgta taacgccatc    720
atcggcggct tcgtgaccga gagcggcgag aagatcaagg gcctgaacga gtacatcaac    780
ctgtataatc agaaaaccaa gcagaagctg cctaagttta agccactgta taagcaggtg    840
ctgagcgatc gggagtctct gagcttctac ggcgagggct atacatccga tgaggaggtg    900
ctggaggtgt ttagaaacac cctgaacaag aacagcgaga tcttcagctc catcaagaag    960
ctggagaagc tgttcaagaa ttttgacgag tactctagcg ccggcatctt tgtgaagaac   1020
ggccccgcca tcagcacaat ctccaaggat atcttcggcg agtggaacgt gatccgggac   1080
aagtggaatg ccgagtatga cgatatccac ctgaagaaga aggccgtggt gaccgagaag   1140
tacgaggacg atcggagaaa gtccttcaag aagatcggct ccttttctct ggagcagctg   1200
caggagtacg ccgacgccga tctgtctgtg gtggagaagc tgaaggagat catcatccag   1260
aaggtggatg agatctacaa ggtgtatggc tcctctgaga agctgttcga cgccgatttt   1320
gtgctggaga agagcctgaa gaagaacgac gccgtggtgg ccatcatgaa ggacctgctg   1380
gattctgtga agagcttcga gaattacatc aaggccttct ttggcgaggg caaggagaca   1440
aacagggacg agtccttcta tggcgatttt gtgctggcct acgacatcct gctgaaggtg   1500
gaccacatct acgatgccat ccgcaattat gtgacccaga agccctactc taaggataag   1560
ttcaagctgt attttcagaa ccctcagttc atgggcggct gggacaagga taaggagaca   1620
gactatcggg ccaccatcct gagatacggc tccaagtact atctggccat catggataag   1680
aagtacgcca agtgcctgca gaagatcgac aaggacgatg tgaacggcaa ttacgagaag   1740
atcaactata agctgctgcc cggccctaat aagatgctgc caaaggtgtt cttttctaag   1800
aagtggatgg cctactataa ccccagcgag gacatccaga agatctacaa gaatggcaca   1860
ttcaagaagg gcgatatgtt taacctgaat gactgtcaca agctgatcga cttctttaag   1920
gatagcatct cccggtatcc aaagtggtcc aatgcctacg atttcaactt ttctgagaca   1980
gagaagtata aggacatcgc cggcttttac agagaggtgg aggagcaggg ctataaggtg   2040
```

```
agcttcgagt ctgccagcaa gaaggaggtg gataagctgg tggaggaggg caagctgtat   2100

atgttccaga tctataacaa ggacttttcc gataagtctc acggcacacc caatctgcac   2160

accatgtact tcaagctgct gtttgacgag aacaatcacg gacagatcag gctgagcgga   2220

ggagcagagc tgttcatgag gcgcgcctcc ctgaagaagg aggagctggt ggtgcaccca   2280

gccaactccc ctatcgccaa caagaatcca gataatccca agaaaaccac aaccctgtcc   2340

tacgacgtgt ataaggataa gaggttttct gaggaccagt acgagctgca catcccaatc   2400

gccatcaata agtgccccaa gaacatcttc aagatcaata cagaggtgcg cgtgctgctg   2460

aagcacgacg ataaccccta tgtgatcggc atcgataggg gcgagcgcaa tctgctgtat   2520

atcgtggtgg tggacggcaa gggcaacatc gtggagcagt attccctgaa cgagatcatc   2580

aacaacttca acggcatcag gatcaagaca gattaccact ctctgctgga caagaaggag   2640

aaggagaggt tcgaggcccg ccagaactgg acctccatcg agaatatcaa ggagctgaag   2700

gccggctata tctctcaggt ggtgcacaag atctgcgagc tggtggagaa gtacgatgcc   2760

gtgatcgccc tggaggacct gaactctggc tttaagaata gccgcgtgaa ggtggagaag   2820

caggtgtatc agaagttcga gaagatgctg atcgataagc tgaactacat ggtggacaag   2880

aagtctaatc cttgtgcaac aggcggcgcc ctgaagggct atcagatcac caataagttc   2940

gagagcttta agtccatgtc tacccagaac ggcttcatct tttacatccc tgcctggctg   3000

acatccaaga tcgatccatc taccggcttt gtgaacctgc tgaaaaccaa gtataccagc   3060

atcgccgatt ccaagaagtt catcagctcc tttgacagga tcatgtacgt gcccgaggag   3120

gatctgttcg agtttgccct ggactataag aacttctctc gcacagacgc cgattacatc   3180

aagaagtgga agctgtactc ctacggcaac cggatcagaa tcttccggaa tcctaagaag   3240

aacaacgtgt tcgactggga ggaggtgtgc ctgaccagcg cctataagga gctgttcaac   3300

aagtacggca tcaattatca gcagggcgat atcagagccc tgctgtgcga gcagtccgac   3360

aaggccttct actctagctt tatggccctg atgagcctga tgctgcagat gcggaacagc   3420

atcacaggcc gcaccgacgt ggattttctg atcagccctg tgaagaactc cgacggcatc   3480

ttctacgata gccggaacta tgaggcccag gagaatgcca tcctgccaaa gaacgccgac   3540

gccaatggcg cctataacat cgccagaaag gtgctgtggg ccatcggcca gttcaagaag   3600

gccgaggacg agaagctgga taaggtgaag atcgccatct ctaacaagga gtggctggag   3660

tacgcccaga ccagcgtgaa gcacaaaagg ccggcggcca cgaaaaaggc cggccaggca   3720

aaaaagaaaa agggatccta cccatacgat gttccagatt acgcttatcc ctacgacgtg   3780

cctgattatg catacccata tgatgtcccc gactatgcct aa                      3822
```

<210> SEQ ID NO 39
<211> LENGTH: 1305
<212> TYPE: PRT
<213> ORGANISM: Artificial Sequence
<220> FEATURE:
<223> OTHER INFORMATION: Porphyromonas crevioricanis (PcCpf1; pY017), including NLS and HA tag

<400> SEQUENCE: 39

```
Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30

Lys Ala Gly Ile Leu Lys Glu Asp Glu His Arg Ala Glu Ser Tyr Arg
        35                  40                  45
```

-continued

```
Arg Val Lys Lys Ile Ile Asp Thr Tyr His Lys Val Phe Ile Asp Ser
    50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
    290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
            340                 345                 350

Thr Gln Gln Leu Met Thr Ser Ile Ser Glu Tyr Asp Leu Ser Arg Ile
        355                 360                 365

Tyr Val Arg Asn Asp Ser Gln Leu Thr Asp Ile Ser Lys Lys Met Leu
    370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
            420                 425                 430

Cys Ile Ala Phe Leu Asp Asn Val Arg Asp Cys Arg Val Asp Thr Tyr
        435                 440                 445

Leu Ser Thr Leu Gly Gln Lys Glu Gly Pro His Gly Leu Ser Asn Leu
    450                 455                 460
```

-continued

```
Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
            500                 505                 510

Leu Lys Pro Leu Trp Gly Met Gly Asp Glu Pro Asp Lys Asp Glu Arg
        515                 520                 525

Phe Tyr Gly Glu Tyr Asn Tyr Ile Arg Gly Ala Leu Asp Gln Val Ile
    530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605

Phe Glu Asn Lys Met Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670

Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
        835                 840                 845

Asn Phe Lys Cys Ser Ala Gly Ser Lys Val Asn Asp Met Val Asn Ala
    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
```

-continued

```
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
        915                 920                 925

Gln Thr Ile Glu Gly Ile Lys Glu Leu Lys Gln Gly Tyr Leu Ser Gln
    930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990

Asn Tyr Leu Val Asp Lys Lys Lys  Arg Pro Glu Asp Ile  Gly Gly Leu
        995                 1000                1005

Leu Arg  Ala Tyr Gln Phe Thr  Ala Pro Phe Lys Ser  Phe Lys Glu
    1010                1015                1020

Met Gly  Lys Gln Asn Gly Phe  Leu Phe Tyr Ile Pro  Ala Trp Asn
    1025                1030                1035

Thr Ser  Asn Ile Asp Pro Thr  Thr Gly Phe Val Asn  Leu Phe His
    1040                1045                1050

Val Gln  Tyr Glu Asn Val Asp  Lys Ala Lys Ser Phe  Phe Gln Lys
    1055                1060                1065

Phe Asp  Ser Ile Ser Tyr Asn  Pro Lys Lys Asp Trp  Phe Glu Phe
    1070                1075                1080

Ala Phe  Asp Tyr Lys Asn Phe  Thr Lys Lys Ala Glu  Gly Ser Arg
    1085                1090                1095

Ser Met  Trp Ile Leu Cys Thr  His Gly Ser Arg Ile  Lys Asn Phe
    1100                1105                1110

Arg Asn  Ser Gln Lys Asn Gly  Gln Trp Asp Ser Glu  Glu Phe Ala
    1115                1120                1125

Leu Thr  Glu Ala Phe Lys Ser  Leu Phe Val Arg Tyr  Glu Ile Asp
    1130                1135                1140

Tyr Thr  Ala Asp Leu Lys Thr  Ala Ile Val Asp Glu  Lys Gln Lys
    1145                1150                1155

Asp Phe  Phe Val Asp Leu Leu  Lys Leu Phe Lys Leu  Thr Val Gln
    1160                1165                1170

Met Arg  Asn Ser Trp Lys Glu  Lys Asp Leu Asp Tyr  Leu Ile Ser
    1175                1180                1185

Pro Val  Ala Gly Ala Asp Gly  Arg Phe Phe Asp Thr  Arg Glu Gly
    1190                1195                1200

Asn Lys  Ser Leu Pro Lys Asp  Ala Asp Ala Asn Gly  Ala Tyr Asn
    1205                1210                1215

Ile Ala  Leu Lys Gly Leu Trp  Ala Leu Arg Gln Ile  Arg Gln Thr
    1220                1225                1230

Ser Glu  Gly Gly Lys Leu Lys  Leu Ala Ile Ser Asn  Lys Glu Trp
    1235                1240                1245

Leu Gln  Phe Val Gln Glu Arg  Ser Tyr Glu Lys Asp  Lys Arg Pro
    1250                1255                1260

Ala Ala  Thr Lys Lys Ala Gly  Gln Ala Lys Lys Lys  Lys Gly Ser
    1265                1270                1275

Tyr Pro  Tyr Asp Val Pro Asp  Tyr Ala Tyr Pro Tyr  Asp Val Pro
    1280                1285                1290
```

Asp Tyr Ala Tyr Pro Tyr Asp Val Pro Asp Tyr Ala
1295 1300 1305

<210> SEQ ID NO 40
<211> LENGTH: 3918
<212> TYPE: DNA
<213> ORGANISM: Artificial Sequence
<220> FEATURE:
<223> OTHER INFORMATION: Porphyromonas crevioricanis (PcCpf1; pY017), including NLS and HA tag

<400> SEQUENCE: 40
atggacagcc tgaaggattt caccaacctg taccccgtgt ccaagacact gcggtttgag 60
ctgaagcctg tgggcaagac cctggagaat atcgagaagg ccggcatcct gaaggaggat 120
gagcacagag ccgagagcta ccggagagtg aagaagatca tcgatacata tcacaaggtg 180
ttcatcgaca gctccctgga gaacatggcc aagatgggca tcgagaatga gatcaaggcc 240
atgctgcagt ccttttgcga gctgtataag aaggaccaca ggaccgaggg agaggacaag 300
gccctggata agatcagggc cgtgctgagg ggcctgatcg tgggagcctt caccggcgtg 360
tgcggccggc gggagaacac agtgcagaat gagaagtatg agagcctgtt taaggagaag 420
ctgatcaagg agatcctgcc agatttcgtg ctgtctacag aggccgagtc cctgcccttt 480
tctgtggagg aggccaccag aagcctgaag gagttcgact cctttacatc ttacttcgcc 540
ggcttttatg agaaccggaa gaatatctac tctaccaagc cccagagcac agccatcgcc 600
tatagactga tccacgagaa cctgcctaag ttcatcgata atatcctggt gtttcagaag 660
atcaaggagc caatcgccaa ggagctggag cacatcaggg cagacttcag cgccggcggc 720
tacatcaaga aggatgagcg cctggaggac atcttttccc tgaactacta tatccacgtg 780
ctgtctcagg ccggcatcga gaagtacaat gccctgatcg gcaagatcgt gaccgagggc 840
gatggcgaga tgaagggcct gaacgagcac atcaacctgt ataatcagca gaggggccgc 900
gaggaccggc tgccactgtt cagacccctg tataagcaga tcctgtctga tagggagcag 960
ctgtcctatc tgccagagtc tttcgagaag gacgaggagc tgctgagggc cctgaaggag 1020
ttttacgatc acatcgcaga ggacatcctg ggaaggaccc agcagctgat gacaagcatc 1080
tccgagtacg atctgtcccg gatctatgtg agaaacgata gccagctgac cgacatctcc 1140
aagaagatgc tgggcgattg gaatgccatc tacatggccc gggagagagc ctatgaccac 1200
gagcaggccc ccaagcgcat cacagccaag tacgagaggg accgcatcaa ggccctgaag 1260
ggcgaggagt ctatcagcct ggccaacctg aacagctgca tcgccttcct ggacaacgtg 1320
agggattgtc gcgtggacac ctatctgtct acactgggac agaaggaggg acctcacggc 1380
ctgagcaacc tggtggagaa cgtgttcgcc tcctaccacg aggccgagca gctgctgtct 1440
tttccctatc ctgaggagaa caatctgatc caggacaagg ataacgtggt gctgatcaag 1500
aacctgctgg ataatatcag cgacctgcag aggttcctga agccactgtg gggcatgggc 1560
gatgagcccg acaaggatga gaggttttac ggcgagtaca attatatcag gggcgccctg 1620
gaccaggtca tccctctgta taacaaggtg cggaattatc tgacccgcaa gccatactcc 1680
acacgcaagg tgaagctgaa cttcggcaat agccagctgc tgtccggctg ggataggaac 1740
aaggagaagg acaattcttg cgtgatcctg cgcaagggcc agaacttcta cctggccatc 1800
atgaacaatc ggcacaagcg gagcttcgag aataagatgc tgcccgagta taaggagggc 1860
gagccttact tcgagaagat ggattataag tttctgccag accccaacaa gatgctgccc 1920

-continued

```
aaggtgttcc tgtctaagaa gggcatcgag atctacaagc ctagcccaaa gctgctggag   1980

cagtatggcc acggcaccca caagaagggc gataccttca gcatggacga tctgcacgag   2040

ctgatcgact tctttaagca ctccatcgag gcccacgagg attggaagca gttcggcttt   2100

aagttcagcg acaccgccac atacgagaac gtgagcagct tctaccggga ggtggaggac   2160

cagggctaca agctgtcttt tagaaaggtg tccgagtctt acgtgtatag cctgatcgat   2220

cagggcaagc tgtacctgtt ccagatctat aacaaggact ttagcccttg ttccaagggc   2280

accccaaatc tgcacacact gtactggcgg atgctgttcg atgagagaaa cctggccgac   2340

gtgatctata agctggatgg caaggccgag atcttctttc gggagaagtc cctgaagaat   2400

gaccacccaa cccaccctgc aggcaagccc atcaagaaga agagccggca gaagaagggc   2460

gaggagagcc tgttcgagta cgatctggtg aaggaccgga gatataccat ggataagttt   2520

cagttccacg tgccaatcac aatgaacttt aagtgctctg ccggcagcaa ggtgaacgac   2580

atggtgaatg cccacatcag ggaggccaag gacatgcacg tgatcggcat cgataggggc   2640

gagcgcaatc tgctgtatat ctgcgtgatc gacagccgcg gcaccatcct ggatcagatc   2700

tccctgaaca caatcaatga catcgattat cacgatctgc tggagtccag ggacaaggat   2760

cgccagcagg agcacaggaa ctggcagacc atcgagggca tcaaggagct gaagcagggc   2820

tacctgtctc aggccgtgca ccgcatcgcc gagctgatgg tggcctataa ggccgtggtg   2880

gccctggagg acctgaacat gggcttcaag cggggcagac agaaggtgga gagcagcgtg   2940

taccagcagt ttgagaagca gctgatcgac aagctgaatt atctggtgga taagaagaag   3000

cggcccgagg acatcggagg cctgctgaga gcctaccagt tcaccgcccc tttcaagagc   3060

tttaaggaga tgggcaagca gaacggcttt ctgttctata tccctgcctg gaacacatcc   3120

aatatcgacc caaccacagg cttcgtgaac ctgtttcacg tgcagtacga gaatgtggat   3180

aaggccaaga gcttctttca gaagttcgac agcatctcct acaaccctaa gaaggattgg   3240

tttgagttcg cctttgacta taagaacttc accaagaagg ccgagggctc taggagcatg   3300

tggattctgt gcacccacgg ctcccggatc aagaacttca gaaattctca gaagaatggc   3360

cagtgggata gcgaggagtt tgccctgacc gaggccttca agtccctgtt tgtgcggtac   3420

gagatcgatt ataccgccga cctgaaaacc gccatcgtgg acgagaagca gaaggatttc   3480

tttgtggacc tgctgaagct gttcaagctg accgtgcaga tgagaaactc ctggaaggag   3540

aaggacctgg attacctgat ctctccagtg gccggcgccg atggcaggtt ctttgacaca   3600

cgcgagggca ataagagcct gcccaaggac gcagatgcaa acggagccta taatatcgcc   3660

ctgaagggcc tgtgggcact gaggcagatc agacagacct ccgagggcgg caagctgaag   3720

ctggccatct ctaacaagga gtggctgcag tttgtgcagg agagatccta cgagaaggac   3780

aaaaggccgg cggccacgaa aaaggccggc caggcaaaaa agaaaaaggg atcctaccca   3840

tacgatgttc cagattacgc ttatccctac gacgtgcctg attatgcata cccatatgat   3900

gtccccgact atgcctaa                                                 3918
```

<210> SEQ ID NO 41
<211> LENGTH: 1368
<212> TYPE: PRT
<213> ORGANISM: Artificial Sequence
<220> FEATURE:
<223> OTHER INFORMATION: Prevotella disiens (PdCpf1; pY018), including NLS and HA tag

<400> SEQUENCE: 41

-continued

```
Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Lys Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Asn Ala Glu Leu
    370                 375                 380

Gln Thr Phe Asn Asn Tyr Glu Leu Ile Ala Asn Ala Leu Arg Ala Lys
385                 390                 395                 400

Ile Lys Lys Glu Thr Lys Gln Gly Arg Lys Ser Phe Glu Lys Tyr Glu
                405                 410                 415

Glu Tyr Ile Asp Lys Lys Val Lys Ala Ile Asp Ser Leu Ser Ile Gln
```

```
            420                 425                 430

Glu Ile Asn Glu Leu Val Glu Asn Tyr Val Ser Glu Phe Asn Ser Asn
        435                 440                 445

Ser Gly Asn Met Pro Arg Lys Val Glu Asp Tyr Phe Ser Leu Met Arg
    450                 455                 460

Lys Gly Asp Phe Gly Ser Asn Asp Leu Ile Glu Asn Ile Lys Thr Lys
465                 470                 475                 480

Leu Ser Ala Ala Glu Lys Leu Leu Gly Thr Lys Tyr Gln Glu Thr Ala
                485                 490                 495

Lys Asp Ile Phe Lys Lys Asp Glu Asn Ser Lys Leu Ile Lys Glu Leu
            500                 505                 510

Leu Asp Ala Thr Lys Gln Phe Gln His Phe Ile Lys Pro Leu Leu Gly
        515                 520                 525

Thr Gly Glu Glu Ala Asp Arg Asp Leu Val Phe Tyr Gly Asp Phe Leu
    530                 535                 540

Pro Leu Tyr Glu Lys Phe Glu Glu Leu Thr Leu Leu Tyr Asn Lys Val
545                 550                 555                 560

Arg Asn Arg Leu Thr Gln Lys Pro Tyr Ser Lys Asp Lys Ile Arg Leu
                565                 570                 575

Cys Phe Asn Lys Pro Lys Leu Met Thr Gly Trp Val Asp Ser Lys Thr
            580                 585                 590

Glu Lys Ser Asp Asn Gly Thr Gln Tyr Gly Gly Tyr Leu Phe Arg Lys
        595                 600                 605

Lys Asn Glu Ile Gly Glu Tyr Asp Tyr Phe Leu Gly Ile Ser Ser Lys
    610                 615                 620

Ala Gln Leu Phe Arg Lys Asn Glu Ala Val Ile Gly Asp Tyr Glu Arg
625                 630                 635                 640

Leu Asp Tyr Tyr Gln Pro Lys Ala Asn Thr Ile Tyr Gly Ser Ala Tyr
                645                 650                 655

Glu Gly Glu Asn Ser Tyr Lys Glu Asp Lys Lys Arg Leu Asn Lys Val
            660                 665                 670

Ile Ile Ala Tyr Ile Glu Gln Ile Lys Gln Thr Asn Ile Lys Lys Ser
        675                 680                 685

Ile Ile Glu Ser Ile Ser Lys Tyr Pro Asn Ile Ser Asp Asp Asp Lys
    690                 695                 700

Val Thr Pro Ser Ser Leu Leu Glu Lys Ile Lys Lys Val Ser Ile Asp
705                 710                 715                 720

Ser Tyr Asn Gly Ile Leu Ser Phe Lys Ser Phe Gln Ser Val Asn Lys
                725                 730                 735

Glu Val Ile Asp Asn Leu Leu Lys Thr Ile Ser Pro Leu Lys Asn Lys
            740                 745                 750

Ala Glu Phe Leu Asp Leu Ile Asn Lys Asp Tyr Gln Ile Phe Thr Glu
        755                 760                 765

Val Gln Ala Val Ile Asp Glu Ile Cys Lys Gln Lys Thr Phe Ile Tyr
    770                 775                 780

Phe Pro Ile Ser Asn Val Glu Leu Glu Lys Glu Met Gly Asp Lys Asp
785                 790                 795                 800

Lys Pro Leu Cys Leu Phe Gln Ile Ser Asn Lys Asp Leu Ser Phe Ala
                805                 810                 815

Lys Thr Phe Ser Ala Asn Leu Arg Lys Lys Arg Gly Ala Glu Asn Leu
            820                 825                 830

His Thr Met Leu Phe Lys Ala Leu Met Glu Gly Asn Gln Asp Asn Leu
        835                 840                 845
```

-continued

```
Asp Leu Gly Ser Gly Ala Ile Phe Tyr Arg Ala Lys Ser Leu Asp Gly
    850                 855                 860

Asn Lys Pro Thr His Pro Ala Asn Glu Ala Ile Lys Cys Arg Asn Val
865                 870                 875                 880

Ala Asn Lys Asp Lys Val Ser Leu Phe Thr Tyr Asp Ile Tyr Lys Asn
                885                 890                 895

Arg Arg Tyr Met Glu Asn Lys Phe Leu Phe His Leu Ser Ile Val Gln
            900                 905                 910

Asn Tyr Lys Ala Ala Asn Asp Ser Ala Gln Leu Asn Ser Ser Ala Thr
        915                 920                 925

Glu Tyr Ile Arg Lys Ala Asp Asp Leu His Ile Ile Gly Ile Asp Arg
    930                 935                 940

Gly Glu Arg Asn Leu Leu Tyr Tyr Ser Val Ile Asp Met Lys Gly Asn
945                 950                 955                 960

Ile Val Glu Gln Asp Ser Leu Asn Ile Ile Arg Asn Asn Asp Leu Glu
                965                 970                 975

Thr Asp Tyr His Asp Leu Leu Asp Lys Arg Glu Lys Glu Arg Lys Ala
            980                 985                 990

Asn Arg Gln Asn Trp Glu Ala Val  Glu Gly Ile Lys Asp  Leu Lys Lys
        995                 1000                1005

Gly Tyr  Leu Ser Gln Ala Val  His Gln Ile Ala Gln  Leu Met Leu
    1010                1015                1020

Lys Tyr  Asn Ala Ile Ile Ala  Leu Glu Asp Leu Gly  Gln Met Phe
    1025                1030                1035

Val Thr  Arg Gly Gln Lys Ile  Glu Lys Ala Val Tyr  Gln Gln Phe
    1040                1045                1050

Glu Lys  Ser Leu Val Asp Lys  Leu Ser Tyr Leu Val  Asp Lys Lys
    1055                1060                1065

Arg Pro  Tyr Asn Glu Leu Gly  Gly Ile Leu Lys Ala  Tyr Gln Leu
    1070                1075                1080

Ala Ser  Ser Ile Thr Lys Asn  Asn Ser Asp Lys Gln  Asn Gly Phe
    1085                1090                1095

Leu Phe  Tyr Val Pro Ala Trp  Asn Thr Ser Lys Ile  Asp Pro Val
    1100                1105                1110

Thr Gly  Phe Thr Asp Leu Leu  Arg Pro Lys Ala Met  Thr Ile Lys
    1115                1120                1125

Glu Ala  Gln Asp Phe Phe Gly  Ala Phe Asp Asn Ile  Ser Tyr Asn
    1130                1135                1140

Asp Lys  Gly Tyr Phe Glu Phe  Glu Thr Asn Tyr Asp  Lys Phe Lys
    1145                1150                1155

Ile Arg  Met Lys Ser Ala Gln  Thr Arg Trp Thr Ile  Cys Thr Phe
    1160                1165                1170

Gly Asn  Arg Ile Lys Arg Lys  Lys Asp Lys Asn Tyr  Trp Asn Tyr
    1175                1180                1185

Glu Glu  Val Glu Leu Thr Glu  Glu Phe Lys Lys Leu  Phe Lys Asp
    1190                1195                1200

Ser Asn  Ile Asp Tyr Glu Asn  Cys Asn Leu Lys Glu  Glu Ile Gln
    1205                1210                1215

Asn Lys  Asp Asn Arg Lys Phe  Phe Asp Asp Leu Ile  Lys Leu Leu
    1220                1225                1230

Gln Leu  Thr Leu Gln Met Arg  Asn Ser Asp Asp Lys  Gly Asn Asp
    1235                1240                1245
```

Tyr Ile Ile Ser Pro Val Ala Asn Ala Glu Gly Gln Phe Phe Asp
    1250                1255                1260

Ser Arg Asn Gly Asp Lys Lys Leu Pro Leu Asp Ala Asp Ala Asn
    1265                1270                1275

Gly Ala Tyr Asn Ile Ala Arg Lys Gly Leu Trp Asn Ile Arg Gln
    1280                1285                1290

Ile Lys Gln Thr Lys Asn Asp Lys Lys Leu Asn Leu Ser Ile Ser
    1295                1300                1305

Ser Thr Glu Trp Leu Asp Phe Val Arg Glu Lys Pro Tyr Leu Lys
    1310                1315                1320

Lys Arg Pro Ala Ala Thr Lys Lys Ala Gly Gln Ala Lys Lys Lys
    1325                1330                1335

Lys Gly Ser Tyr Pro Tyr Asp Val Pro Asp Tyr Ala Tyr Pro Tyr
    1340                1345                1350

Asp Val Pro Asp Tyr Ala Tyr Pro Tyr Asp Val Pro Asp Tyr Ala
    1355                1360                1365

<210> SEQ ID NO 42
<211> LENGTH: 4107
<212> TYPE: DNA
<213> ORGANISM: Artificial Sequence
<220> FEATURE:
<223> OTHER INFORMATION: Prevotella disiens (PdCpf1; pY018), including NLS and HA tag

<400> SEQUENCE: 42
atggagaact atcaggagtt caccaacctg tttcagctga ataagacact gagattcgag 60
ctgaagccca tcggcaagac ctgcgagctg ctggaggagg gcaagatctt cgccagcggc 120
tcctttctgg agaaggacaa ggtgagggcc gataacgtga gctacgtgaa gaaggagatc 180
gacaagaagc acaagatctt tatcgaggag acactgagct ccttctctat cagcaacgat 240
ctgctgaagc agtactttga ctgctataat gagctgaagg ccttcaagaa ggactgtaag 300
agcgatgagg aggaggtgaa gaaaaccgcc ctgcgcaaca agtgtacctc catccagagg 360
gccatgcgcg aggccatctc tcaggccttt ctgaagagcc cccagaagaa gctgctggcc 420
atcaagaacc tgatcgagaa cgtgttcaag gccgacgaga atgtgcagca cttctccgag 480
tttaccagct atttctccgg ctttgagaca aacagagaga atttctactc tgacgaggag 540
aagtccacat ctatcgccta taggctggtg cacgataacc tgcctatctt catcaagaac 600
atctacatct tcgagaagct gaaggagcag ttcgacgcca agaccctgag cgagatcttc 660
gagaactaca agctgtatgt ggccggctct agcctggatg aggtgttctc cctggagtac 720
tttaacaata ccctgacaca gaagggcatc gacaactata atgccgtgat cggcaagatc 780
gtgaaggagg ataagcagga gatccagggc ctgaacgagc acatcaacct gtataatcag 840
aagcacaagg accggagact gcccttcttt atctccctga agaagcagat cctgtccgat 900
cgggaggccc tgtcttggct gcctgacatg ttcaagaatg attctgaagt gatcaaggcc 960
ctgaagggct tctacatcga ggacggcttt gagaacaatg tgctgacacc tctggccacc 1020
ctgctgtcct ctctggataa gtacaacctg aatggcatct ttatccgcaa caatgaggcc 1080
ctgagctccc tgtcccagaa cgtgtatcgg aatttttcta tcgacgaggc catcgatgcc 1140
aacgccgagc tgcagacctt caacaattac gagctgatcg ccaatgccct gcgcgccaag 1200
atcaagaagg agacaaagca gggccggaag tctttcgaga agtacgagga gtatatcgat 1260
aagaaggtga aggccatcga cagcctgtcc atccaggaga tcaacgagct ggtggagaat 1320

```
tacgtgagcg agtttaactc taatagcggc aacatgccaa gaaaggtgga ggactacttc   1380
agcctgatga ggaagggcga cttcggctcc aacgatctga tcgaaaatat caagaccaag   1440
ctgagcgccg cagagaagct gctgggcaca aagtaccagg agacagccaa ggacatcttc   1500
aagaaggatg agaactccaa gctgatcaag gagctgctgg acgccaccaa gcagttccag   1560
cactttatca agccactgct gggcacaggc gaggaggcag atcgggacct ggtgttctac   1620
ggcgattttc tgcccctgta tgagaagttt gaggagctga ccctgctgta taacaaggtg   1680
cggaatagac tgacacagaa gccctattcc aaggacaaga tccgcctgtg cttcaacaag   1740
cctaagctga tgacaggctg ggtggattcc aagaccgaga agtctgacaa cggcacacag   1800
tacggcggct atctgtttcg gaagaagaat gagatcggcg agtacgatta ttttctgggc   1860
atctctagca aggcccagct gttcagaaag aacgaggccg tgatcggcga ctacgagagg   1920
ctggattact atcagccaaa ggccaatacc atctacggct ctgcctatga gggcgagaac   1980
agctacaagg aggacaagaa gcggctgaac aaagtgatca tcgcctatat cgagcagatc   2040
aagcagacaa acatcaagaa gtctatcatc gagtccatct ctaagtatcc taatatcagc   2100
gacgatgaca aggtgacccc atcctctctg ctggagaaga tcaagaaggt gtctatcgac   2160
agctacaacg gcatcctgtc cttcaagtct tttcagagcg tgaacaagga agtgatcgat   2220
aacctgctga aaaccatcag ccccctgaag aacaaggccg agtttctgga cctgatcaat   2280
aaggattatc agatcttcac cgaggtgcag gccgtgatcg acgagatctg caagcagaaa   2340
accttcatct actttccaat ctccaacgtg gagctggaga aggagatggg cgataaggac   2400
aagcccctgt gcctgttcca gatcagcaat aaggatctgt ccttcgccaa gacctttagc   2460
gccaacctgc ggaagaagag aggcgccgag aatctgcaca caatgctgtt taaggccctg   2520
atggagggca accaggataa tctggacctg ggctctggcg ccatcttcta cagagccaag   2580
agcctggacg gcaacaagcc cacacaccct gccaatgagg ccatcaagtg taggaacgtg   2640
gccaataagg ataaggtgtc cctgttcacc tacgacatct ataagaacag gcgctacatg   2700
gagaataagt tcctgtttca cctgagcatc gtgcagaact ataaggccgc caatgactcc   2760
gcccagctga acagctccgc caccgagtat atcagaaagg ccgatgacct gcacatcatc   2820
ggcatcgata ggggcgagcg caatctgctg tactattccg tgatcgatat gaagggcaac   2880
atcgtggagc aggactctct gaatatcatc aggaacaatg acctggagac agattaccac   2940
gacctgctgg ataagaggga gaaggagcgc aaggccaacc ggcagaattg ggaggccgtg   3000
gagggcatca aggacctgaa gaagggctac ctgagccagg ccgtgcacca gatcgcccag   3060
ctgatgctga agtataacgc catcatcgcc ctggaggatc tgggccagat gtttgtgacc   3120
cgcggccaga agatcgagaa ggccgtgtac cagcagttcg agaagagcct ggtggataag   3180
ctgtcctacc tggtggacaa gaagcggcct tataatgagc tgggcggcat cctgaaggcc   3240
taccagctgg cctctagcat caccaagaac aattctgaca agcagaacgg cttcctgttt   3300
tatgtgccag cctggaatac aagcaagatc gatcccgtga ccggctttac agacctgctg   3360
cggcccaagg ccatgaccat caaggaggcc caggacttct ttggcgcctt cgataacatc   3420
tcttacaatg acaagggcta tttcgagttt gagacaaact acgacaagtt taagatcaga   3480
atgaagagcg cccagaccag gtggacaatc tgcaccttcg gcaatcggat caagagaaag   3540
aaggataaga actactggaa ttatgaggag gtggagctga ccgaggagtt caagaagctg   3600
tttaaggaca gcaacatcga ttacgagaac tgtaatctga aggaggagat ccagaacaag   3660
gacaatcgca agttctttga tgacctgatc aagctgctgc agctgacact gcagatgcgg   3720
```

aactccgatg acaagggcaa tgattatatc atctctcctg tggccaacgc cgagggccag 3780
ttctttgact cccgcaatgg cgataagaag ctgccactgg atgcagacgc aaacggagcc 3840
tacaatatcg cccgcaaggg cctgtggaac atccggcaga tcaagcagac caagaacgac 3900
aagaagctga atctgagcat ctcctctaca gagtggctgg atttcgtgcg ggagaagcct 3960
tacctgaaga aaaggccggc ggccacgaaa aaggccggcc aggcaaaaaa gaaaaaggga 4020
tcctacccat acgatgttcc agattacgct tatccctacg acgtgcctga ttatgcatac 4080
ccatatgatg tccccgacta tgcctaa 4107

<210> SEQ ID NO 43
<211> LENGTH: 1291
<212> TYPE: PRT
<213> ORGANISM: Artificial Sequence
<220> FEATURE:
<223> OTHER INFORMATION: Porphyromonas macacae (PmCpf1; pY09), including NLS and HA tag

<400> SEQUENCE: 43

Met Lys Thr Gln His Phe Phe Glu Asp Phe Thr Ser Leu Tyr Ser Leu
1 5 10 15

Ser Lys Thr Ile Arg Phe Glu Leu Lys Pro Ile Gly Lys Thr Leu Glu
20 25 30

Asn Ile Lys Lys Asn Gly Leu Ile Arg Arg Asp Glu Gln Arg Leu Asp
35 40 45

Asp Tyr Glu Lys Leu Lys Lys Val Ile Asp Glu Tyr His Glu Asp Phe
50 55 60

Ile Ala Asn Ile Leu Ser Ser Phe Ser Phe Ser Glu Glu Ile Leu Gln
65 70 75 80

Ser Tyr Ile Gln Asn Leu Ser Glu Ser Glu Ala Arg Ala Lys Ile Glu
85 90 95

Lys Thr Met Arg Asp Thr Leu Ala Lys Ala Phe Ser Glu Asp Glu Arg
100 105 110

Tyr Lys Ser Ile Phe Lys Lys Glu Leu Val Lys Lys Asp Ile Pro Val
115 120 125

Trp Cys Pro Ala Tyr Lys Ser Leu Cys Lys Lys Phe Asp Asn Phe Thr
130 135 140

Thr Ser Leu Val Pro Phe His Glu Asn Arg Lys Asn Leu Tyr Thr Ser
145 150 155 160

Asn Glu Ile Thr Ala Ser Ile Pro Tyr Arg Ile Val His Val Asn Leu
165 170 175

Pro Lys Phe Ile Gln Asn Ile Glu Ala Leu Cys Glu Leu Gln Lys Lys
180 185 190

Met Gly Ala Asp Leu Tyr Leu Glu Met Met Glu Asn Leu Arg Asn Val
195 200 205

Trp Pro Ser Phe Val Lys Thr Pro Asp Asp Leu Cys Asn Leu Lys Thr
210 215 220

Tyr Asn His Leu Met Val Gln Ser Ser Ile Ser Glu Tyr Asn Arg Phe
225 230 235 240

Val Gly Gly Tyr Ser Thr Glu Asp Gly Thr Lys His Gln Gly Ile Asn
245 250 255

Glu Trp Ile Asn Ile Tyr Arg Gln Arg Asn Lys Glu Met Arg Leu Pro
260 265 270

Gly Leu Val Phe Leu His Lys Gln Ile Leu Ala Lys Val Asp Ser Ser
275 280 285

-continued

```
Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
        435                 440                 445

Ile Trp Asp Glu Val Leu Ile Ala Phe Arg Asp Leu Gln Val Ile Leu
    450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
    530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
    690                 695                 700
```

```
Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
    770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845

Ala Gln Asn Asp Asp Leu Gln Ile Ile Gly Ile Asp Arg Gly Glu Arg
    850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
                885                 890                 895

Asp Tyr Gln Lys Ile Leu Gly Asp Arg Glu Gln Glu Arg Leu Arg Arg
            900                 905                 910

Arg Gln Glu Trp Lys Ser Ile Glu Ser Ile Lys Asp Leu Lys Asp Gly
        915                 920                 925

Tyr Met Ser Gln Val Val His Lys Ile Cys Asn Met Val Val Glu His
    930                 935                 940

Lys Ala Ile Val Val Leu Glu Asn Leu Asn Leu Ser Phe Met Lys Gly
945                 950                 955                 960

Arg Lys Lys Val Glu Lys Ser Val Tyr Glu Lys Phe Glu Arg Met Leu
                965                 970                 975

Val Asp Lys Leu Asn Tyr Leu Val Val Asp Lys Lys Asn Leu Ser Asn
            980                 985                 990

Glu Pro Gly Gly Leu Tyr Ala Ala  Tyr Gln Leu Thr Asn  Pro Leu Phe
        995                 1000                1005

Ser Phe  Glu Glu Leu His Arg  Tyr Pro Gln Ser Gly  Ile Leu Phe
    1010                 1015                 1020

Phe Val  Asp Pro Trp Asn Thr  Ser Leu Thr Asp Pro  Ser Thr Gly
    1025                 1030                 1035

Phe Val  Asn Leu Leu Gly Arg  Ile Asn Tyr Thr Asn  Val Gly Asp
    1040                 1045                 1050

Ala Arg  Lys Phe Phe Asp Arg  Phe Asn Ala Ile Arg  Tyr Asp Gly
    1055                 1060                 1065

Lys Gly  Asn Ile Leu Phe Asp  Leu Asp Leu Ser Arg  Phe Asp Val
    1070                 1075                 1080

Arg Val  Glu Thr Gln Arg Lys  Leu Trp Thr Leu Thr  Thr Phe Gly
    1085                 1090                 1095

Ser Arg  Ile Ala Lys Ser Lys  Lys Ser Gly Lys Trp  Met Val Glu
    1100                 1105                 1110

Arg Ile  Glu Asn Leu Ser Leu  Cys Phe Leu Glu Leu  Phe Glu Gln
```

```
    1115                1120                1125

Phe Asn  Ile Gly Tyr Arg Val  Glu Lys Asp Leu Lys  Lys Ala Ile
    1130                1135                1140

Leu Ser  Gln Asp Arg Lys Glu  Phe Tyr Val Arg Leu  Ile Tyr Leu
    1145                1150                1155

Phe Asn  Leu Met Met Gln Ile  Arg Asn Ser Asp Gly  Glu Glu Asp
    1160                1165                1170

Tyr Ile  Leu Ser Pro Ala Leu  Asn Glu Lys Asn Leu  Gln Phe Asp
    1175                1180                1185

Ser Arg  Leu Ile Glu Ala Lys  Asp Leu Pro Val Asp  Ala Asp Ala
    1190                1195                1200

Asn Gly  Ala Tyr Asn Val Ala  Arg Lys Gly Leu Met  Val Val Gln
    1205                1210                1215

Arg Ile  Lys Arg Gly Asp His  Glu Ser Ile His Arg  Ile Gly Arg
    1220                1225                1230

Ala Gln  Trp Leu Arg Tyr Val  Gln Glu Gly Ile Val  Glu Lys Arg
    1235                1240                1245

Pro Ala  Ala Thr Lys Lys Ala  Gly Gln Ala Lys Lys  Lys Lys Gly
    1250                1255                1260

Ser Tyr  Pro Tyr Asp Val Pro  Asp Tyr Ala Tyr Pro  Tyr Asp Val
    1265                1270                1275

Pro Asp  Tyr Ala Tyr Pro Tyr  Asp Val Pro Asp Tyr  Ala
    1280                1285                1290


<210> SEQ ID NO 44
<211> LENGTH: 3876
<212> TYPE: DNA
<213> ORGANISM: Artificial Sequence
<220> FEATURE:
<223> OTHER INFORMATION: Porphyromonas macacae (PmCpf1; pY09), including
      NLS and HA tag

<400> SEQUENCE: 44

atgaaaaccc agcacttctt tgaggacttc acaagcctgt actctctgag caagaccatc     60

cggtttgagc tgaagccaat cggcaagacc ctggagaaca tcaagaagaa tggcctgatc    120

cggagagatg agcagagact ggacgattac gagaagctga agaaagtgat cgacgagtat    180

cacgaggatt tcatcgccaa catcctgagc tccttttcct tctctgagga gatcctgcag    240

tcctacatcc agaatctgag cgagtccgag gccagggcca agatcgagaa aaccatgcgc    300

gacacactgg ccaaggcctt ctctgaggat gagaggtaca agagcatctt taagaaggag    360

ctggtgaaga aggacatccc cgtgtggtgc cctgcctata agagcctgtg caagaagttc    420

gataacttta ccacatctct ggtgcccttc cacgagaaca ggaagaacct gtataccagc    480

aatgagatca cagcctctat cccttatcgc atcgtgcacg tgaacctgcc aaagtttatc    540

cagaatatcg aggccctgtg cgagctgcag aagaagatgg gcgccgacct gtacctggag    600

atgatggaga acctgcgcaa cgtgtggccc agcttcgtga aaaccccaga cgacctgtgc    660

aacctgaaaa cctataatca cctgatggtg cagtctagca tcagcgagta caacaggttt    720

gtgggcggct attccaccga ggacggcaca aagcaccagg gcatcaacga gtggatcaat    780

atctacagac agaggaataa ggagatgcgc ctgcctggcc tggtgttcct gcacaagcag    840

atcctggcca aggtggactc ctctagcttc atcagcgata cactggagaa cgacgatcag    900

gtgttttgcg tgctgagaca gttcaggaag ctgttttgga ataccgtgtc ctctaaggag    960

gacgatgccg cctccctgaa ggacctgttc tgtggcctgt ctggctatga ccctgaggcc   1020
```

atctacgtga gcgatgccca cctggccaca atctccaaga acatctttga cagatggaat 1080
tacatctccg atgccatcag gcgcaagacc gaggtgctga tgccacggaa gaaggagagc 1140
gtggagagat atgccgagaa gatctccaag cagatcaaga agagacagtc ttacagcctg 1200
gccgagctgg acgatctgct ggcccactat agcgaggagt ccctgcccgc aggcttctct 1260
ctgctgagct actttacatc tctgggcggc cagaagtatc tggtgagcga cggcgaagtg 1320
atcctgtacg aggagggcag caacatctgg gacgaggtgc tgatcgcctt cagggatctg 1380
caggtcatcc tggacaagga cttcaccgag aagaagctgg gcaaggatga ggaggccgtg 1440
tctgtgatca agaaggccct ggacagcgcc ctgcgcctgc ggaagttctt tgatctgctg 1500
tccggcacag gcgcagagat caggagagac agctccttct atgccctgta taccgaccgg 1560
atggataagc tgaagggcct gctgaagatg tatgataagg tgagaaacta cctgaccaag 1620
aagccttatt ccatcgagaa gttcaagctg cactttgaca acccatccct gctgtctggc 1680
tgggataaga ataaggagct gaacaatctg tctgtgatct tccggcagaa cggctactat 1740
tacctgggca tcatgacacc caagggcaag aatctgttca agaccctgcc taagctgggc 1800
gccgaggaga tgttttatga gaagatggag tacaagcaga tcgccgagcc tatgctgatg 1860
ctgccaaagg tgttctttcc caagaaaacc aagccagcct tcgccccaga ccagagcgtg 1920
gtggatatct acaacaagaa aaccttcaag acaggccaga agggctttaa taagaaggac 1980
ctgtaccggc tgatcgactt ctacaaggag gccctgacag tgcacgagtg gaagctgttt 2040
aacttctcct tttctccaac cgagcagtat cggaatatcg gcgagttctt tgacgaggtg 2100
agagagcagg cctacaaggt gtccatggtg aacgtgcccg cctcttatat cgacgaggcc 2160
gtggagaacg gcaagctgta tctgttccag atctacaata aggacttcag cccctactcc 2220
aagggcatcc ctaacctgca cacactgtat tggaaggccc tgttcagcga gcagaatcag 2280
agccgggtgt ataagctgtg cggaggagga gagctgtttt atagaaaggc cagcctgcac 2340
atgcaggaca ccacagtgca ccccaagggc atctctatcc acaagaagaa cctgaataag 2400
aagggcgaga caagcctgtt caactacgac ctggtgaagg ataagaggtt taccgaggac 2460
aagttctttt tccacgtgcc tatctctatc aactacaaga ataagaagat caccaacgtg 2520
aatcagatgg tgcgcgatta tatcgcccag aacgacgatc tgcagatcat cggcatcgac 2580
cgcggcgagc ggaatctgct gtatatcagc cggatcgata caaggggcaa cctgctggag 2640
cagttcagcc tgaatgtgat cgagtccgac aagggcgatc tgagaaccga ctatcagaag 2700
atcctgggcg atcgcgagca ggagcggctg aggcgccggc aggagtggaa gtctatcgag 2760
agcatcaagg acctgaagga tggctacatg agccaggtgg tgcacaagat ctgtaacatg 2820
gtggtggagc acaaggccat cgtggtgctg gagaacctga atctgagctt catgaagggc 2880
aggaagaagg tggagaagtc cgtgtacgag aagtttgagc gcatgctggt ggacaagctg 2940
aactatctgg tggtggataa gaagaacctg tccaatgagc caggaggcct gtatgcagca 3000
taccagctga ccaatccact gttctctttt gaggagctgc acagataccc ccagagcggc 3060
atcctgtttt tcgtggaccc atggaacacc tctctgacag atcccagcac aggcttcgtg 3120
aatctgctgg gcagaatcaa ctacaccaat gtgggcgacg cccgcaagtt tttcgatcgg 3180
tttaacgcca tcagatatga cggcaagggc aatatcctgt tcgacctgga tctgtccaga 3240
tttgatgtga gggtggagac acagaggaag ctgtggacac tgaccacatt cggctctcgc 3300
atcgccaaat ccaagaagtc tggcaagtgg atggtggagc ggatcgagaa cctgagcctg 3360

-continued

```
tgctttctgg agctgttcga gcagtttaat atcggctaca gagtggagaa ggacctgaag   3420

aaggccatcc tgagccagga taggaaggag ttctatgtgc gcctgatcta cctgtttaac   3480

ctgatgatgc agatccggaa cagcgacggc gaggaggatt atatcctgtc tcccgccctg   3540

aacgagaaga atctgcagtt cgacagcagg ctgatcgagg ccaaggatct gcctgtggac   3600

gcagatgcaa acggagcata caatgtggcc cgcaagggcc tgatggtggt gcagagaatc   3660

aagaggggcg accacgagtc catccacagg atcggaaggg cacagtggct gagatatgtg   3720

caggagggca tcgtggagaa aaggccggcg gccacgaaaa aggccggcca ggcaaaaaag   3780

aaaaagggat cctacccata cgatgttcca gattacgctt atccctacga cgtgcctgat   3840

tatgcatacc catatgatgt ccccgactat gcctaa                            3876


<210> SEQ ID NO 45
<211> LENGTH: 7
<212> TYPE: PRT
<213> ORGANISM: Artificial Sequence
<220> FEATURE:
<223> OTHER INFORMATION: Nuclear Localization Signal

<400> SEQUENCE: 45

Pro Lys Lys Lys Arg Lys Val
1               5


<210> SEQ ID NO 46
<211> LENGTH: 16
<212> TYPE: PRT
<213> ORGANISM: Artificial Sequence
<220> FEATURE:
<223> OTHER INFORMATION: Nuclear Localization Signal

<400> SEQUENCE: 46

Lys Arg Pro Ala Ala Thr Lys Lys Ala Gly Gln Ala Lys Lys Lys Lys
1               5                   10                  15


<210> SEQ ID NO 47
<211> LENGTH: 16
<212> TYPE: PRT
<213> ORGANISM: Artificial Sequence
<220> FEATURE:
<223> OTHER INFORMATION: Nuclear Localization Signal
<220> FEATURE:
<221> NAME/KEY: misc_feature
<222> LOCATION: (3)..(12)
<223> OTHER INFORMATION: X is any amino acid.

<400> SEQUENCE: 47

Lys Arg Xaa Xaa Xaa Xaa Xaa Xaa Xaa Xaa Xaa Xaa Lys Lys Lys Lys
1               5                   10                  15


<210> SEQ ID NO 48
<211> LENGTH: 4
<212> TYPE: PRT
<213> ORGANISM: Artificial Sequence
<220> FEATURE:
<223> OTHER INFORMATION: Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 48

Lys Lys Xaa Lys
1
```

<210> SEQ ID NO 49
<211> LENGTH: 4
<212> TYPE: PRT
<213> ORGANISM: Artificial Sequence
<220> FEATURE:
<223> OTHER INFORMATION: Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 49

Lys Arg Xaa Lys
1

<210> SEQ ID NO 50
<211> LENGTH: 4
<212> TYPE: PRT
<213> ORGANISM: Artificial Sequence
<220> FEATURE:
<223> OTHER INFORMATION: Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 50

Lys Lys Xaa Arg
1

<210> SEQ ID NO 51
<211> LENGTH: 4
<212> TYPE: PRT
<213> ORGANISM: Artificial Sequence
<220> FEATURE:
<223> OTHER INFORMATION: Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 51

Lys Arg Xaa Arg
1

<210> SEQ ID NO 52
<211> LENGTH: 20
<212> TYPE: PRT
<213> ORGANISM: Artificial Sequence
<220> FEATURE:
<223> OTHER INFORMATION: Nuclear Localization Signal

<400> SEQUENCE: 52

```
Ala Val Lys Arg Pro Ala Ala Thr Lys Lys Ala Gly Gln Ala Lys Lys
1               5                   10                  15

Lys Lys Leu Asp
            20
```

<210> SEQ ID NO 53
<211> LENGTH: 25
<212> TYPE: PRT
<213> ORGANISM: Artificial Sequence
<220> FEATURE:
<223> OTHER INFORMATION: Nuclear Localization Signal

<400> SEQUENCE: 53

```
Met Ser Arg Arg Arg Lys Ala Asn Pro Thr Lys Leu Ser Glu Asn Ala
1               5                   10                  15
```

-continued

Lys Lys Leu Ala Lys Glu Val Glu Asn
20 25

<210> SEQ ID NO 54
<211> LENGTH: 9
<212> TYPE: PRT
<213> ORGANISM: Artificial Sequence
<220> FEATURE:
<223> OTHER INFORMATION: Nuclear Localization Signal

<400> SEQUENCE: 54

Pro Ala Ala Lys Arg Val Lys Leu Asp
1 5

<210> SEQ ID NO 55
<211> LENGTH: 9
<212> TYPE: PRT
<213> ORGANISM: Artificial Sequence
<220> FEATURE:
<223> OTHER INFORMATION: Nuclear Localization Signal

<400> SEQUENCE: 55

Lys Leu Lys Ile Lys Arg Pro Val Lys
1 5

<210> SEQ ID NO 56
<211> LENGTH: 15591
<212> TYPE: DNA
<213> ORGANISM: Homo sapiens

<400> SEQUENCE: 56
taggggatga cagtgggctc tccgctttct cctccatgaa gtaacttaca tgcccctcac 60
cctctgtggg aggggtgttg cagggggtgc agaactcccc tcgccgggta gttcaagcaa 120
tggggaccat atcaattcca tctataggga aactgaggcc tggagtaggg cgaggcctct 180
gggaacccag ccctattctg tctctttccc tggcatttcc catccacaca tagagcttca 240
gattctcttt ctttccccag agaccctcaa atatcctctc actcacagaa tggtgtctct 300
gcctgcctcg ggttggccct gtgatttatt ttagttcttt tcccttgttt tttttttttc 360
aaactctata cacttttgtt ttaaaaactg tggtttctca tgagccctat tatctcattg 420
atacctctca cctctgtggt gaggggaaga aatcatattt tcagatgact cgtaaagggc 480
aaagaaaaaa acccaaaatt tcaaaatttc cgtttaagtc tcataatcaa gaaaaggaga 540
aacacagaga gagagaaaaa aaaaactatg agaacccctc cccaccccgt gattatcagc 600
gcacacactc atcgaaaaaa atttggatta ttagaagaga gaggtctgcg gcttccacac 660
cgtacagcgt ggtttttctt ctcggtataa aagcaaagtt gtttttgata cgtgacagtt 720
tcccacaagc caggctgatc cttttctgtc agtccacttc accaaggtga gtgtccctgc 780
tctcccctac cagatgtggg ccccattgga ggagatggca gggaggtagg cacggcgggg 840
gggtcagggg ccctctggta cagtgggatg tacccagcta ccgtgattcc agccaggtaa 900
ggtctttaaa aaaataatag aataaatggc agaagactta aaggtgaagt acttaatgca 960
tgggcagggg caaaaataaa tgaattcatc aattgatacg tagatggata ggatttttaa 1020
aatatgtcag ctgccagtct ttatggattt cagagctttg aacaacttga aatgctgtcc 1080
aggtgcaact gaaaatttca actgcatctc tctcatctct ttgtctctta gctcttgatg 1140
cctctcatcc ttctctgtct ctctgctcac cctgtcttgc tcttttacat gtttctctgc 1200
ctctctttct cccgccatct gtctgtcgct acactcagac tctctttccc cgcatctctc 1260

-continued

```
ctggcctctg accatctccc ctatctctgt ctcctccatc ttgaccacac tccatcgatc   1320
tcctttcctc catctctccc gctctctttt cttgccttcc cccacctgcc ttcccagcca   1380
gcatccagcc tagagctttg tacacagctg gcgtttaata atagtaatgt cgccgaggac   1440
ctttacattt tatgagagtg agcatcagtt ctgttcaccc tagtagcagg aggattgcaa   1500
ggtgccgggg caagctgagc acttaactga actttgcttg tatcgcttta gaggagaccc   1560
ttggggcggg ggggcaggga gcacttcaca ccattgtcaa ccgtagttta gctgtgtgga   1620
cctaccccag gactgcatgt gtgtgaccag agtccatatt caggaagcaa acaggttgtt   1680
cagggctggg gtgagctcga ttctgcaggc ttagcacagc gtttggcaca aagtaagtgc   1740
tcacgaagtg ttagctatta gtatttctgt aaccaaatta gaatcatgct atatattggt   1800
tttgttcctg ctttattcaa ttaacagtag tgtttttgaa gcttactaaa aattgtttga   1860
acacatgatc tttcatgatg gacaagactg tcctcacatc agcatgaact ttgattgatt   1920
tgaccaagtg ccgattgttg gacattccgg ttgtttctcg tttttttcta taaacatccc   1980
tgactgcttc cttggattcc tgaaaaggga gttgctgggg caaagggggc gtgcattttt   2040
aaagtttatg accctctctg ctaattctcc ttccaaaagg ttgtcctatt ttatgctccc   2100
tctacttaag ctaaccctag gtgagtatta ttatgtttta attatttccc aacatgacag   2160
gtaagaaaaa cacattatca cattgttgaa atttgcatct tgtgattact tttactattc   2220
attggccatt catgcttttt tttttttttt tttggttgtc tggtcatgtc cttactccta   2280
atagggtgtt catcttattt ttcccttatt gatttgccac agctctttat ttggaatggt   2340
tattaacctt tcatcagcca ttacatatat agcaaatatt ttccccaatt catcatttgc   2400
tttttttcta tttgtttatg gtgtttttttg tgatgcttat gatggtttta tacagtcaaa   2460
taggttagtc ttttttttctg tggcttctgt ctctggtttt gtgcttagaa agtcctttcc   2520
tacttgaaaa tgagataaat gttcacctat gttggcttct agtctctttt atggcttcat   2580
tttttccatt tactatagag gttaagagtg tgggtactgg agccagactg tctgggacaa   2640
acccagcgtc accccaagcc ctatgtgtga tttttagcca ggcacttaac ctctccatac   2700
ctccatttcc tcatatgtac tgcaatggtt ataatagtac cttcctcagg agtctttgtt   2760
tagattaaaa tttttaacca cagtaaatac ttagcacaag gcctgacaca caataaaccc   2820
aagatcagca ttaggtgtta aaacttatat cttgaatgga tctgggcatt ttagggtata   2880
tgatgatggt gacatttcaa actgggcagg gaggggttgt tgggataatg gactgactat   2940
tcactcaata actttatctt ctccctaatt atctcagaca catttgttaa accatactcc   3000
atggtcctcc agtttgaaat gccacattca tcacaaattc agttctctcc atatgtgggt   3060
ccatgtccaa gctttctatt ctgttctctt ccccagtatc tgttcttata ccagggccac   3120
actgttttgc tgattgttgc tttgcaatac aattcaatac ccagccatgg gtgtccctgg   3180
caccttgccc ttctttattc ttgattattt caggcagcat cagttgaacc agccagagac   3240
cagcaaatgt tcttatttga ggcaatcctc ctctcgcaca catgcactct ggctctccat   3300
gcatgtgtcc atttctctca atgtctctca ctatctcttg ttctctcttg ctcgctcttt   3360
gtgtgtgtct ctttgtctct atgtatccct atctctcagc cagtcccctg gatagagggg   3420
caattgtcaa cttgaagccc tgcagacacc taatgactta accagacagc gtagaagggc   3480
cctggccctt gtctactcca cgcctctccg tgctcagtgt agaagggcaa attgaagacc   3540
agagatctca gggcctcacc gaaatgcagc ggcagagttg aaatccaagc ctagatctca   3600
ggactctagg tgggaccctg gttctggctc tctccccaac tgcaggcctc agtttacccc   3660
```

tcagcaccca gaagggggaa ggggaacctg ggctaccatt ccccttctg ccttctcaca 3720 cgttggaccc caacttccca caggttggac gatccacgat cacagtgtgg ggcccagcct 3780
cacaagagct gggctaggtg aggccccgga ctccataggt caggaggcct agttggccag 3840
agcgtggtga tgatggaggc atgtcagtca gtcaggctgt gtgtccccag agctggtgct 3900
ggtccccgaa aaccttgatt gtggggcccc tctagagagt ctgatgatgg gctctgtatt 3960
ggcgaaggct gaggcttttc cagctccccc catgaggccc agaccaaagg cacaccagcc 4020
tcaacctcct cctcccctg ttgccatctc tggcggagtg gccatgtatt tgggaacgtt 4080
gttccagagt ggacagggag actgaggccc tagggaggct ggctctgttt ccaggcctgg 4140
taggcaagag gccctatgaa gcagcaagct gcctgacttt cagatggttc caaggagttt 4200
ggacaccagg gacactggcc tacacatact gagactttgg gaccgtagac cccacagtct 4260
gtggttttga gattctagga tcctttaaat ctaagaaatg ctgttctatg attctgaggt 4320
cctggtgtta tactatttga agaccccagg ggtcccagta tctgtggagc ctgcctggca 4380
ctctcagagc ttcaaacctg ggtcctctcc acaacccaag aagggccagg tcttcagagc 4440
taggggcttg tcatagtggc cagatggaca tcacctacca catccaccag cacccatgtc 4500
accccacctg ggccaagcct gctgcaggac agggcagcca gttctcggaa cgaaacctgt 4560
ggggtggggt atctgccctc ttctcttcct ccgtggtgtc gatgaagccc ggcgcatccg 4620
gccgccatga cgtcaatggc ggaaaaatct gggcaagtcg gggctgtga caacagggcc 4680 cagatgcaga ccccgatatg aaaacataat ctgtgtccca gaaacatccc ccattcagct 4740
tctgagaaac ccagtcagaa agggacgtcc caacagacag tgcaggaagc cggctgccca 4800
gcccggccct ctaggtcctc taccccccaga cagatcatct ccatgtccct gtctgagaat 4860
gtatctatgc tttgctgagt caggccatcc cacatgtgtt tggggagaat tcttagctct 4920
ggccaagtgt ccaggcagct tcagaagtga ccacaggcca gccacatggg ccaggccaga 4980
gtggtggaaa acatccattt gcaccgaaat cggtattagt ttgttctggc tgctataaca 5040
aagtaccaca actgagtggc ttcagcaaca gaaattgatc atctcacagt tctggaggcc 5100
agagtccaag atcaaggtgt tgccagggtt ggttccttct gggggccata agggagaagc 5160
tgctccaggc ctctccccca gcttctggtg gttgctggca atctttgtta tttcttggct 5220
tgaaggagca tcaccccatc tctggcttca ttcattcact caccttctca tctcaccagt 5280
gctctcccag gcccttgttc ggagcctcca cagacccaca ctcctgtttc tcacgcagta 5340
atgttctaag cccccaggag actaagaact taatacctgg attctcacac tcatctccct 5400
cagcaccaca gctctgacaa ccacccccag gaggtgacag caaagaaagg aaggagcaac 5460
tgctccccca gaaccccttct atactccccc gggctgctct cagcagctgt gtgcccaact 5520
cagtgctgtg aggtggaacg gggagatgga gacacacaca cacacacacc agagagttta 5580
taaaatgtgc acacggaaac acttcctaaa gaaagaagtg gagttctcaa gtcactatgg 5640
gactacggaa ctcggcatct gagcatcccc ttctgtataa tggggttggc tgggcagtcc 5700
cttccagctc tggcttcctc tcagaccagg attataggat cctgaaaagc cagtgcttcc 5760
ctcagggagt ggaaggttct ggggctcagc agggggcccg gagccattgt ggagggcttt 5820
caaggtgagg acaatagaag agcaggtctt gcgtggcttg gacagggaaa gaggagaagg 5880
agtgggcatt tgaggcaggg ggtgtagcat gagccaggct tgagggccag aaattggggt 5940
gaactctgat gggggctggg tagagaagct tctacaggcc ccagctcaag agaccccatc 6000

-continued

```
tctcctcctc tctgtcactt gccatgctgg atccgtgcat gatcacactc ctggactcgc   6060
ctccttgccc tgagatccag acccccgtat tcagctgccc cctcagctcc tccactcaca   6120
tatttaatgc cagactcttc atgtctatct acacctgcac ttttgcaccc aatccaactc   6180
cccgccatgt cccccatctc aggtaatgtc agctcggtcc ttccagctgc tcaagctaaa   6240
acccatgtca ctttgactct ccctcttgcc cactacatcc aagctgctag cactgctcct   6300
gatccagctt cagattaagt ctcagaatct acccacttct cgccttctcc actgccacca   6360
gcccattctg tgccagcatc atcacttgcc aggactgtta caatagcctc ctcactagcc   6420
ccactcacag cagccagatg aatcttttga gtccatgcct agtcactggg gcaaaatagg   6480
actccgagga gaaagtccga gaccagctcc ggcaagatga gcaaacacag cctgtgcagg   6540
gtgcagggag ggctagaggc ctgaggcttg aaacagctct caagtggagg gggaaacaac   6600
cattgccctc atagaggaca catccacacc agggctgtgc tagcgtgggc aggcaagcca   6660
ggtgctggac ctctgcacgt ggggcatgtg tgggtatgta catgtacctg tgttcttggt   6720
gtgtgtgtgt gtgtgtgtgt gtgtgtgtgt ctagagctgg ggtgcaacta tggggcccct   6780
cgggacatgt cccagccaat gcctgctttg accagaggag tgtccacgtg gctcaggtgg   6840
tcgagtatct cataccgccc tagcacacgt gtgactcctt tcccctattg tctacgcagc   6900
ctgcccttgg acaaggaccc gatgcccaac cccaggcctg gcaagccctc ggccccttcc   6960
ttggcccttg gcccatcccc aggagcctcg cccagctgga gggctgcacc caaagcctca   7020
gacctgctgg gggcccgggg cccaggggga accttccagg gccgagatct tcgaggcggg   7080
gcccatgcct cctcttcttc cttgaacccc atgccaccat cgcagctgca ggtgaggccc   7140
tgggcccagg atggggcagg cagggtgggg tacctggacc tacaggtgcc gacctttact   7200
gtggcactgg gcgggagggg ggctggctgg ggcacaggaa gtggtttctg ggtcccaggc   7260
aagtctgtga cttatgcaga tgttgcaggg ccaagaaaat ccccacctgc caggcctcag   7320
agattggagg ctctccccga cctcccaatc cctgtctcag gagaggagga ggccgtattg   7380
tagtcccatg agcatagcta tgtgtcccca tccccatgtg acaagagaag aggactgggg   7440
ccaagtaggt gaggtgacag ggctgaggcc agctctgcaa cttattagct gtttgatctt   7500
taaaaagtta ctcgatctcc atgagcctca gtttccatac gtgtaaaagg gggatgatca   7560
tagcatctac catgtgggct tgcagtgcag agtatttgaa ttagacacag aacagtgagg   7620
atcaggatgg cctctcaccc acctgccttt ctgcccagct gcccacactg cccctagtca   7680
tggtggcacc ctccggggca cggctgggcc ccttgcccca cttacaggca ctcctccagg   7740
acaggccaca tttcatgcac caggtatgga cggtgaatgg gcagggagga gggagcaggt   7800
gggagaactg tggggagggg ccccgagtca ggctgaacca cagcccacat gtgcccccca   7860
gctctcaacg gtggatgccc acgcccggac ccctgtgctg caggtgcacc ccctggagag   7920
cccagccatg atcagcctca caccacccac caccgccact ggggtcttct ccctcaaggc   7980
ccggcctggc ctcccacctg gtaacacctc agcccgtacc ccatggcttc acagaacccc   8040
caagtcccca gatccttggc tgtgagcagt gtaggctatt ctgaattgca gtactctggg   8100
ggtcaaaggt gtcaggtctc agaggcttgg aaactccacc ctccaaaaaa cgtcaggtgc   8160
agaaccttaa agatgcagaa tgtcaaaatc acaaaaccac agagctttac aaagctagtc   8220
aaaatgtcag cacctgcgaa tggccgtctt taagcttctc tgccagaagc ctgggacttt   8280
ggggacagca gagccccctg ggagtcaggg ttttcgaggc tcaggagggt gggaagctca   8340
aaatgagagg ccttgtgggc caagctccag agcccagccc acagcctcca taggtgccct   8400
```

```
gtccccaccc acagggatca acgtggccag cctggaatgg gtgtccaggg agccggcact   8460
gctctgcacc ttcccaaatc ccagtgcacc caggaaggac aggtcagtgg acagggctgg   8520
gaaggatcct cgccctccta tcccctcccc tgacaccctc tgtcccccca gcaccctttc   8580
ggctgtgccc cagagctcct acccactgct ggcaaatggt gtctgcaagt ggcccggatg   8640
tgagaaggtc ttcgaagagc cagaggactt cctcaagtga gtggcccagg cctgtgccag   8700
tctaccggcc ctggcttgtg gggagaggtc tagggtgcag atctcagctc aggcttcatc   8760
ccaataagta gtaagatgca agagctaaac tctgagactg tgggttcaaa tcccagctcc   8820
atccctgact ggctgtgtga ccttggacaa attacttagc ttctctcgac ctcagttttc   8880
tcgtatgtat aataagaaac gtttgtgctg ttatttaccc ccattttaca gacaaggaga   8940
ctgaggccaa agaggttaag tgtcttgatc aaaatctccc agttcctgag tgacagagct   9000
gggatttgaa cccatgtagc caggctctag aatctgcact cctgctttgc cctgctactc   9060
ctcatgccaa catgccagcc ttattccact gttcccaaag ttctagctcc tctagatggc   9120
tgctgctgcc tcccctcagt ccccccatat gtctctctct ctctctctct ctctctctct   9180
ctctctctct ctctctctct ctctctttct ctctctctca cacacacaca cacacaaata   9240
cacaccacac tacacacaac ccttagcagc aaccccacat gtcctgtcct ccttgcagcc   9300
aggcctttgc acaggccgtc cctccaccca gaatgctttg cccactctca cctccctggc   9360
ccattctcaa ctcaccacac ttccaacatt atctccagca ctctggccag gctcaagtgg   9420
tgagttcagg cctgacatgc agtaggtgct gaggggcatg tgttaaggga acgaggggtg   9480
tgagagggag actgaggtag agaggggagg ggagctgggg ctcagaggag agaactccca   9540
gagggtctgg gccctcccca ttcagagcat tgagccagac caggcctgtc gtggtcacct   9600
gcatggaatc ttctccctac ttaggcactg ccaggcggac catcttctgg atgagaaggg   9660
cagggcacaa tgtctcctcc agagagagat ggtacagtct ctggagcagc aggtaatgcc   9720
agggcggtgg agggtaaggg atagggatag tgcgcaaaac cttctgtcca ccatgtgcca   9780
gaaaccaagt tcacctggga cgagggctgg tataaaggaa ggaagaggag cgggcactcc   9840
cagggaagac cgtagcctgg gcaaagatgt ggcagagaag ggccaggctg aggcctcatg   9900
tttgtgccat ttcacagctg gtgctggaga aggagaagct gagtgccatg caggcccacc   9960
tggctgggaa aatggcactg accaaggctt catctgtggt gagcgacccc aggactggtg  10020
gtggcagact cagactgctg gggggcaggg aggaggtctg cacggtgcag ggaacctaac  10080
ctcacattca ggtcctgaga gctaggggcc cctgtcccca gctccaaaca tgcccagacc  10140
tggaaatctg tccccttcta cttacaaacc ctctgacccc ggctgggcgt ggtggctcac  10200
gcctgtaatc ccagcacttt gggaggccga ggcgggtgga tcacgaggtc aggagttcaa  10260
gaccagcctc gccaagatgg tgaaaccctg tgtctactaa aagtacaaaa aattagccag  10320
gcgtggtggc aggtgtctgt agtcccaact acttgggagg ctgaggcaga gaattgcttg  10380
aacctgggag gcggagtttg cagtgagctg agatcatacc actgcactcc agcctaggcg  10440
acagatcaag actccgtctc aagaaaaaaa aaaaaaaaaa accctctgac tctaagatcc  10500
ccaaacactg tgatcctgag ttgttaaagc aaatgcaaat agccagactt gccagatgca  10560
ggctgtgtgc cagcaggacc agctatgtaa cctgcagggc cccttgttca gatttcaaga  10620
tggcgaccac agagcattaa acaaagcaca gggtgccaca taaccacata ggtcacacgc  10680
ccatgaagcc agccctggag gccaggcact gtttctgagc gctttgctgg tggtaattta  10740
```

-continued

```
tttctcatga tgcgaatgta cagatgagga atattgaggc caggggggtt taggtgactt  10800
tcccaaggtc acagttgggt ggtaaagagc cctattcaac cccagttcat ggtcccagca  10860
tcagtggcca catacgacat ccgcacctgt gctctaataa atacggctca tgctgttttg  10920
tgggattcca cctcagactg gaatttagaa gagggcgtcc ttgctttgaa aaacactgat  10980
ttaaaaataa agtggagcca ggcgcagtgg ctcatgcctg taatcccagc actttgggag  11040
gctgaagcgg gtggatcaca tgaggtcagg agttcgagac cagcctggct aacatggtga  11100
aaccccatct ctaccaaaaa tacaaaaatt agctgggcgt agtgacgggc acctgtagtc  11160
ccagctactc gggaggctga ggcagaagac ttgcttgaat ctgggaggtg gggttgcag  11220
tgagccgaga ttgcaccact gcactccagc ctgggcgaca gagcaagact cagtatcaaa  11280
aaaaataaaa aacataaaat agaaagtaaa aagtgggaag tttaagcctc tgggtcacca  11340
gcctctcccc ctcacccagg catcatccga caagggctcc tgctgcatcg tagctgctgg  11400
cagccaaggc cctgtcgtcc cagcctggtc tggcccccgg gaggcccctg acagcctgtt  11460
tgctgtccgg aggcacctgt ggggtagcca tggaaacagc acattcccag gtaagaatgg  11520
tccttgcact acacggtgcc cccaagctcc taatcctgac aggctctggg tggagggtgc  11580
aaaggagctc catgctgccc cttcccacca ccaccaccac tgcagctgcc gccactcagc  11640
ctttgggaaa atgcatccgc tcacaaaagc ttcctttcgg gatgtccgtg gcctgaaagc  11700
cccccatatg gtctcgagtg tcgggcccct agccctgact cccttgggga ttggggccat  11760
gcctcaccca ctctggactc cagctactat attcggccat cagaagggag ggaccctgct  11820
aagtaattcc aggagcacct cctttcctcc cctgaccaag gaaaatcggg gtggattcgc  11880
ccgagctcac ctatccactg ctctccacca ggcctggcct gtgggcttag cagggatcag  11940
agaccttgac tgtcatcctg gctctgccat ttaacctctt gcatcctttg gtgtgcaagt  12000
tactccgctt cttttcaacc tcggggagaa ctattttggc agaagtggtg caaagaataa  12060
atgatacaac ttatgtcagg tgctcagcaa acagtacctg tgcccgtgga cacgggtgtt  12120
gacggtgaga tctcaggcct gtagactcac cttgtagggg gaggggacag ggagctagct  12180
aggaggtcct gcatggggct tgattcatcc ccaccctctg acagagttcc tccacaacat  12240
ggactacttc aagttccaca acatgcgacc ccctttcacc tacgccacgc tcatccgctg  12300
ggtaagcagg gcagctcggc cccaaggagg aggaagacaa agatggggtg ggggacctgc  12360
ctcccaaact cctgtctccc tctgagtgcc ctcagagtgg gttcctccat tcccaagccc  12420
cagccccaag gatccccaag ccgtgcctca aatgtgaccc ctcatgctgg cttcacccca  12480
aacctgtccg caaatccaaa cctaaaccac catccaggcc agagcatgcc aaattctgac  12540
cctaaaccta cccctttcca gatgtccacc tcagccccat acctaaccct ctcctggacc  12600
cataaaatag cctaaagcta accccatctc tgcaccttgc cctaaacgta ccccagctct  12660
tactctaact ccttccccag cctttatgcc aacccaaccc catctccttc cctggcccca  12720
acgtacccca gtatgtcaat acaccccca ctgggcacca ttcccaacct ttccttgtaa  12780
cacccatttg atccttaact tcatcacccc atcccaactc cttcatctca gcctccccaa  12840
tgccttctca gaaccttcat cctagcgcca cacctaaccc caaacctgaa cctcacccct  12900
acatgatacc agatattccc cgactgtctc tgaactgaaa ccctgaccta gccccatcct  12960
gactgatagc ctcactgcaa tcatcatcgc tgactctgta atcccattcc tgaatccaaa  13020
ctgatcaaat tccctgaccc tcagcctcac tccacaccga accccacaac taacctcatc  13080
cttgccctga gcctaaccac ctaaccatgt ccctgacacg taagatactc gataattcaa  13140
```

accatctctg gcttctgacc taaagccaag tcatcccatc cctcacccct agacccccca 13200
cctgagtcca ccccagcctg actcttaacc caccccttcc ctgaccctta agttggcctg 13260
gccctttacc ccttccaaat ccttgacccc acttctgacc cttcaccttc cccaaccctg 13320
aaatgtcacc tccacagaga accccaactc caactccatc ccagaccttt cacctcactt 13380
cagccctagc cctgaacaag accccactcc caacctcagt cctgatccct tacctaatcc 13440
cagaacaacc atacccacac ccatctaacc ctgcccaacc cgacacttca ccccttttct 13500
aaccccatct ttgaccccat gcttcacccc acatctagtc ctgtccctga ttacctgccc 13560
ctacaattcc gcccccatgt cagatggctc ggggtaggtc atagcccctc taaaccccaa 13620
gtttggggaa tgtgcccctt accccacccc ccaacttcca ggccatcctg gaggctccag 13680
agaagcagcg gacactcaat gagatctacc actggttcac acgcatgttt gccttcttca 13740
gaaaccatcc tgccacctgg aaggtgagct cctctgaggt ggcggtgact gggatggcct 13800
caagtgccat cgcagctcaa agtgggcagg cctgggtctg ggctcatagg cacattgggg 13860
aggaacggga tgtgggttgt tggtggtggc tgctggcctc agaggttgac gcccacctgc 13920
tccctgtccc cggccttcca cagaacgcca tccgccacaa cctgagtctg cacaagtgct 13980
ttgtgcgggt ggagagcgag aagggggctg tgtggaccgt ggatgagctg gagttccgca 14040
agaaacggag ccagaggccc agcaggtgtt ccaaccctac acctggcccc tgacctcaag 14100
atcaaggaaa ggaggatgga cgaacagggg ccaaactggt gggaggcaga ggtggtgggg 14160
gcagggatga taggccctgg atgtgcccac agggaccaag aagtgaggtt tccactgtct 14220
tgcctgccag ggcccctgtt cccccgctgg cagccacccc ctcccccatc atatcctttg 14280
ccccaaggct gctcagaggg gccccggtcc tggccccagc cccccacctcc gccccagaca 14340
caccccccag tcgagccctg cagccaaaca gagccttcac aaccagccac acagagcctg 14400
cctcagctgc tcgcacagat tacttcaggg ctggaaaagt cacacagaca cacaaaatgt 14460
cacaatcctg tccctcactc aacacaaacc ccaaaacaca gagagcctgc ctcagtacac 14520
tcaaacaacc tcaaagctgc atcatcacac aatcacacac aagcacagcc ctgacaaccc 14580
acacaccccca aggcacgcac ccacagccag cctcagggcc cacaggggca ctgtcaacac 14640
aggggtgtgc ccagaggcct acacagaagc agcgtcagta ccctcaggat ctgaggtccc 14700
aacacgtgct cgctcacaca cacggcctgt tagaattcac ctgtgtatct cacgcatatg 14760
cacacgcaca gccccccagt gggtctcttg agtcccgtgc agacacacac agccacacac 14820
actgccttgc caaaaatacc ccgtgtctcc cctgccactc acctcactcc cattccctga 14880
gccctgatcc atgcctcagc ttagactgca gaggaactac tcatttattt gggatccaag 14940
gcccccaacc cacagtaccg tccccaataa actgcagccg agctccccac atgctggact 15000
atcaccccat ataagggttg cggtcagtgg gcaggggtct gggtccaagg ccgcagcagg 15060
aggaactgga cagcggagga agtagctagg gcatgtgctt ggccactgcc tccagcaccc 15120
caaatccctg cctgaggctg gggagagacc tctgccggcg gctcctcagg cctcccggac 15180
ccggcctagg aggccagcgt tctcctggcg gagggctcgg tagtcctccc ggatcttctc 15240
caggttgctg agggtcttct tgcccagctc tgtctcgatc tgaggcaatg tgaacacatg 15300
ccccctcagc acacacagcc cctttcccag ctcctgctca ccagccccca tcacagccac 15360
tctgggcccc tcccaccaac tccaacagcc tgctctgtcc catggccagg cctcgtgtgg 15420
tgttccctct acccaaagca tccttcgcca tgtggcagga ttccccctac atctttaagc 15480

```
tgaagcctct gcccatggcc ctgggaggca gacaggaggg cccttggggt ggaagctggg  15540

gctcacagta ggccacttgc ctgtcccagg tcacaggcac taaggggcag g           15591


<210> SEQ ID NO 57
<211> LENGTH: 431
<212> TYPE: PRT
<213> ORGANISM: Homo sapiens

<400> SEQUENCE: 57

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
```

```
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430


<210> SEQ ID NO 58
<211> LENGTH: 16049
<212> TYPE: DNA
<213> ORGANISM: Homo sapiens

<400> SEQUENCE: 58

catgaccctg ccaccccatg ggcctgctgc tggtggcagc gtggccgcct cctgagagtt      60

ggccctccct tgtgccactg ccaggggagg aaaggccttg atgttccaga caataataaa     120

tgcgcctgtg acttagcctt ggtgtcagtc tcttgcggac ctgacaaccc ccatctctcc     180

ttccctgatt ccctctgcct ttccaggccc catccccctg aacagctcct ccctatggtc     240

ctggctgggc ctaaccctgc cccagggcct aaccctacct gaggctcctc cccttccccc     300

ggggcaggtt gagaggctgg agtgggtccc tcagcgccct gggtgggtgg gcctgcacag     360

ggggtacctc cttctctgag gaactgggct gttagggatt ttccttaggc cctttggttt     420

ccgcctacgg agaggtttcc cccattggtt gctcttcctc agccagggtt acttcctggt     480

ctgttcccct acccaatacc ccgccgctct gtcagcttga gctccaggtg gagctccagg     540

tggctcctcc tctcccgggg gaaggcggcc ctggaccagc aggcgggcct gctgtactcc     600

cgctttgggg ctgcagggaa gctggccgct gtgggcggtc tcgggccagc cccgccccac     660

ctgtcctttt cctggagact attagtccag ggtttgtccc tgcagtgcca ttggcctggc     720

aggcaggatc gaggaggaag tggctgatta ctgagcggtt cttcctcacc tggcttgggc     780

cactgtgcac agctgtgccg ctggctcagc cccgcccccct gcggccctct gccgtggctt     840

ccccctccct acagagagat gctgtcccgt gggtaagtcc cgggcaccat cggggtccca     900

gtctcctgtt agttttggag ggagggaggg ctttgttgat gctcactccg acgtgtgtga     960

acgtgagtgc gatctgccgc tgccctgcgc ctgtttccgg tccctatgaa cttccccttc    1020

ccgcaaggtg tgaggacccc cggctcactc atgctcctct gccccctctt taacattttc    1080

ccctggacaa gtgtgtatct gttctctcca ttgcatttct acttccagcc tctgggctcc    1140

tgcttctgcc tcctgcttag gacctgtccc cctgggtagc tcacaacacc tcaaacatag    1200

cagtcagagg ccacccgcga aggccctccc acgtccagcc aacttctccg cacttcccaa    1260

catcagactt tggtcccatc ttctttgttt cctttcactt ccctttcccc tgcatcattc    1320

attcaacagg tacgtgttga gcatctatta tgcaccaggt gctgtttaag atgctggtaa    1380

tactggagtg aacaagacag acatggtctc tgctctcacg gagcttacat tccagtggga    1440

ggttacagac cgaacaaata acccaataaa ttggatcatt gcagattctc agaagtatta    1500

cgcagaaaat agacagcctt ggccgggtgt agtggttcac acctgtgatc ccagcactgt    1560

gggaggctga ggcgagagga ttgcttgagc ccaggagttt gagaccagcc tggccaatat    1620

agtgagaccc tgtctctaca aaaaataaga aattagctgg gtgtggtggc acacgtcctg    1680

tggttccagc tatggagagg ctaaggtgag aggcttgctt gagcctggga ggtcaaggct    1740
```

```
gcagtcagcg atgattgcac cactgcacac cagcctgggc gacagagtga gaccttgtct   1800
caaaaaaaaa aaaaaaaaaa gaaaatgaac cagcttcata tgctagcaag tgactgggtg   1860
tgcaggtgac attactagct ggagggatca gggaggcctt cccgaggagg tgacatttga   1920
gctgagaccc ggatgaggag gaagaggagc tggccatgtg acgtagtgat caagagtcaa   1980
gcatctctgg gcagaggaga tggtgagcac aaagccctaa tgtgggaaca aacaaaaaaa   2040
ggacagtgtg cccgtggcag aggaccctag tggagcggag gcagggccac agcaggttag   2100
accatgttgg agctaggatg ttgaaagtga aaacctgacg agatgaggtg gcgcacgtct   2160
gtgatcccag cactttggga ggccgaaggg ggaagattgc ttgagctcag gagtttaaaa   2220
ccagcctggg caacatagag agaccccatc tctattaaaa aaaaatactg ggtatgatgg   2280
cccaagcatg tggtagtcct agcagtttgg gaggctgagg tgggaggatc acttgagccc   2340
aagagttcaa gaccaccctg ggcaacatag ggagagacct catctctact acgactacga   2400
ctactactac tactaataaa tagctggatg tagtggcatg cacctgtggt ctcagttact   2460
tggaaggctg aggcaggagg atcacctgag ccaaggaggt cgacgctgca gtgagttgga   2520
ttgtgacact gcacttcagc ctgggtgata aagcaagatt ctgtgtcaaa aaaaaaaaaa   2580
aaagagaggg aaggaaagaa ggaagggaag gaagaaagaa aaagagaaag aaggaaaaaa   2640
aggaaagagc gagaaagaag aaagaaaagg aaggaaggaa agaaagaaaa gaaaggaaag   2700
aaaaagaaaa agtgacaccc agtcgaaaga agaaaggaaa gaaaaagaaa aagtgacaac   2760
cggtcgaaag aaaaaagaaa aagtgacaac cggctgggca tggtggctca agcctgtaat   2820
cccagcactt tgggaggccg aggcaggtgg atcacgaggt caggagttca agaccagcct   2880
ggccaacatg gtgaaaccct gtctcaacta aagatacaaa aaaaaaatta ggctggcaca   2940
gtggtgcgca cctgtgagtc ccagctacta gggaggctga ggcaggagaa ttgcttgaac   3000
ccaggaggcg gaggttgcag tgagccgaga ttgcgtcact gcactccagc ctgagtgcag   3060
cgggagagac tccatctcaa aaaaaaaaaa aaaagaaaag aaaaagtgac aacctgctta   3120
cagagtactg gcgagtttgt gggtgggtgg ctccctagcc ctgctgattc ttgcttctca   3180
cactcatgtc tgcccctgcc ccagtgcaca tcttgtcact gtcggcccca ccgatggggt   3240
tcctactgag tcttctggtc cctgatcccg tctgtggtca ttttcctgcc aggtagcttg   3300
gccaggcctc ccctggtgca gatttcatcc ttggtttctc agcctggcct tgaatgaccc   3360
tctacagcag ggtccccacc tctcagaaca actttgctcc agccacatgg cttgctcacg   3420
gccaggcact gcccatgtgg actctgtgcg tgccacctct ttgccctgac ccatgttgcc   3480
tctgggggag cacttcttcc tccaccttcc atcatgggct gtggcagtgc ccatcccatc   3540
tgcccccgac gctgtctgct gcagtatggt tgttggggga aagggcacca ggctccggcg   3600
tctgacagcc gtgttttacc caccttccta ctcactagct tgtgaccttg ggcaattact   3660
taacatctct gagtcttagt ttctgtttct aaaattgggt gaataacacc tactaagtag   3720
ggttggcctg aggattaata gtataatgta aaagctggca gcactgaaac cctgccactt   3780
accagctttt cacatcagta tttgggaaat attgttaagc tcatttgtca ggcggggatt   3840
ctgaggctca gagcagttcc agaactttct acagattatt ttgccttgtt tgcgcttcca   3900
gactgcctat cttcttgtat caccattgat cttgatctgt atggttttta attttttttt   3960
ttttgagacg gagtttcact ctgttgccca ggctggagtg cggtggcatg atctcggctc   4020
actgcaacct ccacctcctg agaagctggg attacaggca tgtgccacca cacccggcta   4080
```

-continued

```
atctttgtat ttttagtaga gttggggttt cactatgttg gccaggctgg tctcgatctc   4140
ctgacctcgt gatccgccag ccttggcctc ccaaagtgct gggattacag gcgtgagcca   4200
ctgcgcccgg ccaacttcac gtttatacac acccatgcaa acagcatcca gatagagaca   4260
aagagccttc cctgtaccct aaaagtttcc cagaaattgt tcccagttag catatttatt   4320
tttataaagg taatgcatgc ccatcatata acattcaaaa aggtatgtag agaaccaagt   4380
gtctccccca gccctgtcct ccagccaccc agtttccctc cctaggggaa gccaccaata   4440
tgtgtttctt atgtatcccc tgttgagctg cttttcctcg ttttggtttg gcggtgttga   4500
tgtttgtatt tggaattaca ggtaggcagc atcatatacc ttagtgttta gggcctctaa   4560
gatcaaccag ccctgagaaa atcagccatg gtgaggacct tgtcccccag ccccccagga   4620
gataggcccc ctggtgggag tgctggggca gggcagaggc ctagggacaa gaattagaaa   4680
ggacccatgt tgacagggct gctcagggtc atgttgtcca tccctctgcc acagtggcat   4740
ggacaaactg catatgttgg ttagaggagg gcacccttct ctcttgcaag cattggcaag   4800
gtcttaacta ttagtctcct gctcccatgg cagccccttt ggacaaggag gctcttaatc   4860
tctgttcttt gaagccctga gggctggtgt ataggagttc aaagcactgg ctttggaacc   4920
ggactgtctg ggtttgaatc ctggcactgc agctgactca ctgatggact caggcaatgc   4980
cttaaactcc ctgagcctca ggttccttgt ctgtaaaatg ataaagatag cccctgtttc   5040
atagggctgt ggtgagaaac caatcagaca aggcatgtga acgccattat agcacagcgc   5100
ccggcatcca gcaggactca ctcgatgaca gttgtcaccg ccatcattgt tattagcgtg   5160
ggccagggag ggctgcgtaa aagcagctgg tggaggaggg agagatgccg tgggaccgtc   5220
tgggttcgca tgcgtgaagt attatctggg cctggagtgt gcaaggcaca catgtgtcct   5280
tactgcatgt gttgtcacat atgtgcaatg ccatgctcct gagcctttga ttgcagacgt   5340
gtgggaagtg ggccccgtcc ccacccccag tgccaccctg ctctgcttct cttcccttgc   5400
tgtgctctaa aacgagaagt acaagtgagt tcccccaagg ggtcggccgc gcctcttcct   5460
gtccccgccc tgccggctgc cccaggccag tggagtggca gccccagaac tgggaccacc   5520
gggggtggtg aggcggcccg gcactgggag ctgcatctga ggcttagtcc ctgagctctc   5580
tgcctgccca gactagctgc acctcctcat tccctgcgcc cccttcctct ccggaagccc   5640
ccaggatggt gaggtaaggg cctgccaccc acggtagaca ggaggcaagg gtgcctggtg   5700
cccacgggac ccctcctcac tgccctgcct gggccgccca ggtggtttca ccgagacctc   5760
agtgggctgg atgcagagac cctgctcaag ggccgaggtg tccacggtag cttcctggct   5820
cggcccagtc gcaagaacca gggtgacttc tcgctctccg tcaggtaggt gggccccccg   5880
caaccccggg cattttggcc actctcttgt gccatccagg ccctgaacca ctcattcctg   5940
gttccccgtg gcagtgctga ctccccgtct gttcccttgc ccccaacccc cacactcccc   6000
atccctgtct gtgcccaccc atgcccatgt gtgcccccac ccaggacctc agccgatccc   6060
tgccctcctg cctctactcc tgcaccgact ggcctcaccg cctggtgccc tgcagggtgg   6120
gggatcaggt gacccatatt cggatccaga actcagggga tttctatgac ctgtatggag   6180
gggagaagtt tgcgactctg acagagctgg tggagtacta cactcagcag cagggtgtcc   6240
tgcaggaccg cgacggcacc atcatccacc tcaagtaccc gctgaactgc tccgatccca   6300
ctagtgagag gtgagggctc cgcacccccg ccattcccaa gcagggatga gccggctccc   6360
accctgaaca gccagggagg cagggagact ggcagccggc gctgcctacc ctccatcccc   6420
tcccctccct gcaccagctg ggctctcaa tgtccctcct ccctgctgtc ctggacctg   6480
```

```
gtgtctcaga gcctaaccta ccaccctttc cacctaaccc cgaggaagcc acagaaagct   6540
gcctcgccct actccgggag ccctggccgc tgcaacccag gtcccactgg agacagggag   6600
gccactgctg gtggccagca tgtcgtgcag gccagctctg ttgttagaaa gctcttcttc   6660
ctctggaatc gagcctgcct tcctccgtct gcccctcacc ccagcacatg ttaggacagt   6720
gaggagctga cactggggtg aagatgggga tgaatgcttg ccaagacact tgatgccttg   6780
tcccagccgc cccgtgggga tgggtctgtc ctgtggggtc aaataggtct ccggcccaaa   6840
cagagatcat tgagagcacg atgtgaagtg ttcacctgtg taaagtgtct cacgctgtcc   6900
cgggcacaga gtaatactcc aggcatttcc ttcctgtggc ctccccgact cctcctgtgg   6960
tctcccaaag gcatgggctg gggctgggg gctctgaatg ctcctcatga caccatggct   7020
cctttcagca gccgcatctc aatgccagat cccccttagag taaagggcag cggaataacg   7080
ctagggggtt ttcacatgca cccctgggcc aagccgactt gcccttgccg tggatccctg   7140
cattcatgga tcggttattg aaatgatcgg gaaccttgct cctgccagct tgcagcctct   7200
ctgagattcg ggcctccaaa ctgcatcaat atttttggtc aaggcactga ttgaaactta   7260
gagctggatt cggtcacggt gcagccctgt ggcccacctg ggaggcctcc tttcctggat   7320
cggcctcctt caaggccttc cctctctctg tgagcctcac atggctggct ccgtgtctgc   7380
cccctgccct tcctcttccc caccgcaaca ctcagggggc ttttggcacc gagaccctct   7440
aaagctcatg tcctctcttt ctccttgcct ccagccagga gaggaggacg ggctgaccag   7500
tgcctggagg tggaagagag gagcagggcc ccaggaggcc cctgcagagg aggctgaggc   7560
ctgggttcaa ggagaagaga gaagagagag aaggaaggga gggcagtgcc ggggcgggag   7620
gttaagacca gggaagccgc actggaggcc cttttgggtg acccgtccca ggagccagtg   7680
tcacccctga gcctgggagt gtgtgagagg ctctttctcc caggttctgc tgtgtcctct   7740
gccttgtctg tgcgcctcct cctctgcgag aatttgcatc tgtccctcgg tggctctgcg   7800
cttcctgtgg tcagcctgac atttgcatgg agacttcctc atcctggggc ctgagggaag   7860
gggctcagcc ccctccccgc tacctggggt cctagcctgt ccccaggcgg tgggctgaag   7920
tagcccagtg gggttaggag gctctggggg tctctcggct ggagtcacct ccgggcaggg   7980
gtgagatggg ttgggacaga ctggtcctcc cctccttccc cccatccctg cggttggaaa   8040
atttgcccgc cctcccctcg tccctgggct gaggaaacct cacaacctca cttctcactc   8100
tctccccaga aggagttttg tgtttttttcc atcacgtggt ttcctgtggg gctgggcttt   8160
gtggggctac agtttcctcc tgggaaaggg gtgtgcttcg gggaaagggc ttagttctgc   8220
tttctgccct gacagcccct tcaaatccgt ttgaaccctg ggctcccctt cagtgacatc   8280
atccagggca ccccagaacc ccctacacca ctctttcccc agtggggttg tcttccccgc   8340
ctccctggcg gagcgcaccc catccgcctt ccttgtgact tgagtctgtg tgtccatctc   8400
ccaccactcc ctgtggtgtg gcctcggtct gcgtttctct ttgcctctgg tctctgctgg   8460
ggcacagtcc catccttcac ggagattcat ccttagcttc tctcctccaa atattttgaa   8520
tattgccagc ctttctgcct ttcagaggtg ggctctgggt tcgaagcccg gttagaactc   8580
tggaggctag gatggcttga acctgggagg tcgaggctgc agagagctgt aaccgcgcca   8640
ctgcactcca gcctgggcaa cagagctctg gaagcttgcc ctagagtcag tcaagggccc   8700
taggccagtg agtaacagct cagcgtcagt ttcctcatct ataaaatggg ggtaatatca   8760
tacctagctc tcagcatgtt tgtgagagac ctaaatgagg tggtggattt ggaagcatgt   8820
```

agcgcagtgc ctggcacaca gtaggtgctt gatttccggc ccctctctgt gaatgtctct 8880
gctcagcgcc ttcccctgtg gcctgggtct taccttccct gacgctgcct tctctaggtg 8940
gtaccatggc cacatgtctg gcgggcaggc agagacgctg ctgcaggcca agggcgagcc 9000
ctggacgttt cttgtgcgtg agagcctcag ccagcctgga gacttcgtgc tttctgtgct 9060
cagtgaccag cccaaggctg gcccaggctc cccgctcagg gtcacccaca tcaaggtcat 9120
gtgcgaggta aggcagccag gcggcggggg agcctctgct gaggctcctg tctgtgacca 9180
cagtgtgggt ggcagggagg gtctgcctgg gcttgaattc aaggctgggg acccagggag 9240
ggagactcaa gtcctgtgaa tggcctaatt tggctccccc cagggtggac gctacacagt 9300
gggtggtttg gagaccttcg acagcctcac ggacctggtg gagcatttca agaagacggg 9360
gattgaggag gcctcaggcg cctttgtcta cctgcggcag gtcaggggtg ggcccagctg 9420
cctccccact tcccctgagc tgtcccccag atgtgagctt ctgggatctc tgagttgctg 9480
acttctcgct cttccccacc ccagccgtac tatgccacga gggtgaatgc ggctgacatt 9540
gagaaccgag tgttggaact gaacaagaag caggagtccg aggatacagc caaggctggc 9600
ttctgggagg agtttgaggt gcatggtggg gaccggcagg gctggggcag ctgaggtggt 9660
ggcagcggcc tggggcccca ggcggacacc ttcccctcct tgcccacctc tgctcctgac 9720
ccaccccacg tgagctcccc cgatggatgc cctctttggg agctgatgct catttcccca 9780
cccacatctc agagtttgca gaagcaggag gtgaagaact tgcaccagcg tctggaaggg 9840
cagcggccag agaacaaggg caagaaccgc tacaagaaca ttctcccctg tgagcaccca 9900
ggctgcccca ttcacccagg ataccgcccc tgccccagct gcctcccctc atctcacagg 9960
tctccaccct ccacgccagg aggggccatc tccccacacc ccccacagag cctcccccctt 10020
ctccaaaagg cctctactcc tcccagaagt gcctccccac caccagcagg caggttgccc 10080
cctgctccca acctccttgt gaactccctc actccctcca tacagatgat cccccacccc 10140
tgctgcccac agtcccccgc aagcctcatg gcttctgaga ccagaatggc ctgttagctc 10200
aggagggtct gacccaggtg tggtgagtcc ctggctaacc cagaccatct cgcctcctct 10260
ccgcccactc ccagttgacc acagccgagt gatcctgcag ggacgggaca gtaacatccc 10320
cgggtccgac tacatcaatg ccaactacat caaggtcagc agtgtgggcc acgtgggagg 10380
agaggctggg ccctgggaat tccctgtctg gtggggggac cctagatcca gagacagctg 10440
ggcaaagccg aagctggctt cttgcatggg tgagggtggc agtggttcag ggcctgtgct 10500
gggccaaggg gctcactgtc ttggggtgcg tctctccacg cttgcgtcca gaaccagctg 10560
ctaggccctg atgagaacgc taagacctac atcgccagcc agggttgtct ggaggccacg 10620
gtcaatgact tctggcagat ggcgtggcag gagaacagcc gtgtcatcgt catgaccacc 10680
cgagaggtgg agaaaggccg ggtagggcgc ccccccttcc ccgcatccgc ccccgtgctt 10740
gtggtcatgc cattaagtcg aagagcagtc agatgccagg gcagaaaggg atctcagggg 10800
tgagggtccg gcccttgttg ggaaactgag ggctagtgac aaagtctcga ctacacaacg 10860
tgacccccag atccctgcat gcatccctgg gctcttctga gctccagacc caggttccag 10920
gctgtcctcc ttcctcctac ccctgcccca cctgtctgca tccaggcccc tcctgtcctc 10980
cctgccccat agatctctct ggagtctgcc ccttaccctg caggctcccc ctacacagca 11040
ccctctgtgc tgccattgaa gtgatcccat ccgtgacaca aactgggtca agttccttcc 11100
tttctgaaat ctcttccatg gctcctggtc acctttggga taaagtcgca ctctaaggcc 11160
tggcattcaa ggtctggtgg cttccctctg acccgcacgc ttctcttgaa ggctcaccgc 11220
ccccagcagc cccagctctt tcaggttccc agcctttctt tgcacaagct cattttctgc 11280
taggaaatga ctctctccac actatctctg cctggcagat gcctcgtttt tgaagacaca 11340
gccggagcgc tgcctcctct gtgaatccag gtcttgtttc ctccaggacc tagagggaga 11400
attacgtctt tcccagccac gctcctcagc gcggtgtctc cccggtcac ctgtctctgt 11460 gagctcctcg aggcacaggg gcacagactg ggtgttattt gtgtctgtga agctgtgtgg 11520
tttgcacagc ttcggggaca atgcctgccc tggcaacgtt tgttgaatga caaacggatg 11580
taccggtgaa gtggctggcc aggcctcacc acctgttggt ggttgatctg agacgagagc 11640
ccaggtctcc tgcctctctg ccagcccatc cgtccatcca acaaatgttt gggccggtgc 11700
caggcactca gaacatagag caggacctgg gatgggccac agtgccctgc tctgtgcctc 11760
atccccaccc gaccctccct ttccagaaca aatgcgtccc atactggccc gaggtgggca 11820
tgcagcgtgc ttatgggccc tactctgtga ccaactgcgg ggagcatgac acaaccgaat 11880
acaaactccg taccttacag gtctccccgc tggacaatgt gagtggcccc cacgccctgc 11940
cccattccgg gagtccctcc ctggacttgt tctcctctct ggtcgggtag ggtgagatgg 12000
atgaggtgtt ccgagagagg agggggcact gaccctatgt cctcggctta gggagacctg 12060
attcgggaga tctggcatta ccagtacctg agctggcccg accatggggt ccccagtgag 12120
cctgggggtg tcctcagctt cctggaccag atcaaccagc ggcaggaaag tctgcctcac 12180
gcagggccca tcatcgtgca ctgcaggtga ggatgataat cctgatggta gtagtgacag 12240
ctgagaagta aatactgcta agtgccatga gctgttataa gcaatataaa cgttagctcg 12300
cacattgagt gccctccgct cacccccggc ttctcctggg tcccctcatg gctccagaac 12360
cctgggtgga tcgtggctgg aaccagcccc actttggccc tctgcctgtg ggtatcttcc 12420
tcagagccct ctccggatgt accatctcgc ccaaccctgc caaatacaga ggaggagccc 12480
gggacccagt tgctggccag gcccaagcta gtcagggcaa ggccgggcag gcacccacag 12540
taggcctgtg tcccggctgc tccgctttct ctcgaggtcc cattctgttg gtttcttctc 12600
ccaggaacat ctatgaggca tgtgctcccc attcctcctc tttttccatc ggtagccgca 12660
gggcttcggc ttcttcctga ctctgccctc tctcccagct tccccaggca gtgccccatc 12720
ctggccccca gggctgtgtg gggatgggtg atgcttcttt ggggctgcac ataactcctc 12780
tgtctatcta cccgcatgtt tgtgatcagg agacctctgg taaggtgcag aggtgggggc 12840
tgcaaggagg agcaggggtt ccacaggtga gcccactgag ctggcctggc ctgggtggat 12900
gagaggcagt gggtgcaggg cccctccgct taccagctgt gtggtcttgg acaaattact 12960
taacttttct aaccctcagc ttcctcatct gtaaaatcag gatctcaggg ttgtcgtgag 13020
aactcaatga gaccctatcg ttgtggctgg aattccgtca gccctcaaaa actgggcgct 13080
gttactagtt tagtaactca catcaggcag agaatagggg aatgggaacc tgccttgccc 13140
cggtcccttc ccactccctc cgtggacccc aggcctgcga cggcctctgg cttcctcctc 13200
ttcccccagc agctgtttgt cctgggacag ggcaagtcgg ctgaatctag aggtgccccc 13260
gatgggctgt ccggggacgc ggctctgtcc tgtgctctct cagggacagg cccatccccg 13320
agagctaccc tcctgctcac ccgccacaca cacattcaca cacttcttga aagccccatg 13380
gcctttattt agacgttaca ggaaggaagt gggtgtgggg ggttattttt gacaatctgg 13440
gtttgaaatt agacagcgcg actcagggca tcagcttgct gggctcagct gagggtgggc 13500
ctggggtctc cctgaggtct gtttgcccag ggctgggaaa ggagagaaac ttcctactgc 13560
actgctcccc tgagtcccct gaccctgtgc cccgcaccc tgctgtctca gggctatcct 13620
ttccctgacg tcagggtttg aaggaaaagg gaagtgaagc catgctgaga gacgctccat 13680
aactccttca gggagaggcg gggagggctc agggtacctg ggagccggca ggacagtggt 13740
gggatttggg ggtcccaggt cttccggggt gggggcagcc actcactagg agtgaggagt 13800
cggcgcgagg agtggaggag ggaaggatgg tggcagctgg ggagccagcg tcagcaccgc 13860
agagcccgag gtggagcgtg tccatgcaga gctgggcaaa cctccatcat cacttgcccg 13920
gtgaccctgg gcacattccc tcccatcact ggaggctcag gctgctcctg tggtgcctgg 13980
ggctggagct gagcgctggg taccccccctt cccggggagg gcttgactgg cctctgatgg 14040
cacccccgtc tttccccagc gccggcatcg gccgcacagg caccatcatt gtcatcgaca 14100
tgctcatgga gaacatctcc accaagggtg aggggcacct gggggtttgg gggtgggggg 14160
tgagcagccc ctcggtgtcc gcctatgcct ggacctgagg tttgactgcc ccccacccag 14220
gcctggactg tgacattgac atccagaaga ccatccagat ggtgcgggcg cagcgctcgg 14280
gcatggtgca gacggaggcg cagtacaagt tcatctacgt ggccatcgcc cagttcattg 14340
aaaccactaa gaagaagctg gaggtcctgc aggtgcgtgc agagcagggc ctgggggggg 14400
ggggggctgc agtgcaggat gggtgccacc tggccctgct gggaccacca ccttcccact 14460
gtccctctgc ccacagtcgc agaagggcca ggagtcggag tacgggaaca tcacctatcc 14520
cccagccatg aagaatgccc atgccaaggc ctcccgcacc tcgtccaagt gagtggccct 14580
gactgccact gcccggcatc cacccctttg tcctgcccag cccgatcctc actttctgga 14640
gaggacaagt gttgcagctg gggggacctg gcttcaagtt caggcttggt tctcacccct 14700
tctgttcata agcatttcct gagtgcccac acgtgtgggc ctctgctagg taccagcagc 14760
gcactcgtgt atgagatgta gcctctgtcc tctaggagct tggagtctag tgcagggacc 14820
gtggctgcgt cacctgtgag acggggtggc cagaggggac tgccagtgcc gggtcccccct 14880
gtgctgtctc ctgacctgca ccaactgcct gtacttgccc ccctgcaccc ggctgcagac 14940
acaaggagga tgtgtatgag aacctgcaca ctaagaacaa gagggaggag aaagtgaaga 15000
agcagcggtc agcagacaag gagaagagca agggttccct caagaggaag tgagcggtgc 15060
tgtcctcagg tggccatggt acagctcttc tgcctgggtg tcctccctgc cctgccctgt 15120
gtccttggct ccactgcctt ccctgggtgg atggggtggc cgcagcctca ttctgtgctt 15180
cccagctgcc ccagaccctc ttgttccacc tccaggttcc agctaccctc tcactccctc 15240
actcccttct cttggcagcc tcagccctga ccctgtggaa gcatttcgcg atggacagac 15300
tcacaacctg aacctaggag tgccccattc ttttgtaatt taaatggctg catccccccc 15360
acctctccct gaccctgtat atagcccagc caggccccag gcagggccaa cccttctcct 15420
cttgtaaata aagccctggg atcactgtgt gtcgcctctg agccctttgc ttgcccagtg 15480
agtgggcggc cagagggcag ggcaggatgg gtaactgtgt gtgcctccgt gcgtgcctcg 15540
cgtgaaagct ccgccttccg tcagacggac gtgggtcggg actccgcctc gcacgtggga 15600
gggtgaccgt gggtgaagct ccccagtctc cttctttaaa atggagggcg atcataacag 15660
ggtggttgtg aaaagcaccg agatgacggc tgacgataag acgggcacag tgactcatca 15720
cacgcttgcc atgtgcccag gcactaaaag actacacacg ttagttcagt ctaggcactt 15780
ctgtcattct cattttaccg tggcggaaac tgagggacag aaaaactaag taacttggtc 15840
acttgcccaa ggtcacaggg ctatggaaca gtgaggctgg gattcgaacc caggctgtct 15900
gaccccagag cccacactcc ttaccctgga gttgcagctg ggccaccct cagggggcc 15960 ctgatcacac tcccctgatg ctgagttcca gatctgaact aagaagagta gttaacagcc 16020
ggaagcgcag acctgaggcc agcccggct 16049

<210> SEQ ID NO 59
<211> LENGTH: 624
<212> TYPE: PRT
<213> ORGANISM: Homo sapiens

<400> SEQUENCE: 59

Met Val Arg Trp Phe His Arg Asp Leu Ser Gly Leu Asp Ala Glu Thr
1 5 10 15

Leu Leu Lys Gly Arg Gly Val His Gly Ser Phe Leu Ala Arg Pro Ser
20 25 30

Arg Lys Asn Gln Gly Asp Phe Ser Leu Ser Val Arg Val Gly Asp Gln
35 40 45

Val Thr His Ile Arg Ile Gln Asn Ser Gly Asp Phe Tyr Asp Leu Tyr
50 55 60

Gly Gly Glu Lys Phe Ala Thr Leu Thr Glu Leu Val Glu Tyr Tyr Thr
65 70 75 80

Gln Gln Gln Gly Val Leu Gln Asp Arg Asp Gly Thr Ile Ile His Leu
85 90 95

Lys Tyr Pro Leu Asn Cys Ser Asp Pro Thr Ser Glu Arg Trp Tyr His
100 105 110

Gly His Met Ser Gly Gly Gln Ala Glu Thr Leu Leu Gln Ala Lys Gly
115 120 125

Glu Pro Trp Thr Phe Leu Val Arg Glu Ser Leu Ser Gln Pro Gly Asp
130 135 140

Phe Val Leu Ser Val Leu Ser Asp Gln Pro Lys Ala Gly Pro Gly Ser
145 150 155 160

Pro Leu Arg Val Thr His Ile Lys Val Met Cys Glu Gly Gly Arg Tyr
165 170 175

Thr Val Gly Gly Leu Glu Thr Phe Asp Ser Leu Thr Asp Leu Val Glu
180 185 190

His Phe Lys Lys Thr Gly Ile Glu Glu Ala Ser Gly Ala Phe Val Tyr
195 200 205

Leu Arg Gln Pro Tyr Tyr Ala Thr Arg Val Asn Ala Ala Asp Ile Glu
210 215 220

Asn Arg Val Leu Glu Leu Asn Lys Lys Gln Glu Ser Glu Asp Thr Ala
225 230 235 240

Lys Ala Gly Phe Trp Glu Glu Phe Glu Ser Leu Gln Lys Gln Glu Val
245 250 255

Lys Asn Leu His Gln Arg Leu Glu Gly Gln Arg Pro Glu Asn Lys Gly
260 265 270

Lys Asn Arg Tyr Lys Asn Ile Leu Pro Phe Asp His Ser Arg Val Ile
275 280 285

Leu Gln Gly Arg Asp Ser Asn Ile Pro Gly Ser Asp Tyr Ile Asn Ala
290 295 300

Asn Tyr Ile Lys Asn Gln Leu Leu Gly Pro Asp Glu Asn Ala Lys Thr
305 310 315 320

Tyr Ile Ala Ser Gln Gly Cys Leu Glu Ala Thr Val Asn Asp Phe Trp
325 330 335

Gln Met Ala Trp Gln Glu Asn Ser Arg Val Ile Val Met Thr Thr Arg
340 345 350

```
Glu Val Glu Lys Gly Arg Asn Lys Cys Val Pro Tyr Trp Pro Glu Val
        355                 360                 365

Gly Met Gln Arg Ala Tyr Gly Pro Tyr Ser Val Thr Asn Cys Gly Glu
    370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
        435                 440                 445

Ile Ile Val His Cys Ser Ala Gly Ile Gly Arg Thr Gly Thr Ile Ile
    450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
        515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Ser Lys Ser Leu
545                 550                 555                 560

Glu Ser Ser Ala Gly Thr Val Ala Ala Ser Pro Val Arg Arg Gly Gly
                565                 570                 575

Gln Arg Gly Leu Pro Val Pro Gly Pro Pro Val Leu Ser Pro Asp Leu
            580                 585                 590

His Gln Leu Pro Val Leu Ala Pro Leu His Pro Ala Ala Asp Thr Arg
        595                 600                 605

Arg Met Cys Met Arg Thr Cys Thr Leu Arg Thr Arg Gly Arg Arg Lys
    610                 615                 620
```

<210> SEQ ID NO 60
<211> LENGTH: 92763
<212> TYPE: DNA
<213> ORGANISM: Homo sapiens

<400> SEQUENCE: 60

```
aggctcaagc aatcctctca cctcagcctc ccgagtagct gggactacag gcgcgcgcca      60

ccacgcccgg ctaatttttg tattttttgt agagatggga tttcactatt ttgcccgggc     120

tggttcccaa ctcctggact caagcgattc gcccgcctca gcctcccaaa gggaagtgct     180

gggatttcag gcgtgtgcca ccgctcccac cccaaagtag tatttattgt aattattatt     240

attattttga gacggagtct cgctctattg ccaggctgga gtgcagtggc gcgatctcgg     300

ctcaatgcaa cctctgcctc ccgggttcaa gcgattctcc tgcttcagac tcccaagcag     360

ctgggactac aggcgccccc caccacgcca ggctaattct tgaattttta gtggagacgg     420

ggtttcacca tgttggccag gatggtctcg atctcttgac ctcgtgatcc gcccacctcg     480

gcctcccaaa gtgctgggat tacaggcgtg agccaccgcg cccagcctat tattattttt     540

ttaggcagtg tcttgccctg tcgctcaggg tgtagtgcag tggcgtgatc acgactcact     600
```

-continued

```
gcagccccga cttctcgggc ttaagttatc ttcccgccgc agcctccacg cccggttagt    660
tttttgcatt ttttgtagag atgaggtctt gctttttttgc ccaggctggc ctcgaactcc    720
ttggcttaag cgaacctctt gccgcagcct cccaaagtgt tgggattacg ggcgtgaacc    780
accgcgccca gcctactatc tttatcttac agaaagaaaa gaatggagga aaccgaggct    840
cggagacagt aggtaatttc cccaaggttc cacagctaat gagtggagcg gcgatttgtg    900
gaacgaaatg aatgaaatcg atgtggcagc gggcccggac gggtcggtgg cgtagacgcg    960
gagcgcgcag ctcacacctg gcggccgcgg tttccaggag gaagcaagga tgctttggac   1020
actgtgcgtg gcgcctccgc ggagcccccg cgctgccatt cccggccgtc gctcggtcct   1080
ccgctgacgg gaagcaggaa gtggcggcgg gcgtcgcgag cggtgacatc acgggggcga   1140
cggcggcgaa gggcgggggc ggaggaggag cgagccgggc cggggggcag ctgcacagtc   1200
tccgggatcc ccaggcctgg agggggtct gtgcgcggcc ggctggctct gccccgcgtc   1260
cggtcccgag cgggcctccc tcgggccagc ccgatgtgac cgagcccagc ggagcctgag   1320
caaggagcgg gtccgtcgcg gagccggagg gcgggaggaa catgacatcg cggaggtgag   1380
gagccccgag gggcccggcg cgggcctcgg cccggccacc gccgcgttcg gttagccccg   1440
tccggaaggg ggcgccccgg ccgggcttcg ggctcccgcc ccgggtcggg gttgggggcc   1500
ggttccctcc tcgtcccctc gccctccagg ggccgggggc cggcccccacc gcgcccccac   1560
ccctcgggtc cccattcatt tcctgcctcc ccgagttccg gctgcggcag ccccggggat   1620
gcccgtcagg cccggggcag gtagagccgc cgagggaacc acgggtgcca gcggccaggc   1680
tcagcgccgc attcctgacc cattgcctca tgagaattgc ctcatggtga ttccgaaata   1740
accctgctca cttggggagg ctccttggga cacgagaggg gagttgcgcg gggccgggcc   1800
cccagtggtc tagtcgttct ggctcactgt gccactttcg tgcatttggg gacttcacgc   1860
aggacccctg accctttat atgcctcttt gtgtcttctt ttcctcctac ccctcacgtg   1920
ccagaaatgg aaaaactgac tgtatctgca gccactagaa gtatttcctt cctctgcgat   1980
cttcgctttg ggagatggaa aggaagggag ccgcatctcg ttatttaatc cttcactgca   2040
accttaacag tcaggtcact ttactggtac ccgttttatg gatgaggaaa ccgaggccca   2100
gaagcaacat gctagtaaat gacaagattt gaaacttagg aggattagtg agttaatgag   2160
atcctttgaa aggtcagggt aatactacta ctaatagcta acatttgctt agttctgacc   2220
acagccctat cagatggcta ctattatccc cattgtaaag atgagtaaac cgagtttcag   2280
aggttaagta aattgcctaa cctcacagct agtaggtggt ggagacagaa tccctacttt   2340
taatcactat gttgcttcta ttattttgta actattgcta accatttgta agccttaatt   2400
ttgttgtcaa acagtagtgt gacctgttgt tttcagatag tgatcctgct attttgtata   2460
gtcactctat ataccactca cacttaagac ccattgtcta ttcttttcca tgattgttca   2520
attatggtca ctgtctcaga catttaaaaa acgattcaag ctattgaggc tatttgaatg   2580
agattttctt ttcttttttt cttttttttt ttggagacgg aggctcactc tgttgcccag   2640
gctggagtgc agtggcgcaa tctcggctca ccacaatctc cgcctcctag gttcaagcga   2700
ttctcctgcc tcagcctccc aagtaactag gactacaggc gcaccactat gcccggctaa   2760
tttttgtatt tttagtagag acagggtttc actatgttgg ccaggctggt ctcaaactcc   2820
tgacctcgtg atccgcccgc cttggcctcc caaagtgctg gaattacagg cgtgagccac   2880
cgtacccagc ctgaatgaga tttttcaaaa tattaggaat gtctcctcca aacacacctg   2940
gcatgttatt catacatgga tctggaattt aaaaagggga gaaaaagaaa actgagaact   3000
```

```
cgtaggaagt gagtgacttg gacaggtcgg ttggcaagtg cttacagatc tgggtaatat   3060
ataactgcat ttcaacagaa cagtgtatag cctcaaatgt tctaattctt tagggagctt   3120
ttaaataaac agttgtctat tctttaatct gtcaaatagt cattgagcct tttgttcctg   3180
gtgtctgctc ttccagacaa gtaaggatct gctgctttag gagacatcag acggggctgg   3240
gggttgggaa aaggtctggg tagtaataga ccctacattg tccagtttgt tcatttagaa   3300
gcatagaagt gtgggcatag tcaaagtagc aagtggtaaa gatgacagtt tgaaatggag   3360
taattccttc tcccctccag ccctggtatt atgcaccacc caaaaagccg ggttatgaac   3420
ataatacaca taattttgaa tgattcatta ttttttggat tataagcctg ttttatttgt   3480
taaccagcct taatgaggta taaatgacat gcaattaatt gcatatattt aaatgtacaa   3540
tttgatcagt tttgacatac atatacactt gggaaaccac caccatagtc aagataatga   3600
acacatctat cacccctggt aattttgcct tatgttcttt ataatccttc ctttgttctt   3660
aggcagccac tattctgctt tctgtcacta tgtattagtt tgcatttcct agaattttat   3720
ttttaaaaat tttaaaattg tttgaataga gatggggtct cactgtgttg cccagggcag   3780
tctcaaactc ctgggttcaa gtgatcctct caccttggcc tcctgaagtg ttgggattat   3840
aggcatgaga caccctgccc agccctagaa ttttattatt attgttatta ttgtgttttt   3900
ttgagatagg gtctcacttt gttgcccagg ctggagtgca gtggtgcaat cactgcagcc   3960
ttgttttcct aggctcaatc catccccccct cctcagcttt ccggttactg gggctacagg   4020
tgtgcaccac cacacccggc taatttttgt attttttttat agagacaggg ttttgccatg   4080
ttggccaggc tggtctcaaa ctcccgggct caagcgatct tcctgcctcg gcctcccaaa   4140
gtgctgggat tacaggcatg agctattgcg tcccgccttc aaattacttt aacctagtat   4200
taattcattc aacaggaagt taatgagcca ggcaggataa agcagtaaga taggaaaata   4260
ttgctatttt catggctgag agagagcaga caaacacatg actaaatagg gcaatttcag   4320
gtagtaataa attctaggag ggaaaaaatc ccacagaaat gtgaggatgg gagaatgcag   4380
ttagttttga taggtggttt agagaaggtg atcgtgtgag ctgacacctg aatgacaatt   4440
agtagtctga attttgtttt gcttaattat caaaataact cctcttgggt tcggctttta   4500
tatgcatcca gtaattaaaa tgtaagtata ttcaatgtac tgatatctct cagcatcata   4560
ggtaggaaaa ctaaggcatt cagcaattaa gtgactcctc ccttgatcat gtagcagtga   4620
tagtactgga tttagatttt gaggttgctt ctctgccctt ttctgccttt gtgaaaccaa   4680
caaagctgcc tgtattttcc aactcttcct tcagcatgtg gtacctcctt tacatctgtt   4740
tttgttgctc tgaaatccat acgcgacgat gagctgagag ggcagaaaaa ttgagcttgt   4800
tctgagactg gaggcttttg gtttatctct tgcaggtcaa gtacattttg tcctgggctc   4860
tccctggtgg ccacgtttgt ttatctcctg cgggagtaaa taaacttgcc ttgctgaaaa   4920
ataacagttc tgtgtctttg cagtggaaac tgggatgtct ttattaacgt taggtcctga   4980
tgtaaggcca agtttttggt tagagttgct caagtgcaga ggccactgct aagatgactt   5040
acccctcgtg tccatggtca atgtggagac tgttatgagt ggcacatgat gctggaaaag   5100
cagagccaac tcatgtttgt aattgtccta gcaggccgtg gtgtactttg ttaggcagcc   5160
acagaacaat agagaaactc agcttattcc ccttccctct gggaaacaca gacagtactt   5220
gccatccaac gccaatgttt ttaaggaaga aagaggcaaa aagtgatgtt ggcaaggtct   5280
ctgggagttg tggaccccaa ccaaggattg gagaccctga aatggattca gatgccctaa   5340
```

-continued

```
aatgcagccc agttcattac tatgaatttt ggaggacttt gtgccttgag caaatgtgta   5400
tatgtgacgc tctttgacaa cactgaaata ggaaaaatac tatccatgtt cgcgaggagc   5460
actgaattta gagagggaga cagactttta tgccagcatc aaatgaattt gataaagcta   5520
gtaccaaaat gaaatttgaa attttttttt tttgaaatag agtcttactc agtcacccag   5580
gctggagtgc agtgatacaa tattggctca ctgcaacctc cacctcttgg gttcaaacaa   5640
ttcttgtgcc tcagtctcct gagtagctgg gattacaggt gcgtgccacc atgtctggct   5700
aatttttata tttttagtag ggatggggtt tcaccatgtt ggccaggccg gtcttgaact   5760
cctggcctca agtgatctgc ccaccttggc cttccaaagt gctgggatta taggcatgag   5820
ctaccacaca agcctgaaat ttgaaatgta ttggtataga atatactgtt tagaatgtat   5880
gtgtatatat gtatatttgt atactcatat aaacacaaat acacattgta tgtgtttctg   5940
taatatgtat atctgtctac acatacatgt atatacacac atacaatgtc tttttttttt   6000
tttttttttt ttgagacagg gtcttaccct gttgcccagg ctggagactg cagtggcata   6060
atcttggctc actgcagcct cgacctcctg ggctcaagtg atcctcccat ctcagcctcc   6120
tgagtagctg ggactgacta caggcacgtg gcatcaaact tgtccaattt ttctattttt   6180
ttgtagagtt agggtcttgc tctgttgccc aggctggtct caaattcctg ggctcaagct   6240
gtctgcctgc ctcggccttc caaagtacta ggattacaga tgtgaaccac tgtacctggc   6300
ctttacaatg tctattttaa agataatggt tcaagttttt atcatcccac tggcctactc   6360
taatgaaaca tctatccatt cattgaagaa ttatttatgg tgggataact ctgtgccagg   6420
taccgtgcta ggcattgagt attccaggtt ttaggaaaca gcacatgcaa aagtgctgaa   6480
gtgggagaag atctcggagt gattgaaggc taggagagag caagtgtggg agctgtgagg   6540
ctgggaaggt gggaggtagg tgggagcaga ccacataggg attcttaatg tctttagtgt   6600
catgtggacc atggagagga gtgtagattg tatttttaga gcaatgcaaa atcatagaag   6660
gatgtgatcg ggggagtggc atgagctgat ctatttaaaa atatttctct ggctgctgtg   6720
aaggaaggat tgtaggaggc aggagtagat tcagggagat gagacaagtg atgagagagg   6780
ctttgaactt gggtaaaagt agtttgtgga aagtcttttt tggaggtagt ttttgtttat   6840
tgccttgtca tcaaagcaga gatgctgacc aatgaaactc catgagaaaa tagtgattta   6900
taaagacata tctatgcact gccattaaaa agctgcttgg aaaaaaagga taaaaagctg   6960
ctttaacaac tttttttttt gagatggggt cttactctgt cacccaggct cacgacctca   7020
gctcactgca acctctgcct cccaggctca agcattctcc cacctcagcc tcccgagtgg   7080
ctgggactgc aggcacacgc caccatgtca ggctaattgt gtgtgtgtgt gtgtgtgtgt   7140
atgtgtgtgt gtgtgtgtgt gtgtgtgtgc tgggactgca ggcacacacc accatgtcag   7200
gctaattgtg tgtgtgtgtg tgtgtgtgtg tgtgtgtgtg tgtgtgtgtg tgtgtgtgta   7260
tgtagagatg gggttttgcc atgttgccca ggctggtctc aaaatgttgc ccaggctggt   7320
ctcaaactcc tgagctcagg tgatccaccc gcctcggcct ccaaagtgct ggagattaca   7380
gacgtgagcc actgtgccca cctaacaact ttaaaaaaat tttgacattt agtaggatat   7440
ttattgcatt attgttgaga tggcaaaata ttggagacaa ctgaaatgtt catcagtggg   7500
gggggctagt taaatgaaat acagtgtagc atgcattaga acacttttca agaatttaac   7560
tttttttgta gccttttact tataatgctt gtccctattg atgccttttt tttcagcatg   7620
acttactctt ttactatagg atattaaaat ttaattagat tagaaatgag gaatattctt   7680
gtaatctgta gaaagtaaca aactataaac ttattcccca agaacaaata taataatttt   7740
```

```
tctggagtag caggtaagaa agatataaat ttatatgtat acaagaaact gaaattagac   7800
tttatacatt taaaggttac aagtgcagtt ttattacatg aatgtattat ccagcattga   7860
agtctgggct tttagtgtaa ccagcacctg aataacatac attgtaccca ttaagtaatt   7920
tctcatccct caaacccctc ccaccctgaa attagacttt ggatccctag tttaaattcc   7980
acccctctct ttttttgaga caaggtctca ctctgtcacc caggctggag ggcaatgttg   8040
caatgatagc ttactgtagc ctcaacctcc tgggctcaag ggatacaccc tcctcagcct   8100
cctgagtagc tggaactgca ggcgtgcacc accacattca gctaattttt tgattttttt   8160
atagagatga ggtcggaact cctgggctca agcgattctc cccaagtgct ggggttacac   8220
acatgggcca ctgcccccag cctaaacctc ctttctcagt atagcagcct tgagatgaag   8280
ttcctgaaat tactggccag cttgactgtt tccccacatc actggaggag ggggatgcat   8340
agataaaaca aaatattcag catcattgta ttttcttttt gtttcatcag catctttttt   8400
taaaactcac ttgacataag tccctagcct caaagagtaa agcctttgca gaatctgcat   8460
tcagatttcg ggtgtgattt cctgacagat agttcaggtt tgtaaactct ttttttttttc   8520
tttgagacag agtttcactc ttgtagcgca ggctggagtg cagtggcacc atcttgcctc   8580
actgcaactt ctgcccccctt gattcacgcg attctcctgc ctcagcctcc tgagtagctg   8640
ggattacagg catgcgccac cacacctggg taatttttgt atttttagta gagatggggt   8700
ttcaccatgt tggccaggct ggttttgaac tcctgacttc aggtgatcta cctgcctcag   8760
cctcccaaag tgatgggatt acaggtgtga gccaccgcag ccggccaaaa ctttgttttt   8820
tttcctcttt ttgttgctga gaaatgtaaa ctcttacaga cacaaattat gtctcccatt   8880
ttttaaaacc cactcaacac aggggtcatg tgtaataggc cctggagctt attttagaca   8940
ttgatttgag gctcttttcc ccaagtgctg gtttgtgtgt gtgtgtatgt gtgtgtaagt   9000
ctttctatga gatgagtggt acctacctgg gctgtgtgat ctttttttatt ttatttattt   9060
tatttttgta gatacgaggt ctcactatgt tgctcaggct ggtcttgaac tctggggctc   9120
aacctatcct ccctccttgg cctcctagag tgctgagatt acaggtgtga gccactgcac   9180
ctggccagcg atccttaata aatatagata atggccgggc gtggtggctc acacctataa   9240
taccagtact ttgaggggcc gaggctggca ggtcacctga gctgaggagt ttgagaccag   9300
cctgggtaac gtgggtgaaa ccctgtctct acagaaaata gaaaaattag ccaggtgtgg   9360
tggtgcatgc ctgtagtcac agctacttgg gaggttgaga caggagaatt gcttgaacct   9420
ggaaggtgga ggttgcagtg agccgagatc gtgtctttga actccagcct gggtgacaga   9480
gtgagacctt gtctcaaaaa aaaatataga tataggctgg gcgtggtggc tcacacctgt   9540
aatcccagca ctttgggagg ccgaggcggg tggatcagga ggtcaggaga tcgagaccat   9600
cctagctaac atggtgaaac cctgtctcta ctaaaaatac aaacaattag ccaggcctgg   9660
tggtgggtgc ctgtagtccc agctactcgg gaggctgagg caggagaatg gcgtgaaccc   9720
gggaggtgga ggttgcagtg agccgagact gtgccactgc cctccagcct gggcgacaga   9780
gcgagactct gtctcaaaaa aaaaaaatct atatatctat atatctatat ctatatagat   9840
atagatatag ataatgccag atgatggctg gttagaaggg attgtcaggg gctggcaggt   9900
tttgcaggtg ttagaatgag caagatgagg agaaggatgc ttacttccct ctccttgtaa   9960
ctctctaccc cctcccctca gtgttttttt atttttattt ttatttattt atttttttttg  10020
agacaaggtc ttgctctgtc acccacactg gattgcagtg atgcaatcat agctcattga  10080
```

agcccaaact cctgggctca agtgatcctc ttgcctcagc ctcccaagta actgggacca 10140
caggtgcgta caactatgcc cagttaagtt tttcattttt tatacagacg gggtcttgct 10200
atgctgtcca ggctggactt gcacttctgg cttcaagtga ttctcttgcc tcagtttccc 10260
aaagtgctgg cattatgggc ataagccact gtgcctagcc catcagtgtc tttttatcct 10320
ttactcctat caaaattcat tcactcagca gccattgatc aagtgcctac tatatacatg 10380
ttgaggactg gaaatttatt tgtctcttct catcttatct ggaccctctg tgttaattgt 10440
aattaactgt aatcattctg tattaattgt aataaacttg ttgataaact caaatgaggc 10500
cataccgttt tgccacttcc cctccttcca ggttatatgg atgtacttac attgcaggtt 10560
tcatttgttg gttcagtttt taaactaagc cctattgtgt caaattatgc taggtgtgag 10620
atggggagtt caagctgtgt gttgtctttt tttttttttt ttttttgcc tcacttacta 10680 atatacaagc gcttataacc tttgaggctg gccctataca ttaagatttt tattaattcc 10740
actgttcttt atcttctctt actaagttct cagggtcgaa tgaactctaa ctgctccttg 10800
ctagtgataa gcaagttgca aattacagaa ttgtcagtga ttgaatacac gtattaaacc 10860
tgtaactggg aagcattttt ggtaattatg aatacttttg gaaaaaaaaa agctatggaa 10920
ggaaagttta aaatctacga aagctcaagt agatggtcat ggaatagcta tttcaatttc 10980
taactatata ttacttattt atttatttat ttttgagacg gagtttagct cttgttgccc 11040
aggctggagt gtaatggcgt gatctcagct cactgcaacc tccacctccc gggttcaagc 11100
tattctcctg cctcagcctc ccgagtagct gggattatag acatgtgcca ccacgccagg 11160
ctaattttgt atttttagta gagacggggt ttctccacat tggtcaggct ggtctcgaac 11220
tcccaacctc agctgatccg cctgcctcgg cctcccaaag tgctgggatt acaggcgtga 11280
gccaccgcgt ccggcctctt aactattgtt tgaaataatg tagagacagc tccagagcca 11340
tgaagaagtg tatgaagaag cagtgttagc ttaaatgaca tacatgtcac aattgcctat 11400
gtgaaactat cataattatg catgagaagt atctatcctg cataacctcc accaataata 11460
ataatgttaa taatagtgaa aactaatgtt tattaagtcc ttactgtctc cagcctctgt 11520
gctaaatact ggttactaag tttccctgaa aatactattc tcatctgttt gttcttaata 11580
acaggatagc ataattgtaa gttgtaaatg aaataataca gtttatgtaa taaaagggta 11640
aaagagaaga ccacctacct tatcttctgt tgctgatctg gatggatgta ggtggtgttt 11700
acctagtttc acctttggca gttgaaacta cttttttttt tttttttttt tttttaaga 11760 gacagggtgg gccaggcgca gtggctcacg cctgtaatcc ccgcactttg ggaggctgag 11820
gcggacagat cacttgaggt cagaagttcg agaccagcct ggccaacatg gtgaaaccct 11880
gtctctacta aaaatacaga aaaattaact gggtgtggtg gtacacacct gtaattccag 11940
ctacgtggga ggctgaagca ggagaatcgc ttgaacccgg gagtggaggt tgcagtgagc 12000
tgagattgtg ccactgcact ccagcctggg tgacagagca ggactccgtc tcaaaaaaaa 12060
aaacaacaac aaaaaaagaa atttttagaa atatgagatg acagcaagaa tgagggtatt 12120
aaaaagaaat ttttagaact aaatagcaga atgtaatggt gaaaagtttg atttctcaag 12180
tctgctttgc acacaggcat gtggcaaaca ttcagtaagt atagctgtaa ttttaaccag 12240
ctgtaatgta taatagccaa catatcacat ttttcttttt tctttttga gacagagtct 12300 tgctctgttg cccaggctgg agtgcagtgg caccatctcg gctcactgca acctctgcct 12360
cctgagttca agtgattctt gtgcctcagc ctctcaagta gctgggatta caggtgtgtg 12420
ccaccacact cggctatttt ttgcattttt agtagagatg ggctggtct tgaactccca 12480 gcctcaggtg atctgcctgc ctcagcctcc caaagtgctg agattacagg tgtgagccac 12540
agcgcctggc catatattgc tttttttctta ttatcagagc cagttcataa ttgtggaaaa 12600
atagtgtttg taacaatgta agtatggata aatcatcttt ttaattttgt gattcatata 12660
ggtttgttgt tgttgttgtt gttttgtttt tatcttgaga cagagtcttg gtctgtcacc 12720
caggctggag tgtaatggca caaccatggc tcactgcagc ctcagatgcc tgggttcaag 12780
caatcctccc gtctcagcct ctagagtaga tgggaccaca ggtgtgggcc accatgcctg 12840
ggtaattaca aaactttttt ttttttttct agagatgagg tctcactatg ttgcccaggc 12900
tggtctcaaa cctttgacct cgcttcagcc tttagagtag ctatgactat aggcatgtgc 12960
catcacccag ctaattaaaa tttttttct ttttttttt ggtggagatg cggtcttact 13020
ttgttaccca gactgcaagt tagtttcaga tatcaacatt tggtgtttcc aaatgcacgg 13080
ggaggctttg gagcaagttt ttggctcata tgcataggtg tcctagacat tcactttgca 13140
aattcttatt aaaatgacta cagtagcata cagataggga aaaatatcct tgtcagtacc 13200
accgattggg tgagaagaga ctgtatatta aaaacaatga ccatcttttt gccacataaa 13260
ttgctggtgg ggccagtttg aagagggctt tgtcagctgc cttctgcctc ttcctcttga 13320
gtacgtggag ttggagtcat ccttgacagc ctcctgttga caccacccgg gtcacagatg 13380
tgaaactgtg tggatgtagg agagagcagt gatggggctt accccaaggt tgctcttcct 13440
tccctctggc cacaaatgtt tagtaaggaa ctgctctgta ttaaccattt gctaggggct 13500
gcagatacgg tggtgaagaa atagacatgt tcctactcgg gatgctgagg tgggaggatt 13560
gcttgagccc aggagttgga gctgcagtga gccatgatca caccactgca ctccagcctg 13620
ggggacagag cgagacccta tctctaaaaa acaataaaag aaatagatgt gtccttcacc 13680
ctcatggaac tgccagtcta gccttcaacc tggtgactgt agaaatgtgt gattagatgc 13740
tatattgcca tgttgagtgt cacccctgag aagcagggtt ttttttgaga aggtaggatg 13800
ggggatctga ctgtgggacc accagaggga aaagcacatg taaaagctgc gtgtaccaac 13860
tggaggaaat cggagacgtg atcagagaac cagagtcaac caggggccat gccgtacagg 13920
gtcctgttaa gatctgtgac ttttttctaa acgttttctt ctggataaca tctaaatttc 13980
tagttccaaa tgtgaaactc caagggcgtt ctgtgctaaa cattttgcat gtattaatta 14040
atttccacca cacaacattg ctgtgaatta agacagtttc taagcatggc aagaaaccca 14100
gaaatcataa tggaaaaatc tgataaattt aacaatgcca acatgaacct ctgtaggaaa 14160
aaaaatacca cagactaaaa aggggggaaa aaaaccagag acaaatattt gcaacacata 14220
cagtaaaggg taattttctg gttatatcaa gagctcctac aaatcagtaa gaaaaaaaat 14280
ctaataggaa atgagcaacg acaaactgac aactcataga aaaggaaaca caagtggtct 14340
gaaaacatga aaaagtgctc agtctcacaa agaaatgcaa actaacatgg taccattttc 14400
cattaatcag atagacaaag atgaaagagt ttggtaatgt atgtagtatt ggcacaagtg 14460
agggaaaaca ggggatttca cactctatgc ccgtccaaac cagtacctta ttttgagggt 14520
ggtttgacaa tatttgtcaa aataaaaaaa ttatatatag tcatttgcca cataatgatg 14580
gttcagttga tgatggacgg catacataat ggtggtccca taagaatata atgggctggg 14640
tgcagtggct ctcacctgca atcccagcac tttgggaggc cgaggtgggt ggattgcctg 14700
aggtcaggag tttgagacca gcctggccaa catggtgaaa ccctgtctct gctaaaaaca 14760
tacaaacaat tagccaggca tggtggcggg tgcctgtaat cccagctact caggaggcag 14820
aggcaggaga atcgcttgaa cccggaaggc ggaggttgca gtgaggtgag attgggccac 14880
tgcactccca tctagatgac aaggcaaaac tccatctcaa aaaaaaaaaa aaaaaagaat 14940
attatgggcc cagccacagt ggctcacacc tgtaatccca gtactttggt aggccaaggc 15000
aggagaatca tttgaactca ggagtttgag actagtgggg acaacatagc aagaccccat 15060
ctcaaaaaaa aaagattatg gtggagctgt cctgtataga cataccattt ttaacttttt 15120
tttttttga gatggagtct tgctgtgtca cccaggctga tgtgtagtgg cgtgatctgg 15180
gcttactgaa acctccacct cctgggttca agcgattctc ctgcctcagc ttcctgagta 15240
gctgggactg caggcgcagg acaccatatc tggctaattt ttatatattt agtagagatg 15300
gggtttcacc atgttggcca ggctggtctt gaactcctga cctcaagtga tccgcctgcc 15360
tcagcctccc aaagtgctgg gattacaggc attagccacc atttacaggc acctggccac 15420
catttttaat cttttatatt gtatttaaac tgtacctttt ctatgtatgg atgtgtttag 15480
atacacaaat accattgtgt tacagttact tacagtattc agtacagtag catgctgtac 15540
aggtgtgtag cctaggagca ataggttata ccatatagcc caggtgtgta gtaggctctg 15600
ccatctaggt ttgtgtaagt acgctccatg atgttaccac agtgacgaaa tcgcctaatg 15660
atgcatttct cagaacatat tcctgttgtt aagcaatgca tgaccgtatc ttgacaaagc 15720
cattttattt ctaaaacttt aattttacag atttatttgt aaaagtatgt aaaaatgatt 15780
gtaaaggata tgttctgctg cattatttgt aataacaaaa aaccagagga taacataaat 15840
gtcctataag aagggttaga ttatggatgg cacattcata caatggggta ttatgtagcc 15900
attgaataaa agggtactgg ctgggcgcag tggctcatgc ctataatctc aacactttgg 15960
gtggccaaag aaggaggatt gcttgaagcc aggagcttgg ggccagcctg ggcaacatag 16020
caagacccta tctctacaaa ggaaaaataa aacaattagc caggtttggt attggacacc 16080
ttcatggtcc cagctactga ggaggctgag attggaggga tcgcttgtgc ctggcaggtt 16140
gaggctgtag tgagccatga ttgtgccact gcactccagg ctgggagata gagtgggacc 16200
ctatctcaaa aaaacaaaaa caaaaacaaa acctcctgta aaatgtcaag aagtcctaga 16260
tgtgggccag gtgtggtggc tcacacttgt aatccctgca ctttgggagg ctgaggccag 16320
gagtttgaga ccaggcagag caagatagca agactccatt tctacaaaaa ataaaaaaaa 16380
ttagttgggc atagtggtgc attcctgtag tcccagctac tcaggaggct gaggtgggag 16440
gattgcttga gcctgggagg ttgaggctgc agtgagccat gatcacacct ctgcactcca 16500
acctgcgcaa cagagtgaga ccctgtctct aaaaacaaca accaaaaaaa cccagcaaag 16560
tactgataaa gatctttggc tgggcgcagt ggctcacacc tgtaatccca acacttcagg 16620
aggctgaggc gggcaggtca caagatcaag agatcaagac catcctggcc aacatggtga 16680
aacccggtct ctactaaaaa tacaaaaatt agctgggcat ggtggcgtgc acctgtagtc 16740
tctgctactc gggaggctga ggcaggagaa tcacttgaac ccaggtggca gaggttgcag 16800
tgagccgaga tcacgccact gcattccagc ctggcgacag agcaagactc cgtctcaaaa 16860
aaaaaaaaaa gagagaaaga tcttcaagtt gtagtatgtg aaaaaatcag ggtgtaaaac 16920
aagagaatcc catttgtgtg tgtgtcgagt gtgtttcaca caggctcaga gggagtagtg 16980
tgtatatgca catgaacata cgtgtcagtg tatatatgta tatatacaag gttgtgggtt 17040
tgtttgtttt ttttgagaca gagtcttact ctgttgccca ggctggggtg cagtggtgca 17100
atcttgaccc actgcaacct tcacctccca ggttcaagtg attcttgtgc ctcagcctcc 17160
caagtagctg agactacagg cacgcaccac catgcccagt taatttttgt atttttagta 17220

```
gagatggggt ttcatcatgt tgcccaggct ggtctggaac tcctggcctc aagtgctctg  17280
cccgccttgg cctccgaaag tgctgttgcc caggctggag ctcagtggca caatcgcagc  17340
tcactgcaac cccgacgtcc caggctcagg caatctttcc gtcttagctt cccaagtaac  17400
tgggactaca ggtgtgtgcc atcaatgccc caccaatttt ttaatttttt gtagagatgg  17460
ggtttcccta cgttgcccag gctgatcttg aactcctggt ctcaagcaat cctcccacct  17520
cagcctccca aagtgctgcg attacaggtg tgagccacct tgccctgccc tgtacaaaga  17580
tctgcataaa agcagttaat aatactatgt ttgaggctgc catcacaggg gtgaggtcaa  17640
ggacaagtgt gagaaattct tttagaatct attttaaaaa aagaagagat gacagtggtg  17700
acagtcaggg aacagataag caggtagatt gtgggggtct aggctgtcta actggtgttt  17760
aaaatgaagc aaccgctgag cctgctgtat ttcatttaat ggagactagt aaaacaacag  17820
ccagaaattc ttcactttcc atctaagaga ggcaaaagtt attttccctt caataacctg  17880
ggactgtagg attaaggttt tttttttttt ttttttaaat actacaatat gactaccagt  17940
ataatttaaa aatgattaga attctatttg agtaagaaat aggtgtctgc ctgaagtaga  18000
cagtcactga agtcactaag tggcaaaaga cagaaaaaaa attgaaagta ggaaacaatc  18060
agcagatatg ataccaaaca tgagctgtca gtgataatgg attaagtcct tcaataatgg  18120
ctgagccaga tggaattaaa agaaaaaatc caggccgggc atggtggctc acacctgtaa  18180
tcccagcact ttgggaggct gaggtgggag gatcacttga gtccaggagt ttgagaccag  18240
cctgaacaac atagtgggac cccatctcta ttttataaaa atattttgaa aaaagaaaaa  18300
aaaattcagt tgtgttctgc tttaaaaaga caaattggca cagaatgtca aagaataaat  18360
aaaacaaaca tgggcaaaag agattcaggt ggtaccaata tcgggctaag tagcattcaa  18420
gataaagatt attaaataat aagttagtta atactagagt aattgcatat taatgaaaca  18480
taatctatgg tagagatatt atagtcaata attgttttat gtattcatta aggtaacaac  18540
aagcaaacaa gctttaatag ttttaaatgc tttatatgct ttatagttct tttatgtgca  18600
ttaattcatt aattctcatt tcctatgagg taaacactat tattatccac attttacaga  18660
tgtaaaaacc gaagcagaga gattaattag cttgcccagg agatgtggca ttctgggatt  18720
tgagacagtg gtttggctct gtaggttgct tcaataacca agagatgctt caaatcagat  18780
ttttaaaata tgtttttcag aagcattttc ctgatacttc tccccttaca tgggtgttag  18840
tcttttgggt tgaaaaacat gagtaagtgc tagaagagca aaatatgcat ccagatttaa  18900
tagtatgtct gtttttctga gccttggcat ttcattgctt ttataataga aatgaaggct  18960
tttttttttt tttggctgag aatagcactg aactcagtgg gagggactgt gggttgtaag  19020
ttgtccgcct ctgaatggag ttgaatttaa gtttcttggt ttccaaagaa tgattgattt  19080
aaagaccctc aaattgcaag ttagaactga cttcagtcct tgaggttttt taccatttaa  19140
tgaataatta aatttatggt aataaatggt aataaatggt aaaaatggta ataaatttta  19200
ccatttaatg aatttttctt aaaaagcaat tgaattgttg atgaaaggtg atgttaaaat  19260
tatcccagat ttatcaatct tttttttatt gcccctggat tttgagtcat agaaagcctt  19320
tccttattct aaggttaaca agacattcac ccatgttttc ctctagtatt gcattgtttc  19380
atcttttacg tttattattt attttatttt attttttttga gacagggtct cactgtgtca  19440
ctcaggctgg agtgcagtgg aatgatcttg gctcactgca gcctctgcct cccgcctccc  19500
gggttcaagc gattctgctg cctcggcctc ccaagtagct gggattacag gcacctgcca  19560
```

ccgcgcctgg ctaattttg tatttttttt ttagtacaga tggggttttg ctgttggcca 19620
ggctggtctc gaactcctga ccttaagtga tccacccgcc ttggcctccc aaagtgctgg 19680
gattacaggc atgagccacc gtgcccggcc taaaatttat tctgatatgt gatatgatgt 19740
atggttctaa ctactttgtt acggtgcatt attttctaaa tgtggtattg gattctttta 19800
tattttgttt agaagttctg catcaatatt catgagtacc attggtctct gttgtttttc 19860
ttgtgccatc tttattggta taggtatcag tgttatattt agtttgtaaa aggaagttgg 19920
aagttttcct ttctttttag tactcaggaa tgattttaag aattgagact atttggtctt 19980
tgaaggtttg gtagaagtcc attgggaatc catctgggcc tggtgatttt ctgtgcggta 20040
gttccttaat tgttttccct attttttctt atttttaatc aggtagcctc tgaaccagaa 20100
taggttcaga gaggctccct ctattttttt taatacaagt tggtctgcct aagttttctt 20160
actctaatgg gttaattttt gtagactgca tttccctgaa aaattacacg tttgttctag 20220
gttttctgac ttatttccac aactttttag tctttccccc tggaatcatg cccctttcca 20280
taaacaggac tctgatgtac ctgaagtatt ttcacacttc gggtggactt tctgtttctg 20340
ggggtggttt tagagcaatt ttaggcctgc cactagctac cctgttctct acaccatgct 20400
gtttttctca gaatgctctt cttttgcaca aaggcttgga gtaggaggtt gagcagtcac 20460
tcactgacgt ttggtatatt ttcttttttt tgcttacagg taatctggaa gtttgggcat 20520
tctctttaag ttgagggtgt ggttttcatg tcattttatt tgtttattgt tttcttgtgt 20580
gtgtttctta gagacagggt cccactcttg ccctggctgg agtgcagtgg cgtcttgatc 20640
atagcttact gcatcctcaa gctgctgggc ttagatgaac ctcccacctc agcctcctga 20700
gtagctggga ctacaggagc acaccaccat acctaatttt tttttttttg agacgaagtc 20760
ttgctctgtc ccccagattg gagtgtagtg gtgcaatctc ggctcactgc aacctctgcc 20820
tcccgggttc aagcgattct ctcacctcag cctcccgagt agctgagact gcaggtgcat 20880
gccaccatac ccggctaatt tttgtatttt ttagtagaaa cagggtttca ccatgttggc 20940
taggctggtc tcaaactctt gacctcaagt gatccaccca ccttggcctc ccaaagtgct 21000
gggattacag gcttgagcca ctgtgcctgg tccctggcta atttttaatt tttttgtaga 21060
gatgggatct tgctatgttg cccaggctgg tcttgaacac ctggccttaa gcaatcctcc 21120
caccctagcc tgccaaaaca ctgggattta caggcatgaa ccattgtgcc tggcttgttt 21180
tgtttttaat tctatgttgt ttttgaagga tgtatgggga gagatggatt taggcaatca 21240
tcgttgtcct tggctacctg aaagtccagg cactcttcta gatactttat aaatattaac 21300
tcattttatc ctctcaacaa cactatgaca tgggtactgt tacaccttcc attttatagg 21360
acttaacaga gaggttaaat atgtagccca gggtcacaga gagctgggct tcagaccaag 21420
acaatctggc accagagtct atgtggctac ccctaaggct ttgccaccat gtgttagtga 21480
ttctcagcct gtcatttggg gaggggattg cccttttttt taaacttttt aaaaaattta 21540
ttcttatttt attatatttt tgagacagag tctccctctt ttgccgaggc tggagtggag 21600
tggtgtgatt tcagctcact gtaacctctg cctctggggt tcaagtgatt ctcatgcctc 21660
agcctcccaa gtagctggga ttacagttgc cagccaccat gcccagctaa tttttgtatt 21720
attattatta ttatttgaga cggagtctcg ctcttttgtt caggctggag tgcagtgctg 21780
tgatctcggc tctctgtaac cttcgtctcc tgggttcagg tgattctcct gcctcagcct 21840
ccggagtagc tgggactata ggcgcgcacc accatacttg gctaattttt tgtattttta 21900
gtagagacgg ggtttcacta tgttggccag gctggtctcg aactcctgac ctcaggtgat 21960

-continued

```
ctacctgcct tggccttcca aagtgctggg attacaggtg tgagccacca tgcatggctg  22020
gattgtcctt ttttaaaaaa aaaaacaaaa acaaaaaaaa aaacccaaac cataaaccca  22080
atattctgaa agatttggtc tccacacctg tgttatataa taattagttt ttccattttt  22140
ttcctcttgg tagaaggcac atatgccact cagtttccag ttgccacacc caattaacat  22200
aattgttttg cagccaaaag caaaagagag ttgacatttt aattagctta tgtaggtaga  22260
caaattgagg cctaatgtaa gagtttcatt ataccttttt gaaaaactat aaatagctag  22320
aagccagttg tcattacttt ttgattcctt agaattctgg gcatctttca tctggaacca  22380
cagatgaaag aagctgcaag gaaggatttt ttttcttaac ggaatagttt aaccattctg  22440
aatgcaaaag tattggatgc tagaataata ggtatcacat aaattgaggt tgacgttttc  22500
ccgggtgaaa ttctattctg tctcaatttt cctttttttt tgagacggaa tcttgctctg  22560
tcgcccaggc tggagtgcag tggcatgatc tcggctcact gcaagctcca cctcctgggt  22620
tcatgccatt ttcctgcctc agcctcccga gtagctggga ttacaggggc ctgccacaac  22680
acccagctaa tttttttgta tttttagtag agacggggtt tcccaggatg gtctcaatct  22740
cctgacctcg tgatccgcct gcctcggcct cccaaagtgc cgggattaca ggcgtgagcc  22800
actgtgcctg gccttttttt tttttttttt tttttttttt taagacagag tctcgctttg  22860
ttgcctaggc tggagcgcag tggcatgatc tcagcttatt gcaacctccg cctcccgggt  22920
tcaagtgatt ctcctgcctc agcctcccga gtatctgaga ttacagatgt gtgccaccat  22980
gcctggctaa tttttgtatt tttagtacag atgaggtttt gccatgttgc ccaggctggc  23040
ctcaaactcc tgacctcagg taatcctcct gcctcagctc ttcccaaagt gctgggatta  23100
taggcatgag tcaccgggcc cagactcaat cttctgacaa gctctcagag agagtaaaaa  23160
gcaaatgaat atttcattat tttgatctga gctttacgat ttttcttttc ttttcttttt  23220
tttttttttt tgagatggag ttttgcgttg ttgcccaggc tagagtgcag tggtggcgat  23280
cttggctcac cgcaccctcc gcttcccggg ttcaagcgat tcttctgcct cagcctcctg  23340
agtaactggg attacaggca tgcgccacca tgcccggctg attttgtatt tttagtaggg  23400
acagggtttc tccatgttgg tcaggctggt cttaagctcc cgacctcagg tgatccacct  23460
gcctcggcct cccaaagtgc tgggattaca agcatgagcc accttgccca gccttttttt  23520
tttaaatctg agaagaggtc ttgctcgatt gcctaggctg gagtgcagtg gtgcgatctc  23580
tgctcactgc attctctgcc tcccagactc aagcaatcct cccaccttag cctcctgagt  23640
agctgggact acaggcatat gccaccacac ctggctaatg ttcgtatttt tttgtagaga  23700
cagggttttg ccattttgcc caggctggtc ttgaactcct gacctcaggt gatcctccca  23760
ccttggcctc ccaaagtgct gggattacag gtgtgagcca ctgtgcctgg tctccttcac  23820
tgttgtaaga tacttgaatt gggtcaatat ttgtggagaa gtctcttaaa agttcacttg  23880
attgtcagta ctagaactct acatttaata ttgacatatt cctgggagca tttcagagca  23940
ttctattagc ttagaaaggt ccaggataat ttgactttag aagttactgt taccatgaat  24000
ctcaatgact tttgaaatcc atgaagaata tctttttttt tttttgaga cggagtctca  24060
ctctgtcgcc caggctggag tgcagtggtg atctgggctc actgcaagct ccgcctactg  24120
ggttcacgcc attctcctgc ctcagcctcc cgagtagctg ggattacagg cacatgccac  24180
cacgcctggc taattttttt gcatttttag tagagagggg gtttcactgt gttagccagg  24240
atggtctcga tctcctgacc ttgtgatccg cccgcctcgg cctcccaaag tgctgggatt  24300
```

acaggcgtga gccaccgcgc ctgcccaaga atatcttttt gctggtaact agagaggact 24360
cctctgaagc agatgccatt catgatggat ttcatcattt atgggtttta aaaaacattt 24420
tattttgaaa taatttcaaa tttaaataag agttgcaaaa tagtacaaat aattcgtgtt 24480
aacttttcat ccagatttac aagtcaacct tatacaggtt gagtatccct tatccaaaat 24540
gcttgggacc agaagtgttt tggatttcag attttttcga attttggaat atttttatta 24600
tatacttaag catctctaat ccccaaatct caaatctgaa atatctgaaa tgctatgatg 24660
agcatttcct ttgagtgtta tgtgggcact ttttaaattt atttaattaa tttatttttt 24720
gagatggagt attgctccat cacccaggct ggagtgcagt gagcgatctt ggcttattgc 24780
aaacttcacc ttctgggttc aagtgattct cctgcctcag ccccctgagt agttgggact 24840
ataggcgctt gccaccacgg ccggctaatt tttgtatttt tagtagagac agggtttcac 24900
cgtgttggcc aggctggtct cgaactcctg acctcaggtg gtccacctgc ctccgcctcc 24960
caaagtgctg ggattacagg agtgaaccac cgcgcctggc catggatttt gcagcatttt 25020
agatttggga tactcaacct gtaccatgtt tactctctct cctctctctc tctctctttt 25080
tatatatata tatatatata tatatatata tatatatata tatatataaa ttatatatac 25140
actacacata tatgtatgta tatgtatgta ttttatatat aaaatacata tctacatata 25200
aaatacacat gtatatatac atgtgtacat atatgtgtct ctatatttaa gttttgttgg 25260
aaccacttga gggtaagttg cagacatggc gtctcattgc tccaaaatac ttcagtgtgt 25320
atttcttaaa tacaaggaca cttggttaca taaccacagt atatcaccaa atgtatatta 25380
taacaagact accatcaaat ccttatatct ctttcaaatt gttttagtaa tatccttata 25440
gcaaaagaca aaacaacaac aaaaactgtt ccccttttatt ttgtttgttt tggtccatta 25500
tatgtccagg ttatgcatta atgcattgtg ttacttgcta agtcttgtta ctggccttta 25560
attaggatat ttctttgcat cccgccaaac tcctcttcat ggttgtatct tttttttttt 25620
ttttggagat ggaattttgc ttatgttgcc caggctggag tataatgatg cgatcttggc 25680
tcactgcaac ctccgtctcc cgggttcaag cgattctcct gcctcagcct cccgagtaac 25740
tgggattgca ggcctgcgcc accttgccca gctaattttg gaattttgtg agacggggtt 25800
ttgccatgtt ggtcagacta gtctcgaact cctgacctca tgatccgccc gccttggcct 25860
cccaaactgt tgggattaca ggtgtgagcc actgtgcccg gtcttttttt tttttttttt 25920
gagacagggt cttattctgt tgcctggcct ggagtgcagt ggtatgatct tggctcactg 25980
caacctggac ctcctgggct caggcgatcc tcccacctca gcctccttag tagctgggac 26040
tataggcaca caccaccatg catggctaat ttttatattt ttttgtagag actgggtttc 26100
gccatgttgc ccaagctggt cttgaactcc tgggctcaag tgatccacct gccttggcct 26160
cccaaaatgc taggattaca ggtgtaagcc actgcgcctg gccctaattt ttgcattttt 26220
tgtagagatg gggtttcact atattgccca ggctggtctt gaactcctgg gctcaagtga 26280
tcttcccatc acagcccccct aaagtgctgg gattataggc gtgaaccact gtgcctggct 26340
gaggattaag tttcaacctc aggggagcgg cattcaaact atagcattgt cctttagtga 26400
ctggcttagt tcacttagaa tgtttgtcta ttcatccatc tatagacact gttttctttc 26460 acctttttggc tttgcaaata atgctgctgt gaatatgagt tatagaaaaa taccaatttg 26520
aatccgtgtt ttcaattact ttgagtatat acctggaagt ggaatttctg gatcatatgg 26580
tacttccaag tttttttttt ttctttttg agacaaggtc tcactctgtc acccaggctg 26640
gagtgtagtg gcacgatctt ggctcactgc aacctccgcc tcccgggttc aagcgattct 26700
cctgcctcag cctctcaagt agctgggatt acaggcacgc gccaccacgc ccaactaatt 26760
ttgtattttt agtagagatg ggtttctcca tgttggtcag gctgctcccg aactcccgac 26820
ctcaggtgat ctgcctgcct cagcctccca aaattctggg attacaggtg tgagccaccg 26880
cacctggcct ccatgtttca atttttaaac aaacaattag ttaaaaaaat aggaaactaa 26940
gagaatgaac tatttcctgt tttattcagt gggttataat ctgttactat cattgtttat 27000
tttgaggtac aaattgtccc tactttggcc agcagaggat cctgcagttt gtctcctgtg 27060
tccttttcat agctccttgt tggaactctt actggcccac aataggatgt tccaagttca 27120
tcttcttact tttactgccc caacgctggg atcagccatt tcttcaagga ggccagttcc 27180
tttcattgga gaatggaaaa cccaatatgt agaaaccaag atagaggtgt taggtgtgat 27240
tgctactgga gtgtcattgc ttccaaaccc tttcagaaga gacctaggaa atgtgtgtgt 27300
gtgtgtatat atatatgtgt gtgtgtgtgt gtattcataa aagcacatac acatacacat 27360
accccgaagc atgtatttct gtattattat tattttttg agatggagtc ttgctctgtc 27420
gcccaggctg gagtacagtg gcacgatcat ggctcactgc aacctctgcc tcctggattc 27480
aagcaattct cctgtctcag cctcctgagt agctgggatt acaggtgtcc accaccacgc 27540
ccacctaatt tttgtatttt tagtagagat ggggtttcac cacattggcc aggatggtct 27600
tgaactcctg acgtcaagtg atctgcccgc ctcggcctcc caaagtgctg ggattatagg 27660
cgtgagccac tgttcccatc cagaagcata catatctatt tctatatcta catttctgtc 27720
tttacatgta tatattaaaa attacagttt gcactaatac ctccaattac aatctaacat 27780
catgggattt attctggctt tctcccttct catatttgtg tctccccaac agtgagaaac 27840
ctggcttgct atcctcaaca tggtaactta tttattaaga aacttattct tttttttttt 27900
ttttttctga gattgagttt cgctcttgtt gcccaagctg gagtgcagtg gtgtgatctt 27960
ggctcaccgc aacctctgcc tcctgggttc aagcgattct cctgcctcag cttctcaagt 28020
agctgggatt acaggcatgc accaccatgc ccagctaatt tcgtattttt agtagagatg 28080
ggtttctcca tgttggtcag gctgctctgg aactcccgac cccagctgat ctgcctgcct 28140
cggcctccca aagtcctggg attacaggcg tgagccaccg tgccctgcct ctagtttatt 28200
tatttttatt ccatgtgctc agtcttgcga gcacgtggtc tgttttcttg ggcctggccc 28260
cctcagtgca ctgtcttaat accctagccc ccagtccctc tgatcatatc cccagacacc 28320
cctactgaat cccaggtctc taccaaggga aaggcaggga ggaggcattg accaaggaga 28380
agagggggaa gggacaggga aggtcttgat ttgtattttc taaaattttc tactctgctc 28440
ataatgcgtc ttagctgtgt tgttgtggaa agtagtgctg acagtgtctt gttttttat 28500
tacttacttt gtctttcttt ttaagatggt ttcacccaaa tatcactggt gtggaggcag 28560
aaaacctact gttgacaaga ggagttgatg gcagtttttt ggcaaggcct agtaaaagta 28620
accctggaga cttcacactt tccgttaggt aagttggaat gaaaagagag gatcctgaga 28680
gtgttttcta ggtaggaagt ggtaaaacca tgcttggata gcttgctgcc tgcatttcga 28740
gtttgaaggc cttatctgag ccctgggctg ccttcagggt ttggggagtg gcctcctgga 28800
catttagcag aagaggagta aggagggccc ttcttctccc tctgagacct catggaaggt 28860
gagttggagc aggtcataga agttcttaag ccctccagtg cttgagactt gttccacaca 28920
tcttgaacct ggtttctgca tttttctttt ccttcctgtt gatttattta aaaattttat 28980
ttcttttcaa tttttttttt tttttaaata gaggtgggat cttccaatgt tggccaggtt 29040

```
ggccttgaac ttctggcctc aagcaatcct gcctcggcct cccaaagtgt taggattaca  29100
ggcgtgagcc actatgcctg gccttctttt tttgagacaa gctgttgctc tgttgcccag  29160
gctggagtgc agtggtacga tcacagctta cagcagcctt gaactcctgg gcttaagtga  29220
tcctcccgcc tcagcctccc gggtagctgg gactccaggc ttgtgccacc atgctcagca  29280
tttttaaaaa atatttttg tagagatgag gtctcactgt attaccaagg ctgatcttta  29340
actcttagcc tcaagtgatc ctcctgcctc agcctcccaa agtgttggga ttacaggcat  29400
gagccaccac actcagactt tgttgacttc ttaataagaa aaatacttgt taagagtttc  29460
ttcagatcac tttcctttat caacaagtaa aacatgactg aggaagttgt ggtccccttt  29520
gcttccctgc ccaggcccgt ttccctccct ctttccccag aggaaaccac caagaggttg  29580
gcatatattc ttcctgaacg tgtttttata gttgtactgc acttgtactg tgtatgaaca  29640
atataaagtt ggtttgtgtg tttaaaaaat tcacatacat ggatttataa tgtatgtatc  29700
attttgcaac ttaaaaattt ttttttgagc tccatgctga ttgataacga tctatttttt  29760
tttttgaga tggagtttca gtcttattgc ccaggctgaa gtgcaatggc gtgatctcag  29820
ctcactgcaa cctcagcctc ctgggttcaa gctattctcc tgtctcagcc tccggagtgg  29880
ctgggattac aggtgcatgc caccatgccc agctaatttt tgtattttta gtagagatgg  29940
ggtttcacca tgtcgaccag gctggtctca aactcctgac ctcaggtgat ctgcctgcct  30000
tggcctccca aagtgctgga attacaggca tgagctacca tgcctggcct tttttttttt  30060
ttttttttga gacaaagtct tgctcttttt cccaggctgg agtgcagtgg ccacaatctt  30120
ggctcactgc aacctctgcc tcctgagttc aagcagttct cctgcctcag cctcctgagt  30180
agctgggatt acagacatgt accaccatgc caagttaatt tttgtatttt ttgtagagac  30240
taggttttac catgttggcc aggctggtcc tgaactcctg acttaaagtg atccatctgc  30300
cttggcttcc caaagtgctg ggttacagg catgagctat cgcgcctggc ctgagaaatc  30360
tcattcttac tcctactccc ttgcacacta tctccattct gtaggtagcc atttctatta  30420
atttcttgtt taccccttctg tgtttctttc attcttttc tttttttctt tttttttttt  30480
gagacaatct tgctctgttg cccagactgg agtgcagtgg tgtgatcttg gctcaccgca  30540
acctccacct cctgggttca agtgattttc atgactcagc cacctaagta gttgggatta  30600
cagcgcctgg tgtacactac cacacccagc taatttgtgt atttttagta gagatggggt  30660
ttcaccatgt tgtccaggct aatctccaac tcttggcctc aagggatctg cctgtctcag  30720
cctcccaaag tgctgggatt ataggcatga gccaccatgc ctggccctat gtttcttttt  30780
ataaaaataa gcaaattaat atttttatta ctattttcct tttattttta cacatcaagt  30840
agaacattaa atatatttct ctgtaatttt tttcagttac ctaaatcttt tagtgatctc  30900
tctcatcttt ttaatcagct ggatcgcatt ctatcatgtg aatattttat aacttctata  30960
tactgtcacc agcaggtagc gatttagttg tgtctaatat tttaaaatga tatataatgc  31020
ctcaatgaat atagtaacct tttgcatata ttgttttgtg ctttgggata acactacctc  31080
gtattggaaa ctgtgtcatt acatgtgtct ttaaaattac atgtgtcttt ttatttttat  31140
ttttattttt tttgagtggg agtttcactc ttgttgccca ggctggagtg cagtggtgag  31200
atctcggccg actgcaactt ccgcctcccg ggttcaagcg attctcctgc ctcagcctcc  31260
ccagtaggtg agattacagg tgcctgccac cacgcccagc taatttttgt atttttagta  31320
gggacggggt ttcaccatgt tggccaggct ggtatcggtc tgctgacctc aggtgatcct  31380
cccacctcag cctcccaaag tgctgggatt acagacgtga gccaccatgc ctggccatca  31440
```

```
cttttttttt tttcttaatt gctgcatagt ggccgggcac agtggctcac gcctgtaatc  31500
ccagcacttt gggaggccaa ggcaggcggc ggatcatgag gtcaggagac caataccatc  31560
ctggctaaca tggtgaaacc ccgtctctac taaaaataca aaaaaattta gctgggcgtc  31620
gtggcgggcg cctgtagtcc cagctacttg ggaggttgag gcaggagaat ggtgtgaacc  31680
cgggacgtgg agcttgcagt gagccaagat tgcaccactg cactccagcc tgggtgatgg  31740
agtgagactc tgtctcaaaa acaaacaaac aaacaaaaaa attgctgcat agtattccat  31800
tgtatgagta gtaacacaac aatttttata atgcatagta ttccattgta tgaatagtaa  31860
tgtagcacta tttgtttata catttttatg attaaaaaac aaaatgtttt tctattatga  31920
ataaagtggc aatgaatatt tttgtacaag tgttttggta gctatacagt tattgtcact  31980
taatatatgc aattcgatag gccagtcatt caaaatagaa gatatacaag gtaggccggg  32040
cgtggtggct cacgcctgta atctcagcac tttgggaggc cgaggtgggt ggatcacctg  32100
tggttaggag tttcagacca gcctgaccaa catggagaaa cctcatctct actaaaaata  32160
caaaagtagc tgagcgtggt ggcgcattcc tgtaatccca gcttcttggg aggctgaggt  32220
aggagaatca cttgaacctg gatttataat gtatgtaaat ccaccgcgaa ggttgcggtg  32280
aaccgagatc acgtcattgc actccagcct gggcaataag agcgaaactc catctcaaaa  32340
aaaaaaaaaa aagatatgca aggtaaagat actaataaag acctttgtgt tgagttggtt  32400
gacatgtggt tatttcaccc atcgtatttc ttatagggaa taggtaaatt cgttccttgg  32460
gtttctttca acacttaggt aaaatccgac gtggaagatg agatctgatt ttactggtgt  32520
aactctttat ttgtcccctt gcctcccttt ccaatggact attttagaag aaatggagct  32580
gtcacccaca tcaagattca gaacactggt gattactatg acctgtatgg aggggagaaa  32640
tttgccactt tggctgagtt ggtccagtat tacatggaac atcacgggca attaaaagag  32700
aagaatggag atgtcattga gcttaaatat cctctgaact gtgcagatcc tacctctgaa  32760
aggtcagtaa cattttagtg accacaaagt ctgctgctcc cttgtgccct gagtgtcaga  32820
aatgcatgac ggtctgtgta tgactctctg actccaaagg cttgtgactg ttttttgagc  32880
tgtaatcttt aaagaattac taaagtgaga ctaatagcat caaattattt tcagagtacc  32940
tttttcctgc aaaagtttta atcagtgtta cttacactca tcctataggg gttgcatacc  33000
attcctgcat atacttggta cgtgtattag ttttaagact tattgaactt cagcagataa  33060
tctttgagag ttattagagg aaaacaaatg ataatggaga caccaaaata gcagcagttt  33120
tctatggtgg ctctcgacca gttattcagc aatgtcacca acagatgtca gtttaagctc  33180
agaagtggaa aagcagagag ctcagagggt cagctttttc atcagttctt ttaatgttat  33240
caccacaatt atgtgagaat gaccttgctt agagaaaatt atgttatttt cgagatcttt  33300
ccccctgtgt tggaactagg ctgatgaaag catgggcttg acttatttat tgattgtatt  33360
cgttttgtac attcccaatc tcctctctga cttggtgcaa attcaggatc tcttagttag  33420
tttgtatatt ttgtgtcttc aggtatgatt ttttcagctt ataccttttat gtcagtgcta  33480
ttatgtgctg ataatttgtt tctctagcta ccaccgtagc ttcaggcaaa aggctgtcag  33540
ccaactctgt acagtttatt tctaaatttt actgttttca gttgagtatg gatgaagaat  33600
aactcaaagt ttattctttt gatgatgagc ccttaacacc acctgccatg atagtacttg  33660
ctttctgacc aagatcctga gggaaaaagc cactttatta ttagaactat gttaagatgc  33720
ttcccaaaaa acatggagca gtattgtctc aaagtctgtc cttggatggc tttggatgcc  33780
```

```
tacatcagga ctgtctgatg tgctggttaa aatgcagatt cctgggcctc attcagactt  33840
acatgtattg atattgctgg ttgtggagcc tgggaattca tatttttagc aaaatccctc  33900
atttttactc caagtcttat gtgcattata cagtttgaga tgatcaccca ggatatagtc  33960
caaagacact ggaggctgtt gaagtatagg ttgtatatat ggaaaaggtt ggaatgtttg  34020
aattaattta taatgaagat cctttttaat tgagtgttca catgccaagg caaggacaaa  34080
cattcaaaat gattttctgt ctctgttaca actttttctt tctttttttt aatttattta  34140
tttgagatgg agtctcactc tgtcacccag gctggagtca agtgacgcga tctcggctca  34200
ctacaacctc cgcctcccag attcaagtaa ttctcttgcc tcagcctccc gagtagctgg  34260
gactacaggc atgtgccacc atgcccagtt aatttttgta tttttagtag agacagggtt  34320
ttgtcatgtt tgccaggctg gtctcaaact cctgaactca ggtgatccgc ccaccttgac  34380
ctctcaaagt gctgggatta taggcgtgag ccaccgtgcc tgtctctatt acaacttttt  34440
attacaactt ctttattttg actttatttt tacaaattat ttatttattt tttttgagat  34500
ggagtttcgc tcgtcaccca ggctggagtg caatggtgcg atctcagctc actgcaacct  34560
ccgcctccca ggttcaagtg attctcctgc ctcagcctcc tgagtagctg ggattacagg  34620
cacttgccac cacacccggc caattttgta tttttagcag agacagggtt tcaccatgtt  34680
ggtcaggctg gtctcgaatt cttgacctca ggtgatccac ctgcctcggc ctcccaaagt  34740
gttgggatta caggcatgag ccaccacgtc cggccgactt ttattttttt ttcttgagac  34800
agggtcttgc tctgtcaccc aagctggagt gcggtggcat gatcatagcg cactgcagcc  34860
tcgacctcct ggactcaagt gatcctcctg cctcggcctt gtgtatagct gggattacag  34920
gcagttgcca ccatgccagg ctaattttta attgttttgt gaagatgggg atttcactgt  34980
gttgcccaga ctggtcttga actcctggcc tcaagtgatc ttcctgcctt ggccttccaa  35040
agtgttggga ttacaggcat aagccactat gcatggcctg taacttcttt aaatggctat  35100
aattaaacag ttggtccttt taagattggg caatggacga atggcaaatt gcatttttaa  35160
aagaggaggg atttaaaaaa aaacaggaaa gattggggca tttgtctcta aaggactgtg  35220
gactcattta agaagtttag tggtcattct taccatcttt gtggtttttc ctgcctgcat  35280
gggatgcaga ttttctgtct caggtgggat tgatcaatcc cttggaggaa tgtgtctact  35340
ttttaattgt gtttaggaga gctgactgta tacagtagtt ttgtgaaaga acaacatgaa  35400
cccatagtag agctaaattc ttttttattt tttaaaaact ttaggtggtt tcatggacat  35460
ctctctggga aagaagcaga gaaattatta actgaaaaag gaaaacatgg tagttttctt  35520
gtacgagaga gccagagcca ccctggagat tttgttcttt ctgtgcgcac tggtgatgac  35580
aaaggggaga gcaatgacgg caagtctaaa gtgacccatg ttatgattcg ctgtcaggta  35640
aatctccagt tgaaaaatgg gtctggcaag atgttacctt tgggtgattt ttctgctgac  35700
agaagacaga caccattaca ttcaaagtca gattgtcttt tatttattta tttatttatt  35760
tatttatttg agacagggtc ttgctctatc acctacagat ggggtttcac cacgttgggt  35820
ctggtgaccc aaatctttgg gtgatttttc tgctggaaga ggacaaacac cattacattc  35880
aaagtcagat tttctgtttt tttttttttt ttgtttttgt ttttttaata ttcatttgtt  35940
tattcatttg agactgggtc ttgctctgtc acgcaggctg gagtgcaacc tccctgggct  36000
cagttgatct tccctcagcc tcttgagtag ctgggactac aggtgtgtgc caccatgccc  36060
agctagtgtt tgtatttttt gtggagatgg tgttttgccg cattgcccag tgtggtcttg  36120
aactagtgct caagaggcct gcctccttca acctctcaaa gtgttaggat tacagatgtg  36180
```

aactactgtg cctgatccaa agtcagattt tctttgctta cttagtcaag ttcgtctatg 36240
cttttattat acttaatata ttagtatagt tactgtatta gtatattagc atatttaata 36300
tattattata cttatcatac ttgagtatat tgagtatatt tacactttta gtatatttgt 36360
atacacacac cacattttta ttatttatct tttttttgag acagagtctc cctctgtctc 36420
ccaggctgaa gcacagttgg ctcactgcaa cctctgcctc ttgggctcaa gtgattctcg 36480
tgcctcaccc tcctgagtag cagggattac aggtgtccac caccaagcct ggctaatttt 36540
tgtattttta gtggatatgg ggttttacca tgttggccag gctggtctcg aactcctgac 36600
ctcaaatgat ctgcccgcct tggcctccca aagtgctgga attactggcg tgagccactg 36660
cacccagcct attatctgtc ttttgatgga catttaagtt gtctctatat actagctatt 36720
gtgaataatg ctgcagtgaa catgagagtg cttgaaaaca ctaatgtaac ataaaggtaa 36780
caaataataa atgtcatgtg tttatcttga aaggaactga aatacgacgt tggtggagga 36840
gaacggtttg attctttgac agatcttgtg gaacattata agaagaatcc tatggtggaa 36900
acattgggta cagtactaca actcaagcag gtgagcagat tggaaagctc aagctttctc 36960
cttaaaaact taaaacaaat cctaatagag aattttgcaa acatacagag gtagacagaa 37020
tagtatcatc agcctccatg tacccattgc agcttcaact atcaaatctt tttttttttt 37080
tttttttttg agacagtctt actctgtcac ccagtctgga gtacagtgtt gcaatcttgg 37140
ctcactacaa cctctgcttc ctgggttcaa gcgattctcc tgcctcagcc tcctgagtag 37200
ctgggactac aggtgcccac caccatgccc ggctagtttt tgtgttttta atagagatgg 37260
ggtttcacca tgttggcctg gctggtcttg aattcccgac ctcaggtttt ctgcccgcct 37320
tggcctcccg aagttttggg attacaggcg tgagctacca cgcccggccc taaatctttt 37380
cttattatga ttccactcac tgactgccgc tatagtactt ggaaacatat tccagattta 37440
tattattccc atatttatct gtaaaaggca ttacagaggt tctttttttt tttttttttt 37500
tttgagatgg agttttgctc tgtcgcccag gctggagtgc agtggcgtgt tcttggctca 37560
ctgcaacctc tgcgtcccgg gttcaagagc ttctcctgcc tcagcctcct gagtagctgg 37620
gattataggt ggtgccacta cacccagcta atttttgtat ttttagtaga gatggggttt 37680
caccatgtta gccaggctgg tcttgaactc ctgacctcaa gtgatctgcc tgcctcagcc 37740
tctcaaagtg ctgggattat aggcatgagc cactgcatct ggcctaaggc tgtacagagt 37800
tttaaagcaa gttttcatta tagatccact tctggttacc tttaggtaac ctcacttatt 37860
cactttggca ttgttgctat ttcaaatttc acctttatga tagtggaaaa tgatataatc 37920
tctctaaata atgtggtcta ttcataaaga aaaataggct tgaatttata tcagcagagt 37980
aaagtgtatg tgaagactga agaaagatac attttctggc tgaacagaaa acacggtgaa 38040
acgatttgaa aacttttatt gtgaattaca gggtcctatg aaccctctgt ccgtgccttt 38100
atgaatatca acatagacat gttttttttt ttttttttgc attaacaccg ttttctgtaa 38160
tattttcttt attttacatc aactgctgta ctcgatcagc cccttaacac gactcgtata 38220
aatgctgctg aaatagaaag cagagttcga gaactaagca aattagctga gaccacagat 38280
aaagtcaaac aaggcttttg ggaagaattt gaggtaagtt attaaaaaac tgtttttacg 38340
tgagttgtta tatcctattt ttagtggagg agaagttgct cttgtgtttg gaattggacc 38400
tgagagactt gaaactgacg tcctttttta attcggccat tgattgacac ggagcaagtt 38460
gctgagaggg cttcttcgaa acagaagagc attgtgttct gagggaaggg agttggcagt 38520
gagtagtcaa tggatgtgct agccgctcca tttggctctt ttggtttgga ctggtggcaa 38580
aatctcagag aaacaaaagg atctaatttc ttcgaaagat ttccagcatg cactggggtc 38640
tttagaaaca atctatagcc ttagtgcagc aaatgagtat gagtaaaaga gaaacacctt 38700
gtggtggctt tttttttttt ttttttgaga cagggtctcg ctctgtcgcc gaagctggag 38760
tgtagtggcg tgatctcggt ttactgcagc cccgtcctcc ctgggctcaa gtgatcttcc 38820
catctcagcc tactgagtag ctgggactac aggcacatgc ccctatgcct ggctaatttt 38880
tgtatttttg gtagagatga ggttttgcag tgttgcccag gctggtcttg aactcttggg 38940
ctcaagtgat cctcctactt aagcttcccg agtagctggg actacaggca cacgatacca 39000
tgcccatcta atttttgtat ttttttgtag agatggggtt ttgcagtgtt gcccaggctg 39060
gtcttgaact cttgggctca agtgatcctc cagctttgac gtgccaaatg tggtggcttt 39120
aatttcagag ttcaaattga taactctggt aagttaagtg aactgatttc tttttttttt 39180
aaattatttt tgttgattat actttaagtt ctgggatata tgtgcagaac gtgcaggttt 39240
gtacataggt atacatgtgc catcatggtt tgctgcacac attaacccat catttaggtt 39300
ttaagtcctg catgcattag gtgtttgtcc taatgctctc cctccccttt aatgcatcag 39360
tgaaaaagtg atgataggct gggcgtggtg gctcactcct gtaatctcag cactttgaga 39420
gggtgaggca ggtggaccac ttgaatccag gagtttgccc ccatccccag acagtgtgtg 39480
tgatgttccc ctccctgtgt ccatgtgttc tcattgtttg gttttctgtt cctgtgttag 39540
tttgctgaga atgatggttt ccagcttcat ccatgaccct gcaaaggaca tgaactcatt 39600
ctttttttat ggctgcatag tattccatgg tgtgtatgtg ccacattttc tttatccggt 39660
ctatcattga tgggcatttg ggttggttcc aagtctttgc tattgtaaat agtgctgcaa 39720
taaacatatg tgtgcatatg tctttatagt agaatgtttt ataatccttt gggtatatac 39780
ccagtaatgg gattgctggg tcaaatggta tttctggttc tagatccttg aggagtcacc 39840
acactgtctt ccacaatggt tcaactaatt tacactccca ccaacagtgt aaaagcattc 39900
ctatttctcc acatcttctc cagcatctgt tgtttcctga ctttaagtga actgatctct 39960
ttcctgaaac taacttgggt tggagaatgt ccctgatggg aatgtgctgt gttcccattg 40020
cactcttcta tatcacttac ccattgacaa tgtgatctct ttcattttct cctcatccat 40080
ttgacagaaa acttcaaaaa caaggattct ggcatattta cctttgcagt tgtccccagc 40140
atgtagcacg gtgcctagta cacagaagaa actccataaa tgtttgttga atgagattta 40200
catttaactc atgtttacat cattttattt tcctgttctg ttttatggga atgattattc 40260
tatgcttttt gaggactaca atttataaat atttgtggat tgaatgaata agtgaatact 40320
gggcaaataa agtcctttta gccagagtat gtctgaacaa cttgctgaga tagatatgat 40380
ttcccatttt ccagctgagg ggcctaaggg aggttaagta aattattcaa tcttcatacc 40440
acagtttttg ttttgttttg ttttgttttt tttcctcctg agacagagtc tcactttgct 40500
gccatactgg agtacagtgg tgcaatcata gctcactgca gcgtccaact tctgggctca 40560
cgccatcctc ccacctcagc ctcctgagta gctggtacta caggtgtgca ccaccatagc 40620
cggctaattt ttcatttttt gtagatatgg ggtctcactg tgttactcag gttggtcttg 40680
aacttctgag ctcaaacaat tctcctgtct tggcctctca aagtgttggg attacaggtg 40740
tgagccactg tgcccggccc ataccacaga tattgattga attccagcag tggggaggag 40800
tgtggaatag aacattctca gtccttgctc aacattactg aacagagact tgaatttgag 40860
tttattctct catcccaggc ttcgcgttag gctctgaaga cactagtgaa caagacagac 40920
agggttactg cctttaaagg gagcttttag ttgagagaag gaaaacagtg atgaaaagca 40980
tcagtgaaaa agtgatgata ggctggggcg tagtggctac tcctgtaatc tcagcacttt 41040
tagagggtga ggcaggcagc tcacttgatt ccaggagttt gagaccaggc tgggcaacat 41100
ggtaaaaccc cgtctctaca aaaaatacaa aaagtagctg ggtgtggggg tgcgcaccca 41160
cagtcccagc tactctgggg gttgaggtgg gaggattgct cgagcctggg agattgaggc 41220
tgcagtgagc tgagatcacg tcactgctct ccagcctgag caacagagcc agaacctgtc 41280
ccaaaaaaaa aaaaaattga tgataaacat agtgagacag aattttgaaa tctcagcctc 41340
actgttgcct tccttgtccc ctgcctgcct aaataataaa aggcagcatt tcagcagtca 41400
ttcatttcat tactttcact tcatttcacc ttcataaagc ctcatgaggt aagatgggaa 41460
gatacagaag ttttagaaac cgctcatcaa aattgaatgg aaagccgatt gttccaaaac 41520
tttttagtgt ggaaaatttc tattatatgc aaaagtagag agaatgggat agttatagca 41580
gtatacctga cacccagcat taacaactgt tgataatatg gccaatcttt ttcgactctg 41640
ccccactcac ttccccagcc ctgacttgtc ttgaagcaaa tacttttttt ttttttttga 41700
gatagagttt tgttttgttt tgttttttgt ttttgagatg gagtctcact ctgtccccca 41760
agctggagtg ctgtggcttg atcttggctc actacaacct ccgcctcctg ggttcaagtg 41820
attcttgtgc ctcagcctcc tgagtaactg ggattacagg tgtgtaccac catgcccagc 41880
taatttttgt atttttagta gggacagggt tttcactatg ttggccacgc tggtctcaaa 41940
ctcctgacct caggtgatcc gcctgacttg gcctccgaaa gtgctgggat tgtaggtgtg 42000
agccactgct cccggccttg aagcaaatct taacacatca tttcgtctgt aactatttta 42060
tttcaaaaaa ttataacctg aatagcatta tcatatctaa aactattaac agtatttcct 42120
taatattaac acatatcagt cacattttcc tgattgctac acacacacac acacacacac 42180
acacacacac acttgcaatt tgtgtttttt tctttttaga tggatctcac tctgttgccc 42240
aggctggagt gcaatggtgc attctcagct cactgcaacc tccacctcct gggctcaact 42300
gattctcttg cctcagcctc ctgagtagct gggactacag gtgcccacca cctcacctgg 42360
ctagtttttg tatttttagt agaggtgggg tttcaccatg ttggccaggt tggtctcaaa 42420
cttccgacct caggtgatcc acccaccttg gcctcccaaa gtgctgggat tacaggcatg 42480
agccactgtg cccagcagca atttgtttga attgggagtg ctttcttcca ccttgattat 42540
gaaaaaattt caaatgtgta taaaacagat tcatataaag gatcctgata tgccattatc 42600
agctttatca attatccctg tcatcatatt ttttatttat aaatatttca atatttgtgg 42660
aatccttaaa aatgcatcac ataacccaac attgttcata ttataccaat tgtcttataa 42720
tttaaaaata ttttgttcaa tcatttttca gataagcttc acacactgtg gttggctaag 42780
tctcataata tttctgttgt aaaaatctta agtctgggcg tggtggcaca cggctgtcat 42840
tccagcactt tgggaggctg aggtgggcgg atcacgaggt caagagatcg agaccatcct 42900
ggccaacatg gtgaaacccg gtctctacta aaaatacaaa aattagctgg gcgtggtagt 42960
gcgtgcctgt agtcccagct actcgggagg ctgaggcagg agaatcgctt gaacccagaa 43020
ggtggcagtt gcagtgagcc gagatcgcgc cactgcactc cagcctagag acagagtgcg 43080
gcttcatctc aaaacgaaac aaaacaaaac aatcttaagt ctcttagaat actttgatgc 43140
cccttccatc tctcttttc tgtcttcctt ccccctctcc ctgtcttttc tgctgttgaa 43200
gaaagcagat catttgtcct gagagttact tatagtctga attttgctga gtgcctctct 43260

```
gtggtggact taagcatgta tccatccctt atatttcttg taagttgata tatctagaga  43320
cttcattgga tacaagtttt ctttggcaag atagcatgta tggtggtgta tcaggaggtg  43380
tttatgtcct gttgtttctt ctctgatttt cttagcagct cctgatcatt attacttaga  43440
tccattaatt cataagggac tatatggtag tgatattgta attttatcat tcttcttcat  43500
ttgttaggtt ggcatatttc tataaaaagc ttttcatcgc cgagggttga ttttttcctt  43560
cttactaagc agtttctttt tctttttctt tttttttttt ttgaggtagg tctcactgtg  43620
ttgctcaggc tggtgtgcag tggcgcaaac acacagttgc gaactcttgg gctgaggtga  43680
tcctcctgcc tcagtttcct gtgtagttgg gaccacaggt gcatgccacc atgcctggct  43740
aatttttttga ttcttttgta gagatgaggt ctcactttat ttcccaggct ggtcttgaat  43800
gtctgggctc aagcaatctt tctacctcag cctcctgagt agctgggact acaggcacat  43860
accaccatgc ccagctaatt ttttaatttt tatttttagt agagatgtgg tcgtattatg  43920
ttgctcagga tggtctcgaa ctgcagagct caagtgatcc tcctgcctca gcctcccagt  43980
gtgctgggat tataggtgta ctacaggcaa gagccaatga gcctggtcag attttttttt  44040
cctgatttga aatctgttat gggttcaatt gatacttcca aatcaaactc agggtttcag  44100
gatttttact aacctcattg atcttaccca tgtatctcct ttctctaatg ccaaaaatcc  44160
tacttcttga agccataata agattattca tttgttttat cccacattac acacaacaat  44220
cttagaataa tgacttccca ataatatgat tactgaaaac agtttaattt tttttgcgct  44280
tttcaaaaaa atccttcaga gatgtgtagt caagttactg tattctgctg ggcacagtgg  44340
ctcacgccta taatcccagt actttgggag gacaagaagg gaggatcgct ggacctcagg  44400
agtttgagac cagccggggc aatatagtga gaccctgtct ctacaaaaga aaattaaaaa  44460
ttaaccagac atggtggcat gtccctatag tcccagctat tgagaggctg tggcgagagt  44520
aggcttaagc ccaggagttt gaagctgcag tgagatacga ttgtgacact gtactctagg  44580
gtgacagagc agggaccctg tttttaaaaa aaaaaaatga aaaaacttcc tgtgccttag  44640
actcatttgt aatcgtcctt ctctctgtgt ggctatatgc taactgggta tatggttagt  44700
ttatttgttt catttaaaaa atctctttct gttaagtttt atttataatt acacaaatac  44760
tggctttgat agtcaaattg aaaaaacaaa gtgtattcaa agaagtctac cttctatcct  44820
tgtcctttcc tatgttttag ccatagtata aaaagttatg gtttatcatt atatttcaaa  44880
aatataagaa gatattccca tatcccactt tttcttaaac agtagcataa ctttacatac  44940
ttttttctaa ccttgctttt ttaaatatcc tggacatcct ggatatccat aatagtgtct  45000
agagatagtc ttcattcttt ttttactgta tagtaatcca ctgtgtactt gtaccatagt  45060
ttattcaacc tattgatggg catttgggta gtttccaaat gtatcacaga gaggattaca  45120
gtgaatagcc ttgtgtatgc atcctgcttt acttttgctg actactggta atattaacat  45180
tttttatgtt ctgtatttaa aaaatggtgg ttattattca tctataactt ttattataca  45240
tgactttggt tagcatgctt taacctttta gcataacatt tgcaagctac ttgttttaat  45300
taaaattttg gttaaatgta aaaaatagtg agctattttg taatctagat tcaatagaat  45360
cttatacttc ctttacaaat gatagctgag ttgatcattt gtgtaaatga ctgtgaactt  45420
aaaaattaca gcatttttta aaataaattt ttttaacatt ttaaaattat ttaaaataat  45480
agacacacaa agtaaaaaga gaagaaaaaa aaaagagaca gggtcttgct atgttgccca  45540
ggctggtctc aaactcccag gctcaaatga tcctcctgcc ttggcctcct aaagtgtaag  45600
ccaccacact tggcaaaaat tagtttcttt aaaacaaaaa cattacaggt tatctggtac  45660
```

catggtagct tctttaacac taggttcact tagaacaaag cttaggaaca aagtcagact 45720
ttcacaaaga gcttgtgtgg caatggggta ttttttgcaa attccattgg tggggtcaag 45780
atgtgagttt agaaggaact cttagcctga ctcttctggc catggaaaaa gatggttgct 45840
tctaaatgct gacctggtga ttttacactg tcacatctca aattgtggtc atcttttata 45900
cattattaac aacaaaaggg aaaaattgag ttgactttaa gaggaagtgg aaaataacga 45960
gatcacatct gtactctaca ggctctccac agaggtcaga ctgaggtggt aaaattgttg 46020
tgcactaaat tagggcatta acgtttcatg gaaactgaag ctatatctaa atagctgatg 46080
gcctgctttc tagatctcct atatacctgc ttctcaaatt cagtctgttt taaaaaattg 46140
ccctttgagg ttggaaccag cgaaataagg ctgaaaacag aataagccat tattgaaaaa 46200
attaggaact tggaagcaga tactcataat ctaaatcctc tgaagctaaa gtttgatcca 46260
caatagcaaa gcattatcat tttagtgatt gtaccttagt tgtttcctgg caggtgataa 46320
atttgggatc actttcttct tacagtgtgc tctgatagtc tttaaaacaa accagagctc 46380
taaattgtaa tgccattggt aatttaactc tgatttgtct ctatgcctgt ctcctggtgt 46440
tctgtaaaat tctacacgtc atttcaggta tcactatcca gaagacgtta cttttgcctt 46500
tgatgcactt taaaatgtga agtctcttgt gaagctcttt ggttattttc tcctttgctg 46560
ctgaaataaa ttcaggttga tgattttctt gtaggatatg ttgtgtgatc tagacattgc 46620
aaacccaagt ctttgatttt tttttcccta cagattgcct gtttcttttt tattttaatt 46680
tttattagtt attattattt ttgagatgga gtctcactct gtcacccagg ctggagtgca 46740
gaggtgtgat agctcactgc aacctccacc tcccgggttc ttgtgcctca gccacccagg 46800
tagctgggat tacaggcacg taccaccact ctcagctaat ttttttgtat ttttagtagg 46860
gatgggattt ctccatgttg gccaggctga tctcaaactc ctgaccttaa gtgatcttcc 46920
tgccttggtc tctgaaagtg ttgggattac aggtgtgagc cactgtgcct ggccagttat 46980
taattttttt aaagagatgg ggtctcacta tcttgcccag gctggagtgc agtggctctt 47040
tacaggcact gttgtagtgc actgcagcct tgaactcctg ggctcaagtg atcctcctga 47100
gaggctggaa ttacaggcac acaccactgt gtccaacaga ttgcccattt gtgatctgtg 47160
taaatatctc tcacttcctg cagtatctct gctcaagaat gtaaagagat ggataatatt 47220
tttagatttg ttgaaacaaa gtaaagttct gctcaaatga gaatgacact aactaaatga 47280
aaaggccggt tataattctg taattttgtg cctgcaatgt gtgtgttatt gtacacttga 47340
atcggccctg tgcattgtgg cgaggtgcat attgcatggt tgtattgaaa aggtgcttgg 47400
gccgggcgtg gtggctcaca cctgtaatcc cagcaatttg ggaggctgag gcagctggat 47460
tacctgaggt taggagttca agaccagcct ggccaacatg gtgaaaccct gtttctagta 47520
aaaaatacaa aaaattagct gggtgtggtg gtgggtgcct gtaataccag ctactaggga 47580
ggctaaggca gggagaattg cttaaacctg ggaggcagag gttgcagtga gctgagattg 47640
tgccactgca ctccagcctg agtgtatcac aaaaaaaaaa aaaaaaggtt tttgccctct 47700
ctctgtgcct gctgctccct gttgagtcct ataggcctga gctgccaggg ggtactgtgg 47760
gctgagactg gacattgcaa ccgactgcaa ggcaccgtgg gacccaggtt gtggatggac 47820
tgtctctcgg gctttcttct ttccattcat cttcctcctc taactcccct ctgtatccag 47880
tatccttgct ctccatacac ctgcttcatt ctttttcctt cagtagattt ttctgcttct 47940
tgacttacaa accctacttc tagccccttt cagatattga aactagcaac tttcaggctt 48000

-continued

```
tgtaccaaag tctcagagat tctcattgac tcggatgcca tccatctcta gtccaaagaa  48060
caatgtcaag gacatgaaca tgtggaacaa aagtgtctgc tgtggacacc tttggggaga  48120
aatagttttc agtgatgagg gttgtagtga gttgggcaga tatcccaaaa atatctgcca  48180
aaaactatag acacttctgg ttgcagtgac ttattccttc cttcattcag caaatactga  48240
ttgaacaccg actgtatgtc tggatctatt ctaggttttg ggggtggagc agtgaacaaa  48300
tcagtcttta tctttataga gtgtacagtc aagtgggaga gacaggcagt aaacaaagaa  48360
acagttcaat attcaatctg tgagatggtg ataagtgcta cagagaaaac aaactagtgt  48420
aagataaaaa gggtgttttg ataggccttt actatttagg tctctttgat aaggtggcat  48480
ttgaacaaag ctctgaagga aataatggag ccaaccatgc atataacctc agggagaaca  48540
ttctaggtag agggaacagc aagtgcaaag gccctgaagt gggggtttgt ttaccttgtt  48600
gcacaatctg cacacaggcc agtacaattg gaatggatgg gaaatgtaaa agagagaagt  48660
tgaaaaggcc aggtgcagtg gctcatgcct acaatcccag cattttggga ggctgaagtg  48720
ggaggaattt gagatcagcc tggcaacag aaccagacct cgggctaatt tttgtatttt  48780
tagtagagac agggtttcac catattggcc aggctgatct caaactcctg acctcaggtg  48840
atcctcctgc ctcagcctcc caaagtgcta ggattacagg tgtgagccat ggccccccagc  48900
cgtatctttg tcttaaaaag taatctctgt gcttggtagg ccaagaattt aaaatataaa  48960
aaatttaaga aagaaaaaaa ataagtaaag taactataca ggttggtctg gccgtaatgg  49020
tgagtgtcat tatttttctt ccctaggtat tttggctctg ttgctcagag cagtgcaggc  49080
gaaatggtca ttagggcatc gtcatggtgc ctggggatgc ctggctcagc cagtttattt  49140
tctgtctgcc tctctccttg gtccttttcc tccactttca ttcatgaaat tctagtcaag  49200
agctgggtcc agtggtttc aatccaaggg ctttggaagc ctctggggtc tattttggtc  49260
attgcagtca ctgggctgct gctcctggca tttaggttgg caggggtctg ggctgggaag  49320
caggaatgtt cagtggccat aaatgtaagg gttggtctta catttacata agggagacaa  49380
tgaaaactta actcctccac agtagtggag tagtgccgtt gggtactcac agtcagtagt  49440
gccgttgggt actcacatgt acaacatgga tcaggacatt gactttctgt ggataccttt  49500
taatagttta ttagatgtgt taggctgttt tgcactgctc taaaggaata tctgagtcta  49560
ggtaatttat aaagacaaga ggtttaattg gctcatggtt ctgaaggctg tacaagcatg  49620
gctccagcat ctgcttctgg tgagggcctc aggaagcttc cggtcatagt ggaaggcaaa  49680
aggagggcag acgatcacat ggccggagtg gtggcaaggg tggggtggga gccacgctct  49740
ttttttaatt ttattttaat ttgagacagt gtctcactct tttgcccagc ctggagtgca  49800
gtggcgtgat ctcagctcac tgcagcctct gcctcccagg ttcaagcaat tctcctgcct  49860
cagcctcctg agtagttggg actacaggcg cgcatcacaa tgcccagctg atttttgtat  49920
ttttagcaga gacagggttt caccatgttg gccaggctgg tctcggactc ctgatctcaa  49980
gtaatccgcc tgcctcggcc tcccaaagtg ctgggattac aggcatgagc cactgcgcac  50040
ggccaccaca ctgttttaaa caaccagatt gcacgtgaac ttagagtgag aactcactgt  50100
gaggatggca ccaaaacatt catgaaggat ccaccacctt cctttaggcc ccacctccaa  50160
cactggaggt catatttcaa cttgagattt ggaggggaca gacatccaaa ccgtatcatt  50220
aaatttaata gttttatgca gttttttttgg ctctagatct gtttagactc ctgcagtcag  50280
gtgtctgtaa ctagcctctg gtcctttttg agagttcaca gtttggtgca aaccctttgg  50340
atgtattatt tgggaaaatg ggatatctgg cagcctgtgt ccctgcttta cattatcctt  50400
```

tttgctgcct gccccaagcc tcctcattag catccctgcc aaggccagtg gagaaggatg 50460
gagatgcggt gacattcagc ttgacaggtc attagcagct tttgtgccct agggactgct 50520
ggtgggaggg aggttgtgga agataaaccc tgacaggaat gtattctcct cgagggcagg 50580
gtttatttga tatttttctg gagcttagaa ccataagcct ggtgctgggg aggaagcgcc 50640
cttagcattt ggtagcctct gtgggcagag catggaaagt cacaacttct gaattgtttg 50700
tattttcagt ctcactctag atggatggca tcttctgcta tgggaaatga aatatgttta 50760
ggcaacttga gtcccaggtg cagatgaggc tgggctaatt ggtgcactag ggaaggagcc 50820
gggggagaga tgtgctgtta gctattatca atctgtgaca actgtcagct gctggcagtt 50880
agcacccacc tgagcctggg atgcaggggt gcctctcctg tcctctgtgg aagcctctgg 50940
acccagcagc catcttgact gtgcactgtt caagccccaa gtccgcctgg aagaggtgat 51000
tgagaactta ctgcaggata aggaaagcgc aggacaggtg cagtggctca cgcctgtaat 51060
ctcagtgctt tgggaggctg aggccggagg agggctggag tccttgagtg cgagaccagc 51120
ctgggcaaca tagtgagacc ctgtctttac aaaaaggaaa agaattagcc agatgtggtg 51180
gtgcgtgcct gtagtcccag ccactcaaga ggctgaggtg cgaggatcac ttgagcccag 51240
gagtttgagg ttacagtgag ctatgatcat accactgcat tccagcctgg gtgagagagc 51300
atgactctgt cccaacaaca aaaaaaaaga ttaagggaag cctctggcag acctgatgat 51360
gggtggccca gccaaaatga gtattgatga ggatttccct ggtctggaac tctgaattta 51420
gtctggcaaa gtattccctt tgtgttgtga gatgattctt ggtgttaccc catcacggta 51480
ggtaagatga attagcaaat gagaaaggct ttctcttttt catccttatc tagtccgtag 51540
atgaagcctg aagaaggtct ccatatggta gtagtaagtg tttaacatct acctctaaca 51600
cttgcctgtg tctttttttt tttgcaaagc ctcaggaatg ccccagtatc taggtagaat 51660
ttgataatat ttcatttttg ttatattccc ttttctgttt accttctata tacagcaaaa 51720
tgaaaaaatt tttaaaattt gtgcaagtaa gggcaatttc ttttttcttt ttcttttttt 51780
ttgagacagg gtcttgctct ggcacccagg ctggagtgca gtgacacaat ctcggctcac 51840
tgcaacctct gcttcctggg tttaagcgat tctcctgcct caggcttcca agtagctggg 51900
attacaggtg cctgccacca ctcccagcta attttcatat ttttagtaga gaccaggttt 51960
tgccatgttg actgggctgg tcttgaactc ctgacctcag gtgatccatc caccttggcc 52020
tcccaaagtg ctgggattat aggcttgagc cactgggcct ggctgaggca gtttcttttt 52080
gaaatatatt ttgtgaagga gaaaaagagg agttcagttt aaagaaacaa atgacataag 52140
aggtggtatg cagagatgcc aaagcatctt gaaggtgctt tttttttgg aaacagagtc 52200 ttgcttcatt gcccagtctg gtctgcagtg gtgcaatcat ggttccctgc agccttgacc 52260
ttctgggctc aagtaatcct cccacctcag cctctcaagt agctgggact acagatgcat 52320
gccactatgt ctggctaatc tttaaatttt ttgtagaagc cagctctcac catattgccc 52380
aggctggtct tgacctcctg tcctcgagca aaaataccga ttttgattaa gtctggggta 52440
ggacctgggg ctgggattct aaccagctcc caggtggtgc taatgctgct ggtctacaga 52500
ccacacgtgg agtagccagt gtagagttca tgtagcaata gtgatgtcat agaaatagcc 52560
agtatctgta tacttgcttt gttgtatgtc acgcactgta tagtgatgta catgcatctc 52620
atttgaccct caccccgccc ctttgggggt agaaaggatt gtgctcattt cacactcaag 52680
gaaactgagg cacagacagg caaagtagct tggcgaaaca gaaaggaact tagaggcagg 52740

-continued ccctgattag ctcagagact agaaggcctt gtgcgtcatc ctgaacagct tggacttgat 52800
cttgaaggtg gagggagaaa ttgaagggta attaaacagg aactgtagga aattcacctt 52860
gcatagtgat tgctttggcc acgtgtgccc tgccaccgcc cccccacctc agtgaagtgt 52920
catgcgaagt tgggttcgta aatgaaggcc cgaatgcttt cctgacaagt ttgttttaaa 52980
tcaagctgct aattagtccc agtccccctc ccccggtatg tattttttg ttgatgtcgt 53040 ttcacttcat ttagttgaag tgattgattc agttcagtgt ttgaacttct ttttgaacct 53100
caccttaata acctgtctaa acatcaaggt taaaccttct tgctaacaca gcagtattgc 53160
ttggtaagac tggctcacag tccaaggaaa tgcttgccca gagagggcaa actgccttaa 53220
ctccttaacc tgagctcatt aaaaaaaatt caaatgactg attccttgtc acagttctac 53280
ctacattgtt tttatttttg tccaggtttc agctagttaa atgcttttgt gatgagctta 53340
tgtccaggct gaaggttgca ttttgaaact gagcgtcaaa taccaattta aagtccagac 53400
ctttacactt gtgaaattca gataaatgaa atggaaataa aacagggctg ctgtgttgtg 53460
aaatatgact gtgtttttcc ttgtaggact ctttgagggt agccattttg gcattttata 53520
tataaatttt cttttcttag cctacctttt actttcttga tttgcctatt tgtgatttcc 53580
cattaaacac taggcttttt gtaaaccaat tatcccttga aattgacttt tttttttttt 53640
gagacaggat cttgttttgc cacacaggct ggagtgccgt ggctccatca tatgataaac 53700
agaaagagag agagagagag agagagagag agagagagag accctgtctt atttaaaaca 53760
aaaaaagaag aagaaaaaaa gaatatagat cacagctgtt atttgtatat gctacgccaa 53820
tccttgttgg gtttcattct ttataattgt tatttttaaa gatttttctt atgaatattc 53880
tattgtttca ttgtagaaaa tttaagggag aacacagtgg gaaaaaaaaa acaagaaaag 53940
gacttcataa tcctgctacc ctgggagaaa aaaaaaatca ccattaccta tttggttctt 54000
ctcccacttt tttttttttc gagatggagt ctccctttgt tacccaggct ggagggcagg 54060
gacgtgatct tggctctctg caacctctgc ctcctgggtt caagcgattc tcgtgcctca 54120
gcctcccgag tatctgggat tacaggggtg tgccatcaca cctggctaat ttttgtattt 54180
ttagtagaga cggggttttg tcatgttggc caggctggtt tgttggccat gtctggtttt 54240
ttgtcatatt ggccagtctg tttgtcatgt caggctgaca tgttttgtca tgttggccag 54300
gctggtcttt aactcctgac ttcaggtaat cctgaagtgc taggattata ggcgtgagcc 54360
attgcacctg gccttctgcc ttttttttaa agaaaaaaaa ttaaaacatt tttttctttt 54420
taagatagcg tctcatttg ttgcccaggc tggtcttgaa ctcctgggct caagtgatcc 54480
tccagcctca gcctctggag tagctgggac tacagatgca catcatggtg tccttatgcc 54540
atttcttttg tacgtaggtg aatgcaagtg tatgattaca tcatatgcta ttttggaggt 54600
ttgactttct tttcactttc atcatctttc caaggtgtta ttttcctagt acatcttttt 54660
aaatggacat agaacattct tttgtatgaa caaacaatag ttttatttag gcggtccttt 54720
cctgttggac atttatatta ttttcagcat ttctccacag ttgttgcagc attcagatga 54780
accttctttt tttttttttt tgagacggag tctcgctctt tcgcccaggc tggagtgcag 54840
tggcacaatc tctcctcaag tgattcctgt gtcaccctcc cacgtagctg ggattacagg 54900
tgcccatgtc tggctaattt ttgtgttttt ggtagagctg tggttttacc atgttggcca 54960
ggctggtttc gaactcctgc cctgaagtga tctgcccacc tcagcctccc aaagtgtggg 55020
gattacaggt gtaagccatc acgcctgacc cagatgaaca ttcttgtagc tatcgcacac 55080
aattctgaac atttcctagg atgaattcct taaagaagta atgctgatcc aggcttttt 55140

-continued

```
cttttctgt gactctttga cacgtaataa tattgacttt tctttctttc cagacactac  55200
aacaacagga gtgcaaactt ctctacagcc gaaaagaggg tcaaaggcaa gaaaacaaaa  55260
acaaaaatag atataaaaac atcctgccct gtaagtatca atattccgct cagtaatagt  55320
cactcttgga gattttgatt cctagcacct ctgtaccttt cctcagggtc gtgtgctctt  55380
gttagcacat cggaggcctt agcttcttta attgcaagca gtttccaaaa taatcaacca  55440
tggtgggtgt tgatgacttc attcactgag ctcccgtgat gctgattact gagtaaagtt  55500
gccactaggt ggctttgtct gtggttggtt ccttctgtta attaattttc tgtctgccca  55560
agatagatca tctcaaggct tgggatctct cagtgtcagg gaccttaggg tgccagattt  55620
gtgtcttgac tcctcctcac tgggcctgtg agtcctgggt aaggcctgcc tcctttctgg  55680
gactcagttc ccttaagtgg gaaacagaca aacacctcct gagggctcct agaactgttc  55740
tgcttgctga tcccctgagc tcaagttact ggagaaaggg tatataccta aactgctcag  55800
aagaagactt tgtgggccgg gcgcagtggc tcacacctgt aatcccagca ctttcggagg  55860
ccgaggcaag cggatcacct ctgatcagga gttcaagacc agcctggcca acatggtgaa  55920
accccatctc tactaaaaat acaaaaatta gccatatgtg gtggtgtgcg cctgtaatcc  55980
cagctactcg ggaggctgag gcgggaaatt ggttgaaccc aggagatgga ggttgcagtg  56040
agccgagatg tgccattgca ctccagcctg ggtgacaaga gcaaaactcc gtctcaaaaa  56100
aaaaaaagga agactttgtg aatattcgca aagctgtaaa gctgtacctt tcaatttttt  56160
tttgagacat agtctcactc tgttgctcag ggtgcagtca cagctcactg tagcctcaac  56220
ctcctgggct caagcgattc tcccacctca gcctcctgat tagctgggac aataggcagg  56280
caccagtaca cctggttgat tttacagttt ttctgtaggc cggcgcagtg gcttacgcct  56340
gtaatcccag caccctggga ggccgaggtg ggcggatcac ctgaggttag gagttcgaga  56400
gtagcctggc caacatggtg aaaccccatc tctattaaaa attacaaaaa ttagctgggc  56460
gtggtggtgg atgcctgtaa tcccagctac ttgggaggct gaggctgagg caggagaatc  56520
gcttgaacct gggaggcgga ggttgcaatg agccggaggt gctatgtgca ccactgcact  56580
ccaggctggg cgacagagtg agactctgtc tcaaaacaaa aaacgattta aaaaataata  56640
aaattttttc tagggcgggg tctccctatg ttgcccaggc tggtcttgaa ctcctgggct  56700
caagtagtcc tcctgcctca gcctcccaaa ctgttgggat taccagtgca agccattgtg  56760
cctggctgta ccttctgtaa cacccaaatg ccacctggca aagcccaagt tgaatcatga  56820
ggaaaaaagg cctggaagga tgtagacctt cctttttct acttatttat ttatttattt  56880
ttgagatagg gtcttactct gttgcccagg ctggagtgca gtggcatgat catgggtcac  56940
tgcagcctca acctcccggg ctcaagtggt ccttcccacc ccagcctgca atgtagctgg  57000
gactacaggc atgtgctacc atgcccagct aatttttgta ttttttgtaa ttattttttt  57060
tgtagagaca gggtttcgtc atgttgccta ggctggtctc gaattcctgg gctcaaacga  57120
tctgcctgca tcggcctccc aaagtgttgg gattacaggt gtgaaccact gtgtctggct  57180
atatcttctg taacacccaa atgccaccag gcaaagccca agttgaacca ggagggaaaa  57240
aggcctggca ggatgtaggc cttgcatgag gatctcagaa actgcactaa accagtcaca  57300
gttcctctct cccgaggtct aactctatgc tgaactcttt gcatttttat ctcacttaat  57360
ccatatcaca tgcacaggaa ggaagcattc gtagtatcct ggtttcctag accattttag  57420
caaggttata agtgaagggg agtgggtggg agaactggca ctagagcccc caaagtcact  57480
```

-continued gttcttagca ccactctaat gcatggggtt ctccattgat gtgctatgca aggcagtgca 57540
ctgaggagaa aggaaggaac atttacaact tctctttatt tatatcctgt ccctaaaaaa 57600
aaaagaaaaa gaaaaatttg tctgaggcct agattgattg cagggagtgc ataatgtttt 57660
attgattgat tgattgattg tatatagaga tggggggtct cactatattg cccaggctga 57720
tctcgaactc ctaggctcaa gcaatcctcc tgctttggct tcccaaagtg ctgggattac 57780
aggcatgagc gactgcacct ggctatgcat actatattta tccaacttac aaataaggct 57840
tgcttgcctg tagtgcatat gtgtatacat ttcagcatag aaaaactgtg tgattggggg 57900
ttgtgatcaa atttggagag cattgctctc atgtcttatc aggtcagagt catttttgtca 57960 aatcttgtaa accattcttt gtgtgtgtct atgcatgaaa catagtcttt ctctttctgc 58020
atgcatatgt acatatacat ggtatatatg tatatcatat ctacatggat attgtaatgt 58080
atatgtatga ggatgggga aagtggagac atttgtaata ctgagaaaag gcagtgagga 58140
atttgcagag aagcagtttg agctgtagca tggtactagt gaccttgagg aagccttatc 58200
cttttttttt ggaatttatt ttttcaattt ttagaaatag acaagagttt ctctatgttg 58260
cccaggctgg tcttgacctc ctgggcccaa actatcctcc tgccttggct tcccaaagtg 58320
ccaggattac aggtgtggac caccatgcct ggccaccttg tcctttctat gtctaagttg 58380
tgacatctgc tcaggggtca ggtggtatta aatggtataa aatgtatggg aaagtgaagg 58440
gatcaatggt atgcagtatc taaatagaat atcgcttttt cctcccttaa aggtctcatt 58500
cagatgtttc ctctgatgaa catctcattt ccttaaagat gaggagtctg aagcaaaaaa 58560
gacattattc ttttaagaca catggctgtc ttactaattc ccattgcaaa atatgttgtt 58620
taggtagagc actcagattt ttatacgaat aatagacttt tgtacagaat ttggacagtt 58680
gatactatca gagccttgtg atattccact gcattatgct tcactaaaaa atacctggct 58740
gggtgcggtg gctcacaact gtaatcccag cactttggga ggctgaggtg ggcagatcac 58800
ctgaggtcag gagttcaaga tcagcctggc taacatggca aaaccccatc tctactaaaa 58860
atacaaaaat tagccagatg tggtggcacg ctcctgtaat cccagttact caggaggctg 58920
aggtatgaga attgcttgag cccaggaggc agaggttgca gagagccgag atagtgctat 58980
tgcactccaa cctgggtgac agaggaaaac cctgtctcaa aaaataaatt taaaacaaca 59040
acaacaacaa caacaaaaac ccctctttat tatggaaatt ttcaaatata ttcaagagca 59100
taaagaaccc acatgtaccc atcacccagc ttcaacaatt atcaactcat gcccagtctt 59160
ggtttcatct atactctgat ccacatctcc tctctccttg aattattttg aagcccatct 59220
cagacatcat gtcatatatg tatacttcaa tcttcttttt ttttaaaact ccccctcccc 59280
ttttcttttt tcttgagact gtgtctcact ctgtcatcca ggctggagtg atcttggctc 59340
actgcaatgt ccgcctctcg ggttcaagcg atttttgtac ctcagcctcc ctagtagcta 59400
ggattacaga tgtggaccaa catgcctggc taatttttgt atttttaata gagacagggt 59460
tttgtcatgt tggccaggct ggtcttgacc tcctgacctc atatgatcca cctgccttgg 59520
cctcccaaag tgctgaaatt ataggccact gcgcccagcc caaaatttct tggtttgaaa 59580
taattttgga actcataaga agttacacat atagtagaga gaattttctt gtaccttctc 59640
tgagcttcct atatacccaa tgataacatc ctatataccc atagtatatg atcaaaacta 59700
ggaaattgtg aagatggcat tttgagacat caggcagtgt tcacgttact gttttgctta 59760
cctgggcttt aatttttatg tgtttttttt tcaatcattg aatgaacaaa acttggacta 59820
ggctggggag taactgattt gaactgtttt ttcctgaagc agtccaggac ttatgtgacc 59880
gtggtctctt tttcttctag ttgatcatac cagggttgtc ctacacgatg gtgatcccaa 59940
tgagcctgtt tcagattaca tcaatgcaaa tatcatcatg gtaagctttg cttttcacag 60000
tgttttctga ccatacattt ctagcctatt tttgtatttt aaatccttcc tcatgtcctg 60060
aaagtaactt taaggtgttt gaaggatttt cttcctaaat ttctagcctg aatttgaaac 60120
caagtgcaac aattcaaagc ccaaaaagag ttacattgcc acacaaggct gcctgcaaaa 60180
cacggtgaat gacttttggc ggatggtgtt ccaagaaaac tcccgagtga ttgtcatgac 60240
aacgaaagaa gtggagagag gaaaggtaaa tcacagaaac ttcttttctg ctaaactgtt 60300
tttaaagtat cagacatgtc agattggcca tgtttaggaa ttgaataaat gaattaagct 60360
tactgtaact gattctctgg aaaaaaggga ctaggagaaa tttgattatg ttattccttg 60420
gtgtagtttt ctttatgttt cttctgcttg ggatttgttg agcttcttgg ctccatggat 60480
ttgtagtttt ccttaaattt ggataatgtt cagtcttagt ttcttcagat acatatcctg 60540
ggctgggcat ggtggctcat gcctgtagtc ccagcactgt ggggtgttga ggtgggcgga 60600
tcacttgagg tcaggagttt gagaccagcc tgggcaatgt agtaagaccc catctcttaa 60660
aaaaaaaaaa tgtaccctgc acaaccttgt cctaggacag cagtcatacg tgtattagac 60720
tacttgaagt tgtctcatag cccactgata cttggtttat tttattcagt tttttctccc 60780
cgtgtttcat ttcgaatagc ttcttttgct atgtctccaa gttaatcttc tgcaatatgt 60840
catccgctct taatcctatc cagagtattt ttcatcacag acattgtatt tttcatctct 60900
agaagtgtta atgtcatcta tagctttcct tttaacatgt gtagcatttt ccttaccttt 60960
tgaatgtatg gagtatttct gttgttgttt tttgttttgt agagacaggg tctcggtctg 61020
ttgcccaggc cggagtgcag tggcatgatc tcagctcact gcagcctctg cctcccggtt 61080
caaatgattc tcatgcctca gcctcccaag tagctgggac tacaggtgcg tgccaccacg 61140
cctggctaat tttgtattt ttagtagaga tggggttttg ccatgttggc caggctggtt 61200
ttggaacccc tgagcttagg tgatccacct tccttgacct cccaaagtgt tgggattata 61260
ggtgtgagcc accatgcctg gccatgttgt ctgttttaat taactctgcc taactgtcct 61320
cccaaatggt tgctgcagtg ctcactccca ccagcagcac ctgcctagga ctcattactc 61380
catactcttc aagacacttc agattaaaaa aataaattgt aacaccccac acctacagaa 61440
gagcggacag atcttattga gtgacagccc tctgtgttat ctcaaagtga gcccaccatg 61500
gtggtttttt ttttaaatat ggaaaagttc tgtgtttttg tttgtgttct agtgaaagtt 61560
ctttttaga tatcctttaa ttggtttata taagatttta tgtggaatgt agcagtcata 61620
cctataaatt aaacctaagg cagatggaga actttggagt tgagccttcc tactgtaatt 61680
ttcatattgg atgtgaaggg cagtgtgatt ttcataagac tttcattgtt gtactcctag 61740
ttggtatact tctgaatacc tttgaggcca gttctggtca tcgtgaaaca aaggtttcct 61800
tcagcaaatg cctgtggtaa cattaggtgt tcttgaatta atggaccaat gaaaacatct 61860
ttgtagtttc tgcttcaggc aagggttttt tgccctaaat gtggatagga agaatgaagc 61920
ccttcatcct cctttttgcc tgattatagc tataggaggt tcacctgttc tcagaagaca 61980
tgaggattgt gaagagaggg gtcttgtgtt gcttcagagg aatcagtatc agtccctttc 62040
agaagctctc ctggatagac aggcattagg gccaaatcac tctgccccac ccctcaccac 62100
catgtcctac tctctgctcc ctgtctcatt cttcctcttt actttggtgg tgccgagagg 62160
atgacatgat gggtattgat tctctccaca gacctttctg acatcctact ttcagtatcc 62220

```
ccccagtgca cagaagacaa gccagactgt ggactgtgtt tgattcctgg gctctatttt  62280
aaaagacagt gtattagttc tcacatttta gaatttgttt gccaaggttt ccacgggagt  62340
ttagaaacta gggggagggc tgatgtttaa agttagctaa aatgttcttt tcagggtcat  62400
gatttaattt tatattctct ggtgagttcc ctatagtgac tgggagcagt cctcagtctt  62460
gattggccag tgacagcata gagtacaatt aatattagga gtgctcattt ggggaaacta  62520
aaatttgcat caaatctgtc agaggtgttt ggatctacaa aataccggag ggaaagctga  62580
attgagaatc ataataaata aaagaccaca tcgttctttt tttttttttt ttttgggact  62640
gtatcttgct ctgtcactca ggctgcagtg cagtggcact atcttggatc actgcaggct  62700
ccgcctcccg gattcaagcg attttcctgc ctcagtgcct gagtagctgg gattacaggc  62760
gtgtgccact acacctggct aatttttgta attttagtag agacaggttt caccatgttg  62820
gccaggctgg tctcaaactc ctggcctcaa gtgatccacc cggcttccca aagtgctggg  62880
attacaggcg tgagccactg cgcccaacca agaccacatc cttttattga acgttcctcc  62940
taccatgttt tctttttttct ttcaattaat cattgactca ttgactctca ctgttgatgt  63000
ctgtagctgc tctcttattt ccagttttat agctgtaaat ttctctgtct tcctaagata  63060
caaggtaaat ttctcttgct gatattggtg gttttggaaa gtgagtggtg tggatgactg  63120
cccagaaaac aacagaacac aaaagcattc tctgcccaga acacatcacc aaatagatac  63180
aaactcatct cttactgagt gaaatagctt cctttttggc agcaagaatg attttcttgg  63240
tgccatattt ttcaatccgc ctgctcttga agccagcagc tattgcagac ttggcattcc  63300
caggcaccca gttaagggaa agtgacgtgt agaggaggta tcagatgggt ctggatatag  63360
aaaaagcagc tggttcaaaa ccccatgggc tgcctttctg tgatagagtt attcacactt  63420
gggttagata aggcacagag tcctcctaca ctggtgcgga aatgaaacag acagtctggc  63480
tcgttgggca gcctagcctc ctccagaatc tgtgcttgcc ttccctatgg agtgactggt  63540
agatcttaga attcagacct cagtggttgc tagccagcac tctcacattg gttggtcctt  63600
ctctctgcat ctttgattct ttagagatag ataaaccaag caccgactct cctttgacat  63660
gtgcttggaa cagacacctg cacgagctgc ctttctcctc ccacttctgc ctggtcttcc  63720
aaacacctgc ttttcttgtt tgaactcttc cttttttttt gagacagaac ctctctctgt  63780
cacccaggct ggagtgcagt ggcatgatct cagctcactg caacctctgc ctcccaggtt  63840
caaataattc tcctgcctca gcctcccaag tagctgggat tacaggtgcc tgctatcacg  63900
cctggctaat ttttgtattt ttagtagaga cacggtttca ccatttggcc aggttggtct  63960
caaacctctg gtctcaagtg atctgcccgc ctcggccacc cgaactgctg ggattacagg  64020
catgagccac tgcgccccag ctgattcttt acagataaac aaacattgac tctgctttga  64080
catgtgcttg gatcaggtaa ctgcaccagc tgcctttctc ctcccacttc tgcctggtcc  64140
tccgaatgcc tgcttttctt atttgaactc ttctgtcctt ttctgaaaac ctaacagatg  64200
cgaaacaggc cattttccat gttggtggtt attaagcaag acttgaacat ttgtttgttg  64260
cttgtttagg cttttatttc agagttcaca gaattaactt tctttttttc tgatctcttc  64320
cagagtaaat gtgtcaaata ctggcctgat gagtatgctc taaaagaata tggcgtcatg  64380
cgtgttagga acgtcaaaga aagcgccgct catgactata cgctaagaga acttaaactt  64440
tcaaaggttg gacaagtaag tatattgtcg tattctagag actttgggaa ctgttgatgg  64500
tgtgtaggaa ttcagggtct tgccgttact catgtttgca tacatgcatg cattcgctca  64560
ctcattgatt cagtagccat ttattagctt ccttctatgt gccaggtaca gtttaagcag  64620
```

tactggtaca ttgtgaacaa ggcaggtagt gttcctgccc tcatcgagcc tagggagata 64680
gacaatttaa aaacaaataa ctggccaggc gccgtggctc aggcctgtaa tcccagcact 64740
ttgggaggct gaggtgggtg gatcgcttga gccggggagt tcgagaccag ccctgggtgg 64800
gagactggga tagggtgacc tgagtggcta caaggtctgt taggaggcct ccgcaggggc 64860
ctatgttgat ggcctcctct ccaagtatcc acagacttca gcagttgttc tttttgttc 64920
cttcctttgg aatggaatat tatataaaat ggcagaataa actggaagag aagcagtaga 64980
tgtgagaggt gccgggggt gaagtctgca ggatgtgggg attgtttggc ttttggagga 65040
ggaaggaggg attcaagaca cattgtagag gtttgagtct gagcggacag tggtgctgtg 65100
gcagacacca caaaagctgg aaggagaact gatgtgggca gtgatttgtt ttcttctgga 65160
tgtgttcagc tgggcatctg aacagtcatg tggacattca tctattcatt cagagatatt 65220
tgttcaatga cctcttggtt cctggcacca tgctgcttgc tggagataga gctggggaac 65280
aaaacagatg gaatccctgc actcccaagt gtacactata ctggccagta atctaccagc 65340
ccagtaattg cacatataaa tatatcatta taaactgtaa tcagggctag aaagaaaaaa 65400
tgcaggagtt tagggttcat ttggaggggg aagggacttt tttttttttt tttttgaaac 65460
agaatcttgt tctgtcaccc agactggagt gcactggtgc attcacggct cactgcagcc 65520
acaacctcct aagctcaagt gatcctctca cctcagcctc ccatgtagct gggggctaca 65580
ggtgtgtgcc accatgccca cccaattgtt aaattttta tagagacggt tgtctcatta 65640
tgttgcccag gctggtcttg aactcctggg cttaagcgat cctgctgcca catgcagcct 65700
cccaaggtgc tggaattaca ggcgtgagcc agcgcacccg gccaagggag gggaggttct 65760
taaggcatag ggaacaatgt gtttgagtca gcaaaggagg ttgtgggggt ttgtcctaag 65820
tgtggtaagc agccagagtt ggatttaagt ttttaagaga ttcccctcca ccctgtagag 65880
actggagggg gcaggagttg ttctagggat taggaccaat ttggaggtag tgcagccgtc 65940
agagtaaaaa ataataggga ttgaactagg ccagtgccca gggtgcctga aagaagagga 66000
cccagtagag ctgactggag gcagacatgc agggattcag tgaaggagtg taccaagggc 66060
gagggtggtg tgcagggtga ctggcaattt tctagcttga gaaaggtccg gggggatggc 66120
agtggagttg aggaagctgg gaggatcaag gacctttttg tgaacacaca aagtttgaga 66180
tgccttggac acattgaagt ggagcggtca gggaggcaag ggtggaggtg ggatgcggag 66240
gggaggtggg atgcagagcg tcgtggatgg atcagttttg ctcgatagag ggacatgttt 66300
ttctgtggca acaggagggc aaaaggagaa ggtggccaca gatgccggta gatgagctga 66360
gagtgattgt attccctatc ctctcggaag cttgaggcaa ggccatcaac agacaatcag 66420
agggaataag aagagataga atatatgaag aaagggagaa aagatgaaat cgtaattgtg 66480
tagcagggca agaagtccag aaatttctgt gctgtgccaa gttcccagtt gaggcggtga 66540
acatgaaaat atactgatac ccattgcctg gtttttctcc aaggacactt ggctcctagg 66600
gcacaaaaca gaaagtacgt ggtttgtcca ggccgagggc tttgcatagt tgcagtggat 66660
ggagaggagg tcaaggaatg gaggcacatg gtagagagag actgtcccca gagcacgggg 66720
actcctggcc ggatgagggg gacaggggca ggaggaggca ggtggaaagt agagggaggg 66780
ctcagtggtc tggaggctac aggaagtgac ggggggacca gaaggagctg gaaaccagtg 66840
tggttgtggc ccagggtggg atgtttggat ttctgatgtc agagagggtc cagtccttct 66900
gatgatgggg aggggtggag gctgaatcta tggtagagat agtgagagga actggaacaa 66960

```
tgtagctgtc aagtggaaat gggagaaagg gctgggcgtg gtggctcacg cctgtaatcc  67020
cagcatattg ggaggctgag gcaagaggat cgtgttagct caggagttct gggctgcatt  67080
gagctgtgat tgtgccactg cactccagcc ttggcaacag agtgcccagt taaaaataaa  67140
aataaaataa aataaaaaaa ttaaaaaaaa aagaagaaga aaaaagagaa aagtgtcctt  67200
ttacatccct tttaaaaatg tcacttaagg ctgggcaaag tggctcatgc ctgtaatccc  67260
tgcactttgg gaggctgaag tgggtggatt acttgaggtc aggagtacaa gaccagcctg  67320
gccaacatgg cgaaactcct tctctactaa aattagctgg atgtggtaca tgcctgtagt  67380
cccagctact cgggagtcga gtctgaggcc caagaattgc ttgaatcggg gaggcgtagg  67440
ttgcagtgag ctgtgatcag gtcactgtgc accagcctgg atgacagagt gagactctgt  67500
ctcaaaaaaa aaagtcactt agcttagatt gtctctacat atataggaag aagatgtagg  67560
aatgaatggt gctgctacaa ttacgtcatc tggatagacc cagaaacatg atactttttg  67620
gttttctgta gccttggtgc cattgttgat ctttattaat tatcattatc ctcaaaatag  67680
ccataatgtg ctgagtctct tcctatttgc tgggcagagg ctgagtattt cagcgagctc  67740
actgagtcct taaaattgca ttatgataga gagaaagaga ttattatttg cattttgcaa  67800
aatgaagaaa ttgaggttta gagataccca agggccacgt gagtgtgagt gcctggaatt  67860
ggagcctaaa tctagtcatc tgatagcaaa gcctgttttc ttatctgctt tgcattaaat  67920
ataagtttaa aatagaacaa tactggccag gctgggtggc tcacgcctgt aatcccagca  67980
ctttgggagg tcgaggcagg cagatcacct gaggtcagga gtttgcaacc agcctggcca  68040
atatggcgaa agaaacccca tcgctactaa aaatacaaaa attagccagg catggtgatg  68100
tgtgcctgta atcccagcta cttgggaggc tgaggcagga gaatggcttg aacccgggag  68160
gcagaggttg cagtgagcca agatcacgcc actgcactcc agcctgggca acagagtaag  68220
actctgtctt ggaaaaaaaa aaaaaaaaga atgatactat agtctgtgtt tatatggtgg  68280
ggaaggttga gtatcaaaaa aataacaaag aggaatgaat gtcttaagtg aatgcctgtt  68340
tccccatctg cttcctcttc tgctgggagg agagacctgg atccctagag gtttcagttg  68400
cctccagagc tgagtgccac agggatgcag gggaataggg atgttacctg tcgctggtaa  68460
ttcagagaga tgattcaggg tatagttacc tgaaagaaca aattgccatg ccagacgtct  68520
tggttcttat gacagaggca aagagttgcc tccaggattg cccaaaagga gacgagttct  68580
gggaacctca cgaagaggac ctttcagtgg aacctgggga gattctcttc ctctccattg  68640
gatttaggaa agcttagaac cggtgattc ctcaacctct tgatttattt aattcttttc  68700
tggtttttct tggctctact ccaggggaat acggagagaa cggtctggca ataccacttt  68760
cggacctggc cggaccacgg cgtgcccagc gaccctgggg gcgtgctgga cttcctggag  68820
gaggtgcacc ataagcagga gagcatcatg gatgcagggc cggtcgtggt gcactgcagg  68880
tgacagctcc tgctgcccct ctaggccaca gcctgtccct gtctcctagc gcccagggct  68940
tgcttttacc tacccactcc tagctcttta actgtaggaa gaatttaata tctgtttgag  69000
gcatagagca actgcattga gggacatttt gatcccaagg catatttctc ctagacccta  69060
cagcactgcc attggccatg gccatggcaa catgctcagt taaaacagca aagactaagt  69120
cagcattatc tctgagtcca ccagaagttg tgcattaaac aacttcatcc tggctctgca  69180
gtttctcctt attcttcatg atgtttgctt tgtagctgtt gactgctttg taggtattga  69240
ggtggtgggg gtgtggtgga aataggcctg actcttgagg atcccttaag tcatttttgc  69300
ttggttctct ttttccttct tttcttctac tcttctatga ttcatctctt tgattgtgat  69360
```

tctgttctct ctctctctct ctcttttttt tttttcgttt ttgagacaga gtcttgtttt 69420
gttgcccagg ctagagtgca gtggtgccat cttggctcac tgcaacctcc gcctcccggg 69480
ttcaggccat tctcctgcct cagcctccca agtagctggg attacaggca tctgacacta 69540
cgcccggcta atttttgtat tttaatagag acaaggtttt gtcatgttgg ccaggctggt 69600
ctcgaaccct tgacctcagg tgatccacct gccttgtcct tccaaagtgc tgggattaca 69660
ggtatgagct accatgcccg gcccattctg ttctcttcta ccataaatat atttctcccc 69720
taacactata tttgtttgct tcacaagatt ccagctgctt ttccaccaag gcctttgatg 69780
gaagctgtgc tgtgacctct gtaatgagtc tgtgggctgc tgattctcca gtttgggctt 69840
catgattata ctggggaata ttgggtttcc taaatctcat tcatttcttg ggcaagtaga 69900
tatatgtgaa agtgtttatt tgtccagttg ttaaagaagc taccatttat tgagccagcc 69960
tctgagcaca atgtttttttg ttttgttttg tttttaattt ttaaaattat ttacttcttc 70020
tatttcaata actttattat tattattttt tgagacagag tctcactctg tcacccaggc 70080
tagagtgcaa ttgagcgatc ttagctcact gcaacctctg ctttctgggt tcaagcaatt 70140
ctcatgtctc agcctcccga gtagctggga ttactggtac gtgacaacat gcctggctaa 70200
tttttgtgtt tttagtagag acgaggtttt gctatgttgg ccaggctggt ctggaactcc 70260
tggccccaag tgatcctcct gcctcggcct cccaaagtgc tggtattata ggtgagagcc 70320
actgcgcccg gccctctttc agtaattttg atgtattttt ttgtatatga ttcctgtttc 70380
attctgtcca accagcactc tgtatggtat gtgctgttgt ccccatttca cagatgcaga 70440
aattaagggt cagagaggtt aagggactta cctcaggcac gttgtactgg agaagctgaa 70500
ctccaagagc aggtttgggc tgactccaaa gccctatgct ttttgccaac atattttcaa 70560
acataaatag acaattttat aaatagctcc aaagagtaga cattgtttct gttgatatta 70620
atggcttggt tttgagtctg aaacccccat gaatgattct gttgtccctg ctttttgtcc 70680
ttctgcccgc agtgctggaa ttggccggac agggacgttc attgtgattg atattcttat 70740
tgacatcatc agagagaaag gtgggtcatc tggtgggcaa gaagcgacag tttctgtttt 70800
tagtttatgg aaggaaagtg ctcacgaaaa cagtctgggg aagagaggtt gaatgggaaa 70860
attctttcac aaaaatctgg gctgaagact tcagtgtgtc tgcctgagaa cagaagtgac 70920
actatttgag cttttggcat aaaatgaagt ctaggagctg cagaacccac tgccatggcc 70980
ttttgttgca tacacagtgg tggtctctat ccagccacct gaccttgttt acagtatggg 71040
gtgatttgtt ggcaagtgag ggaatcctga cttctgccac ttcgttattt atgtagtctt 71100
ctgggatcat tggtattggt cagaagttca acactgtagc cattgcaaca tgctcagtta 71160
aaacagcaaa gactaaatta gcattgtctc tgagtccact aaaagttgtg cattaaacaa 71220
cttcatcctg gctctgcagt ttctctttat tcttcatgat gtttccttcg taggtgttga 71280
ctgcgatatt gacgttccca aaaccatcca gatggtgcgg tctcagaggt cagggatggt 71340
ccagacagaa gcacagtacc gatttatcta tatggcggtc cagcattata ttgaaacact 71400
acagcgcagg attgaagaag agcaggtacc agcctgaggg ctggcatgcg gattctcatt 71460
ctcttgctag gcctcttgga tacgctctcc ttttgagcag gaggacaggc tctgatagac 71520
aactgtttga tttcggaatg ggaaacaaac tcccaactaa aagggcctct ggaaactgtc 71580
aattattctc cacttctcag ctctgatttt tcactgcaga ggagcttagg gaagggcacc 71640
atcctatcag cctggcctgc cagattgaag aactgccatg cagaaaggtt ctgatgttct 71700

-continued

```
caggctcatg tggcaagcgt aaaactcaaa gccttgaagt ttctagcctg ttccagcctt  71760
gatccaggcc atgtttatcc tgattccatc ctttaaaacg aatgcctcac tcttaatagc  71820
gcacggcagt ttgaaccact aatttggtcg agttggaaac agtgaaattt caattttaat  71880
aagctgtgca taatgaagag gaatgtggaa ttggagcctt tccatctgaa gctattcata  71940
acaggcacaa agctgagtta attaggaata tgctgagatg aaggaaatga ggagagctgc  72000
tcttttgggg gctgtgcttc tctccccaac ccctcaaccc cattgccatg ctgcagatgg  72060
ggtggtgtct aaacatcagt ggcgagtgcc tgcattactc tgctcgttgc cttccagaga  72120
actcagcttc tccaaatgct gagctctttt cagaatggga cctgccacca gtatttgaaa  72180
gatttctagc ctagcagaac agcagccacg ttatcaaagt ttggttggcc aaaggaaggt  72240
acttgctaat tagtttagta ggttttcagt ccgcacagac atacgggatt gttttattgt  72300
acatagacat cttcagaaac agtgtatgta tagaaatgta aggtcaaaat ttgaacctca  72360
gtgctttaaa tctgaatttg tattaactga tatgaaatat ttagacggtt actttatttt  72420
atatctgtct tccattatac ttaatttggc tcaagaatag ttaggcaaaa agttgcccaa  72480
agagaaggat ctcctagtaa atacaaagag aatgtaacat agttgctaca agttggagca  72540
tgttcaggga tgtctttttt tttttttttt tttgagagag aggtctctct ctgttgccca  72600
ggctggagtg cagtggtgta atcatggctc actgcagcct caatctccca ggcttaagcg  72660
atcctcccac ctcagcctcc caagtagctg ggactatagg catgcgccac cacacctagc  72720
taattttcgc atttttgta gtgtcacagt ttcgccatgt tgcccaggct agtctcgaat  72780
tcctaggctc aagcagtgct tctgcctcag cctctctgag tagttaggac tacaaatttg  72840
tggctccatg cccggctaat ttttttatct ttattttgta gagacaaggt ctcactgtgt  72900
tgcccaggct agtcttgaac tcctgggctc aaacaaccct cccactttgg gtttccaaag  72960
tgctgggatt acaagtgtga gccactgagc ccagtgacct ctgggtttta aaaatgtgta  73020
ggcttcaatt atttatttta aaaaatgaaa tcctgcaata tatagttttc tgcgttgtgt  73080
ggtttgaatc aatctgggaa ctggcttgct ggctgattgt ggtaaagtaa gaagtactta  73140
atttagtaga aagtttaaat ggcagacata acattaaacc cagctgattt ataaatgaag  73200
caaaagaaca aaactcattc aggataattg gttattctaa aatacagtca tttctaaaat  73260
tatgaagtgt tcaggacctt tgggagtgaa agaatttgct aaagaaggat cagtgaaaaa  73320
aaggaatgat gggtgaagag ctgtggagaa ggaagagaag aaacagcaca aggaaggaag  73380
aatataaaat cagatgtggg aatccagggg aaagtgcaaa cgaagcaaga ttgagaaaat  73440
tctcaagttt ttataaacag ttctcacact ctgccagttc cttggaggta gactttttg  73500
ttaacttcca actacagtag tgaaaaaaaa aaaaaaaccc tcaaatttgc aaaagcagtc  73560
tgtggaattt tctttaccca gctttcctga ctgttaactt tttagcacac ttaactttat  73620
cattcgttta ttctctctgt ttaaaattaa aaatgtaaat tttaaaaagt aaaatgtttg  73680
ttggttacaa acatttatac ccctttgtct ctaaatatca tttcatttta aaaaatgaat  73740
aatctaagcc tacacattct aaaatgtgta tattttctaa aaataagggc attctcttac  73800
ataaccaatg tcacaattat ttgatacagt gatcaaaatc aggaaactaa cattgatata  73860
acactattat ctaacctaca gaccatcttc aaattttgtc ctgctagtat cttttatggg  73920
tccagggtca cacagtgcat ttggctataa tgtatctttt ttctcttttt ttgagacagg  73980
gtctcacttt gttgcccagg ttggagtgca gtggtgcaat tatggctcac ggcagccttg  74040
acctccttgg gctcaggtga tcctcccacc tcagcctctc gagtagctgg agaccacagg  74100
```

tgtgcaccac catgcctggc taagttttgt attttttgta gagatggagc ttcgccgtgt 74160
tgccccggct ggccttgaac tcctgggctc aagtgaccct cccgccttgg cctcccaaag 74220
tgctgggatt acaggcgtga gtcaccacac ctggccagtt attagtatgt ttagtctctt 74280
taatctggaa cagtttctca gtcattcttt atttttcatg acctggatgt ttttgaagag 74340
tttaggccag ctatttagca gaatgccttt cagtttggat ttgtccagtg ttttctcttg 74400
actatattct agtcatgcat ttttggcagg actgtcacag aaatgttgtt gtagtcttct 74460
tagtacatca catcaggtac acactgttga tctgattcat tactagtggt gttaactttg 74520
atcacttgaa taaggtggtg tctgtcaaat ttgtccaccg taaagttact tgagcaaaac 74580
gtagctggga ctacaggcgt agcaaaaaat gtagcaaaaa gtagtatttt tgctacattt 74640 ttttttttagg aacaaagtat ttttcccttt taagttaatc tcttgtccat aaagttatta 74700
tttttccctt ttaagttaat atcttgtggg tagatactgg agactgcgta aattacctat 74760
ttctcataat actttttttt tttttgagat ggagtctcgc accgtctccc aggctggagt 74820
gcagtggtgc aatctcgggt cactgcaagc tccacctccc gggttgacgc cattctcctg 74880
cctcagcctc ccaagtagtt gggactacag gcgcccgcca tcacacctgg ctaatttttt 74940
gtatttttag tagagacggg gtctcaccgt gttagccagg atggtcttga tctcctgacc 75000
ttgtgatctg cccgccttgg cctcccaaag tgctgggatt acagatgtga gtcactgcgc 75060
ccggctctca taatactttt tgcctactaa ttttatattc attgattaaa ttcttgcctg 75120
aaaaaattat tactgtggta tttgccaaat ggcaattttc tgtttccatc attgcctttc 75180
ccccgctttt aaaagtataa gtgacaaaga aaaactgtat ataaagtgta caccatgata 75240
ttttgatata tgtatacttt gtgaaatgat tatcaaaatt gagttaaata atgcatccaa 75300
catctcagtt actttttttt ttttttgaga cagagtcttg gtttgtcact aaggctggag 75360
tgcagtgcca caatctcggc tcattacaac ctccacctcc caggttcaag tgattctcct 75420
gccttggcct ccccagtagc tgggattaca ggtgcccacc atcacacccg gctaattttt 75480
gtatttttag tagaggtggg gtttcactac gttggccagg ctggtctcga actcctgacc 75540
tcaaatgatc ctcccgtctc agctttccaa agtggtggga ttacaggcgt gagccactgt 75600
gcccggccac tcttagtaaa ttttaagtgt acattttttt tttttttttt ttgagatgga 75660
gtctcacttt gtcaccctgg ctggagtgca gtggcatgat cttgccacac tggaacctct 75720
gcctcctggg ttcattcagg tgcttctccc acctcagcct cccaagtagc tgagactaca 75780
ggtacccgcc accatgcctg gctaattatt gtatttttag tagagatggg ggttcaccat 75840
gttagccagg ctggcctcaa actcctgacc tcaggtgatc tacccacctc ggcctcccaa 75900
agtactgaga ttacaggcat gagccaccac acccagccac attacgttag tattaactat 75960
aatcaccatg ctgtacatta gatctccaaa atgtattcat cttatgtaac ttcaagtttg 76020
taccctttga ccaaagtctc cttgttttcc ctaccccaa cccctggtaa tcactgcttt 76080
aatctcagtt tttatgagtt tgactggttt agattccaca tacaaatgag atcaggcagt 76140
gatggtttat ttcacttagc ataatgtcat ccatgttctt gcaaatgaca ggattttctt 76200
ctttttaaaa ctaatatcca tgctggacac ggtggctcat gcctgtaatc ccagcacttt 76260
ggaaggctga ggagggtgga tcacttgagg tcaggagttc gagaccagcc tggccaacat 76320
ggtgaaaccc catctctacc aaaaatataa aaaattagct ggatgtggtg gcgcacacct 76380
gtgatcccag ctacttggga cactgaggca ggaggatcgc ttgaacccgg gaggcggagg 76440
ttgcagtgag ccaagatggt gccactgcac tttagcctgg atgttgatgt tgttccactt 76500
gtttattttt attttgttcc ctgtgctttt ggtatcaaat cctaaaaacc attgccatga 76560
ccattgtcat gttactttcc ccatatgctt tcttctagaa cttttaaggt tcatcattcc 76620
cttttctgtt tttagttgca agcctactat aaggaagggc ttttctttct tccttattta 76680
tttattcatg tctatcagaa tgggcacctt actactattt ttgttgttat tgcttgaatt 76740
gacttgaatt tggctagtgg aaaccttttc agatcgggta ctctgtcctt ttgatctctt 76800
tccattttca agcacttctt tagacttaag atggtctagg ctcatcttct cctttcccag 76860
ccatttttca aaggaacctg attcctttta gtgaagagca gtatttgaa accaagatct 76920
gggcactggg tctacttgtt tgtactggta cagtgttctt tgaattgcta attagctgat 76980
caattactgc tctatttgag ttccctcttt ctaaaacctc acatatgtgt acagacggtc 77040
cctgacttat gatggttcga cttatgattt ttgattttat gatggtttga gagcaataca 77100
tccattctgt ttttcacttt tcattcaaca ctttatttta aaatagggat tgtgagatga 77160
tattgcccac gtgtaggcta atgtaagtgt tctgagcacg tttaaagtag gctaggctaa 77220
gctgtggtgt ttggtaggtt agatatgtta aatgcatttt cgactagtga tattttcaac 77280
ttatgatgag tttattggga tgtatcccca taaagtcgag gagcattata catatctctg 77340
tataacagag tgagttcctt atacctttca tccactttcc cctgaagtta acattttacc 77400
taaccatgat acatttatca aaactaaaac attaacatca atacattgct attaactaaa 77460
ctagagttta attggatttt gccagttttc caatgaatat cctttttctg ttccttgatc 77520
caattcatgg tcacacactg agtttggtca cttgtcactg tagtcttctc caatctgcga 77580
cagcttctta ggctttcctt gtttttcatg tactcttgac gatttttaag agtactggtc 77640
agatatcttg taggatatcc cacaacttgt gtttaatctt atgttttctc atgattagac 77700
ttgagtaatg gatttttggg aagaatacca cagaggtata ttgttaagtg ttctcatcac 77760
ttggaggtaa atgttatcaa catggcctgg tgatgttaaa cttgtcagtt tgtttagtta 77820
gtatctgcca gatttttctc actgcataat tacaaatcct ccttaactta tgatggggtt 77880
acagcctgat aagcccatca taaattgaaa atatcataag tcaaaaatgc atttaatgca 77940
tctaaactac taaacatcac agcttagcct agcctgcctt gaacgtattc aggacactta 78000
cattagccta cagttgggca aaatcatctc atgggaagcc tgttttataa tgtgttgcat 78060
atcttatgta atgtgttgag tactgtactc agaatgaaaa acagaagggt tgtattgctt 78120
ttgcaccatc ataaaatcaa aaaaaccata aggcaaacca tcatgaagtt ggggactgcc 78180
tgtacttttt tcctctttcc ctgttcaatt ccttggaaga aagtcattta gttcagacca 78240
tactcaagaa aagggaaata aagctccatc tcttggagct taattgaaac tggaatgact 78300
agtttctata tacattattt agaatccttt tgtaagaaag atttgttcct tctctccatt 78360
tatttattcc attatttata ttgatagaga cgcatgtaca tttattttat actttgggtt 78420
ataatctatt tttcttgctc aaattgttac agctttggtc actgggaggt tcttcagatt 78480
ggctcctgtg tcatttgaca tgtccccacc ctctcgtttc tgagtacttc tctactttgg 78540
cattacaaaa gatgttccag gctcctctta tatttttccc tgccgcagcc ctagaatcat 78600
ccattttttct atggtgccct ggttcctttt actttagatg gggtttaga aaccaatctg 78660
ggtgttgggt gtgctcattg ctactggaat cactgcttct aggccctctc agcagataga 78720
gctagaaaac atatggctgt atatgaatcc atggattcat atatatctat aattgttttc 78780
tgtatctggc catctatata tatattaagc taaacatgaa ttcatactga tgtctcagac 78840

```
tcgaatccat tgccgcaggg ctcattcttg ccttcctctt gcttatttgt gacttctttc  78900
tctaacaggg agaaacccca gtctcattat caccaaccta tctactcatt tgttcaaccc  78960
tggtataggt gtaaagtagt ttcagaatta ctaacctata cccatgtgag aattgtattt  79020
gcacttcttg tttgaaggaa atacatacaa cacaggtagc gtctctacac ttcagtatac  79080
agagatctga acagtgttct ctctgagtga atcatattgc aggacagaaa ttacttttaa  79140
aaattctgta atgggtcagg cctataatcc tagcactttg ggaggctgag gtgggcagat  79200
cacctgaggt caggagttcg agaccagcct ggccaaaatg gtaaaacccc atctctacaa  79260
aaaatacaaa aattagccag gcgtagtggt gtgtgcctgt aatcccagct actcaggagg  79320
ctgaggcacg agaatcactt gaacctggga ggcagagctt gcagtgagct gagattgagc  79380
cactgcactc cagtctgggc gacagagcga gactctgtct caaaaaaaaa aaaaaaaaaa  79440
aattccataa tgatagcaga gctggaatag aaatgggatt gcacaggctg aatctgagtt  79500
gttgcaacag taaacgagca agatttaaac tggccttgtg tagcacttgc tatttggctc  79560
ctcatatttt attagacgct tattcttttt tgtttggtgt cattcctttg agaaatattt  79620
gagtgccttt tctgttgcag acattgatta gatgctgagg ttgtaacaat gaagaagata  79680
gccatcgctg ttgcctcatg gaactgaagt tttactagat gtaaaatttg agttaacatg  79740
aggccgtgcc cctatgtgcc ctattgtttc ttcacacagc tcccttcatc tccttggtcc  79800
aatgaaaagg ttttttcata cttgttcatt cattcctgca ttaattaaag taggttgtac  79860
tgtgccaggc actgggaata tttaagtagt tgtgttcctg aattggaaat gaatccagca  79920
tggttggagt agaaggagct ggggggcaat gtggagtgtg atggggagat tggaaaagta  79980
agctgagacc agatttttca gtttggaggg agaggtgggc cttgtaggcc atattacaga  80040
ttgtagactt tatttggagg gacatggaag tcattgagga gtctgaagca ggggaatgac  80100
ataaaaagat cctcatttta ggccggatgt ggtggctcac gcctgtaatc ccagcacttt  80160
gggaggttga agtgggtgga ttgcttgagg ccaagagttt gagactagcc tgggcaacat  80220
ggtgaaaccc tgtctctatc aaaaatacaa aaattagctg ggcatggtgg ctcacacctg  80280
tagtcccagc tacttgggag gctgaggcat gagaatcgct tgaacccggg aggcagagat  80340
tgcagtgagc cgagattgtg ccactgcatt ccagcctggg tgacagagtg agacttcgtg  80400
tcaaaaaaaa aacaaaaaac ccctcatttt gaaagggaac cctggcttga gggtgaagaa  80460
tgggtgggca ctaggctaga gcagctgcag ggtcagtgag gagctgccgc agtgctgcac  80520
gtgagaaccc gtcatggttt ggtcagggtg ggcaggactg acagtgagca cagagcgaag  80580
taaaaccagc aaaatttcat gattggatag tggaaggaat catggtgttt gtagtcttca  80640
aatgtgaacc cagagtgcac tggacaagta gtctaggctg ctctgtaacc aaggcaagtg  80700
ttttcatttt accctctctt cctgctcttg gcctttggat tttttgtaat ttaaggttta  80760
tgaatgtaat cagttactta acatggaaag atacttaata ccagatgatt ttggagtctt  80820
gtgatcaata ccttctctca atcttgggtg tgtgtcagtt ggcaaggcca taaaatttgt  80880
tataaacatt gcagaaggct tggttactgt gctgtgacgt tgaatttggg tggagataga  80940
tcaatttcag ttgattttct aggcttcaga aacacattac cctctactcc acaaacacaa  81000
atcaaaacaa aacaatccct attccctgag catttctctt gatctataac acagcctggg  81060
ctgtcacagt actaagacaa gcccatctga tttgtgagtc agttttattt cttggtcttc  81120
tacataagct aaaaagtttc aacattttaa tgcttttcct tggattcctt tgagtcattg  81180
```

aagtaattcc tgtttcattt gtactaatta ttccacacta gaaaattctg ttgtaatcac 81240
tttatgtatt aatagaaata ctgattttta ttttcaagga agtattgagt agggaggggg 81300
aaatagggat ttgctgttca atgggtatag agtttcagta atacaagaca aaaaacttca 81360
gagatcttct atacagcagt gggtatatag ttaacaatac tgcacatcta acagtttgtt 81420
aagagggtag atctcatgtc atgtgttttt aaaaattgct tttaaaaaaa gtatcgagta 81480
aaaaagcagt tttactcctc agtttctatt tatatttaaa atttttattt aaaaagtgag 81540
ttgagatttt taaacctcag gataagtttt attttttaaa aaatttattt tttattattt 81600
tttgagatgg agtctcactc catctcaagt cacccaggct ggagtgcagt ggtgtcttgg 81660
ctcactgcga cctctatctc ccaggttcaa gtgtttctgc tgcttcagcc tcctgagtag 81720
ctgggattac aggtctgcac caccacgcct ggctaatttt tgtattttta gtagagatgg 81780
ggtgtcacca tgttggccag gtttgtcttg aactcctaac ctcaagtgac cacctgcctt 81840
ggcctctcaa agtgctggga ttacaggtat gagccacagt gcccggcggg ataagtttta 81900
aaataatatt ctctgctggc tgggcatggt ggctcatgcc tgtaaaccca gcactttggg 81960
aggctgaggc aggagcatca ctcgaggcca agagtttgag accagtctgg gcaacataat 82020
gagacccccct ctctacaaaa aataaaaaaa atttggctga gtgtggcatg ttcctgtagc 82080
tatcgggagg ctgagatggg aggattgctt gagcccagga gtttgaggct gcagtgagct 82140
atgattgcac cactgcgctc tagtctgggt gacagtgtga gaccctgtct cttaaaaaaa 82200
aaaaaaaaaa aggccaggca cagtggctca ggcctgtaac cccagcactt tgggaggccg 82260
aggcgggtgg atcacttgag gccaggaatt tgagaccagg ctggccaaca tgatgaaacc 82320
ccgtctctac taaaaataca aaaataagct gggtgttgtg gtgcacacct gtaatcccag 82380
ctacttggga ggctgaggga gagaattgct tgaacctggg aggcagaggc tacagtgagc 82440
cgagatcaca ccactgcact ccagcctggg tgacagagca agactccatc tcaaaaacaa 82500
caacaacaaa aaaaccaaat gttcttgcca attcttccat ttaatattta attttgaatt 82560
atattgtatc tttctaagga ttgtttctta tataagcaaa gatttttcag tgctaaacat 82620
ttacgactgc tattcagaaa tggttattta caagtctttt tgttttaaga aaatggctgt 82680
tcaaaaaatt aaaatagtat ataaaccaaa caaaatattt ttgctttgga tgtctgtttt 82740
gcagcttctt ccctacacta taagttctta ctgactgctt tatcacttaa taaattggtt 82800
tggctacttt aacagaggca aatagtatca ggcaaaaaat tattttttat ttttattttt 82860
tgagacagtc tcactccatc acccaggctg cagtgcagtg gcctgatctt ggctcactgc 82920
aacctccacc tcccaggttc aagcgattct catgcctcag cctcctgagt agctggaatt 82980
ataggcatgc accaccacac tcagctaatt tttgtatttt tagtagagac agggttttgc 83040
catgttgacc aggctagtct tgaactcctg acctcaagtg atccatctgc tttggcctcc 83100
caaagtgctg ggataacagg catgagccac catgcccagc cctatttttt attttttaga 83160
gatgggtctc gctttttaga gatgggtctt gttgcccagg ccagagtgca gtggtgcgat 83220
catagcttac tgcagccttg aattcctggg ctcaagcaat tctcctgcct cagcctcccg 83280
agtagctggg actacaggcc tgtgccacca ggcctggctt gtacattagt atttgatatg 83340
gctaccctaa gggcaatcct atagtgaagt caacattaga taatgatgct catctgatgg 83400
attagatttt cagagttggc tgtttccagg tgcctatagg agtagaaaag ggtgacaaac 83460
ctcctaacta gatgtcctac caaatatagt tcactccaca tctgagatga gactgcatga 83520
ctgctggttt tctttgcctt ttcccccca gggtatcatc agaaccaaaa ataaagtttt 83580

-continued

```
aaaggtgggt caggtgtgtg ttggctcatg cctgtaatcc tagcactttg ggaggctgag  83640
gcaggtggat catctgagct caggagttca agaccagcct ggctaataac atggttaagc  83700
cccatctcta ctaaaataca aaaagttagc tgggcatggt ggtgggcacc tgtaatccca  83760
gctactcagg aggctgaggc atgaaaatcg cttgaacccc agaggcgggg gttgcagtga  83820
gccgagatca tgccactgca cactagcctg aacaacagag caaggctctg tctccaaaca  83880
aacaaaaatg gtgccagagt cttttccagg gctgagggga gatacaatga agtgtgttat  83940
tttttctgat aagagtgcta ccatctttca ttcttgtgtg ccatttctag ttggggtgaa  84000
tttgttttcg gagttccttt cccagctgtt tgcctgaaaa accatgaaat gtgttccaca  84060
tgaactatga aatgattaga tgctaatgtg gcaaagaaag tgtgaattct cttgtagaaa  84120
cagggacatt tggttcggta cagtaagttg ttaatgcgtg actctgtgct ttcaaattct  84180
gtggttcaaa agtacttttc actcctactg tgtatttacc ttgagaaggt gaatccccta  84240
acaatttggt caatgtatca gtattctcaa cccgtctatc aatttttttt tctttctccc  84300
tcttttttct tttttgggc aaaatacctt ttttgctttt tatcccctta aaataaccat  84360
tgtccctcac atgtgcactc ttccaaattt cagaaaagca agaggaaagg gcacgaatat  84420
acaaatatta agtattctct agcggaccag acgagtggag atcagagccc tctcccgcct  84480
tgtactccaa cgccaccctg tgcagagtaa gtagtgctga aggaaattct ttttacctgg  84540
tcatggtggt ttaaaaaggt ttaaaaaaca aaaacaaaaa caaaacacaa gtttgtagca  84600
catgcctttc actggtgcac gttcctgttg ccctactgtt agtgtatctg tgactggtga  84660
tatctattga ttgtgttaat gctatctcaa ccacgtttta attttcctaa gctggccagg  84720
cacggtggct aacgcctgta atcccagtgc tttgggaggc cgaggttcat ggattacttt  84780
gaagtcagga gttcgagacc agcctggcca acatggtgaa accctgtctc tactaaaaat  84840
acaaaaatta gccgggcatg gtggcgcatg cctgtaatcc cagctactca ggaggctgag  84900
gcaggagaat cgcttgaacc caggaaacgg atgttgcagt gagccgagat catgccactg  84960
cactccagcc tgggcgatag agtgagcctc tgtctaaaaa taaaataaaa taaaataaat  85020
tcctaaactg aaggctgact gctatgctag ctaggattat atgggatttt aagtatatca  85080
agtggtggtt ctccaagaag aatctaattt ttcttttgat gggctgggga ttgtaacaaa  85140
ggaaggtcat atgtcttaat gatgtgttaa ggctctttgc aaaatcaaag taaataaatt  85200
gaccactaat gtgtcagccc agccatgttc tgctcatttg ccaccagtca acagaaatct  85260
actttgggtg tttaaaccag gagtcagcaa actacagctc acaaggccag atgtgggcca  85320
tggcctgtta ctgtatggcc tgttaatggt tttaaagggt tgtaaaacaa aagaacacaa  85380
aacaaagacc caataacaaa acaaagcccg aagaataata tgcgacagag accatgtatg  85440
gcatatagag cctaaaatac tgactctcaa gcccttccca gaaatccttc ccgactcctt  85500
gttgaaaaca cggtaggaaa gcatttgtca aattgaggat atgaatagca attgtaagtt  85560
attatttttc tatatattcg aaagtcactt gctagtataa catttacctt ttatttttcc  85620
ctaagaatct tctctctgtt tgctttcgac atggattttt aaacccctgc agattttaat  85680
attctatata aatgttttag gtggcatata tgaggtttgt attaacattt gctttctatt  85740
taacattgaa atgaaattat acagcagagg tattttctcg tccaagttgc cacttctttc  85800
tatctttttt cttttctttc ccagtggact gcctgggaaa attgatattt taaattgctc  85860
tctgcaataa tttgcaatgg aactggaatg ccagggttct gagtccttgc cagacagctc  85920
```

```
gtccctcctg ttggcatgac tgagtcagct gtcatgattc cctcagtacc agtggcatgc  85980
ctgtgacaga cagcctgtct gcctttcatt cccgtcgtct cccttgtagg gttcagatcc  86040
aggatacact ggtcctggag cccctctcag cctggcaccc acagctgctg ggttccttac  86100
tctcctggac tgctctgatg tcatctccct gctcagcaga aagaagtctg ggatcttgat  86160
gctttggccc tctgtcctag gccctaaacc acccattgcc cttcacataa cctgagctgg  86220
ggctaaatag atctctcatc actgcctgcc tgctcctgta ttttcccttc ttggagcttt  86280
tgcctgttca gatccctcta ctggaaatta ataggatttc attctatgtg tgcatttcca  86340
acctttcttc acagtgcgat ccaaatgcct catcctacag gcctccttaa aacaacctgc  86400
tttctgccag accccaggga gcaccaggac ttgaggcttt tattgcactt ctgttgtttt  86460
tttgagatgg agtctcgctc tgtcgcccag gctggagtgc agtggcacga tctctgctca  86520
ctgcaacctc catctcccga gttcaagaga ttcttctgcc tcagcctctc aagcagctgg  86580
gactacaggc atgtgccatg acacccggat aatttttgta tttttagtag agacggggtt  86640
caccatattg gccaggctgg tctcaaactc ctgacctcgt gatccaccca cctgggcctc  86700
ccaaagttct gggattacag gcgtgagcca ccatgcccag cgttatttca cttctgcctc  86760
tgtaattata ttgctgtatg gctatctctt ctctccctgg gaatgtcagg tcctaggcac  86820
aggaactgtg tctgtaccat atctggtgcc caaagaatgt agtatgtgtt ttatagatat  86880
catgtaagct taaacagcgt ggtctacatt tttgtaaatg tctttctttt tcttttctct  86940
ccagaatgag agaagacagt gctagagtct atgaaaacgt gggcctgatg caacagcaga  87000
aaagtttcag atgagaaaac ctgccaaaac ttcagcacag aaataggtat ttaaatgcaa  87060
gtgctctatt ggttaattgt ttatataatt ggcagtattt ttaagcaggc aagcaatttg  87120
ggaatgtttt agcaaagtgt accataattg agttttacaa accaggctcc tttttcctct  87180
ccctgtactt ctttttccaa gatggtttta gtttagagtt cattaaacat taaaatcaaa  87240
cacagaatta attctgcatg aggcaaggct agcacttatt ccagagaaat ggctgatact  87300
ggtggtagag tgcaggtatc actgttcctg caatttttat tagagttggt tagcccaggc  87360
tgtgctgggg gatgatctgt agggatctgg gaagcatcgg gactcagcac tgggtggttg  87420
ggagtcagga agcctgagtt ctcatttcag tcagtctctg accaactgtg tggcatgggg  87480
tgctagacca cttggctgcc gactgggtca ccgacatccc ttccagctct gctgctggaa  87540
attcatctct cccatatgtt gcctccccat caattacgtt ttttaagtgt gacccaagta  87600
tatgatgtat gttttcatga taaattagaa acttatctgg gcatggtggc tcatacctgt  87660
aatcccagca ctttgggagg ctgaggtggg cggatcacct gaggtcagga gttcgagacc  87720
agcctgacca actaaaatag tagagaccaa cccgtctcta ctaaaaatag aaaattagct  87780
gagcatggtg gtgcatgcct ataatcccag ctactcagga ggctgaggca ggagaggcag  87840
cggttgcagt gtgccaagat cgcgccattg cactccacct gggccacaag agtgaaactc  87900
catctcaaaa aaaaaaaaaa aaaaaaaaaa actcagtgtc agtatttcat gtcgaaattc  87960
cacttcaatg ggtagtgtag ttaaaagctc taagtctacc ttaaaatcac ctaatgcttt  88020
gttaagcttt tagatatatg ttccttaaaa actcttaact tatttcttcc ccagatgtgg  88080
actttcaccc tctccctaaa aagatcaaga acagacgcaa gaaagtttat gtgaagacag  88140
aatttggatt tggaaggctt gcaatgtggt tgactacctt ttgataagca aaatttgaaa  88200
ccatttaaag accactgtat tttaactcaa caatacctgc ttcccaatta ctcatttcct  88260
cagataagaa gaaatcatct ctacaatgta gacaacatta tattttatag aatttgtttg  88320
```

aaattgagga agcagttaaa ttgtgcgctg tattttgcag attatgggga ttcaaattct 88380
agtaataggc ttttttattt ttatttttat acccttaacc agtttaattt tttttttcct 88440
cattgttggg gatgatgaga agaaatgatt tgggaaaatt aagtaacaac gacctagaaa 88500
agtgagaaca atctcattta ccatcatgta tccagtagtg gataattcat tttgatggct 88560
tctatttttg gccaaatgag aattaagcca gtgcctgaga ctgtcagaag ttgacctttg 88620
cactggcatt aaagagtcat agaaaaagaa tcatggatat ttatgaatta aggtaagagg 88680
tgtggctttt tttttttct tttttccagc cgttgaccaa ttatagttcg gctgttgact 88740
gagaagtttg tggtgggaaa acgtttgcca tatttttcttt gcatttgaat aattgtcttg 88800
tacttagaaa aaaggcgtct atgaatgacc agtgtttttg gtcgccaaat gttgctgaca 88860
aacttatccc aaaactttag tggcttaaaa aaacctgccc ccaactgtta gtcaatctga 88920
gctgggctca gctgggctgt tcttctgcca gcctgcaggt ggccactcat gtggtcagca 88980
ggtcggcgga gagactggga tggctgggct tctctctctg cctgcagtcc tgagtctctc 89040
cttcttcgtg tagtctcttt cagtggcctg gctggcaggg tagctagacc tctcacatgc 89100
agctcagagc tcccaagagc tcaaaagcag aaatggccag gccttctgaa aacttaagtc 89160
cagaattgtc acagtgtccc ttctacttcc ctctattgat gatgatgatg atgatgatga 89220
tgatgatgat gatgatgatg atggtttttt ctaatcagaa gaaagctggg gtatgccctc 89280
tacttactaa acaagtcaca agcccagctc agattcaaga aaagggtgtg aagtagaggt 89340
gcagttaagt ggggggccac tagtctaaca gacggtcaca accagtgcca tggaaaacca 89400
aggatattag caaaagcaga agttgctagt gaccttggga agccgaagct gcttacagta 89460
gctgggacaa gctgaaagtc agactaagaa ataaagagag ggccttcaag aagcttcctg 89520
aatgatttct gctagccctg agcctatttt tggaaccagc acttggggaa actgatcttg 89580
tgaggatgga tgtgtttagg gacacagggc ttttgagagc agcaccaccc cactggggca 89640
tccccagact tgggaaacgt gactctttct taatgccact gggttttagt caggccacag 89700
tgagaaggaa cagccctaac aggcctccag ccaggttgaa tgagctcatt tttgttgtag 89760
ccaaccagta agatttgcta atgttctaca ttaagtgcct tctccaaaga catccctctt 89820
tgcctcatat gttgaatcat ccagtgcgga tatttcaatg aaaatatcat tggttgactt 89880
ttgtgatggt aataatgcta tggcatcttt gccatgaagt tgtggcctcc ttggattctt 89940
ctgactttgg cttctgaaag gaaggcctag atccagccct ggtggtagtt cctttctgag 90000
gtctctcagt cccttgagac tttggggtag tttggctgcc attctcactg acaaaatgta 90060
tatcagcccc cacctccacc ccccaatatt ccttgaactt tgaattgctt cagaacacag 90120
gtgtggcctg aaggtattcc cttattaggg aagtgtcact gctgtcttct agtcaaactt 90180
gtaaagaaaa agattccagt tcagtatttg cagcaagaag cttgaatgct gttcttttta 90240
tcgcattgtt acatcgactc attctccatt ttgctttggt tttgtcttga cttgacttga 90300
ctttgggggt aaagtctttc accagcacac aagagtttga ttgtacaaat atatcttctg 90360
cattaacatc tctgcctgtt gcttaagatc agttgctttt atactcagaa tggaaatacc 90420
tgatcttggc tagttttgtt ataagatatt gatttcattt agatttccct ccacgaggtc 90480
agcaaactat catgttctta tgtaaactta ggccaaggcc agagttatca tagtccctag 90540
gttgctacgg cttatcatgt gcttggtaaa aggtgatcgc aggttctcag acgagtttac 90600
tttacatgag atggaatcag gcagagaggc tgggatgatg gagaaagctc gaggtgaagt 90660

```
tttaaaaaaa aagttgtgga aaggaaagtt ccaaagaggt ggtttctgag gaagtcagag  90720
cgcccagggc cagagcagtc agtaatgggt gaatgaggtt gtttggaaag tcggtgtgac  90780
agacacatgg atgccatcta cttctaggtt gctggtgggt attaaatatg cacaatattc  90840
catagctcac tgaggatttt aaaattataa gcataggatt ttatattttg gggtgaaaga  90900
attatctggc acattaggta ttggagttta aaaaaaaagc caaatttcac agtcttaata  90960
actttttta aaaaaaacta aaaggcgctt catgtccagt gtgtggccct tctgaaactt  91020
atggtcatct ctcccactga aaccaaggtc ttttcaaatg tggctaaatg gggatgagga  91080
gacacgggta ggactttctt ggtgtgtgtg cattctttaa agagccaagt tgcttcgggg  91140
aaacagccag gaaaatggtc aagattattt ttagaggtta ttttattggg gattttaaga  91200
actaataaca tcttgagtta tttttaattc agggggatgt ggaaaggttt gcaattgtca  91260
agtgttttgt tgtagcttag tatccataag ggaaacttag actatagaca taactacaaa  91320
gccagtgcag cttttgtttt ctgtatgttg ttgggggatc aactttcaca catagcaagc  91380
acatggcctc cctgatgtca ggatgccttt gttaggatct gtatttgccc ttaattttgt  91440
tgaaatcttt tttccttctt cctcttgaaa agttccaaaa tatagtttat tgtatctttc  91500
atcactaaaa atttgttcct ttttcactat gggcagttca cacaaggcaa aaactattga  91560
acagttggtt ttagtgtgtt gtataacttt gctgtatatc aaactaattt tgacaagttt  91620
tcatcctaag cctcaaatca tgtaattaat aatttgcctg tttatttatg acctaattgt  91680
gattctttta ttaataaaag ctaatgggaa aaggatccct gattaagctg atgactagac  91740
ctacaattaa ttttcctgca gtatatgaag tattgtacca gagtattaaa agatatgtaa  91800
tattttattg ataaatctat cctttaaaag gaatacgttt taggatgtca tcattttgat  91860
gtgaatcatg taaatgttga taatatgctg tttattatac atttagtgtt tcaagagatt  91920
cacttaattg cctttttgcc cacgtatatt atgtagtcta tttgcaactg ttcttaaaaa  91980
aatgacatta aaagaatagt ttatgtagag aaacattagt ggatgttaat tgtctcccca  92040
cctatattta tgggtgttag cgcaactgct ttgctagttg caaagctgta ttatcagagt  92100
aaaagtgtat ttgtaaactg tatgggaact aaaaattagg aataaaacca ttttcttata  92160
tgatggcatt tgtcgtttgc ttcatcagaa atgtccagga aaaaaatggg attattggtc  92220
actccacctc tcacactggc aaaatactga catttagcag ctcttatcta gaagtgactt  92280
ggaacataga ataaaggcat gagttcctga agaattcatt gagtgtttcc tgtagaaata  92340
gctttaggag atagggagtt ctatctggga gaacatatga gtaactcaag agtaaaaagt  92400
atagtctgtg taaactatag aagaaatgct gggcatggtg gcgcgcccct gtaatctcag  92460
ctacttggag gctgagacgg gaggattcct tgaacccagg agcccaggag ttttagacca  92520
gtctgggtaa catagtgaga ccctttctca cctactctca ctgcatgccc cccaaaaata  92580
tatatgtgcg cgcacgcgcg cgcacacaca catacacaca cacacacaca cacacacaca  92640
cagaggaaat tgttagaaaa cacacagaac tgaatgtaaa tagtattagg tgggaataag  92700
aagtaaaggg atggtaagga ggcttggagg aggagtaaat tatctgctat gggacatcag  92760
ctc                                                                92763
```

<210> SEQ ID NO 61
<211> LENGTH: 593
<212> TYPE: PRT
<213> ORGANISM: Homo sapiens

<400> SEQUENCE: 61

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415
```

-continued

```
Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val Val His Cys Ser Ala Gly Ile Gly
    450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Glu Gln Lys Ser Lys Arg Lys Gly His Glu Tyr Thr Asn
    530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Gln Lys Ser Phe
            580                 585                 590

Arg
```

<210> SEQ ID NO 62
<211> LENGTH: 1296
<212> TYPE: DNA
<213> ORGANISM: Homo sapiens

<400> SEQUENCE: 62

```
atgcccaacc ccaggcctgg caagccctcg gccccttcct tggcccttgg cccatcccca     60

ggagcctcgc ccagctggag ggctgcaccc aaagcctcag acctgctggg ggcccggggc    120

ccagggggaa ccttccaggg ccgagatctt cgaggcgggg cccatgcctc ctcttcttcc    180

ttgaacccca tgccaccatc gcagctgcag ctgcccacac tgcccctagt catggtggca    240

ccctccgggg cacggctggg ccccttgccc cacttacagg cactcctcca ggacaggcca    300

catttcatgc accagctctc aacggtggat gcccacgccc ggacccctgt gctgcaggtg    360

cacccccctgg agagcccagc catgatcagc ctcacaccac ccaccaccgc cactggggtc    420

ttctccctca aggcccggcc tggcctccca cctgggatca acgtggccag cctggaatgg    480

gtgtccaggg agccggcact gctctgcacc ttcccaaatc ccagtgcacc caggaaggac    540

agcacccttt cggctgtgcc ccagagctcc tacccactgc tggcaaatgg tgtctgcaag    600

tggcccggat gtgagaaggt cttcgaagag ccagaggact tcctcaagca ctgccaggcg    660

gaccatcttc tggatgagaa gggcagggca caatgtctcc tccagagaga gatggtacag    720

tctctggagc agcagctggt gctggagaag gagaagctga gtgccatgca ggcccacctg    780

gctgggaaaa tggcactgac caaggcttca tctgtggcat catccgacaa gggctcctgc    840

tgcatcgtag ctgctggcag ccaaggccct gtcgtcccag cctggtctgg cccccgggag    900

gcccctgaca gcctgtttgc tgtccggagg cacctgtggg gtagccatgg aaacagcaca    960

ttcccagagt tcctccacaa catggactac ttcaagttcc acaacatgcg accccctttc   1020

acctacgcca cgctcatccg ctgggccatc ctggaggctc cagagaagca gcggacactc   1080
```

```
aatgagatct accactggtt cacacgcatg tttgccttct tcagaaacca tcctgccacc   1140

tggaagaacg ccatccgcca caacctgagt ctgcacaagt gctttgtgcg ggtggagagc   1200

gagaaggggg ctgtgtggac cgtggatgag ctggagttcc gcaagaaacg gagccagagg   1260

cccagcaggt gttccaaccc tacacctggc ccctga                             1296


<210> SEQ ID NO 63
<211> LENGTH: 1875
<212> TYPE: DNA
<213> ORGANISM: Homo sapiens

<400> SEQUENCE: 63

atggtgaggt ggtttcaccg agacctcagt gggctggatg cagagaccct gctcaagggc     60

cgaggtgtcc acggtagctt cctggctcgg cccagtcgca agaaccaggg tgacttctcg    120

ctctccgtca gggtgggga tcaggtgacc catattcgga tccagaactc aggggatttc    180

tatgacctgt atggaggga gaagtttgcg actctgacag agctggtgga gtactacact    240

cagcagcagg gtgtcctgca ggaccgcgac ggcaccatca tccacctcaa gtacccgctg    300

aactgctccg atcccactag tgagaggtgg taccatggcc acatgtctgg cgggcaggca    360

gagacgctgc tgcaggccaa gggcgagccc tggacgtttc ttgtgcgtga gagcctcagc    420

cagcctggag acttcgtgct ttctgtgctc agtgaccagc ccaaggctgg cccaggctcc    480

ccgctcaggg tcacccacat caaggtcatg tgcgagggtg gacgctacac agtgggtggt    540

ttggagacct tcgacagcct cacggacctg gtggagcatt tcaagaagac ggggattgag    600

gaggcctcag gcgcctttgt ctacctgcgg cagccgtact atgccacgag ggtgaatgcg    660

gctgacattg agaaccgagt gttggaactg aacaagaagc aggagtccga ggatacagcc    720

aaggctggct tctgggagga gtttgagagt ttgcagaagc aggaggtgaa gaacttgcac    780

cagcgtctgg aagggcagcg gccagagaac aagggcaaga accgctacaa gaacattctc    840

ccctttgacc acagccgagt gatcctgcag ggacgggaca gtaacatccc cgggtccgac    900

tacatcaatg ccaactacat caagaaccag ctgctaggcc ctgatgagaa cgctaagacc    960

tacatcgcca gccagggttg tctggaggcc acggtcaatg acttctggca gatggcgtgg   1020

caggagaaca gccgtgtcat cgtcatgacc acccgagagg tggagaaagg ccggaacaaa   1080

tgcgtcccat actggcccga ggtgggcatg cagcgtgctt atgggcccta ctctgtgacc   1140

aactgcgggg agcatgacac aaccgaatac aaactccgta ccttacaggt ctccccgctg   1200

gacaatggag acctgattcg ggagatctgg cattaccagt acctgagctg gcccgaccat   1260

ggggtcccca gtgagcctgg gggtgtcctc agcttcctgg accagatcaa ccagcggcag   1320

gaaagtctgc ctcacgcagg gcccatcatc gtgcactgca gcgccggcat cggccgcaca   1380

ggcaccatca ttgtcatcga catgctcatg gagaacatct ccaccaaggg cctggactgt   1440

gacattgaca tccagaagac catccagatg gtgcgggcgc agcgctcggg catggtgcag   1500

acggaggcgc agtacaagtt catctacgtg gccatcgccc agttcattga aaccactaag   1560

aagaagctgg aggtcctgca gtcgcagaag ggccaggagt cggagtacgg gaacatcacc   1620

tatcccccag ccatgaagaa tgcccatgcc aaggcctccc gcacctcgtc caagagcttg   1680

gagtctagtg cagggaccgt ggctgcgtca cctgtgagac ggggtggcca gaggggactg   1740

ccagtgccgg gtccccctgt gctgtctcct gacctgcacc aactgcctgt acttgccccc   1800

ctgcacccgg ctgcagacac aaggaggatg tgtatgagaa cctgcacact aagaacaaga   1860

gggaggagaa agtga                                                    1875
```

<210> SEQ ID NO 64
<211> LENGTH: 1782
<212> TYPE: DNA
<213> ORGANISM: Homo sapiens

<400> SEQUENCE: 64
atgacatcgc ggagatggtt tcacccaaat atcactggtg tggaggcaga aaacctactg 60
ttgacaagag gagttgatgg cagttttttg gcaaggccta gtaaaagtaa ccctggagac 120
ttcacacttt ccgttagaag aaatggagct gtcacccaca tcaagattca gaacactggt 180
gattactatg acctgtatgg aggggagaaa tttgccactt tggctgagtt ggtccagtat 240
tacatggaac atcacgggca attaaaagag aagaatggag atgtcattga gcttaaatat 300
cctctgaact gtgcagatcc tacctctgaa aggtggtttc atggacatct ctctgggaaa 360
gaagcagaga aattattaac tgaaaaagga aaacatggta gttttcttgt acgagagagc 420
cagagccacc ctggagattt tgttctttct gtgcgcactg gtgatgacaa aggggagagc 480
aatgacggca agtctaaagt gacccatgtt atgattcgct gtcaggaact gaaatacgac 540
gttggtggag gagaacggtt tgattctttg acagatcttg tggaacatta taagaagaat 600
cctatggtgg aaacattggg tacagtacta caactcaagc agccccttaa cacgactcgt 660
ataaatgctg ctgaaataga aagcagagtt cgagaactaa gcaaattagc tgagaccaca 720
gataaagtca aacaaggctt ttgggaagaa tttgagacac tacaacaaca ggagtgcaaa 780
cttctctaca gccgaaaaga gggtcaaagg caagaaaaca aaaacaaaaa tagatataaa 840
aacatcctgc cctttgatca taccagggtt gtcctacacg atggtgatcc caatgagcct 900
gtttcagatt acatcaatgc aaatatcatc atgcctgaat ttgaaaccaa gtgcaacaat 960
tcaaagccca aaaagagtta cattgccaca caaggctgcc tgcaaaacac ggtgaatgac 1020
ttttggcgga tggtgttcca agaaaactcc cgagtgattg tcatgacaac gaaagaagtg 1080
gagagaggaa agagtaaatg tgtcaaatac tggcctgatg agtatgctct aaaagaatat 1140
ggcgtcatgc gtgttaggaa cgtcaaagaa agcgccgctc atgactatac gctaagagaa 1200
cttaaacttt caaaggttgg acaagggaat acggagagaa cggtctggca ataccacttt 1260
cggacctggc cggaccacgg cgtgcccagc gaccctgggg gcgtgctgga cttcctggag 1320
gaggtgcacc ataagcagga gagcatcatg gatgcagggc cggtcgtggt gcactgcagt 1380
gctggaattg gccggacagg gacgttcatt gtgattgata ttcttattga catcatcaga 1440
gagaaaggtg ttgactgcga tattgacgtt cccaaaacca tccagatggt gcggtctcag 1500
aggtcaggga tggtccagac agaagcacag taccgattta tctatatggc ggtccagcat 1560
tatattgaaa cactacagcg caggattgaa gaagagcaga aaagcaagag gaaagggcac 1620
gaatatacaa atattaagta ttctctagcg gaccagacga gtggagatca gagccctctc 1680
ccgccttgta ctccaacgcc accctgtgca gaaatgagag aagacagtgc tagagtctat 1740
gaaaacgtgg gcctgatgca acagcagaaa agtttcagat ga 1782

<210> SEQ ID NO 65
<211> LENGTH: 930
<212> TYPE: PRT
<213> ORGANISM: Artificial Sequence
<220> FEATURE:
<223> OTHER INFORMATION: Generic TALEN amino acid sequence (to recognize
15bp DNA sequences)
<220> FEATURE:
<221> NAME/KEY: misc_feature

```
<222> LOCATION: (187)..(188)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (221)..(222)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (255)..(256)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (289)..(290)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (323)..(344)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (356)..(357)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (390)..(391)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (424)..(425)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (458)..(459)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (492)..(493)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (526)..(527)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (560)..(561)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (594)..(595)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (628)..(629)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (662)..(663)
<223> OTHER INFORMATION: To recognize C: XX = HD; To recognize T: XX =
      NG; To recognize A: XX = NI; To recognize G: XX = NK

<400> SEQUENCE: 65

Met Asp Tyr Lys Asp His Asp Gly Asp Tyr Lys Asp His Asp Ile Asp
1               5                   10                  15
```

-continued

```
Tyr Lys Asp Asp Asp Asp Lys Met Ala Pro Lys Lys Lys Arg Lys Val
            20                  25                  30

Gly Ile His Gly Val Pro Ser Arg Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Thr Tyr Cys His Ile Ile Thr Ala Leu Pro Glu Ala Thr His Glu Asp
            100                 105                 110

Ile Val Gly Val Gly Lys Gln Trp Ser Gly Ala Arg Ala Leu Glu Ala
        115                 120                 125

Leu Leu Thr Asp Ala Gly Glu Leu Arg Gly Pro Pro Leu Gln Leu Asp
    130                 135                 140

Thr Gly Gln Leu Val Lys Ile Ala Lys Arg Gly Gly Val Thr Ala Met
145                 150                 155                 160

Glu Ala Val His Ala Arg Asn Ala Leu Thr Gly Ala Pro Leu Asn Leu
                165                 170                 175

Thr Pro Glu Gln Val Val Ala Ile Ala Ser Xaa Xaa Gly Gly Lys Gln
            180                 185                 190

Ala Leu Glu Thr Val Gln Arg Leu Leu Pro Val Leu Cys Gln Ala His
        195                 200                 205

Gly Leu Thr Pro Glu Gln Val Val Ala Ile Ala Ser Xaa Xaa Gly Gly
    210                 215                 220

Lys Gln Ala Leu Glu Thr Val Gln Arg Leu Leu Pro Val Leu Cys Gln
225                 230                 235                 240

Ala His Gly Leu Thr Pro Glu Gln Val Val Ala Ile Ala Ser Xaa Xaa
                245                 250                 255

Gly Gly Lys Gln Ala Leu Glu Thr Val Gln Arg Leu Leu Pro Val Leu
            260                 265                 270

Cys Gln Ala His Gly Leu Thr Pro Glu Gln Val Val Ala Ile Ala Ser
        275                 280                 285

Xaa Xaa Gly Gly Lys Gln Ala Leu Glu Thr Val Gln Arg Leu Leu Pro
    290                 295                 300

Val Leu Cys Gln Ala His Gly Leu Thr Pro Glu Gln Val Val Ala Ile
305                 310                 315                 320

Ala Ser Xaa Xaa Gly Gly Lys Gln Ala Leu Glu Thr Val Gln Arg Leu
                325                 330                 335

Leu Val Leu Cys Gln Ala His Gly Leu Thr Pro Glu Gln Val Val Ala
            340                 345                 350

Ile Ala Ser Xaa Xaa Gly Gly Lys Gln Ala Leu Glu Thr Val Gln Arg
        355                 360                 365

Leu Leu Pro Val Leu Cys Gln Ala His Gly Leu Thr Pro Glu Gln Val
    370                 375                 380

Val Ala Thr Ala Ser Xaa Xaa Gly Gly Lys Gln Ala Leu Glu Thr Val
385                 390                 395                 400

Gln Arg Leu Leu Pro Val Leu Cys Gln Ala Asn Gly Leu Thr Pro Glu
                405                 410                 415

Gln Val Val Ala Ile Ala Ser Xaa Xaa Gly Gly Lys Gln Ala Leu Glu
            420                 425                 430

Thr Val Gln Arg Leu Leu Pro Val Leu Cys Gln Ala His Gly Leu Thr
```

```
        435                 440                 445

Pro Glu Gln Val Val Ala Ile Ala Ser Xaa Xaa Gly Gly Lys Gln Ala
    450                 455                 460

Leu Glu Thr Val Gln Arg Leu Leu Pro Val Leu Cys Gln Ala His Gly
465                 470                 475                 480

Leu Thr Pro Glu Gln Val Val Ala Ile Ala Ser Xaa Xaa Gly Gly Lys
                485                 490                 495

Gln Ala Leu Glu Thr Val Gln Arg Leu Leu Pro Val Leu Cys Gln Ala
            500                 505                 510

His Gly Leu Thr Pro Glu Gln Val Val Ala Ile Ala Ser Xaa Xaa Gly
        515                 520                 525

Gly Lys Gln Ala Leu Glu Thr Val Gln Arg Leu Leu Pro Val Leu Cys
    530                 535                 540

Gln Ala His Gly Leu Thr Pro Glu Gln Val Val Ala Ile Ala Ser Xaa
545                 550                 555                 560

Xaa Gly Gly Lys Gln Ala Leu Glu Thr Val Gln Arg Leu Leu Pro Val
                565                 570                 575

Leu Cys Gln Ala His Gly Leu Thr Pro Glu Gln Val Val Ala Ile Ala
            580                 585                 590

Ser Xaa Xaa Gly Gly Lys Gln Ala Leu Glu Thr Val Gln Arg Leu Leu
        595                 600                 605

Pro Val Leu Cys Gln Ala His Gly Leu Thr Pro Glu Gln Val Val Ala
    610                 615                 620

Thr Ala Ser Xaa Xaa Gly Gly Lys Gln Ala Leu Glu Thr Val Gln Arg
625                 630                 635                 640

Leu Leu Pro Val Leu Cys Gln Ala His Gly Leu Thr Pro Glu Gln Val
                645                 650                 655

Val Ala Thr Ala Ser Xaa Xaa Gly Gly Arg Pro Ala Leu Glu Ser Ile
            660                 665                 670

Val Ala Gln Leu Ser Arg Pro Asp Pro Ala Leu Ala Ala Leu Thr Asn
        675                 680                 685

Asp His Leu Val Ala Leu Ala Cys Leu Gly Gly Arg Pro Ala Met Asp
    690                 695                 700

Ala Val Lys Lys Gly Leu Pro His Ala Pro Glu Leu Ile Arg Arg Val
705                 710                 715                 720

Asn Arg Arg Ile Gly Glu Arg Thr Ser His Arg Val Ala Gly Ser Gln
                725                 730                 735

Leu Val Lys Ser Glu Leu Glu Glu Lys Lys Ser Glu Leu Arg His Lys
            740                 745                 750

Leu Lys Tyr Val Pro His Glu Tyr Ile Glu Leu Ile Glu Ile Ala Arg
        755                 760                 765

Asn Pro Thr Gln Asp Arg Ile Leu Glu Met Lys Val Met Glu Phe Phe
    770                 775                 780

Met Lys Val Tyr Gly Tyr Arg Gly Glu His Leu Gly Gly Ser Arg Lys
785                 790                 795                 800

Pro Asp Gly Ala Ile Tyr Thr Val Gly Pro Ile Asp Tyr Gly Val Ile
                805                 810                 815

Val Asp Thr Lys Ala Tyr Ser Gly Gly Tyr Asn Leu Pro Ile Gly Gln
            820                 825                 830

Ala Asp Glu Met Gln Arg Tyr Val Lys Glu Asn Gln Thr Arg Asn Lys
        835                 840                 845

His Ile Asn Pro Asn Glu Trp Trp Lys Val Tyr Pro Ser Ser Val Thr
    850                 855                 860
```

```
Glu Phe Lys Phe Leu Phe Val Ser Gly His Phe Lys Gly Asn Tyr Lys
865                 870                 875                 880

Ala Gln Leu Thr Arg Leu Asn Arg Lys Thr Asn Cys Asn Gly Ala Val
                885                 890                 895

Leu Ser Val Glu Glu Leu Leu Ile Gly Gly Glu Met Ile Lys Ala Gly
            900                 905                 910

Thr Leu Thr Leu Glu Glu Val Arg Arg Lys Phe Asn Asn Gly Glu Ile
        915                 920                 925

Asn Phe
    930


<210> SEQ ID NO 66
<211> LENGTH: 933
<212> TYPE: PRT
<213> ORGANISM: Artificial Sequence
<220> FEATURE:
<223> OTHER INFORMATION: Generic TALEN amino acid sequence (to recognize
      15bp DNA sequences)
<220> FEATURE:
<221> NAME/KEY: misc_feature
<222> LOCATION: (188)..(189)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (222)..(223)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (256)..(257)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (290)..(291)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (324)..(325)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (358)..(359)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (392)..(393)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (426)..(427)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (460)..(461)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (494)..(495)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (528)..(529)
<223> OTHER INFORMATION: To recognize C: XX = HD; To recognize T: XX =
      NG; To recognize A: XX = NI; To recognize G: XX = NN
```

<220> FEATURE:
<221> NAME/KEY: misc_feature
<222> LOCATION: (562)..(563)
<223> OTHER INFORMATION: To recognize C: XX = HD; To recognize T: XX = NG; To recognize A: XX = NI; To recognize G: XX = NN
<220> FEATURE:
<221> NAME/KEY: misc_feature
<222> LOCATION: (596)..(597)
<223> OTHER INFORMATION: To recognize C: XX = HD; To recognize T: XX = NG; To recognize A: XX = NI; To recognize G: XX = NN
<220> FEATURE:
<221> NAME/KEY: misc_feature
<222> LOCATION: (630)..(631)
<223> OTHER INFORMATION: To recognize C: XX = HD; To recognize T: XX = NG; To recognize A: XX = NI; To recognize G: XX = NN
<220> FEATURE:
<221> NAME/KEY: misc_feature
<222> LOCATION: (664)..(665)
<223> OTHER INFORMATION: To recognize C: XX = HD; To recognize T: XX = NG; To recognize A: XX = NI; To recognize G: XX = NK

<400> SEQUENCE: 66

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Arg Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Thr Tyr Gln His Ile Ile Thr Ala Leu Pro Glu Ala Thr His Glu Asp
            100                 105                 110

Ile Val Gly Val Gly Lys Gln Trp Ser Gly Ala Arg Ala Leu Glu Ala
        115                 120                 125

Leu Leu Thr Asp Ala Gly Glu Leu Arg Gly Pro Pro Leu Gln Leu Asp
    130                 135                 140

Thr Gly Gln Leu Val Lys Ile Ala Lys Arg Gly Gly Val Thr Ala Met
145                 150                 155                 160

Glu Ala Val His Ala Ser Arg Asn Ala Leu Thr Gly Ala Pro Leu Asn
                165                 170                 175

Leu Thr Pro Glu Gln Val Val Ala Ile Ala Ser Xaa Xaa Gly Gly Lys
            180                 185                 190

Gln Ala Leu Glu Thr Val Gln Arg Leu Leu Pro Val Leu Cys Gln Ala
        195                 200                 205

His Gly Leu Thr Pro Glu Gln Val Val Ala Ile Ala Ser Xaa Xaa Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser Xaa
                245                 250                 255

Xaa Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Xaa Xaa Gly Gly Lys Gln Ala Leu Glu Thr Val Gln Arg Leu Leu
    290                 295                 300
```

-continued

Pro Val Leu Cys Gln Ala His Gly Leu Thr Pro Glu Gln Val Val Ala
305 310 315 320

Ile Ala Ser Xaa Xaa Gly Gly Lys Gln Ala Leu Glu Thr Val Gln Arg
325 330 335

Leu Leu Pro Val Leu Cys Gln Ala His Gly Leu Thr Pro Glu Gln Val
340 345 350

Val Ala Ile Ala Ser Xaa Xaa Gly Gly Lys Gln Ala Leu Glu Thr Val
355 360 365

Gln Arg Leu Leu Pro Val Leu Cys Gln Ala His Gly Leu Thr Pro Glu
370 375 380

Gln Val Val Ala Ile Ala Ser Xaa Xaa Gly Gly Lys Gln Ala Leu Glu
385 390 395 400

Thr Val Gln Arg Leu Leu Pro Val Leu Cys Gln Ala His Gly Leu Thr
405 410 415

Pro Glu Gln Val Val Ala Ile Ala Ser Xaa Xaa Gly Gly Lys Gln Ala
420 425 430

Leu Glu Thr Val Gln Arg Leu Leu Pro Val Leu Cys Gln Ala His Gly
435 440 445

Leu Thr Pro Glu Gln Val Val Ala Ile Ala Ser Xaa Xaa Gly Gly Lys
450 455 460

Gln Ala Leu Glu Thr Val Gln Arg Leu Leu Pro Val Leu Cys Gln Ala
465 470 475 480

His Gly Leu Thr Pro Glu Gln Val Val Ala Ile Ala Ser Xaa Xaa Gly
485 490 495

Gly Lys Gln Ala Leu Glu Thr Val Gln Arg Leu Leu Pro Val Leu Cys
500 505 510

Gln Ala His Gly Leu Thr Pro Glu Gln Val Val Ala Ile Ala Ser Xaa
515 520 525

Xaa Gly Gly Lys Gln Ala Leu Glu Thr Val Gln Arg Leu Leu Pro Val
530 535 540

Leu Cys Gln Ala His Gly Leu Thr Pro Glu Gln Val Val Ala Ile Ala
545 550 555 560

Ser Xaa Xaa Gly Gly Lys Gln Ala Leu Glu Thr Val Gln Arg Leu Leu
565 570 575

Pro Val Leu Cys Gln Ala His Gly Leu Thr Pro Glu Gln Val Val Ala
580 585 590

Ile Ala Ser Xaa Xaa Gly Gly Lys Gln Ala Leu Glu Thr Val Gln Arg
595 600 605

Leu Leu Pro Val Leu Cys Gln Ala His Gly Leu Thr Pro Glu Gln Val
610 615 620

Val Ala Ile Ala Ser Xaa Xaa Gly Gly Lys Gln Ala Leu Glu Thr Val
625 630 635 640

Gln Arg Leu Leu Pro Val Leu Cys Gln Ala His Gly Leu Thr Pro Glu
645 650 655

Gln Val Val Ala Ile Ala Ser Xaa Xaa Gly Gly Arg Pro Ala Leu Glu
660 665 670

Ser Ile Val Ala Gln Leu Ser Arg Pro Asp Pro Ala Leu Ala Ala Leu
675 680 685

Thr Asn Asp His Leu Val Ala Leu Ala Cys Leu Gly Gly Arg Pro Ala
690 695 700

Met Asp Ala Val Lys Lys Gly Leu Pro His Ala Pro Glu Leu Ile Arg
705 710 715 720

-continued

```
Arg Val Asn Arg Arg Ile Gly Glu Arg Thr Ser His Arg Val Ala Gly
                725                 730                 735

Ser Gln Leu Val Lys Ser Glu Leu Glu Glu Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Pro Thr Gln Asp Arg Ile Leu Glu Met Lys Val Met Glu
    770                 775                 780

Phe Phe Met Lys Val Tyr Gly Tyr Arg Gly Glu His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Glu Arg Tyr Val Glu Glu Asn Gln Thr
        835                 840                 845

Arg Asp Lys His Leu Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe
    930
```